United States Patent
Zeng et al.

(10) Patent No.: US 7,514,566 B2
(45) Date of Patent: Apr. 7, 2009

(54) THIAZOLE COMPOUNDS AND METHODS OF USE

(75) Inventors: Qingping Zeng, Thousand Oaks, CA (US); John G. Allen, Newbury Park, CA (US); Matthew P. Bourbeau, Woodland Hills, CA (US); Celia Dominguez, Los Angeles, CA (US); Christopher H. Fotsch, Thousand Oaks, CA (US); Nianhe Han, Thousand Oaks, CA (US); Fang-Tsao Hong, Thousand Oaks, CA (US); Xin Huang, Roslindale, MA (US); Matthew R. Lee, Calabasas, CA (US); Aiwen Li, Westlake Village, CA (US); Qingyian Liu, Camarillo, CA (US); James T. Rider, Camarillo, CA (US); Seifu Tadesse, Simi Valley, CA (US); Andrew S. Tasker, Simi Valley, CA (US); Vellarkad N. Viswanadhan, Thousand Oaks, CA (US); Xianghong Wang, Moorpark, CA (US); Kurt E. Weiler, Thousand Oaks, CA (US); George E. Wohlhieter, Lake Balboa, CA (US); Guomin Yao, Newbury Park, CA (US); Chester Chenguang Yuan, Newbury Park, CA (US)

(73) Assignee: Amgen, Inc., Thousand Oaks, CA (US)

( * ) Notice: Subject to any disclaimer, the term of this patent is extended or adjusted under 35 U.S.C. 154(b) by 0 days.

(21) Appl. No.: 11/652,728

(22) Filed: Jan. 11, 2007

(65) Prior Publication Data
US 2007/0173506 A1    Jul. 26, 2007

Related U.S. Application Data

(60) Provisional application No. 60/759,546, filed on Jan. 18, 2006.

(51) Int. Cl.
A61K 31/425 (2006.01)
C07D 277/00 (2006.01)

(52) U.S. Cl. ..................... 548/198; 514/370

(58) Field of Classification Search ............ 548/198
See application file for complete search history.

(56) References Cited

U.S. PATENT DOCUMENTS

| | | | |
|---|---|---|---|
| 3,591,600 A | 7/1971 | Fancher | |
| 3,932,400 A | 1/1976 | Hibino et al. | |
| 4,086,239 A | 4/1978 | Fancher | |
| 4,297,365 A | 10/1981 | Rajappa et al. | |
| 4,451,471 A | 5/1984 | Ferrini et al. | |
| 4,496,560 A | 1/1985 | Farge et al. | |
| 4,886,833 A | 12/1989 | Gayer et al. | |
| 5,086,053 A | 2/1992 | Brodin et al. | |
| 5,145,860 A | 9/1992 | Takasugi et al. | |
| 5,232,921 A | 8/1993 | Biziere et al. | |
| 5,302,608 A | 4/1994 | Sohda et al. | |
| 5,550,138 A | 8/1996 | Sohda et al. | |
| 5,856,347 A | 1/1999 | Hashiguchi et al. | |
| 6,521,643 B1 | 2/2003 | Tomishima et al. | |
| 6,720,427 B2 | 4/2004 | Sanner et al. | |
| 6,894,054 B2 | 5/2005 | Laborde et al. | |
| 6,962,933 B1 | 11/2005 | Ohkawa et al. | |
| 2001/0044545 A1 | 11/2001 | Dhanoa et al. | |
| 2002/0025976 A1 | 2/2002 | Chu et al. | |
| 2003/0078252 A1 | 4/2003 | Sanner et al. | |
| 2003/0216403 A1 | 11/2003 | Lively et al. | |
| 2004/0053948 A1 | 3/2004 | McDonald et al. | |
| 2004/0053973 A1 | 3/2004 | Ohkawa et al. | |
| 2004/0097555 A1 | 5/2004 | Ohkawa et al. | |
| 2004/0116439 A1 | 6/2004 | Lively et al. | |
| 2004/0122016 A1 | 6/2004 | Cao et al. | |
| 2004/0152747 A1 | 8/2004 | Chen et al. | |
| 2004/0157827 A1 | 8/2004 | Pevarello et al. | |
| 2004/0171643 A1 | 9/2004 | De Cointet et al. | |
| 2005/0004134 A1 | 1/2005 | Tsutsumi et al. | |
| 2005/0038059 A1 | 2/2005 | Mueller et al. | |
| 2005/0080113 A1 | 4/2005 | Ohkawa et al. | |

(Continued)

FOREIGN PATENT DOCUMENTS

CA      1045136 A1    12/1978

(Continued)

OTHER PUBLICATIONS

International Search Report and Written Opinion from PCT/US2007/000871 (2007).

(Continued)

*Primary Examiner*—Laura L. Stockton
(74) *Attorney, Agent, or Firm*—Bernard P. Friedrichsen

(57) ABSTRACT

The invention relates to thiazole compounds of Formula I and Formula II and compositions thereof useful for treating diseases mediated by protein kinase B (PKB) where the variables have the definitions provided herein.

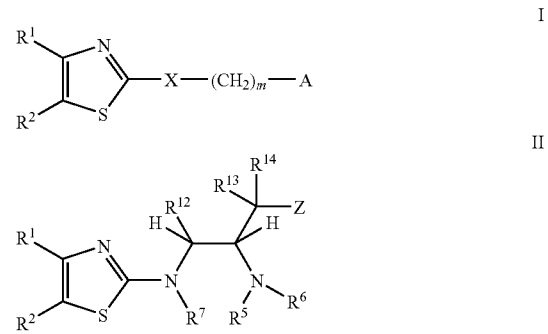

The invention also relates to the therapeutic use of such thiazole compounds and compositions thereof in treating disease states associated with abnormal cell growth, cancer, inflammation, and metabolic disorders.

48 Claims, No Drawings

U.S. PATENT DOCUMENTS

| | | | |
|---|---|---|---|
| 2005/0119320 | A1 | 6/2005 | Bruce et al. |
| 2005/0176789 | A1 | 8/2005 | Ruah et al. |
| 2005/0182104 | A1 | 8/2005 | Balter et al. |
| 2005/0192300 | A1 | 9/2005 | Wang et al. |
| 2005/0256121 | A1 | 11/2005 | Jefferson et al. |
| 2006/0003944 | A1 | 1/2006 | Glinka et al. |
| 2006/0052426 | A1 | 3/2006 | Despeyroux et al. |
| 2006/0154961 | A1 | 7/2006 | Zeng et al. |
| 2006/0178388 | A1 | 8/2006 | Wrobleski et al. |
| 2006/0205731 | A1 | 9/2006 | Kodama et al. |
| 2006/0287317 | A1 | 12/2006 | Smith et al. |
| 2006/0293365 | A1 | 12/2006 | Baltzer et al. |
| 2006/0293366 | A1 | 12/2006 | Baltzer et al. |
| 2007/0032487 | A1 | 2/2007 | Bruce et al. |

FOREIGN PATENT DOCUMENTS

| | | |
|---|---|---|
| GB | 2022085 A | 12/1979 |
| JP | 01075475 A2 | 3/1989 |
| JP | 2002053565 A2 | 2/2002 |
| JP | 2002053566 A2 | 2/2002 |
| WO | WO 99/65884 | 12/1999 |
| WO | WO 00/45635 | 8/2000 |
| WO | WO 03/068227 | 8/2003 |
| WO | WO 2004/089937 | 10/2004 |
| WO | WO 2005/052147 | 6/2005 |
| WO | WO 2005/068444 | 7/2005 |
| WO | WO 2005/116025 | 12/2005 |
| WO | WO 2006/020767 | 2/2006 |
| WO | WO 2006/038734 | 4/2006 |
| WO | WO 2006/051270 | 5/2006 |
| WO | WO 2007/008541 | 1/2007 |
| WO | WO 2007/033780 | 3/2007 |
| WO | WO 2007/066805 | 6/2007 |
| WO | WO 2007/070600 | 6/2007 |
| WO | WO 2008/036308 | 3/2008 |

OTHER PUBLICATIONS

Pathak, V. N. et al., "Synthesis and Biological Activities of Some New 2-(N-Arylamino)-4-(Fluoroaryl) thiazoles," J. Indian Chem. Soc., vol. LVI, pp. 1010-1012 (1979).

Mankad, P.R. et al., "Analgesic & Muscle Tension Relaxing Agents: Part 1—Synthesis of Some New 2-β-Hydroxyphenethylaminothiazoles," Indian Journal of Chemistry, 1 (10), 441-442 (1963).

Senapti, R.M. et al., "Studies on Thiadiazoles," Proceedings of the Institution of Chemists (India), 37(3), 111-113 (1965).

Beyer, Hans et al., "Folgeprodukte der Thiazolyl-(2)-cyanamide," Chemische Berichte, 99(9), 2937-2943 (1966).

Ghattas, A.G. et al., "Synthesis of Some New Heterocyclic 1,3,4-Oxadiazoles with Antibacterial Activity," Fac. Sci., Assuit University, 37(6), 410-412 (1982).

Shah, V.H. et al., "Studies on Acetamide Derivatives: Preparation and Antimicrobial Activity of 2-α-Arylaminoacetamido/α-Carbamoyl benzylamino/Arylcarbamoylmethylamino-5-o-Nitrophenyl/Benzoylaminomethyl1-1,3,4-Thiadiazole," J. Indian Chem. soc., LIX, 678-690 (1982).

Kalpana Pande et al., "Anti-Inflammatory and AntiProteolytic Activities of Substituted Imidazolones," Indian Drugs 23(1), 13-17 (1985).

Kulkarni, R.A. et al., "O,O-Dialkyl-S-(4-substituted-phenyl-5-phenylacetamido-thiazol-2-yl)phosphorothiaotes and O,O-Dialkyl-s-(4-substituted-phenyl-5-phenylthiazol-2-yl)phosphorothioate," Journal of the Indian Chemical Society, 65(6), 432-434 (1988).

V.L. Pachhaima et al., "Studies on Thiadiazoles: Part I: Preparation and Antimicrobial Activity of 2-(α Carbamylarylmethylamino)-5-(4'-Pyridyl)-1,3,4-Thiadiazoles," J. Inst. Chemists (India), 61, 54-56 (1989).

S.P. Hiremath et al., "Synthesis of Substituted indolythiadiazolines and indolylisoxazolines," Indian Journal of Chemistry, 30B, 744-748 (1991).

Jin Quan Cheng et al., "AKT2, a putative oncogene encoding a member of a subfamily of protein-serine/threonine kinases, is amplified in human ovarian carcinomas," Proc. Natl. Acad. Sci., U.S.A., 89 9267-9271 (1992).

S.P. Hiremath et al., "Synthesis of 2-Phenyl(indol3-yl)Isothiocyanates, 1-Substituted-3-(Substituted-2'-Phenylindol-3'-yl) Thiosemicarbazides and their Reacations," Indian Journal of Heterocyclic Chemistry, 2, 119-124 (1992).

Gioacchino Mazzone et al., "Synthesis and Local Anesthetic Activity of Alkylaminoacyl Derivatives of 2-Amino-1,3,4-Thiadiazole," IL Farmaco, 48(9), 1207-1224 (1993).

H. Singh et al., "Synthesis, characterization and fungitoxicity of manganese (II), iron (II), colbalt (II), nickel (II), copper (II), and zinc (II) complexes of N-phenyl-5-phenyl-1,3,4-oxadiazole-2-sulphonamide and 5-phenyl-1,3,4-oxadiazole-2-imino sulphonamide," Indian Journal of Chemistry, 33A, 350-353 (1994).

Tanaka, Akito et al., "Antiplatelet Agents Based on Cyclooxygenase Inhibition without Ulcerogenesis. Evaluation and Synthesis of 4,5-Bis (4-methoxyphenyl)-2-substituted-thiazoles," Journal of Medicinal Chemistry, 37(8), 1189-1199 (1994).

Alfonso Bellacosa et al., "Molecular Alterations of the AKT2 Oncogene in Ovarian and Breast Carcinomas," Int. J. Cancer (Pred. Oncol.), 64, 280-285 (1995).

L.D.S. Yadav et al.,, "A facile ring transformation of 5-oxazolone derivatives to new 1,3,4-oxa(thia)diazolo[3,2-a]pyrimidin-5-ones," Indian Journal of Chemistry Section B: Including Medicinal Chem.,, 34B, 500-503 (1995).

Jin Quan Cheng et al., "Amplification of AKT2 in human pancreatic cancer cells and inhibition of AKT2 expression and tumorigenicity by antisense RNA," Proc. Natl. Acad. Sci. U.S.A., 93, 3636-3641 (1996).

Brian A. Hemmings, "Akt Signaling: Linking Membrane Events to Life and Death Decisions," Science, 275, 628-630 (1997).

George Kulik et al., "Antiapoptotic Signalling by the Insulin-Like Growth Factor I Receptor, Phosphatidylinositol 3-Kinase, and Akt," Molecular and Cellular Biology, 17, 1595-1606 (1997).

Da-Ming Li et al., "TEP1, Encoded by a Candidate Tumor Suppressor Locus, Is a Novel Protein Tyrosine Phosphatase Regulated by Transforming Growth Factor $\beta^1$," Cancer Research, 57, 2124-2129 (1997).

Masakazu, Ban et al., "Novel Antiallergic and Antiinflammatory Agents. Part I: Synthesis and Pharmacology of Glycolic Amide Derivatives," Biorganic & Medicinal Chemistry, 6, 1069-1076 (1998).

Robin K. Pettit et al., "Specific Activities of Dolastatin 10 and Peptide Derivatives against Cryptococcus neoformans," Antimicrobial Agents and Chemotherapy, 42, 2961-2965 (1998).

Michael P. Czech et al., "Signaling Mechanisms That Regulate Glucose Transport," The Journal of Biological Chemistry, 274, 1865-1868 (1999).

Daniela Brodbeck et al., "A Human Protein Kinase Bγ with Regulatory Phosphorylation Sites in the Activation Loop and in the C-terminal Hydrophobic Domain," J. Biol. Chem., 274, 9133-9136 (1999).

Arnaud Besson et al., "PTEN/NMAC1/TEP1 in signal transduction and tumorigenesis," Eur. J. Biochem., 263, 605-611 (1999).

Maria J. Arevalo et al., "Expeditious formation of 1,2,4-triazine derivatives via a thioisomunchnone cycloaddition reaction," Tetrahedron Letters, 40, 8675-8678 (1999).

Asim Khwaja, "Akt is more than just a Bad kinase," Nature, 401, 33-34 (1999).

Javier Verdu et al., "Cell-autonomous regulation of cell and organ growth in Drosophila by Akt/PKB," Nat. Cell Biol., 1, 500-506 (1999).

Sandeep Robert Datta et al., "Cellular survival: a play in three Akts," Genes Dev., 13, 2905-2927 (1999).

Zeng Qiang Yuan et al., "Frequent activation of AKT2 and induction of apoptosis by inhibition of phosphoinositide-3-OH kinase/ Akt pathway in human ovarian cancer," Oncogene, 19, 2324-2330 (2000).

Kazuhiko Namikawa et al., "Akt/Protein Kinase B Prevents Injury-Induced Motoneuron Death and Accelerates Axonal Regeneration," J. Neurosci., 20(8), 2875-2886 (2000).

Zhengyu Luo et al., "Acute modulation of endothelial Akt/PKB activity alters nitric oxide-dependent vasomotor activity in vivo," *J. Clin. Invest.*, 106, 493-499 (2000).

Yasuko Kureishi et al., "The HMG-CoA reductase inhibitor simvastatin activates the protein kinase Akt and promotes angiogenesis in normocholesterolemic animals," *Nat. Med.*, 6, 1004-1010j (2000).

Wenfeng Miao et al., "Intracoronary, Adenovirus-mediated Akt Gene Transfer in Heart Limits Infarct Size Following Ischemia-reperfusion Injury in Vivo," *J. Mol. Cell. Cardiol.*, 32, 2397-2402 (2000).

Cunming Duan et al., "Phosphatidylinositol 3-Kinase Is Required for Insulin-Like Growth Factor-1—Induced Vascular Smooth Muscle Cell Proliferatioin and Migration," *Circ. Res.*, 86, 15-23 (2000).

Peter Blume-Jensen et al., "*Oncogenic kinase signalling*," Nature, 411, 355-365 (2001).

Hui-Kuan Lin et al., "Akt suppresses androgen-induced apoptosis by phosphorylating and inhibiting androgen receptor," *Proc. Natl. Acad. Sci. U.S.A.*, 98, 7200-7205 (2001).

Joseph R. Testa et al., "AKT plays a central role in tumorigenesis," *Proc. Natl. Acad. Sci.*, 98, 10983-10985 (2001).

Derek P. Brazil et al., "Ten years of protein kinase B signalling: a hard Akt to follow," *Trends Biochem Sci.*, 11, 657-664 (2001).

Mazaahir Kidwai et al., "Microwave Induced Synthesis and Antibacterial Activity of Cephalosporin Derivatives Using Solid Support," *Bioorganic Chemistry*, 29, 380-386 (2001).

Margaret A. Lawlor et al., "PKB/Akt: a key mediator of cell proliferation, survival and insulin responses?" *J. Cell Sci.*, 114, 2903-2910 (2001).

Michelle M. Hill et al., "Identification of a Plasma Membrane Raft-Associated PKB Ser473 Kinase Activity that Is Distinct from ILK and PDK1," *Current Biology*, 12, 1251-1255 (2002).

Igor Vivanco et al., "The Phosphatidylinositol 3-Kinase-AKT Pathway In Human Cancer," *Nat. Rev. Cancer*, 2, 489-501 (2002).

Corinne J. Hackbarth et al., "N-Alkyl Urea Hydroxamic Acids as a New Class of Peptide Deformylase Inhibitors with Antibacterial Activity," *Antimicrobial Agents and Chemotherapy*, 46(9), 2752-2764 (2002).

Mitsuo Kodomari et al., "One-pot synthesis of 2-aminothiazoles using supported reagents," *Tetrahedron Letters*, 43(9), 1717-1720 (2002).

Karleen M. Nicholson et al., "The protein kinase B/Akt signalling pathway in human malignancy," *Cell. Signal.*, 14, 381-395 (2002).

B.J. Fennell et al., "Effects of the antimitotic natural product dolastatin 10, and related peptides, on the human malarial parasite *Plasmodium falciparum*," *J. Antimicrobial Chemotherapy*, 51, 833-841 (2003).

Richard C. Hresko et al., "Phosphionositide-dependent Kinase-2 Is a Distinct Protein Kinase Enriched in a Novel Cytoskeletal Fractioin Associated with Adipocyte Plasma Membranes," *J. Biol. Chem.*, 278, 21615-21622 (2003).

Mazaahir Kidwai et al., "Solid Supported Reaction of Substituted 2-Oxazoline and Amines under Microwave Irradiation," *J. Chinese Chem. Soc.*, 50, 1075-1078 (2003).

Lin Yang et al., "Akt/Protein Kinase B Signaling Inhibitor-2, a Selective Small Molecule Inhibitor of Akt Signaling with Antitumor Activity in Cancer Cells Overexpressing Akt," *Cancer Res.*, 64, 4394-4399 (2004).

Cheol-Min Park et al., "Non-peptidic small molecule inhibitors of XIAP," *Bioorganic & Medicinal Chemistry Letters*, 15(3), 771-775 (2005).

Tadashi Aoyama et al., "One pot synthesis using supported reagents system $KSCN/SiO_2$-$RNH_3OAc/Al_2O_3$ :synthesis of 2-aminothiazoles and *N*-Allythioureas," *Tetrahedron* 62(14), 3201-3213 (2006).

Fathalla et al., "Synthesis of Some New 1,8-Naphthyridine Derivatives of Expected Biological Activity", *Egyptian J, Chem.*, 46(1), 135-152 (2003).

Suzuki, Norio, et al., "Synthesis and Antiallergy Activity of [1,3,4]Thiadiazole[3,2-a]-1,2,3-triazolo[4,5-d]pyrimindin-9(3H)-one Derivatives. I," *Chem. Pharm. Bull.*, 40(2), 357-363 (1992).

Yadav L. et al., "One-Pot Annulation of Pyrimidine Ring on Azoles Under Microwave Irradiation and Solvent-Free Conditions," *Synthesis*, 1, 63-66 (2003).

Grehn, Leif, "A Method for Nitration of Thiazoles," *J. Heterocyc. Chem.*, 14, 917-919 (1977).

SEQUENCE LISTING

<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide

<400> SEQUENCE: 1

Ala Arg Lys Arg Glu Arg Thr Tyr Ser Phe Gly His His Ala
1               5                   10

THIAZOLE COMPOUNDS AND METHODS OF USE

CROSS REFERENCES TO RELATED APPLICATIONS

This application claims the benefit of U.S. Provisional Application No. 60/759,546, filed on Jan. 18, 2006, which is hereby incorporated by reference in its entirety and for all purposes as if fully set forth herein.

FIELD OF THE INVENTION

The invention relates to thiazole compounds useful for treating diseases mediated by protein kinase B (PKB). The invention also relates to the therapeutic use of such thiazole compounds and compositions thereof in treating disease states associated with abnormal cell growth, cancer, inflammation, and metabolic disorders.

BACKGROUND OF THE INVENTION

Protein kinases represent a large family of proteins which play a central role in the regulation of a wide variety of cellular processes, maintaining control over cellular function. A partial list of such kinases includes ab1, bcr-ab1, Blk, Brk, Btk, c-kit, c-met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, GSK3α, GSK3β, Hck, IGF-1R, INS-R, Jak, KDR, Lck, Lyn, MEK, MK2, MSK1, p38, PDGFR, PIK, PKB, PKA, PIM1, PIM2, PRAK, PRK2, PKC, PYK2, P70S6, ROCK2, ros, tie, tie2, TRK, Yes, and Zap70. Inhibition of such kinases has become an important therapeutic approach.

AKT (also known as protein kinase B (PKB) or RAC-PK), including three isoforms AKT1/PKBα/RAC-PKα, AKT2/PKBα/RAC-PKβ, AKT3/PKBγ/RAC-PKγ, has been identified as a serine/threonine protein kinase. Testa et al., *Proc. Natl. Acad. Sci.*, 2001, 98, 10983-10985; Brazil et al., *Trends Biochem Sci.*, 2001, 11, 657-64; Lawlor et al., *J. Cell Sci.*, 2001, 114, 2903-2910; Cheng, *Proc. Natl. Acad. Sci. USA*, 1992, 89, 9267-9271; Brodbeck, et al., *J. Biol. Chem.* 1999, 274, 9133-9136. PKB mediates many effects of IGF-1 and other growth factors on tumor growth and inhibition of apoptosis. Nicholson, et al., *Cell. Signal.*, 2002, 14, 381-395. PKB plays an important role in cell proliferation, apoptosis and response to insulin. For these reasons, modulation of PKBs is of interest in the treatment of tumorigenesis, abnormal cell proliferation, and diabetes.

The molecular structure of the PKBs comprises a regulatory site near the carboxy terminus of the polypeptide, a catalytic domain with an activation loop having a threonine, and an amino-terminal pleckstrin homology domain. The pleckstrin homology domain permits anchorage of the enzyme to the cell membrane through interaction with phospholipids, which triggers the activation of the PKBs. The role of the pleckstrin homology domain requires phosphorylation of phosphatidylinositol at the D-3 position via phosphatidylinositol 3-kinase PI3K, an SH2 domain protein that associates with activated receptor tyrosine kinases, particularly IGF-1R. In particular, phosphoinositol-3-kinase, when activated by receptor tyrosine kinase, catalyzes the synthesis of phosphoinositol-3,4-diphosphate and phosphatidylinositol 3,4,5-triphosphate. The pleckstrin homology domain binds 3-phosphoinositides, which are synthesized by PI3K upon stimulation by growth factors such as platelet derived growth factor (PDGF), nerve growth factor (NGF) and insulin-like growth factor (IGF-1). Kulik et al., *Mol. Cell. Biol.*, 1997, 17, 1595-1606; Hemmings, *Science*, 1997, 275, 628-630; Datta, et al. *Genes Dev.*, 1999, 13, 2905-2927. Lipid binding to the pleckstrin homology domain promotes translocation of PKB to the plasma membrane. Further activation of PKB occurs by phosphorylation by another protein kinase, PDK1 at Thr308, Thr309, and Thr305 for the PKB isoforms α, β and γ, respectively. A third step of activation is catalyzed by a kinase that phosphorylates Ser473, Ser474 or Ser472 in the C-terminal tails of PKBα, β, and γ respectively. The Ser473 kinase activity has been identified to be associated with plasma membrane and is not due to PKB and PDK1 kinase activity. Hill et al., *Current Biology*, 2002, 12, 1251-1255; Hresko et al., *J. Biol. Chem.*, 2003, 278, 21615-21622. The process produces the fully activated form of PKB.

Activation of PKB can also occur by inhibiting the D-3 phosphoinositide specific phosphatase, PTEN, which is a membrane-associated FYVE finger phosphatase commonly inactivated in many cancers due to genetic alteration, including prostate cancer. Besson, et al., *Eur. J. Biochem.*, 1999, 263, 605-611; Li, et al., *Cancer Res.*, 1997, 57, 2124-2129.

The catalytic domain of PKB is responsible for the phosphorylation of serine or threonine in the target protein.

Once activated, PKB mediates several cellular functions including proliferation, cell growth, and promotion of survival. Intracoronary, adenovirus-mediated akt gene transfer in heart limits infarct size following ischemia-reperfusion injury in vivo. Miao et al., *J. Mol. Cell. Cardiol.*, 2000, 32, 2397-2402. The antiapoptotic function of PKB is reported to be mediated by its ability to phosphorylate apoptosis regulatory molecules including BAD, caspase 9, IKK-, and the forkhead transcriptional factor FKHRL1. Datta et al., at 2905. PKB signaling is also implicated in the physiological regulation of organ size (Verdu, et al., *Nat. Cell Biol.*, 1999, 1, 500-506), glucose homeostasis (Czech, et al., *J. Biol. Chem.*, 1999, 274, 1865-1868), vasomotor tone (Luo, et al. *J. Clin. Invest.* 1999, 106, 493-499), and angiogenesis (Kureishi, et al., *Nat. Med.*, 2000, 6, 1004-1010).

Manifestations of altered PKB regulation appear in both injury and disease, the most important role being in cancer. PKB kinase activity is constitutively activated in tumors with PTEN mutation, PI 3-kinase mutation and overexpression, and receptor tyrosine kinase overexpression. PKB is also a mediator of normal cell functions in response to growth factor signaling. Expression of the PKB gene was found to be amplified in 15% of human ovarian carcinoma cases. Cheng, et al., *Proc. Natl. Acad. Sci. U.S.A.*, 1992, 89, 9267-9271. PKB has also been found to be over expressed in 12% of pancreatic cancers. Cheng, et al., *Proc. Natl. Acad. Sci. U.S.A.*, 1996, 93, 3636-3641. In particular, PKBβ is over-expressed in 12% of ovarian carcinomas and in 50% of undifferentiated tumors, suggesting that PKB may be associated with tumor aggressiveness. Bellacosa, et al., *Int. J. Cancer*, 1995, 64, 280-285. PKB is also a mediator of normal cell functions. Khwaja, *Nature*, 1999, 401, 33-34; Yuan, et al., *Oncogene*, 2000, 19, 2324-2330; Namikawa, et al., *J Neurosci.*, 2000, 20, 2875-2886.

Elucidation of the role of PKB in the increase of growth and inhibition of apoptosis is complicated by the many protein substrates of PKB, including BAD, Forkhead (FOXO family), GSK3, Tuberin (TSC2), p27 Kip1, p21Cip1/WAF1, Raf, Caspase-9, and Mdm2. Lin, et al., *Proc. Natl. Acad. Sci. U.S.A.*, 2001, 98, 7200-7205; Blume-Jensen, et al., *Nature* 2001, 411, 355-365; Vivanco, et al., *Nat. Rev. Cancer*, 2002, 2, 489-501.

The various PKBs vary in their abundance in different mammalian cell types. For example, PKBβ is especially abundant in highly insulin-responsive tissues, including brown fat; PKBα is widely expressed in most of the tissues; and PKBγ is more abundant in brain and testes.

Modulation of PKB by small molecules can be achieved by identifying compounds that bind to and activate or inhibit one or more PKBs. Cao et al. in United States Publication No. 2004/0122016, published Jun. 24, 2004, disclose certain thiophene derivatives and thiophene analogs as inhibitors of protein kinases. In particular, the disclosure addresses compositions effective as inhibitors of Rho-associated coiled-coil forming protein serine/threonine kinase (ROCK), extracellular signal regulated kinase (ERK), glycogen synthase kinase (GSK), and members of the AGC sub-family of protein kinases. Id. at 4. The AGC sub-family of kinases includes protein kinase A (PKA), PDK, $p70^{S6K}$-1, $p70^{S6K}$-2, and PKB. Id.

Triciribine has been reported to inhibit cell growth in PKBβ overexpressing cells, transformed cells, and was effective at a concentration of 50 nM. Yang et al., *Cancer Res.*, 2004, 64, 4394-4399.

In other work, U.S. Pat. No. 5,232,921, issued Aug. 3, 1993, discloses thiazole derivatives that are active on the cholinergic system. The patent does not address modulation of PKB.

U.S. Patent Publication No. US 2005/0004134, published Jan. 6, 2005, discloses certain thiazole derivatives, a method of obtaining them, and pharmaceutical compositions containing them. The derivatives are described as adenosine antagonists useful in the prevention and/or treatment of cardiac and circulatory disorders, degenerative disorders of the central nervous system, respiratory disorders, and many diseases for which diuretic treatment is suitable.

Derivatives of thiazole were synthesized and used in treating conditions alleviated by antagonism of a 5-HT2b receptor in International Publication No. WO 03/068227. Thiazolyl substituted aminopyrimidines were also made and tested as fungicides in U.S. Patent Publication No. US 2005/0038059, published February, 2005. Derivatives of thiazole were also synthesized by Sanner et al. and indicated to have activity inhibiting cdk5, cdk2, and GSK-3. U.S. Patent Publication No. US 2003/0078252, published Apr. 24, 2003.

Thiadiazole compounds useful for treating diseases mediated by PKB are disclosed in WO 2006/044860, published on Apr. 27, 2006, and in U.S. Patent Publication No. US 2006/0154961, published on Jul. 13, 2006.

A need exists for new compounds that can be used to modulate PKB and can be used to treat various disease conditions associated with PKB.

SUMMARY OF THE INVENTION

This invention encompasses novel compounds useful for treating diseases or conditions mediated by PKB. The invention also encompasses the therapeutic use of such compounds and compositions thereof in the treatment of disease states associated with abnormal cell growth, such as cancer, or metabolic disease states, such as diabetes, or inflammation. The invention further provides pharmaceutical compositions that include the compounds of the invention and the use of the compounds in the preparation of medicaments for treating various conditions and disease states.

In one aspect the invention comprises a compound of Formula I

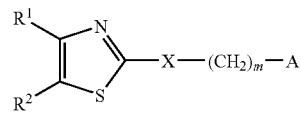

wherein:
A is

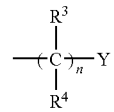

or aryl;
Y is —N($R^5$)$R^6$ or —O$R^6$;
X is O, S, or —N($R^7$);
$R^1$ is $R^8$, —CH$R^{11}$—N(H)—$R^8$, —CH$R^{11}$—O—$R^8$, $C_2$-$C_6$ alkynyl, $C_2$-$C_6$ hydroxyalkynyl, or —C≡N;
$R^2$ is aryl or heteroaryl;
$R^3$ is —H, $C_1$-$C_6$ alkyl which may be interrupted by one or more hetero atoms, —(C$R^9R^{10}$)$_t$(aryl), —(C$R^9R^{10}$)$_t$(heteroaryl), —(C$R^9R^{10}$)$_t$(cycloalkyl), or —(C$R^9R^{10}$)$_t$(heterocyclyl);
$R^4$ is $C_1$-$C_6$ alkyl which may be interrupted by one or more hetero atoms, —(C$R^9R^{10}$)$_t$(aryl), —(C$R^9R^{10}$)$_t$(heteroaryl), —(C$R^9R^{10}$)$_t$(cycloalkyl), or —(C$R^9R^{10}$)$_t$(heterocyclyl),
or $R^3$ and $R^4$, together with the carbon atom to which they are both attached, join to form a $C_3$-$C_{10}$ heterocyclic or carbocyclic ring system,
or $R^4$ and $R^7$ join to form a $C_3$-$C_{10}$ heterocyclic ring;
$R^5$ is —H, $C_1$-$C_8$ alkyl, —C(O)(C$R^9R^{10}$)$_t$)N($R^7$)$_2$, —(C$R^9R^{10}$)$_t$(aryl), —(C$R^9R^{10}$)$_t$(heteroaryl), —(C$R^9R^{10}$)$_t$(cycloalkyl), or —(C$R^9R^{10}$)$_t$(heterocyclyl),
or $R^4$ and $R^5$ join to form a $C_3$-$C_{10}$ heterocyclic ring;
$R^6$ and $R^7$ are independently selected from —H, $C_1$-$C_8$ alkyl, —($C_1$-$C_6$ alkyl)aryl, or —C(O)($C_1$-$C_6$ alkyl), or $R^6$ and $R^7$, together with the atoms to which they are linked, join to form a 5 to 6-membered heterocyclic ring, or
$R^5$ and $R^6$, together with the nitrogen atom to which they are linked, join to form a 5 to 6-membered heterocyclic or heteroaryl ring;
$R^8$ is —H, $C_1$-$C_6$ alkyl, —($C_1$-$C_6$ alkyl)aryl, aryl, or heteroaryl; and
$R^9$, $R^{10}$, and $R^{11}$ are independently selected from —H, $C_1$-$C_6$ alkyl, or aryl;
wherein n is an integer from 1 to 6; m is an integer from 0 to 2; and each t is independently an integer from 0 to 3;
wherein each of the above alkyl, aryl, heteroaryl, cycloalkyl, and heterocyclyl moieties and heterocyclic and carbocyclic rings are optionally and independently substituted by 1-3 substituents selected from
amino,
aryl, heteroaryl, cycloalkyl, or heterocyclyl optionally substituted by 1-5 substituents selected from
$C_1$-$C_6$ alkoxy,
$C_1$-$C_6$ alkyl optionally substituted by halo,
aryl,
halo,
hydroxyl,
heteroaryl, $C_1$-$C_6$ hydroxyalkyl, or —NHS(O)$_2$—($C_1$-$C_6$ alkyl);

$C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamino, $C_2$-$C_6$ alkenyl, or $C_2$-$C_6$ alkynyl, wherein each of which may be interrupted by one or more hetero atoms, cyano, halo, hydroxyl, nitro, or —O-aryl;

or a pharmaceutically acceptable salt, hydrate, or stereoisomer thereof.

In one embodiment, the invention comprises a compound of Formula I, wherein A is

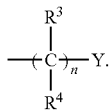

In another embodiment, the invention comprises a compound of Formula I, wherein A is

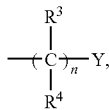

and m, n, and t are 1.

In another embodiment, the invention comprises a compound of Formula I, wherein A is

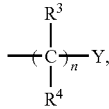

and X is —N(R$^7$), Y is —N(R$^5$)(R$^6$), and m, n, and t are 1.

In another embodiment, the invention comprises a compound of Formula I, wherein A is

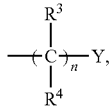

and X is —N(R$^7$), Y is —N(R$^5$)(R$^6$), R$^2$ is heteroaryl, R$^3$ is —H, R$^4$ is —(CR$^9$R$^{10}$)$_t$(aryl) or —(CR$^9$R$^{10}$)$_t$(heteroaryl), m, n, and t are 1, R$^5$, R$^6$, and R$^7$ are —H, and R$^9$ and R$^{10}$ are independently selected from H or $C_1$-$C_3$ alkyl.

In another embodiment, the invention comprises a compound of Formula I, wherein A is

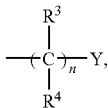

and X is —N(R$^7$), Y is —N(R$^5$)(R$^6$), R$^2$ is bicyclic heteroaryl, R$^3$ is —H, R$^4$ is —(CR$^9$R$^{10}$)$_t$(monocyclic aryl) or —(CR$^9$R$^{10}$)$_t$(bicyclic heteroaryl), m, n, and t are 1, and R$^5$, R$^6$, R$^7$, R$^9$ and R$^{10}$ are —H.

In another embodiment, the invention comprises a compound of Formula I, wherein A is

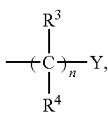

and X is —N(R$^7$), Y is —N(R$^5$)(R$^6$), R$^2$ is bicyclic heteroaryl, R$^3$ is —H, R$^4$ is —(CR$^9$R$^{10}$)$_t$(monocyclic aryl) or —(CR$^9$R$^{10}$)$_t$(bicyclic heteroaryl), m, n, and t are 1, and R$^5$, R$^6$, R$^7$, R$^9$ and R$^{10}$ are —H, wherein the bicyclic heteroaryl group of R$^2$ is isoquinolinyl, 1H-indazolyl, thiazolo[5,4-c]pyridinyl, benzo[d]thiazole-2(3H)-onyl, phthalazinyl, indolin-2-onyl, 3,4-dihydroquinolin-2(1H)-onyl, benzo[d]isoxazolyl, benzo[d]oxazol-2(3H)-onyl, benzo[d]imidazol-2(3H)-onyl, or 1,6-naphthyridinyl; and the monocyclic aryl group of R$^4$ is phenyl, chlorophenyl, (trifluoromethyl)phenyl, or ($C_1$-$C_6$)alkoxyphenyl, or the bicyclic heteroaryl group of R$^4$ is 1H-indolyl. In some embodiments, the bicyclic heteroaryl group of R$^2$ is isoquinolin-6-yl, 3-aminoisoquinolin-6-yl, 1H-indazol-5-yl, 1H-indazol-6-yl, 3-amino-1H-indazol-5-yl, 3-amino-1H-indazol-6-yl, 3-amino-1-methyl-1H-indazol-6-yl, 3-methylamino-1H-indazol-5-yl, 3-methyl-1H-indazol-5-yl, thiazolo[5,4-c]pyridin-2-yl, benzo[d]thiazole-2(3H)-on-6-yl, 1-hydroxyphthalazin-6-yl, phthalazin-6-yl, indolin-2-on-5-yl, 3-methylindolin-2-on-5-yl, 3-(furan-2-ylmethylene)indolin-2-on-5-yl, 3-(1H-imidazol-5-ylmethylene)indolin-2-on-5-yl, 3,3-difluoroindolin-2-on-5-yl, 3,4-dihydroquinolin-2(1H)-on-6-yl, benzo[d]isoxazol-5-yl, 3-aminobenzo[d]isoxazol-5-yl, benzo[d]oxazol-2(3H)-on-6-yl, 1-methyl-1H-benzo[d]imidazol-2(3H)-on-6-yl, or 1,6-naphthyridin-2-yl. In some such embodiments, the monocyclic aryl group of R$^4$ is phenyl, 3-chlorophenyl, 4-chlorophenyl, 4-methoxyphenyl, 3-(trifluoromethyl)phenyl, or 4-(trifluoromethyl)phenyl, or the bicyclic heteroaryl group of R$^4$ is 1H-indol-3-yl.

In another embodiment, the invention comprises a compound of Formula I, wherein A is

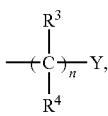

and X is —N(R$^7$), Y is —N(R$^5$)(R$^6$), R$^2$ is bicyclic heteroaryl, R$^3$ is —H, R$^4$ is —(CR$^9$R$^{10}$)$_t$(monocyclic aryl), m, n, and t are 1, and R$^5$, R$^6$, R$^7$, R$^9$ and R$^{10}$ are —H, wherein the bicyclic heteroaryl group of R$^2$ is isoquinolin-6-yl, 3-aminoisoquinolin-6-yl, 1H-indazol-5-yl, 3-methyl-1H-indazol-5-yl, thiazolo[5,4-c]pyridin-2-yl, benzo[d]oxazol-2(3H)-on-6-yl, or 1,6-naphthyridin-2-yl, and the monocyclic aryl group of $R^4$ is 4-chlorophenyl, 3-(trifluoromethyl)phenyl or 4-(trifluoromethyl)phenyl.

In other embodiments, the invention comprises a compound of Formula I having any of the features of any of the embodiments described above in which $R^1$ is —H, —CH$_3$, —CH$_2$CH$_3$, —CH$_2$OCH$_3$, —CH$_2$OCH$_2$CH$_3$, —CH$_2$OH, —CH$_2$OCH$_2$CF$_3$, —CH$_2$N(H)CH$_3$, —CH(CH$_3$)OCH$_3$, furanyl, phenyl, pyridyl, or —C≡N. In some such embodiments, $R^1$ is —H, —CH$_3$, —CH$_2$OCH$_3$, —CH$_2$OCH$_2$CH$_3$, —CH$_2$OH, or furan-2-yl. In other embodiments, $R^1$ is —CH$_3$, —CH$_2$CH$_3$, —CH$_2$OCH$_3$, —CH$_2$OCH$_2$CH$_3$, —CH$_2$OH, —CH$_2$OCH$_2$CF$_3$, —CH$_2$N(H)CH$_3$, —CH(CH$_3$) OCH$_3$, furanyl, phenyl, pyridyl, or —C≡N. In some such embodiments, $R^1$ is —CH$_3$, —CH$_2$OCH$_3$, —CH$_2$OCH$_2$CH$_3$, —CH$_2$OH, or furan-2-yl. In other embodiments, $R^1$ is —(C$_1$-C$_6$ alkyl), —(C$_1$-C$_6$ alkyl)aryl, aryl, heteroaryl, —CHR$^{11}$—N(H)—R$^8$, —CHR$^{11}$—O—R$^8$, or —C≡N. In some such embodiments, $R^1$ is —(C$_1$-C$_6$ alkyl), aryl, heteroaryl, —CHR$^{11}$—N(H)—R$^8$, —CHR$^{11}$—O—R$^8$, or —C≡N. In still other such embodiments, $R^1$ is —(C$_1$-C$_6$ alkyl), heteroaryl, or —CHR$^{11}$—O—R$^8$.

In another embodiment, the invention comprises a compound of Formula I, wherein A is aryl, X is —N(R$^7$), $R^2$ is heteroaryl, and m is 1.

In another embodiment, the invention comprises a compound of Formula I, wherein A is aryl, X is —N(R$^7$), $R^2$ is a bicyclic heteroaryl, m is 1, and $R^7$ is —H.

In another embodiment, the invention comprises a compound of Formula I, wherein A is a monocyclic aryl, X is —N(R$^7$), $R^1$ is —H, $R^2$ is thiazolo[5,4-c]pyridin-2-yl, m is 1, and $R^7$ is —H.

In another aspect, the invention provides a compound of Formula II

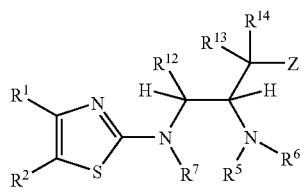

II wherein:
$R^1$ is —H, halo, —OR$^8$, C$_1$-C$_6$ alkyl, —(C$_1$-C$_6$ alkyl)-O—R$^8$, —(C$_1$-C$_6$ haloalkyl)-O—R$^8$, —(C$_2$-C$_6$ alkenyl)-O—R$^8$, —(C$_1$-C$_6$ alkyl)N(R$^7$)$_2$, —(C$_1$-C$_6$ alkyl)aryl, —C(O)R$^8$, —C(O)O—R$^8$, —C(O)N(R$^7$)$_2$, —CHR$^{11}$—N(H)—R$^8$, —CHR$^{11}$—O—R$^8$, C$_2$-C$_6$ alkynyl, (C$_2$-C$_6$ alkynyl)-O—R$^8$, —C≡N, —(C$_2$-C$_6$ alkynyl)(C$_3$-C$_8$ cycloalkyl), —(C$_2$-C$_6$ alkynyl)(C$_5$-C$_8$ cycloalkenyl), —(C$_2$-C$_6$ alkynyl)-N(R$^7$)S(O)$_2$—R$^8$, aryl, heteroaryl, cycloalkyl, or heterocyclyl;

$R^2$ is a carbocyclic ring system or is a heterocyclic ring system;

$R^5$ is —H, C$_1$-C$_8$ alkyl, —C(O)(CR$^9$R$^{10}$)$_t$)N(R$^7$)$_2$, —(CR$^9$R$^{10}$)$_t$(aryl), —(CR$^9$R$^{10}$)$_t$(heteroaryl), —(CR$^9$R$^{10}$)$_t$(cycloalkyl), or —(CR$^9$R$^{10}$)$_t$(heterocyclyl);

$R^6$ and $R^7$, in each instance, are independently selected from —H, C$_1$-C$_8$ alkyl, —(C$_1$-C$_6$ alkyl)aryl, or —C(O)(C$_1$-C$_6$ alkyl);

$R^8$ is selected from —H, C$_1$-C$_6$ alkyl, C$_1$-C$_6$ haloalkyl, —(C$_1$-C$_6$ alkyl)aryl, aryl, heteroaryl, C$_1$-C$_6$ hydroxyalkyl, or —(C$_1$-C$_6$ alkyl)-O—(C$_1$-C$_6$ alkyl), cycloalkyl, or heterocyclyl;

$R^9$ and $R^{10}$, in each instance, and $R^{11}$ are independently selected from —H, C$_1$-C$_6$ alkyl, or aryl;

$R^{12}$ is —H, —OR$^8$, —O—(C$_1$-C$_6$ alkyl)-O—R$^8$, C$_1$-C$_6$ alkyl, C$_2$-C$_6$ alkenyl, —(C$_1$-C$_6$ alkyl)-O—R$^8$, or —(C$_1$-C$_6$ alkyl)-O—C(O)—R$^8$;

$R^{13}$ is —H, or C$_1$-C$_6$ alkyl;

$R^{14}$ is —H, —OR$^8$, —O—(C$_1$-C$_6$ alkyl)-O—R$^8$, C$_1$-C$_6$ alkyl, C$_2$-C$_6$ alkenyl, —(C$_1$-C$_6$ alkyl)-O—R$^8$, or —(C$_1$-C$_6$ alkyl)-O—C(O)—R$^8$;

each t is independently selected from 0, 1, 2, or 3; and

Z is aryl or heteroaryl;

wherein each of the above alkyl, aryl, heteroaryl, cycloalkyl, and heterocyclyl moieties and heterocyclic and carbocyclic rings are optionally and independently substituted by 1-3 substituents selected from amino, aryl, heteroaryl, cycloalkyl, or heterocyclyl optionally substituted by 1-5 substituents selected from
  C$_1$-C$_6$ alkoxy,
  C$_1$-C$_6$ alkyl optionally substituted by halo,
  aryl,
  halo,
  hydroxyl,
  heteroaryl,
  C$_1$-C$_6$ hydroxyalkyl, or
  —NHS(O)$_2$—(C$_1$-C$_6$ alkyl);

C$_1$-C$_6$ alkyl, C$_1$-C$_6$ haloalkyl, C$_1$-C$_6$ hydroxyalkyl, C$_1$-C$_6$ alkoxy, C$_1$-C$_6$ haloalkoxy, C$_1$-C$_6$ hydroxyalkoxy, C$_1$-C$_6$ alkylamino, C$_2$-C$_6$ alkenyl, or C$_2$-C$_6$ alkynyl, wherein each of which may be interrupted by one or more hetero atoms, cyano,
halo,
hydroxyl,
nitro,
oxo,
—NH(CO)—O—(C$_1$-C$_6$ alkyl)aryl, —NH(CO)—O—(C$_1$-C$_6$ alkyl), —N(C$_1$-C$_6$ alkyl)(CO)—O—(C$_1$-C$_6$ alkyl)aryl, —N(C$_1$-C$_6$ alkyl)(CO)—O—(C$_1$-C$_6$ alkyl), —C(O)OH, —C(O)O(C$_1$-C$_6$ alkyl), —C(O)NH$_2$, —C(O)N(H)—(C$_1$-C$_6$ alkyl), —C(O)N(C$_1$-C$_6$ alkyl)$_2$, —NH(C$_1$-C$_6$ alkyl), —N(C$_1$-C$_6$ alkyl)$_2$, —(C$_2$-C$_4$ alkenyl)heterocyclyl, or —(C$_2$-C$_4$ alkenyl)cycloalkyl, or —O-aryl;

or a pharmaceutically acceptable salt, hydrate, stereoisomer, or mixture thereof.

In some embodiments, the compound of Formula II has the Formula IIA

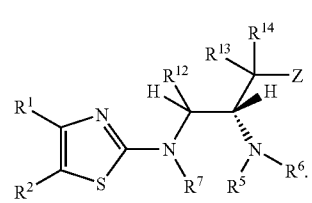

IIA

In some embodiments, the compound of Formula II has the Formula IIB

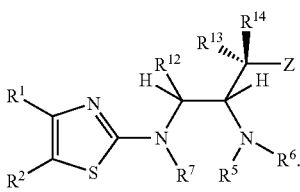

IIB

In some embodiments, the compound of Formula II has the Formula IIC

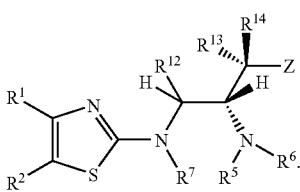

IIC

In some embodiments, the compound of Formula II has the Formula IID

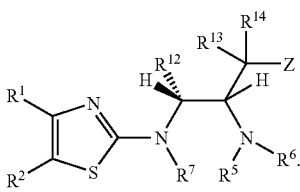

IID

In some embodiments, the compound of Formula II has the Formula IIE

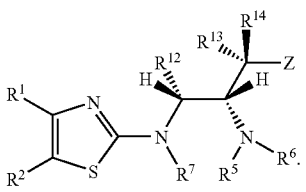

IIE

In some embodiments of the compound of Formula II, $R^1$ is —H.

In some embodiments of the compound of Formula II, $R^{12}$ is —H or $C_1$-$C_6$ alkyl. In some such embodiments, $R^{12}$ is —H or methyl.

In some embodiments of the compound of Formula II, $R^{13}$ is —H.

In some embodiments of the compound of Formula II, $R^{14}$ is —H.

In some embodiments of the compound of Formula II, $R^{14}$ is —$OR^8$, —O—($C_1$-$C_6$ alkyl)—O-$R^8$, $C_1$-$C_6$ alkyl, $C_2$-$C_6$ alkenyl, —($C_1$-$C_6$ alkyl)—O—$R^8$, or —($C_1$-$C_6$ alkyl)-O—C(O)—$R^8$.

In some embodiments of the compound of Formula II, $R^{14}$ is selected from —H, methyl, ethyl, propyl, ethenyl, propenyl, hydroxymethyl, methoxymethyl, —$CH_2$—O—C(O)—($C_1$-$C_6$ alkyl), 1-hydroxyethyl, or methoxymethoxy.

In some embodiments of the compound of Formula II, Z is selected from optionally substituted phenyl, optionally substituted indolyl, optionally substituted naphthyl, optionally substituted pyridyl, or optionally substituted thiophenyl. In some such embodiments, Z is selected from phenyl, indolyl, naphthyl, pyridyl, or thiophenyl, each of which is optionally substituted with 1-3 substituents selected from —Cl, —F, —$CF_3$, —OH, —O—($C_1$-$C_6$ alkyl), —O—($C_1$-$C_6$ alkyl)-Cl, —O—($C_1$-$C_6$ alkyl)-OH, —$C_1$-$C_6$ alkyl, —$OCF_3$, —NH(CO)—O—($C_1$-$C_6$ alkyl)aryl, or —NH(CO)—O—($C_1$-$C_6$ alkyl).

In some embodiments of the compound of Formula II, Z is selected from phenyl, indoyl, naphthyl, pyridyl, thiophenyl, 4-chlorophenyl, 4-trifluoromethylphenyl, 3-chlorophenyl, 3-trifluoromethylphenyl, 4-methoxyphenyl, 3-fluoro-4-trifluoromethylphenyl, 4-chloro-3-fluorophenyl, 4-(3- chloropropoxy)phenyl, 4-(3-hydroxypropoxy)phenyl, 3,4-dichlorophenyl, 4-fluorophenyl, 2,4-dichlorophenyl, 4-methylphenyl, 3,4-difluorophenyl, 3-fluoro-4-methoxyphenyl, 3,5-difluorophenyl, 6-trifluoromethylpyridin-3yl, 5-methoxy-6-trifluoromethylpyridin-3-yl, 2-fluoro-4-trifluoromethylphenyl, 4-trifluoromethoxyphenyl, 2,3-difluoro-4-trifluoromethylphenyl, 4-hydroxyphenyl, 3-methoxy-4-trifluoromethylphenyl, 3-hydroxy-4-trifluoromethylphenyl, 5-chlorothiophen-2-yl, 3-fluoro-4-hydroxyphenyl, or a phenyl substituted in the 4 position with —NH—C(O)-O—$CH_2$-phenyl.

In some embodiments of the compound of Formula II, $R^7$ is H. In some such embodiments, $R^5$ and $R^6$ are both H.

In some embodiments of the compound of Formula II, $R^5$ and $R^6$ are both H.

In some embodiments of the compound of Formula II, $R^{12}$ is —H or $C_1$-$C_6$ alkyl, $R^{13}$ is —H, and $R^{14}$ is —H, —$OR^8$, —O—($C_1$-$C_6$ alkyl)-O—$R^8$, $C_1$-$C_6$ alkyl, $C_2$-$C_6$ alkenyl, —($C_1$-$C_6$ alkyl)-O—$R^8$, or —($C_1$-$C_6$ alkyl)-O—C(O)—$R^8$. In some such embodiments, $R^{14}$ is —$OR^8$, —O—($C_1$-$C_6$ alkyl)-O—$R^8$, $C_1$-$C_6$ alkyl, $C_2$-$C_6$ alkenyl, —($C_1$-$C_6$ alkyl)-O—$R^8$, or —($C_1$-$C_6$ alkyl)-O—C(O)—$R^8$. In further such embodiments, $R^5$, $R^6$, and $R^7$ are all H.

In some embodiments of the compound of Formula II, the carbocyclic ring system or the heterocyclic ring system of $R^2$ includes at least one aromatic ring.

In some embodiments of the compound of Formula II, $R^2$ is selected from optionally substituted phenyl, pyridyl, indazolyl, isoquinolinyl, thiazolopyridinyl, benzothiazolonyl, dihydroquinolinonyl, benzoisoxazolyl, benzooxazolonyl, indolinonyl, benzoimidazolonyl, phthalazinyl, naphthyridinyl, thienopyridinyl, benzodioxolyl, isoindolinonyl, quinazolinyl, or cinnolinyl. In other embodiments, $R^2$ is selected from isoquinolinyl, 1H-indazolyl, thiazolo[5,4-c]pyridinyl, benzo[d]thiazole-2(3H)-onyl, phthalazinyl, indolin-2-onyl, 3,4-dihydroquinolin-2(1H)-onyl, benzo[d]isoxazolyl, benzo[d]oxazol-2(3H)-onyl, benzo[d]imidazol-2(3H)-onyl, 1,6-naphthyridinyl, quinazolin-7-yl, or cinnolin-6-yl. In other embodiments, $R^2$ is isoquinolin-6-yl, 3-aminoisoquinolin-6-yl, 1H-indazol-5-yl, 1H-indazol-6-yl, 3-amino-1H-indazol-5-yl, 3-amino-1H-indazol-6-yl, 3-amino-1-methyl-1H-indazol-6-yl, 3-methylamino-1H-indazol-5-yl, 3-methyl-1H-indazol-5-yl, thiazolo[5,4-c]pyridin-2-yl, benzo[d]thiazole-2(3H)-on-6-yl, 1-hydroxyphthalazin-6-yl, phthalazin-6-yl, indolin-2-on-5-yl, 3-methylindolin-2-on-5-yl, 3-(furan-2-ylmethylene)indolin-2-on-5-yl, 3-(1H-imidazol-5-ylmethylene)indolin-2-on-5-yl, 3,3-difluoroindolin-2-on-5-yl, 3,4-dihydroquinolin-2(1H)-on-6-yl, benzo[d]isoxazol-5-yl, 3-aminobenzo[d]isoxazol-5-yl, benzo[d]oxazol-2(3H)-on-6-yl, 1-methyl-1H- benzo[d]imidazol-2(3H)-on-6-yl, 1,6-naphthyridin-2-yl, quinazolin-7-yl, or cinnolin-6-yl.

In some embodiments of the compound of Formula II, $R^2$ is selected from the following groups which may optionally be substituted and where the wavy line the point of attachment to the thiazole:

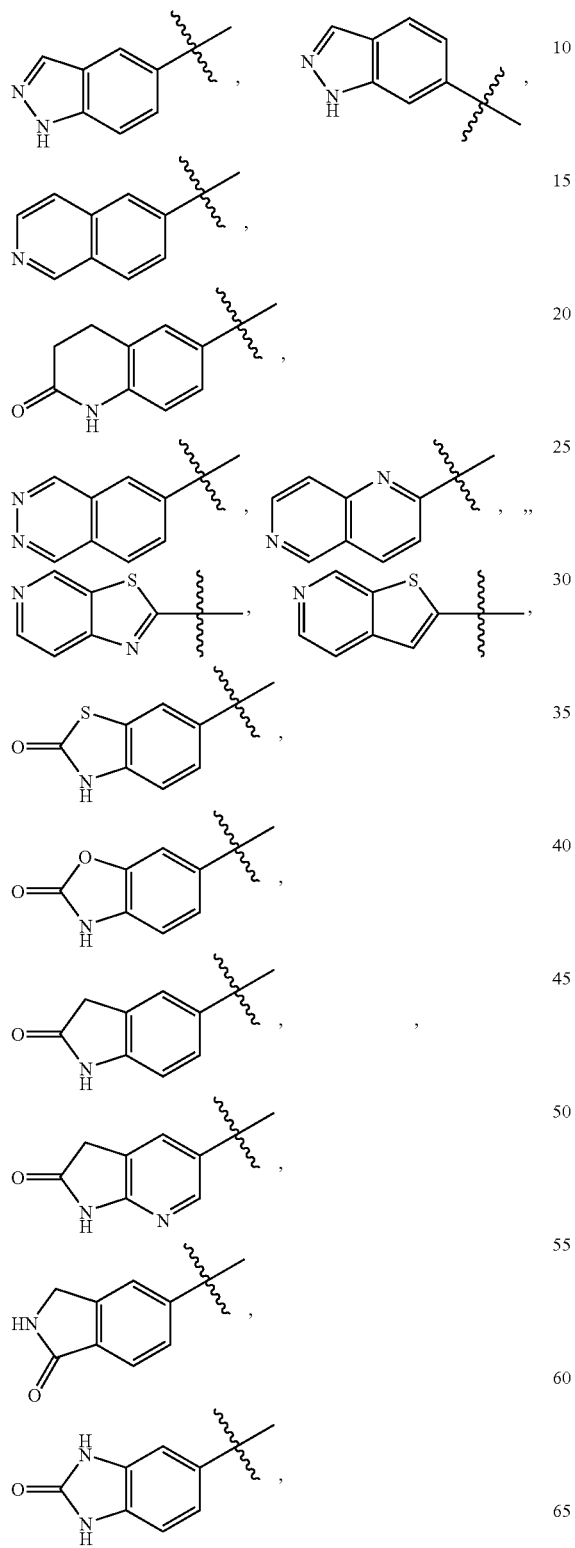

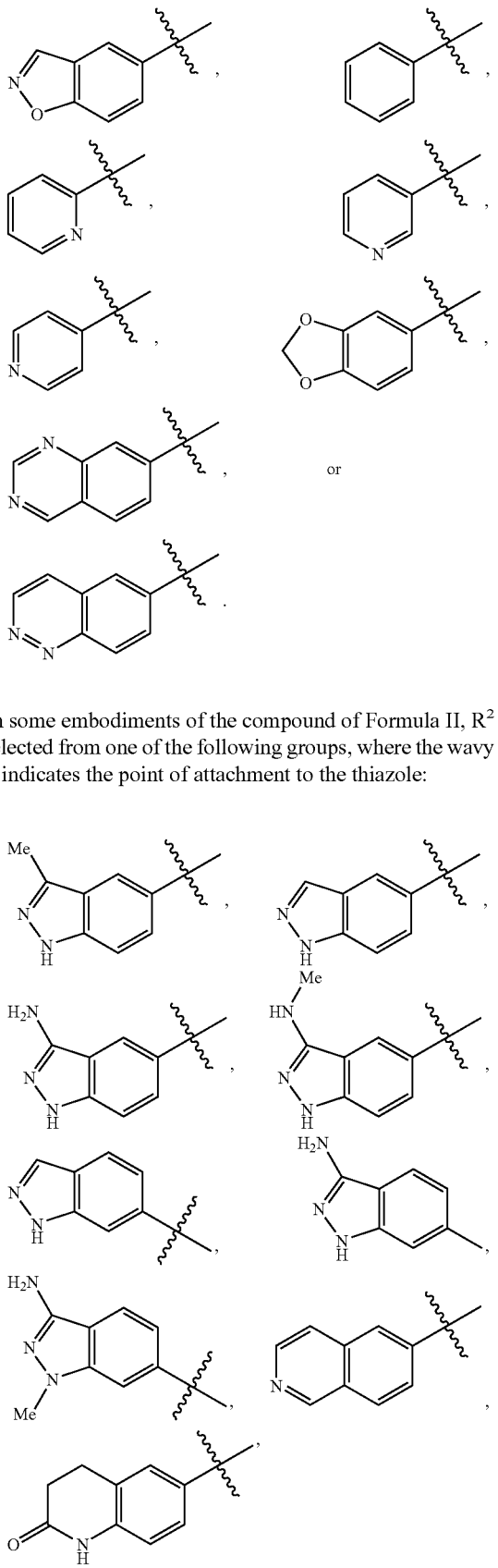

In some embodiments of the compound of Formula II, $R^2$ is selected from one of the following groups, where the wavy line indicates the point of attachment to the thiazole:

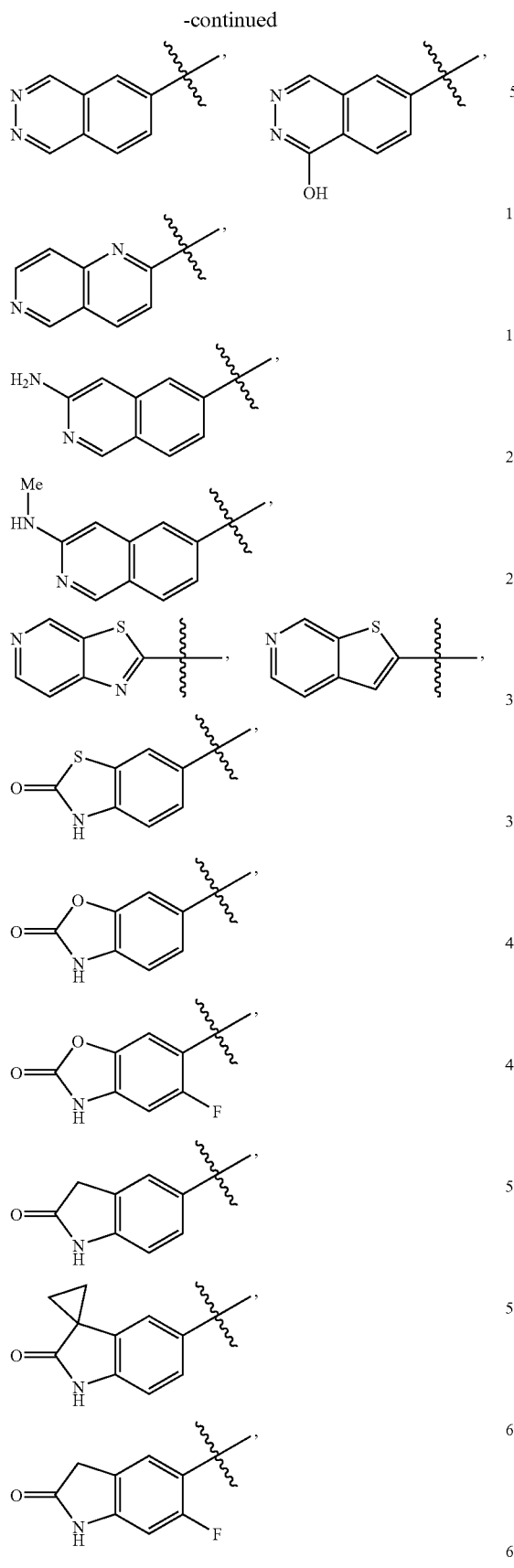
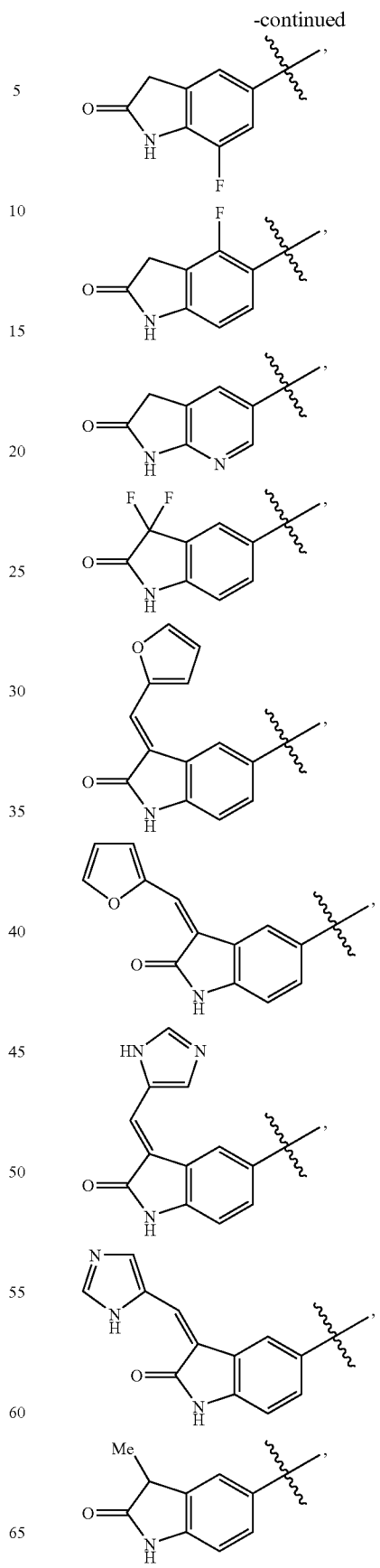

-continued

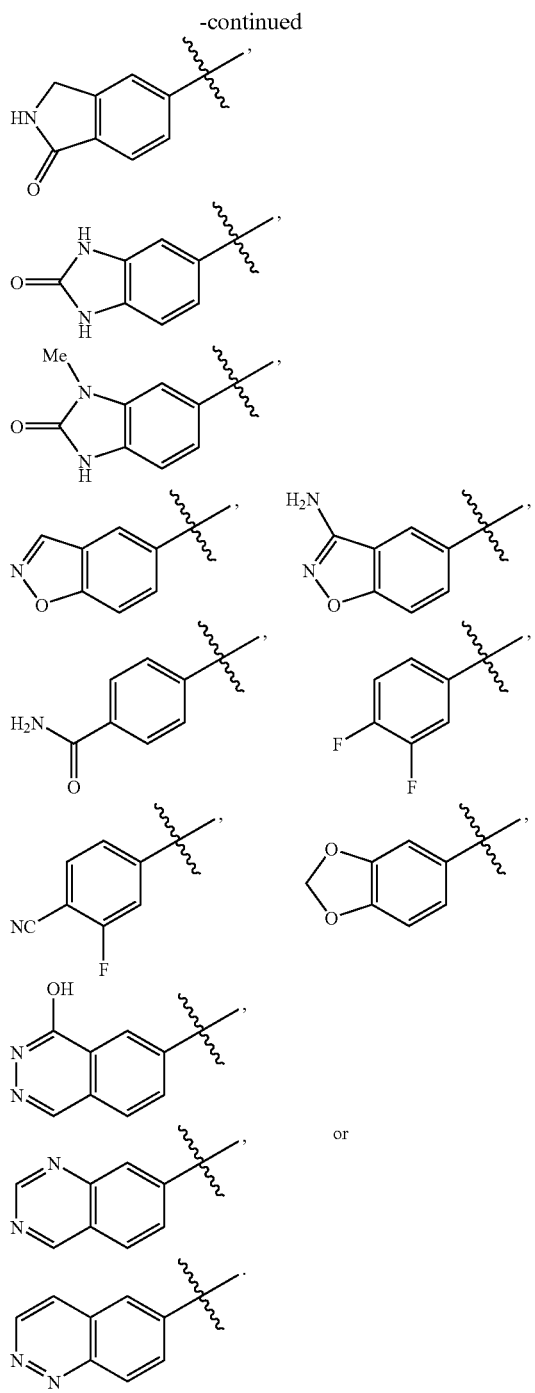

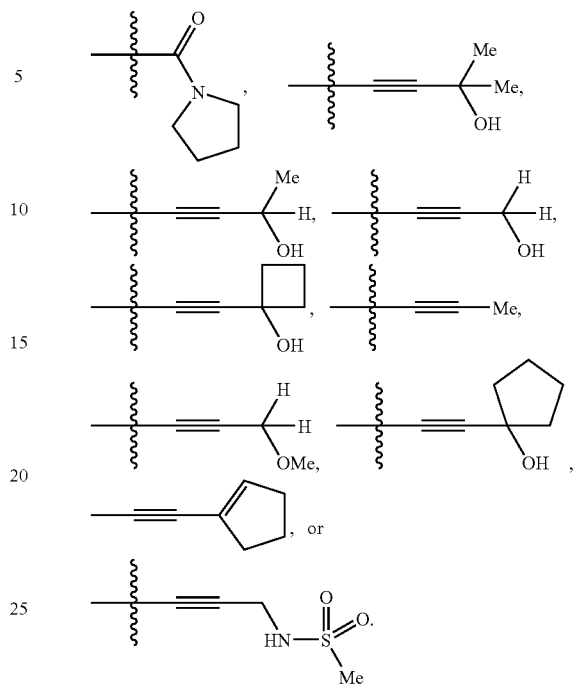

In some embodiments of the compound of Formula II, $R^1$ is selected from —H, —C≡N, —Br, —Cl, —OH, —CF$_3$, —CH$_3$, —CH$_2$CH$_3$, —CH$_2$CH$_2$OH, —C(H)(CH$_3$)OCH$_3$, —CH$_2$OCH$_2$CF$_3$, —CH$_2$N(H)CH$_3$, —CH$_2$N(CH$_3$)$_2$, —CF$_2$CH$_2$OH, cyclopropyl, furanyl, tetrahydrofuranyl, phenyl, 2,3-difluorophenyl, 3,4-difluorophenyl, 4-fluorophenyl, 3-fluorophenyl, 2-fluorophenyl, pyridyl, oxazolyl, hydroxymethyl, methoxymethyl, ethoxymethyl, —C(O)OMe, —C(O)N(H)CH$_2$CH$_2$OH, —C(O)N(H)CH$_3$, —C(O)NH$_2$, —C(O)N(CH$_3$)$_2$, or a group selected from one of the following groups where the wavy line indicates the point of attachment to the thiazole:

In another aspect, the invention comprises a pharmaceutically acceptable salt, hydrate, or solvate of a compound of Formula I or Formula II or any of the compounds listed above. In one embodiment, the pharmaceutically acceptable salts of Formula I compounds or Formula II compounds are selected from ammonium trifluoroacetate and ammonium chloride.

In another aspect, the invention comprises a pharmaceutical composition comprising a pharmaceutically-acceptable carrier and a compound of Formula I or Formula II, a compound of any of the embodiments described herein, and/or a salt of any of the compounds of any of the embodiments. In some embodiments, the invention also provides the use of a compound of any of the embodiments in the manufacture of a medicament for carrying out any of the methods of any of the embodiments of the invention. Such compositions and medicaments may further include one or more additional therapeutic agent. Therefore, in some embodiments, the composition or medicament includes at least one additional therapeutic agent.

In another aspect, the invention comprises a method for treating a kinase-mediated disorder in a mammal comprising administering to the mammal a therapeutically effective amount of a compound of Formula I or Formula II or a pharmaceutical composition of the invention. In some embodiments, the invention provides the use of a compound of Formula I or Formula II or a pharmaceutical composition of the invention for treating a kinase-mediated disorder in a mammal. The disorder can be one that is mediated by kinases including IGF-1R, Insulin Receptor, KDR, Tie2, EGFR, PKA, PKB, PKC, FKHR, TSC1/2, SGK, LCK, BTK, Erk, MSK, MK2, MSK, p38, P70S6K, PIM1, PIM2, ROCK2, GSK3, or a CDK complex. In some embodiments, the disorder is mediated by PKB, and in some embodiments is mediated by PKBα. In some embodiments, the method comprises selective inhibition of PKB. In some such embodiments, the method comprises selective inhibition of PKBα.

In another embodiment, the invention encompasses Formula I compounds or Formula II compounds that have selective kinase activity—i.e., they possess significant activity against one specific kinase while possessing less or minimal activity against a different kinase. In some embodiments, the compounds have selective PKB inhibition activity. In some such embodiments, the compounds have selective PKBα inhibition activity. In other embodiments, the invention provides the use of a compound of Formula I or Formula II or a pharmaceutical composition of the invention for selectively inhibiting a kinase activity. In some embodiments, PKB is selectively inhibited. In some such embodiments, PKBα is selectively inhibited.

In one embodiment, the invention provides a method of treating a proliferation-related disorder in a mammal in need thereof. Such methods include administering to the mammal a therapeutically effective amount of a compound of any of the embodiments described herein or a pharmaceutical composition comprising the compound. Another embodiment of the invention comprises treating abnormal cell growth by administering a therapeutically effective amount of a compound of the invention or a pharmaceutical composition of the invention to a subject in need thereof. In some embodiments, the invention provides the use of a compound of Formula I or Formula II or a pharmaceutical composition of the invention for treating abnormal cell growth. The abnormal cell growth can be a benign growth or a malignant growth. In particular, the abnormal cell growth can be a carcinoma, sarcoma, lymphoma, or leukemia. In one embodiment of this method, the abnormal cell growth is a cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. The method of the invention also comprises treating a patient having cancer wherein the cancer is selected from the group consisting of small cell lung carcinoma, non-small cell lung carcinoma, esophageal cancer, kidney cancer, pancreatic cancer, melanoma, bladder cancer, breast cancer, colon cancer, liver cancer, lung cancer, sarcoma, stomach cancer, cholangiocarcinoma, mesothelioma, or prostate cancer. In another embodiment of said method, said abnormal cell growth is a benign proliferative disease, including, but not limited to, psoriasis, benign prostatic hypertrophy or restenosis.

In another embodiment, the invention comprises a method of administering a therapeutically effective amount of a Formula I or Formula II compound to a mammal for treating disease states or conditions selected from diabetes, inflammation, and metabolic disorders. In other embodiments, the invention provides the use of a compound of Formula I or Formula II or a pharmaceutical composition of the invention for treating a disease state or a condition selected from diabetes, inflammation, and metabolic disorders.

In another embodiment, the invention encompasses a method for treating or preventing cancer in a patient in need thereof, comprising administering to the patient a therapeutically or prophylactically effective amount of a compound according to Formula I or Formula II and a pharmaceutically acceptable excipient, carrier, or vehicle. In other embodiments, the invention provides the use of a compound of Formula I or Formula II or a pharmaceutical composition of the invention for treating or preventing cancer in a patient such as in a human cancer patient. In some embodiments, the cancer is a tumor.

In another aspect, the invention encompasses a method for treating or preventing cancer in a patient in need thereof, comprising administering to the patient a therapeutically or prophylactically effective amount of a Formula I or Formula II compound and at least one additional therapeutic agent.

Further objects, features, and advantages of the invention will be apparent from the following detailed description.

DETAILED DESCRIPTION OF THE INVENTION 1.1 Definitions

Where the following terms are used in this specification, they are used as defined below:

The terms "comprising" and "including" are used herein in their open, non-limiting sense.

As used herein, unless otherwise specified, the term "alkyl" means a saturated straight chain or branched non-cyclic hydrocarbon having from 1 to 20 carbon atoms, preferably 1-10 carbon atoms and most preferably 1-4 carbon atoms. Representative saturated straight chain alkyls include, but are not limited to, -methyl, -ethyl, -n-propyl, -n-butyl, -n-pentyl, -n-hexyl, -n-heptyl, -n-octyl, -n-nonyl and -n-decyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. An alkyl group can be unsubstituted or substituted. An alkyl group may be designated as having a certain number of carbon atoms. For example, an alkyl group having from 1 to 8 carbon atoms may be designated as a $C_1$-$C_8$ alkyl group whereas an alkyl group having from 1 to 6 carbon atoms may be designated as a $C_1$-$C_6$ alkyl group. When such terms are used in conjunction with others such as in the term "—($C_1$-$C_6$ alkyl)aryl", the "-" symbol indicates the point of attachment to the rest of the molecule, and the term indicates that one of the hydrogens of the alkyl group is replaced by a bond to an aryl group. For example, a —($C_1$-$C_2$ alkyl)aryl includes such groups as —$CH_2$Ph, —$CH_2CH_2$Ph, and —CH(Ph)$CH_3$.

When so designated, an alkyl group can be interrupted by one or more heteroatoms such as N, O, S, or Si atoms. Insertion of a heteroatom in the alkyl group forms a heteroalkyl group. In some embodiments, the heteroatom is a N, O, or S atom. The term "heteroalkyl," by itself or in combination with another term, means, unless otherwise stated, a stable straight or branched chain radical, or combination thereof, that includes carbon atoms and from one to three heteroatoms selected from the group consisting of O, N, and S. The nitrogen and sulfur atoms may optionally be oxidized, and the nitrogen heteroatom may optionally be quaternized. The heteroatom(s) O, N, and S may be placed at any position in the heteroalkyl group. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, and —$CH_2$—$CH_2$—S(O)$_2$—$CH_3$. Up to two heteroatoms may be consecutive or adjacent to one another, such as, for example, in —$CH_2$—NH—$OCH_3$. When a prefix such as ($C_2$-$C_8$) is used to refer to a heteroalkyl group, the number of carbons (2 to 8, in this example) is meant to include the heteroatoms as well. For example, a $C_2$-heteroalkyl group is meant to include, for example, —$CH_2OH$ (one carbon atom and one heteroatom replacing a carbon atom) and —$CH_2SH$.

To further illustrate the definition of a heteroalkyl group, where the heteroatom is oxygen, a heteroalkyl group is an oxyalkyl group. For instance, ($C_2$-$C_5$)oxyalkyl is meant to include, for example —$CH_2$-O—$CH_3$ (a $C_3$-oxyalkyl group with two carbon atoms and one oxygen replacing a carbon atom), —$CH_2CH_2CH_2CH_2OH$, and the like.

As used herein, unless otherwise specified, the term "alkenyl" means an unsaturated straight chain or branched noncyclic hydrocarbon having from 2 to 20 carbon atoms and at least one carbon-carbon double bond. Preferably, an alkenyl has 2 to 10 carbon atoms and most preferably has 2 to 4 carbon atoms. Exemplary straight chain alkenyls include, but are not limited to, -but-3-ene, -hex-4-ene, and -oct-1-ene. Exemplary branched chain alkenyls include, but are not limited to, -2-methyl-but-2-ene, -1-methyl-hex-4-ene, and -4-ethyl-oct-1-ene. An alkenyl group can be substituted or unsubstituted. An alkenyl group may be designated as having a certain number of carbon atoms. For example, an alkenyl group having from 2 to 8 carbon atoms may be designated as a $C_2$-$C_8$ alkenyl group whereas an alkenyl group having from 2 to 6 carbon atoms may be designated as a $C_2$-$C_6$ alkenyl group.

As used herein, and unless otherwise specified, the term "alkynyl" means an alkyl group in which one or more carbon-carbon single bonds is replaced with an equivalent number of carbon-carbon triple bonds. An alkynyl group must comprise at least two carbon atoms, and can be substituted or unsubstituted. An alkynyl group may be designated as having a certain number of carbon atoms. For example, an alkynyl group having from 2 to 8 carbon atoms may be designated as a $C_2$-$C_8$ alkynyl group whereas an alkynyl group having from 2 to 6 carbon atoms may be designated as a $C_2$-$C_6$ alkynyl group.

As used herein, the term "halo" means a halogen atom such as a fluorine, chlorine, bromine, or iodine atom (—F, —Cl, —Br, or —I).

As used herein, unless otherwise specified, the term "haloalkyl" means an alkyl group in which one or more hydrogens has been replaced by a halogen atom. A halogen atom is a fluorine, chlorine, bromine, or iodine atom. The number of halogen atoms in a haloalkyl group may range from one to (2m'+1), where m' is the total number of carbon atoms in the alkyl group. For example, the term "halo($C_1$-$C_4$)alkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms). The term "perhaloalkyl" means, unless otherwise stated, an alkyl substituted with (2m'+1) halogen atoms, where m' is the total number of carbon atoms in the alkyl group. For example, the term "perhalo($C_1$-$C_4$)alkyl", is meant to include trifluoromethyl, pentachloroethyl, 1,1,1-trifluoro-2-bromo-2-chloroethyl, and the like.

As used herein, the term "cyano" means a —C≡N group.
As used herein, the term "nitro" means a —$NO_2$ group.
As used herein, the term "oxo" means a =O group.
As used herein, the terms "hydroxy" and "hydroxyl" mean an —OH group.

As used herein, unless otherwise specified, the term "hydroxyalkyl" means an alkyl group in which one or more hydrogens has been replaced with a hydroxyl group.

As used herein, unless otherwise specified, the term "hydroxyalkenyl" means an alkenyl group in which one or more hydrogens has been replaced with a hydroxyl group.

As used herein, unless otherwise specified, the term "hydroxyalkynyl" means an alkynyl group in which one or more hydrogens has been replaced with a hydroxyl group.

The term "alkoxy" means a structure of the formula —O-alkyl where alkyl has the meaning set forth above.

The term "haloalkoxy" means an alkoxy group in which one or more hydrogen is replaced by a halogen atom.

The term "hydroxyalkoxy" means an alkoxy group in which one or more hydrogen is replaced by a hydroxy group.

The term "alkylsulfonyl" means a structure of the formula —S(O)$_2$-alkyl.

The term "amino" means an —$NH_2$ group.

The terms "alkylamino" and "dialkylamino" mean a structure of the formula —NH-alkyl and —N(alkyl)alkyl, respectively, wherein the alkyl is as defined above. The alkyl groups in dialkylamino groups may be the same or different.

The term "alkanoyl", alone or in combination with another term, means a radical of the type "R—C(O)—" wherein "R" is an alkyl radical as defined above and "—C(O)—" is a carbonyl radical. Examples of such alkanoyl radicals include, but are not limited to, acetyl, trifluoroacetyl, hydroxyacetyl, propionyl, butyryl, valeryl, 4-methylvaleryl, and the like. The terms "alkanoylamino," and "alkanoyloxy" mean —NH-alkanoyl and —O-alkanoyl, respectively.

The term "alkoxy carbonyl amino" means a structure of the formula —NHC(O)O-alkyl.

The term "alkylsulfonyl amino" means a structure of the general formula —NHS(O)$_2$-alkyl.

As used herein, the terms "carbocyclic ring system" and "carbocyclic" mean a ring system in which all the ring members are carbon atoms. Carbocyclic ring systems typically include from 3 to 14 ring atoms. Carbocyclic ring systems may be aromatic or may be non-aromatic. Carbocyclic ring systems include cycloalkyl rings and may also include fused ring systems. Examples of fused ring carbocyclic ring systems include, but are not limited to, decalin, norbornane, tetrahydronaphthalene, naphthalene, indene, and adamantane. The ring atoms in a carbocyclic ring system may be substituted or unsubstituted.

As used herein, the terms "heterocyclic ring system", "heterocyclic" and "heterocyclyl" means a carbocyclic ring system in which at least one ring atom is a heteroatom such as a N, O, S, or Si. In some embodiments, the heterocyclic ring system includes from 1 to 4 heteroatoms. In some embodiments, the heteroatom is selected from N, O, or S. Heterocyclic ring systems may include one ring or may include fused ring systems. By way of nonlimiting example, heterocyic ring systems may include two six membered rings that are fused to one another or may include one five membered ring and one six membered ring that are fused to one another. Heterocyclic ring systems may be aromatic or may be non-aromatic and may be unsaturated, partially unsaturated, or saturated. The ring atoms in a heterocyclic ring system may be substituted or unsubstituted.

As used herein, unless otherwise specified the term "aryl" means a carbocyclic ring or ring system containing from 6 to 14 ring atoms wherein at least one ring is aromatic. The ring atoms of a carbocyclic aryl group are all carbon atoms. Aryl groups include mono-, bi-, and tricyclic groups as well as benzo-fused carbocyclic moieties such as, but not limited to, 5,6,7,8-tetrahydronaphthyl and the like. In some embodiments, the aryl group is a monocyclic ring or is a bicyclic ring. Representative aryl groups include, but are not limited to, phenyl, tolyl, anthracenyl, fluorenyl, indenyl, azulenyl, phenanthrenyl and naphthyl. An aryl group can be unsubstituted or substituted.

The term "heteroaryl" means an aryl group in which one or more, but not all, of the ring carbon atoms in any ring, whether aromatic or not, is replaced by a hetero atom. For example pyridine is a heteroaryl group as is a compound in which benzene is fused to a nonaromatic ring that includes at least one heteroatom. Exemplary heteroatoms are N, O, S, and Si. In some embodiments, the heteroatoms are N, O, or S. A heteroaryl group can be unsubstituted or substituted. Non-limiting examples of aryl and heteroaryl groups include phenyl, 1-naphthyl, 2-naphthyl, 4-biphenyl, 1-pyrrolyl, 2-pyrrolyl, 3-pyrrolyl, 1-pyrazolyl, 3-pyrazolyl, 5-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furanyl, 3-furanyl, dibenzofuryl, 2-thienyl(2-thiophenyl), 3-thienyl(3-thiophenyl), 2-pyridyl, 3-pyridyl, 4-pyridyl, 2-pyrimidinyl, 4-pyrimidinyl, 5-pyrimidinyl, 3-pyridazinyl, 4-pyridazinyl, 5-benzothiazolyl, 2-benzoxazolyl, 5-benzoxazolyl, benzo[c][1,2,5]oxadiazolyl, purinyl, 2-benzimidazolyl, 5-indolyl, 1H-indazolyl, carbazolyl, α-carbolinyl, β-carbolinyl, γ-carbolinyl, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl, and 8-quinolyl. Non-limiting examples of other heteroaryl groups include pyridyl, indazolyl, isoquinolinyl, thiazolopyridinyl, benzothiazolonyl, dihydroquinolinonyl, benzoisoxazolyl, benzooxazolonyl, indolinonyl, benzoimidazolonyl, phthalazinyl, naphthyridinyl, thienopyridinyl, benzodioxolyl, isoindolinonyl, quinazolinyl, or cinnolinyl. The nonaromatic rings in aryl and heteroaryl groups that include nonaromatic rings may be substituted with various groups as described herein including the oxo (=O) group for example in groups such as, but not limited to, the benzo[d]thiazol-2 (3H)-onyl group.

The term "cycloalkyl" means an unsaturated or saturated hydrocarbon that forms at least one ring, having from 3 to 20 ring carbon atoms, and in some embodiments, from 3 to 10 ring, from 3 to 8, or from 3 to 6 carbon atoms. The rings in a cycloalkyl group are not aromatic. A cycloalkyl group can be unsubstituted or substituted.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "PKB" refers to protein kinase B, also known as AKT.

The term "treating" refers to:
(i) preventing a disease, disorder, or condition from occurring in a mammal that may be predisposed to the disease, disorder and/or condition, but may not yet have been diagnosed as having it;
(ii) inhibiting the disease, disorder, or condition, i.e., arresting its development; and
(iii) relieving the disease, disorder, or condition, i.e., causing regression of the disease, disorder, and/or condition, or one or more of its symptoms.

The term "preventing" refers to the ability of a compound or composition of the invention to prevent a disease identified herein in mammals diagnosed as having the disease or who are at risk of developing such disease. The term also encompasses preventing further progression of the disease in mammals that are already suffering from or have symptoms of the disease.

The term "mammal" refers to non-human animals or humans.

As used herein, the term "patient" or "subject" means an animal (e.g., cow, horse, sheep, pig, chicken, turkey, quail, cat, dog, mouse, rat, rabbit, guinea pig, etc.) or a mammal, including chimeric and transgenic animals and mammals. In the treatment or prevention of a cancer, the term "patient" or "subject" preferably means a monkey or a human, most preferably a human. In a specific embodiment, the patient or subject is afflicted by a cancer.

As used herein, a "therapeutically effective amount" refers to an amount of a compound of the invention, or prodrug thereof, sufficient to provide a benefit in the treatment or prevention of a condition or disease such as cancer, to delay or minimize symptoms associated with the condition or disease, or to cure or ameliorate the disease or cause thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

As used herein, a "prophylactically effective amount" refers to an amount of a compound of the invention or other active ingredient sufficient to result in the prevention of a condition or disease such as cancer, or recurrence or metastasis of cancer. A prophylactically effective amount may refer to an amount sufficient to prevent initial disease or the recurrence or spread of the disease. The term preferably encompasses a non-toxic amount that improves overall prophylaxis or enhances the prophylactic efficacy of or synergies with another prophylactic or therapeutic agent.

As used herein, "in combination" refers to the use of more than one prophylactic and/or therapeutic agents simultaneously or sequentially. The agents may be selected and administered in such a manner that their respective effects are additive or synergistic.

As used herein, the term "pharmaceutically acceptable salts" refers to salts prepared from pharmaceutically acceptable non-toxic acids or bases including inorganic and organic acids and bases. If the Formula I or Formula II compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the Formula I or Formula II compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The neutral forms of the compounds may be regenerated from the salt by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. The term "prodrug" is intended to mean any chemical entity that, after administration, is converted to a different therapeutically effective chemical entity. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound.

As used herein, "solvate" refers to a compound of the present invention or a salt thereof, that further includes a stoichiometric or non-stoichiometric amount of solvent bound by non-covalent intermolecular forces. Where the solvent is water, the solvate is a hydrate.

The compounds of this invention may contain one or more asymmetric centers and thus occur as racemates and racemic mixtures, scalemic mixtures, single enantiomers, individual diastereomers, and diastereomeric mixtures. All such isomeric forms of these compounds are expressly included in the present invention.

As used herein and unless otherwise indicated, the term "optically pure" or "stereomerically pure" means a composition that comprises one stereoisomer of a compound and is substantially free of other stereoisomers of that compound. For example, a stereomerically pure compound having one chiral center will be substantially free of the opposite enantiomer of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-lnterscience, New York, 1981); Wilen, S. H., et al. (1997) *Tetrahedron* 33:2725; Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

The compounds of the invention may exhibit the phenomenon of tautomerism. While the structural formulas set forth herein cannot expressly depict all possible tautomeric forms, it is to be understood that these structures are intended to represent all tautomeric forms of the depicted compound and are not to be limited merely to the specific compound form depicted by the formula drawings.

Certain compounds of the invention may exist in multiple crystalline or amorphous forms. In general, all physical forms are equivalent for the uses contemplated by the invention and are intended to be within the scope of the invention.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, research reagents, e.g., assay reagents, and diagnostic agents, e.g., in vivo imaging agents. All isotopic variations of the compounds of the invention, whether radioactive or not, are intended to be encompassed within the scope of the invention.

1.2 Compounds

The compounds described herein are useful for treating diseases or conditions mediated by various kinases such as PKB. The invention encompasses the therapeutic use of such compounds and compositions thereof in the treatment of disease states associated with abnormal cell growth, such as cancer, or metabolic disease states, such as diabetes, or inflammation. The invention further provides pharmaceutical compositions that include the compounds of the invention and the use of the compounds in the preparation of medicaments or pharmaceutical formulations or compositions for treating various conditions and disease states.

In one aspect the invention comprises a compound of Formula I

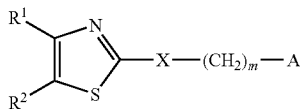

wherein:

A is

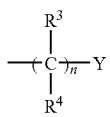

or aryl;

Y is —N(R$^5$)R$^6$ or —OR$^6$;

X is O, S, or —N(R$^7$);

R$^1$ is R$^8$, —CHR$^{11}$—N(H)—R$^8$, —CHR$^{11}$—O—R$^8$, C$_2$-C$_6$ alkynyl, C$_2$-C$_6$ hydroxyalkynyl, or —C≡N;

R$^2$ is aryl or heteroaryl;

R$^3$ is —H, C$_1$-C$_6$ alkyl which may be interrupted by one or more hetero atoms, —(CR$^9$R$^{10}$)$_t$(aryl), —(CR$^9$R$^{10}$)$_t$(heteroaryl), —(CR$^9$R$^{10}$)$_t$(cycloalkyl), or —(CR$^9$R$^{10}$)$_t$(heterocyclyl);

R$^4$ is C$_1$-C$_6$ alkyl which may be interrupted by one or more hetero atoms, —(CR$^9$R$^{10}$)$_t$(aryl), —(CR$^9$R$^{10}$)$_t$(heteroaryl), —(CR$^9$R$^{10}$)$_t$(cycloalkyl), or —(CR$^9$R$^{10}$)$_t$(heterocyclyl), or R$^3$ and R$^4$, together with the carbon atom to which they are both attached, join to form a C$_3$-C$_{10}$ heterocyclic or carbocyclic ring system, or R$^4$ and R$^7$ join to form a C$_3$-C$_{10}$ heterocyclic ring;

R$^5$ is —H, C$_1$-C$_8$ alkyl, —C(O)(CR$^9$R$^{10}$)$_t$)N(R$^7$)$_2$, —(CR$^9$R$^{10}$)$_t$(aryl), —(CR$^9$R$^{10}$)$_t$(heteroaryl), —(CR$^9$R$^{10}$)$_t$(cycloalkyl), or —(CR$^9$R$^{10}$)$_t$(heterocyclyl), or R$^4$ and R$^5$ join to form a C$_3$-C$_{10}$ heterocyclic ring;

R$^6$ and R$^7$ are independently selected from —H, C$_1$-C$_8$ alkyl, —(C$_1$-C$_6$ alkyl)aryl, or —C(O)(C$_1$-C$_6$ alkyl), or R$^6$ and R$^7$, together with the atoms to which they are linked, join to form a 5 to 6-membered heterocyclic ring, or R$^5$ and R$^6$, together with the nitrogen atom to which they are linked, join to form a 5 to 6-membered heterocyclic or heteroaryl ring;

R$^8$ is —H, C$_1$-C$_6$ alkyl, —(C$_1$-C$_6$ alkyl)aryl, aryl, or heteroaryl; and R$^9$, R$^{10}$, and R$^{11}$ are independently selected from —H, C$_1$-C$_6$ alkyl, or aryl;

wherein n is an integer from 1 to 6; m is an integer from 0 to 2; and each t is independently an integer from 0 to 3;

wherein each of the above alkyl, aryl, heteroaryl, cycloalkyl, and heterocyclyl moieties and heterocyclic and carbocyclic rings are optionally and independently substituted by 1-3 substituents selected from amino, aryl, heteroaryl, cycloalkyl, or heterocyclyl optionally substituted by 1-5 substituents selected from C$_1$-C$_6$ alkoxy, C$_1$-C$_6$ alkyl optionally substituted by halo, aryl, halo, hydroxyl, heteroaryl, C$_1$-C$_6$ hydroxyalkyl, or —NHS(O)$_2$—(C$_1$-C$_6$ alkyl);

C$_1$-C$_6$ alkyl, C$_1$-C$_6$ haloalkyl, C$_1$-C$_6$ hydroxyalkyl, C$_1$-C$_6$ alkoxy, C$_1$-C$_6$ alkylamino, C$_2$-C$_6$ alkenyl, or C$_2$-C$_6$ alkynyl, wherein each of which may be interrupted by one or more hetero atoms, cyano, halo, hydroxyl, nitro, or —O-aryl;

or a pharmaceutically acceptable salt, hydrate, or stereoisomer thereof.

In one embodiment, the invention comprises a compound of Formula I, wherein A is

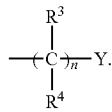

In another embodiment, the invention comprises a compound of Formula I, wherein A is

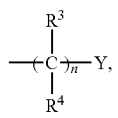

and m, n, and t are 1.

In another embodiment, the invention comprises a compound of Formula I, wherein A is

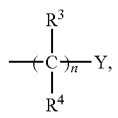

and X is —N(R$^7$), Y is —N(R$^5$)(R$^6$), and m, n, and t are 1.

In another embodiment, the invention comprises a compound of Formula I, wherein A is

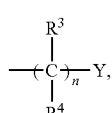

and X is —N(R$^7$), Y is —N(R$^5$)(R$^6$), R$^2$ is heteroaryl, R$^3$ is —H, R$^4$ is —(CR$^9$R$^{10}$)$_t$(aryl) or —(CR$^9$R$^{10}$)$_t$(heteroaryl), m, n, and t are 1, R$^5$, R$^6$, and R$^7$ are —H, and R$^9$ and R$^{10}$ are independently selected from H or C$_1$-C$_3$ alkyl.

In another embodiment, the invention comprises a compound of Formula I, wherein A is

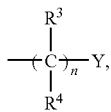

and X is —N(R$^7$), Y is —N(R$^5$)(R$^6$), R$^2$ is bicyclic heteroaryl, R$^3$ is —H, R$^4$ is —(CR$^9$R$^{10}$)$_t$(monocyclic aryl) or —(CR$^9$R$^{10}$)$_t$(bicyclic heteroaryl), m, n, and t are 1, and R$^5$, R$^6$, R$^7$, R$^9$ and R$^{10}$ are —H.

In another embodiment, the invention comprises a compound of Formula I, wherein A is

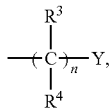

and X is —N(R$^7$), Y is —N(R$^5$)(R$^6$), R$^2$ is bicyclic heteroaryl, R$^3$ is —H, R$^4$ is —(CR$^9$R$^{10}$)$_t$(monocyclic aryl) or —(CR$^9$R$^{10}$)$_t$(bicyclic heteroaryl), m, n, and t are 1, and R$^5$, R$^6$, R$^7$, R$^9$ and R$^{10}$ are —H, wherein the bicyclic heteroaryl group of R$^2$ is isoquinolinyl, 1H-indazolyl, thiazolo[5,4-c]pyridinyl, benzo[d]thiazole-2(3H)-onyl, phthalazinyl, indolin-2-onyl, 3,4-dihydroquinolin-2(1H)-onyl, benzo[d]isoxazolyl, benzo[d]oxazol-2(3H)-onyl, benzo[d]imidazol-2(3H)-onyl, or 1,6-naphthyridinyl; and the monocyclic aryl group of R$^4$ is phenyl, chlorophenyl, (trifluoromethyl)phenyl, or (C$_1$-C$_6$)alkoxyphenyl, or the bicyclic heteroaryl group of R$^4$ is 1H-indolyl. In some embodiments, the bicyclic heteroaryl group of R$^2$ is isoquinolin-6-yl, 3-aminoisoquinolin-6-yl, 1H-indazol-5-yl, 1H-indazol-6-yl, 3-amino-1H-indazol-5-yl, 3-amino-1H-indazol-6-yl, 3-amino-1-methyl-1H-indazol-6-yl, 3-methylamino-1H-indazol-5-yl, 3-methyl-1H-indazol-5-yl, thiazolo[5,4-c]pyridin-2-yl, benzo[d]thiazole-2(3H)-on-6-yl, 1-hydroxyphthalazin-6-yl, phthalazin-6-yl, indolin-2-on-5-yl, 3-methylindolin-2-on-5-yl, 3-(furan-2-ylmethylene)indolin-2-on-5-yl, 3-(1H-imidazol-5-ylmethylene)indolin-2-on-5-yl, 3,3-difluoroindolin-2-on-5-yl, 3,4-dihydroquinolin-2(1H)-on-6-yl, benzo[d]isoxazol-5-yl, 3-aminobenzo[d]isoxazol-5-yl, benzo[d]oxazol-2(3H)-on-6-yl, 1-methyl-1H-benzo[d]imidazol-2(3H)-on-6-yl, or 1,6-naphthyridin-2-yl. In some such embodiments, the monocyclic aryl group of R$^4$ is phenyl, 3-chlorophenyl, 4-chlorophenyl, 4-methoxyphenyl, 3-(trifluoromethyl)phenyl, or 4-(trifluoromethyl)phenyl, or the bicyclic heteroaryl group of R$^4$ is 1H-indol-3-yl.

In another embodiment, the invention comprises a compound of Formula I, wherein A is

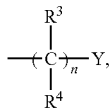

and X is —N(R$^7$), Y is —N(R$^5$)(R$^6$), R$^2$ is bicyclic heteroaryl, R$^3$ is —H, R$^4$ is —(CR$^9$R$^{10}$)$_t$(monocyclic aryl), m, n, and t are 1, and R$^5$, R$^6$, R$^7$, R$^9$ and R$^{10}$ are —H, wherein the bicyclic heteroaryl group of R$^2$ is isoquinolin-6-yl, 3-aminoisoquinolin-6-yl, 1H-indazol-5-yl, 3-methyl-1H-indazol-5-yl, thiazolo[5,4-c]pyridin-2-yl, benzo[d]oxazol-2(3H)-on-6-yl, or 1,6-naphthyridin-2-yl, and the monocyclic aryl group of R$^4$ is 4-chlorophenyl, 3-(trifluoromethyl)phenyl or 4-(trifluoromethyl)phenyl.

In other embodiments, the invention comprises a compound of Formula I having any of the features of any of the embodiments described above in which R$^1$ is —H, —CH$_3$, —CH$_2$CH$_3$, —CH$_2$OCH$_3$, —CH$_2$OCH$_2$CH$_3$, —CH$_2$OH, —CH$_2$OCH$_2$CF$_3$, —CH$_2$N(H)CH$_3$, —CH(CH$_3$)OCH$_3$, furanyl, phenyl, pyridyl, or —C≡N. In some such embodiments, R$^1$ is —H, —CH$_3$, —CH$_2$OCH$_3$, —CH$_2$OCH$_2$CH$_3$, —CH$_2$OH, or furan-2-yl. In other embodiments, R$^1$ is —CH$_3$, —CH$_2$CH$_3$, —CH$_2$OCH$_3$, —CH$_2$OCH$_2$CH$_3$, —CH$_2$OH, —CH$_2$OCH$_2$CF$_3$, —CH$_2$N(H)CH$_3$, —CH(CH$_3$)OCH$_3$, furanyl, phenyl, pyridyl, or —C≡N. In some such embodiments, R$^1$ is —CH$_3$, —CH$_2$OCH$_3$, —CH$_2$OCH$_2$CH$_3$, —CH$_2$OH, or furan-2-yl. In other embodiments, R$^1$ is —(C$_1$-C$_6$ alkyl), —(C$_1$-C$_6$ alkyl)aryl, aryl, heteroaryl, —CHR$^{11}$—N(H)—R$^8$, —CHR$^{11}$—O—R$^8$, or —C≡N. In some such embodiments, R$^1$ is —(C$_1$-C$_6$ alkyl), aryl, heteroaryl, —CHR$^{11}$—N(H)—R$^8$, —CHR$^{11}$—O—R$^8$, or —C≡N. In still other such embodiments, R$^1$ is —(C$_1$-C$_6$ alkyl), heteroaryl, or —CHR$^{11}$—O—R$^8$.

In another embodiment, the invention comprises a compound of Formula I, wherein A is aryl, X is —N(R$^7$), R$^2$ is heteroaryl, and m is 1.

In another embodiment, the invention comprises a compound of Formula I, wherein A is aryl, X is —N(R$^7$), R$^2$ is a bicyclic heteroaryl, m is 1, and R$^7$ is —H.

In another embodiment, the invention comprises a compound of Formula I, wherein A is a monocyclic aryl, X is —N(R$^7$), R$^1$ is —H, R$^2$ is thiazolo[5,4-c]pyridin-2-yl, m is 1, and R$^7$ is —H.

In another embodiment, the invention comprises a compound of Formula I selected from N-((S)-2-amino-3-phenylpropyl)-5-(3-methyl-1H-indazol-5-yl)thiazol-2-amine, N-((S)-2-amino-3-(1H-indol-3-yl)propyl)-5-(3-methyl-1H-indazol-5-yl)thiazol-2-amine, N-((S)-2-amino-3-(4-chlorophenyl)propyl)-5-(3-methyl-1H-indazol-5-yl)thiazol-2-amine, N-((S)-2-amino-3-(4-chlorophenyl)propyl)-5-(1H-indazol-5-yl)thiazol-2-amine, N-((S)-2-amino-3-(1H-indol-3-yl)propyl)-5-(isoquinolin-6-yl)thiazol-2-amine, N-((S)-2-amino-3-(4-(trifluoromethyl)phenyl)propyl)-5-(isoquinolin-6-yl)thiazol-2-amine, N-((S)-2-amino-3-phenylpropyl)-4-methyl-5-(3-methyl-1H-indazol-5-yl)thiazol-2-amine, N-((S)-2-amino-3-phenylpropyl)-5-(1H-indazol-5-yl)-4-methylthiazol-2-amine, N-((S)-2-amino-3-(4-(trifluoromethyl)phenyl)propyl)-4-(furan-2-yl)-5-(isoquinolin-6-yl)thiazol-2-amine, N-((S)-2-amino-3-(4-(trifluoromethyl)phenyl)propyl)-5-(isoquinolin-6-yl)-4-phenylthiazol-2-amine, (2-((S)-2-amino-3-(4-(trifluoromethyl)phenyl)propylamino)-5-(isoquinolin-6-yl)thiazol-4-yl)methanol, (2-((S)-2-amino-3-(4-(trifluoromethyl)phenyl)propylamino)-5-(3-methyl-1H-indazol-5-yl)thiazol-4-yl)methanol, (2-((S)-2-amino-3-(4-(trifluoromethyl)phenyl)propylamino)-5-(1H-indazol-5-yl)thiazol-4-yl)methanol, N-((S)-2-amino-3-(4-(trifluoromethyl)phenyl)propyl)-5-(isoquinolin-6-yl)-4-(methoxymethyl)thiazol-2-amine, N-((S)-2-amino-3-(4-(trifluoromethyl)phenyl)propyl)-5-(1H-indazol-5-yl)-4-(methoxymethyl)thiazol-2-amine, N-((S)-2-amino-3-(4-(trifluoromethyl)phenyl)propyl)-4-(methoxymethyl)-5-(3-methyl-1H-indazol-5-yl)thiazol-2-amine,
N-((S)-2-amino-3-(4-(trifluoromethyl)phenyl)propyl)-5-(isoquinolin-6-yl)-4-(1-methoxyethyl)thiazol-2-amine,
N-((S)-2-amino-3-(3-chlorophenyl)propyl)-N-(4-(methoxymethyl)-5-(thiazolo[5,4-c]pyridin-2-yl)thiazol-2-yl)acetamide,
N-((S)-2-amino-3-(3-chlorophenyl)propyl)-4-(methoxymethyl)-5-(thiazolo[5,4-c]pyridin-2-yl)thiazol-2-amine,
N-((S)-2-amino-3-(4-chlorophenyl)propyl)-4-(methoxymethyl)-5-(thiazolo[5,4-c]pyridin-2-yl)thiazol-2-amine,
N-((S)-2-amino-3-(3-chlorophenyl)propyl)-5-(thiazolo[5,4-c]pyridin-2-yl)-4-((2,2,2-trifluoroethoxy)methyl)thiazol-2-amine,
N-((S)-2-amino-3-(4-chlorophenyl)propyl)-4-(ethoxymethyl)-5-(thiazolo[5,4-c]pyridin-2-yl)thiazol-2-amine,
N-((S)-2-amino-3-(4-(trifluoromethyl)phenyl)propyl)-4-(methoxymethyl)-5-(thiazolo[5,4-c]pyridin-2-yl)thiazol-2-amine,
N-((S)-2-amino-3-(4-(trifluoromethyl)phenyl)propyl)-4-ethyl-5-(thiazolo[5,4-c]pyridin-2-yl)thiazol-2-amine,
N-((S)-2-amino-3-(4-(trifluoromethyl)phenyl)propyl)-4-methyl-5-(thiazolo[5,4-c]pyridin-2-yl)thiazol-2-amine,
N-((S)-2-amino-3-(4-chlorophenyl)propyl)-N-(4-(methoxymethyl)-5-(thiazolo[5,4-c]pyridin-2-yl)thiazol-2-yl)acetamide,
N-((S)-2-amino-3-(4-(trifluoromethyl)phenyl)propyl)-N-(4-(methoxymethyl)-5-(thiazolo[5,4-c]pyridin-2-yl)thiazol-2-yl)acetamide,
N-((S)-2-amino-3-(1H-indol-3-yl)propyl)-4-(methoxymethyl)-5-(thiazolo[5,4-c]pyridin-2-yl)thiazol-2-amine,
N-benzyl-5-(thiazolo[5,4-c]pyridin-2-yl)thiazol-2-amine,
N-((S)-2-amino-3-(3-(trifluoromethyl)phenyl)propyl)-N-benzyl-5-(thiazolo[5,4-c]pyridin-2-yl)thiazol-2-amine,
N-((S)-2-amino-3-(4-(trifluoromethyl)phenyl)propyl)-N-benzyl-5-(thiazolo[5,4-c]pyridin-2-yl)thiazol-2-amine,
N-((S)-2-amino-3-(3-(trifluoromethyl)phenyl)propyl)-5-(thiazolo[5,4-c]pyridin-2-yl)thiazol-2-amine,
N-((S)-2-amino-3-(4-(trifluoromethyl)phenyl)propyl)-5-(thiazolo[5,4-c]pyridin-2-yl)thiazol-2-amine,
N-(4-(methoxymethyl)-5-(thiazolo[5,4-c]pyridin-2-yl)thiazol-2-yl)-N-((S)-2-(2-morpholinoethylamino)-3-(4-(trifluoromethyl)phenyl)propyl)acetamide,
4-(methoxymethyl)-N-((S)-2-(2-morpholinoethylamino)-3-(4-(trifluoromethyl)phenyl)propyl)-5-(thiazolo[5,4-c]pyridin-2-yl)thiazol-2-amine,
6-(2-((S)-2-amino-3-(4-(trifluoromethyl)phenyl)propylamino)thiazol-5-yl)-3,4-dihydroquinolin-2(1H)-one,
6-(2-((S)-2-amino-3-(1H-indol-3-yl)propylamino)thiazol-5-yl)benzo[d]thiazol-2(3H)-one,
5-(2-((S)-2-amino-3-(1H-indol-3-yl)propylamino)thiazol-5-yl)-1H-indazol-3-amine,
5-(2-((S)-2-amino-3-(1H-indol-3-yl)propylamino)thiazol-5-yl)benzo[d]isoxazol-3-amine,
6-(2-((S)-2-amino-3-(1H-indol-3-yl)propylamino)thiazol-5-yl)benzo[d]oxazol-2(3H)-one,
6-(2-((S)-2-amino-3-(4-(trifluoromethyl)phenyl)propylamino)thiazol-5-yl)benzo[d]oxazol-2(3H)-one,
5-(2-((S)-2-amino-3-(4-(trifluoromethyl)phenyl)propylamino)thiazol-5-yl)-3,3-difluoroindolin-2-one,
5-(2-((S)-2-amino-3-(4-(trifluoromethyl)phenyl)propylamino)thiazol-5-yl)indolin-2-one,
6-(2-((S)-2-amino-3-(4-(trifluoromethyl)phenyl)propylamino)thiazol-5-yl)benzo[d]thiazol-2(3H)-one,
5-(2-((S)-2-amino-3-(3-(trifluoromethyl)phenyl)propylamino)thiazol-5-yl)indolin-2-one,
5-(2-((S)-2-amino-3-(1H-indol-3-yl)propylamino)thiazol-5-yl)-N-methyl-1H-indazol-3-amine),
6-(2-((S)-2-amino-3-(3-(trifluoromethyl)phenyl)propylamino)thiazol-5-yl)benzo[d]oxazol-2(3H)-one,
5-(2-((S)-2-amino-3-(4-(trifluoromethyl)phenyl)propylamino)thiazol-5-yl)-3-methylindolin-2-one,
N-((S)-2-amino-3-(4-(trifluoromethyl)phenyl)propyl)-5-(1H-indazol-6-yl)thiazol-2-amine,
(S)-4-(2-(2-amino-3-(4-(trifluoromethyl)phenyl)propylamino)thiazol-5-yl)benzamide,
5-(2-((S)-2-amino-3-(4-(trifluoromethyl)phenyl)propylamino)thiazol-5-yl)-1H-indazol-3-amine,
5-(2-((S)-2-amino-3-(4-(trifluoromethyl)phenyl)propylamino)thiazol-5-yl)benzo[d]isoxazol-3-amine,
6-(2-((S)-2-amino-3-(4-(trifluoromethyl)phenyl)propylamino)thiazol-5-yl)-1H-indazol-3-amine,
6-(2-((S)-2-amino-3-(4-(trifluoromethyl)phenyl)propylamino)thiazol-5-yl)-1-methyl-1H-indazol-3-amine,
5-(2-((S)-2-Amino-3-(4-chlorophenyl)propylamino)thiazol-5-yl)indolin-2-one,
6-(2-((S)-2-Amino-3-(4-chlorophenyl)propylamino)thiazol-5-yl)benzo[d]oxazol-2(3H)-one,
N-((S)-2-amino-3-(4-(trifluoromethyl)phenyl)propyl)-5-(isoquinolin-6-yl)-4-((methylamino)methyl)thiazol-2-amine,
6-(2-((S)-2-amino-3-(4-(trifluoromethyl)phenyl)propylamino)thiazol-5-yl)-1-methyl-1H-benzo[d]imidazol-2(3H)-one,
6-(2-((S)-2-amino-3-(4-(trifluoromethyl)phenyl)propylamino)-4-(methoxymethyl)thiazol-5-yl)-1-methyl-1H-benzo[d]imidazol-2(3H)-one,
6-(2-((S)-2-amino-3-(4-(trifluoromethyl)phenyl)propylamino)-4-(methoxymethyl)thiazol-5-yl)benzo[d]oxazol-2(3H)-one,
2-((S)-2-amino-3-(4-(trifluoromethyl)phenyl)propylamino)-5-(2-oxoindolin-5-yl)thiazole-4-carbonitrile,
2-((S)-2-amino-3-(4-(trifluoromethyl)phenyl)propylamino)-5-(3-methyl-2-oxo-2,3-dihydro-1H-benzo[d]imidazol-5-yl)thiazole-4-carbonitrile,
2-((S)-2-amino-3-(4-(trifluoromethyl)phenyl)propylamino)-5-(isoquinolin-6-yl)thiazole-4-carbonitrile,
N-((S)-2-amino-3-(4-(trifluoromethyl)phenyl)propyl)-5-(phthalazin-6-yl)thiazol-2-amine,
6-(2-((S)-2-amino-3-(4-(trifluoromethyl)phenyl)propylamino)thiazol-5-yl)phthalazin-1-ol,
N-((S)-2-amino-3-(3-chlorophenyl)propyl)-5-(isoquinolin-6-yl)thiazol-2-amine,
5-(2-((S)-2-amino-3-(4-methoxyphenyl)propylamino)thiazol-5-yl)indolin-2-one,
N-((S)-2-amino-3-(4-(trifluoromethyl)phenyl)propyl)-5-(1,6-naphthyridin-2-yl)thiazol-2-amine,
5-(2-((S)-2-amino-3-(4-(trifluoromethyl)phenyl)propylamino)-4-(methoxymethyl)thiazol-5-yl)indolin-2-one,
5-(2-((S)-2-amino-3-phenylpropylamino)thiazol-5-yl)-3-methylindolin-2-one,
N-((S)-2-amino-3-(4-(trifluoromethyl)phenyl)propyl)-4-(methoxymethyl)-5-(1,6-naphthyridin-2-yl)thiazol-2-amine,
(E)-5-(2-((S)-2-amino-3-(1H-indol-3-yl)propylamino)thiazol-5-yl)-3-(furan-2-ylmethylene)indolin-2-one ditrifluoroacetates,
(Z)-5-(2-((S)-2-amino-3-(1H-indol-3-yl)propylamino)thiazol-5-yl)-3-(furan-2-ylmethylene)indolin-2-one ditrifluoroacetates,
(E)-3-((1H-imidazol-5-yl)methylene)-6-(2-((S)-2-amino-3-(1H-indol-3-yl)propylamino)thiazol-5-yl)indolin-2-one, 5-(2-((S)-2-amino-3-(1H-indol-3-yl)propylamino)thiazol-5-yl)indolin-2-one,
6-(2-((S)-2-Amino-3-(4-(trifluoromethyl)phenyl)propylamino)thiazol-5-yl)isoquinolin-3-amine,
6-(2-((S)-2-Amino-3-(4-chlorophenyl)propylamino)thiazol-5-yl)isoquinolin-3-amine,
6-(2-((S)-2-amino-3-(4-methoxyphenyl)propylamino)thiazol-5-yl)benzo[d]oxazol-2(3H)-one, or
4-(2-((S)-2-amino-3-(4-(trifluoromethyl)phenyl)propylamino)-5-(isoquinolin-6-yl)thiazole-4-yl)-2-methylbut-3-yn-2-ol, or a pharmaceutically acceptable salt, hydrate, or stereoisomer thereof.

In another aspect, the invention provides a compound of Formula II

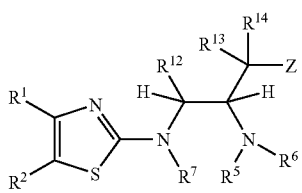

wherein:
$R^1$ is —H, halo, —$OR^8$, $C_1$-$C_6$ alkyl, —($C_1$-$C_6$ alkyl)-O—$R^8$, —($C_1$-$C_6$ haloalkyl)-O—$R^8$, —($C_2$-$C_6$ alkenyl)-O—$R^8$, —($C_1$-$C_6$ alkyl)N($R^7$)$_2$, —($C_1$-$C_6$ alkyl)aryl, —C(O)$R^8$, —C(O)O—$R^8$, —C(O)N($R^7$)$_2$, —$CHR^{11}$—N(H)$R^8$, —$CHR^{11}$—O—$R^8$, $C_2$-$C_6$ alkynyl, ($C_2$-$C_6$ alkynyl)-O—$R^8$, —C≡N, —($C_2$-$C_6$ alkynyl)($C_3$-$C_8$ cycloalkyl), —($C_2$-$C_6$ alkynyl)($C_5$-$C_8$ cycloalkenyl), —($C_2$-$C_6$ alkynyl)-N($R^7$)S(O)$_2$—$R^8$, aryl, heteroaryl, cycloalkyl, or heterocyclyl;
$R^2$ is a carbocyclic ring system or is a heterocyclic ring; system;
$R^5$ is —H, $C_1$-$C_8$ alkyl, —C(O)($CR^9R^{10}$)$_t$N($R^7$)$_2$, —C(O)($CR^9R^{10}$)$_t$, —C(O)$_2$($CR^9R^{10}$)$_t$, —($CR^9R^{10}$)$_t$(aryl), —($CR^9R^{10}$)$_t$(heteroaryl), —($CR^9R^{10}$)$_t$(cycloalkyl), or —($CR^9R^{10}$)$_t$(heterocyclyl);
$R^6$ and $R^7$, in each instance, are independently selected from —H, $C_1$-$C_8$ alkyl, —($C_1$-$C_6$ alkyl)aryl, or —C(O)($C_1$-$C_6$ alkyl);
$R^8$ is selected from —H, $C_1$-$C_6$ alkyl, $C_1$-$C_6$ haloalkyl, —($C_1$-$C_6$ alkyl)aryl, aryl, heteroaryl, $C_1$-$C_6$ hydroxyalkyl, or —($C_1$-$C_6$ alkyl)-O—($C_1$-$C_6$ alkyl), cycloalkyl, or heterocyclyl;
$R^9$ and $R^{10}$, in each instance, and $R^{11}$ are independently selected from —H, $C_1$-$C_6$ alkyl, or aryl;
$R^{12}$ is —H, —$OR^8$, —O—($C_1$-$C_6$ alkyl)-O—$R^8$, $C_1$-$C_6$ alkyl, $C_2$-$C_6$ alkenyl, —($C_1$-$C_6$ alkyl)-O—$R^8$, or —($C_1$-$C_6$ alkyl)-O—C(O)—$R^8$;
$R^{13}$ is —H, or $C_1$-$C_6$ alkyl;
$R^{14}$ is —H, —$OR^8$, —O—($C_1$-$C_6$ alkyl)-O—$R^8$, $C_1$-$C_6$ alkyl, $C_2$-$C_6$ alkenyl, —($C_1$-$C_6$ alkyl)-O—$R^8$, or —($C_1$-$C_6$ alkyl)-O—C(O)—$R^8$;
each t is independently selected from 0, 1, 2, or 3; and
Z is aryl or heteroaryl;
wherein each of the above alkyl, aryl, heteroaryl, cycloalkyl, and heterocyclyl moieties and heterocyclic and carbocyclic rings are optionally and independently substituted by 1-3 substituents selected from
amino,
aryl, heteroaryl, cycloalkyl, or heterocyclyl optionally substituted by 1-5 substituents selected from
$C_1$-$C_6$ alkoxy,
$C_1$-$C_6$ alkyl optionally substituted by halo,
aryl,
halo,
hydroxyl,
heteroaryl,
$C_1$-$C_6$ hydroxyalkyl, or
—NHS(O)$_2$—$C_1$-$C_6$ alkyl);
$C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ hydroxyalkoxy, $C_1$-$C_6$ alkylamino, $C_2$-$C_6$ alkenyl, or $C_2$-$C_6$ alkynyl, wherein each of which may be interrupted by one or more hetero atoms,
cyano,
halo,
hydroxyl,
nitro,
oxo,
—NH(CO)—O—($C_1$-$C_6$ alkyl)aryl, —NH(CO)—O—($C_1$-$C_6$ alkyl), —N($C_1$-$C_6$ alkyl)(CO)—O—($C_1$-$C_6$ alkyl)aryl, —N($C_1$-$C_6$ alkyl)(CO)—O—($C_1$-$C_6$ alkyl), —C(O)OH, —C(O)O($C_1$-$C_6$ alkyl), —C(O)NH$_2$, —C(O)N(H)—($C_1$-$C_6$ alkyl), —C(O)N($C_1$-$C_6$ alkyl)$_2$, —NH($C_1$-$C_6$ alkyl), —N($C_1$-$C_6$ alkyl)$_2$, —($C_2$-$C_4$ alkenyl)heterocyclyl, or —($C_2$-$C_4$ alkenyl)cycloalkyl, or
—O-aryl;

or a pharmaceutically acceptable salt, hydrate, stereoisomer, or mixture thereof.

In some embodiments of the compound of Formula II,
$R^1$ is —H, halo, —$OR^8$, $C_1$-$C_6$ alkyl, —($C_1$-$C_6$ alkyl)-O—$R^8$, —($C_1$-$C_6$ haloalkyl)-O—$R^8$, —($C_2$-$C_6$ alkenyl)-O—$R^8$, —($C_1$-$C_6$ alkyl)N($R^7$)$_2$, —($C_1$-$C_6$ alkyl)aryl, —C(O)$R^8$, —C(O)O—$R^8$, —C(O)N($R^7$)$_2$, —$CHR^{11}$—N(H)—$R^8$, —$CHR^{11}$—O—$R^8$, $C_2$-$C_6$ alkynyl, ($C_2$-$C_6$ alkynyl)-O—$R^8$, —C≡N, —($C_2$-$C_6$ alkynyl)($C_3$-$C_8$ cycloalkyl), —($C_2$-$C_6$ alkynyl)($C_5$-$C_8$ cycloalkenyl), —($C_2$-$C_6$ alkynyl)-N($R^7$)S(O)$_2$—$R^8$, aryl, heteroaryl, cycloalkyl, or heterocyclyl;
$R^2$ is a carbocyclic ring system or is a heterocyclic ring; system optionally substituted by 1-3 substituents independently selected from —F, —Cl, —Br, —I, —CN, —NO$_2$, —OH, =O, —NH$_2$, —NH($C_1$-$C_6$ alkyl), —N($C_1$-$C_6$ alkyl)$_2$, —C(O)OH, —C(O)O($C_1$-$C_6$ alkyl), —C(O)NH$_2$, —C(O)N(H)($C_1$-$C_6$ alkyl), —C(O)N($C_1$-$C_6$ alkyl)$_2$, $C_1$-$C_6$ alkyl, cycloalkyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ hydroxyalkoxy, $C_1$-$C_6$ alkylamino, $C_2$-$C_6$ alkenyl, —($C_2$-$C_4$ alkenyl)heterocyclyl, or —($C_2$-$C_4$ alkenyl)cycloalkyl;
$R^5$ is —H, $C_1$-$C_8$ alkyl, —C(O)($CR^9R^{10}$)$_t$N($R^7$)$_2$, —($CR^9R^{10}$)$_t$(aryl), —($CR^9R^{10}$)$_t$(heteroaryl), —($CR^9R^{10}$)$_t$(cycloalkyl), or —($CR^9R^{10}$)$_t$(heterocyclyl);
$R^6$ and $R^7$, in each instance, are independently selected from —H, $C_1$-$C_8$ alkyl, —($C_1$-$C_6$ alkyl)aryl, or —C(O)($C_1$-$C_6$ alkyl);
$R^8$ is selected from —H, $C_1$-$C_6$ alkyl, $C_1$-$C_6$ haloalkyl, —($C_1$-$C_6$ alkyl)aryl, aryl, heteroaryl, $C_1$-$C_6$ hydroxyalkyl, or —($C_1$-$C_6$ alkyl)-O—($C_1$-$C_6$ alkyl), cycloalkyl, or heterocyclyl;
$R^9$ and $R^{10}$, in each instance, and $R^{11}$ are independently selected from —H, $C_1$-$C_6$ alkyl, or aryl;
$R^{12}$ is —H, —$OR^8$, —O—($C_1$-$C_6$ alkyl)-O—$R^8$, $C_1$-$C_6$ alkyl, $C_2$-$C_6$ alkenyl, —($C_1$-$C_6$ alkyl)-O—$R^8$, or —($C_1$-$C_6$ alkyl)-O—C(O)—$R^8$;
$R^{13}$ is —H, or $C_1$-$C_6$ alkyl;

$R^{14}$ is —H, —$OR^8$, —O—($C_1$-$C_6$ alkyl)-O—$R^8$, $C_1$-$C_6$ alkyl, $C_2$-$C_6$ alkenyl, —($C_1$-$C_6$ alkyl)-O—$R^8$, or —($C_1$-$C_6$ alkyl)-O—C(O)—$R^8$;

each t is independently selected from 0, 1, 2, or 3; and

Z is aryl or heteroaryl optionally substituted with from 1-3 substituents independently selected from —F, —Cl, —Br, —I, —CN, —$NH_2$, —$NO_2$, —$CF_3$, —OH, —O—($C_1$-$C_6$ alkyl), —O—($C_1$-$C_6$ alkyl)-Cl, —O—($C_1$-$C_6$ alkyl)-OH, —$C_1$-$C_6$ alkyl, —$OCF_3$, —NH($C_1$-$C_6$ alkyl), —N($C_1$-$C_6$ alkyl)$_2$, —C(O)OH, —C(O)O($C_1$-$C_6$ alkyl), —C(O)$NH_2$, —C(O)N(H)—($C_1$-$C_6$ alkyl), —C(O)N($C_1$-$C_6$ alkyl)$_2$, —NH(CO)—O—($C_1$-$C_6$ alkyl)aryl, or —NH(CO)—O—($C_1$-$C_6$ alkyl).

In some embodiments, the compound of Formula II has the Formula IIA

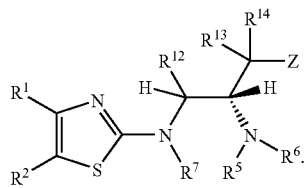

IIA

In some embodiments, the compound of Formula II has the Formula IIB

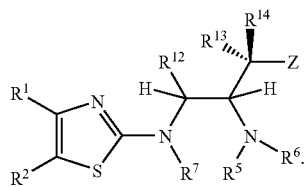

IIB

In some embodiments, the compound of Formula II has the Formula IIC

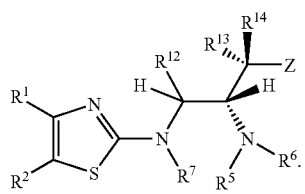

IIC

In some embodiments, the compound of Formula II has the Formula IID

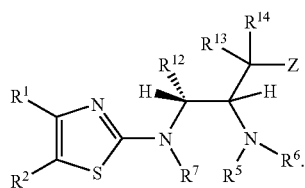

IID

In some embodiments, the compound of Formula II has the Formula IIE

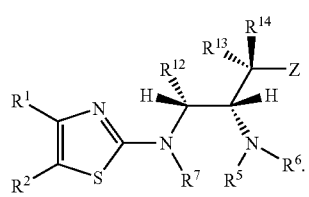

IIE

In some embodiments of the compound of Formula II, $R^1$ is —H.

In some embodiments of the compound of Formula II, $R^{12}$ is —H or $C_1$-$C_6$ alkyl. In some such embodiments, $R^{12}$ is —H or methyl.

In some embodiments of the compound of Formula II, $R^{13}$ is —H.

In some embodiments of the compound of Formula II, $R^{14}$ is —H.

In some embodiments of the compound of Formula II, $R^{14}$ is —$OR^8$, —O—($C_1$-$C_6$ alkyl)-O—$R^8$, $C_1$-$C_6$ alkyl, $C_2$-$C_6$ alkenyl, —($C_1$-$C_6$ alkyl)-O—$R^8$, or —($C_1$-$C_6$ alkyl)-O—C(O)—$R^8$.

In some embodiments of the compound of Formula II, $R^{14}$ is selected from —H, methyl, ethyl, propyl, ethenyl, propenyl, hydroxymethyl, methoxymethyl, —$CH_2$—O—C(O)—($C_1$-$C_6$ alkyl), 1-hydroxyethyl, or methoxymethoxy.

In some embodiments of the compound of Formula II, Z is selected from optionally substituted phenyl, optionally substituted indolyl, optionally substituted naphthyl, optionally substituted pyridyl, or optionally substituted thiophenyl. In some such embodiments, Z is selected from phenyl, indolyl, naphthyl, pyridyl, or thiophenyl, each of which is optionally substituted with 1-3 substituents selected from —Cl, —F, —$CF_3$, —OH, —O—($C_1$-$C_6$ alkyl), —O—($C_1$-$C_6$ alkyl)-Cl, —O—($C_1$-$C_6$ alkyl)-OH, —$C_1$-$C_6$ alkyl, —$OCF_3$, —NH(CO)—O—($C_1$-$C_6$ alkyl)aryl, or —NH(CO)—O—($C_1$-$C_6$ alkyl).

In some embodiments of the compound of Formula II, Z is selected from phenyl, indolyl, naphthyl, pyridyl, thiophenyl, 4-chlorophenyl, 4-trifluoromethylphenyl, 3-chlorophenyl, 3-trifluoromethylphenyl, 4-methoxyphenyl, 3-fluoro-4-trifluoromethylphenyl, 4-chloro-3-fluorophenyl, 4-(3- chloropropoxy)phenyl, 4-(3-hydroxypropoxy)phenyl, 3,4-dichlorophenyl, 4-fluorophenyl, 2,4-dichlorophenyl, 4-methylphenyl, 3,4-difluorophenyl, 3-fluoro-4-methoxyphenyl, 3,5-difluorophenyl, 6-trifluoromethylpyridin-3-yl, 5-methoxy-6-trifluoromethylpyridin-3-yl, 2-fluoro-4-trifluoromethylphenyl, 4-trifluoromethoxyphenyl, 2,3-difluoro-4-trifluoromethylphenyl, 4-hydroxyphenyl, 3-methoxy-4-trifluoromethylphenyl, 3-hydroxy-4-trifluoromethylphenyl, 5-chlorothiophen-2-yl, 3-fluoro-4-hydroxyphenyl, or a phenyl substituted in the 4 position with —NH—C(O)—O—$CH_2$-phenyl.

In some embodiments of the compound of Formula II, $R^7$ is H. In some such embodiments, $R^5$ and $R^6$ are both H.

In some embodiments of the compound of Formula II, $R^5$ and $R^6$ are both H.

In some embodiments of the compound of Formula II, $R^{12}$ is —H or $C_1$-$C_6$ alkyl, $R^{13}$ is —H, and $R^{14}$ is —H, —$OR^8$, —O—($C_1$-$C_6$ alkyl)-O—$R^8$, $C_1$-$C_6$ alkyl, $C_2$-$C_6$ alkenyl, —($C_1$-$C_6$ alkyl)-O—$R^8$, or —($C_1$-$C_6$ alkyl)-O—C(O)—$R^8$. In some such embodiments, $R^{14}$ is —$OR^8$, —O—($C_1$-$C_6$ alkyl)-O—$R^8$, $C_1$-$C_6$ alkyl, $C_2$-$C_6$ alkenyl, —($C_1$-$C_6$ alkyl)-O—$R^8$, or —($C_1$-$C_6$ alkyl)-O—C(O)—$R^8$. In further such embodiments, $R^5$, $R^6$, and $R^7$ are all H.

In some embodiments of the compound of Formula II, the carbocyclic ring system or the heterocyclic ring system of $R^2$ is optionally substituted with from 1-3 substituents selected from —F, —Cl, —Br, —I, —CN, —$NO_2$, —OH, =O, —$NH_2$, —NH($C_1$-$C_6$ alkyl), —N($C_1$-$C_6$ alkyl)$_2$, —C(O)$NH_2$, —C(O)N(H)($C_1$-$C_6$ alkyl), —C(O)N($C_1$-$C_6$ alkyl)$_2$, $C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ hydroxyalkoxy, $C_1$-$C_6$ alkylamino, $C_2$-$C_6$ alkenyl, —($C_2$-$C_4$ alkenyl)heterocyclyl, or —($C_2$-$C_4$ alkenyl)cycloalkyl.

In some embodiments of the compound of Formula II, the carbocyclic ring system or the heterocyclic ring system of $R^2$ includes at least one aromatic ring. In such embodiments, the aromatic ring may be carbocyclic, or the aromatic ring may include one or more heteroatoms such as, but not limited to, in pyridine or pyrimidine rings. In some embodiments, the at least one aromatic ring in the carbocyclic ring system or the heterocyclic ring system of $R^2$ is a phenyl ring or is a pyridyl ring. In some embodiments, the carbocyclic ring system or the heterocyclic ring system of $R^2$ includes an aromatic ring, and the aromatic ring is bonded to the thiazole shown in the structure of Formula II. In some embodiments, the carbocyclic ring system or the heterocyclic ring system of $R^2$ is a fused ring system comprising at least two rings. In some such embodiments, $R^2$ is a heterocyclic ring system comprising two six membered rings or one six membered ring and one 5 membered ring.

In some embodiments of the compound of Formula II, $R^2$ is selected from optionally substituted phenyl, pyridyl, indazolyl, isoquinolinyl, thiazolopyridinyl, benzothiazolonyl, dihydroquinolinonyl, benzoisoxazolyl, benzooxazolonyl, indolinonyl, benzoimidazolonyl, phthalazinyl, naphthyridinyl, thienopyridinyl, benzodioxolyl, isoindolinonyl, quinazolinyl, or cinnolinyl. In other embodiments, $R^2$ is selected from isoquinolinyl, 1H-indazolyl, thiazolo[5,4-c]pyridinyl, benzo[d]thiazole-2(3H)-onyl, phthalazinyl, indolin-2-onyl, 3,4-dihydroquinolin-2(1H)-onyl, benzo[d]isoxazolyl, benzo[d]oxazol-2(3H)-onyl, benzo[d]imidazol-2(3H)-onyl, 1,6-naphthyridinyl, quinazolin-7-yl, or cinnolin-6-yl. In other embodiments, $R^2$ is isoquinolin-6-yl, 3-aminoisoquinolin-6-yl, 1H-indazol-5-yl, 1H-indazol-6-yl, 3-amino-1H-indazol-5-yl, 3-amino-1H-indazol-6-yl, 3-amino-1-methyl-1H-indazol-6-yl, 3-methylamino-1H-indazol-5-yl, 3-methyl-1H-indazol-5-yl, thiazolo[5,4-c]pyridin-2-yl, benzo[d]thiazole-2(3H)-on-6-yl, 1-hydroxyphthalazin-6-yl, phthalazin-6-yl, indolin-2-on-5-yl, 3-methylindolin-2-on-5-yl, 3-(furan-2-ylmethylene)indolin-2-on-5-yl, 3-(1H-imidazol-5-ylmethylene)indolin-2-on-5-yl, 3,3-difluoroindolin-2-on-5-yl, 3,4-dihydroquinolin-2(1H)-on-6-yl, benzo[d]isoxazol-5-yl, 3-aminobenzo[d]isoxazol-5-yl, benzo[d]oxazol-2(3H)-on-6-yl, 1-methyl-1H-benzo[d]imidazol-2(3H)-on-6-yl, 1,6-naphthyridin-2-yl, quinazolin-7-yl, or cinnolin-6-yl.

In some embodiments of the compound of Formula II, $R^2$ is selected from one of the following groups which may optionally be substituted and where the wavy line indicates the point of attachment to the thiazole:

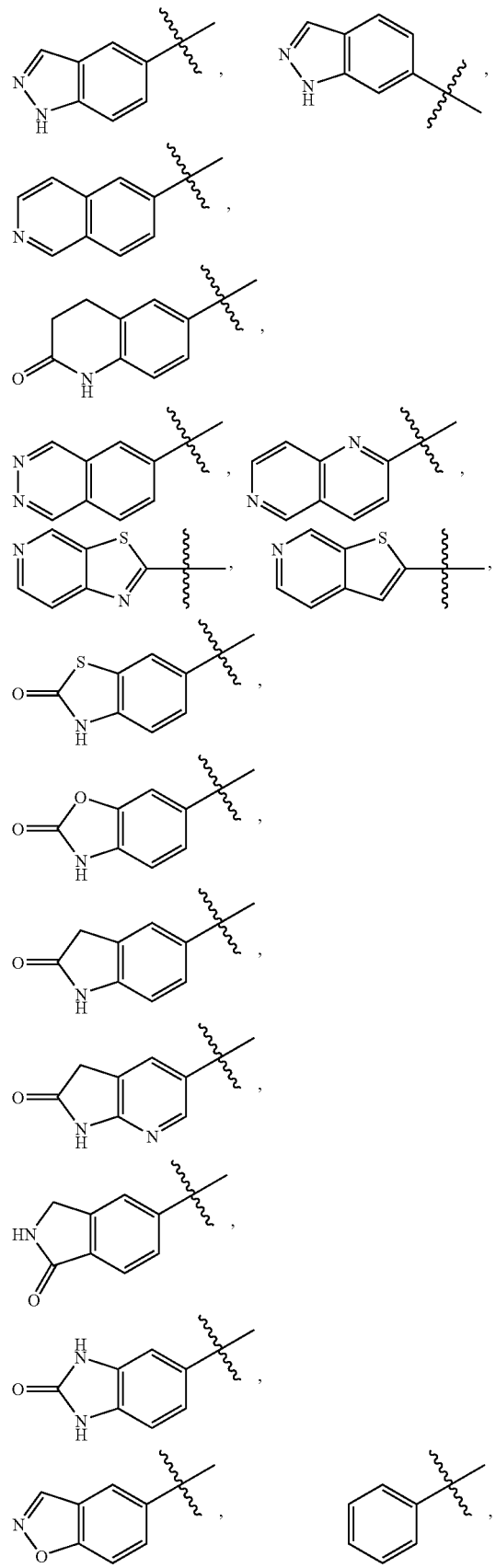

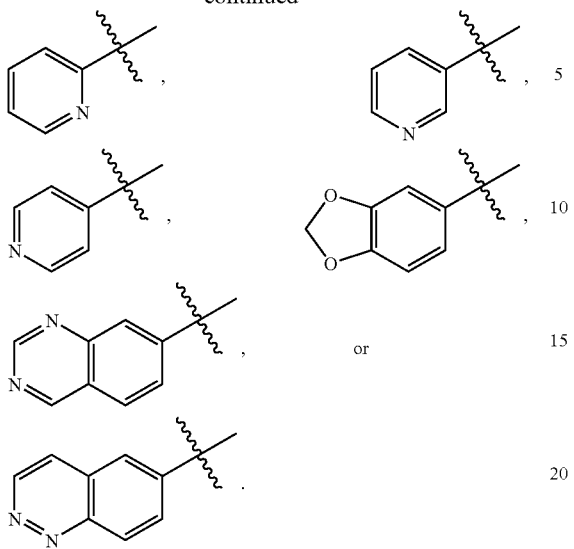
In some embodiments of the compound of Formula II, $R^2$ is selected from one of the following groups, where the wavy line indicates the point of attachment to the thiazole:
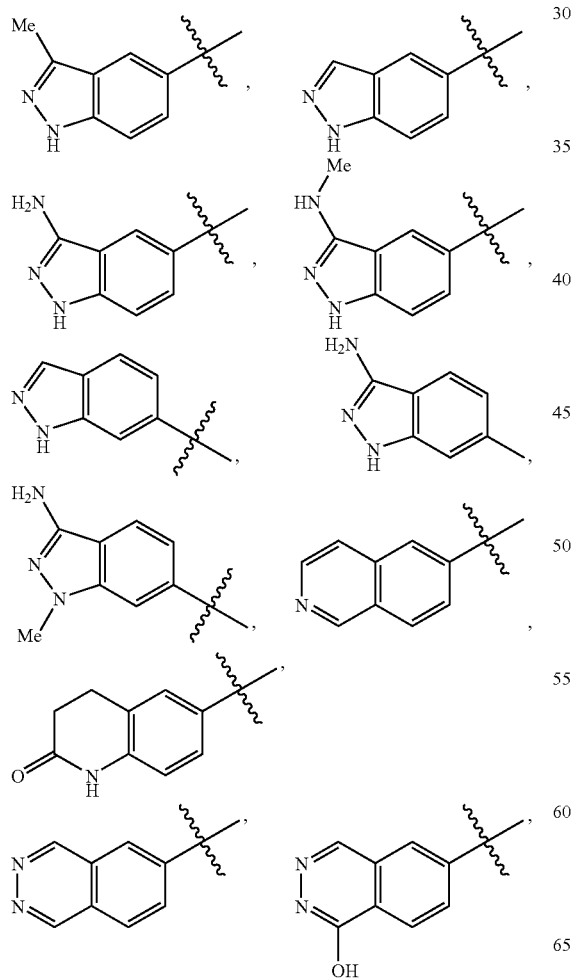
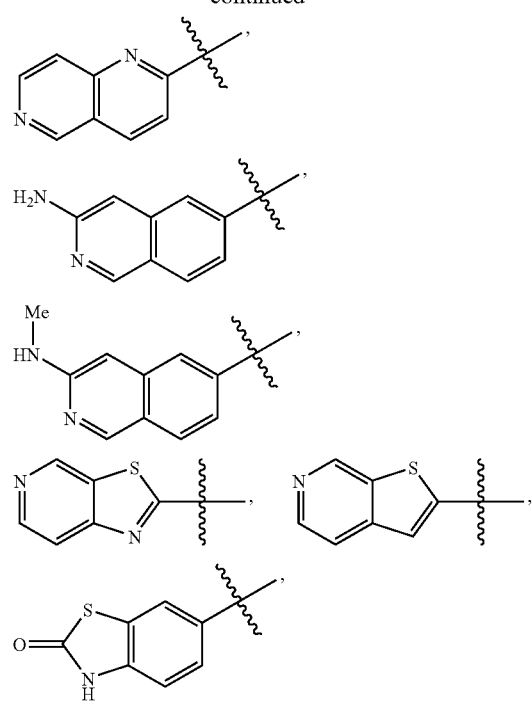

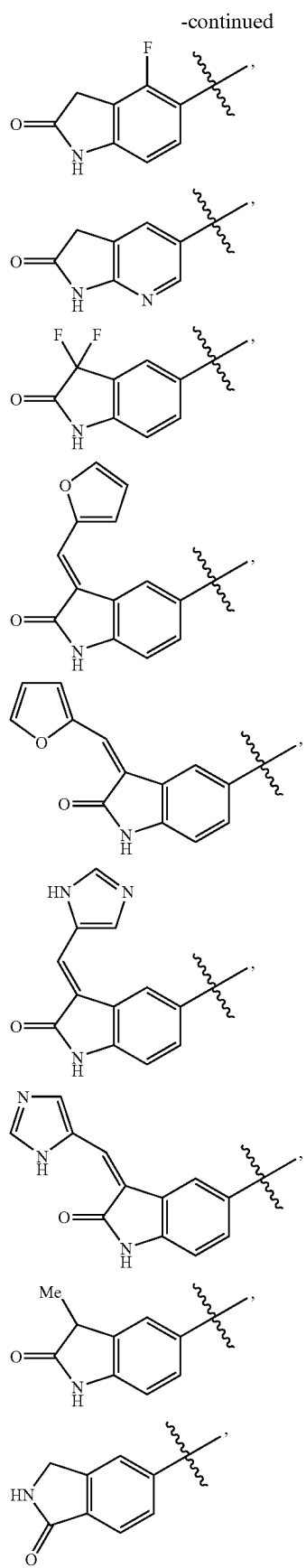
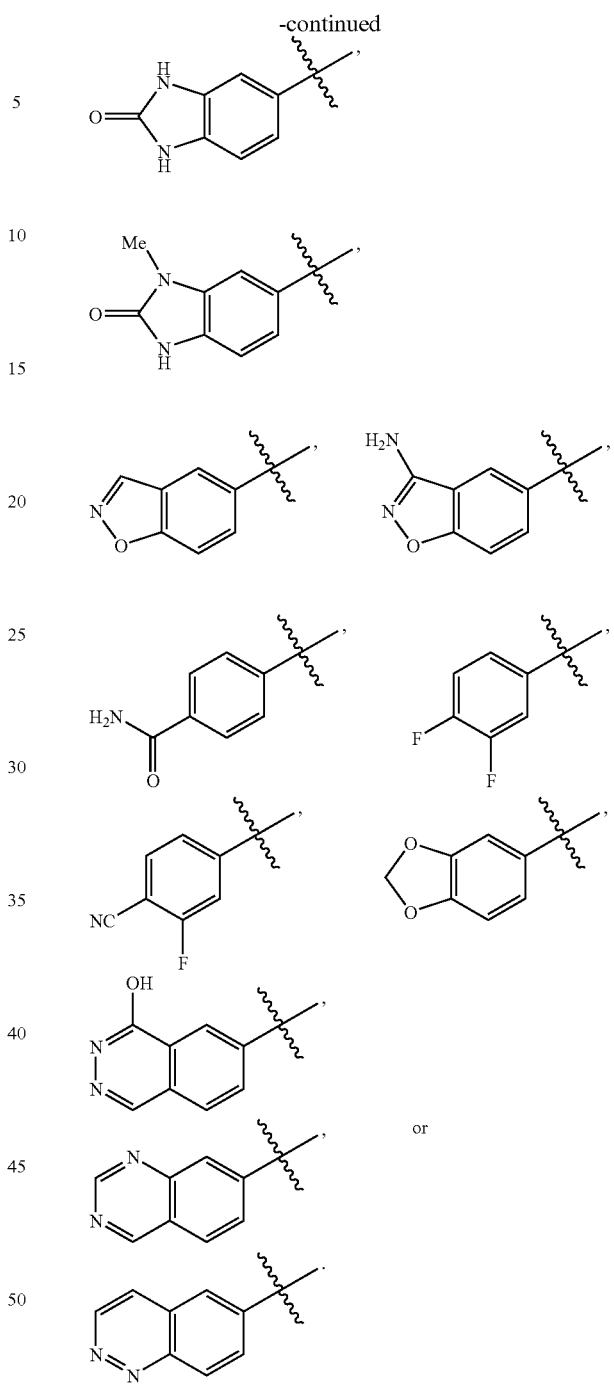

In some embodiments of the compound of Formula II, $R^1$ is selected from —H, —C≡N, —Br, —Cl, —OH, —$CF_3$, —$CH_3$, —$CH_2CH_3$, —$CH_2CH_2OH$, —C(H)($CH_3$)$OCH_3$, —$CH_2OCH_2CF_3$, —$CH_2N(H)CH_3$, —$CH_2N(CH_3)_2$, —$CF_2CH_2OH$, cyclopropyl, furanyl, tetrahydrofuranyl, phenyl, 2,3-difluorophenyl, 3,4-difluorophenyl, 4-fluorophenyl, 3-fluorophenyl, 2-fluorophenyl, pyridyl, oxazolyl, hydroxymethyl, methoxymethyl, ethoxymethyl, —C(O)OMe, —C(O)N(H)$CH_2CH_2OH$, —C(O)N(H)$CH_3$, —C(O)$NH_2$, —C(O)N($CH_3$)$_2$, or a group selected from one of the following groups where the wavy line indicates the point of attachment to the thiazole:

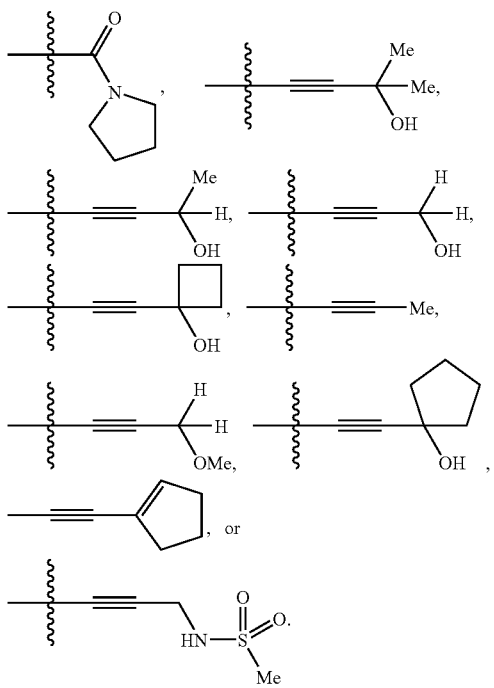

In one embodiment, the invention comprises one or more compound selected from any one or all of Examples 1-255 shown in Table 1, or a pharmaceutically acceptable salt, hydrate, or stereoisomer thereof. Each of the different groups of Examples 1-255 that correspond to any of the variables in the compounds of Formula I and/or Formula II is preferred.

In another aspect, the invention comprises a pharmaceutically acceptable salt, hydrate, or solvate of a compound of Formula I or Formula II or any of the compounds of any of the embodiments described herein. In one embodiment, the pharmaceutically acceptable salt is selected from a chloride or trifluoroacetate salt. In some such embodiments, the salt is an ammonium trifluoroacetate, ammonium chloride, or hydrochloride salt.

1.3 Pharmaceutical Compositions and Dosage Forms

Compounds of Formula I and Formula II or any of the embodiments thereof, or a pharmaceutically acceptable salt, hydrate, or stereoisomer thereof may be used to prepare pharmaceutical compositions and single unit dosage forms. Therefore, in some embodiments, the invention provides a pharmaceutical composition that includes a compound of Formula I or Formula II, or a pharmaceutically acceptable salt, hydrate, or stereoisomer thereof. Pharmaceutical compositions and individual dosage forms of the invention may be suitable for oral, mucosal (including sublingual, buccal, rectal, nasal, or vaginal), parenteral (including subcutaneous, intramuscular, bolus injection, intra-arterial, or intravenous), transdermal, or topical administration. Pharmaceutical compositions and dosage forms of the invention typically also comprise one or more pharmaceutically acceptable carrier, excipient, or diluent. Sterile dosage forms are also contemplated.

The term "composition" as used herein is intended to encompass a product comprising the specified ingredients (and in the specified amounts, if indicated), as well as any product which results, directly or indirectly, from combination of the specified ingredients. The term "pharmaceutically acceptable" carrier, excipient, or diluent means that the carrier, excipient, or diluent is compatible with the other ingredients of the formulation and is not deleterious to the recipient thereof. Composition formulation may improve one or more pharmacokinetic properties (e.g., oral bioavailability, membrane permeability) of a compound of the invention (herein referred to as the active ingredient).

The pharmaceutical compositions of the invention may conveniently be presented in unit dosage form and may be prepared by any of the methods well known in the art. All methods include the step of bringing the active ingredient such as a compound of any of the embodiments into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect in the subject.

In some embodiments, pharmaceutical compositions include a Formula I or Formula II compound of the invention, or a pharmaceutically acceptable salt, hydrate or stereoisomer thereof, and at least one additional therapeutic agent. Examples of additional therapeutic agents include, but are not limited to, those listed above. Such compositions may include one or more pharmaceutically acceptable carrier, excipient, or diluent.

The composition, shape, and type of dosage forms of the invention will typically vary depending on their use. For example, a dosage form used in the acute treatment of a disease or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences,* 20th ed., Mack Publishing, Easton Pa. 2000. Examples of dosage forms include, but are not limited to, tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms particularly suitable for parenteral administration to a patient; and sterile solids (e.g., crystalline or amorphous solids) that can be reconstituted to provide liquid dosage forms suitable for parenteral administration to a patient.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

Like the amounts and types of excipients, the amounts and specific types of active ingredients in a dosage form may differ depending on factors such as, but not limited to, the route by which it is to be administered to patients. However, typical dosage forms of the invention comprise a Formula I or Formula II compound of the invention, or a pharmaceutically acceptable salt, hydrate, or stereoisomer thereof in an amount of from 0.1 mg to 1500 mg per unit to provide doses of about 0.01 to 200 mg/kg per day.

The invention further provides the use of a compound of Formula I or Formula II or any of the embodiments thereof, or a pharmaceutically acceptable salt, hydrate, or stereoisomer thereof, in the preparation of a pharmaceutical composition or medicament. In some embodiments, the composition or medicament may be used to treat a disease mediated by a kinase such as PKB. In some embodiments, the disease is mediated by PKBα. In some embodiments, the disease is cancer and in some such embodiments, the cancer is a solid tumor.

1.4 Methods of Treatment and Prevention of Disease States

The compounds of the invention may be used to treat or prevent various kinase-related disorders. Thus, the present invention provides methods for treating or preventing such disorders. In some embodiments, the invention provides a method for treating a kinase-mediated disorder in a subject that includes administering a therapeutically effective amount of a compound of any of the embodiments of the invention or a pharmaceutical composition to the subject. In some embodiments, the subject is a mammal, and in some such embodiments is a human. In some embodiments the disorder is mediated by IGF-1R, Insulin Receptor, KDR, Tie2, EGFR, PKA, PKB, PKC, FKHR, TSC1/2, SGK, LCK, BTK, Erk, MSK, MK2, MSK, p38, P70S6K, PIM1, PIM2, ROCK2, GSK3, or a CDK complex. In some such embodiments, the disorder is mediated by PKB. In some such embodiments, the administration of the compound or pharmaceutical composition produces selective inhibition of PKB, and in some cases PKBα, in the subject after administration. In some embodiments, the disorder is cancer. The present invention thus provides methods for treating or preventing PKB-mediated disease states, such as cancer. In some embodiments, the cancer is a tumor such as a solid tumor.

The compounds of the invention may also be used to treat proliferation-related disorders. Thus, the invention further provides methods for treating such proliferation-related disorders in a subject. Such methods include administering to a subject in need thereof a therapeutically effective amount of the compound or pharmaceutical composition of any of the embodiments. In some embodiments, the subject is a mammal. In some such embodiments, the mammal is a human. In some embodiments, the proliferation-related disorder is abnormal cell growth. In other embodiments, the disorder is inflammation or an inflammation-related disorder. In still other embodiments, the disorder is a metabolic disease such as diabetes. In still other embodiments, the disorder is cancer. In some such embodiments, the cancer is a solid tumor.

The magnitude of a prophylactic or therapeutic dose of a Formula I or Formula II compound of the invention or a pharmaceutically acceptable salt, solvate, hydrate, or stereoisomer thereof in the acute or chronic treatment or prevention of a cancer or other disease or condition will vary with the nature and aggressiveness of the condition, and the route by which the active ingredient is administered. The dose, and in some cases the dose frequency, will also vary according to the condition to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. In general, the dose per day is in the range of from about 0.001 to 100 mg/kg, preferably about 1 to 25 mg/kg, more preferably about 1 to about 5 mg/kg. For treatment of humans having a cancer, about 0.1 mg to about 15 g per day is administered in about one to four divisions a day, preferably 10 mg to 12 g per day, more preferably from 40 mg to 500 mg per day. In one embodiment the compounds of the invention are administered from 40 mg to 500 mg per day in about one to four divisions a day. Additionally, the recommended daily dose can be administered in cycles as single agents or in combination with other therapeutic agents. In one embodiment, the daily dose is administered in a single dose or in equally divided doses. In a related embodiment, the recommended daily dose can be administered one time per week, two times per week, three times per week, four times per week or five times per week.

The compounds of the invention can be administered to provide systemic distribution of the compound within the patient. Therefore, in some embodiments, the compounds of the invention are administered to produce a systemic effect in the body.

The compounds of the invention may also be administered directly to a site affected by a condition, as, for example, an in the treatment of an accessible area of skin or an esophageal cancer.

As indicated above, the compounds of the invention may be administered via oral, mucosal (including sublingual, buccal, rectal, nasal, or vaginal), parenteral (including subcutaneous, intramuscular, bolus injection, intra-arterial, or intravenous), transdermal, or topical administration. In some embodiments, the compounds of the invention are administered via mucosal (including sublingual, buccal, rectal, nasal, or vaginal), parenteral (including subcutaneous, intramuscular, bolus injection, intra-arterial, or intravenous), transdermal, or topical administration. In other embodiments, the compounds of the invention are administered via oral administration. In still other embodiments, the compounds of the invention are not administered via oral administration.

Different therapeutically effective amounts may be applicable for different conditions, as will be readily known by those of ordinary skill in the art. Similarly, amounts sufficient to treat or prevent such conditions, but insufficient to cause, or sufficient to reduce, adverse effects associated with conventional therapies are also encompassed by the above described dosage amounts and dose frequency schedules.

Some methods of the invention comprise the administration of a compound of the invention and an additional therapeutic agent (i.e., a therapeutic agent other than a compound of the invention). Thus, the compounds of the invention can be used in combination with at least one other therapeutic agent. Examples of additional therapeutic agents include, but are not limited to, antibiotics, anti-emetic agents, antidepressants, antifungal agents, anti-inflammatory agents, antineoplastic agents, antiviral agents, cytotoxic agents, and other anticancer agents, immunomodulatory agents, alpha-interferons, β-interferons, alkylating agents, hormones, and cytokines. In one embodiment, the invention encompasses administration of an additional therapeutic agent that demonstrates anti-cancer activity. In another embodiment, an additional therapeutic agent that demonstrates cytotoxic activity is administered to a subject such as a cancer patient.

The compounds of the invention and the other therapeutics agent can act additively or, preferably, synergistically. In some embodiments, a composition comprising a compound of the invention is administered concurrently with the administration of another therapeutic agent, which can be part of the same composition or can be in a different composition from the one that comprises the compound of the invention. In other embodiments, a compound of the invention is administered prior to, or subsequent to, administration of another therapeutic agent. In still other embodiments, a compound of the invention is administered to a patient who has not previously undergone or is not currently undergoing treatment with another therapeutic agent. A compound of the invention may be administered to a subject that has had, is currently undergoing, or is scheduled to receive radiation therapy. In some such embodiments, the subject is a cancer patient.

When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent. Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I or Formula II may also be administered sequentially with known anticancer or cytotoxic agents when a combination formulation is inappropriate. The invention is not limited in the sequence of administration as compounds of the invention may be administered either prior to, simultaneous with, or after administration of a known anticancer or cytotoxic agent.

There are large numbers of antineoplastic agents available in commercial use, in clinical evaluation and in pre-clinical development, which may be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from, but are not limited to, the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT, and uricytin.

A second family of antineoplastic agents which may be used in combination with compounds of the present invention consists of alkylating-type antineoplastic agents. Suitable alkylating-type antineoplastic agents may be selected from, but are not limited to, the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, and trimelamol.

A third family of antineoplastic agents which may be used in combination with compounds of the present invention consists of antibiotic-type antineoplastic agents. Suitable antibiotic-type antineoplastic agents may be selected from, but are not limited to, the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024, and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from, but not limited to, the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemin-B, dihaematoporphirin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US)MAP, marycin, Merrel Dow MDL-27048, Medco MEDR-340, merbarone, merocyanine derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. No. 6,630,500, U.S. Pat. No. 6,515,004, U.S. Pat. No. 6,713,485, U.S. Pat. No. 5,521,184, U.S. Pat. No. 5,770,599, U.S. Pat. No. 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProIX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT I (vascular endothelial growth factor receptor 1), (Merck & Co, USA); Tie-2 ligands, (Regeneron, USA); and, thrombospondin I inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, KDR inhibitors, EGF inhibitors and CDK inhibitors, TNF inhibitors, matrix metalloproteinases (MMP) inhibitors, COX-2 inhibitors including celecoxib, NSAID's, or $\alpha_v\beta_3$ inhibitors.

2. WORKING EXAMPLES

The compounds of Formula I and Formula II were prepared according to the following synthetic schemes and individual examples detailed herein. The compounds were named using Chemdraw Ultra, v.8.07. These schemes and examples are provided for the purpose of illustration only and are not intended to limit the scope of the invention.

Unless otherwise noted, all materials were obtained from commercial suppliers and were used without further purification. Anhydrous solvents such as DMF, THF, DCM, and toluene were obtained from the Aldrich Chemical Company. All reactions involving air- or moisture-sensitive compounds were performed under a nitrogen atmosphere. Flash chromatography was performed using Aldrich Chemical Company silica gel (200-400 mesh, 60A) or Biotage pre-packed column. Thin-layer chromatography (TLC) was performed with Analtech gel TLC plates (250 mµ.). Preparative TLC was performed with Analtech silica gel plates (1000-2000.mu.). Preparative HPLC was conducted on a Varian, Shimadzu, Beckman, or Waters HPLC system with 0.1% TFA/H$_2$O and 0.1% TFA/CH$_3$CN as mobile phase. The flow rate was at 20 mL/minute and the gradient method was used. $^1$H NMR spectra were obtained with super conducting FT NMR spectrometers operating at 400 MHz or a Varian 300 MHz instrument. Chemical shifts are expressed in ppm downfield from the tetramethylsilane internal standard. All compounds showed NMR spectra consistent with their assigned structures. Mass spectra (MS) were obtained using a Perkin Elmer-SCIEX API 165 electrospray mass spectrometer (positive and/or negative) or an HP 1100 MSD LC-MS with electrospray ionization and quadrupole detection. All parts are by weight and temperatures are in degrees centigrade unless otherwise indicated.

The following abbreviations are used: AcOH (acetic acid), ATP (adenosine triphosphate), Boc (tert-butyloxycarbonyl), Boc$_2$O (Boc anhydride), Br$_2$ (bromine), t-BuOH (tert-butanol), CH$_3$CN or ACN (acetonitrile), MeI (iodomethane or methyl iodide), CCl$_4$ (carbon tetrachloride), CHCl$_3$ (chloroform), CDCl$_3$ (deuterated chloroform), CD$_3$OD (d$_4$-methanol), CO$_2$ (carbon dioxide), Cs$_2$CO$_3$ (cesium carbonate), DIAD (diisopropyl azodicarboxylate), CuI (copper iodide), DCM (dichloromethane), dppf (1,1-diphenylphosphinoferrocene), DMAP (4-(dimethylamino)pyridine), DMF (dimethylformamide), DMSO (dimethylsulfoxide), EDC 1-(3-dimethylaminopropyl)-3 (ethylcarbodiimide hydrochloride), EtOAc (ethyl acetate), EtOH (ethanol), Et$_2$O (diethyl ether), Fe (iron), g (gram), h (hour), H$_2$ (hydrogen), H$_2$O (water), HCl (hydrochloric acid), H$_2$SO$_4$ (sulfuric acid), K$_2$CO$_3$ (potassium carbonate), KOAc (potassium acetate), KOH (potassium hydroxide), LAH (lithium aluminum hydride), LCMS (liquid chromatography mass spectrometry), LiCl (lithium chloride), MeOH (methanol), MgSO$_4$ (magnesium sulfate), mg (milligram), min (minute), mL (milliliter), NBS (N-bromosuccinimide), NMP (N-methylpyrrolidone), Na$_2$SO$_4$ (sodium sulfate), NaHCO$_3$ (sodium bicarbonate), Na$_2$CO$_3$ (sodium carbonate), NaCl (sodium chloride), NaH (sodium hydride), NaHMDS (sodium hexamethylsilazane), NaOH (sodium hydroxide), NaBH$_4$ (sodium borohydride), NH$_4$Cl (ammonium chloride), Pd/C (palladium on carbon), PdCl$_2$(PPh$_3$)$_2$ (palladium chloride bis(triphenylphosphine)), Pd$_2$(dba)$_3$ (palladium dibenzylideneacetone), PdCl$_2$(dppf) (1,1-bis(diphenylphosphino)ferrocene, palladium chloride), Pd(PPh$_3$)$_4$ (palladium tetrakis triphenylphosphine), Pd(OH)$_2$ (palladium hydroxide), Pd(OAc)$_2$ (palladium acetate), PMB (para methoxybenzyl), PPh$_3$ (triphenylphosphine), RT (room temperature), SiO$_2$ (silica), SOCl$_2$ (thionyl chloride), TEA (triethylamine), TFA (trifluoroacetic acid), THF (tetrahydrofuran), and Zn (zinc).

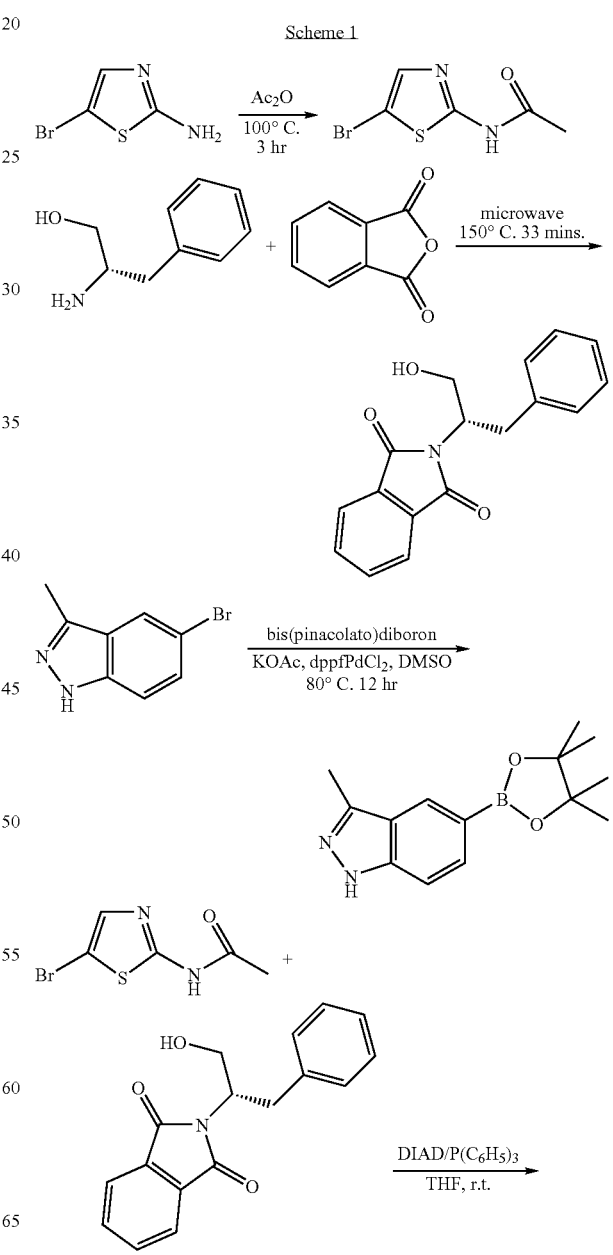

Scheme 1

-continued

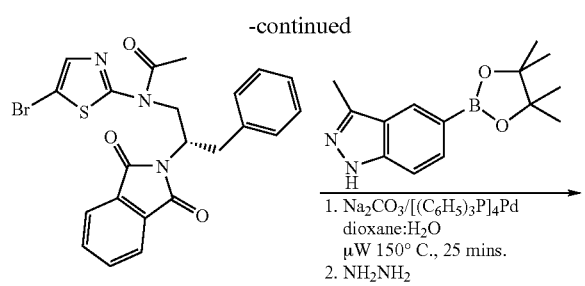

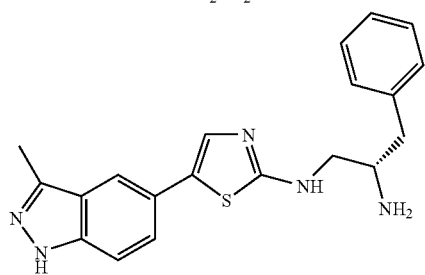

Example 1

N-((S)-2-amino-3-phenylpropyl)-5-(3-methyl-1H-indazol-5-yl)thiazol-2-amine

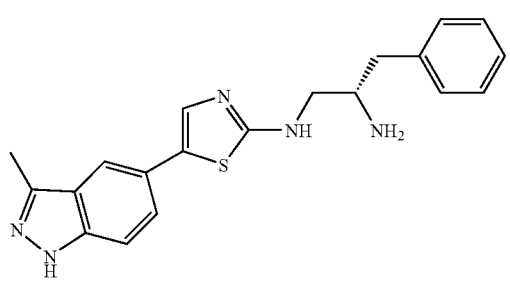

As shown in Scheme 1, Example 1 was synthesized starting with commercially available 5-bromothiazol-2-amine and (S)-2-amino-3-phenylpropan-1-ol. HRMS Theoretical (M+H) 364.15904, found 364.15915.

N-(5-bromothiazol-2-yl)acetamide

5-Bromothiazol-2-amine (6.0 g, 23 mmol) and acetic anhydride (50 g, 490 mmol) were charged into a 250 mL round bottom flask. The suspension in the flask was heated to 100° C. After stirring for 3 hours, the reaction mixture was cooled and filtered to yield the crude product. The crude product was charged into a round bottom flask, 50 mL MeOH was added, and the mixture was heated to reflux. The mixture was cooled, and the product N-(5-bromothiazol-2-yl)acetamide (4.5 g, 93%) was obtained by filtration. The collected product was then washed with hexane. The product was used directly in the next step without further purification. LCMS (API-ES) m/z (%): 221.0 (100%, M$^+$+H).

(S)-2-(1-hydroxy-3-phenylpropan-2-yl)isoindoline-1,3-dione

Isobenzofuran-1,3-dione (4.40 g, 29.76 mmol) and (S)-2-amino-3-phenylpropan-1-ol (4.50 g, 29.76 mmol) were charged into a 20 mL microwave tube along with 10 mL dioxane. The microwave tube was heated at 150° C. for 33 minutes in a Smith Synthesizer. After the reaction was complete, dioxane was evaporated off and the residue was passed through a short pad of silica gel with DCM. The resulting product (7.50 g, 89%) was used in the following step. LCMS (API-ES) m/z (%): 282.2 (100%, M$^+$+H).

(S)-N-(5-bromothiazol-2-yl)-N-(2-(1,3-dioxoisoindolin-2-yl)-3-phenylpropyl)acetamide N-(5-Bromo-thiazol-2-yl)-acetamide) (442.0 mg, 2.0 mmol), (S)-2-(1-hydroxy-3-phenylpropan-2-yl)isoindoline-1,3-dione (281.0 mg, 1.0 mmol), triphenylphosphine (303.0 mg, 1.5 mmol) and THF (15.0 mL) were charged into a 100 mL round bottom flask. The resulting reaction mixture was a suspension. The flask was immersed in an ice-water bath. After stirring for 15 minutes under nitrogen, a solution of DIAD (421.5 mg, 1.5 mmol) in 3.0 mL THF was slowly added to the flask through a syringe. The reaction mixture became a clear solution after the addition was complete. After 10 minutes, the reaction mixture was brought to room temperature by removing the ice water bath and the stirring was continued for 16 hours. THF was evaporated off, and the residue was diluted with 40 mL saturated sodium bicarbonate and extracted with DCM (75 mL×2). The residue was subjected to a silica gel column chromatography purification with hexane-EtOAc (7:3) as the eluant to afford a compound as a white solid (S)-N-(5-bromothiazol-2-yl)-N-(2-(1,3-dioxoisoindolin-2-yl)-3-phenylpropyl)acetamide (20 mg, yield 17%). LCMS (API-ES) m/z (%): 484.0 (100%, M$^+$+H).

3-Methyl-5-(4,4,5,5-tetramethyl-1,3,2-dioxaborolan-2-yl)-1H-indazole

5-Bromo-3-methyl-1H-indazole (13.24 g, 62.75 mmol), bis(pinacolato)diboron (16.74 g, 65.89 mmol), potassium acetate (18.5 g, 188.25 mmol) and anhydrous 240 mL DMSO were charged into a 500 mL round bottom flask. After degassing the resulting reaction mixture with nitrogen for 15 minutes, 1, 1-[Bis(diphenylphosphino)ferrocene]-dichloropalladium(II) (2.56 g, 3.14 mmol) was added. The reaction was then heated to 86° C. under nitrogen. After stirring for 20 hours, the black reaction mixture was cooled to room temperature and slowly poured into 1.2 L of diethyl ether. The resulting mixture was transferred to a 2 L separation funnel, and the lower layer was discarded. The upper layer was washed with 1.0 M magnesium sulfate (500 mL×2) and brine solution, dried over sodium sulfate, and concentrated to dryness. The residue was subjected to a silica gel column chromatography purification with hexane-EtOAc (4:1) as the eluant to afford the desired compound 3-methyl-5-(4,4,5,5-tetramethyl-1,3,2-dioxaborolan-2-yl)-1H-indazole (10.0 g, 61.7%) as a colorless solid. LCMS (API-ES) m/z (%): 259.2 (100%, M$^+$+H).

N-((S)-2-amino-3-phenylpropyl)-5-(3-methyl-1H-indazol-5-yl)thiazol-2-amine

To a solution of 1.0 mL dioxane, 0.5 mL distilled water and sodium carbonate (35.0 mg, 0.33 mmol) in a 5 mL microwave tube, were added 3-methyl-5-(4,4,5,5-tetramethyl-1,3,2-dioxaborolan-2-yl)-1H-indazole (32.0 mg, 0.124 mmol) and (S)-N-(5-bromothiazol-2-yl)-N-(2-(1,3-dioxoisoindolin-2-yl)-3-phenylpropyl)acetamide (40.0 mg, 0.0826 mmol). The reaction mixture was degassed by bubbling nitrogen into the microwave tube for 30 seconds. Subsequently, tetrakis(triphenylphosphine)palladium(0) (10.0 mg, 0.0083 mmol) was added to the tube, and the mixture was heated at 150° C. in a Smith microwave synthesizer. After heating for 25 minutes, the reaction mixture was filtered through a pad of Celite and washed with MeOH. The filtrate was evaporated off, and the resulting residue was diluted with 1.5 mL MeOH, 1.5 mL water, and 1.5 mL hydrazine. The resulting mixture was transferred to a 5 mL microwave tube and heated at 150° C. After heating for 33 minutes, silica gel (10.0 g) was added to the reaction mixture, and the mixture was concentrated to dryness. The resulting solid was directly loaded on a silica gel column and chromatography separation was performed with DCM:MeOH (97:3) as the eluant to afford the desired compound N-((S)-2-amino-3-phenylpropyl)-5-(3-methyl-1H-indazol-5-yl)thiazol-2-amine as a colorless solid (8.0 mg, 26.6%). HRMS Theoretical (M+H) 364.15904, found 364.15915.

Examples 2-3

Examples 2-3 were synthesized in a manner similar to that shown in Scheme 1.

Example 2

N-((S)-2-amino-3-(1H-indol-3-yl)propyl)-5-(3-methyl-1H-indazol-5-yl)thiazol-2-amine HRMS Theoretical (M+H) 403.16994, found 403.16939.

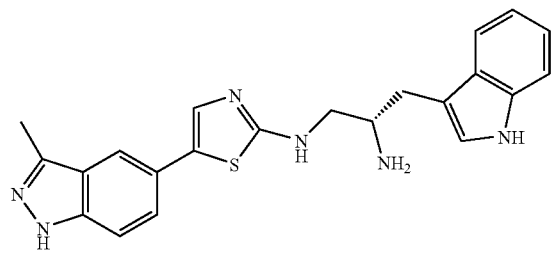

Example 3

N-((S)-2-amino-3-(4-chlorophenyl)propyl)-5-(3-methyl-1H-indazol-5-yl)thiazol-2-amine HRMS Theoretical (M+H) 398.12007, found 398.11981.

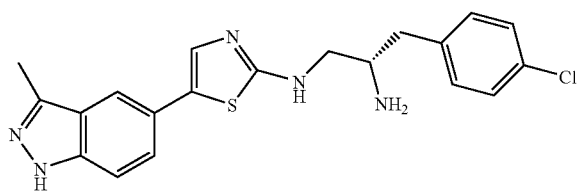

Example 4

N-((S)-2-amino-3-(4-chlorophenyl)propyl)-5-(1H-indazol-5-yl)thiazol-2-amine

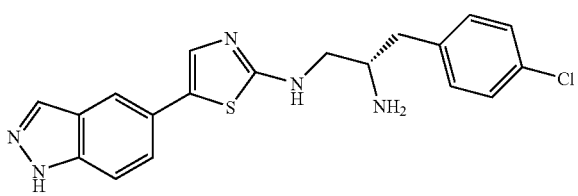

This compound was prepared in a manner similar to that shown in Scheme 1 using 5-(4,4,5,5-tetramethyl-1,3,2-dioxaborolan-2-yl)-1H-indazole to couple with the corresponding thiazole bromide. HRMS Theoretical (M+H) 384.10449, found 384.10449.

Examples 5-6

Examples 5-6 were synthesized in a manner similar to that shown in Scheme 1 using isoquinolin-6-ylboronic acid to couple with the corresponding amino thiazole bromide. Isoquinolin-6-ylboronic acid was prepared as shown in Scheme 2.

Scheme 2

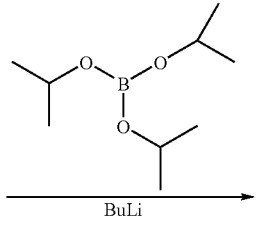

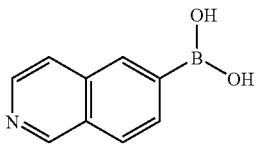

Isoquinolin-6-ylboronic acid

A flame-dried 100 mL round bottom flask was charged with 10 mL THF, triisopropyl borate (1 g, 5.8 mmol) and 6-bromoisoquinoline (1 g, 4.8 mmol). The mixture was cooled to −78° C., and butyllithium (3.6 mL, 5.8 mmol) was added dropwise to the reaction over about 1 hour. The mixture was stirred for 0.5 hours at −78° C. and then warmed to −20° C. After 5.0 mL 2.0 N HCl was added to the reaction mixture, it was concentrated under reduced pressure in a rotary evaporator until a precipitate formed. The white solid (0.6 g) HCl salt of isoquinolin-6-ylboronic acid was obtained by filtration. The product was used directly in the next step. LCMS (API-ES) m/z (%): 174 (100%, M+H).

Example 5

N-((S)-2-amino-3-(1H-indol-3-yl)propyl)-5-(isoquinolin-6-yl)thiazol-2-amine

LCMS (M+H$^+$) 400.2, calculation: 400.15.

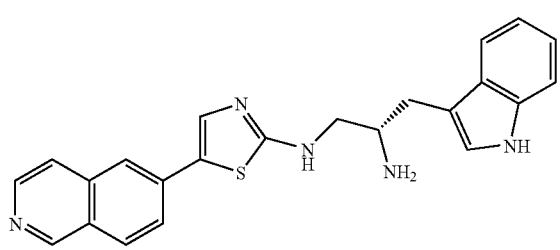

Example 6

N-((S)-2-amino-3-(4-(trifluoromethyl)phenyl)propyl)-5-(isoquinolin-6-yl)thiazol-2-amine HRMS Theoretical (M+H$^+$) 429.13553, found 429.13594.

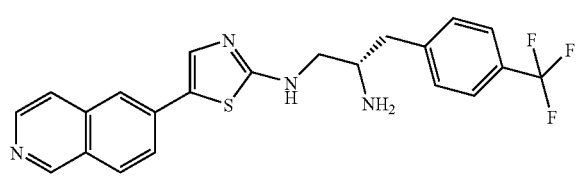

Examples 7-10

Examples 7-10 were synthesized using a procedure similar to that shown in Scheme 1 with a coupling reaction between the corresponding bromothiazole intermediate and the boronic acid or esters. The 4-substituted 2-aminothiazoles were prepared by treating the commercially available 2-bromo-ketones with thiourea as shown in a similar manner in Scheme 3.

Example 7

N-((S)-2-amino-3-phenylpropyl)-4-methyl-5-(3-methyl-1H-indazol-5-yl)thiazol-2-amine HRMS Theoretical (M+H) 378.17469, found 378.17453.

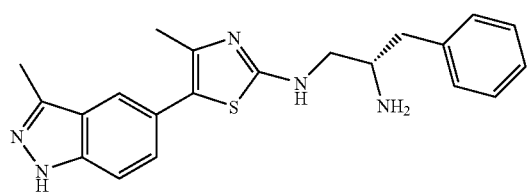

Example 8

N-((S)-2-amino-3-(4-(trifluoromethyl)phenyl)propyl)-4-(furan-2-yl)-5-(isoquinolin-6-yl)thiazol-2-amine HRMS Theoretical (M+H) 495.14609, found 495.14677.

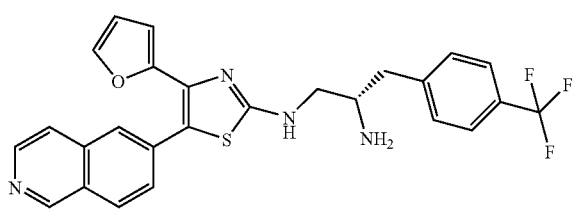

Example 9

N-((S)-2-amino-3-(4-(trifluoromethyl)phenyl)propyl)-5-(isoquinolin-6-yl)-4-phenylthiazol-2-amine HRMS Theoretical (M+H) 505.16683, found 505.16754.

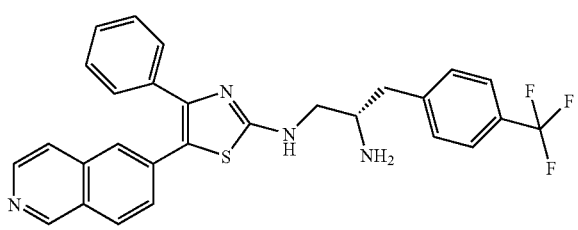

Examples 10-12

Examples 10-12 were synthesized using a procedure similar to that shown in Scheme 1 with a coupling reaction between the corresponding bromothiazole intermediate and the boronic acid or esters. The 4-hydroxymethyl-2-aminothiazole intermediate was prepared as shown in Scheme 3.

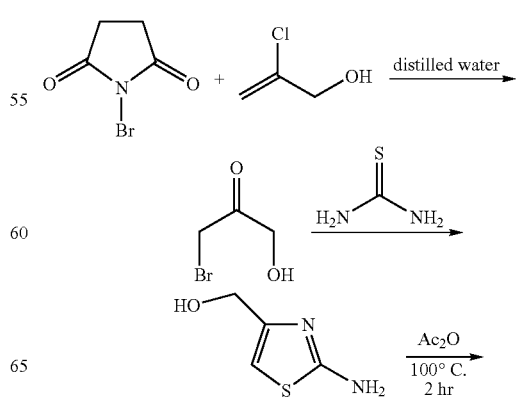

Scheme 3

-continued

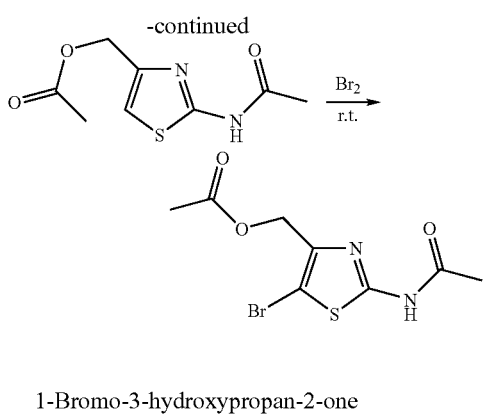

1-Bromo-3-hydroxypropan-2-one

2-Chloroprop-2-en-1-ol (75 g, 811 mmol) and 100 mL distilled water were charged into a 2 L round bottom flask. 1-bromopyrrolidine-2,5-dione (69 mL, 811 mmol) was added in portions along with more distilled water. The total volume of distilled water used was 800 mL. The reaction was complete after stirring at 20° C. for two hours. The reaction mixture was extracted by ether, washed with brine solution once, and dried over sodium sulfate. The crude product was obtained as an oil after the solvent was removed. It was used directly in the next step.

(2-Aminothiazol-4-yl)methanol

1-Bromo-3-hydroxypropan-2-one (60 g, 392 mmol) and thiourea (34 g, 451 mmol) were charged into a 1 L round bottom flask containing 400 mL of EtOH. The resulting mixture was heated to reflux for 90 minutes. The reaction mixture was then cooled and concentrated under reduced pressure, and a precipitate formed. The product was obtained as a solid (40 g, yield=80%) after filtration and washing three times with hexane. The product was used directly in the next step without further purification. LCMS (API-ES) m/z (%) 131.2 (100%, M$^+$+H).

(2-Acetamidothiazol-4-yl)methyl acelate

2-Aminothiazol-4-yl-methanol (17 g, 131 mmol) and acetic anhydride (927 g, 261 mmol) were mixed in 100 mL dioxane in a 500 mL round bottom flask. The mixture was heated at reflux for 1 hour. After the solvent was evaporated, 300 mL saturated sodium bicarbonate was added to the flask. The mixture was extracted twice with 200 mL EtOAc. The combined organic layers were washed with brine and dried over sodium sulfate. After evaporating the solvent, the remaining residue was washed with hexane and ether three times each. This procedure provided 10 g of (2-acetamidothiazol-4-yl)methyl acetate (yield=30%). LCMS (API-ES) m/z (%) 215.2 (100%, M$^+$+H).

(2-Acetamido-5-bromothiazol-4-yl)methyl acetate (2-Acetamidothiazol-4-yl)methyl acetate (9.00 g, 42 mmol) was dissolved in 30 mL AcOH. A mixture of Br$_2$ (9.0 g, 56.7 mmol) in 20 mL AcOH was added dropwise to the (2-acetamidothiazol-4-yl)methyl acetate/AcOH mixture. The reaction was complete in 10 minutes. After 200 mL distilled water was added to the reaction mixture, the mixture was extracted with EtOAc. The organic layer was washed a few times with water and saturated sodium bicarbonate. The organic layer was then washed with brine solution and dried over sodium sulfate. Evaporation of the solvent provided the product as a yellow solid (10 g, yield=80%). LCMS (API-ES) m/z (%) 293.2 (100%, M$^+$+H).

Example 10

(2-((S)-2-amino-3-(4-(trifluoromethyl)phenyl)propylamino)-5-(isoquinolin-6-yl)thiazol-4-yl)methanol HRMS Theoretical (M+H) 459.14609, found 459.14670.

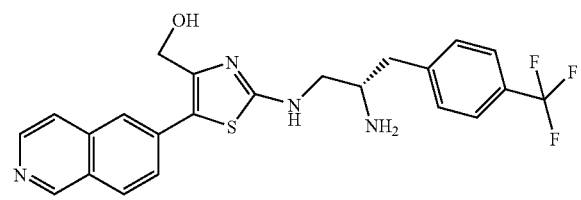

Example 11

(2-((S)-2-amino-3-(4-(trifluoromethyl)phenyl)propylamino)-5-(3-methyl-1H-indazol-5-yl)thiazol-4-yl)methanol HRMS Theoretical (M+H) 462.15699, found 462.15753.

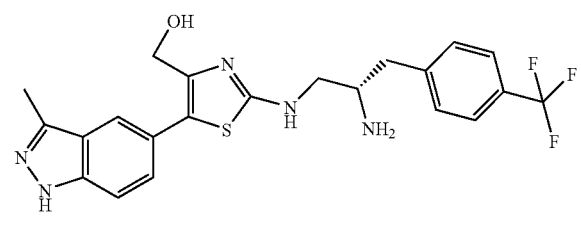

Example 12

(2-((S)-2-amino-3-(4-(trifluoromethyl)phenyl)propylamino)-5-(1H-indazol-5-yl)thiazol-4-yl)methanol HRMS Theoretical (M+H) 448.14134, found 448.14205.

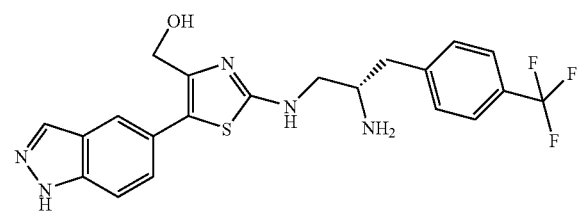

Examples 13-15

Examples 13-15 were synthesized using a procedure similar to that shown in Scheme 1 using a coupling reaction between the corresponding bromothiazole intermediate and the boronic acid or esters. The 4-methoxylmethyl-2-aminothiazole intermediate was prepared as shown in Scheme 4.

Scheme 4

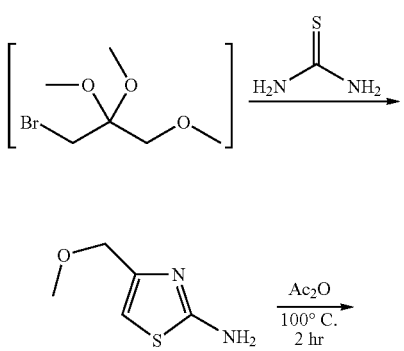

4-(Methoxymethyl)thiazol-2-amine

1-Methoxypropan-2-one (40 g, 454 mmol) was dissolved in 300 mL of anhydrous MeOH in a 1 L round bottom flask. The flask was cooled in an ice-water bath. Br$_2$ (73 g, 454 mmol) was added to the flask dropwise through an addition funnel. After the addition, an additional 50 mL MeOH was added to the mixture. After stirring for 20 minutes, the ice water bath was removed and the reaction was stirred until the brown color disappeared. Thiourea (34.6 g, 454 mmol) was then added into the flask. The reaction mixture was then heated at reflux for 2 hours. The reaction mixture was then cooled and the solvent was evaporated. Saturated sodium bicarbonate was then added into the reaction flask. The resulting mixture was extracted twice with EtOAc, and the combined organic layers were washed with brine and dried over sodium sulfate. After removing the solvent, the crude 4-(methoxymethyl)thiazol-2-amine was obtained. LCMS (API-ES) m/z (%) 145.2 (100%, M$^+$+H).

N-(4-(methoxymethyl)thiazol-2-yl)acetamide

This compound was made using the same procedure as that used in preparing (2-acetamidothiazol-4-yl)methyl acetate.

N-(5-bromo-4-(methoxymethyl)thiazol-2-yl)acetamide

This compound was made using the same procedure as that used in preparing (2-acetamido-5-bromothiazol-4-yl)methyl acetate.

Example 13

N-((S)-2-amino-3-(4-(trifluoromethyl)phenyl)propyl)-5-(isoquinolin-6-yl)-4-(methoxymethyl)thiazol-2-amine HRMS Theoretical (M+H) 473.16174, found 473.16147.

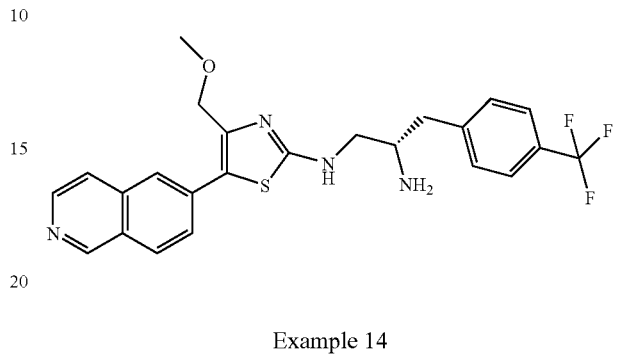

Example 14

N-((S)-2-amino-3-(4-(trifluoromethyl)phenyl)propyl)-5-(1H-indazol-5-yl)-4-(methoxymethyl)thiazol-2-amine HRMS Theoretical (M+H) 462.15699, found 462.15711.

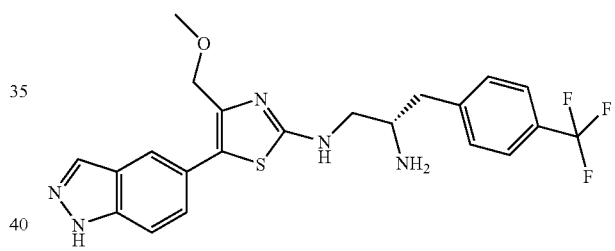

Example 15

N-((S)-2-amino-3-(4-(trifluoromethyl)phenyl)propyl)-4-(methoxymethyl)-5-(3-methyl-1H-indazol-5-yl)thiazol-2-amine HRMS Theoretical (M+H) 476.17264, found 476.17384.

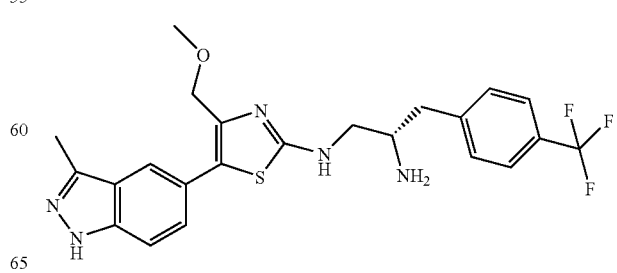

Example 16

N-((S)-2-amino-3-(4-(trifluoromethyl)phenyl)propyl)-5-(isoquinolin-6-yl)-4-(1-methoxyethyl)thiazol-2-amine LCMS Theoretical (M+H) 486.17, found 486.20.

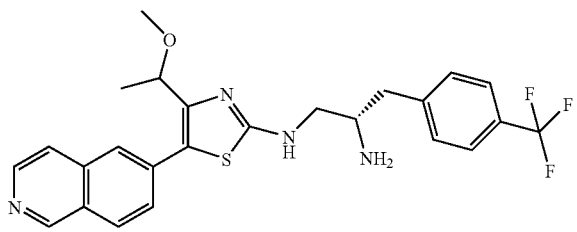

This compound was synthesized using a procedure similar to that shown in Scheme 1 with a coupling reaction between the corresponding bromothiazole intermediate and the boronic acid or esters. The 4-(1-methoxyethyl)-2-aminothiazole intermediate was prepared as shown in Scheme 5.

Scheme 5

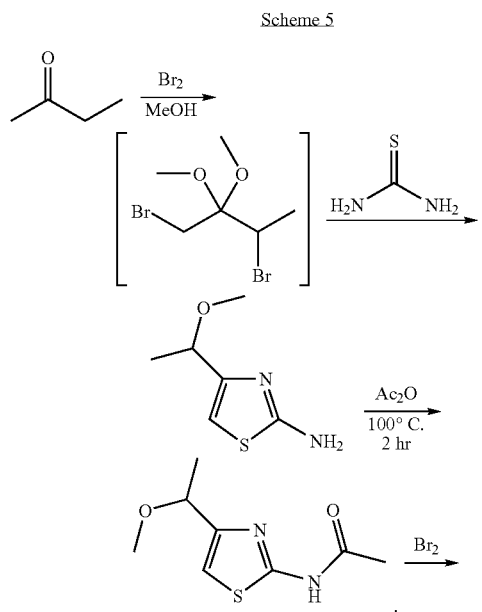

4-(1-Methoxyethyl)thiazol-2-amine

Butan-2-one (20 g, 277 mmol) and 200 mL MeOH were charged into a 1 L round bottom flask. A small amount of $Br_2$ (5 mL) was added to the flask to initiate the reaction. The reaction initiated, and the mixture was stirred at 20° C. until the orange color disappeared. The reaction flask was immersed in an ice-water bath and $Br_2$ was slowly added through an addition funnel. A total of 6 to 8 g (554 mmol) of $Br_2$ was added. Thiourea (21 g, 278 mmol) was then added in portions to the reaction flask. After addition, the reaction mixture was heated at reflux for 2 hours. After the solvent was evaporated, the remaining residue was mixed with saturated sodium bicarbonate. The resulting mixture was extracted with EtOAc, and the combined organic layers were washed with brine and dried over sodium sulfate. The product 4-(1-methoxyethyl)-thiazol-2-amine (22 g, yield=50%) was obtained and used in the next step without further purification. LCMS (API-ES) m/z (%) 159.2 (100%, $M^++H$).

N-(4-(1-methoxyethyl)thiazol-2-yl)acetamide

This compound was made using the same procedure used in preparing (2-acetamidothiazol-4-yl)methyl acetate.

N-(5-bromo-4-(1-methoxyethyl)thiazol-2-yl)acetamide

This compound was made using the same procedure used in preparing (2-acetamido-5-bromothiazol-4-yl)methyl acetate.

Example 17

N-((S)-2-amino-3-(3-chlorophenyl)propyl)-N-(4-(methoxymethyl)-5-(thiazolo[5,4-c]pyridin-2-yl)thiazol-2-yl)acetamide

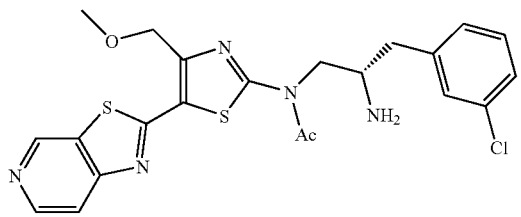

Example 17 was synthesized as shown in Scheme 6.

Scheme 6

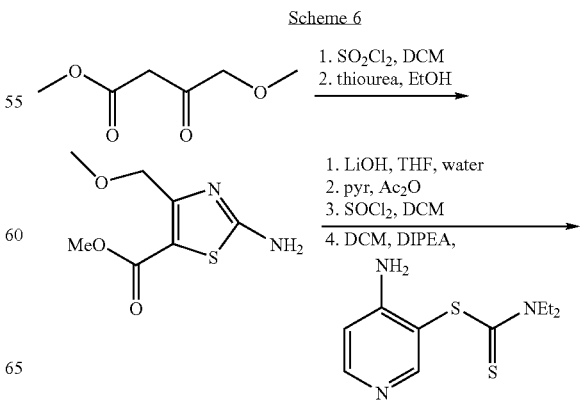

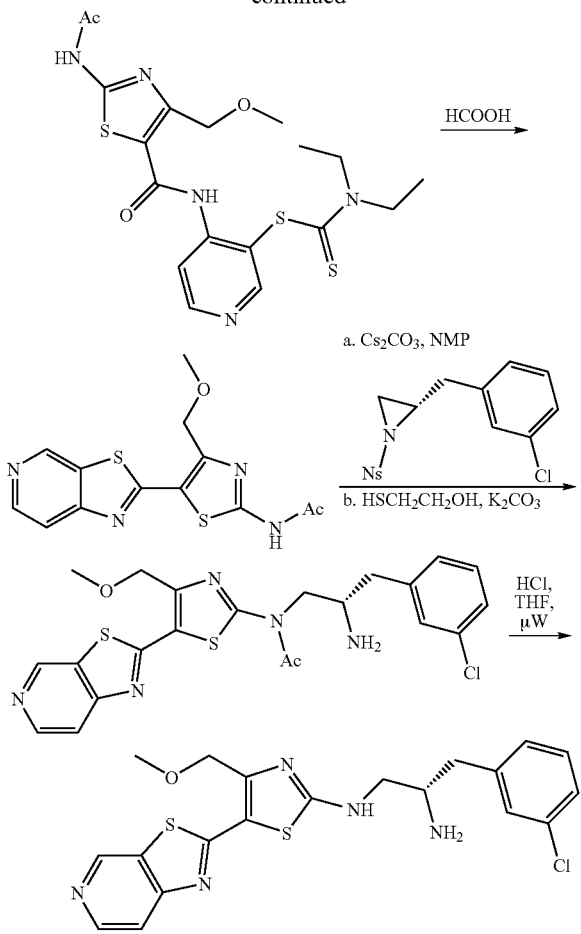

Methyl 2-amino-4-(methoxymethyl)thiazole-5-carboxylate

To a 100 mL round-bottomed flask was added methyl 4-methoxy-3-oxobutanoate (4.43 mL, 34.2 mmol) and DCM (30.00 mL). Sulfuryl chloride (2.91 mL, 35.9 mmol) was added dropwise with a syringe to the reaction mixture. The mixture was then stirred for 1 hour at 20° C. The solution was reduced to an oil under reduced pressure and dissolved in EtOH (50 mL). To this solution was added methyl 2-chloro-4-methoxy-3-oxobutanoate (6.18 g, 34 mmol) and thiourea (1.9 mL, 34 mmol). The reaction was then stirred at reflux for approximately 12 hours. LCMS indicated that the reaction was complete, and the solvent was removed under reduced pressure. Saturated aqueous sodium bicarbonate was added, and the resulting solid was filtered and recrystallized from water and <5 mL EtOH to give methyl 2-amino-4-(methoxymethyl)thiazole-5-carboxylate as rust colored crystals (4.85 g, 68%). LCMS (M+H) 203 calc. for $C_7H_{11}N_2O_3S$ 203.2. $^1$H NMR (400 MHz, $CD_3OD$): δ ppm 4.64 (s, 2H), 3.77 (s, 3H), 3.37 (s, 3H).

4-(2-Acetamido-4-(methoxymethyl)thiazole-5-carboxamido)pyridin-3-yl diethylcarbamodithioate Methyl 2-amino-4-(methoxymethyl)thiazole-5-carboxylate (2.0 g, 9.9 mmol) and THF (75 mL, 925 mmol) were added to a 250 mL round-bottomed flask. The resulting suspension was then sonicated until clear. Water (75 mL, 9.9 mmol) and then lithium hydroxide (0.71 g, 30 mmol) were added, and the mixture was stirred at 80° C. for approximately 30 minutes. LCMS indicated that the reaction was complete, and the solvent was removed under reduced pressure. The resulting residue was dissolved in pyridine (75.00 mL, 0.9273 mol). Acetic anhydride (1.026 mL, 0.01088 mol) was added to the pyridine solution, and the mixture was stirred at reflux for approximately 2 hours until LCMS showed that the reaction was complete. The mixture was concentrated under reduced pressure to provide crude 2-acetamido-4-(methoxymethyl)thiazole-5-carboxylic acid which was then taken up in DCM (200 mL). Thionyl chloride (2.164 mL, 29.67 mmol) was then added, and the mixture was stirred at reflux for approximately 2 hours. The reaction was followed by LCMS, (aliquots were removed and quenched with MeOH). Once the reaction was complete, the solvents were removed under reduced pressure and the crude product 2-acetamido-4-(methoxymethyl)thiazole-5-carbonyl chloride was taken up in DCM (50.00 mL). A DCM suspension of 4-aminopyridin-3-yl diethylcarbamodithioate (1.9 g, 7.9 mmol) and DIPEA (6.9 mL, 40 mmol) were added, and the suspension was stirred for 1 hour until LCMS indicated that the reaction was complete. The solvent was reduced, and the resulting oil was passed through a plug of silica gel, and washed with approximately 700 mL of 10% MeOH in DCM to give crude 4-(2-acetamido-4-(methoxymethyl)thiazole-5-carboxamido)pyridin-3-yl diethylcarbamodithioate (4.4 g, 9.7 mmol, 98% yield), which was used in the next step without further purification. LCMS (M+H) 454 calc. for $C_{18}H_{24}N_5O_3S_3$ 454.6.

N-(4-(methoxymethyl)-5-(thiazolo[5,4-c]pyridin-2-yl)thiazol-2-yl)acetamide

Crude 4-(2-acetamido-4-(methoxymethyl)thiazole-5-carboxamido)pyridin-3-yl diethylcarbamodithioate (4.485 g, 9.89 mmol) and formic acid (0.379 mL, 9.89 mmol) were added to a 150 mL round-bottomed flask, and the solution was stirred at reflux for approximately 24 hours until LCMS indicated that the reaction was complete. The formic acid was removed, and the reaction was quenched by addition of 1 N NaOH. No precipitate formed, and the solution was made neutral with HCl and extracted with EtOAc (5×75 mL) to provide crude product. The organic solution was adsorbed onto a plug of silica gel and chromatographed through a Redi-Sep® pre-packed silica gel column (40 g), eluting with a gradient of 2% to 10% 2 M $NH_3$.MeOH in DCM, to provide N-(4-(methoxymethyl)-5-(thiazolo[5,4-c]pyridin-2-yl)thiazol-2-yl)acetamide (0.446 g, 1.39 mmol, 14.1% yield). LCMS (M+H) 321.1 calc. for $C_{13}H_{13}N_4O_2S_2$ 321.39, $^1$H NMR (400 MHz, $CD_3OD$): δ ppm 9.42 (s, 1H), 8.61 (d, J=6.5 Hz, 1H), 8.18 (d, J=6.5 Hz, 1H), 4.82 (s, 2H), 3.51 (s, 3H), 2.27 (s, 3H).

Example 17

N-((S)-2-amino-3-(3-chlorophenyl)propyl)-N-(4-(methoxymethyl)-5-(thiazolo[5,4-c]pyridin-2-yl)thiazol-2-yl)acetamide N-(4-(methoxymethyl)-5-(thiazolo[5,4-c]pyridin-2-yl)thiazol-2-yl)acetamide (0.120 g, 0.375 mmol), $Cs_2CO_3$ (0.244 g, 0.749 mmol), and DMF (0.0289 mL, 0.375 mmol) were added to a 50 mL round-bottomed flask. The mixture was stirred at 50° C., and a DMF solution of (S)-2-(3-chlorobenzyl)-1-(4-nitrophenylsulfonyl)aziridine (0.264 g, 0.749 mmol) was added dropwise using an addition funnel. The reaction was stirred for 1 hour, and LCMS indicated very little remaining starting material. $K_2CO_3$ (0.259 g, 1.87 mmol) and 2-mercaptoethanol (0.293 g, 3.75 mmol) were added to the reaction mixture, and the reaction was stirred again for approximately 1 hour at 25° C. The color slowly changed from dark red-brown to a more clear orange and LCMS indicated that the nosyl group had been removed. The majority of the DMF was removed under reduced pressure, and the residue was extracted with EtOAc and washed with saturated sodium bicarbonate. The organic layer was dried over sodium sulfate, filtered, and loaded onto a plug of silica gel and chromatographed using a Redi-Sep® pre-packed silica gel column (12 g), eluting with a gradient of 2% to 10% 2 M $NH_3$.MeOH in DCM, to provide semi-pure N-((S)-2-amino-3-(3-chlorophenyl)propyl)-N-(4-(methoxymethyl)-5-(thiazolo[5,4-c]pyridin-2-yl)thiazol-2-yl)acetamide (0.111 g, 0.227 mmol, 60.7% yield). The crude material was used without further purification, but a fraction was purified using reverse phase HPLC to give pure compound N-((S)-2-amino-3-(3-chlorophenyl)propyl)-N-(4-(methoxymethyl)-5-(thiazolo[5,4-c]pyridin-2-yl)thiazol-2-yl)acetamide. LCMS (M+H) 487.8 calc. for $C_{22}H_{23}ClN_5O_2S_2$ 488.1. $^1$H NMR (400 MHz, $CD_3OD$): δ ppm 9.39 (s, 1H), 8.61 (d, J=6.6 Hz, 1H), 8.16 (d, J=6.6 Hz, 1H), 7.27 (m, 2H), 7.19 (m, 2H), 4.74 (s, 2H), 3.66 (m, 1H), 3.52 (s, 3H), 3.45 (dd, J=13.8, 7.8 Hz, 1H), 2.91 (dd, J=13.9, 5.8 Hz, 1H), 2.76 (dd, J=613.9, 8.7 Hz, 1H), 1.85 (s, 3H).

Example 18

N-((S)-2-amino-3-(3-chlorophenyl)propyl)-4-(methoxymethyl)-5-(thiazolo[5,4-c]pyridin-2-yl)thiazol-2-amine

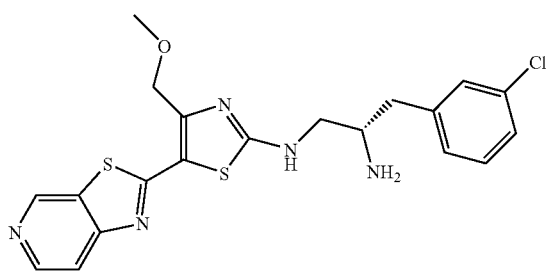

A glass microwave reaction vessel was charged with N-((S)-2-amino-3-(3-chlorophenyl)propyl)-N-(4-(methoxymethyl)-5-(thiazolo[5,4-c]pyridin-2-yl)thiazol-2-yl)acetamide (0.090 g, 0.1 8 mmol), THF (2.0 mL, 24 mmol), and 5 N HCl (2.0 mL, 10.0 mmol). The reaction mixture was stirred and heated in a Smith Synthesizer® microwave reactor (Personal Chemistry, Inc., Upssala, Sweden) at 150° C. for 11 minutes. The solution was then made basic with 10 N NaOH and extracted with EtOAc. The solvent was removed, and the compound was purified by reverse phase HPLC to give the title compound (31 mg, 38%). LCMS (M+H) 445.7 calc. for $C_{20}H_{21}ClN_5OS_2$ 446.09. $^1$H NMR (400 MHz, $CD_3OD$): δ ppm 9.12 (s, 1H), 8.50 (d, J=5.7 Hz, 1H), 7.83 (d, J=5.7 Hz, 1H), 7.34 (s, 1H), 7.23 (m, 3H), 4.70 (dd, J=12.4, 17.4 Hz, 2H), 4.46 (m, 1H), 3.47 (s, 3H), 3.25 (dd, J=3.7, 13.2 Hz, 1H), 3.15 (dd, J=9.9, 13.2 Hz, 1H), 2.98 (m, 2H).

Examples 19-27

Examples 19-27 were prepared in a manner similar to that shown in Scheme 6.

Example 19

N-((S)-2-amino-3-(4-chlorophenyl)propyl)-4-(methoxymethyl)-5-(thiazolo[5,4-c]pyridin-2-yl)thiazol-2-amine LCMS (M+H) 445.7 calc. for $C_{20}H_{21}ClN_5OS_2$ 446.09. $^1$H NMR (400 MHz, $CD_3OD$): δ ppm 9.22 (s, 1H), 8.42 (d, J=6.6 Hz, 1H), 7.98 (d, J=6.6 Hz, 1H), 7.14 (d, J=8.4 Hz, 2H), 7.09 (d, J=8.0 Hz, 2H), 4.53 (s, 2H), 3.55 (m, 2H), 3.39 (dd, J=7.5, 15.3 Hz, 1H), 3.07 (s, 3H), 2.77 (d, J=7.3 Hz, 2H).

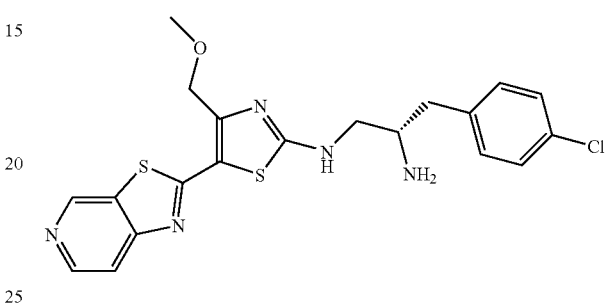

Example 20

N-((S)-2-amino-3-(3-chlorophenyl)propyl)-5-(thiazolo[5,4-c]pyridin-2-yl)-4-((2,2,2-trifluoroethoxy)methyl)thiazol-2-amine LCMS (M+H) 513.7 calc. for $C_{21}H_{20}ClF_3N_5OS_2$ 514.07. $^1$H NMR (400 MHz, $CD_3OD$): δ ppm 9.09 (s, 1H), 8.48 (d, J=5.6 Hz, 1H), 7.80 (d, J=5.6 Hz, 1H), 7.21 (m, 4H), 4.90 (s, 2H), 4.10 (m, 2H), 3.42 (m, 1H), 3.33 (m, 2H), 2.83 (m, 1H), 2.65 (dd, J=6.9, 13.6 Hz, 1H).

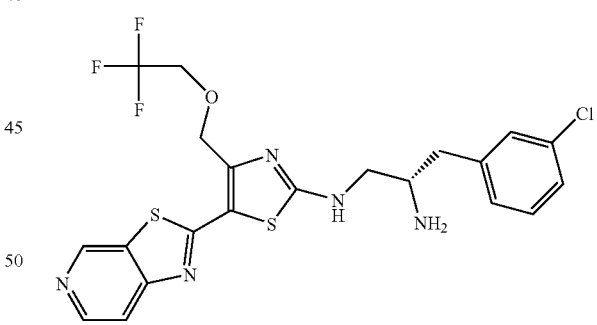

Example 21

N-((S)-2-amino-3-(4-chlorophenyl)propyl)-4-(ethoxymethyl)-5-(thiazolo[5,4-c]pyridin-2-yl)thiazol-2-amine LCMS (M+H) 460.1 calc. for $C_{21}H_{23}ClN_5OS_2$ 460.10. $^1$H NMR (400 MHz, $CD_3OD$): δ ppm 9.14 (s, 1H), 8.50 (d, J=5.7 Hz, 1H), 7.83 (d, J=5.7 Hz, 1H), 7.31 (d, J=8.4 Hz, 2H), 7.24 (d, J=8.4 Hz, 2H), 4.74 (s, 2H), 3.70 (q, J=7.0 Hz, 2H), 3.45 (m, 1H), 3.33 (dd, J=6.9, 16.0 Hz, 2H), 2.84 (dd, J=5.6, 13.6 Hz, 1H), 2.66 (dd, J=7.1, 13.6 Hz, 1H), 1.26 (t, J=7.0 Hz, 3H).

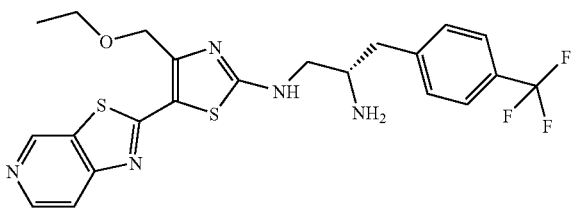

Example 22

N-((S)-2-amino-3-(4-(trifluoromethyl)phenyl)propyl)-4-(methoxymethyl)-5-(thiazolo[5,4-c]pyridin-2-yl)thiazol-2-amine LCMS (M+H) 480.0 calc. for $C_{21}H_{21}F_3N_5OS_2$ 480.11. $^1$H NMR (400 MHz, CD$_3$OD): δ ppm 9.13 (s, 1H), 8.50 (d, J=5.7 Hz, 1H), 7.83 (d, J=5.7 Hz, 1H), 7.61 (d, J=8.0 Hz, 2H), 7.45 (d, J=8.0 Hz, 2H), 4.70 (s, 2H), 3.49 (s, 3H), 3.46 (m, 1H), 3.36 (m, 2H), 2.95 (dd, J=5.3, 13.6 Hz, 1H), 2.75 (dd, J=6.8, 13.6 Hz, 1H).

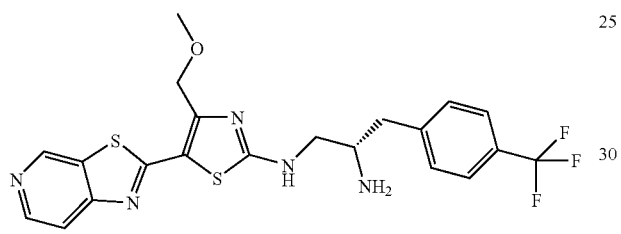

Example 23

N-((S)-2-amino-3-(4-(trifluoromethyl)phenyl)propyl)-4-ethyl-5-(thiazolo[5,4-c]pyridin-2-yl)thiazol-2-amine LCMS (M+H) 464.0 calc. for $C_{21}H_{21}F_3N_5S_2$ 464.12. $^1$H NMR (400 MHz, CD$_3$OD): δ ppm 9.08 (s, 1H), 8.48 (d, J=5.6 Hz, 1H), 7.78 (d, J=5.6 Hz, 1H), 7.60 (d, J=8.0 Hz, 2H), 7.45 (d, J=8.0 Hz, 2H), 3.45 (m, 1H), 3.34 (m, 2H), 3.01 (q, J=7.4 Hz, 2H), 2.93 (dd, J=5.1, 13.3 Hz, 1H), 2.76 (dd, J=6.9, 13.3 Hz, 1H), 1.33 (t, J=7.4 Hz, 3H).

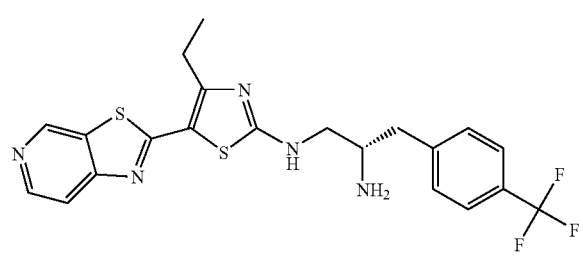

Example 24

N-((S)-2-amino-3-(4-(trifluoromethyl)phenyl)propyl)-4-methyl-5-(thiazolo[5,4-c]pyridin-2-yl)thiazol-2-amine LCMS (M+H) 450.0 calc. for $C_{20}H_{19}F_3N_5S_2$ 450.10. $^1$H NMR (400 MHz, CD$_3$OD): δ ppm 9.07 (s, 1H), 8.46 (d, J=5.6 Hz, 1H), 7.75 (d, J=5.6 Hz, 1H), 7.60 (d, J=8.0 Hz, 2H), 7.45 (d, J=8.0 Hz, 2H), 3.43 (m, 1H), 3.34 (m, 2H), 2.94 (dd, J=5.1, 13.5 Hz, 1H), 2.74 (dd, J=7.2, 13.5 Hz, 1H), 2.58 (s, 3H).

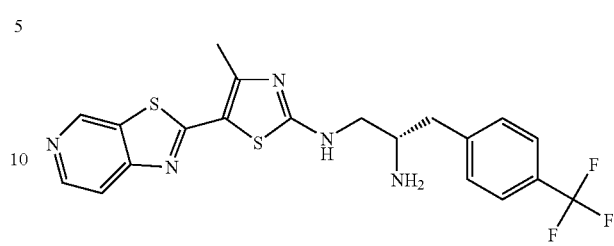

Example 25

N-((S)-2-amino-3-(4-chlorophenyl)propyl)-N-(4-(methoxymethyl)-5-(thiazolo[5,4-c]pyridin-2-yl)thiazol-2-yl)acetamide LCMS (M+H) 487.8 calc. for $C_{22}H_{23}ClN_5O_2S_2$ 488.1. $^1$H NMR (400 MHz, CD$_3$OD): δ ppm 9.39 (s, 1H), 8.61 (d, J=6.6 Hz, 1H), 8.17 (d, J=6.6 Hz, 1H), 7.28 (d, J=8.5 Hz, 2H), 7.23 (d, J=8.5 Hz, 2H), 4.73 (s, 2H), 4.37 (m, 1H), 3.68 (m, 1H), 3.52 (s, 3H), 3.45 (dd, J=13.8, 7.8 Hz, 1H), 2.90 (dd, J=13.9, 5.9 Hz, 1H), 2.75 (dd, J=13.8, 8.7 Hz, 1H), 1.85 (s, 3H).

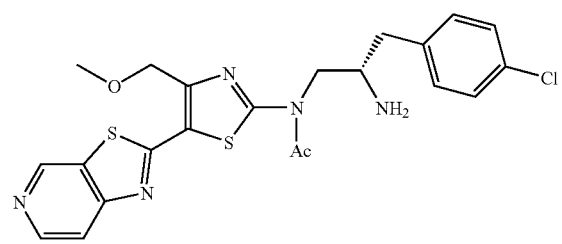

Example 26

N-((S)-2-amino-3-(4-(trifluoromethyl)phenyl)propyl)-N-(4-(methoxymethyl)-5-(thiazolo[5,4-c]pyridin-2-yl)thiazol-2-yl)acetamide LCMS (M+H) 521.8 calc. for $C_{23}H_{23}F_3N_5O_2S_2$ 522.12. $^1$H NMR (400 MHz, CD$_3$OD): δ ppm 9.34 (s, 1H), 8.59 (d, J=6.3 Hz, 1H), 8.10 (d, J=6.3 Hz, 1H), 7.58 (d, J=7.8 Hz, 2H), 7.44 (d, J=7.8 Hz, 2H), 4.73 (s, 2H), 4.42 (m, 1H), 3.70 (m, 1H), 3.52 (s, 3H), 3.47 (m, 1H), 3.01 (dd, J=13.4, 5.0 Hz, 1H), 2.85 (dd, J=13.4, 8.9 Hz, 1H), 1.84 (s, 3H).

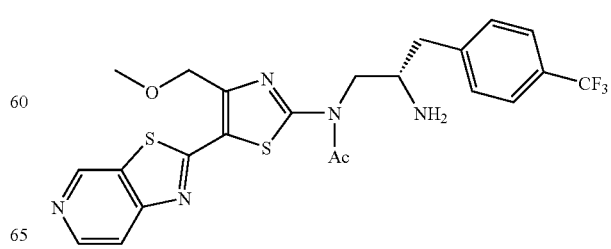

Example 27

N-((S)-2-amino-3-(1H-indol-3-yl)propyl)-4-(methoxymethyl)-5-(thiazolo[5,4-c]pyridin-2-yl)thiazol-2-amine LCMS (M+H) 451.1 calc. for $C_{22}H_{23}N_6OS_2$ 451.14. $^1$H NMR (400 MHz, $CD_3OD$): δ ppm 9.42 (m, 1H), 8.65 (m, 1H), 8.20 (m, 1H), 7.62 (m, 1H), 7.35 (m, 1H), 7.26 (s, 1H), 7.06 (m, 2H), 4.74 (s, 2H), 3.90 (m, 1H), 3.82 (m, 1H), 3.51 (s, 3H), 3.16 (m, 3H).

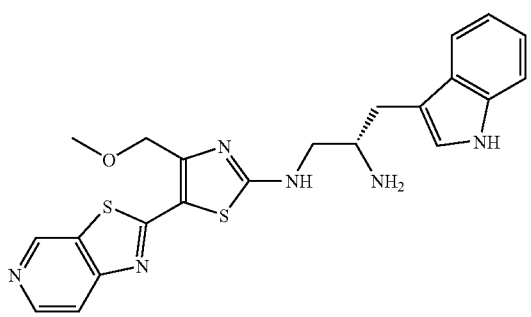

Examples 28-30

Examples 28-30 were made using a procedure similar to that shown in Scheme 6, but starting from readily available 2-(benzylamino)thiazole-5-carboxylic acid as shown in Scheme 7.

Scheme 7

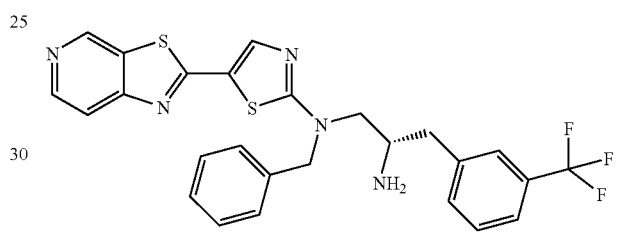

Example 28

N-benzyl-5-(thiazolo[5,4-c]pyridin-2-yl)thiazol-2-amine

LCMS (M+H) 325.0 calc. for $C_{16}H_{13}N_4S_2$ 325.06. $^1$H NMR (400 MHz, $CDCl_3$): δ ppm 8.85 (s, 1H), 8.33 (d, J=5.5 Hz, 1H), 7.72 (s, 1H), 7.61 (d, J=5.5 Hz, 1H), 7.15 (m, 5H), 4.40 (s, 2H).

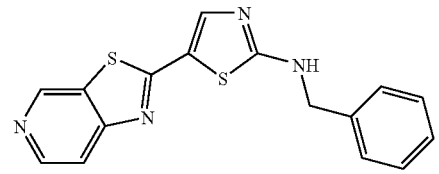

Example 29

N-((S)-2-amino-3-(3-(trifluoromethyl)phenyl)propyl)-N-benzyl-5-(thiazolo[5,4-c]pyridin-2-yl)thiazol-2-amine LCMS (M+H) 526.1 calc. for $C_{26}H_{23}F_3N_5S_2$ 526.13. $^1$H NMR (400 MHz, $CD_3OD$): δ ppm 9.32 (s, 1H), 8.62 (d, J=6.4 Hz, 1H), 8.27 (s, 1H), 8.07 (d, J=6.4 Hz, 1H), 7.57 (m, 5H), 7.32 (m, 3H), 7.20 (m, 1H), 4.67 (s, 2H), 4.12 (dd, J=8.5, 14.8 Hz, 1H), 3.90 (m, 1H), 3.75 (dd, J=3.9, 14.8 Hz, 1H), 3.08 (m, 2H).

Example 30

N-((S)-2-amino-3-(4-(trifluoromethyl)phenyl)propyl)-N-benzyl-5-(thiazolo[5,4-c]pyridin-2-yl)thiazol-2-amine LCMS (M+H) 526.1 calc. for $C_{26}H_{23}F_3N_5S_2$ 526.13. $^1$H NMR (400 MHz, $CD_3OD$): δ ppm 9.45 (s, 1H), 8.68 (d, J=6.6 Hz, 1H), 8.39 (s, 1H), 8.21 (d, J=6.6 Hz, 1H), 7.65 (d, J=7.9 Hz, 2H), 7.43 (d, J=57.9 Hz, 2H), 7.32 (m, 3H), 7.19 (m, 2H), 4.70 (s, 2H), 4.16 (dd, J=8.9, 14.9 Hz, 1H), 3.94 (m, 1H), 3.73 (dd, J=3.9, 14.9 Hz, 1H), 3.14 (m, 1H), 3.03 (dd, J=8.5, 14.1 Hz, 1H).

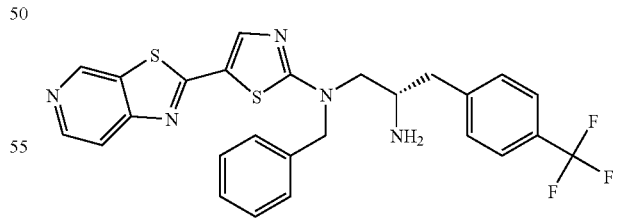

Examples 31-32

Examples 31-32 were made using a procedure similar to that shown in Scheme 6, but starting from readily available methyl 2-aminothiazole-5-carboxylate to make the intermediate N-(5-(thiazolo[5,4-c]pyridin-2-yl)thiazol-2-yl)acetamide.

Example 31

N-((S)-2-amino-3-(3-(trifluoromethyl)phenyl)propyl)-5-(thiazolo[5,4-c]pyridin-2-yl)thiazol-2-amine LCMS (M+H) 436.0 calc. for $C_{19}H_{17}F_3N_5S_2$ 436.09. $^1$H NMR (400 MHz, $CD_3OD$): δ ppm 9.08 (s, 1H), 8.50 (d, J=5.6 Hz, 1H), 7.88 (s, 1H), 7.79 (d, J=5.6 Hz, 1H), 7.60 (s, 1H), 7.54 (m, 1H), 7.48 (m, 2H), 3.94 (dd, J=5.1, 13.9 Hz, 1H), 3.73 (dd, J=8.0, 13.9 Hz, 1H), 3.55 (m, 1H), 2.98 (d, J=11.4 Hz, 1H), 2.73 (dd, J=8.3, 13.7 Hz, 1H).

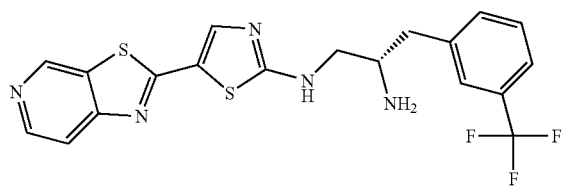

Example 32

N-((S)-2-amino-3-(4-(trifluoromethyl)phenyl)propyl)-5-(thiazolo[5,4-c]pyridin-2-yl)thiazol-2-amine LCMS (M+H) 436.0 calc. for $C_{19}H_{17}F_3N_5S_2$ 436.09. $^1$H NMR (400 MHz, $CD_3OD$): δ ppm 9.06 (s, 1H), 8.49 (d, J=5.6 Hz, 1H), 7.93 (s, 1H), 7.78 (d, J=5.6 Hz, 1H), 7.60 (d, J=7.9 Hz, 2H), 7.44 (d, J=7.9 Hz, 2H), 3.46 (m, 1H), 3.34 (m, 2H), 2.95 (dd, J=4.6, 13.5 Hz, 1H), 2.73 (dd, J=6.9, 13.5 Hz, 1H).

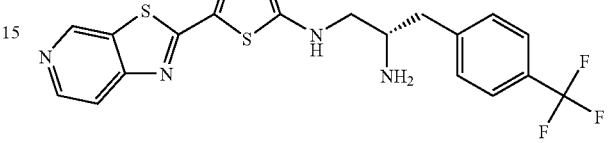

Examples 33-34

Examples 33-34 were made using the procedure shown in Scheme 8 starting from N-(4-(methoxymethyl)-5-(thiazolo[5,4-c]pyridin-2-yl)thiazol-2-yl)acetamide that was prepared as shown in Scheme 6.

Scheme 8

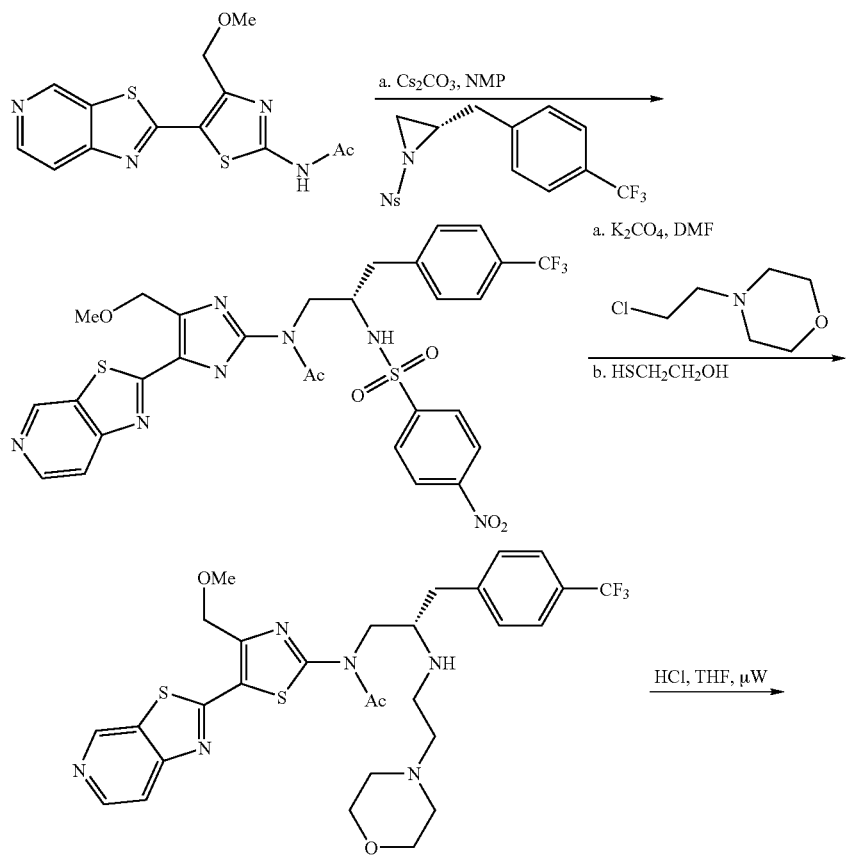

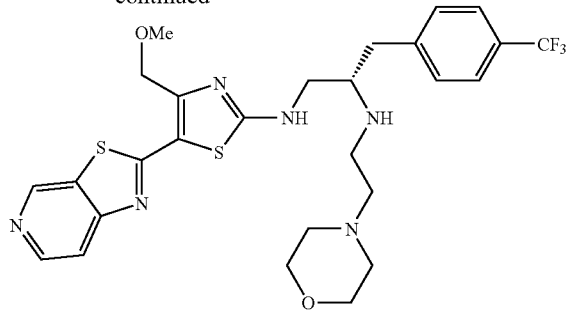

Example 33

N-(4-(methoxymethyl)-5-(thiazolo[5,4-c]pyridin-2-yl)thiazol-2-yl)-N-((S)-2-(2-morpholinoethylamino)-3-(4-(trifluoromethyl)phenyl)propyl)acetamide

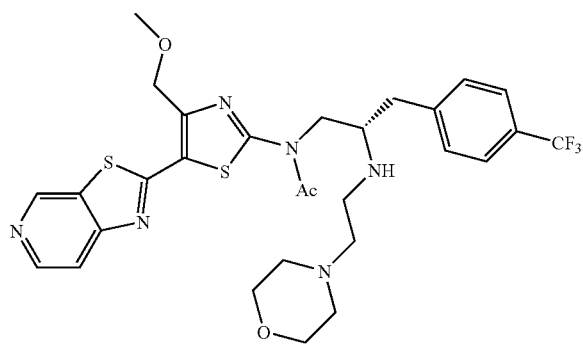

N-(4-(methoxymethyl)-5-(thiazolo[5,4-c]pyridin-2-yl)thiazol-2-yl)-N-((S)-2-(4-nitrophenylsulfonamido)-3-(4-(trifluoromethyl)phenyl)propyl)acetamide:

To a 50 mL round-bottomed flask was added N-(4-(methoxymethyl)-5-(thiazolo[5,4-c]pyridin-2-yl)thiazol-2-yl)acetamide (0.300 g, 0.936 mmol), $Cs_2CO_3$ (0.610 g, 1.87 mmol), and DMF (0.0721 mL, 0.936 mmol). The resulting solution was heated to 50° C. A DMF solution of (S)-2-(4-(trifluoromethyl)benzyl)-1-(4-nitrophenylsulfonyl)aziridine (0.724 g, 1.87 mmol) was added to the reaction dropwise, and the reaction mixture was monitored by LCMS. After approximately 30 minutes, the solvent was removed and the residue was taken up in EtOAc and washed with saturated sodium bicarbonate. The solution was dried over sodium sulfate, filtered and loaded onto a plug of silica gel. Chromatography through a Redi-Sep® pre-packed silica gel column (40 g), eluting with a gradient of 1% to 10% 2 M $NH_3$.MeOH in DCM, to provide N-(4-(methoxymethyl)-5-(thiazolo[5,4-c]pyridin-2-yl)thiazol-2-yl)-N-((S)-2-(4-nitrophenylsulfonamido)-3-(4-(trifluoromethyl)phenyl)propyl)acetamide (0.290 g, 0.410 mmol, 43.8% yield). LCMS (M+H) 707 calc. for $C_{29}H_{26}F_3N_6O_6S_3$ 707.1.

N-(4-(methoxymethyl)-5-(thiazolo[5,4-c]pyridin-2-yl)thiazol-2-yl)-N-((S)-2-(2-morpholinoethylamino)-3-(4-(trifluoromethyl)phenyl)propyl)acetamide To a 100 mL round-bottomed flask was added N-(4-(methoxymethyl)-5-(thiazolo[5,4-c]pyridin-2-yl)thiazol-2-yl)-N-((S)-2-(4-nitrophenylsulfonamido)-3-(4-(trifluoromethyl)phenyl)propyl)acetamide (0.090 g, 0.13 mmol), n-(2-chloroethyl)morpholine hydrochloride (0.026 g, 0.14 mmol), $K_2CO_3$ (0.070 g, 0.51 mmol), and DMF (0.0098 mL, 0.13 mmol). The resulting solution was stirred at 80° C. for 12 hours. LCMS indicated formation of the desired product, so additional $K_2CO_3$ (0.070 g, 0.51 mmol) and 2-mercaptoethanol were added, and the reaction was stirred approximately 30 minutes to remove the nosyl group. The solution was reduced to an oil under reduced pressure, and the residue was partitioned between EtOAc and saturated sodium bicarbonate. The organic layer was washed with saturated sodium bicarbonate, dried over sodium sulfate, and filtered. The crude product was adsorbed onto a plug of silica gel and chromatographed through a Redi-Sep® pre-packed silica gel column (12 g), eluting with a gradient of 1% to 10% 2 M $NH_3$.MeOH in DCM, to provide N-(4-(methoxymethyl)-5-(thiazolo[5,4-c]pyridin-2-yl)thiazol-2-yl)-N-((S)-2-(2-morpholinoethylamino)-3-(4-(trifluoromethyl)phenyl)propyl)acetamide (0.013 g, 0.017 mmol, 14% yield). LCMS (M+H) 635.2 calc. for $C_{29}H_{34}F_3N_6O_3S_2$ 635.21. $^1$H NMR (400 MHz, $CD_3OD$): δ ppm 9.21 (s, 1H), 8.42 (d, J=6.7 Hz, 1H), 7.98 (d, J=6.7 Hz, 1H), 7.41 (d, J=8.0 Hz, 2H), 7.27 (d, J=8.0 Hz, 2H), 4.52 (s, 2H), 4.36 (m, 1H), 3.82 (m, 2H), 3.53 (m, 7H), 3.30 (s, 3H), 3.10 (m, 2H), 2.89 (m, 5H), 1.62 (s, 3H).

Example 34

4-(Methoxymethyl)-N-((S)-2-(2-morpholinoethylamino)-3-(4-(trifluoromethyl)phenyl)propyl)-5-(thiazolo[5,4-c]pyridin-2-yl)thiazol-2-amine

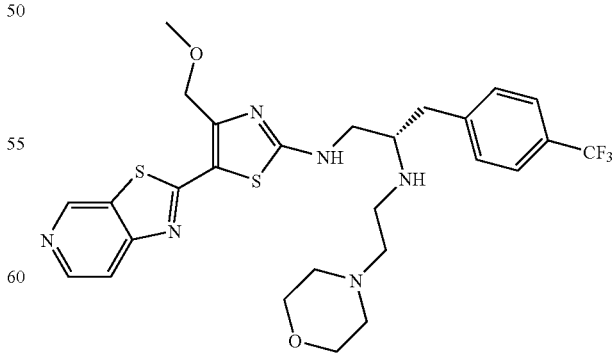

A glass microwave reaction vessel was charged with N-(4-(methoxymethyl)-5-(thiazolo[5,4-c]pyridin-2-yl)thiazol-2-yl)-N-((S)-2-(2-morpholinoethylamino)-3-(4-(trifluoromethyl)phenyl)propyl)acetamide (0.111 g, 0.2 mmol), THF (2.0 mL, 24 mmol), and HCl (2.0 mL, 10 mmol). The reaction mixture was stirred and heated in a Smith Synthesizer® microwave reactor (Personal Chemistry, Inc., Upssala, Sweden) at 150° C. for 12 minutes. The mixture was then made basic with NaOH, extracted with EtOAc, and the organics were adsorbed onto a plug of silica gel and chromatographed through a Redi-Sep® pre-packed silica gel column (4 g), eluting with a gradient of 1% to 10% 2 M $NH_3$.MeOH in DCM, to provide the title compound, 4-(methoxymethyl)-N-((S)-2-(2-morpholinoethylamino)-3-(4-(trifluoromethyl)phenyl)propyl)-5-(thiazolo[5,4-c]pyridin-2-yl)thiazol-2-amine (0.008 g, 8% yield). LCMS (M+H) 593.2 calc. for $C_{27}H_{32}F_3N_6O_2S_2$ 593.20. $^1$H NMR (400 MHz, $CD_3OD$): δ ppm 9.13 (s, 1H), 8.50 (d, J=5.7 Hz, 1H), 7.83 (d, J=5.7 Hz, 1H), 7.62 (d, J=8.1 Hz, 1H), 7.48 (d, J=8.1 Hz, 1H), 4.69 (s, 2H), 3.50 (s, 3H), 3.47 (m, 6H), 3.14 (m, 1H), 2.95 (dd, J=6.0, 13.6 Hz, 1H), 2.84 (dd, J=7.9, 13.6 Hz, 1H), 2.77 (dd, J=5.8, 11.9 Hz, 1H), 2.68 (m, 1H), 2.40 (m, 2H), 2.29 (s, 4H).

Example 35

6-(2-((S)-2-amino-3-(1H-indol-3-yl)propylamino)thiazol-5-yl)benzo[d]thiazol-2(3H)-one

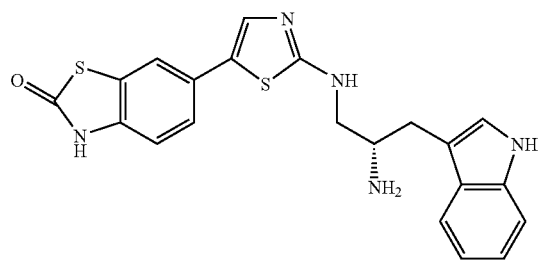

This compound was synthesized using a procedure similar to that shown in Scheme 1 with a coupling reaction between (S)-tert-butyl 3-(1H-indol-3-yl)-2-(4-nitrophenylsulfonamido)propyl(5-bromothiazol-2-yl)carbamate and commercially available 2-oxo-2,3-dihydrobenzo[d]thiazol-6-ylboronic acid using $PdCl_2(PPh_3)_2$ as the catalyst instead of tetrakis-(triphenylphosphine)palladium. MS m/z: 422 (M+1). $^1$H NMR (400 MHz, $CD_3OD$): δ ppm 3.11-3.20 (m, 2H), 3.57 (d, J=7.04 Hz, 2H), 3.66-3.72 (m, 1H), 3.76-3.86 (m, 1H), 7.05-7.18 (m, 3H), 7.25 (s, 1H), 7.33-7.42 (m, 3H), 7.52 (d, J=1.56 Hz, 1H), 7.60 (d, J=7.82 Hz, 1H).

(S)-tert-butyl 3-(1H-indol-3-yl)-2-(4-nitrophenylsulfonamido)propyl(5-bromothiazol-2-yl)carbamate was prepared as shown in Scheme 9. The final de-protection step used a similar condition to that shown in Scheme 6 and as described for Example 17.

Scheme 9

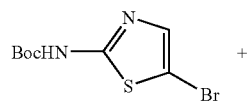

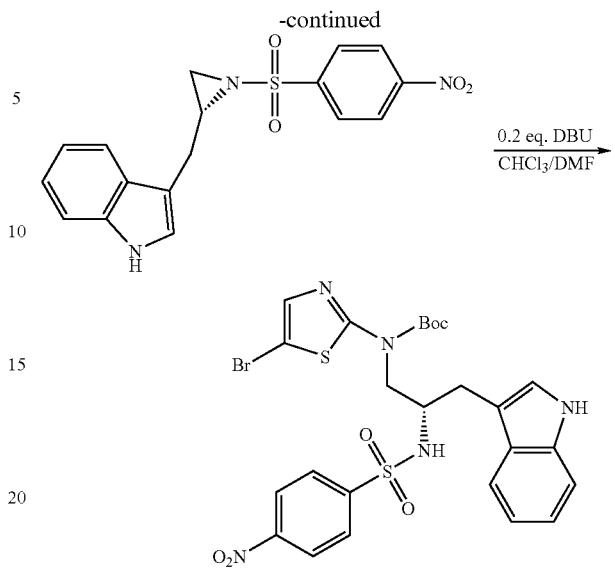

Example 36

6-(2-((S)-2-amino-3-(4-(trifluoromethyl)phenyl)propylamino)thiazol-5-yl)-3,4-dihydroquinolin-2(1H)-one

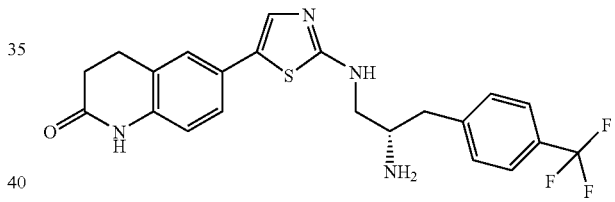

The title compound was synthesized using a procedure similar to that shown in Scheme 1 with a coupling reaction between (S)-tert-butyl 1-(N-(5-bromothiazol-2-yl)-tert-butoxylcarbonylamino)-3-(4-(trifluoromethyl)phenyl)propan-2-ylcarbamate as shown in Scheme 10 and 6-(4,4,5,5-tetramethyl-1,3,2-dioxaborolan-2-yl)-3,4-dihydroquinolin-2(1H)-one, which was prepared from commercially available 6-bromo-3,4-dihydroquinolin-2(1H)-one in a similar manner to the procedure shown in Scheme 1. MS m/z: 447 (M+1). $^1$H NMR (400 MHz, $CD_3OD$): δ ppm 2.55-2.60 (m, 2H), 2.97 (t, J=7.63 Hz, 2H), 3.09 (dd, J=14.97, 7.34 Hz, 2H), 3.52 (d, J=6.85 Hz, 1H), 3.62 (d, J=3.72 Hz, 1H), 3.70 (m, 1H), 6.86 (d, J=8.22 Hz, 1H), 7.23-7.34 (m, 3H), 7.53 (d, J=8.02 Hz, 2H), 7.69 (d, J=8.02 Hz, 2H).

Scheme 10

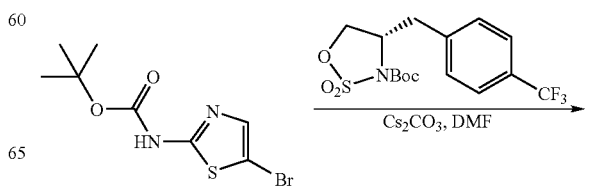

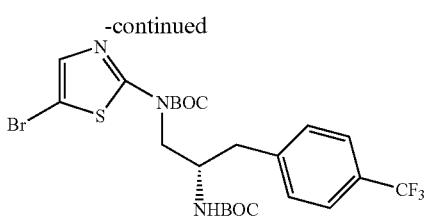

(S)-tert-butyl 1-(N-(5-bromothiazol-2-yl)-tert-butoxylcarbonylamino)-3-(4-(trifluoromethyl)phenyl)propan-2-ylcarbamate To a solution of tert-butyl 5-bromothiazol-2-ylcarbamate (2.4 g, 8.6 mmol) in 90 mL of DMF, was added $Cs_2CO_3$ (5.6 g, 17 mmol). The mixture was heated to 50° C., and the cyclic sulfamidate (3.9 g, 10 mmol) was added slowly in 25 mL of DMF. The cyclic sulfamidate was prepared as described by Posakony J. in JOC 2002, 67 5164-5169. After 1 hour, the reaction was concentrated under reduced pressure. The residue was taken up in 70 mL of EtOAc, and 70 mL of 1 M aqueous HCl was added. The mixture was stirred for 1 hour and was then transferred to a separatory funnel. The mixture was partitioned, and the aqueous portion was extracted twice with 75 mL of EtOAc. The combined organic extracts were washed with 50 mL of brine and dried over $MgSO_4$. Filtration and concentration under reduced pressure, followed by a silica gel column chromatography separation eluting with 1% to 20% EtOAc in hexanes gave the title compound (4.7 g, 94% yield) as a white solid. MS m/z: 582 (M+1).

Examples 37-40

Examples 37-40 were synthesized using a procedure similar to that shown in Scheme 1 using a coupling reaction between the corresponding bromothiazole intermediate as described in Example 35 or Example 36 and the corresponding boronic acids or esters.

Example 37

5-(2-((S)-2-amino-3-(1H-indol-3-yl)propylamino)thiazol-5-yl)-1H-indazol-3-amine

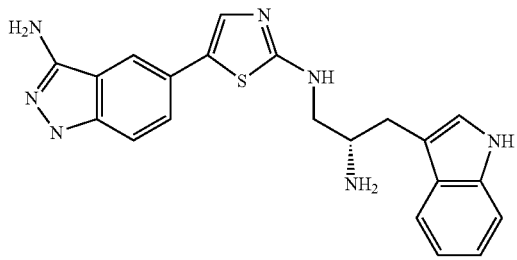

The title compound was synthesized using a procedure similar to that shown in Scheme 1. MS m/z: 404 (M+1). $^1$H NMR (400 MHz, $CD_3OD$): δ ppm 3.12-3.10 (m, 1H), 3.25-3.12 (m, 1H), 3.61-3.55 (m, 1H), 3.72-3.68 (m, 1H), 3.81-3.72 (m, 1H), 7.06 (m, 1H), 7.15 (m, 1H), 7.25 (s, 1H), 7.39 (d, J=1.96 Hz, 3H), 7.58 (d, J=17.2, 1H), 7.60 (d, J=16.4, 1H), 7.86 (s, 1H).

Example 38

5-(2-((S)-2-amino-3-(1H-indol-3-yl)propylamino)thiazol-5-yl)benzo[d]isoxazol-3-amine MS m/z: 405 (M+1). $^1$H NMR (400 MHz, $CD_3OD$): δ ppm 2.82-2.91 (m, 1H), 3.12-3.19 (m, 1H), 3.54-3.60 (m, 1H), 3.66-3.72 (m, 1H), 3.77 (t, J=6.55 Hz, 1H), 7.06 (t, J=7.53 Hz, 1H), 7.12-7.16 (m, 1H), 7.24 (s, 1H), 7.37-7.41 (m, 3H), 7.59 (d, J=7.82 Hz, 1H), 7.66 (dd, J=8.80, 1.76 Hz, 1H), 7.81 (d, J=1.17 Hz, 1H).

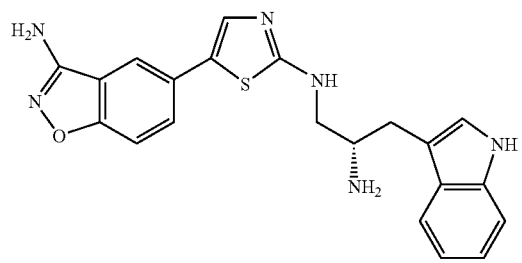

Example 39

6-(2-((S)-2-amino-3-(1H-indol-3-yl)propylamino)thiazol-5-yl)benzo[d]oxazol-2(3H)-one MS m/z: 406 (M+1). $^1$H NMR (400 MHz, $CD_3OD$): δ ppm 3.10-3.23 (m, 2H), 3.54-3.61 (m, 1H), 3.66-3.71 (m, 1H), 3.76-3.85 (m, 1H), 7.04-7.09 (m, 2H), 7.15 (t, J=7.63 Hz, 1H), 7.22 (dd, J=8.22, 1.56 Hz, 1H), 7.25 (s, 1H), 7.33-7.41 (m, 31H), 7.59 (d, J=8.02 Hz, 1H).

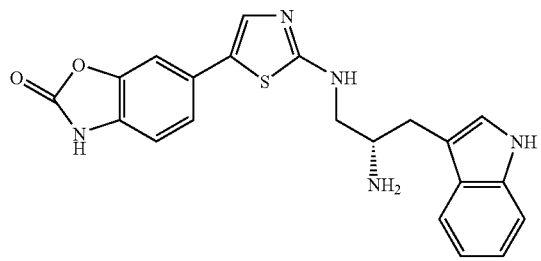

Example 40

6-(2-((S)-2-amino-3-(4-(trifluoromethyl)phenyl)propylamino)thiazol-5-yl)benzo[d]oxazol-2(3H)-one MS m/z: 435 (M+1). $^1$H NMR (400 MHz, $CD_3OD$): δ ppm 3.08-3.19 (m, 2H), 3.56-3.72 (m, 2H), 3.87 (dt, J=11.20, 7.02 Hz, 1H), 7.08 (d, J=8.22 Hz, 1H), 7.24 (d, J=8.02 Hz, 1H), 7.37 (s, 1H), 7.44 (s, 1H), 7.55 (d, J=8.02 Hz, 2H), 7.69 (d, J=8.22 Hz, 2H).

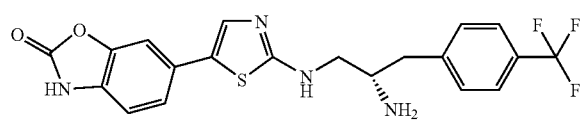

Example 41

5-(2-((S)-2-amino-3-(4-(trifluoromethyl)phenyl)propylamino)thiazol-5-yl)-3,3-difluoroindolin-2-one

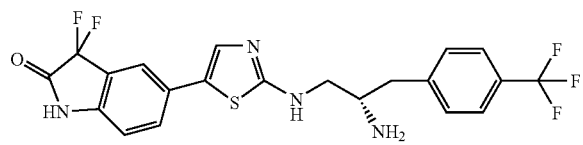

The title compound was obtained by treating 5-(2-((S)-2-amino-3-(1H-indol-3-yl)propylamino)thiazol-5-yl)-3,3-difluoro-1-(methoxymethyl)indolin-2-one with 4N HCl in dioxane in a glass microwave reaction vessel and heated in a Discover® model microwave reactor (CEM, Matthews, N.C.) at 100° C. for 5 minutes to remove the MOM group. The reaction mixture was concentrated and directly purified by preparative HPLC to give the title compound. MS m/z: 469 (M+1). $^1$H NMR (400 MHz, CD$_3$OD): δ ppm 3.02-3.12 (m, 2H), 3.46-3.53 (m, 1H), 3.64 (d, J=36.4 Hz, 1H), 3.80 (br s, 1H), 6.97 (d, J=8.41 Hz, 1H), 7.40 (s, 1H), 7.52 (d, J=7.83 Hz, 3H), 7.65-7.70 (m, 3H).

5-(2-((S)-2-Amino-3-(1H-indol-3-yl)propylamino)thiazol-5-yl)-3,3-difluoro-1-(methoxymethyl)indolin-2-one was synthesized using a procedure similar to that shown in Scheme 1 using a coupling reaction between the corresponding bromothiazole intermediate as in Example 35 and 3,3-difluoro-1-(methoxymethyl)-5-(4,4,5,5-tetramethyl-1,3,2-dioxaborolan-2-yl)indolin-2-on. 3,3-difluoro-1-(methoxymethyl)-5-(4,4,5,5-tetramethyl-1,3,2-dioxaborolan-2-yl)indolin-2-on was prepared using a procedure similar to that shown in Scheme 1 using 5-bromo-3,3-difluoro-1-(methoxymethyl)indolin-2-one as the starting material. 5-Bromo-3,3-difluoro-1-(methoxymethyl)indolin-2-one was prepared using a two step procedure as described below.

5-Bromo-1-(methoxymethyl)indoline-2,3-dione

To a 500 mL round-bottomed flask, was added 5-bromoisatin (5.00 g, 22.1 mmol), formaldehyde dimethyl acetal (111 mL, 22.1 mmol), and boron trifluoride diethyl etherate (16.7 mL, 133 mmol). The resulting mixture was heated at 40° C. TLC (1:1 hexane:EtOAc) showed starting material was consumed. The mixture was then diluted with EtOAc (100 mL) and washed with brine/water (60 mL), brine (60 mL) and brine/bicarbonate (60 mL). The organic layer was dried over sodium sulfate and evaporated to provide an orange solid. The solid was taken up in EtOAc (50 mL) with heating, and hexane (10 mL) was added until the mixture became cloudy. A black precipitate formed immediately that should have been removed. The mixture was heated to reflux and allowed to stand at room temperature and then at −20° C. Orange red crystals were filtered washing with hexane and manually separated from the black precipitate to provide the title compound (2.97 g, 49.7% yield) as a red crystalline solid. $^1$H NMR (400 MHz, DMSO-d$_6$) δ ppm 3.29 (s, 3H), 5.08 (s, 2H), 7.19 (d, J=8.22 Hz, 1H), 7.77 (s, 1H), 7.85 (s, 1H).

5-Bromo-3,3-difluoro-1-(methoxymethyl)indolin-2-one

To a 100 mL round-bottomed flask, was added 5-bromo-1-(methoxymethyl)indoline-2,3-dione (1.50 g, 5.6 mmol), DCM (14 mL, 5.6 mmol), deoxo-fluor(r) (3.1 mL, 17 mmol), and EtOH (0.0097 mL, 0.17 mmol). After addition, the mixture was stirred at room temperature 16 hours when TLC (1:1 hexane:EtOAc) showed that the reaction was complete. The mixture was cooled to 0° C. and saturated aqueous sodium carbonate (50 mL) was added in portions. The mixture was then stirred for 8 hours and then extracted with DCM (3×75 mL). The organic layer was dried over sodium sulfate, evaporated onto a plug of silica gel, and purified by chromatography through a Redi-Sep® pre-packed silica gel column (120 g), eluting with a gradient of 0% to 100% EtOAc in hexane, to provide 5-bromo-3,3-difluoro-1-(methoxymethyl)indolin-2-one (1.36 g, 84% yield) as a off-white crystalline. $^1$H NMR (400 MHz, CDCl$_3$) δ ppm 3.35 (s, 3H), 5.10 (s, 2H), 7.01 (d, J=8.41 Hz, 1H), 7.64 (d, J=9.00 Hz, 1H), 7.71 (d, J=1.37 Hz, 1H).

Examples 42-44

Examples 42-44 were synthesized using a procedure similar to that used in Examples 35 and 36.

Example 42

5-(2-((S)-2-amino-3-(4-(trifluoromethyl)phenyl)propylamino)thiazol-5-yl)indolin-2-one MS m/z: 433 (M+1). $^1$H NMR (400 MHz, CD$_3$OD): δ ppm 3.12-3.34 (m, 2H), 3.46-3.52 (m, 1H), 3.54 (s, 2H), 3.60-3.65 (m, 1H), 3.78 (br s, 1H), 6.87 (d, J=7.82 Hz, 1H), 7.28 (s, 2H), 7.37(s, 1H), 7.52 (d, J=8.22 Hz, 2H), 7.69 (d, J=8.02 Hz, 2H).

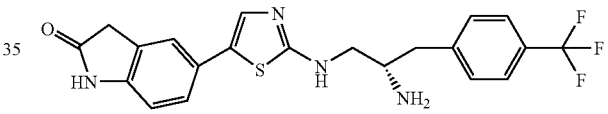

Example 43

6-(2-((S)-2-amino-3-(4-(trifluoromethyl)phenyl)propylamino)thiazol-5-yl)benzo[d]thiazol-2(3H)-one MS m/z: 451 (M+1). $^1$H NMR (400 MHz, CD$_3$OD): δ ppm 3.02-3.15 (m, 2H), 3.46-3.53 (m, 1H), 3.62-3.65 (m, 1H), 3.80 (m, 1H), 7.11 (d, J=8.41 Hz, 1H), 7.34-7.37 (m, 2H), 7.53 (d, J=8.22 Hz, 2H), 7.58 (d, J=1.57 Hz, 1H), 7.69 (d, J=8.22 Hz, 2H).

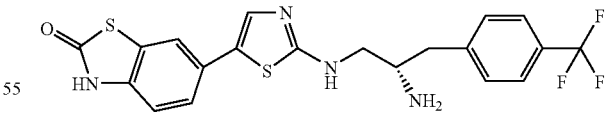

Example 44

5-(2-((S)-2-amino-3-(3-(trifluoromethyl)phenyl)propylamino)thiazol-5-yl)indolin-2-one MS m/z: 433 (M+1). $^1$H NMR (400 MHz, CD$_3$OD): δ ppm 3.03-3.15 (m, 2H), 3.48-3.56 (m, 3H), 3.61-3.67 (m, 1H), 3.81 (d, J=6.85 Hz, 1H), 6.89 (d, J=8.02 Hz, 1H), 7.31 (s, 2H), 7.38 (s, 1H), 7.58-7.70 (m, 4H).

Example 45

5-(2-((S)-2-amino-3-(1H-indol-3-yl)propylamino)thiazol-5-yl)-N-methyl-1H-indazol-3-amine

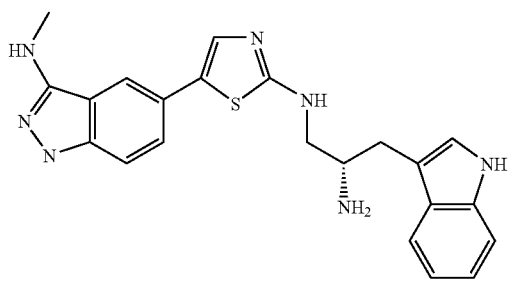

The title compound was synthesized using a procedure similar to that of Example 35 using tert-butyl 5-bromo-3-(tert-butoxycarbonyl)-1H-indazole-1-carboxylate as one of the starting material that led to the product. tert-Butyl 5-bromo-3-(tert-butoxycarbonyl)-1H-indazole-1-carboxylate was synthesized from commercially available 5-bromo-2-fluorobenzonitrile. MS m/z: 418 (M+1). $^1$H NMR (400 MHz, CD$_3$OD): δ ppm 3.08 (s, 3H), 3.11-3.25 (m, 2H), 3.59-3.62 (m, 1H), 3.69-3.74 (m, 1H), 3.84 (dt, J=7.09, 3.59 Hz, 1H), 7.05 (t, J=7.53 Hz, 1H), 7.14 (t, J=7.53 Hz, 1H), 7.25 (s, 1H), 7.37-7.45 (m, 3H), 7.59 (d, J=7.82 Hz, 1H), 7.78 (dd, J=8.90, 1.66 Hz, 1H), 7.89 (d, J=0.78 Hz, 1H).

5-Bromo-1H-indazol-3-amine

To a 250 mL round-bottom flask was added 5-bromo-2-fluorobenzonitrile (15.54 g, 77.7 mmol) and hydrazine (124 g, 3885 mmol). The reaction mixture was heated to 100° C. for 5 minutes. The hydrazine was then removed under reduced pressure to give 5-bromo-1H-indazol-3-amine (16.4 g, 99.5% yield). MS m/z: 213 (M+1).

5-Bromo-N,N-dimethyl-1H-indazol-3-amine

To a 25 mL round-bottom flask, was added 5-bromo-1H-indazol-3-amine (2.0 g, 9432 μmol), 2.0 M iodomethane in tert-butyl methyl ether (587 μL, 9432 μmol), 1.5 g of Na$_2$CO$_3$, and 5 mL of DMF. The reaction mixture was heated to 80° C. for 6 hours. The reaction mixture was then diluted with 30 mL of water and extracted twice with 50 mL of EtOAc. The organic layers were combined, concentrated, and purified by a silica gel column chromatography separation on an ISOC instrument, eluting with 0-60% EtOAc in hexane to give 5-bromo-N,N-dimethyl-1H-indazol-3-amine (45 mg, 2.0% yield), MS m/z: 241 (M+1); and 5-bromo-N-methyl-1H-indazol-3-amine (550 mg, 26% yield), MS m/z: 227 (M+1).

tert-Butyl 5-bromo-3-(tert-butoxycarbonyl)-1H-indazole-1-carboxylate

To a 25 mL round-bottom flask was added (Boc)$_2$O (386 mg, 1769 μmol), 5-bromo-N-methyl-1H-indazol-3-amine (200 mg, 885 μmol), N,N-dimethylpyridin-4-amine (216 mg, 1769 μmol), 1 mL of TEA, and 3 mL of MeCN. The reaction mixture was stirred for 15 hours and then concentrated and purified with silica gel column chromatography, eluting with 0-20% EtOAc/hexane to give tert-butyl 5-bromo-3-(tert-butoxycarbonyl)-1H-indazole-1-carboxylate (330 mg, 87.5% yield). $^1$H NMR (400 MHz, CDCl$_3$) δ ppm 1.46 (s, 9H), 1.71 (d, J=1.57 Hz, 9H), 3.44 (d, J=1.76 Hz, 3H), 7.56-7.60 (m, 1H), 7.85 (s, 1H), 7.99 (d, J=8.80 Hz, 1H).

Example 46

6-(2-((S)-2-amino-3-(3-(trifluoromethyl)phenyl)propylamino)thiazol-5-yl)benzo[d]oxazol-2(3H)-one

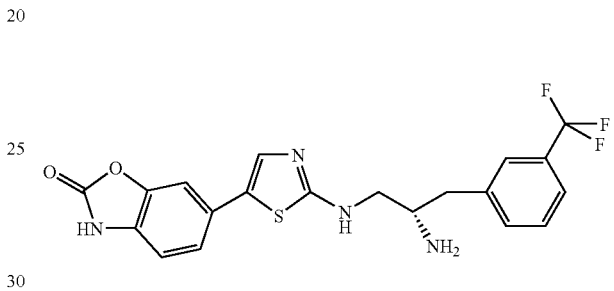

The title compound was synthesized using a procedure similar to that used in Example 36. MS m/z: 435 (M+1). $^1$H NMR (400 MHz, CD$_3$OD): δ ppm 3.12-3.34 (m, 2H), 3.46-3.52 (m, 1H), 3.54 (s, 2H), 3.60-3.65 (m, 1H), 3.78 (br s, 1H), 6.87 (d, J=7.82 Hz, 1H), 7.28 (s, 2H), 7.37(s, 1H), 7.52 (d, J=8.22 Hz, 2H), 7.69 (d, J=8.02 Hz, 2H).

Example 47

5-(2-((S)-2-amino-3-(4-(trifluoromethyl)phenyl)propylamino)thiazol-5-yl)-3-methylindolin-2-one

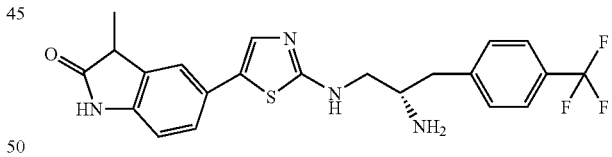

The title compound was synthesized using a procedure similar to that used for Example 36 using 5-bromo-3-methylindolin-2-one as one of the starting material that led to the product. 5-bromo-3-methylindolin-2-one was prepared using commercially available 5-bromoindolin-2-one as the starting material. MS m/z: 447 (M+1). $^1$H NMR (400 MHz, CD$_3$OD): δ ppm 1.45 (d, J=7.63 Hz, 3H), 3.06-3.17 (m, 2H), 3.47 (q, J=7.63 Hz, 1H), 3.54-3.69 (m, 2H), 3.81-3.88 (m, 1H), 6.90 (d, J=8.22 Hz, 1H), 7.29 (dd, J=8.02, 1.17 Hz, 1H), 7.37-7.41 (m, 2H), 7.54 (d, J=8.22 Hz, 2H), 7.69 (d, J=8.02 Hz, 2H).

5-Bromo-3-methylindolin-2-one

To a 250 mL round-bottom flask, was added 5-bromoindolin-2-one (2 g, 9 mmol), N,N'-tetramethylethylenediamine (4 mL, 28 mmol) and 70 mL of THF. The reaction mixture

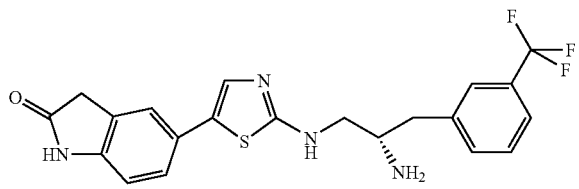

was cooled to −78° C. 2.5 M n-butyllithium in hexanes (8.4 mL, 21 mmol) was then added slowly to the reaction mixture. The reaction mixture was stirred for 15 hours, 5 mL of saturated NH$_4$Cl solution was added to the reaction mixture, and then the reaction mixture was extracted twice with 30 mL of EtOAc. The combined organic layers were concentrated and purified with silica gel column chromatography, eluting with 0-40% EtOAc/hexane to give 5-bromo-3-methylindolin-2-one (0.37 g, 17% yield). MS m/z: 227 (M+1).

Example 48

N-((S)-2-amino-3-(4-(trifluoromethyl)phenyl)propyl)-5-(1H-indazol-6-yl)thiazol-2-amine

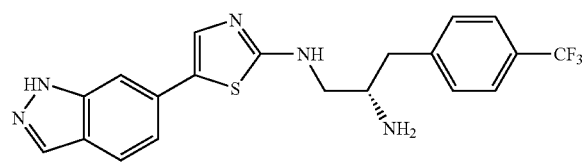

The title compound was synthesized using a procedure similar to that described in Example 42 using 6-bromo-1H-indazole as one of the starting material that led to the product. 6-bromo-1H-indazole was prepared using commercially available 4-bromo-2-fluorobenzaldehyde. LCMS (M+H) 418.1 calc. for C$_{20}$H$_{18}$F$_3$N$_5$S 417.5, $^1$H NMR (400 MHz, CD$_3$OD): δ ppm 7.99 (s, 1H), 7.72 (d, J=8.5 Hz, 1H), 7.63 (d, J=29 Hz, 2H), 7.32-7.42 (m, 3H), 7.29 (d, J=1.2 Hz, 1H), 3.46-3.49 (m, 2H), 3.30-3.35 (m, 1H), 2.85-2.98 (m, 3H).

6-bromo-1H-indazole

To a 100 mL round-bottomed flask was added hydrazine (30 mL, 832 mmol) and 4-bromo-2-fluorobenzaldehyde (4.69 g, 23 mmol). The solution was stirred at 125° C. for 3 hours. After cooling to ambient temperature, the solution was concentrated under reduced pressure. The solution was quenched by pouring it into a mixture of ice water (100 mL), and then extracting with EtOAc (3×100 mL). The organic layers were combined, dried over sodium sulfate, and filtered. The solution was evaporated to dryness, and adsorbed onto silica gel. The crude product was purified using column chromatography through a Redi-Sep® pre-packed silica gel column (40 g), eluting with a gradient of 0% to 100% EtOAc in hexanes, to provide 6-bromo-1H-indazole (4.6 g, 18 mmol, 76% yield). LCMS (M+H) 197.9 calc. for C$_7$H$_5$BrN$_2$ 197.0, $^1$H NMR (400 MHz, CD$_3$OD): δ ppm 8.03 (s, 1H), 7.67-7.72 (2H, m), 7.24-7.26 (m, 1H).

Example 49

(S)-4-(2-(2-amino-3-(4-(trifluoromethyl)phenyl)propylamino)thiazol-5-yl)benzamide

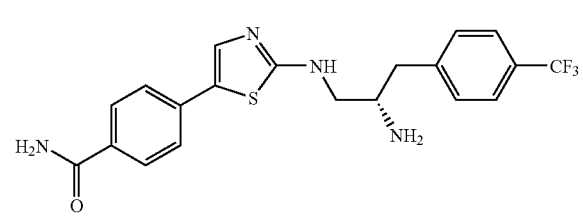

The title compound was synthesized using a procedure similar to that described for Example 36. LCMS (M+H) 421 calc. for C$_{20}$H$_{20}$F$_3$N$_4$OS 421.45. $^1$H NMR (400 MHz, DMSO-d$_6$) δ ppm 7.83 (d, J=8.4 Hz, 2H), 7.60 (d, J=8.4 hz, 2H), 7.50-7.44 (m, 5H), 3.40 (dd, J=4.4, 12.2 Hz, 1H), 3.36-3.25 (m, 2H), 2.96 (dd, J=4.8, 13.3 Hz, 1H), 2.72 (dd, J=7.2, 13.3 Hz, 1H).

Example 50

5-(2-((S)-2-amino-3-(4-(trifluoromethyl)phenyl)propylamino)thiazol-5-yl)-1H-indazol-3-amine

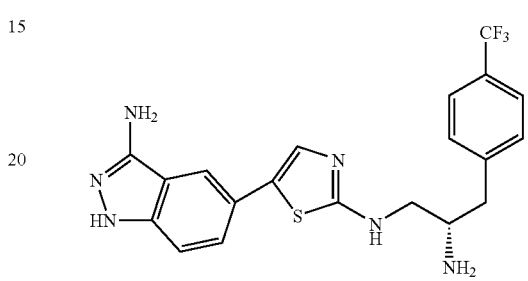

The title compound was synthesized using the procedure shown in Scheme 11. 2-Fluoro-5-(4,4,5,5-tetramethyl-1,3,2-dioxaborolan-2-yl)benzonitrile was prepared as shown in Scheme 1 using commercially available 5-bromo-2-fluorobenzonitrile as the starting material. (S)-tert-butyl 1-(N-(5-bromothiazol-2-yl)-tert-butoxylcarbonylamino)-3-(4-(trifluoromethyl)phenyl)propan-2-ylcarbamate was prepared as described in Example 36.

Scheme 11

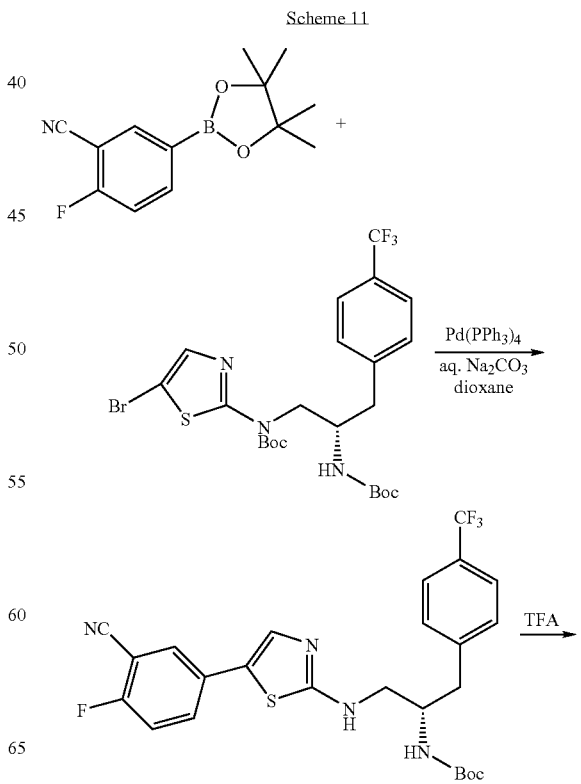

89

-continued

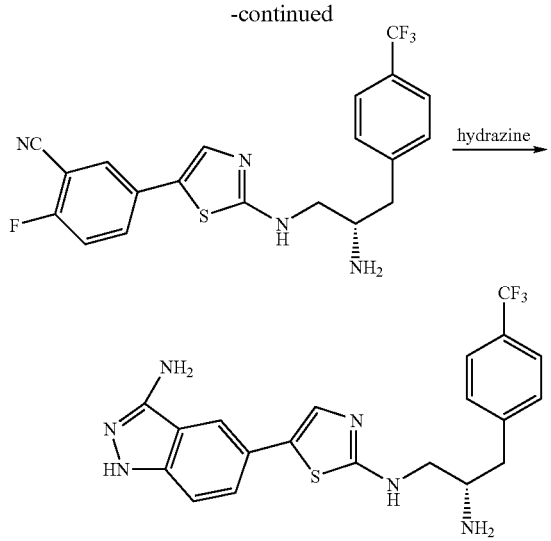

5-(2-((S)-2-amino-3-(4-(trifluoromethyl)phenyl)
propylamino)thiazol-5-yl)-2-fluorobenzonitrile To a solution of (S)-tert-butyl 1-(N-(5-bromothiazol-2-yl)-tert-butoxylcarbonylamino)-3-(4-(trifluoromethyl)phenyl)propan-2-ylcarbamate (0.20 g, 0.34 mmol) in 3 mL of dioxane in a microwave safe tube, was added 2-fluoro-5-(4,4,5,5-tetramethyl-1,3,2-dioxaborolan-2-yl)benzonitrile (0.13 g, 0.52 mmol), sodium carbonate, 2 M in water (0.69 mL, 1.4 mmol), and tetrakis(triphenylphosphine) palladium (0.020 g, 0.017 mmol). The mixture was purged with nitrogen for 30 seconds and the tube was sealed. The tube was then heated to 120° C. in a Personal Chemistry microwave unit for 20 minutes. The mixture was diluted with 5 mL of water and extracted twice with 8 mL of EtOAc. The combined organic extracts were washed with 7 mL of brine and dried over MgSO$_4$. Filtration and concentration under reduced pressure afforded tert-butyl (S)-1-(5-(3-cyano-4-fluorophenyl)thiazol-2-ylamino)-3-(4-(trifluoromethyl)phenyl)propan-2-ylcarbamate, mixed with the other two products. The crude mixture was carried on to the next reaction without any further purification.

To a solution of tert-butyl (S)-1-(5-(3-cyano-4-fluorophenyl)thiazol-2-ylamino)-3-(4-(trifluoromethyl)phenyl)propan-2-ylcarbamate (0.18 g, 0.35 mmol) in 7 mL of DCM was added TFA (0.40 mL, 5.2 mmol). After 30 minutes, 2 mL of additional TFA was added. The mixture was stirred for 30 minutes and was then concentrated under reduced pressure. The residue was taken up in 30 mL of 1:1 EtOAc to 2 N aqueous Na$_2$CO$_3$. The mixture was partitioned in a separatory funnel, and the aqueous portion was extracted with 25 mL of EtOAc. The combined organic extracts were washed with brine and dried over MgSO$_4$. Filtration and concentration under reduced pressure, followed by flash chromatography on silica gel (2.5% to 10% MeOH/DCM) afforded 5-(2-((S)-2-amino-3-(4-(trifluoromethyl)phenyl)propylamino)thiazol-5-yl)-2-fluorobenzonitrile (0.14 g, 0.33 mmol, 96% yield) as a yellow solid. $^1$H NMR (400 MHz, CD$_3$OD) δ ppm 7.83 (dd, J=5.8, 2.4 Hz, 1H), 7.76 (ddd, J=8.7, 5.0, 2.4 Hz, 1H), 7.68 (d, J=8.2 Hz, 2H), 7.52 (d, J=7.8 Hz, 2H), 7.48 (s, 1H), 7.35 (t, J=9.0 Hz, 1H), 3.84-3.78 (m, 1H), 3.68-3.63 (m, 1H), 3.55-3.47 (m, 1H), 3.14-3.04 (m, 2H) LCMS (M+H) 421 calc. for C$_{20}$H$_{19}$F$_3$N4OS 420.43.

90

5-(2-((S)-2-amino-3-(4-(trifluoromethyl)phenyl)
propylamino)thiazol-5-yl)-1H-indazol-3-amine 5-(2-((S)-2-amino-3-(4-(trifluoromethyl)phenyl)propylamino)thiazol-5-yl)-2-fluorobenzonitrile (0.042 g, 0.100 mmol) was taken up in hydrazine (0.50 mL) in a microwave safe tube. The tube was sealed and heated in a Personal Chemistry microwave unit to 100° C. for 5 minutes. The hydrazine was then removed under reduced pressure, and the residue was purified by HPLC (95:5 to 70:30 water:MeCN over 45 minutes), affording 5-(2-((S)-2-amino-3-(4-(trifluoromethyl)phenyl)propylamino)thiazol-5-yl)-1H-indazol-3-amine (0.027 g, 0.062 mmol, 62% yield) as a yellow amorphous solid. $^1$H NMR (400 MHz, CD$_3$OD) δ ppm 7.75-7.71 (m, 1H), 7.67-7.60 (m, 2H), 7.51-7.45 (m, 3H), 7.34-7.25 (m, 2H), 3.64-3.48 (m, 2H), 3.42-3.34 (m, 1H), 3.09-3.00 (m, 1H), 2.89 (dd, J=13.8, 7.1 Hz, 1H), 1.95-1.91 (m, 1H). HRMS (M+H) for C$_{25}$H$_{27}$F$_3$N$_6$O$_2$S calc. 433.14168, obs. 433.14225.

Example 51

5-(2-((S)-2-amino-3-(4-(trifluoromethyl)phenyl)
propylamino)thiazol-5-yl)benzo[d]isoxazol-3-amine

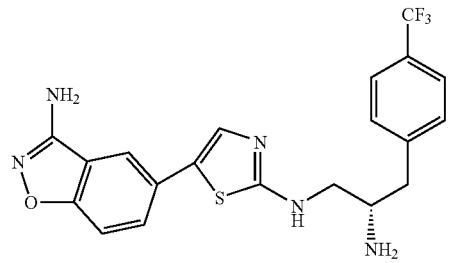

The title compound was synthesized using the procedure shown in Scheme 12 using the same intermediate 5-(2-((S)-2-amino-3-(4-(trifluoromethyl)phenyl)propylamino)thiazol-5-yl)-2-fluorobenzonitrile as in Example 50.

Scheme 12

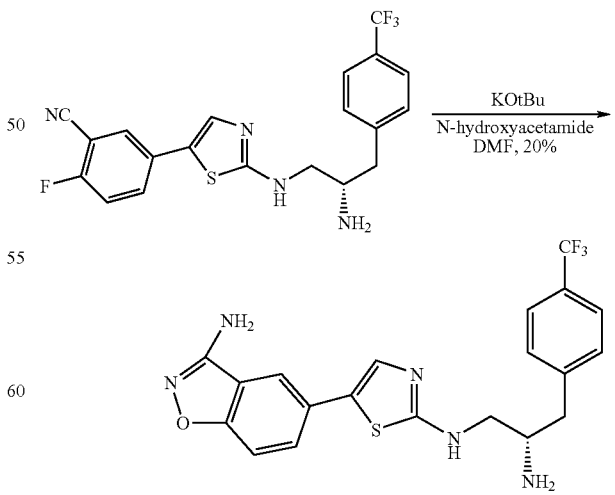

To a solution of N-hydroxyacetamide (0.02 g, 0.3 mmol) in 1.5 mL of DMF, was added potassium tert-butoxide (1.0 M in THF (0.3 mL, 0.3 mmol)). The mixture was stirred for 30 minutes and then 5-(2-((S)-2-amino-3-(4-(trifluoromethyl)phenyl)-propylamino)thiazol-5-yl)-2-fluorobenzonitrile (0.086 g, 0.2 mmol) was added in 1.5 mL of DMF. The mixture was stirred for 12 hours and was then diluted with 20 mL of EtOAc. The organic layer was washed with 10 mL of brine and was then dried over MgSO$_4$. Filtration and concentration under reduced pressure, followed by HPLC purification (95:5 to 70:30 water:MeCN over 50 minutes) afforded 5-(2-((S)-2-amino-3-(4-(trifluoromethyl)phenyl)-propylamino)thiazol-5-yl)benzo[d]isoxazol-3-amine (0.018 g, 0.04 mmol, 20% yield) as an amorphous solid. $^1$H NMR (400 MHz DMSO-d$_6$) δ ppm 7.84 (s, 1H), 7.63-7.67 (m, 1H), 7.65 (d, 9.1 Hz, 2H), 7.50 (d, J=8.0 Hz, 2H), 7.40 (d, J=8.7 Hz, 1H), 7.25 (s, 1H), 5.51 (s, 2H), 3.52-3.43 (m, 2H), 3.38-3.32 (m, 1H), 3.03 (dd, J=5.3, 13.7 Hz, 1H), 2.82 (dd, J=7.5, 13.7 Hz, 1H). HRMS (M+H) for C$_{20}$H$_{18}$F$_3$N$_5$OS calc. 434.12569, obs. 434.12614.

Example 52

6-(2-((S)-2-amino-3-(4-(trifluoromethyl)phenyl)propylamino)thiazol-5-yl)-1H-indazol-3-amine

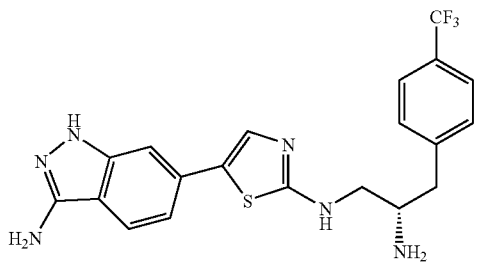

The title compound was synthesized using a procedure similar to that used to prepare Example 50 using commercially available 4-bromo-2-fluorobenzonitrile as the starting material in stead of 5-bromo-2-fluorobenzonitrile. LCMS (M+H) 433 calc. for C$_{20}$H$_{20}$F$_3$N$_6$S 433.47. $^1$H NMR (400 MHz, CD$_3$OD) δ ppm 7.64-7.61 (m, 3H), 7.47 (d, J=8.1 Hz, 2H), 7.38 (s, 1H), 7.25 (s, 1H), 7.14 (d, J=9.7 Hz, 1H), 3.47-3.42 (m, 2H), 3.15-3.10 (m, 1H), 3.02-2.97 (m, 1H), 2.80-2.77 (m, 1H).

Example 53

6-(2-((S)-2-amino-3-(4-(trifluoromethyl)phenyl)propylamino)thiazol-5-yl)-1-methyl-1H-indazol-3-amine

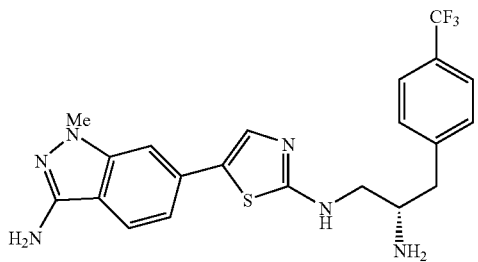

This compound was synthesized using a procedure similar to that of Example 52 using methyl hydrazine instead of hydrazine as the reagent in the last step. LCMS (M+H) 447 calc. for C$_{21}$H$_{22}$F$_3$N$_6$S 447.15. $^1$H NMR (400 MHz, CD$_3$OD) δ ppm 7.62 (d, J=8.4 Hz, 3H), 7.47 (d, J=8.0 Hz, 2H), 7.43 (s, 1H), 7.27 (s, 1H), 7.13 (dd, J=8.5, 1.1 Hz, 1H), 3.78 (s, 3H), 3.5-3.0 (m, 3H), 2.97 (s, 1H), 2.76 (s, 1H).

Example 54

5-(2-((S)-2-Amino-3-(4-chlorophenyl)propylamino)thiazol-5-yl)indolin-2-one

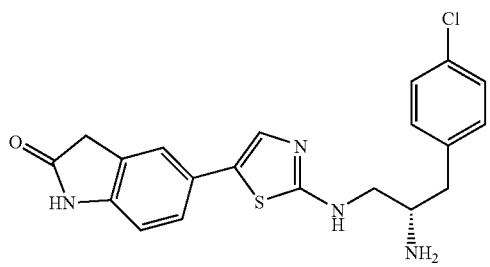

This compound was synthesized using a procedure similar to that of Example 1 and Example 36. The coupling reaction used (tBu$_2$PPh)$_2$PdCl$_2$ as the catalyst with KOAc as the base instead of Pd(PPh$_3$)$_4$ with Na$_2$CO$_3$ as the base as shown in Scheme 1. The reaction started with the commercially available 5-bromoindolin-2-one. LCMS (M+H) 399 calc. for C$_{20}$H$_{20}$ClN$_4$OS 399.1; $^1$H NMR (400 MHz, DMSO-d$_6$) δ ppm 10.57 (s, 1H), 7.89-7.83 (m, 1H), 7.56-7.35 (m, 7H), 6.95 (d, J=8.0 Hz, 1H), 3.66 (s, 2H), 3.44-3.37 (m, 1H), 3.30-3.22 (m, 2H), 2.91 (dd, J=13.3, 4.7 Hz, 1H), 2.73-2.66 (m, 1H).

Example 55

6-(2-((S)-2-Amino-3-(4-chlorophenyl)propylamino)thiazol-5-yl)benzo[d]oxazol-2(3H)-one

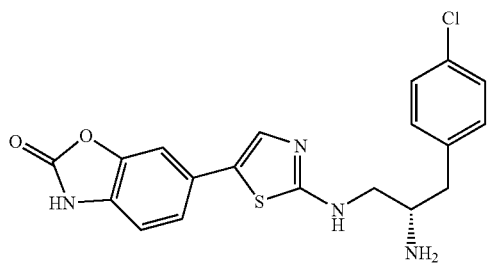

This compound was synthesized using a procedure similar to that of Example 544. It started with the commercially available 6-chlorobenzo[d]oxazol-2(3H)-one. LCMS (M+H) 401 calc. for C$_{19}$H$_{18}$ClN$_4$O$_2$S 401.1; $^1$H NMR (400 MHz, CD$_3$OD) δ ppm 7.35-7.20 (m, 7H), 7.05-7.02 (m, 1H), 3.50-3.10 (m, 3H), 2.87 (dd, J=13.5, 5.9 Hz, 1H), 2.66 (d, J=13.9 Hz, 1H).

Example 56

N-((S)-2-amino-3-(4-(trifluoromethyl)phenyl)propyl)-5-(isoquinolin-6-yl)-4-((methylamino)methyl)thiazol-2-amine

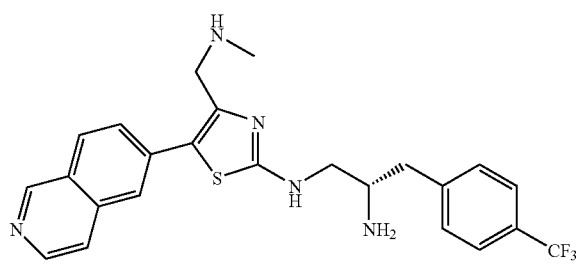

This compound was synthesized in a similar manner to that shown in Scheme 1 using N-((2-acetylamino-5-bromothiazol-4-yl)methyl)-2,2,2-trifluoro-N-methylacetamide (synthesized as shown in Scheme 13) as the starting material to couple with the isoquinolin-6-ylboronic acid. LCMS (M+H$^+$) 472.2 calc. for $C_{24}H_{25}F_3N_5S$ 472.2; $^1$H NMR (400 MHz, CD$_3$OD) δ ppm 2.82 (s, 3H), 3.21 (m, 2H), 3.75 (m, 1H), 3.89 (m, 2H), 4.46 (s, 2H), 7.62 (d, J=8.0 Hz, 2H) 7.70 (d, J=8.0 Hz, 2H), 8.02 (d, J=8.0 Hz, 1H), 8.29 (s, 1H), 8.55 (m, 3H), 9.75 (s, 1H).

Scheme 13

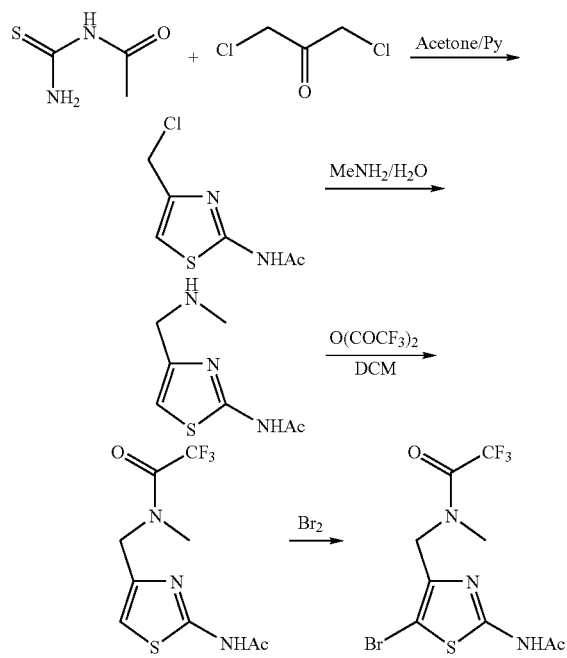

N-((2-acetylamino-5-bromothiazol-4-yl)methyl)-2,2,2-trifluoro-N-methylacetamide 1,3-dichloroacetone (19.8 mL, 216 mmol) and acetothiourea (25.5 g, 216 mmol) were mixed in 200 mL acetone. Pyridine (20 mL) was then added to the solution. A light yellow clear solution formed. The solution was heated to reflux for 30 minutes. After removing most of the solvent under a reduced pressure, the remaining residue was mixed with EtOAc and water. The aqueous phase pH was adjusted to pH=2 with 2 N HCl. After partition, the aqueous phase was extracted twice with EtOAc. The combined EtOAc solution was washed twice with saturated aqueous NH$_4$Cl and dried over anhydrous sodium sulfate. After removing the solvent under reduced pressure, a white solid (19.5 g, 102 mmol) was obtained as the crude product N-(4-(chloromethyl)thiazol-2-yl)acetamide.

To a stirred aqueous aminomethane 40% solution (10 mL, 290 mmol), was added dropwise over 30 minutes the crude N-(4-(chloromethyl)thiazol-2-yl)acetamide (5 g, 26 mmol) in THF (100 mL) through an addition funnel. After addition, the mixture was stirred for an additional 30 minutes. After removing most of the solvent under a reduced pressure, the aqueous solution was mixed with sodium chloride to saturation and was then extracted three times with EtOAc. The EtOAc solution was dried over sodium sulfate. After removing the solvent under a reduced pressure, a yellow oil was obtained of the crude product (2.9 g, 16 mmol) N-(4-((methylamino)methyl)thiazol-2-yl)acetamide.

Crude N-(4-((methylamino)methyl)thiazol-2-yl)acetamide (2.7 g, 15 mmol) was dissolved in 50 mL DCM. To this solution was added trifluoroacetic acid anhydride (6.1 mL, 44 mmol). The mixture was stirred for 10 minutes. To this reaction solution, Br$_2$ (0.77 mL, 15 mmol) was added dropwise. After addition, the DCM solution was washed twice with water and twice with saturated sodium bicarbonate. The DCM solution was then dried over sodium sulfate. After removing the solvent, the residue was subjected to a silica gel column chromatograph separation using 20% EtOAc in hexane to yield an off-white solid as the pure product (1.84 g, 5.1 mmol) N-((2-acetylamino-5-bromothiazol-4-yl)methyl)-2,2,2-trifluoro-N-methylacetamide. LCMS (M+H$^+$) 360.0 calc. for $C_9H_{10}BrF_3N_3O_2S$ 360; $^1$H NMR (400 MHz, CDCl$_3$) δ ppm 2.26 (s, 3H), 3.09 (s, 3H), 4.64 (s, 2H), 9.13 (s, 1H).

Example 57

6-(2-((S)-2-amino-3-(4-(trifluoromethyl)phenyl)propylamino)thiazol-5-yl)-1-methyl-1H-benzo[d]imidazol-2(3H)-one

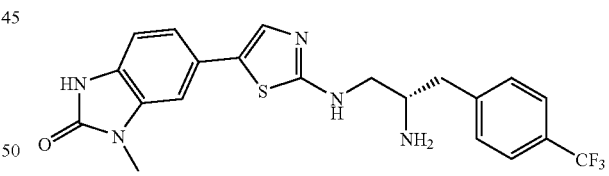

This compound was synthesized using a procedure similar to that shown in Scheme 1 using (S)-N-(5-bromothiazol-2-yl)-N-(2-(1,3-dioxoisoindolin-2-yl)-3-(4-(trifluoromethyl)phenyl)propyl)acetamide as the starting material to couple with 1-methyl-6-(4,4,5,5-tetramethyl-1,3,2-dioxaborolan-2-yl)-1H-benzo[d]imidazol-2(3H)-one, which was prepared in a manner similar to that shown in Scheme 1 using 6-bromo-1-methyl-1H-benzo[d]imidazol-2(3H)-one as the starting material to react with bis(pinacolato)diboron. 6-bromo-1-methyl-1H-benzo[d]imidazol-2(3H)-one was prepared by treating tert-butyl 5-bromo-2-oxo-2,3-dihydrobenzo[d]imidazole-1-carboxylate with dimethyl sulfate in the presence of sodium carbonate followed by a crystallization step in the wet MeOH. tert-Butyl 5-bromo-2-oxo-2,3-dihydrobenzo[d]imidazole-1-carboxylate was prepared as described by Puwen Zhang, et. al., in Bioorganic & Medicinal Chemistry Letters 11 (2001) 2747-2750. LCMS (M+H⁺) 448.1 calc. for $C_{21}H_{21}F_3N_5OS$ 448.1; ¹H NMR (400 MHz, $CD_3OD$) δ ppm 2.72 (dd, J=13.40, 7.53 Hz, 1H), 2.96 (dd, J=13.60, 5.38 Hz, 1H), 3.23-3.28 (m, 2H), 3.36 (m, 1H), 3.40 (s, 3H), 7.02 (d, J=8.22 Hz, 1H), 7.12 (dd, J=8.22, 1.37 Hz, 1H), 7.19 (d, J=1.37 Hz, 1H), 7.45 (d, J=8.02 Hz, 2H) 7.61 (d, J=8.02 Hz, 2H).

Example 58

6-(2-((S)-2-amino-3-(4-(trifluoromethyl)phenyl)propylamino)-4-(methoxymethyl)thiazol-5-yl)-1-methyl-1H-benzo[d]imidazol-2(3H)-one

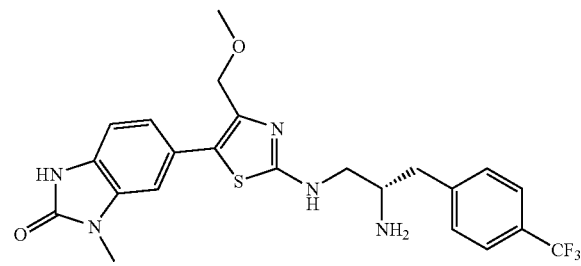

This compound was prepared using a procedure similar to that used in Example 57 using the same starting 5-bromothiazole intermediate used in Example 14. LCMS (M+H⁺) 491.1 calc. for $C_{23}H_{25}F_3N_5O_2S$ 491.1; ¹H NMR (400 MHz, $CD_3OD$) δ ppm 3.12 (dd, J=6.94, 7.47 Hz, 2H), 3.40 (s, 3H), 3.42 (s, 3H), 3.57 (m, 1H), 3.68 (m, 1H), 3.85 (m, 1H), 4.33 (s, 2H), 7.12 (bs, 2H), 7.14 (s, 1H), 7.55 (d, J=8.02 Hz, 2H) 7.69 (d, J=8.02 Hz, 2H).

Example 59

6-(2-((S)-2-amino-3-(4-(trifluoromethyl)phenyl)propylamino)-4-(methoxymethyl)thiazol-5-yl)benzo[d]oxazol-2(3H)-one

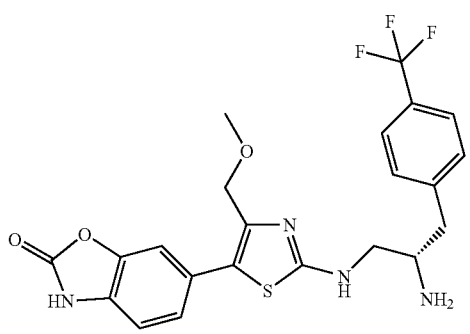

The title compound was prepared using a procedure similar to that used to prepare Example 58. LCMS (M+H⁺) 479.1 calc. for $C_{22}H_{22}F_3N_4O_3S$ 479.1.

Example 60

N-((S)-2-amino-3-(4-(trifluoromethyl)phenyl)propyl)-4-(pyridin-2-yl)-5-(thiazolo[5,4-c]pyridin-2-yl)thiazol-2-amine

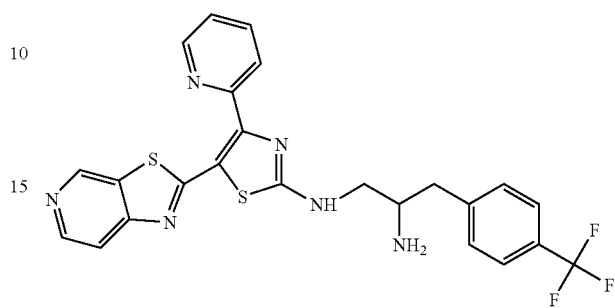

The title compound was prepared using a procedure similar to that used to prepare Example 17 as shown in Scheme 6. LCMS (M+H) 513.1 calc. for $C_{24}H_{20}F_3N_6S_2$ 513.11. ¹H NMR (400 MHz, $CD_3OD$) δ ppm 9.42 (s, 1H), 8.90 (d, J=4.9 Hz, 1H), 8.61 (d, J=6.6 Hz, 1H), 8.19 (m, 1H), 8.08 (m, 1H), 8.01 (m, 1H), 7.71 (d, J=8.2 Hz, 2H), 7.57 (m, 3H), 3.98 (m, 1H), 3.91 (dd, J=4.2, 14.5 Hz, 1H), 3.69 (dd, J=7.4, 14.5 Hz, 1H), 3.57 (m, 1H), 3.45 (m, 1H), 3.14 (m, 2H).

Example 61

2-((S)-2-amino-3-(4-(trifluoromethyl)phenyl)propylamino)-5-(2-oxoindolin-5-yl)thiazole-4-carbonitrile

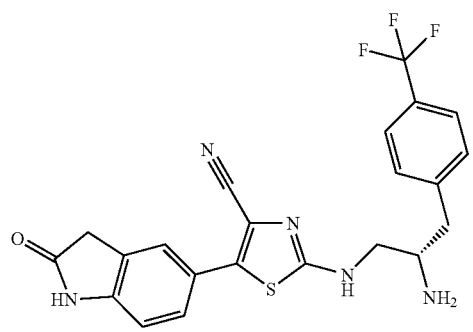

The title compound was prepared using a procedure similar to that used to prepare Example 1 as shown in Scheme 1. LCMS (M+H) 458.1 calculation: 458.1. The starting (S)-tert-butyl 1-(N-(4-cyano-5-bromothiazol-2-yl)-tert-butoxylcarbonylamino)-3-(4-(trifluoromethyl)phenyl)propan-2-ylcarbamate was prepared as described in Scheme 10 using tert-butyl 5-bromo-4-cyanothiazol-2-ylcarbamate as the starting material. tert-Butyl 5-bromo-4-cyanothiazol-2-ylcarbamate was synthesized as shown in Scheme 14.

Scheme 14

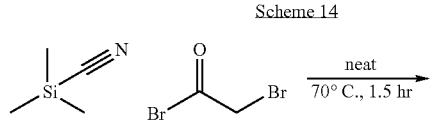

97

-continued

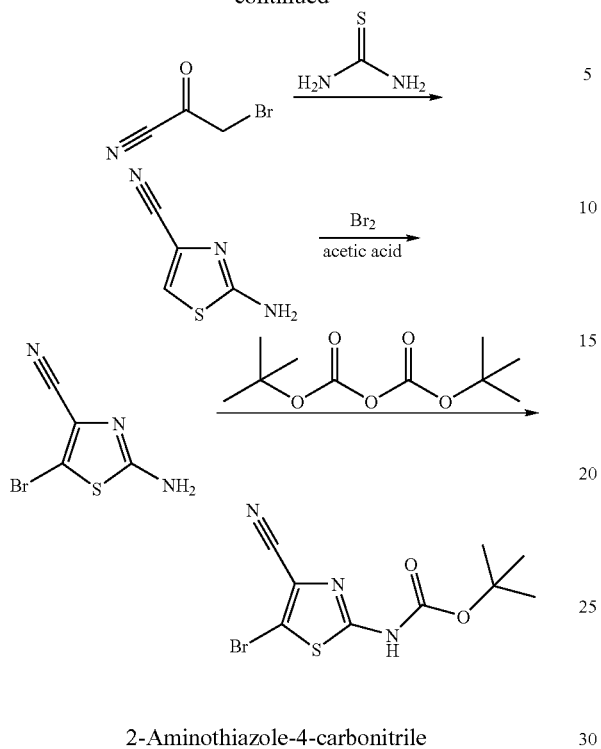

2-Aminothiazole-4-carbonitrile

Bromoacetyl bromide (15.0 g, 74.3 mmol) was added dropwise into trimethylsilyl cyanide (8.85 g, 89.2 mmol). After addition, the reaction mixture was heated to 70° C. for 90 minutes. 50 mL ACN was added to the reaction and then thiourea (6.78 g, 89.16 mmol) was added to the reaction. The reaction was completed after a 2 hour reflux time. Saturated sodium bicarbonate was added to the reaction mixture, and the reaction mixture was extracted with EtOAc (2×100 mL). The organic layers were combined, washed with brine, and dried over sodium sulfate. No further purification was necessary. LCMS (API-ES) m/z (%): 126.2 (100%, M$^+$+H).

2-Amino-5-bromothiazole-4-carbonitrile

2-Aminothiazole-4-carbonitrile (1.40 g, 11.18 mmol) was dissolved in 20 mL AcOH in a 150 mL round bottom flask. Br$_2$ (1.78 g, 11.18 mmol) was added to the reaction in a dropwise manner. After stirring at room temperature for 10 minutes, AcOH was removed under vacuum. Saturated sodium bicarbonate was added to the reaction mixture, and the mixture was extracted with EtOAc (2×100 mL). The combined organic layers were washed with brine and dried over sodium sulfate. 2-amino-5-bromothiazole-4-carbonitrile (1.20 g, yield: 53%) was obtained. LCMS (API-ES) m/z (%): 205.9 (100%, M$^+$+2H).

Tert-butyl 5-bromo-4-cyanothiazol-2-ylcarbamate

2-Amino-5-bromothiazole-4-carbonitrile (1.20 g, 5.88 mmol) was dissolved in 50 mL of dioxane. Di-tert-butyl dicarbonate (2.56 g, 11.76 mmol) and N,N-dimethylpyridin-4-amine (35.9 mg, 0.295 mmol) were added to the reaction mixture. The reaction was complete after heating at 75° C. for 30 minutes. The solvent was evaporated under reduced pressure. Saturated sodium bicarbonate was added into the reaction mixture, and the mixture was extracted with EtOAc

98

(2×100 mL). The organic layers were combined, washed with brine, and dried over sodium sulfate. The crude product was purified by column chromatography (condition: 15% EtOAc in hexane). LCMS (API-ES) m/z (%): 303.9 (100%, M$^+$).

Examples 62-63

Examples 62-63 were synthesized using a procedure similar to that used for Example 61.

Example 62

2-((S)-2-amino-3-(4-(trifluoromethyl)phenyl)propylamino)-5-(3-methyl-2-oxo-2,3-dihydro-1H-benzo[d]imidazol-5-yl)thiazole-4-carbonitrile LCMS (M+H) 473.1 calculation: 473.1.

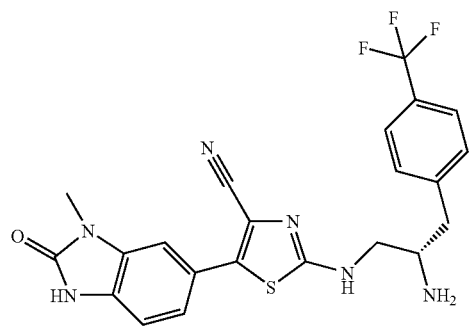

Example 63

2-((S)-2-amino-3-(4-(trifluoromethyl)phenyl)propylamino)-5-(isoquinolin-6-yl)thiazole-4-carbonitrile LCMS (M+H) 454.1 calculation: 454.1.

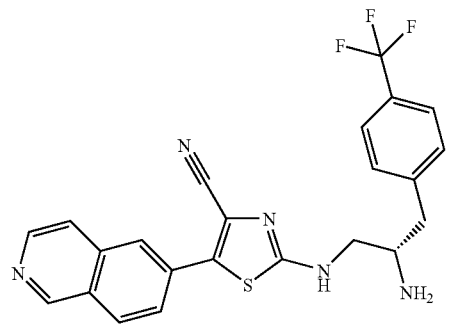

Example 64

N-((S)-2-amino-3-(4-(trifluoromethyl)phenyl)propyl)-5-(phthalazin-6-yl)thiazol-2-amine The title compound was synthesized as shown in Scheme 15.

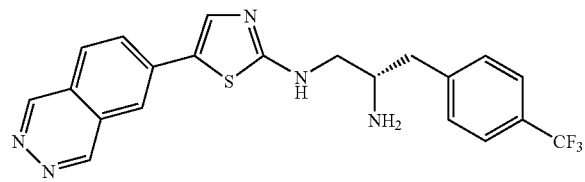

reaction mixture was quenched with a saturated NH₄Cl solution (300 mL). The layers were separated, and the aqueous layer was extracted with ether (3×100 mL). The organic layers were combined, washed with brine (300 mL), dried over MgSO₄, filtered, and concentrated. The crude product was adsorbed onto a plug of silica gel and chromatographed through a Redi-Sep pre-packed silica gel column (330 g), eluting with a gradient of 10% to 20% EtOAc in hexanes, to provide the title compound (30 g, 81%) LCMS (M+H⁺) 490.1 calc. for $C_{20}H_{38}N_2O_2SSn$ 490.1; ¹H NMR (400 MHz,

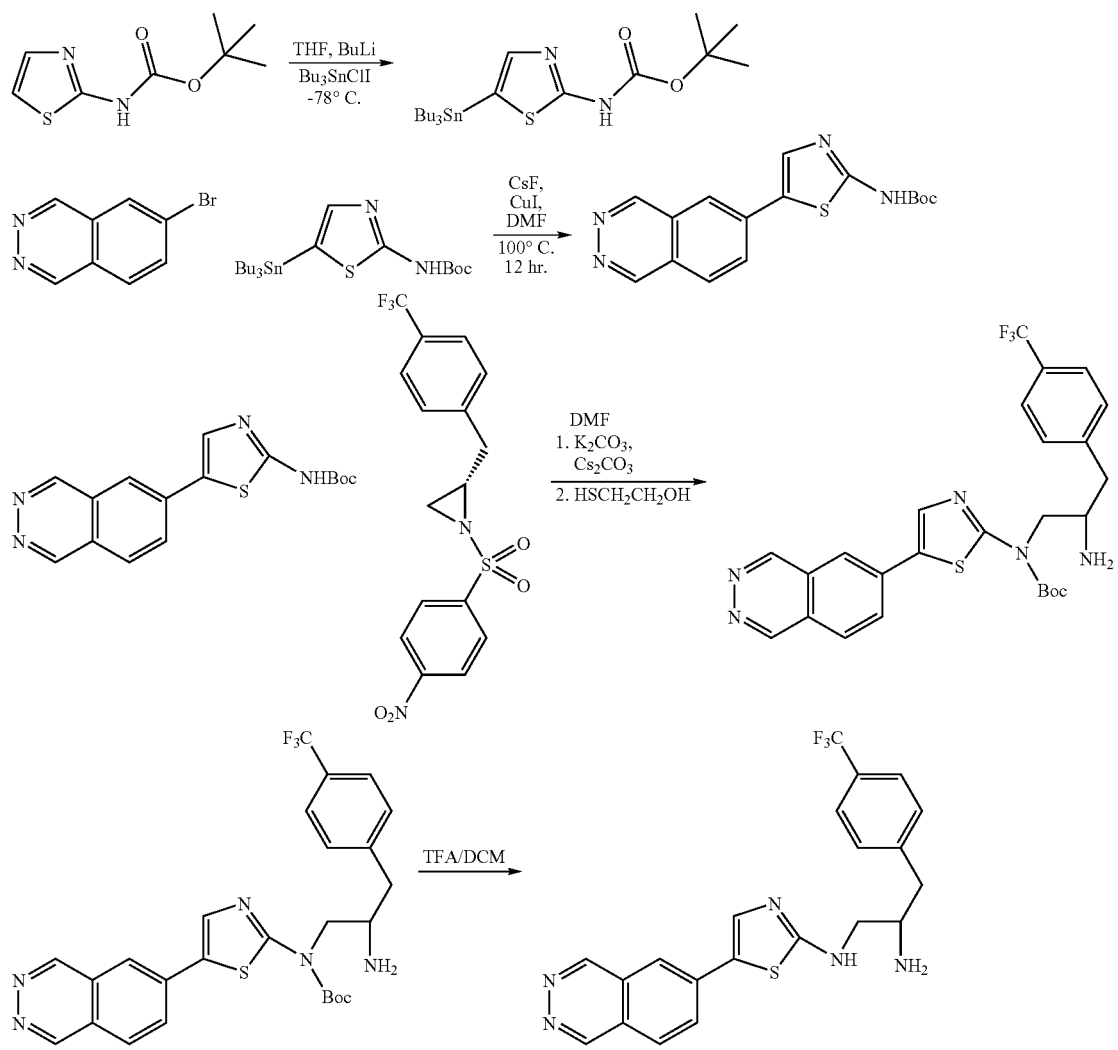

Tert-butyl 5-(tributylstannyl)thiazol-2-ylcarbamate

A solution of tert-butyl thiazol-2-ylcarbamate (15.0 g, 75 mmol), in THF (200 mL) was stirred at −78° C. and then n-butyl lithium (63 mL, 157 mmol) was added dropwise over 15 minutes. The resulting solution was stirred at −78° C. for 30 minutes, and then tributyltin chloride (22 mL, 82 mmol) was then added dropwise. The resulting pale yellow mixture was stirred for 30 minutes at −78° C. The bath was then removed, and the mixture was allowed to warm to room temperature. The reaction was then stirred for 2.5 hours. The CDCl₃) δ ppm 7.31 (s, 1H), 1.59 (s, 9H), 1.30 (tt, 6H), 1.54 (t, 6H), 1.10 (qt, 6H), 0.80 (t, 9H).

Tert-butyl 5-(phthalazin-6-yl)thiazol-2-ylcarbamate

A glass microwave reaction vessel was charged with 6-bromophthalazine (1.0 g, 5 mmol), tert-butyl 5-(tributylstannyl)thiazol-2-ylcarbamate (4.0 g, 7 mmol), DMF (4 mL), cesium fluoride (1.0 g, 10 mmol), copper(I) iodide (0.2 g, 1.0 mmol), and tetrakis(triphenylphosphine)palladium(0) (0.3 g, 0.2 mmol). The reaction mixture was stirred and heated at 100° C.

overnight. The mixture was diluted with DCM (20 mL) and water (5 mL) and filtered through Celite. The organic solution was evaporated under reduced pressure, and the residue was adsorbed onto a plug of silica gel and chromatographed through a Redi-Sep pre-packed silica gel column (40 g), eluting with a gradient of 5% to 10% MeOH in DCM to provide the title compound (1.19 g, 76%). LCMS (M+H$^+$) 329.3 calc. for $C_{16}H_{16}N_4O_2S$ 329.3; $^1$H NMR (400 MHz, CDCl$_3$) δ ppm 9.50 (s, J=13.69 Hz 1H), 9.46 (s, 1H), 8.01 (d, J=1.37, Hz 1H), 7.92 (d, J=8.41 Hz, 1H), 7.81 (s, 1H), 7.58 (s, 1H) 1.40 (s, 9H).

N-((S)-2-amino-3-(4-(trifluoromethyl)phenyl)propyl)-5-(phthalazin-6-yl)thiazol-2-amine A solution of tert-butyl 5-(phthalazin-6-yl)thiazol-2-ylcarbamate (0.320 g, 0.97 mmol) and Cs$_2$CO$_3$ (0.63 g, 1.9 mmol) in DMF was stirred at room temperature for 30 minutes. The resulting solution was treated dropwise with ((S)-2-(4-(trifluoromethyl)benzyl-1-(4-nitrophenylsulfonyl)aziridine in DMF, and was then stirred for 30 minutes. The reaction was treated in portions with K$_2$CO$_3$ (0.67 g, 4.9 mmol) and mercaptoethanol (0.23 g, 2.9 mmol) and stirred for 15 minutes. After removing the solvent under reduced pressure, the residue was adsorbed onto a plug of silica gel and chromatographed through a Redi-Sep pre-packed silica gel column (40 g), eluting with a gradient of 5% to 95% MeOH in DCM. The resulting residue was dissolved in DCM and treated with TFA to provide the title compound (0.100 g, 19% yield). LCMS (M+H$^+$) 430.6 calc. for $C_{21}H_{18}F_3N_5S$ 430.6; $^1$H NMR (400 MHz, CDCl$_3$-d) δ ppm 9.48 (s, 1H), 9.44 (s, 1H), 8.01 (d, 1H), 7.92 (d, 1H), 7.75 (s, 1H), 7.62 (sd, 3H), 7.35 (d, 2H), 3.92 (dd, 2H), 3.55 (dd, 1H), 3.25 (tt, 1H) 2.98 (dd, 1H), 2.89 (t, 2H), 2.72 (b, 1H).

Example 65

6-(2-((S)-2-amino-3-(4-(trifluoromethyl)phenyl)propylamino)thiazol-5-yl)phthalazin-1-ol

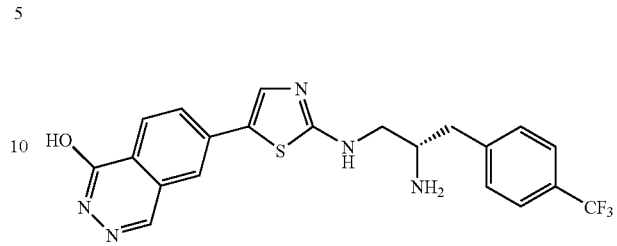

The title compound was prepared in a manner similar to that used for Example 64 using tert-butyl 5-(1-hydroxyphthalazin-6-yl)thiazol-2-ylcarbamate as the starting material. LCMS (M+H$^+$) 446.2 calc. for $C_{21}H_{18}F_3N_5SO$, 446.2; $^1$H NMR (400 MHz, CDCl$_3$) δ ppm 8.29 (s, 1H), 8.27 (d, 1H), 7.95 (d, 1H), 7.85 (s, 1H), 7.68 (s, 1H) 7.62 (d, 2H) 7.47 (d, 2H), 3.92 (dd, 2H), 3.55 (dd, 1H), 3.25 (tt, 1H) 2.98 (dd, 1H), 2.89 (t, 2H), 2.72 (b, 1H).

Example 66

N-((S)-2-amino-3-(3-chlorophenyl)propyl)-5-(isoquinolin-6-yl)thiazol-2-amine

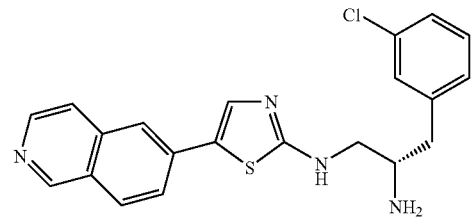

This compound was synthesized as shown in Scheme 16. LCMS (M+H$^+$) 395.1 calc. for $C_{21}H_{2}OClN_4S$ 395.1; $^1$H NMR (400 MHz, DMSO-d$_6$) δ ppm 9.19 (s, 1H), 8.44 (d, J=5.7 Hz, 1H), 8.09 (br s, 1H), 8.04 (d, J=8.0 Hz, 1H), 7.91 (dd, J=8.0, 1.8 Hz, 1H), 7.75-7.77 (m, 3H), 7.20-7.35 (m, 5H), 3.28 (m, 1H), 3.15 (m, 2H), 2.78 (m, 1H), 2.53 (m, 1H).

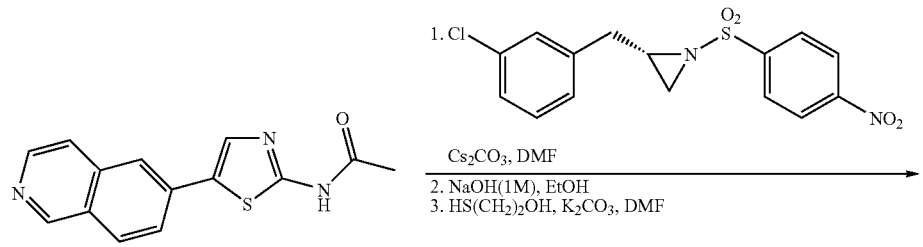

Scheme 16

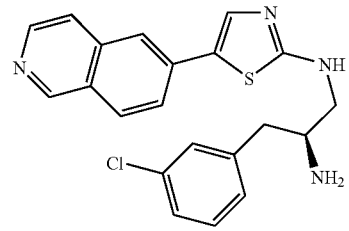

N-(5-(isoquinolin-6-yl)thiazol-2-yl)acetamide

To a mixture of lithium chloride (0.295 g, 6.94 mmol) (flame-dried), 6-bromoisoquinoline (0.1805 g, 0.868 mmol), and Pd(PPh$_3$)$_4$ (0.0501 g, 0.0434 mmol) in a microwave reaction vessel, was added a solution of N-(5-(tributylstannyl)thiazol-2-yl)acetamide (0.561 g, 1.30 mmol) in DMF (2.00 mL, 0.868 mmol). The mixture was sealed and heated at 100° C. (oil bath) overnight. After cooling, the mixture (solidified) was diluted with EtOAc and water (2 mL each) and sonicated for 10 minutes. The resulting mixture was filtered, and the solid was washed with water and more EtOAc to provide N-(5-(isoquinolin-6-yl)thiazol-2-yl)acetamide (0.2177 g, 0.808 mmol) as a yellow solid. LCMS (M+H$^+$) 270.3 calc. for C$_{14}$H$_{12}$N$_3$OS 270.3; $^1$H NMR (400 MHz, DMSO-d$_6$) δ ppm 12.32 (br s, 1H), 9.27 (s, 1H), 8.48 (d, J=5.67 Hz, 1H), 8.13-8.15 (m, 3H), 8.06 (d, J=7.20 Hz, 1H), 7.85 (d, J=5.67 Hz, 1H), 2.20 (s, 3H).

N-((S)-2-amino-3-(3-chlorophenyl)propyl)-5-(isoquinolin-6-yl)thiazol-2-amine To a stirred suspension of N-(5-(isoquinolin-6-yl)thiazol-2-yl)acetamide (0.1441 g, 0.5 mmol) and Cs$_2$CO$_3$ (0.5 g, 2 mmol) in DMF (3 mL, 39 mmol), was added a solution of (S)-2-(3-chlorobenzyl)-1-(4-nitrophenylsulfonyl)aziridine (0.4 g, 1 mmol) in DMF (2 mL) at 0° C. After stirring at the same temperature for 1 hour, the reaction mixture was allowed to warm to room temperature, and was stirred for 4 hours. The reaction was then quenched with NH$_4$Cl (10 mL (aqueous)) and water (10 mL), and diluted with EtOAc (5 mL). The separated aqueous layer was extracted with EtOAc (10 mL×2), and the combined organic layers were washed with water (5 mL×2) and brine. The resulting organic layer was dried over Na$_2$SO$_4$ and concentrated to give the crude residue as a yellow solid, which was used directly without further purification.

To a stirred mixture of crude N-((S)-3-(3-chlorophenyl)-2-(4-nitrophenylsulfonamido)propyl)-N-(5-(isoquinolin-6-yl)thiazol-2-yl)acetamide (0.33 g, 0.535 mmol) in EtOH (3 mL), was added sodium hydroxide (1.1 mL, 1 M aqueous solution, 1.1 mmol) at room temperature. After addition, the reaction mixture was stirred at 80° C. overnight. The reaction mixture was then diluted with NH$_4$Cl (10 mL (aqueous)) and water (10 mL), and diluted with DCM (5 mL). The separated aqueous layer was extracted with EtOAc (5 mL×2), and the combined organic layers were washed with brine, dried over Na$_2$SO$_4$, and concentrated to give the crude residue (0.2233 g, 385 µmol), to which DMF (2 mL), 2-mercaptoethanol (60 mg, 770 µmol), and K$_2$CO$_3$ (160 mg, 1155 µmol) were added sequentially. The resulting mixture was stirred at room temperature for 1.5 hours, and the resulting dark mixture was diluted with NH$_4$Cl (5 mL (aqueous)) and water (5 mL) and diluted with DCM (5 mL). The separated aqueous layer was extracted with DCM (10 mL×2), and the combined organic layers were washed with brine, dried over Na$_2$SO$_4$, and concentrated to give the crude residue which was purified with flash column chromatography (pure DCM→5% MeOH in DCM) to obtain the desired product N-((S)-2-amino-3-(3-chlorophenyl)propyl)-5-(isoquinolin-6-yl)thiazol-2-amine (33 mg, 84 µmol) as a yellow solid.

Example 67

5-(2-((S)-2-amino-3-(4-methoxyphenyl)propylamino)thiazol-5-yl)indolin-2-one

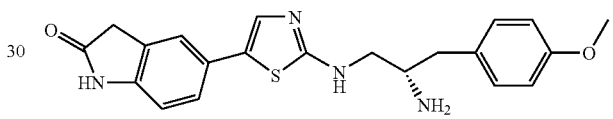

The title compound was prepared in a manner similar to that used for Example 36. LCMS m/z: 395 (M+1). $^1$H NMR (400 MHz, (CD$_3$OD)): δ ppm 2.92 (dd, J=10.27, 7.34 Hz, 2H), 3.44-3.48 (m, 1H), 3.54 (s, 2H), 3.58-3.63 (m, 2H), 6.87 (d, J=8.02 Hz, 1H), 6.93 (d, J=8.61 Hz, 2H), 7.22 (d, J=8.61 Hz, 2H), 7.29 (s, 2H), 7.37 (s, 1H).

Example 68

N-((S)-2-amino-3-(4-(trifluoromethyl)phenyl)propyl)-5-(1,6-naphthyridin-2-yl)thiazol-2-amine

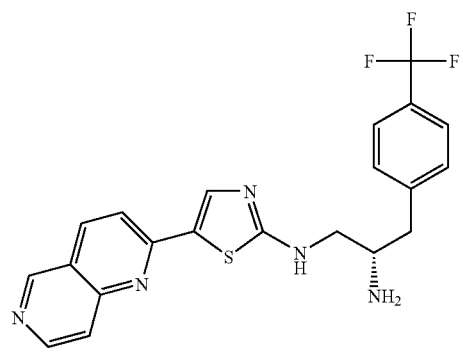

The title compound was prepared in a manner similar to that used for Example 64 by coupling 2-iodo-1,6-naphthyridine with tert-butyl 5-(tributylstannyl)thiazol-2-ylcarbamate. The resulting tert-butyl 5-(1,6-naphthyridin-2-yl)thiazol-2-ylcarbamate, was treated with the cyclic sulfamidate as described in Scheme 10 for Example 36. The intermediate 2-iodo-1,6-naphthyridine was prepared as shown in Scheme 17.

Scheme 17

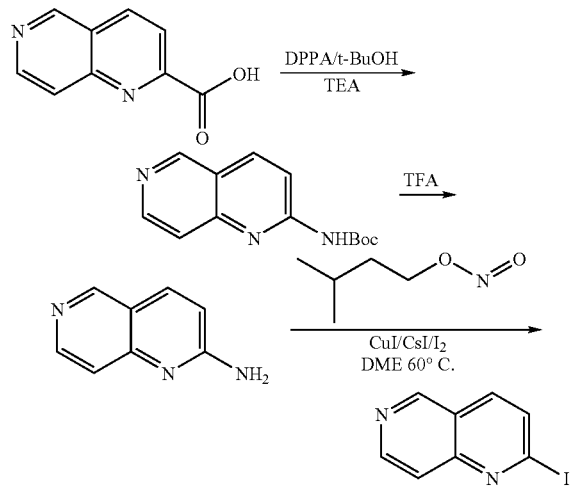

Tert-butyl 1,6-naphthyridin-2-ylcarbamate

To 250 mL round-bottomed flask was added 1,6-naphthyridine-2-carboxylic acid (5 g, 29 mmol), t-BuOH (32 mL, 29 mmol), and TEA (4 mL, 29 mmol). The starting material was dissolved with ultra-sonication. Diphenylphosphoryl azide (7 mL, 34 mmol) was added, and the reaction mixture was then heated to 80° C. The mixture was poured into ice water (20 mL), and was partitioned between brine (100 mL) and EtOAc (100 mL). The EtOAc layer was dried over sodium sulfate, concentrated, and purified by chromatography through a Redi-Sep® pre-packed silica gel column (120 g), eluting with a gradient of 0% to 40% EtOAc in hexane, to provide the title compound (2.7 g, 38%). MS m/z: 245 (M+1). $^1$H NMR (400 MHz, DMSO-d$_6$) δ ppm 1.50 (s, 9H), 7.61 (d, J=6.06 Hz, 1H), 8.17 (d, J=9.19 Hz, 1H), 8.47 (d, J=9.19 Hz, 1H), 8.61 (d, J=5.87 Hz, 1H), 9.20 (s, 1H), 10.48 (s, 1H).

1,6-Naphthyridin-2-amine

A 50% TFA/DCM mixture (10 mL) was added to tert-butyl 1,6-naphthyridin-2-ylcarbamate (2.7 g, 11.0 mmol) from the above step. After 30 minutes, the reaction mixture was concentrated and diluted with 30 mL of water. A saturated NaHCO$_3$ solution (15 mL) was added, and the reaction mixture was extracted twice with 50 mL of EtOAc. The organic layers were combined, concentrated, and purified by chromatography through a Redi-Sep® pre-packed silica gel column (120 g), eluting with a gradient 0-15% MeOH/DCM to give 1,6-naphthyridin-2-amine (1.6 g, 99% yield). MS m/z: 145 (M+1). $^1$H NMR (400 MHz, (CD$_3$OD)): δ ppm 6.93 (d, J=9.00 Hz, 1H), 7.41 (d, J=6.06 Hz, 1H), 8.05 (d, J=9.00 Hz, 1H), 8.37 (d, J=5.87 Hz, 1H), 8.83 (s, 1H).

2-Iodo-1,6-naphthyridine

6-Naphthyridin-2-amine (1.6 g, 5.5 mmol), I$_2$ (0.70 g, 2.8 mmol), copper(I) iodide (0.32 mg, 1.7 mmol), cesium iodide (1.43 g, 5.5 mmol), isoamyl nitrite (3.9 g, 33.1 mmol), and 60 mL of DME were added to a 250 mL round-bottom flask. The reaction mixture was heated to 60° C. for 16 hours and then 70 mL of EtOAc was added to the reaction mixture. The mixture was washed with 70 mL of 20% NH$_3$ solution and 70 mL of 1 M Na$_2$S$_2$O$_3$ solution. The organic layer was concentrated and purified by chromatography through a Redi-Sep® pre-packed silica gel column (120 g), eluting with a gradient 0-15% EtOAc/hexane to give 2-iodo-1,6-naphthyridine (280 mg, 19.8% yield). MS m/z: 257 (M+1).

N-((S)-2-amino-3-(4-(trifluoromethyl)phenyl)propyl)-5-(1,6-naphthyridin-2-yl)thiazol-2-amine To a solution of tert-butyl 5-(1,6-naphthyridin-2-yl)thiazol-2-ylcarbamate (28 mg, 85 μmol) in 5 mL of DFM, was added Cs$_2$CO$_3$ (56 mg, 171 μmol). The mixture was heated to 50° C., and cyclic sulfamidate (47 mg, 128 μmol) was added slowly in 2 mL of DMF. After 1 hour, the reaction was concentrated under reduced pressure. The residue was taken up in 20 mL of EtOAc, and 20 mL of 1 M aqueous HCl was added. The mixture was stirred for 1 hour and then was transferred to a separatory funnel. The mixture was partitioned, and the aqueous portion was extracted twice with 40 mL of EtOAc. The combined organic layers were washed with 25 mL of brine and then were dried over MgSO$_4$. Filtration and concentration under reduced pressure, followed by chromatography through a Redi-Sep® pre-packed silica gel column (40 g), eluting with a gradient 1% to 20% EtOAc/hexanes, provided the desired product as a yellow solid. MS m/z: 630 (M+1). A 70% TFA/DCM solution (3 mL) was added to the Boc-protected intermediate. After 30 minutes, the reaction mixture was concentrated and purified by preparatory LC (10-100% MeCN in water 20-45 mL/min) to give N-((S)-2-amino-3-(4-(trifluoromethyl)phenyl)-propyl)-5-(1,6-naphthyridin-2-yl)thiazol-2-amine (13 mg, 36% yield). MS m/z: 430 (M+1).

Example 69

5-(2-((S)-2-amino-3-(4-(trifluoromethyl)phenyl)propylamino)-4-(methoxymethyl)thiazol-5-yl)indolin-2-one

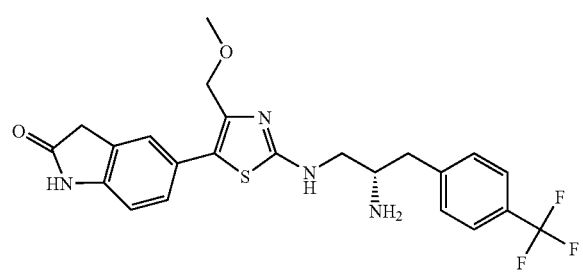

The title compound was prepared in a manner similar to that used for Examples 37-40. MS m/z: 477 (M+1). $^1$H NMR (400 MHz, (CD$_3$OD)): δ ppm 3.05-3.11 (m, 2H), 3.37 (s, 3H), 3.47-3.66 (m , 4H), 3.81 (dd, J=7.24, 3.72 Hz, 1H), 4.29 (s, 2H), 6.93 (d, J=7.82 Hz, 1H), 7.24 (d, J=8.22 Hz, 1H), 7.28 (s, 1H), 7.54 (d, J=7.82 Hz, 2H), 7.69 (d, J=8.22 Hz, 2H).

Example 70

5-(2-((S)-2-amino-3-phenylpropylamino)thiazol-5-yl)-3-methylindolin-2-one

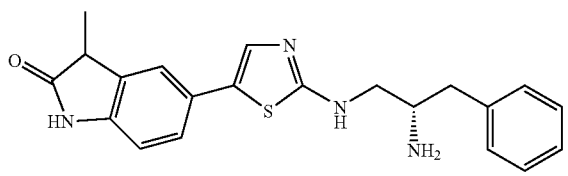

The title compound was prepared in a manner similar to that used for Examples 37-40. MS m/z: 379 (M+1). $^1$H NMR (400 MHz, (CD$_3$OD)): δ ppm 1.46 (d, J=7.43 Hz, 3H), 3.04 (d, J=7.04 Hz, 2H), 3.49 (q, J=7.83 Hz, 1H), 3.57-3.70 (m, 2H), 3.80 (qd, J=7.24, 4.11 Hz, 1H), 6.93 (d, J=7.82 Hz, 1H), 7.30-7.43 (m, 7H), 7.45 (s, 1H).

Example 71

N-((S)-2-amino-3-(4-(trifluoromethyl)phenyl)propyl)-4-(methoxymethyl)-5-(1,6-naphthyridin-2-yl)thiazol-2-amine

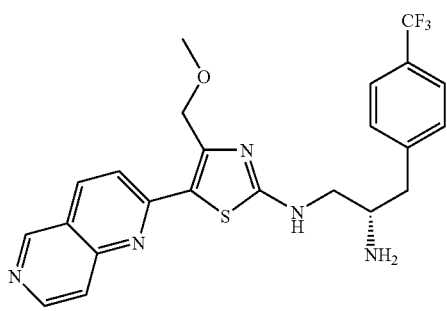

This compound was synthesized in a similar manner to that used for example 68. The intermediate tert-butyl 4-(methoxymethyl)-5-(tributylstannyl)thiazol-2-ylcarbamate was prepared as shown in Scheme 18. LCMS m/z: 474 (M+1). $^1$H NMR (400 MHz, (CD$_3$OD)): δ ppm 3.13 (d, J=1.56 Hz, 2H), 3.51 (s, 3H), 3.60-3.66 (m, 1H), 3.76-3.65 (m, 1H) 3.75 (d, J=3.91 Hz, 1H), 4.82 (s, 2H), 7.49-7.71 (m, 5H), 8.08(d, J=8.96 Hz, 2H), 8.16 (d, j=6.64, 2H), 8.63-8.68 (m, 2H), 9.51 (s, 1H).

Scheme 18

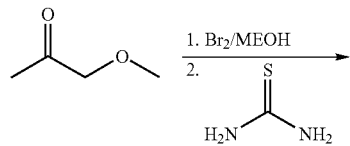

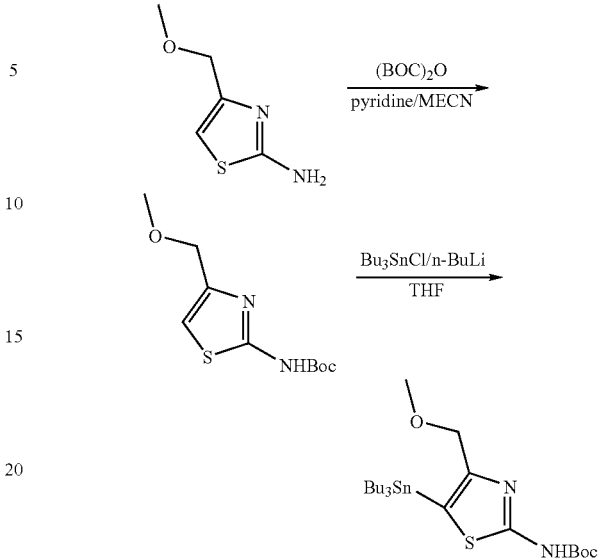

4-(Methoxymethyl)thiazol-2-amine

A solution of 1-methoxypropan-2-one (20.3 g, 231 mmol) in 200 mL of MeOH was added to a 250 mL round-bottom flask. The flask was then immersed in an ice-water bath. Br$_2$ was added dropwise to the reaction mixture through an addition funnel. After the addition, the addition funnel was rinsed with 50 mL MeOH, and the reaction mixture was stirred for 20 minutes at 0° C. The ice-water bath was then removed, and the reaction mixture was stirred for two more hours. Thiourea (18 g, 231 mmol) was then added to the reaction mixture, and the reaction was heated at reflux overnight. The reaction was concentrated, and saturated sodium bicarbonate and solid sodium carbonate were used to adjust the pH to 8-9. The resulting mixture was then extracted three times with 200 mL portions of EtOAc. The organic layers were concentrated and then purified by recrystallization to give 4-(methoxymethyl)thiazol-2-amine (11 g, 33% yield over two steps). MS m/z: 145 (M+1).

Tert-butyl 4-(methoxymethyl)thiazol-2-ylcarbamate

A suspension of 4-(methoxymethyl)thiazol-2-amine (7.6 g, 53 mmol) in ACN (400 mL) was stirred at room temperature and treated with pyridine (13 mL, 158 mmol) and then di-tert-butyl dicarbonate (23 g, 105 mmol). The reaction mixture was stirred at room temperature overnight. The solvent was reduced in vacuo to approximately 20 mL, and the mixture was partitioned between EtOAc (200 mL) and 1 N HCl (150 mL). The aqueous layer was extracted again with EtOAc (150 mL), and the combined organic phases were washed with 1 N HCl (75 mL), saturated NaHCO$_3$ (75 mL), and saturated NaCl (50 mL). The resulting mixture was dried over Na$_2$SO$_4$, filtered, concentrated, and purified by chromatography through a Redi-Sep® pre-packed silica gel column (40 g), eluting with a gradient 0-25% EtOAc/hexane to give tert-butyl 4-(methoxymethyl)thiazol-2-ylcarbamate (7.5 g, 58%). MS m/z: 245 (M+1).

Tert-Butyl 4-(methoxymethyl)-5-(tributylstannyl)thiazol-2-ylcarbamate

To a 250 mL flame-dried 3-neck round-bottomed flask was added tert-butyl 4-(methoxymethyl)thiazol-2-ylcarbamate (1.75 g, 7.2 mmol) and 200 mL of dry THF. The resulting solution was stirred at −78° C. and treated dropwise with 1.6 M n-BuLi in THF (9.4 mL, 15 mmol) over 15 minutes. The resulting pale yellow solution was stirred at −78° C. for 30 minutes and was then treated dropwise with tributyltin chloride (2.1 mL, 7.9 mmol). The reaction mixture was stirred at −78° C. for 30 minutes. The bath was then removed, and the mixture was allowed to warm to room temperature and was stirred at room temperature for 2.5 hours. The reaction was quenched by the addition of saturated NH$_4$Cl (150 mL). The layers were separated, and the aqueous layer was washed with Et$_2$O (3×100 mL). The organic phases were combined and washed with NaCl (100 mL) dried over MgSO$_4$, filtered, and concentrated in vacuo to provide the crude produce as a viscous oil which was then purified by column chromatography using a Redi-Sep® pre-packed silica gel column (120 g), eluting with a gradient of 10% to 20% EtOAc in hexane, to provide tert-butyl 4-(methoxymethyl)-5-(tributylstannyl)thiazol-2-ylcarbamate (2.5 g, 65% yield) as waxy oil. MS m/z: 535 (M+1).

Example 72

(E)- and (Z)-5-(2-((S)-2-amino-3-(1H-indol-3-yl)propylamino)thiazol-5-yl)-3-(furan-2-ylmethylene)indolin-2-one ditrifluoroacetates

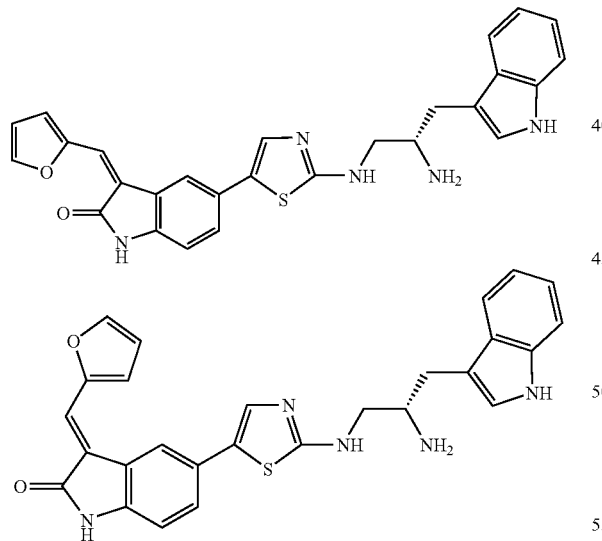

This compound was synthesized in a manner similar to that used for Examples 37-40 using (E)-3-(furan-2-ylmethylene)-5-(4,4,5,5-tetramethyl-1,3,2-dioxaborolan-2-yl)indolin-2-one as the starting material which was prepared as shown in Scheme 19. LCMS (M+H) 482.1 calc. for C$_{27}$H$_{26}$N$_5$O$_2$S 482.2; $^1$H NMR (400 MHz, CD$_3$OD) δ ppm 3.16 (s, 6H) 3.34 (s, 1H) 3.69 (s, 1H) 3.83 (s, 2H) 6.77 (dd, J=3.42, 1.66 Hz, 2H) 6.92 (d, J=8.02 Hz, 2H) 7.07 (d, J=7.63 Hz, 2H) 7.14 (d, J=2.93 Hz, 5H) 7.25 (s, 3H) 7.35-7.43 (m, 9H) 7.60 (d, J=7.82 Hz, 3H) 7.96 (s, 2H) 8.56 (s, 2H).

Scheme 19

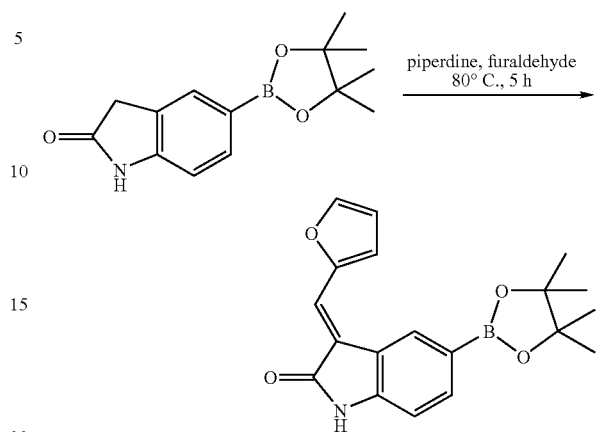

5-(4,4,5,5-Tetramethyl-1,3,2-dioxaborolan-2-yl)indolin-2-one (2.00 g, 7.7 mmol), ethyl alcohol (77 mL), piperidine (0.15 mL, 1.5 mmol), and 2-furaldehyde (0.77 mL, 9.3 mmol) were added to a 250 mL round-bottomed flask. The flask was sealed under a septum and heated to 80° C. for 5 hours. The mixture was cooled and filtered through a medium glass frit. The filtrate was adsorbed onto a plug of silica gel and chromatographed through a Redi-Sep® pre-packed silica gel column (120 g), eluting with a gradient of 0% to 70% EtOAc in hexane. The combined fractions were evaporated, and the product was crystallized out of EtOAc and hexanes at −20° C. to give (E)-3-(furan-2-ylmethylene)-5-(4,4,5,5-tetramethyl-1,3,2-dioxaborolan-2-yl)indolin-2-one (1.02 g, 39%) as an orange solid. LCMS (M+H) 338.1 calc. for C$_{19}$H$_{21}$BNO$_4$ 338.1.

Example 73

(E)-3-((1H-imidazol-5-yl)methylene)-6-(2-((S)-2-amino-3-(1H-indol-3-yl)propylamino)thiazol-5-yl)indolin-2-one ditrifluoroacetates

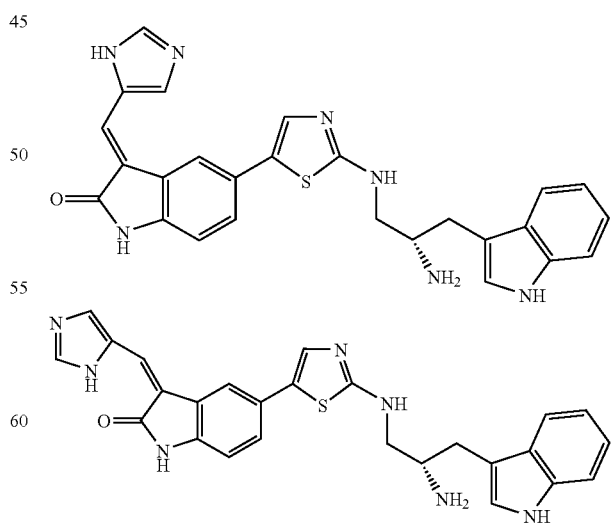

The title compound was prepared in a manner similar to that used for Example 72. HRMS (M+H) 482.17598 calcd for $C_{26}H_{24}N_7OS$ 482.17576; $^1$H NMR (400 MHz, $CD_3OD$) δ ppm 2.65 (s, 1H) 2.80-2.87 (m, 3H) 2.98 (s, 1H) 3.07 (ddd, J=13.45, 6.60, 6.36 Hz, 2H) 3.20 (s, 1H) 3.21 (d, J=2.54 Hz, 1H) 3.42-3.49 (m, 1H) 3.61-3.80 (m, 6H) 3.89 (dd, J=7.04, 4.30 Hz, 1H) 4.64 (t, J=6.36 Hz, 2H) 6.95-7.16 (m, 4H) 7.25-7.42 (m, 4H) 7.47 (s, 1H) 7.52 (s, 1H) 7.60 (d, J=8.02 Hz, 1H) 7.83 (d, J=1.37 Hz, 1H) 7.86 (s, 1H) 8.08-8.11 (m, 1H) 8.99 (s, 1H).

Example 74

5-(2-((S)-2-amino-3-(1H-indol-3-yl)propylamino)thiazol-5-yl)indolin-2-one ditrifluoroacetate

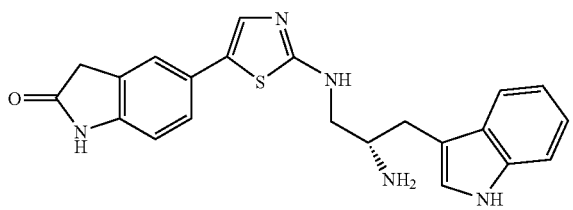

The title compound was prepared in a manner similar to that used for Example 35 to provide it as an off-white amorphous solid: HRMS 404.15396 calcd for $C_{22}H_{22}N_5OS$ 404.15396; $^1$H NMR (400 MHz, $CD_3OD$) δ ppm 3.18 (d, J=7.24 Hz, 2H), 3.54-3.72 (m, 4H), 3.84 (td, J=7.09, 4.01 Hz, 1H), 6.89 (d, J=8.22 Hz, 1H), 7.06 (t, J=7.14 Hz, 1H), 7.15 (t, J=7.24 Hz, 1H), 7.22-7.27 (m, 2H), 7.30-7.41 (m, 3H), 7.60 (d, J=8.02 Hz, 1H).

Example 75

6-(2-((S)-2-Amino-3-(4-(trifluoromethyl)phenyl)propylamino)thiazol-5-yl)isoquinolin-3-amine

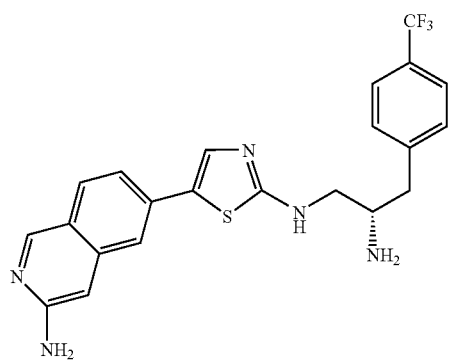

The title compound was prepared in a manner similar to that used for Examples 37-40. LCMS (M+H) 444.1 calcd for $C_{22}H_{21}F_3N_5S$ 444.1.

Example 76

6-(2-((S)-2-Amino-3-(4-chlorophenyl)propylamino)thiazol-5-yl)isoquinolin-3-amine

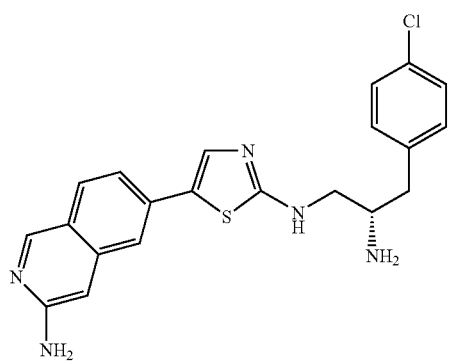

The title compound was prepared in a manner similar to that used for Examples 37-40. LCMS (M+H) 410.1 calcd for $C_{21}H_{21}ClN_5S$ 410.1.

Example 77

N-((S)-2-amino-3-(4-chlorophenyl)propyl)-4-(ethoxymethyl)-5-(thiazolo[5,4-c]pyridin-2-yl)thiazol-2-amine

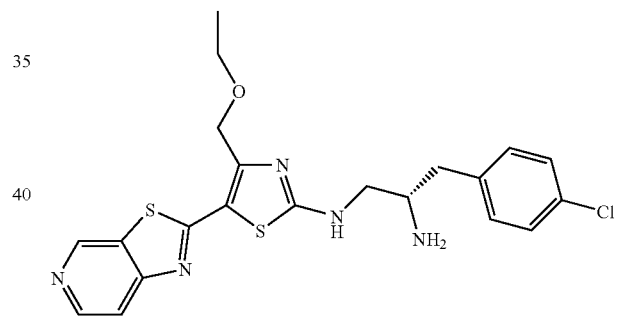

The title compound was prepared in a manner similar to that used for Example 21. LCMS (M+H) 460.1 calcd for $C_{21}H_{23}ClN_5OS_2$ 460.09.

Example 78

6-(2-((S)-2-amino-3-(4-methoxyphenyl)propylamino)thiazol-5-yl)benzo[d]oxazol-2(3H)-one

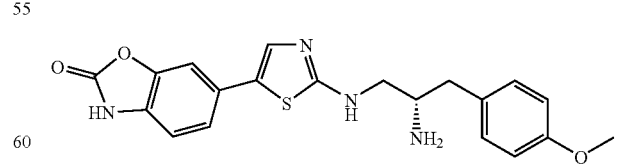

The title compound was prepared in a manner similar to that used for Example 36. LCMS m/z: 397 (M+1). $^1$H NMR (400 MHz, ($CD_3OD$)): δ ppm 2.87-2.98 (m, 2H), 3.47-3.52 (m, 1H), 3.59-3.69 (m, 2H), 3.78 (s, 3H), 6.93 (d, J=8.61 Hz, 2H), 7.06 (d, J=8.22 Hz, 1H), 7.21-7.25 (m, 3H), 7.36 (s, 2H).

Example 79
4-(2-((S)-2-Amino-3-(4-(trifluoromethyl)phenyl)propylamino)-5-(isoquinolin-6-yl)thiazole-4-yl)-2-methylbut-3-yn-2-ol
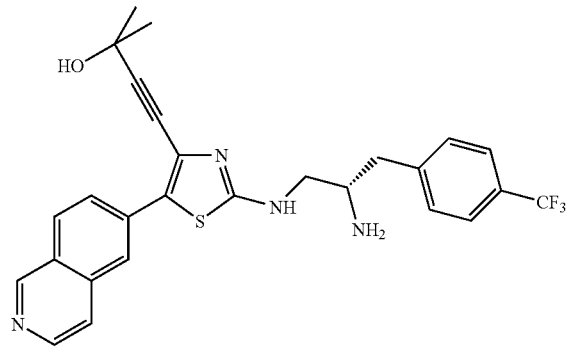
4-(2-((S)-2-Amino-3-(4-(trifluoromethyl)phenyl)propylamino)-5-(isoquinolin-6-yl)thiazole-4-yl)-2-methylbut-3-yn-2-ol was synthesized as shown in Scheme 20.
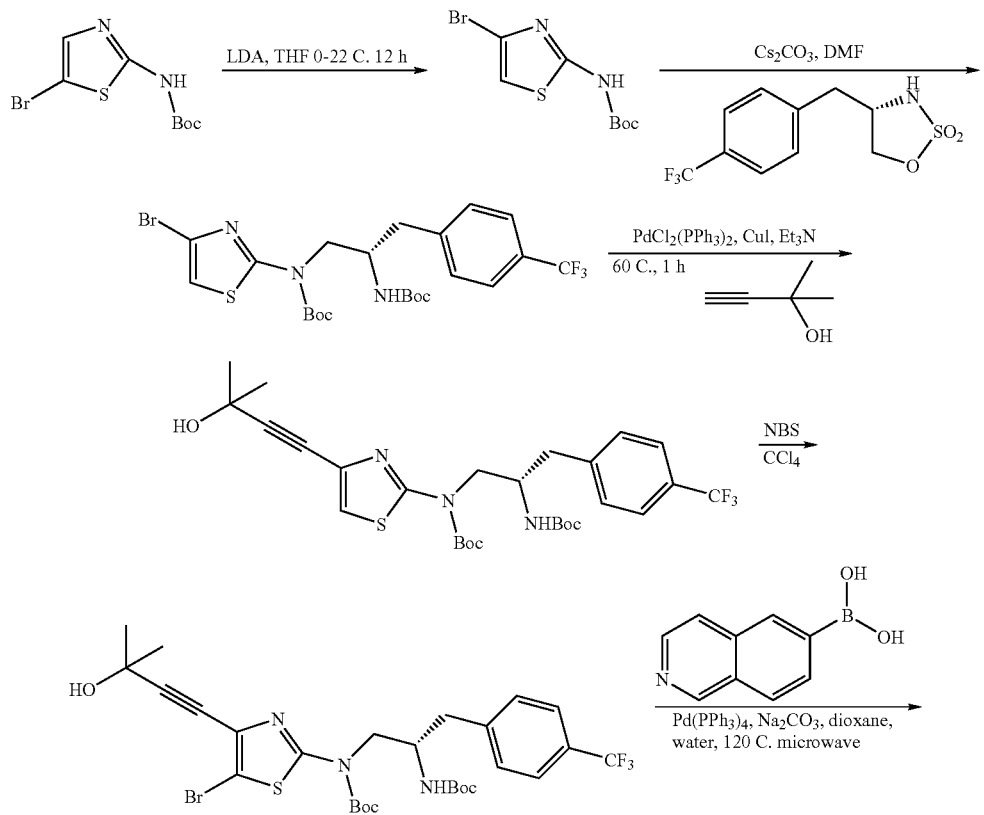

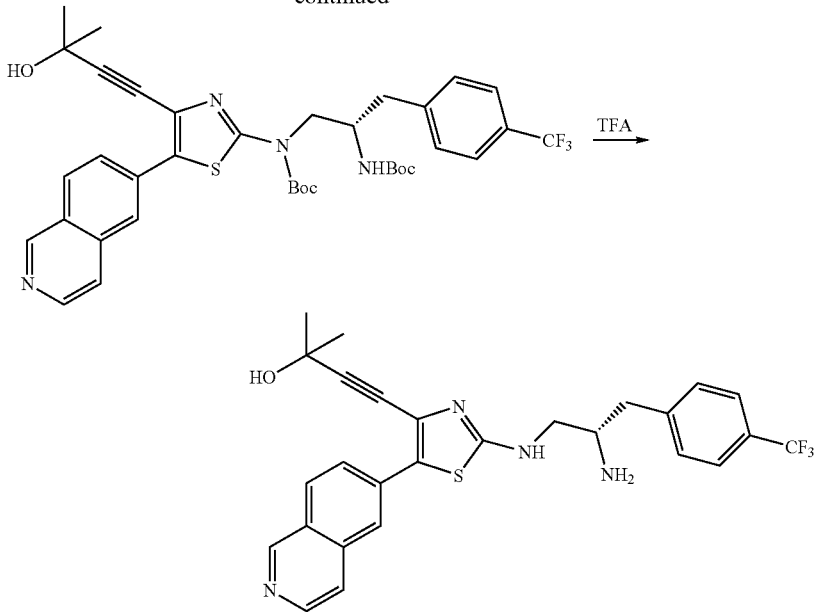

t-Butyl 4-bromothiazol-2-ylcarbamate

Diisopropylamine (2.3 mL, 16 mmol) was taken up in 30 mL of THF and chilled to 0° C. Butyllithium, 2.5M in hexane (6.4 mL, 16 mmol), was added to the reaction mixture, and the mixture was stirred for 20 minutes. tert-Butyl 5-bromothiazol-2-ylcarbamate (1.5 g, 5.4 mmol) was then added slowly in 8 mL of THF. After 15 minutes, approximately 2 mL of water was added, and the mixture was warmed to room temperature and stirred for 12 hours. The mixture was diluted with 30 mL of 1/2 saturated aqueous $NH_4Cl$ and transferred to a separatory funnel. The mixture was extracted twice with 5 mL of EtOAc, and the combined organic extracts were washed with brine and dried over $MgSO_4$. Filtration and concentration under reduced pressure afforded tert-butyl 4-bromothiazol-2-ylcarbamate (1.5 g, 100% yield) as a brown solid.

(S)-tert-Butyl 1-(N-(4-bromothiazol-2-yl)-tert-butoxylcarbonylamino)-3-(4-(trifluoromethyl)phenyl)propan-2-ylcarbamate t-Butyl 4-bromothiazol-2-ylcarbamate (0.91 g, 3.3 mmol) was taken up in 15 mL of DMF. $Cs_2CO_3$ (2.1 g, 6.6 mmol) was added, and the mixture was heated to 50° C. The cyclic sulfamidate (1.5 g, 3.9 mmol) was added slowly in 8 mL of 2:1 DMF:THF, and the mixture was stirred for 1 hour. The solvent was then removed under reduced pressure, and the residue was taken up in 20 mL of EtOAc. 20 mL of 10% aqueous HCl was then added carefully, and the mixture was stirred for 30 minutes. 5% aqueous NaOH was next added until the pH was greater than 7, and the mixture was partitioned in a separatory funnel. The aqueous portion was extracted twice with 20 mL of EtOAc, and the combined organic extracts were washed with 30 mL of brine and dried over $MgSO_4$. Filtration and concentration under reduced pressure, followed by flash chromatography on silica gel (2.5% to 10% EtOAc/hexanes), afforded (S)-tert-butyl 1-(N-(4-bromothiazol-2-yl)-tert-butoxylcarbonylamino)-3-(4-(trifluoromethyl)phenyl)propan-2-ylcarbamate (1.4 g, 74% yield) as a sticky white solid: LCMS (M+H) 580, 582 calc. for $C_{23}H_{30}BrF_3N_3O_4S$ 580, 582.

(S)-tert-butyl 1-(N-(4-(3-hydroxy-3-methylbut-1-ynyl)thiazol-2-yl)-tert-butoxylcarbonylamino)-3-(4-(trifluoromethyl)phenyl)propan-2-ylcarbamate (S)-tert-butyl 1-(N-(4-bromothiazol-2-yl)-tert-butoxylcarbonylamino)-3-(4-(trifluoromethyl)phenyl)propan-2-ylcarbamate (0.25 g, 0.43 mmol) was taken up in 4 mL of $Et_3N$. 2-Methylbut-3-yn-2-ol (0.21 mL, 2.2 mmol), dichlorobis(triphenylphosphino)-palladium(II) (0.030 g, 0.043 mmol), and copper(I) iodide (0.025 g, 0.13 mmol) were added. The mixture was stirred for 20 minutes. No reaction was observed, and the mixture was heated to 60° C. for 1 hour. The reaction was judged to be complete by LC/MS, the solvent was removed under reduced pressure, and the residue was purified by flash chromatography on silica gel (5% to 30% EtOAc/hexanes), to provide (S)-tert-butyl 1-(N-(4-(3-hydroxy-3-methylbut-1-ynyl)thiazol-2-yl)-tert-butoxylcarbonylamino)-3-(4-(trifluoromethyl)phenyl)propan-2-ylcarbamate (0.23 g, 91% yield): LCMS (M+H) 584 calc. for $C_{28}H_{37}F_3N_3O_5S$ 583.6.

(S)-tert-butyl 1-(N-(5-bromo-4-(3-hydroxy-3-methylbut-1-ynyl)thiazol-2-yl)-tert-butoxylcarbonylamino)-3-(4-(trifluoromethyl)phenyl)propan-2-ylcarbamate (S)-tert-butyl 1-(N-(4-(3-hydroxy-3-methylbut-1-ynyl)thiazol-2-yl)-tert-butoxylcarbonylamino)-3-(4-(trifluoromethyl)phenyl)propan-2-ylcarbamate (0.18 g, 0.31 mmol) was taken up in 5 mL of $CCl_4$ and NBS (0.11 g, 0.62 mmol) was added. After 3 hours, the solvent was removed under reduced pressure, and the residue was purified by flash chromatography on silica gel (5% to 40% EtOAc/hexanes) to afford (S)-tert-butyl 1-(N-(5-bromo-4-(3-hydroxy-3-methylbut-1-ynyl)thiazol-2-yl)-tert-butoxylcarbonylamino)-3-(4-(trifluoromethyl)phenyl)propan-2-ylcarbamate (0.05 g, 24% yield) as a white solid.

(S)-tert-butyl 1-(N-(4-(3-hydroxy-3-methylbut-1-ynyl)-5-(isoquinolin-6-yl)thiazol-2-yl)-tert-butoxylcarbonylamino)-3-(4-(trifluoromethyl)phenyl)propan-2-ylcarbamate (S)-tert-butyl 1-(N-(5-bromo-4-(3-hydroxy-3-methylbut-1-ynyl)thiazol-2-yl)-tert-butoxylcarbonylamino)-3-(4-(trifluoromethyl)phenyl)propan-2-ylcarbamate (0.025 g, 0.038 mmol) was taken up in 1 mL of dioxane in a microwave safe tube. Isoquinolin-6-ylboronic acid (0.0098 g, 0.057 mmol), sodium carbonate, 2M in water (0.075 mL, 0.15 mmol), and tetrakistriphenylphosphine palladium(0) (0.0044 g, 0.0038 mmol) were added. The mixture was degassed with nitrogen and the tube was sealed. The tube was then heated to 120° C. in a Personal Chemistry microwave unit for 20 minutes. The mixture was diluted with 10 mL of EtOAc, washed with 5 mL of water and 5 mL of brine, and then dried over MgSO$_4$. Filtration and concentration under reduced pressure, followed by flash chromatography on silica gel (pipette column, 25% to 70% EtOAc/hexanes), afforded (S)-tert-butyl 1-(N-(4-(3-hydroxy-3-methylbut-1-ynyl)-5-(isoquinolin-6-yl)thiazol-2-yl)-tert-butoxylcarbonylamino)-3-(4-(trifluoromethyl)phenyl)propan-2-ylcarbamate (0.010 g, 37% yield) as a white solid.

4-(2-((S)-2-amino-3-(4-(trifluoromethyl)phenyl)propylamino)-5-(isoquinolin-6-yl)thiazole-4-yl)-2-methylbut-3-yn-2-ol (S)-tert-butyl 1-(N-(4-(3-hydroxy-3-methylbut-1-ynyl)-5-(isoquinolin-6-yl)thiazol-2-yl)-tert-butoxylcarbonylamino)-3-(4-(trifluoromethyl)phenyl)propan-2-ylcarbamate (0.010 g, 0.01 mmol) was taken up in 1 mL of DCM and TFA (0.2 mL) was added. After 1.5 hours, the solvent was removed under reduced pressure. The residue was loaded onto a Varian Mega Bond ELUT SCX column in MeOH, and eluted with 1M NH$_3$ in MeOH to provide the free base. The solvent was removed under reduced pressure, and the residue was purified by flash chromatography on silica gel (pipette column, 2.5% to 10% MeOH/DCM) to afford 4-(2-((S)-2-amino-3-(4-(trifluoromethyl)phenyl)propylamino)-5-(isoquinolin-6-yl)thiazol-4-yl)-2-methylbut-3-yn-2-ol (0.002 g, 28% yield) as a yellow oil: LCMS (M+H) 511 calc. for C$_{27}$H$_{26}$F$_3$N$_4$OS 510.6. $^1$H NMR (400 MHz, CD$_3$OD) δ ppm 9.17 (s, 1H) 8.41 (d, J=5.87 Hz, 1H) 8.28 (s, 1H) 8.07-8.13 (m, 2H) 7.79 (d, J=5.87 Hz, 1H) 7.62 (d, J=8.02 Hz, 2H) 7.47 (d, J=8.02 Hz, 2H), 3.47-3.25 (m, 3H) 2.95 (d, J=4.89 Hz, 1H) 2.73 (dd, J=13.40, 7.34 Hz, 1H) 1.60 (s, 6H).

Example 80

2-((S)-2-Amino-3-(4-chlorophenyl)propylamino)-5-(3,4-difluorophenyl)thiazol-4-ol dihydrochloride

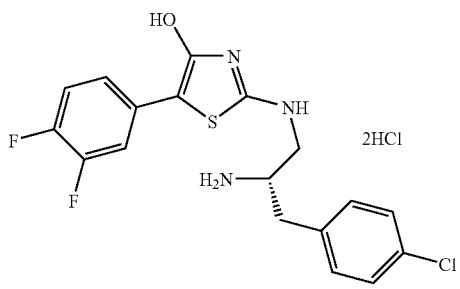

2-((S)-2-Amino-3-(4-chlorophenyl)propylamino)-5-(3,4-difluorophenyl)thiazol-4-ol dihydrochloride was synthesized as shown in Scheme 21 starting with commercially available ethyl 2-(3,4-difluorophenyl)acetate and (S)-3-(4-chlorophenyl)propane-1,2-diamine dihydrochloride.

Scheme 21

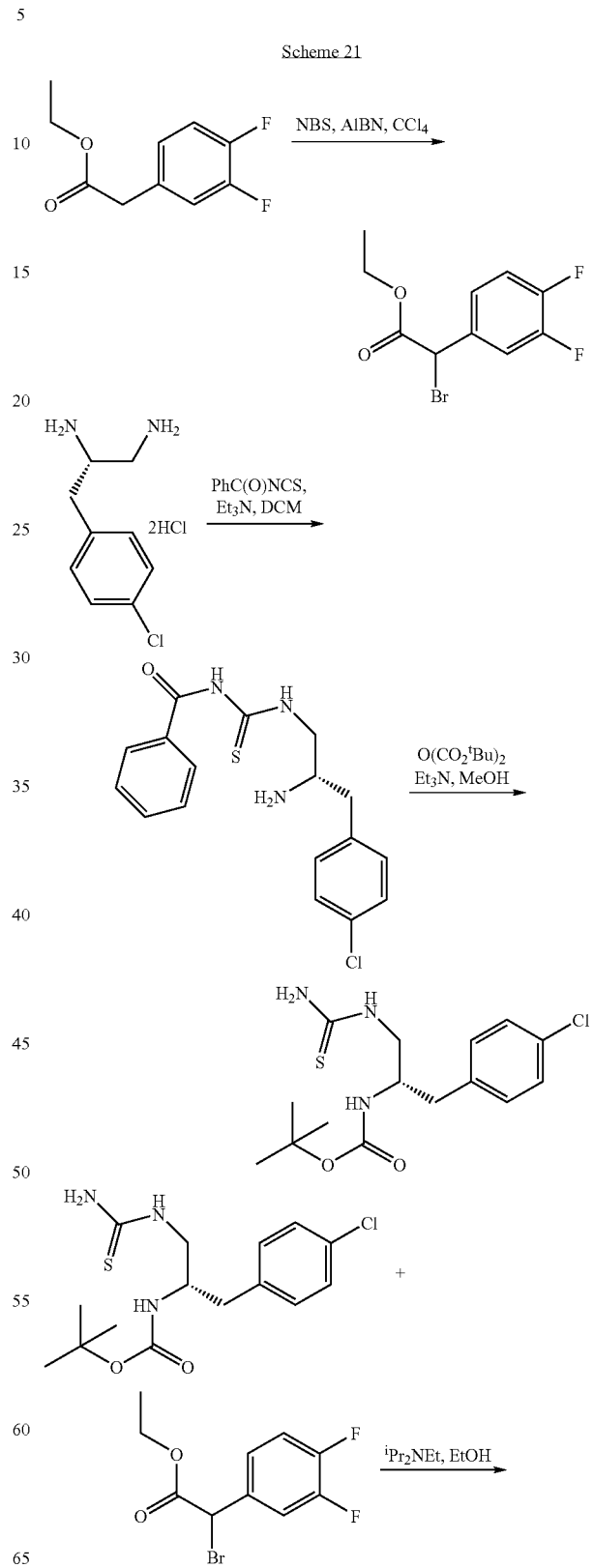

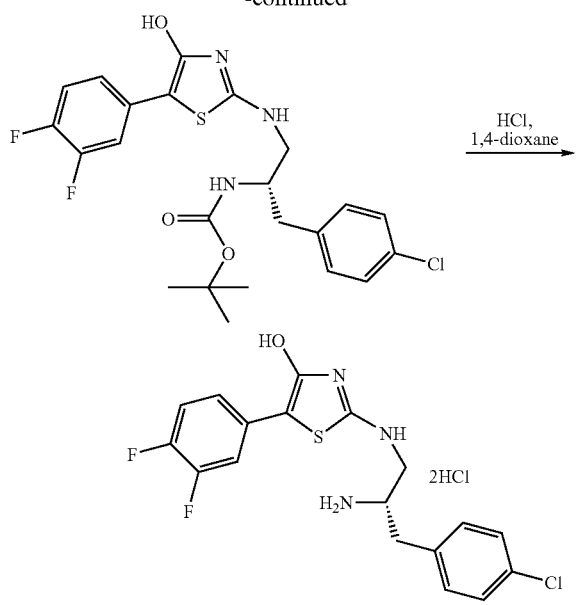

Ethyl 2-bromo-2-(3,4-difluorophenyl)acetate

A mixture of ethyl 2-(3,4-difluorophenyl)acetate (1.20 g, 5.99 mmol), N-bromosuccinimide (1.17 g, 6.59 mmol), and 2,2'-azobis(isobutyronitrile) (0.148 g, 0.899 mmol) in CCl$_4$ (20 mL) was gradually heated to reflux and stirred at this temperature overnight. The solvent was removed in vacuum. The residue was purified by flash column chromatography (100% hexanes for 5 minutes, then 0 to 5% of EtOAc in hexanes over 23 minutes). The desired product was obtained as a colorless oil (1.14 g, 68%). $^1$H NMR (300 MHz, CDCl$_3$) δ 1.31 (d, J=6.0 Hz, 3H), 4.17-4.35 (m, 2H), 5.27 (s, 1H), 7.11-7.20 (m, 1H), 7.24-7.30 (m, 1H), 7.42-7.52 (m, 1H).

(S)-1-(2-Amino-3-(4-chlorophenyl)propyl)-3-benzoylthiourea

A solution of benzoyl isothiocyanate (2.94 mL, 21.9 mmol) in DCM (50 mL) was added dropwise via an addition funnel to the mixture of (S)-3-(4-chlorophenyl)propane-1,2-diamine dihydrochloride (5.63 g, 21.9 mmol) and TEA (7.60 mL, 54.6 mmol) in DCM (200 mL) at −10° C. under nitrogen. The addition took 30 minutes. The mixture was then gradually warmed to ambient temperature and stirred overnight. The solvent was removed in vacuo. The residue was partitioned between EtOAc and water. The combined organic portions were washed with brine. The crude product was purified by flash column chromatography (20 to 100% of EtOAc in hexanes, Biotage Si 40M). The product was obtained as an off-white foamy solid, 5.53 g, 73%. $^1$H NMR (300 MHz, CDCl$_3$) δ 1.84 (broad, NH$_2$), 2.57-2.71 (m, 1H), 2.82-2.94 (m, 1H), 3.34-3.48 (m, 1H), 3.51-3.65 (m, 1H), 3.82-3.99 (m, 1H), 7.13-7.21 (m, 2H), 7.28-7.34 (m, 2H), 7.49-7.58 (m, 2H), 7.59-7.68 (m, 1H), 7.80-7.91 (m, 2H), 9.00 (broad, NH), 11.07 (broad, NH). LCMS (API-ES): 348.1/350.1 (M$^+$+H), chloro pattern.

(S)-tert-Butyl 3-(4-chlorophenyl)-1-thioureidopropan-2-ylcarbamate

A mixture of (S)-1-(2-amino-3-(4-chlorophenyl)propyl)-3-benzoylthiourea (5.50 g, 15.8 mmol), di-tert-butyl dicarbonate (3.80 g, 17.4 mmol), and TEA (3.30 mL, 23.7 mmol) in MeOH (60 mL) was stirred at room temperature overnight. The solvent was removed in vacuo. The residue was then partitioned between EtOAc and water. The combined organic portions were washed with brine, and the solvent was removed in vacuo. The mixture was then stirred with K$_2$CO$_3$ (6.56 g, 47.4 mmol) in MeOH (20 mL) at room temperature overnight. The solvent was removed in vacuo, and the residue was partitioned between EtOAc and water. The combined organic portions were washed with brine. The crude product was purified by flash column chromatography (0 to 70% of EtOAc in hexanes). The product was obtained as a white foamy solid, 4.04 g, 74%. $^1$H NMR (300 MHz, CD$_3$OD) δ 1.27-1.45 (m, 9H), 2.45-2.96 (m, 2H), 3.34-3.97 (m, 3H), 7.14-7.34 (m, 4H). LCMS (API-ES): 344.1/346.1 (M$^+$+H), chloro pattern.

(S)-tert-Butyl-3-(4-chlorophenyl)-1-(5-(3,4-difluorophenyl)-4-hydroxythiazol-2-ylamino)propan-2-ylcarbamate A mixture of (S)-tert-butyl 3-(4-chlorophenyl)-1-thioureidopropan-2-ylcarbamate (0.585 g, 1.70 mmol) and ethyl 2-bromo-2-(3,4-difluorophenyl)acetate (0.500 g, 1.79 mmol) in ethyl alcohol (2 mL) and diisopropylethylamine (0.3 mL) in a sealed vial (Biotage microwave vial, 5 mL) with a magnetic stirring bar was heated in a microwave oven (Initiator, Biotage) at 120° C. for 15 minutes. After cooling to ambient temperature, the volatiles were removed in vacuum. The residue was partitioned between EtOAc and water. The combined organic portions were washed with brine. The crude product was purified by flash column chromatography (20% of EtOAc in hexanes for 5 minutes, 20% to 100% of EtOAc in hexanes over 23 minutes). The product was obtained as a white solid, 0.201 g, 24%. $^1$H NMR (300 MHz, CD$_3$OD) δ 1.22-1.39 (m, 9H), 2.52-2.97 (m, 2H), 3.35-3.60 (m, 1H), 3.64-3.85 (m, 1H), 3.92-4.24 (m, 1H), 7.11-7.46 (m, 7H). LCMS (API-ES): 496.1/498.1 (M$^+$+H), chloro pattern.

2-((S)-2-amino-3-(4-chlorophenyl)propylamino)-5-(3,4-difluorophenyl)thiazol-4-ol dihydrochloride Hydrogen chloride (4.0 M solution in 1,4-dioxane, 5 mL) was added to tert-butyl (S)-3-(4-chlorophenyl)-1-(5-(3,4-difluorophenyl)-4-oxo-4,5-dihydrothiazol-2-ylamino)propan-2-ylcarbamate (0.0940 g, 0.190 mmol). The mixture was stirred at room temperature for 90 minutes in a sealed vessel. The solvent was removed in vacuo to give the product as a white solid, 89.3 mgs, 100%. $^1$H NMR (300 MHz, CD$_3$OD) δ 2.90-3.12 (m, 2H), 3.64-3.87 (m, 3H), 7.13-7.44 (m, 7H). LCMS (API-ES): 396.0/398.0 (M$^+$+H), chloro pattern.

Example 81

N-((S)-2-Amino-3-(4-(trifluoromethyl)phenyl)propyl)-4-((dimethylamino)methyl)-5-(isoquinolin-6-yl)thiazol-2-amine

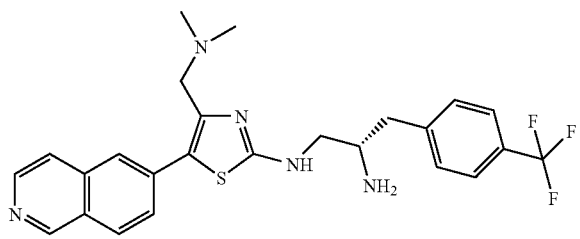

N-((S)-2-Amino-3-(4-(trifluoromethyl)phenyl)propyl)-4-((dimethylamino)methyl)-5-(isoquinolin-6-yl)thiazol-2-amine: MS Theoretical (M+H) 486.19, found 486.2. Example 81 was synthesized in a manner similar to that of Example 36 with a coupling reaction between the corresponding bromothiazole intermediate (S)-tert-butyl 1-(N-(5-bromo-4-((dimethylamino)methyl)thiazol-2-yl)acetamido)-3-(4-(trifluoromethyl)phenyl)propan-2-ylcarbamate and the boronic acid to yield the Boc protected intermediate tert-butyl (S)-1-(4-((dimethylamino)methyl)-5-(isoquinolin-6-yl)thiazol-2-ylamino)-3-(4-(trifluoromethyl)phenyl)propan-2-ylcarbamate. (S)-tert-butyl 1-(N-(5-bromo-4-((dimethylamino)methyl)thiazol-2-yl)acetamido)-3-(4-(trifluoromethyl)phenyl)propan-2-ylcarbamate was prepared in a manner similar to that shown in Scheme 10 with 5-bromo-4-((dimethylamino)methyl)thiazole as the starting material. 5-bromo-4-((dimethylamino)methyl)thiazole was prepared as shown in Scheme 22.

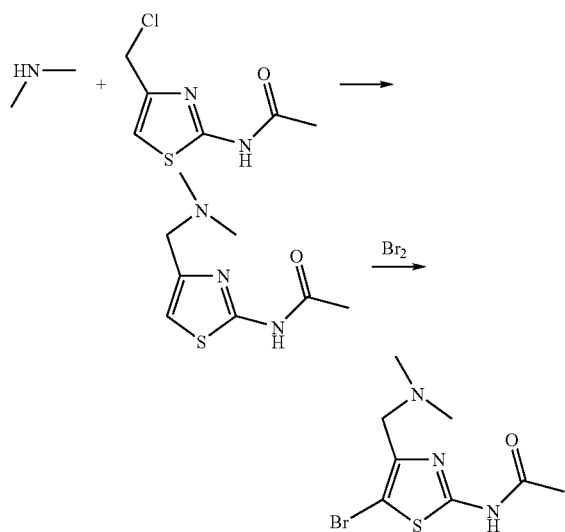

N-(4-((Dimethylamino)methyl)thiazol-2-yl)acetamide

N-(4-(Chloromethyl)thiazol-2-yl)acetamide (2.0 g, 10 mmol) in 20 mL THF was added in portions to dimethylamine (4.7 g, 105 mmol). After addition, the mixture was stirred for an additional 30 minutes. The solvent was removed under reduced pressure. 200 mL distilled water was then added to the resulting residue, and the mixture was extracted with EtOAc. The EtOAc solution was washed with brine solution and dried over sodium sulfate. After removing the solvent, an off-white solid was obtained as the crude product (1.3 g, yield=80%). LCMS (API-ES) m/z (%) 200.1 (100%, M$^+$+H). $^1$H NMR (400 MHz, CDCl$_3$) δ ppm 2.24 (s, 3H) 2.26 (s, 6H) 3.43 (s, 2H) 6.73 (s, 1H).

N-(5-Bromo-4-((dimethylamino)methyl)thiazol-2-yl)acetamide

To a solution of N-(4-((dimethylamino)methyl)thiazol-2-yl)acetamide (1.1 g, 5.5 mmol) in 10 mL AcOH was added Br$_2$ (0.28 mL, 5.5 mmol) dropwise. The resulting mixture discolored instantly, and a precipitate appeared. The precipitate was filtered and washed with AcOH. The collected precipitate was neutralized with saturated sodium bicarbonate and extracted twice with 100 mL EtOAc. The organic layer was combined, washed once with brine, and dried over sodium sulfate. After removing the solvent, the product was obtained as a white solid (1.0 g, yield=65%). LCMS (API-ES) m/z (%) 278.0 (100%, M$^+$+H). $^1$H NMR (400 MHz, CDCl$_3$) δ ppm 2.24 (s, 3H) 2.28 (s, 6H) 3.44 (s, 2H).

Example 82

6-(2-((S)-2-Amino-3-(3-(trifluoromethyl)phenyl)propylamino)thiazol-5-yl)-1-methyl-1H-benzo[d]imidazol-2(3H)-one Example 82 was synthesized in a manner similar to that described for Example 36 and 57 using 3-(trifluoromethyl)-1-phenylalanine purchased from PepTech as the starting material to make the cyclic sulfamidate intermediate similarly shown in Scheme 24. MS theoretical (M+H) 448.13, found 448.2; $^1$H NMR (400 MHz, CD$_3$OD) δ ppm 3.11-3.17 (m, 2H) 3.39 (s, 3H) 3.61-3.68 (m, 2H) 3.86-3.93 (m, 1H) 7.03-7.08 (m, 1H) 7.12-7.17 (m, 1H) 7.22 (d, J=1.17 Hz, 1H) 7.46 (s, 1H) 7.57-7.65 (m, 3H) 7.70 (s, 1H).

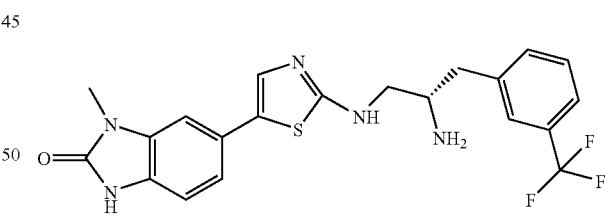

Example 83

N-((S)-2-Amino-3-(3-fluoro-4-(trifluoromethyl)phenyl)propyl)-5-(isoquinolin-6-yl)thiazol-2-amine Example 83 was prepared in a similar manner to that described for Example 82. MS Theoretical (M+H) 447.12, found 447.1; $^1$H NMR (400 MHz, CD$_3$OD) δ ppm 2.68-2.79 (m, 1H) 2.92-3.02 (m, 1H) 3.33-3.39 (m, 2H) 3.39-3.50 (m, 1H) 7.21-7.31 (m, 2H) 7.58-7.68 (m, 2H) 7.72-7.83 (m, 2H) 7.89 (dd, J=8.61, 1.76 Hz, 1H) 8.05 (d, J=8.61 Hz, 1H) 8.39 (d, J=5.87 Hz, 1H) 9.14 (s, 1H).

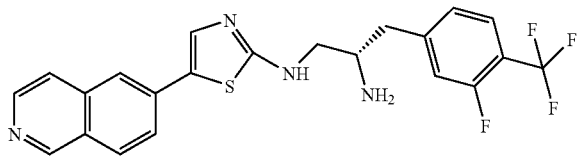

Examples 84-87

Examples 84-87 were synthesized in a similar manner to that described for Example 82 using amino acid ester(S)-methyl 2-(tert-butoxycarbonyl)-3-(4-chloro-3-fluorophenyl) propanoate which was prepared via a coupling reaction between 4-bromo-1-chloro-2-fluorobenzene and (R)-methyl 2-(tert-butoxycarbonyl)-3-iodopropanoate as shown in Scheme 23.

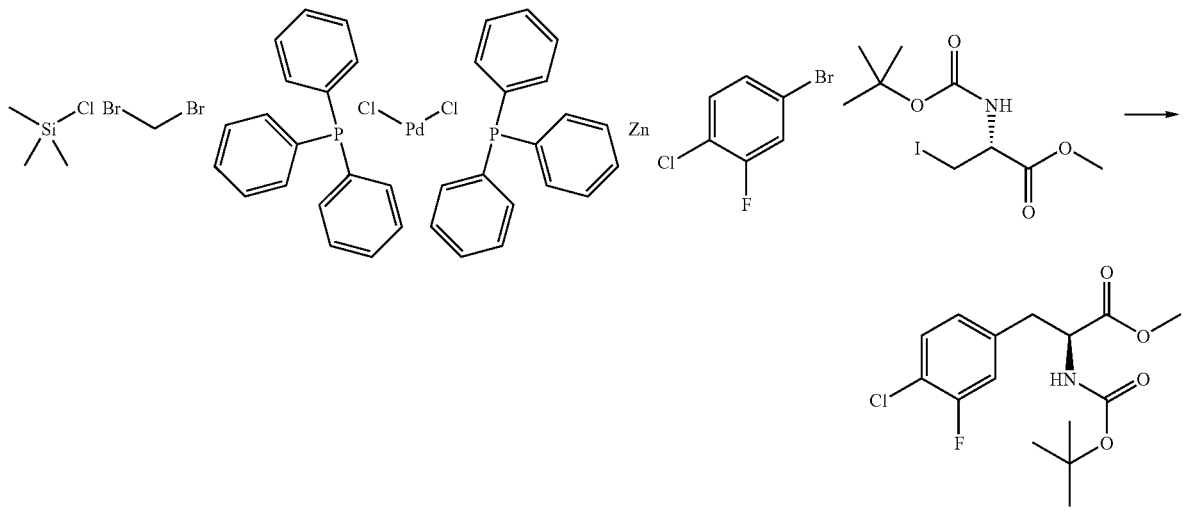

(S)-methyl 2-(tert-butoxycarbonyl)-3-(4-chloro-3-fluorophenyl)propanoate

Zinc (23.8 g, 365 mmol) and 100 mL DMF were charged into a flame-dried 500 mL round bottom flask. Methylene dibromide (3.17 g, 18.2 mmol) was added, and the mixture was heated to 90° C. for 30 minutes. After cooling to room temperature, trimethylsilyl chloride (0.463 mL, 3.65 mmol) was added, and the mixture was stirred at room temperature. After 30 minutes stirring, Boc-3-iodo-1-alanine methyl ester (20.00 g, 60.8 mmol) was added portion wise (5.0 g each time). After stirring at room temperature for 4 hours, dichlorobis(triphenylphosphine)palladium (ii) (2.35 g, 3.34 mmol) and 4-bromo-1-chloro-2-fluorobenzene (19.1 g, 91.1 mmol) in 20 mL DMF was added. After stirring at room temperature for 16 hours, the reaction mixture was filtered through a pad of Celite. The mother liquor was evaporated under high vacuum. The residue was taken up in EtOAc and washed with 200 mL saturated ammonium chloride, and brine, and the resulting mixture was dried over sodium sulfate. The crude product was then chromatographed eluting with 10% EtOAc in hexane. After removing the solvent, a colorless oil was obtained as the desired product (6.5 g, yield=58%). $^1$H NMR (300 MHz, CDCl$_3$) δ ppm 1.45 (s, 9H) 2.96-3.05 (m, 1H) 3.08-3.17 (m, 1H) 3.75 (s, 3H) 4.32 (m, 1H) 6.84-6.97 (m, 2H) 7.31 (t, J=7.91 Hz, 1H). MS Theoretical (M+H) 332.1, found 232.1.

Example 84

6-(2-((S)-2-Amino-3-(4-chloro-3-fluorophenyl)propylamino)thiazol-5-yl)benzo[d]oxazol-2(3H)-one MS Theoretical (M+H) 419.07, found 419.1; $^1$H NMR (400 MHz, CD$_3$OD) δ ppm 2.67 (dd, J=13.60, 7.53 Hz, 1H) 2.89 (dd, J=13.60, 5.38 Hz, 1H) 3.23-3.30 (m, 1H) 3.33 (dd, 2H) 7.02-7.12 (m, 2H) 7.15-7.23 (m, 2H) 7.28 (s, 1H) 7.33 (s, 1H) 7.36-7.45 (m, 1H).

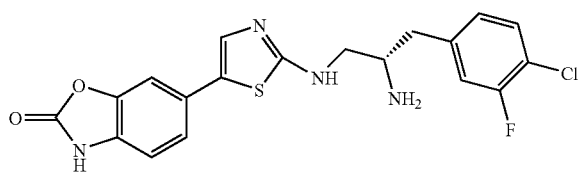

Example 85

N-((S)-2-Amino-3-(4-chloro-3-fluorophenyl)propyl)-5-(isoquinolin-6-yl)thiazol-2-amine MS Theoretical (M+H) 413.09, found 413.1; $^1$H NMR (400 MHz, CD$_3$OD) δ ppm 2.67 (dd, J=13.60, 7.34 Hz, 1H) 2.85-2.93 (m, 1H) 3.34 (d, 2H) 3.43 (t, J=8.12 Hz, 1H) 7.09 (d, J=8.02 Hz, 1H) 7.19 (dd, J=10.27, 1.66 Hz, 1H) 7.41 (t, J=7.92 Hz, 1H) 7.66 (s, 1H) 7.73-7.82 (m, 2H) 7.88 (dd, J=8.61, 1.57 Hz, 1H) 8.05 (d, J=8.61 Hz, 1H) 8.38 (d, J=5.87 Hz, 1H) 9.13 (s, 1H).

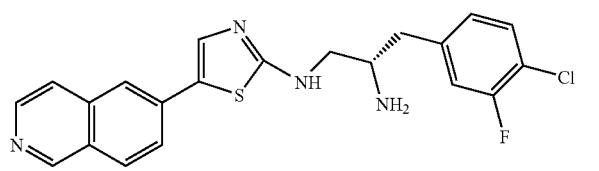

Example 86

5-(2-((S)-2-Amino-3-(4-chloro-3-fluorophenyl)pro-
pylamino)thiazol-5-yl)indolin-2-one MS Theoretical (M+H) 417.09, found 417.1; $^1$H NMR (400 MHz, CD$_3$OD) δ ppm 2.66 (dd, J=13.60, 7.34 Hz, 1H) 2.89 (dd, J=13.69, 5.48 Hz, 1H) 3.22-3.29 (m, 1H) 3.33 (s, 2H) 3.36-3.43 (m, 1H) 3.45-3.56 (m, 1H) 6.87 (d, J=8.02 Hz, 1H) 7.08 (dd, J=8.22, 1.37 Hz, 1H) 7.18 (dd, J=10.37, 1.76 Hz, 1H) 7.22 (s, 1H) 7.28 (dd, J=8.02, 1.56 Hz, 1H) 7.35-7.43 (m, 2H).

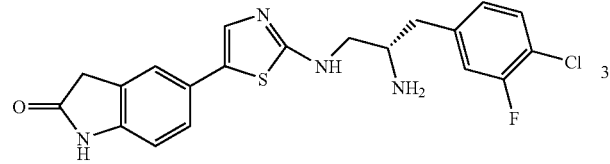

Example 87

6-(2-((S)-2-Amino-3-(4-chloro-3-fluorophenyl)pro-
pylamino)thiazol-5-yl)-1-methyl-1H-benzo[d]imida-
zol-2(3H)-one MS Theoretical (M+H) 432.1, found 432.1; $^1$H NMR (400 MHz, CD$_3$OD) δ ppm 2.96-3.02 (m, 2H) 3.42 (s, 3H) 3.53 (dt, J=14.77, 7.29 Hz, 1H) 3.61-3.70 (m, 1H) 3.73-3.83 (m, 1H) 7.06 (d, J=8.02 Hz, 1H) 7.17 (d, J=8.02 Hz, 2H) 7.23 (s, 1H) 7.26-7.32 (m, 1H) 7.41 (s, 1H) 7.50 (t, J=7.92 Hz, 1H).

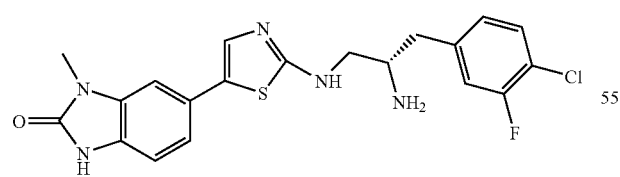

Examples 88-91

Examples 88-91 were synthesized in a manner similar to that described for Example 82 using N-Boc-erythro-L-beta-methylphenylalanine purchased from Acros as the starting material.

Example 88

6-(2-((2S,3S)-2-Amino-3-phenylbutylamino)thiazol-
5-yl)benzo[d]oxazol-2(3H)-one

MS Theoretical (M+H) 381.13, found 381.1.

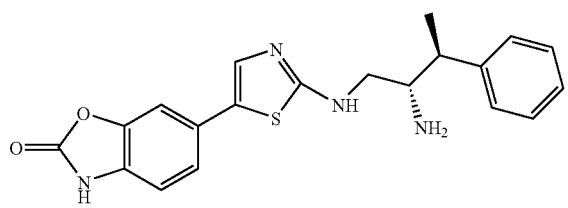

Example 89

6-(2-((2S,3S)-2-Amino-3-phenylbutylamino)thiazol-
5-yl)-1-methyl-1H-benzo[d]imidazol-2(3H)-one MS Theoretical (M+H) 394.16, found 394.2.

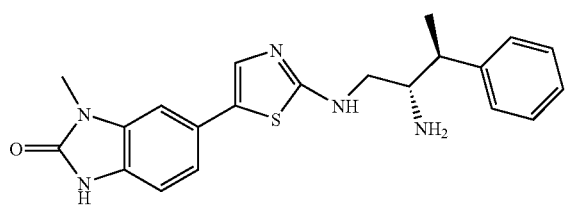

Example 90

5-(2-((2S,3S)-2-Amino-3-phenylbutylamino)thiazol-
5-yl)indolin-2-one

MS Theoretical (M+H) 379.15, found 379.2.

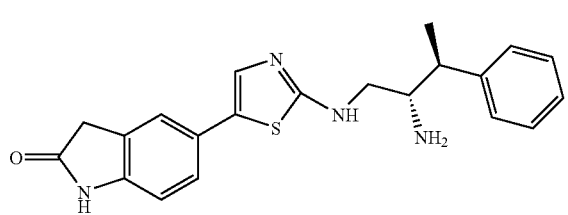

Example 91

N-((2S,3S)-2-Amino-3-phenylbutyl)-5-(isoquinolin-
6-yl)thiazol-2-amine

MS Theoretical (M+H) 375.16, found 375.2.

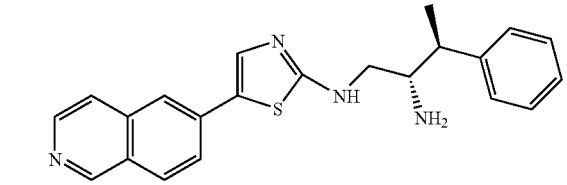

Example 92

5-(2-((2S,3S)-2-Amino-3-(4-(trifluoromethyl)phenyl)butylamino)thiazol-5-yl)indolin-2-one methane sulfonic acid salt Example 92 was synthesized in a manner similar to that described for Example 82 using the cyclic sulfamidate intermediate (S)-tert-butyl 4-((S)-1-(4-(trifluoromethyl)phenyl)ethyl)-1,2,3-oxathiazolidine-3-carboxylate, 2,2-dioxide which was synthesized as shown in Scheme 24. HRMS Theoretical (M+H) 447.14609, found 447.14627; $^1$H NMR (400 MHz, CD$_3$OD) δ ppm 1.49 (d, J=7.03 Hz, 3H) 2.72 (s, 3H) 3.21-3.29 (m, 1H) 3.56 (s, 2H) 3.65-3.72 (m, 1H) 3.74-3.81 (m, 1H) 3.81-3.87 (m, 1H) 6.90 (d, J=8.53 Hz, 1H) 7.29-7.34 (m, 2H) 7.40 (s, 1H) 7.58 (d, J=8.03 Hz, 2H) 7.74 (d, J=8.53 Hz, 2H).

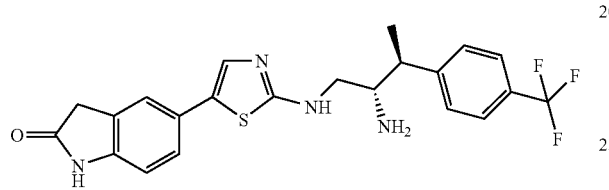

Scheme 24

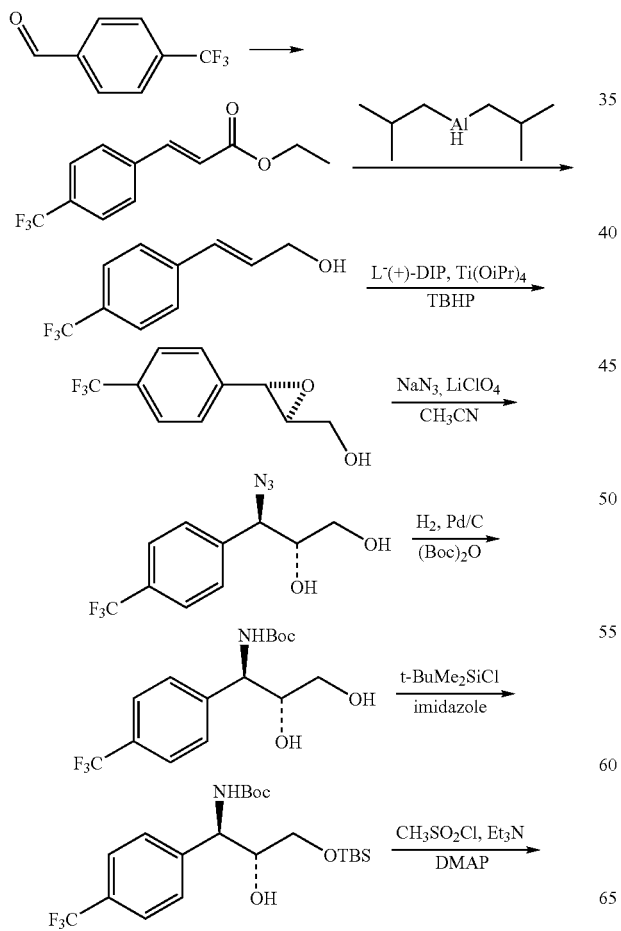

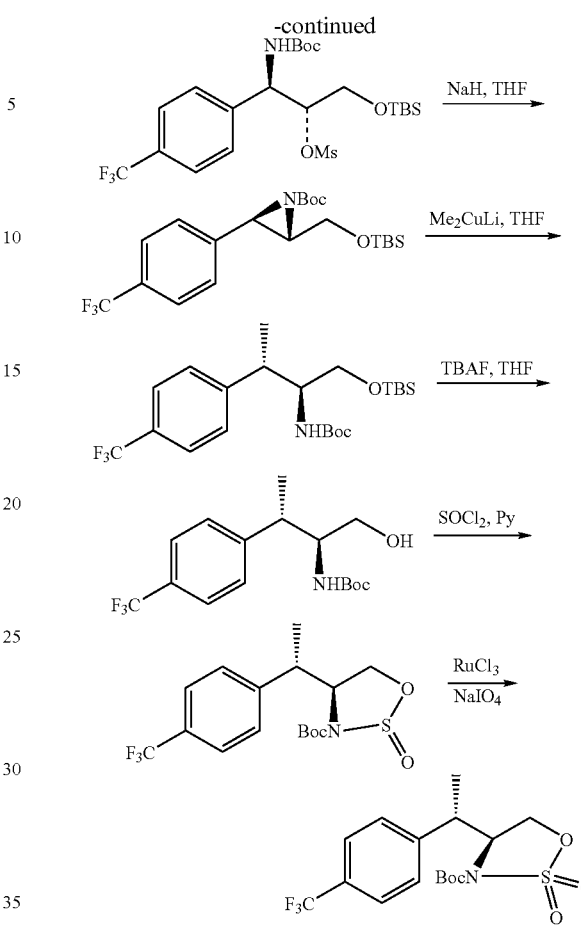

(E)-ethyl 3-(4-(trifluoromethyl)phenyl)acrylate

To a solution of (carbethoxymethylene)triphenylphosphorane (55.3 g, 159 mmol) in 150 mL DCM, alpha,alpha,alpha-trifluoro-p-tolualdehyde (25.00 g, 144 mmol) in 75 mL DCM was added. The reaction is exothermic. The mixture was heated at reflux for 90 minutes. After removing the solvent, hexane was added to the resulting residue. A precipitate appeared and was filtered through filter paper. The collected solid was subjected to a silica gel chromatography with 100% hexane as the eluant to afford a white solid ((E)-ethyl 3-(4-(trifluoromethyl)phenyl)acrylate(25.0 g, yield=71%). LCMS (API-ES) m/z (%): 245.1 (100%, M$^+$+H); $^1$H NMR (400 MHz, CD$_3$OD) δ ppm 1.35 (t, J=7.14 Hz, 3H) 4.28 (q, J=7.04 Hz, 2H) 6.68 (d, J=1 6.04 Hz, 1H) 7.70-7.77 (m, 3H) 7.80-7.84 (m, 2H).

(E)-3-(4-(trifluoromethyl)phenyl)prop-2-en-1-ol (E)-Ethyl 3-(4-(trifluoromethyl)phenyl)acrylate (25.00 g, 102 mmol) in 100 mL ether was cooled in an ice-water bath. To this solution, di-iso-butylaluminum hydride (205 mL, 205 mmol) in hexane was added. After addition, the ice-water bath was removed. After 2 hours of stirring at room temperature, the reaction mixture was diluted with 200 mL diethyl ether, cooled to 0° C. and quenched with careful addition of 200 mL brine and 200 mL of 5.0 M HCl. The aqueous solution was extracted with diethyl ether twice (200 mL each time). The combined organic phases were washed with brine and dried over sodium sulfate. The product was chromatographed eluting with 20% EtOAc in hexane. After removing the solvent, a white solid was obtained as the desired product (15.3 g, yield=74%). $^1$H NMR (400 MHz, CD$_3$OD) δ ppm 4.28 (dd, J=5.28, 1.57 Hz, 2H) 6.55 (dt, J=15.94, 5.23 Hz, H) 6.67-6.75 (m, 1H) 7.58-7.67 (m, 4H).

((2S,3S)-3-(4-(trifluoromethyl)phenyl)oxiran-2-yl) methanol

Into a 2000 mL flame-dried flask were introduced dry powdered 4A molecular sieves (9.0 g) and anhydrous DCM (1000 mL) under nitrogen. After cooling to −20° C., the following reagents were introduced sequentially via cannula under stirring: diisopropyl l-tartrate (5 g, 21 mmol), titanium tetraisopropoxide (4 mL, 14 mmol) and 5.5 M solution of t-butylhydroperoxide (101 mL, 554 mmol). The mixture was stirred 1 hour at −20° C. and a solution of (E)-3-(4-(trifluoromethyl)phenyl)prop-2-en-1-ol (56.0 g, 277 mmol) in 150 mL DCM was added over a 30 minute period. After 8 hours of stirring at the same temperature, the reaction was quenched by addition of 24 mL of a 10% aqueous solution of NaCl saturated with NaCl (100 mL of a 10% solution were prepared by adding 10 g of NaCl to a solution of 10 g of NaOH in 95 mL water). 300 mL ether was added dropwise while the cold bath was maintained at −20° C. After the ether addition, the cold bath was removed, and the mixture was allowed to warm to 10° C. Stirring was maintained for an additional 15 minutes at 10° C., and anhydrous MgSO$_4$ (24 g) and Celite (3 g) were added. After a final 30 minutes of stirring, the mixture was allowed to settle, and the upper portion was filtered through a pad of Celite. The Celite was washed with 20 mL ether. The solvents were evaporated, and tert-butyl hydroperoxide was removed by azeotropic evaporation with toluene (3×100 mL) under high vacuum. The crude product was then chromatographed eluting with 30% EtOAc in hexane. After removing the solvent, a colorless oil was obtained as the desired product (54 g, yield=90%). $^1$H NMR (400 MHz, CD$_3$OD) δ ppm 3.17 (ddd, J=4.74, 2.89, 2.15 Hz, 1H) 3.72 (dd, J=12.72, 4.70 Hz, 1H) 3.90 (dd, J=12.72, 2.93 Hz, 1H) 3.96 (d, J=1.96 Hz, 1H) 7.50 (d, J=8.02 Hz, 2H) 7.66 (d, J=8.22 Hz, 2H).

(2R,3R)-3-azido-3-(4-(trifluoromethyl)phenyl)propane-1,2-diol

To a mixture of ((2S,3S)-3-(4-(trifluoromethyl)phenyl) oxiran-2-yl)methanol (15.00 g, 68.8 mmol) in 400 mL ACN was added lithium perchlorate (75.3 mL, 1719 mmol). The reaction mixture was a suspension. After stirring for 15 minutes, sodium azide (12.1 mL, 344 mmol) was added, and the mixture was heated to 65° C. for 24 hours under nitrogen. After the reaction mixture was cooled, the solvent was evaporated under reduced pressure. 500 mL distilled water was added, and the resulting mixture was extracted 3 times (3×400 mL) with diethyl ether. The combined ether layers were directly dried over MgSO$_4$. After removing the solvent, a colorless oil was obtained as the desired product (14.5 g, yield=81%). $^1$H NMR (400 MHz, CD$_3$OD) δ ppm 3.50-3.56 (m, 1H) 3.58-3.63 (m, 1H) 3.84-3.90 (m, 1H) 4.78 (d, J=6.53 Hz, 1H) 7.62 (d, J=8.03 Hz, 2H) 7.67-7.73 (m, 2H).

tert-butyl (1R,2R)-2,3-dihydroxy-1-(4-(trifluoromethyl)phenyl)propylcarbamate

To (2R,3R)-3-azido-3-(4-(trifluoromethyl)phenyl)propane-1,2-diol (14.50 g, 56 mmol) in 120 mL EtOAc, was added di-t-butyldicarbonate (17 g, 78 mmol) and 10% Pd/C (1.45 g, 14 mmol). The mixture was hydrogenated at atmospheric pressure until no starting material could be observed by TLC (about 36 hours). The reaction mixture was filtered through Celite. The filtrate was washed twice with water and twice with brine solution and then dried over sodium sulfate. After removing the solvent, 100 mL hexane was added into the residue and a precipitate appeared. The resulting precipitate was filtered and washed with cold hexane. The white solid was air-dried and was obtained as the desired product (11.0 g, yield=60%). $^1$H NMR (400 MHz, CD$_3$OD) δ ppm 1.42 (s, 9H) 3.43-3.52 (m, 2H) 3.84 (q, J=5.41 Hz, 1H) 4.75 (d, J=5.67 Hz, 1H) 7.52-7.57 (m, 2H) 7.60-7.64 (m, 2H).

tert-butyl (1R,2R)-3-(tert-butyldimethylsilyloxy)-2-hydroxy-1-(4-(trifluoromethyl)phenyl)propylcarbamate tert-butyl (1R,2R)-2,3-dihydroxy-1-(4-(trifluoromethyl) phenyl)propylcarbamate (11 g, 32.8 mol) in 100 mL DMF was cooled in an ice-water bath. 1H-imidazole (8.2 mL, 72 mol) was added in one portion, and the mixture was stirred for 10 minutes under nitrogen. tert-butyldimethylsilylchloride (5.43 g, 36.0 mmol) in 20 mL DMF was added via syringe. The reaction was monitored by TLC. After 16 hours, DMF was evaporated under high vacuum. 150 mL distilled water was added, and the resulting mixture was extracted into diethyl ether (2×200 mL). The ether layer was washed with saturated aqueous ammonia chloride and dried over sodium sulfate. After removing the solvent, the product was obtained as a white solid (14.0 g, yield=95%). $^1$H NMR (400 MHz, CD$_3$OD) δ ppm 0.08-0.12 (m, 6H) 0.97 (s, 9H) 1.43 (s, 9H) 3.50 (s, 1H) 3.63 (s, 1H) 3.85 (s, 1H) 4.81 (s, 1H) 7.53-7.58 (m, 2H) 7.60-7.66 (m, 2H).

(1R,2R)-1-(tert-butoxycarbonyl)-3-(tert-butyldimethylsilyloxy)-1-(4-(trifluoromethyl)phenyl)propan-2-yl methanesulfonate To a solution of tert-butyl (1R,2R)-3-(tert-butyldimethylsilyloxy)-2-hydroxy-1-(4-(trifluoromethyl)phenyl)propylcarbamate (14.50 g, 32.3 mmol) in 50 mL DCM at −15° C. were added TEA (4.57 g, 45.2 mmol), N,N-dimethylpyridin-4-amine (0.197 g, 1.61 mmol), and methanesulfonyl chloride (3.26 mL, 41.9 mmol). The mixture was allowed to warm to room temperature. 200 mL distilled water was added, and the aqueous phase was extracted into DCM (2×200 mL). The combined organic layer was washed with cold 5% HCl, saturated sodium bicarbonate, and water. The crude product was then chromatographed eluting with 15% EtOAc in hexane. After removing the solvent, the product was obtained as a colorless oil (15 g, yield=88%). $^1$H NMR (400 MHz, CD$_3$OD) δ ppm 0.11 (d, J=3.91 Hz, 6H) 0.93-0.98 (m, 9H) 1.44 (s, 9H) 2.84 (s, 3H) 3.80-3.87 (m, 2H) 4.84-4.86 (m, 1H) 5.13 (d, J=5.28 Hz, 1H) 7.58 (d, J=8.02 Hz, 2H) 7.69 (d, J=8.22 Hz, 2H).

(2R,3R)-tert-butyl 2-((tert-butyldimethylsilyloxy) methyl)-3-(4-(trifluoromethyl)phenyl)aziridine-1-carboxylate To a suspension of 4.0 g sodium hydride (60% dispersion in mineral oil) in 50 mL THF at 0° C. was added a solution (1R,2R)-1-(tert-butoxycarbonyl)-3-(tert-butyldimethylsilyloxy)-1-(4-(trifluoromethyl)phenyl)propan-2-yl methanesulfonate (13.5 g, 25.6 mmol) in 60 mL THF. The reaction progress was monitored by TLC(20% EtOAc in hexane).

When no more starting material could be detected, 4 grams of MeOH was added to the mixture to remove the excess sodium hydride. The solvent was removed at reduced pressure, and 200 mL of distilled water was added to the residue. The aqueous phase was extracted (3×150 mL) with EtOAc. The combined organic layers were washed with brine and dried over sodium sulfate. The crude product was then chromatographed eluting with 3% EtOAc in hexane. After removing the solvent, the product was obtained as a colorless oil (6.5 g, yield=58%). $^1$H NMR (400 MHz, CD$_3$OD) δ ppm 0.14-0.18 (m, 6H) 0.95-0.98 (m, 9H) 1.46 (s, 9H) 2.78 (q, J=2.80 Hz, 1H) 3.64 (d, J=2.93 Hz, 1H) 4.11 (ddd, J=18.19, 11.93, 2.54 Hz, 2H) 7.48 (d, J=8.22 Hz, 2H) 7.66 (d, J=8.02 Hz, 2H).

tert-butyl (2S,3S)-1-(tert-butyldimethylsilyloxy)-3-(4-(trifluoromethyl)phenyl)butan-2-ylcarbamate To a stirred slurry of cuprous iodide (7.9 g, 42 mmol) in 150 mL ether at 0° C. was added methyllithium (1.6 M solution in diethyl ether (52 mL, 83 mmol)). The mixture was stirred at this temperature for 20 minutes. A solution of (2R,3R)-tert-butyl 2-((tert-butyldimethylsilyloxy)methyl)-3-(4-(trifluoromethyl)phenyl)aziridine-1-carboxylate (6.00 g, 14 mmol) in 150 mL ether was added via cannula to the lithium dimethylcuprate solution. The mixture was stirred at 0° C. and monitored by TLC. When no starting material could be detected (ca. 7 hours), 250 mL of an 8:1 mixture of saturated aqueous ammonia chloride and ammonia hydroxide (28-30% in water) was added to the reaction. The resulting reaction mixture was extracted with diethyl ether (2×300 mL). The combined organic layers were washed twice with brine and dried over sodium sulfate. The crude product was then chromatographed eluting with 3% EtOAc in hexane. After removing the solvent, the desired product was obtained as a colorless oil (2.0 g, yield=32%). $^1$H NMR (400 MHz, CD$_3$OD) δ ppm 0.09 (s, 6H) 0.90-0.96 (m, 9H) 1.25-1.33 (m, 12H) 3.00-3.11 (m, 1H) 3.68-3.80 (m, 3H) 7.43 (d, J=8.02 Hz, 2H) 7.56 (d, J=8.02 Hz, 2H).

tert-butyl (2S,3S)-1-hydroxy-3-(4-(trifluoromethyl)phenyl)butan-2-ylcarbamate

To tert-butyl (2S,3S)-1-(tert-butyldimethylsilyloxy)-3-(4-(trifluoromethyl)phenyl)butan-2-ylcarbamate (2000 mg, 4.5 mmol) in 25 mL ether at 0° C. was added 1.0 M tetrabutylammonium fluoride in THF (8.9 mL, 8.9 mmol). After the addition, the ice-bath was taken away. The reaction progress was monitored by TLC. After 60 minutes, the solvent was evaporated and 100 mL diethyl ether was added. The organic layer was washed with water and brine solution, and then dried over sodium sulfate. The crude product was then chromatographed eluting with 30% EtOAc in hexane. After removing the solvent, the desired product was obtained as a white solid (1.25 g, 84%). $^1$H NMR (400 MHz, CD$_3$OD) δ ppm 1.26-1.31 (m, 9H) 1.34 (d, J=7.04 Hz, 3H) 3.02-3.13 (m, 1H) 3.61-3.67 (m, 2H) 3.75 (dd, J=8.71, 4.60 Hz, 1H) 7.44 (d, J=8.02 Hz, 2H) 7.57 (d, J=8.22 Hz, 2H).

Mixture of (R)-tert-butyl 4-((S)-1-(4-(trifluoromethyl)phenyl)-1-S-ethyl)-1,2,3-oxathiazolidine-3-carboxylate, 2-oxide and (S)-tert-butyl 4-((S)-1-(4-(trifluoromethyl)phenyl)-1-S-ethyl)-1,2,3-oxathiazolidine-3-carboxylate, 2-oxide To a solution of thionyl chloride (0.6 mL, 8 mmol) in 10 mL of MeCN at −60° C. was added tert-butyl (2S,3S)-1-hydroxy-3-(4-(trifluoromethyl)phenyl)butan-2-ylcarbamate (1.1 g, 3 mmol) in 20 mL of MeCN dropwise via syringe. After 10 minutes, pyridine (1 mL, 16 mmol) was added dropwise while keeping the cold bath temperature at −60° C. The mixture was allowed to warm to room temperature and stirred overnight. During the warm up period, the reaction mixture was still a suspension. After overnight stirring, the reaction became a clear brown solution. The solvent was then removed under reduced pressure. The residue was taken up in 100 mL of EtOAc. The mixture was transferred to a separatory funnel and washed twice with 100 mL of water and once with 100 mL of brine. The organic layer was dried over Na$_2$SO$_4$. Filtration and concentration under reduced pressure, followed by flash chromatography on silica gel (5% to 10% EtOAc/hexanes) afforded 1.0 g of the mixture of diastereomers. The product is a yellow solid. 900 mg product was obtained, and the yield was 70%. $^1$H NMR (400 MHz, CDCl$_3$) δ ppm 1.40-1.44 (m, 9H) 1.51 (m, 3H) 3.62-3.70 (m, 1H) 4.37-4.46 (m, 2H) 4.79-4.89 (m, 1H) 7.38-7.43 (m, 2H) 7.59 (t, J=8.90 Hz, 2H).

(S)-tert-butyl 4-((S)-1-(4-(trifluoromethyl)phenyl)ethyl)-1,2,3-oxathiazolidine-3-carboxylate, 2,2-dioxide Sodium periodate (2.30 g, 9.5 mmol), ruthenium(III) chloride hydrate (2.67 mg, 0.012 mmol) and sulfomidite (900 mg, 2.37 mmol) were mixed together in a 500 mL round bottom flask. The ratio of the solvent by volume was as follows: ACN:water:EtOAc=30:10:5. 45 mL ACN was used. The mixture was sonicated for 17 minutes and it turned into a nice suspension. The mixture was filtered through filter paper and washed with DCM. The solvent was evaporated. The resulting mixture was taken up in DCM and washed with water and brine solution. The organic layer was dried over sodium sulfate. 840 mg of the white solid product was obtained, and the yield was 88%. $^1$H NMR (400 MHz, CDCl$_3$) δ ppm 1.44-1.49 (m, 12H) 3.51-3.59 (m, J=6.90, 6.90, 6.90, 6.90 Hz, 1H) 4.40-4.50 (m, 3H) 7.43 (d, J=8.22 Hz, 2H) 7.61 (d, J=8.22 Hz, 2H).

Example 93

6-(2-((2S,3S)-2-amino-3-(4-(trifluoromethyl)phenyl)butylamino)thiazol-5-yl)-1-methyl-1H-benzo[d]imidazol-2(3H)-one This compound was synthesized in a manner similar to that described for Example 92. MS Theoretical (M+H) 462.15, found 462.0; $^1$H NMR (400 MHz, CD$_3$OD) δ ppm 1.39 (d, J=7.34 Hz, 3H) 2.93-3.01 (m, 1H) 3.21-3.27 (m, 2H) 3.42 (s, 3H) 3.52-3.60 (m, 1H) 7.04 (d, J=8.22 Hz, 1H) 7.15 (dd, J=8.12, 1.66 Hz, 1H) 7.21 (d, J=1.56 Hz, 1H) 7.30 (s, 1H) 7.50 (d, J=8.02 Hz, 2H) 7.65 (d, J=8.02 Hz, 2H).

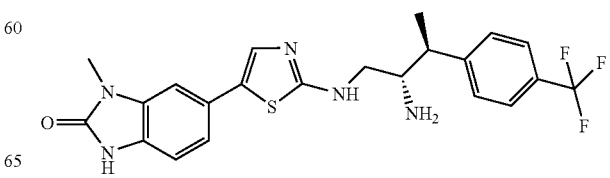

Example 94

5-(2-((S)-2-Amino-3-(4-(3-chloropropoxy)phenyl)propylamino)thiazol-5-yl)indolin-2-one This compound was synthesized in a manner similar to that described for Example 36 using (S)-tert-butyl 3-(4-(3-chloropropoxy)phenyl)-1-hydroxypropan-2-ylcarbamate cyclic sulfamidate prepared according to Scheme 25. HRMS calcd for $C_{23}H_{25}ClN_4O_2S$ 456.13867, found 457.14595 [M+H]; $^1$H NMR (400 MHz, $CD_3OD$) δ ppm 2.16-2.23 (m, J=6.16 Hz, 2H), 2.89-2.99 (m, 2H), 3.47-3.56 (m, 3H), 3.60-3.76 (m, 4H), 4.11 (t, J=5.87 Hz, 2H), 6.87-6.97 (m, 3H), 7.21-7.39 (m, 5H).

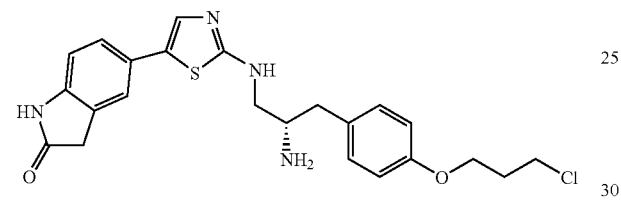

Scheme 25

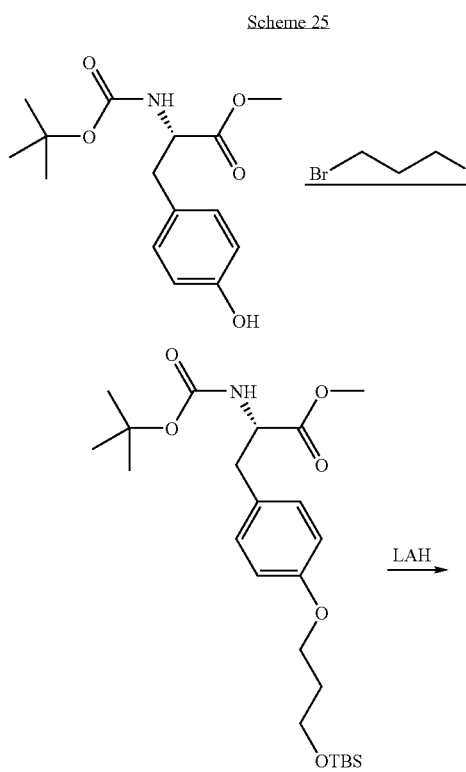

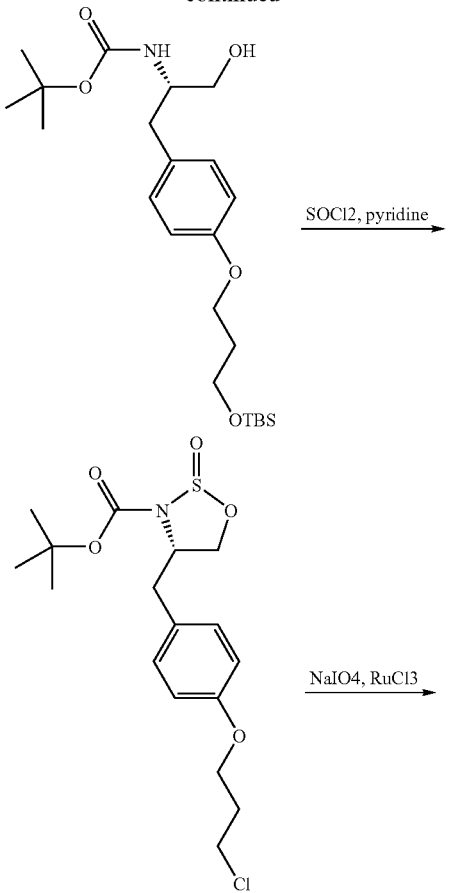

(S)-methyl 2-(tert-butoxycarbonyl)-3-(4-(3-(tert-butyldimethylsilyloxy)propoxy)-phenyl)propanoate (3-Bomopropoxy)-tert-butyldimethylsilane (17.7 mL 76.2 mmol), $K_2CO_3$ (14.0 g, 102 mmol) and n-(tert-butoxycarbonyl)-1-tyrosine methyl ester (15.0 g, 50.8 mmol) were combined in DMF (63 mL and stirred at room temperature for 12 hours and at 80° C. for 7 hours. The mixture was diluted with ether (250 mL) and brine (100 mL) was added. The mixture was passed through a coarse fritted glass funnel. The filtrate was washed with brine (3×100 mL), and the organic layer was dried over sodium sulfate and evaporated to a yellow oil. The oil was soluble in hexane, and was loaded on to a column of silica gel and purified by chromatography through a Redi-Sep® pre-packed silica gel column (330 g), eluting with a gradient of 0% to 50% EtOAc in hexane, to provide (S)-methyl 2-(tert-butoxycarbonyl)-3-(4-(3-(tert-butyldimethylsilyloxy)propoxy)phenyl)propanoate (23.6 g, 100% yield) as a yellow oil. $^1$H NMR (400 MHz, CDCl$_3$) δ ppm 0.0 (s, 6H), 0.85 (s, 9H) 1.38 (s, 9H) 1.89-1.96 (m, 2H) 2.97 (s, 2H) 3.66 (s, 3H) 3.75 (t, J=5.97 Hz, 2H) 3.99 (t, J=6.26 Hz, 2H) 4.49 (m, 1H) 4.90 (m, 1H) 6.78 (d, J=8.61 Hz, 3H) 6.97 (d, J=8.41 Hz, 2H).

(S)-tert-butyl 3-(4-(3-(tert-butyldimethylsilyloxy)propoxy)phenyl)-1-hydroxypropan-2-ylcarbamate To (S)-methyl 2-(tert-butoxycarbonyl)-3-(4-(3-(tert-butyldimethylsilyloxy)propoxy)phenyl)propanoate (10.23 g, 21.9 mmol) in THF (200 mL) at 0° C. was added LAH, 1.0 M solution in THF (21.9 mL, 21.9 mmol) dropwise over 10 minutes. Brine (200 mL) and ether (250 mL) were added, and the organic phase was separated. The aqueous layer was washed with ether (2×100 mL), and the combined organic layers were washed with brine (100 mL), dried over sodium sulfate, and evaporated to provide (S)-tert-butyl 3-(4-(3-(tert-butyldimethylsilyloxy)propoxy)phenyl)-1-hydroxypropan-2-ylcarbamate (8.78 g, 91.3% yield) as a white crystalline solid: $^1$H NMR (400 MHz, CDCl$_3$) δ ppm 0.04 (s, 6H) 0.87 (m, 9H) 1.38 (s, 9H) 1.81 (s, 1H) 1.89-1.96 (m, 2H) 2.73 (d, J=7.04 Hz, 2H) 3.52 (s, 1H) 3.61 (s, 1H) 3.70 (s, 1H) 3.75 (t, J=5.97 Hz, 3H) 4.00 (t, J=6.26 Hz, 2H) 6.80 (d, J=8.41 Hz, 2H) 7.06 (d, J=8.41 Hz, 2H).

(S)-tert-butyl 3-(4-(3-chloropropoxy)phenyl)-1-hydroxypropan-2-ylcarbamate cyclic sulfamidite (S)-tert-butyl 3-(4-(3-(tert-butyldimethylsilyloxy)propoxy)phenyl)-1-hydroxypropan-2-ylcarbamate (8.78 g, 20 mmol) was added in ACN (130 mL) to thionyl chloride (3.6 mL, 50 mmol) at −60° C. over 35 minutes. The dropping funnel was rinsed with 10 mL ACN. The mixture was stirred an additional 30 minutes at −60° C. and pyridine (8.1 mL, 100 mmol) was added and stirring was continued at room temperature. After 23 hours, the solvent was evaporated, and the residue was dissolved in 1:1 brine:EtOAc (500 mL). The aqueous layer was washed with ether (3×100 mL). The combined organic layers were washed with brine (100 mL), dried over sodium sulfate, adsorbed onto a plug of silica gel, and purified by chromatography through a Redi-Sep® pre-packed silica gel column (330 g), eluting with a gradient of 0% to 60% EtOAc in hexane to provide (S)-tert-butyl 3-(4-(3-chloropropoxy)phenyl)-1-hydroxypropan-2-ylcarbamate cyclic sulfamidite (2.64 g, 34% yield) as a mixture of diastereomers: $^1$H NMR (400 MHz, CDCl$_3$) δ ppm 1.26 (t, J=7.14 Hz, 1H) 1.54, 1.56 (2s, 9H) 2.20-2.27 (m, J=6.06 Hz, 2H) 3.75 (t, J=6.26 Hz, 2H) 4.10 (td, J=5.77, 2.15 Hz, 2H) 4.13 (s, 1H) 4.43 (d, J=9.39 Hz, 1H) 4.81 (d, J=8.80 Hz, 1H) 6.83-6.89 (m, 2H) 7.07-7.16 (m, 2H). Minor diastereomer resonances were observed at 2.57, 2.78, 3.11, and 3.54 ppm.

(S)-tert-butyl 3-(4-(3-chloropropoxy)phenyl)-1-hydroxypropan-2-ylcarbamate cyclic sulfamidate To a solution of (S)-tert-butyl 3-(4-(3-chloropropoxy)phenyl)-1-hydroxypropan-2-ylcarbamate cyclic sulfamidite (2.64 g, 6.77 mmol) in ACN (36 mL) and EtOAc (6 mL) at 0° C. was added sodium periodate (1.28 g, 5.98 mmol) in 20 mL of water and ruthenium(iii) chloride (0.0113 g, 0.0544 mmol). The mixture was allowed to warm to room temperature. After 6 hours, ACN was removed by rotary evaporation. The aqueous mixture and precipitate were dissolved in EtOAc (200 mL) and washed with brine (2×100 mL), the brine was extracted with EtOAc (50 mL), the combined organics were dried over sodium sulfate and evaporated providing (S)-tert-butyl 3-(4-(3-chloropropoxy)phenyl)-1-hydroxypropan-2-ylcarbamate cyclic sulfamidate (2.61 g, 95% yield) as a white solid: $^1$H NMR (400 MHz, CDCl$_3$) ppm 1.38-1.45 (m, 9H) 2.05-2.12 (m, 2H) 2.72 (dd, J=13.50, 10.37 Hz, 1H) 3.15 (dd, J=13.60, 4.21 Hz, 1H) 3.59 (t, J=6.26 Hz, 2H) 3.95 (t, J=5.77 Hz, 2H) 4.16 (d, J=9.19 Hz, 1H) 4.24 (s, 1H) 4.31 (d, J=3.33 Hz, 1H) 6.73 (d, J=8.41 Hz, 2H) 6.99 (d, J=8.41 Hz, 2H).

Example 95

5-(2-((S)-2-Amino-3-(4-(3-hydroxypropoxy)phenyl)propylamino)-thiazol-5-yl)indolin-2-one This compound was synthesized in a manner similar to that described for Example 36 using (S)-tert-butyl 3-(4-(3-(tert-butyldimethylsilyloxy)-propoxy)phenyl)-1-hydroxypropan-2-ylcarbamate cyclic sulfamidate. (S)-tert-butyl 3-(4-(3-(tert-butyldimethylsilyloxy)propoxy)phenyl)-1-hydroxypropan-2-ylcarbamate cyclic sulfamidate was prepared according to Scheme 25, but the following procedure was used for the reaction with thionyl chloride. HRMS calcd for C$_{23}$H$_{26}$N$_4$O$_3$S 438.17256, found 439.18018; $^1$H NMR(400 MHz, CD$_3$OD) δ ppm 1.92-2.00 (m, J=6.75, 6.50, 6.38, 6.38 Hz, 3H), 2.94 (d, J=7.24 Hz, 2H), 3.51-3.57 (m, 2H), 3.61-3.74 (m, 4H), 4.07 (q, J=6.06 Hz, 2H), 6.88-6.96 (m, 3H), 7.19-7.25 (m, 2H), 7.30 (dd, J=8.22, 1.37 Hz, 1H), 7.36-7.40 (m, 2H).

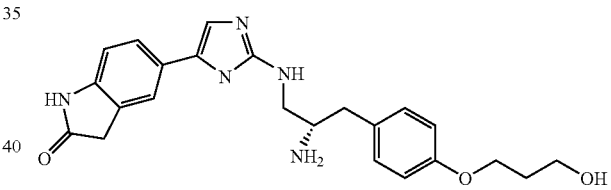

(S)-tert-butyl 3-(4-(3-(tert-butyldimethylsilyloxy)propoxy)phenyl)-1-hydroxypropan-2-ylcarbamate cyclic sulfanidite A mixture of (S)-tert-butyl 3-(4-(3-(tert-butyldimethylsilyloxy)propoxy)phenyl)-1-hydroxypropan-2-ylcarbamate (1.11 g, 2.5 mmol) in ACN (12 mL) was added to thionyl chloride (0.46 mL, 6.3 mmol) and pyridine (2.1 mL, 25 mmol) in ACN (4 mL) at −60° C. The mixture was allowed to warm slowly to room temperature over 3 hours. The mixture was evaporated and the residue taken up in EtOAc, partitioned between brine (100 mL) and ether (100 mL), and washed with brine (2×50 mL). The ether was dried over sodium sulfate, adsorbed onto a plug of silica gel and purified by chromatography through a Redi-Sep® pre-packed silica gel column (120 g), eluting with a gradient of 0% to 100% EtOAc in hexane, to provide (S)-tert-butyl 3-(4-(3-(tert-butyldimethylsilyloxy)propoxy)-phenyl)-1-hydroxypropan-2-ylcarbamate cyclic sulfamidite (0.55 g, 45% yield) as a colorless oil: $^1$H NMR (400 MHz, CDCl$_3$) δ ppm 0.00 (s, 6H) 0.84 (s, 9H) 1.50, 1.51 (2 s, 9H) 1.89-1.97 (m, 2H) 2.47-2.57 (m, 0.5H) 2.67-2.79 (m, 0.5H) 2.99-3.13 (m, 0.5H) 3.46-3.57 (m, 0.5H) 3.75 (t, J=5.97 Hz, 2H) 3.93-4.04 (m, 2H) 4.10-

4.31 (m, 1H) 4.39 (d, J=9.39 Hz, 0.5H) 4.40-4.50 (m, 0.5H) 4.42-4.85 (m, 1H) 6.81 (dd, J=8.22, 5.48 Hz, 2H) 7.01-7.10 (m, 2H).

Example 96

N-((S)-2-Amino-3-(3,4-dichlorophenyl)propyl)-4-(methoxymethyl)-5-(thiazolo[5,4-c]pyridin-2-yl)thiazol-2-amine This compound was synthesized in a manner similar to that described for Example 17. LCMS (M+H) 480 calc. for $C_{20}H_{20}Cl_2N_5OS_2$ 480.05. $^1$H NMR (400 MHz, CD$_3$OD) δ ppm 9.11 (s, 1H) 8.60 (d, J=5.48 Hz, 1H) 7.81 (d, J=5.67 Hz, 1H) 7.39 (dd, J=9.88, 8.31 Hz, 1H) 7.36 (d, J=9.19 Hz, 1H) 7.06 (dd, J=18.58, 8.02 Hz, 1H) 6.30 (s, 1H) 6.14 (s, 1H) 4.74 (d, J=6.46 Hz, 3H) 3.75 (bs, 1H) 3.28-3.37 (m, 1H) 3.20 (m, 1H) 2.94-3.02 (m, 2H) 2.83 (dd, J=13.40, 5.18 Hz, 1H) 2.57 (dd, J=13.60, 8.51 Hz, 1H).

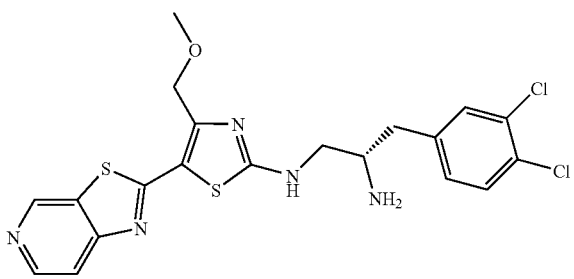

Examples 97-99

Examples 97-99 were synthesized in manner similar to that described for Example 31.

Example 97

N-((S)-2-Amino-3-(3,4-dichlorophenyl)propyl)-5-(thiazolo[5,4-c]pyridin-2-yl)thiazol-2-amine LCMS (M+H) calc. for $C_{18}H_{16}Cl_2N_5S_2$ 436.0. $^1$H NMR (400 MHz, CD$_3$OD): δ ppm 9.13 (s, 1H) 8.55 (d, J=5.67 Hz, 1H) 8.02 (s, 1H) 7.85 (d, J=5.67 Hz, 1H) 7.55-7.58 (m, 1H) 7.54 (s, 1H) 7.29 (dd, J=8.31, 2.05 Hz, 1H) 3.73-3.85 (m, 1H) 3.61 (dd, 1H) 3.01 (dd, J=9.78, 7.24 Hz, 1H) 2 protons obscured under solvent peak at 3.32.

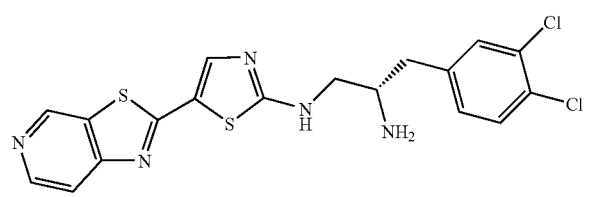

Example 98

N-((S)-2-Amino-3-(4-methoxyphenyl)propyl)-5-(thiazolo[5,4-c]pyridin-2-yl)thiazol-2-amine LCMS (M+H) calc. for $C_{19}H_{20}N_5OS_2$ 398.1. $^1$H NMR (400 MHz, CD$_3$OD): δ ppm 9.38 (s, 1H) 8.67 (s, 1H) 8.24 (s, 1H) 8.15 (d, J=6.26 Hz, 1H) 7.26 (d, J=8.61 Hz, 2H) 6.95 (d, J=8.61 Hz, 2H) 3.81 (s, 3H) 3.79 (m, 2H) 3.71-3.77 (m, 1H) 3.60-3.69 (m, 1H) 2.97 (d, J=6.85 Hz, 1H).

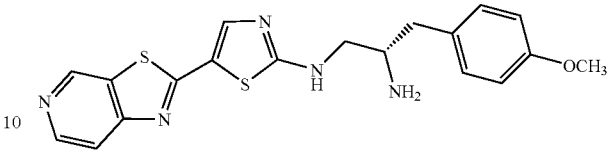

Example 99

N-((S)-2-Amino-3-(4-chlorophenyl)propyl)-5-(thiazolo[5,4-c]pyridin-2-yl)thiazol-2-amine LCMS (M+H) calc. for $C_{18}H_{17}ClN_5S_2$ 402.0. $^1$H NMR (400 MHz, CD$_3$OD): δ ppm 9.43 (s, 1H) 8.69 (d, J=6.46 Hz, 1H) 8.29 (s, 1H) 8.22 (d, J=6.46 Hz, 1H) 7.38-7.44 (m, 2H) 7.22-7.29 (m, 2H) 3.81 (d, J=11.54 Hz, 2H) 3.61-3.71 (m, 1H) 3.02 (d, J=6.85 Hz, 2H).

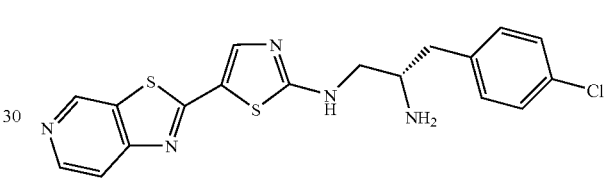

Example 100

N-((S)-2-Amino-3-(4-(trifluoromethyl)phenyl)propyl)-4-(2,3-difluorophenyl)-5-(isoquinolin-6-yl)thiazol-2-amine Example 100 was synthesized in a manner similar to that described for Example 81 by coupling the 5-bromothiazole intermediate shown in Scheme 26 with isoquinolin-6-ylboronic acid. LCMS (M+H) calc. for $C_{28}H_{22}F_5N_4S$ 541.1. $^1$H NMR (400 MHz, CD$_3$OD) δ ppm 9.15 (s, 1H) 8.48 (d, J=5.67 Hz, 1H) 7.78 (d, J=8.61 Hz, 1H) 7.57-7.64 (m, 3H) 7.49 (d, J=5.67 Hz, 1H) 7.31-7.37 (m, 3H) 7.19-7.25 (m, 1H) 7.12-7.18 (m, 1H) 7.04-7.11 (m, 1H) 3.45-3.53 (m, 1H) 3.35-3.42 (m, 1H) 3.17-3.27 (m, 1H) 2.96 (dd, J=13.40, 5.18 Hz, 1H) 2.68 (dd, J=13.50, 8.61 Hz, 1H).

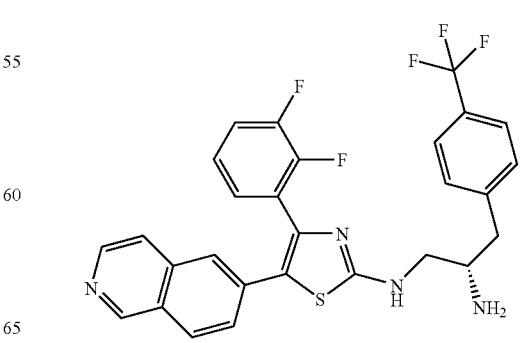

Scheme 26

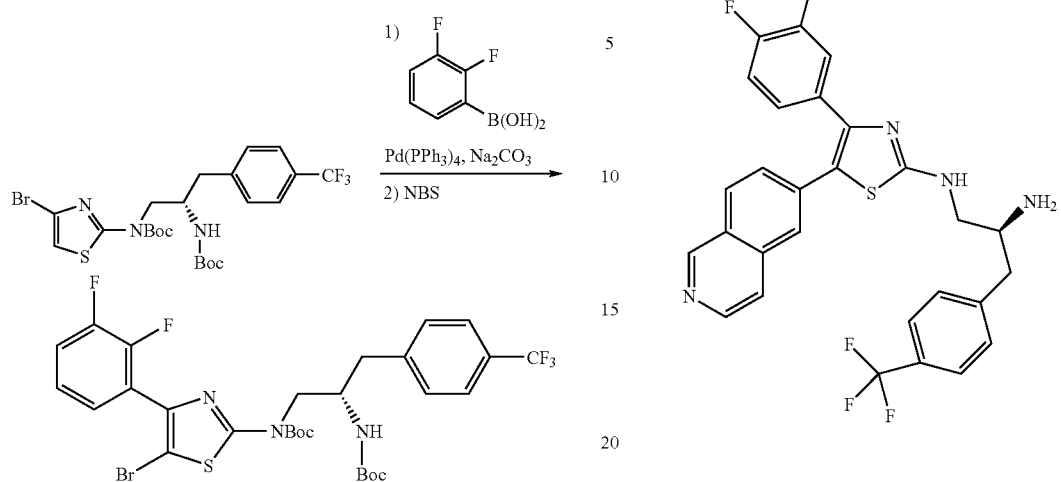

Tert-butyl (S)-1-(5-bromo-4-(2,3-difluorophenyl)thiazol-2-yl-(t-butoxylcarbonyl)amino)-3-(4-(trifluoromethyl)phenyl)propan-2-ylcarbamate A glass microwave reaction vessel was charged with Bis-Bocdiamino-4-bromothiazole (0.500 g, 0.86 mmol), 2,3-difluorophenylboronic acid (0.20 g, 1.3 mmol), tetrakis(triphenylphosphine)palladium(0) (0.100 g, 0.086 mmol), sodium carbonate (0.27 g, 2.6 mmol), and 1,4-dioxane (4.00 mL, 47 mmol) and water (0.400 mL, 22 mmol). The reaction mixture was stirred and heated in a Smith Synthesizer® microwave reactor (Personal Chemistry, Inc., Upssala, Sweden) at 125° C. for 25 minutes. The crude reaction mixture was adsorbed onto a plug of silica gel and chromatographed through a Redi-Sep® pre-packed silica gel column (40 g), eluting with a gradient of 5% to 40% EtOAc in hexane, to provide the crude product (0.87 g).

The material from the above reaction (0.530 g, 0.864 mmol) was added to a 100 mL round-bottomed flask, and CCl$_4$ (0.0833 mL, 0.864 mmol) was added. NBS (0.307 g, 1.73 mmol) was added to the resulting suspension, and the resulting mixture was stirred. The reaction was quenched by the addition of water and DCM. The aqueous portion was extracted with DCM and dried over sodium sulfate, filtered, and adsorbed onto a plug of silica gel and chromatographed through a Redi-Sep® pre-packed silica gel column (12 g), eluting with a gradient of 5% to 40% EtOAc in hexane to provide the product (0.567 g, 94.8%).

Examples 101-107

These compounds were synthesized in a manner similar to that described for Example 100.

Example 101, N-((S)-2-Amino-3-(4-(trifluoromethyl)phenyl)propyl)-4-(3,4-difluorophenyl)-5-(isoquinolin-6-yl)thiazol-2-amine: LCMS (M+H) calc. for $C_{28}H_{22}F_5N_4S$ 541.1. $^1$H NMR (400 MHz, CD$_3$OD) δ ppm 9.20 (s, 1H) 8.52 (d, J=5.67 Hz, 1H) 7.84 (d, J=8.61 Hz, 1H) 7.72 (s, 1H) 7.60 (d, J=8.02 Hz, 3H) 7.55 (d, J=5.67 Hz, 1H) 7.38-7.43 (m, 1H) 7.35 (d, J=7.83 Hz, 2H) 7.13-7.19 (m, 1H) 6.98-7.06 (m, 1H) 5.80 (br. s., 1H) 3.47-3.55 (m, 1H) 3.35-3.43 (m, 1H) 3.19-3.26 (m, 1H) 2.97 (dd, J=13.60, 5.18 Hz, 1H) 2.70 (dd, J=13.40, 8.51 Hz, 1H).

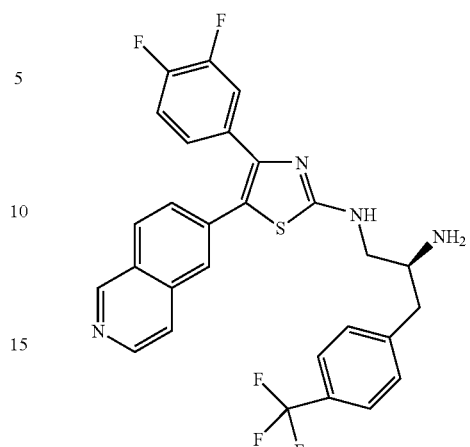

Example 102

N-((S)-2-Amino-3-(4-(trifluoromethyl)phenyl)propyl)-4-(4-fluorophenyl)-5-(isoquinolin-6-yl)thiazol-2-amine LCMS (M+H) calc. for $C_{28}H_{23}F_4N_4S$ 523.1. $^1$H NMR (400 MHz, CD$_3$OD) δ ppm 9.54 (s, 1H) 8.46 (d, J=6.65 Hz, 1H) 8.20-8.26 (m, 2H) 8.05 (s, 1H) 7.65-7.71 (m, 3H) 7.54 (d, J=8.22 Hz, 2H) 7.48 (dd, J=8.51, 5.38 Hz, 2H) 7.10 (dd, J=8.71 Hz, 2H) 3.89-3.96 (m, 1H) 3.72-3.79 (m, 1H) 3.56-3.63 (m, 1H) 3.11 (d, J=7.40 Hz, 2H).

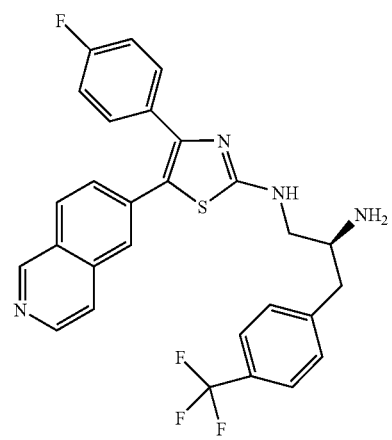

Example 103

N-((S)-2-amino-3-(4-(trifluoromethyl)phenyl)propyl)-4-(3-fluorophenyl)-5-(isoquinolin-6-yl)thiazol-2-amine LCMS (M+H) calc. for $C_{28}H_{23}F_4N_4S$ 523.1. $^1$H NMR (400 MHz, CD$_3$OD) δ ppm 9.57 (s, 1H) 8.48 (d, J=6.46 Hz, 1H) 8.20-8.30 (m, 2H) 8.09 (s, 1H) 7.72 (dd, J=8.80, 1.56 Hz, 1H) 7.67 (d, J=8.02 Hz, 2H) 7.55 (d, J=8.02 Hz, 2H) 7.30-7.38 (m, 1H) 7.19-7.28 (m, 2H) 7.14 (dd, J=8.51 Hz, 1H) 3.91-4.00 (m, 1H) 3.76 (dd, 1H) 3.60 (dd, 1H) 3.12 (d, J=7.24 Hz, 2H).

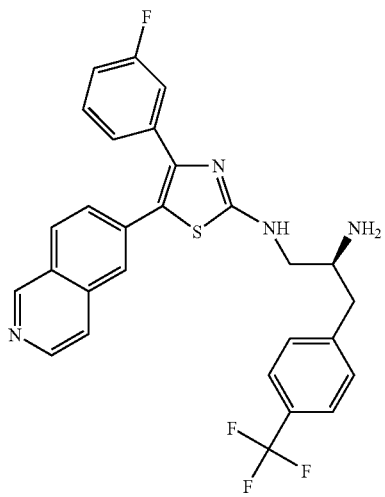

Example 104

N-((S)-2-Amino-3-(4-(trifluoromethyl)phenyl)propyl)-5-(isoquinolin-6-yl)-4-(pyridin-3-yl)thiazol-2-amine LCMS (M+H) calc. for $C_{27}H_{23}F_3N_5S$ 506.1. $^1$H NMR (400 MHz, CD$_3$OD) δ ppm 9.60 (s, 1H) 8.71 (s, 1H) 8.58-8.65 (m, 1H) 8.51 (d, J=6.46 Hz, 1H) 8.32 (d, J=8.61 Hz, 1H) 8.26 (d, J=6.46 Hz, 1H) 8.14 (s, 1H) 7.59-7.79 (m, 5H) 7.55 (d, J=8.22 Hz, 2H) 3.92-3.98 (m, 1H) 3.75-3.82 (m, 1H) 3.59-3.67 (m, 1H) 3.47 (s, 1H) 3.13 (d, J=7.04 Hz, 2H).

Example 105

N-((S)-2-Amino-3-(4-(trifluoromethyl)phenyl)propyl)-4-(2-fluorophenyl)-5-(isoquinolin-6-yl)thiazol-2-amine LCMS (M+H) calc. for $C_{28}H_{23}F_4N_4S$ 523.1. $^1$H NMR (400 MHz, CD$_3$OD) δ ppm 9.11 (s, 1H) 8.37 (d, J=5.87 Hz, 1H) 7.88 (d, J=8.80 Hz, 1H) 7.67 (s, 1H) 7.60-7.64 (m, 3H) 7.41-7.51 (m, 4H) 7.38 (dd, J=8.61, 1.56 Hz, 1H) 7.22-7.26 (m, 1H) 7.08-7.15 (m, 1H) 3.48 (dd, 1H) 3.39-3.45 (m, 1H) 2.99 (dd, J=13.50, 5.67 Hz, 1H) 2.78 (dd, J=13.50, 7.24 Hz, 1H) 1H obscured by solvent at 3.30 ppm.

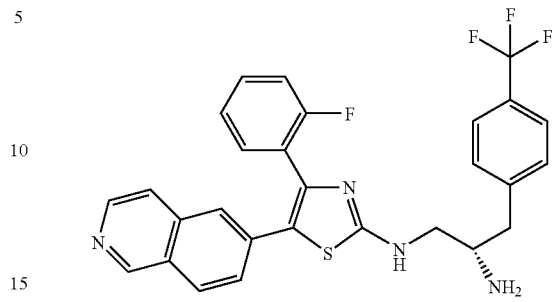

Example 106

N-((S)-2-Amino-3-(4-fluorophenyl)propyl)-4-(2-fluorophenyl)-5-(isoquinolin-6-yl)thiazol-2-amine LCMS (M+H) calc. for $C_{27}H_{23}F_2N_4S$ 473.1. $^1$H NMR (400 MHz, CD$_3$OD) δ ppm 9.11 (s, 1H) 8.36 (d, J=5.87 Hz, 1H) 7.89 (d, J=8.61 Hz, 1H) 7.68 (s, 1H) 7.63 (d, J=5.87 Hz, 1H) 7.40-7.51 (m, 2H) 7.38 (dd, J=8.61, 1.57 Hz, 1H) 7.26-7.33 (m, 2H) 7.24 (t, J=7.53 Hz, 1H) 7.11 (t, J=9.10 Hz, 1H) 7.01-7.07 (m, 2H) 3.40-3.51 (m, 1H) 2.84-2.93 (m, 1H) 2.67 (dd, J=13.60, 6.94 Hz, 1H) 2H obscured by solvent at 3.31.

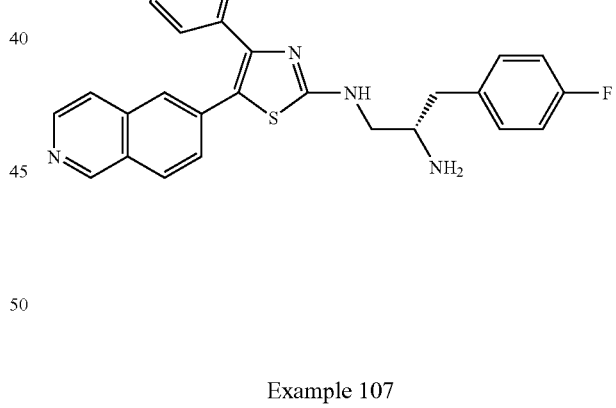

Example 107

5-(2-((S)-2-Amino-3-(4-(trifluoromethyl)phenyl)-propylamino)-4-(2-fluorophenyl)thiazol-5-yl)indolin-2-one LCMS (M+H) calc. for $C_{27}H_{23}F_4N_4OS$ 527.1. $^1$H NMR (400 MHz, CD$_3$OD) δ ppm 7.84 (s, 1H) 7.60 (d, J=8.02 Hz, 2H) 7.46 (d, J=8.02 Hz, 2H) 7.32-7.40 (m, 2H) 7.15 (td, J=7.53, 0.98 Hz, 1H) 7.04-7.10 (m, 1H) 7.02 (d, J=1.37 Hz, 1H) 6.98 (dd, J=8.12, 1.86 Hz, 1H) 6.73 (d, J=8.02 Hz, 1H) 3.35-3.46 (m, 3H) 3.29 (d, J=6.26 Hz, 1H) 2.98 (dd, J=13.60, 5.58 Hz, 1H) 2.76 (dd, J=13.60, 7.53 Hz, 1H) 1H obscured by solvent at 3.35.

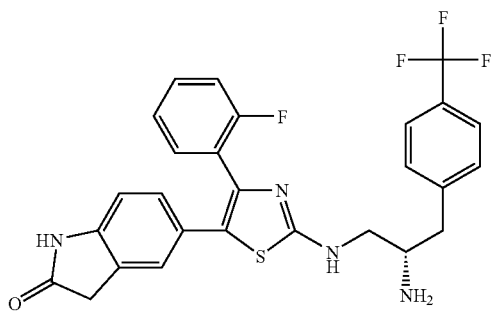

Example 108

N-((S)-2-amino-3-(4-(trifluoromethyl)phenyl)propyl)-5-(thieno[2,3-c]pyridin-2-yl)thiazol-2-amine Example 108 was synthesized in a manner similar to that described in Example 82 using thieno[2,3-c]pyridin-2-ylboronic acid as one of the starting materials. Thieno[2,3-c]pyridin-2-ylboronic acid was prepared by treating commercially available thieno[2,3-c]pyridine with butyl lithium in the presence of diisopropylamine and triisopropyl borate in THF at −70° C. LCMS (M+H) 435.1 for $C_{20}H_{17}F_3N_4S_2$, 434.5; $^1H$ NMR (400 MHz, $CD_3OD$) δ ppm 2.71-2.79 (m, 6H) 2.93-3.01 (m, 7H) 3.35 (d, J=3.33 Hz, 11H) 3.41-3.48 (m, 8H) 7.29 (s, 7H) 7.47 (d, J=8.02 Hz, 17H) 7.51 (s, 6H) 7.58-7.65 (m, 16H) 7.70 (d, J=5.67 Hz, 7H) 8.35 (d, J=5.67 Hz, 7H) 8.97 (s, 7H).

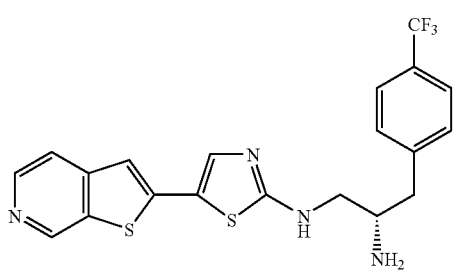

Example 109

6-(2-((2S,3S)-2-Amino-3-(4-(trifluoromethyl)phenyl)butylamino)-thiazol-5-yl)benzo[d]oxazol-2(3H)-one This compound was synthesized in a manner similar to that described in Example 92 except that the intermediate tert-butyl (2S,3S)-1-hydroxy-3-(4-(trifluoromethyl)phenyl)butan-2-ylcarbamate was prepared in a different way as shown in Scheme 27. LCMS (M+H) calc. for $C_{21}H_{20}F_3N_4O_2S$ 449.1. $^1H$ NMR (400 MHz, $CD_3OD$) δ ppm 7.66 (d, J=8.03 Hz, 1H) 7.51 (d, J=8.03 Hz, 1H) 7.35 (s, 1H) 7.30 (s, 1H) 7.24 (d, J=8.53 Hz, 1H) 7.06 (d, J=8.03 Hz, 1H) 3.54-3.62 (m, 1H) 3.24-3.29 (m, 2H) 2.95-3.03 (m, 1H) 1.41 (d, J=7.03 Hz, 3H).

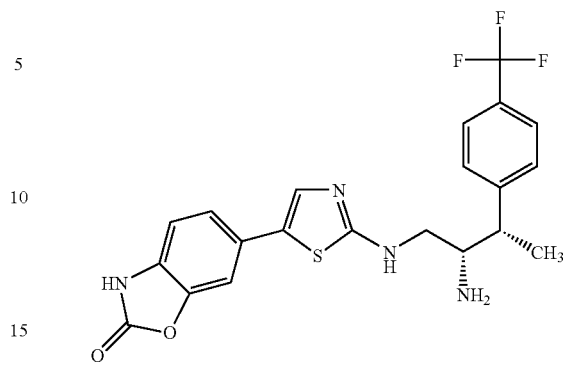

Scheme 27

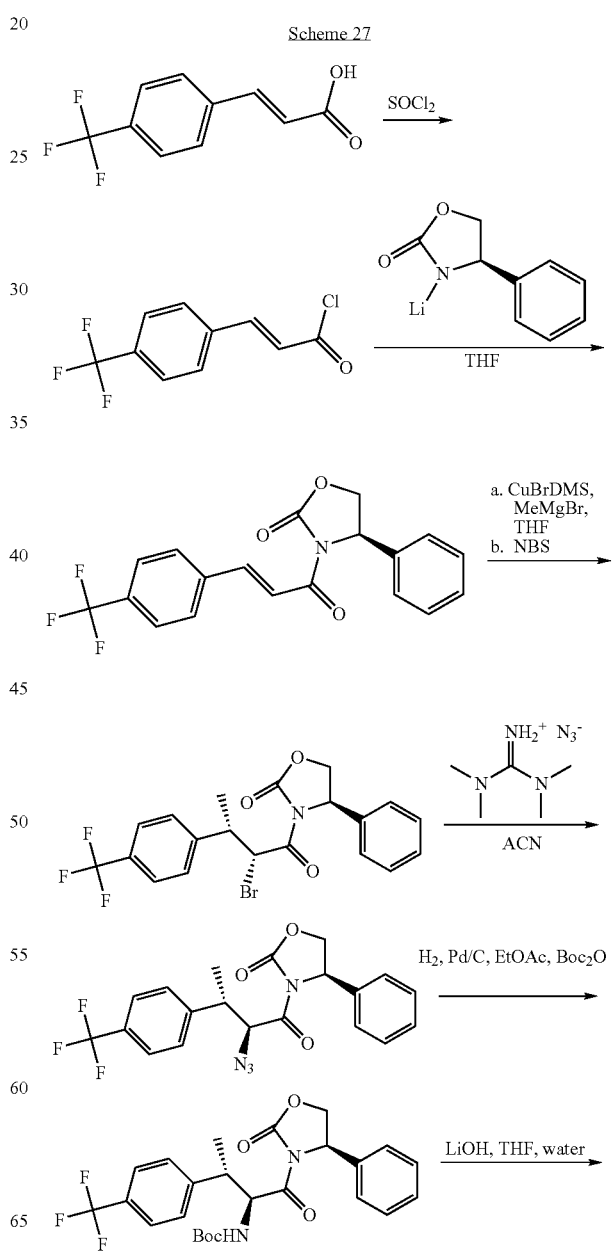

-continued

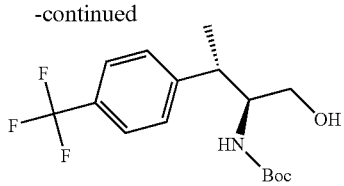

(E)-3-(4-(trifluoromethyl)phenyl)acryloyl chloride

To a 500 mL round-bottomed flask was added 4-(trifluoromethyl)cinnamic acid (231 mL, 116 mmol), DCM (7.44 mL, 116 mmol), thionyl chloride (17.7 mL, 243 mmol), and a few drops of DMF. The resulting mixture was stirred at reflux for about 1.5 hours and followed by LCMS (MeOH quench). Once no starting material was present, the solvents were reduced and the oil was used immediately in the next step.

(R,E)-4-phenyl-3-(3-(4-(trifluoromethyl)phenyl)acryloyl)oxazolidin-2-one

To a 500 mL round-bottomed flask was added (R)-4-phenyloxazolidin-2-one (19 g, 116.00 mmol) and THF (464 mL, 116 mmol). The solution was cooled to −78° C. N-butyllithium (46 mL, 116 mmol) was then added slowly, and the reaction was stirred for about 15 minutes before the addition of a THF solution of (E)-3-(4-(trifluoromethyl)phenyl)acryloyl chloride (27 g, 116 mmol). The cold bath was removed, the reaction was allowed to warm to room temperature, and the progress of the reaction was checked by LCMS. After LCMS indicated that the reaction was complete, the reaction was quenched with water, and the organics were washed with saturated sodium bicarbonate and brine, dried over sodium sulfate, filtered, and reduced to give an orange solid, (R,E)-4-phenyl-3-(3-(4-(trifluoromethyl)phenyl)acryloyl)oxazolidin-2-one (42 g, 100% yield).

(R)-3-((2R,3S)-2-bromo-3-(4-(trifluoromethyl)phenyl)butanoyl)-4-phenyloxazolidin-2-one To a 500 mL round-bottomed flask was added copper (I) bromide-dimethyl sulfide complex (4.63 g, 22.5 mmol), DMS (27.1 mL, 369 mmol), and THF (100 mL). The reaction was then cooled to −78° C. Methylmagnesium bromide, 3.16 M in ether (9.53 mL, 30.1 mmol) was added and the solution was stirred for about 10 minutes and then at 0° C. for 10 minutes. The reaction was then cooled to −78° C. before being transferred via a cannula to a pre-cooled (−78° C.) slurry of (R,E)-4-phenyl-3-(3-(4-(trifluoromethyl)phenyl)acryloyl)oxazolidin-2-one (7.40 g, 20.5 mmol) in THF (300 mL) and DCM (100 mL). The resulting mixture was stirred at −78° C. for about 30 minutes and was then warmed to −10° C. for about 1 hour. The solution was re-cooled to −78° C. and was added via cannula to a pre-cooled (−78° C.) solution of N-bromosuccinimide (65 mmol) in THF (750 mL). The resulting mixture was stirred for about 90 minutes, and it was then quenched with sodium sulfite, washed with water and brine, dried over magnesium sulfate, and reduced in volume. The crude product was adsorbed onto a plug of silica gel and chromatographed through a Redi-Sep® pre-packed silica gel column (120 g), eluting with a gradient of 20% to 60% EtOAc in hexane, to provide (R)-3-((2R,3S)-2-bromo-3-(4-(trifluoromethyl)phenyl)butanoyl)-4-phenyloxazolidin-2-one (5.76 g, 61.6% yield).

(R)-3-((2S,3S)-2-azido-3-(4-(trifluoromethyl)phenyl)butanoyl)-4-phenyloxazolidin-2-one To a 250 mL round-bottomed flask was added (R)-3-((2R,3S)-2-bromo-3-(4-(trifluoromethyl)phenyl)butanoyl)-4-phenyloxazolidin-2-one (5.46 g, 12 mmol), ACN (50.00 mL, 957 mmol) and the reaction is cooled in an ice bath. Then reactant 2 (2.8 g, 18 mmol) is added and the reaction mixture is stirred while warming to RT overnight. The reaction is followed by LCMS, and once complete, quenched by the addition of saturated Sodium Bicarbonate The aqueous layer was extracted with DCM (×3) and the combined organics were washed with water, 1 N HCl, water, Sodium Bicarbonate and brine, and then dried over sodium sulfate, filtered and reduced in vacuum. The crude product was adsorbed onto a plug of silica gel and chromatographed through a Redi-Sep® pre-packed silica gel column (40 g), eluting with a gradient of 5% to 55% EtOAc in hexane, to provide (R)-3-((2S,3S)-2-azido-3-(4-(trifluoromethyl)phenyl)butanoyl)-4-phenyloxazolidin-2-one (4.74 g, 95% yield).

tert-Butyl (2S,3S)-1-oxo-1-((R)-2-oxo-4-phenyloxazolidin-3-yl)-3-(4-(trifluoromethyl)phenyl)butan-2-ylcarbamate To a 250 mL round-bottomed flask was added (R)-3-((2S,3S)-2-azido-3-(4-(trifluoromethyl)phenyl)butanoyl)-4-phenyloxazolidin-2-one (4.08 g, 9.75 mmol), Boc$_2$O (19 g, 14.6 mmol), and EtOAc (60.00 mL, 9.75 mmol). The solution was degassed by evacuation and refilling with nitrogen three times. Palladium on carbon (0.104 g, 0.975 mmol) was added, and a balloon of H$_2$ was added to the reaction. The solution was saturated with hydrogen by evacuating and backfilling with hydrogen four times. The reaction was then allowed to stir for 12 hours. The reaction was filtered through Celite and reduced to an oil which was used immediately in the next step.

tert-Butyl (2S,3S)-1-hydroxy-3-(4-(trifluoromethyl)phenyl)butan-2-ylcarbamate

To a 250 mL round-bottomed flask was added tert-butyl (2S,3S)-1-oxo-1-((R)-2-oxo-4-phenyloxazolidin-3-yl)-3-(4-(trifluoromethyl)phenyl)butan-2-ylcarbamate (4.80 g, 9.7 mmol), diethyl ether (50.00 mL, 481 mmol), and water (0.19 mL, 11 mmol). The resulting solution was cooled in an ice bath. Lithium borohydride (0.23 g, 11 mmol) was added in one portion and gas evolution was observed. The ice bath was removed, and the solution was stirred for about 12 hours. The reaction was followed by LCMS and once completed, was quenched by the addition of brine. The aqueous layer was extracted with EtOAc (×3), and the combined organic layers were washed with brine, dried over magnesium sulfate, filtered, and adsorbed onto a plug of silica gel and chromatographed through a Redi-Sep® pre-packed silica gel column (120 g), eluting with a gradient of 20% to 60% EtOAc in hexane, to provide tert-butyl (2S,3S)-1-hydroxy-3-(4-(trifluoromethyl)phenyl)butan-2-ylcarbamate (2.15 g, 66% yield).

Example 110

N-((2S,3S)-2-Amino-3-(4-(trifluoromethyl)phenyl)butyl)-5-(isoquinolin-6-yl)thiazol-2-amine The title compound was synthesized in a manner similar to that described for Example 109. LCMS (M+H) calc. for $C_{23}H_{22}F_3N_4S$ 443.1. $^1$H NMR (400 MHz, CD$_3$OD) δ ppm 9.14 (s, 1H) 8.40 (d, J=6.02 Hz, 1H) 8.06 (d, J=9.04 Hz, 1H) 7.90 (d, J=9.03 Hz, 1H) 7.83 (s, 1H) 7.78 (d, J=5.52 Hz, 1H) 7.66 (dd, 2H) 7.52 (d, J=8.03 Hz, 2H) 3.58-3.66 (m, 1H) 3.29 (d, J=4.02 Hz, 2H) 2.93-3.04 (m, 1H) 1.42 (d, J=7.03 Hz, 3H).

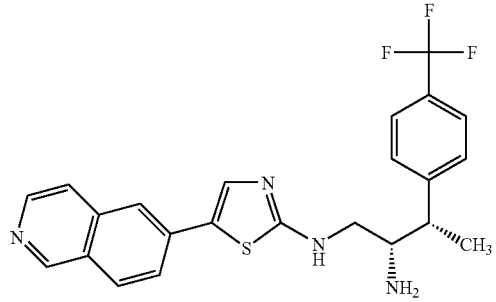

Example 111

N-((S)-2-Amino-3-(4-(trifluoromethyl)phenyl)propyl)-4-bromo-5-(thiazolo[5,4-c]pyridin-2-yl)thiazol-2-amine This compound was synthesized as shown in Scheme 28. LCMS (M+H) calc. for $C_{19}H_{16}BrF_3N_5S_2$ 513.99. $^1$H NMR (400 MHz, CD$_3$OD): δ ppm 9.17 (s, 1H) 8.53 (d, J=5.67 Hz, 1H) 7.84 (d, J=5.67 Hz, 1H) 7.63 (d, J=8.02 Hz, 2H) 7.48 (d, J=8.02 Hz, 2H) 3.44-3.52 (m, 1H) 3.35-3.40 (m, 2H) 2.91-3.02 (m, 1H) 2.76 (dd, J=13.40, 7.53 Hz, 1H).

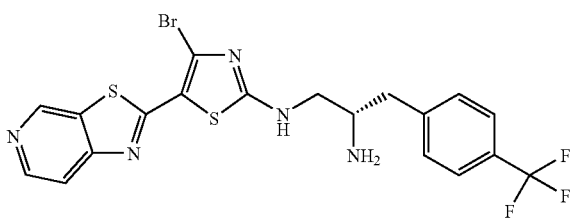

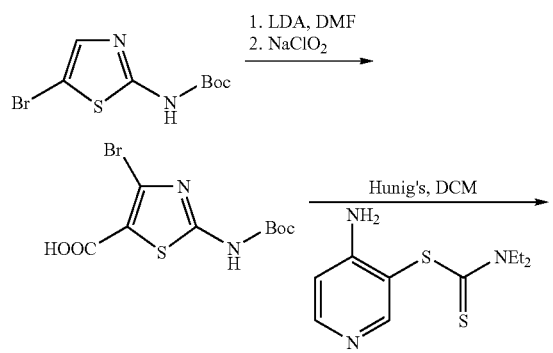

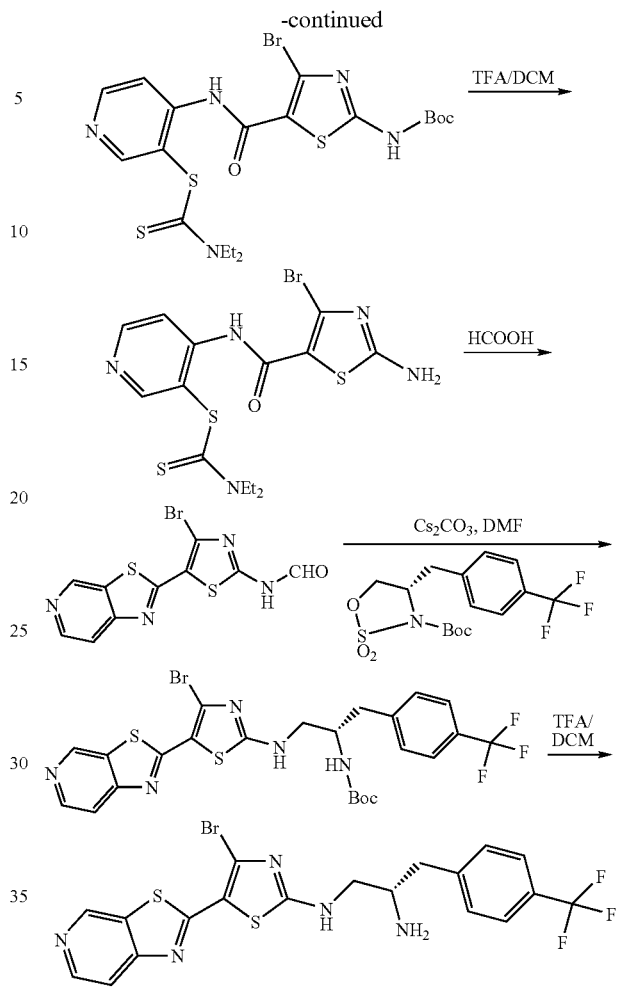

tert-Butyl 4-bromo-5-formylthiazol-2-ylcarbamate

To a 500 mL round-bottomed flask was added diisopropylamine (8.28 mL, 59.1 mmol) in 100 mL of THF (1.29 g, 17.9 mmol). The resulting solution was cooled to 0° C. and butyllithium (2.5 M solution in hexanes, 23.6 mL, 59.1 mmol) was added slowly. The reaction was stirred for about 20 minutes and then a THF solution of tert-butyl 5-bromothiazol-2-ylcarbamate (5.00 g, 17.9 mmol) was slowly added. The mixture was stirred for about 30 minutes and then was quenched by the addition of DMF (4.58 mL, 59.1 mmol). The resulting mixture was stirred for about 12 hours. The reaction was partitioned between water and EtOAc, and the aqueous layer was extracted with EtOAc (2×100 mL) The organic layers were washed with brine, dried over magnesium sulfate, and filtered, and the crude product was adsorbed onto a plug of silica gel and chromatographed through a Redi-Sep® prepacked silica gel column (330 g), eluting with a gradient of 5% to 25% EtOAc in hexane providing tert-butyl 4-bromo-5-formylthiazol-2-ylcarbamate (3.31 g, 60.2% yield).

4-Bromo-2-(tert-butoxycarbonyl)thiazole-5-carboxylic acid

To a 250 mL round-bottomed flask was added sodium chlorite (3.68 g, 40.7 mmol), tert-butyl 4-bromo-5-formylthiazol-2-ylcarbamate (1.18 g, 3.84 mmol), isobutanol (76.8 mL, 3.84 mmol), and an aqueous (30.00 mL, 3.84 mmol) solution of sodium dihydrogen phosphate (3.60 g, 30.0 mmol) followed by 2-methyl-2-butene (4.47 mL, 42.3 mmol). The mixture was stirred vigorously for about 3 hours. LCMS indicated complete conversion to product so the mixture was diluted with water (60 mL) and 120 mL of 1:1 EtOAc/hexanes. The aqueous layer was extracted with 1:1 EtOAc/hexanes, and the combined organic layers were washed with brine, dried over sodium sulfate, and filtered. The solvent was reduced providing the semi-crude product 4-bromo-2-(tert-butoxycarbonyl)thiazole-5-carboxylic acid (1.35 g, 109% yield). The crude product was used immediately without further purification.

tert-Butyl 4-bromo-5-((3-(diethylcarbamothioylthio)pyridin-4-yl)carbamoyl)thiazol-2-ylcarbamate To a 150 mL round-bottomed flask was added the crude 4-bromo-2-(tert-butoxycarbonyl)thiazole-5-carboxylic acid (1.35 g, 4.2 mmol), 4-aminopyridin-3-yl diethylcarbamodithioate (1.0 g, 4.2 mmol), bis(tetramethylene)chloroformamidinium hexafluorophosphate (1.54 g), and DCM (0.27 mL, 4.2 mmol). The resulting mixture was stirred for about 5 minutes. Hunig's Base (1.6 mL, 9.2 mmol) was then added, and the mixture was stirred and followed by LCMS. After about 30 minutes, no more starting material was detected so the mixture was adsorbed onto a plug of silica gel and chromatographed through a Redi-Sep® pre-packed silica gel column (40 g), eluting with a gradient of 1% to 10% MeOH in DCM, to provide tert-butyl 4-bromo-5-((3-(diethylcarbamothioylthio)pyridin-4-yl)carbamoyl)thiazol-2-ylcarbamate (3.126 g) as the crude product.

N-(4-bromo-5-(thiazolo[5,4-c]pyridin-2-yl)thiazol-2-yl)formamide

To a 100 mL round-bottomed flask was added tert-butyl 4-bromo-5-((3-(diethylcarbamothioylthio)pyridin-4-yl)carbamoyl)thiazol-2-ylcarbamate (1.0 g, 1.8 mmol) and a 1:1 mixture of TFA (0.14 mL, 1.8 mmol) and DCM (0.12 mL, 1.8 mmol) with a few drops of triethylsilane. The solution was then stirred at room temperature. LCMS indicated that the reaction was complete after about 1 hour. The solvents were removed, and the resulting oil was used without further manipulation. To a 100 mL round-bottomed flask was added 4-(2-amino-4-bromothiazole-5-carboxamido)pyridin-3-yl diethylcarbamodithioate (0.82 g, 1.8 mmol) and formic acid (0.070 mL, 1.8 mmol), and the mixture was heated at 100° C. for about 2 hours. LCMS indicated no remaining starting material, so the solvent was removed and 2 N ammonia in MeOH was added. An orange precipitate formed which was filtered and determined to be the product N-(4-bromo-5-(thiazolo[5,4-c]pyridin-2-yl)thiazol-2-yl)formamide.

tert-Butyl (S)-1-(N-(4-bromo-5-(thiazolo[5,4-c]pyridin-2-yl)thiazol-2-yl)formamido)-3-(4-(trifluoromethyl)phenyl)propan-2-ylcarbamate To a 100 mL round-bottomed flask was added N-(4-bromo-5-(thiazolo[5,4-c]pyridin-2-yl)thiazol-2-yl)formamide (0.325 g, 0.953 mmol), Cs₂CO₃ (0.621 g, 1.91 mmol), and DMF (0.0696 g, 0.953 mmol). The reaction mixture was stirred at 50° C. To the resulting solution was added a DMF solution of tert-butyl 4-((S)-1-(4-(trifluoromethyl)phenyl)methyl)-1,2,3-oxathiazolidine-3-carboxylate, 2,2-dioxide (0.727 g, 1.91 mmol), and the reaction was stirred for about 2 hours. LCMS showed the desired product, and no remaining starting material so the solvent was removed, and the resulting oil was partitioned between EtOAc and 25 mL of 1N HCl and stirred vigorously for about 30 minutes. The aqueous phase was extracted with EtOAc, and the combined organic layers were dried over sodium sulfate, filtered, and loaded on to a plug of silica gel and chromatographed through a Redi-Sep® pre-packed silica gel column (12 g), eluting with a gradient of 1% to 10% MeOH in DCM, providing tert-butyl (S)-1-(N-(4-bromo-5-(thiazolo[5,4-c]pyridin-2-yl)thiazol-2-yl)formamido)-3-(4-(trifluoromethyl)phenyl)propan-2-ylcarbamate (0.330 g, 53.9% yield).

Example 111

N-((S)-2-Amino-3-(4-(trifluoromethyl)phenyl)propyl)-4-bromo-5-(thiazolo[5,4-c]pyridin-2-yl)thiazol-2-amine To a 150 mL round-bottomed flask was added tert-butyl (S)-1-(4-bromo-5-(thiazolo[5,4-c]pyridin-2-yl)thiazol-2-ylamino)-3-(4-(trifluoromethyl)phenyl)propan-2-ylcarbamate (0.157 g, 0.26 mmol), DCM (25.00 mL, 389 mmol) and TFA (5.00 mL, 65 mmol) with a few drops of triethylsilane, and the resulting solution was stirred for about 15 minutes and followed by LCMS. LCMS showed conversion to product so the solvent was removed, and the oil was dissolved in 2 N ammonia in MeOH and adsorbed on to a plug of silica gel. Chromatography through a Redi-Sep® pre-packed silica gel column (12 g), eluting with a gradient of 1% to 10% 2 M ammonia.MeOH in DCM, provided N-((S)-2-amino-3-(4-(trifluoromethyl)phenyl)propyl)-4-bromo-5-(thiazolo[5,4-c]pyridin-2-yl)thiazol-2-amine (0.086 g, 65% yield).

Example 112

6-(2-((S)-2-Amino-3-(4-(trifluoromethyl)phenyl)propylamino)thiazol-5-yl)-5-fluorobenzo[d]oxazol-2(3H)-one Example 112 was synthesized in a manner similar to that described for Example 40. The boronic ester intermediate was synthesized starting with commercially available 4-bromo-2,5-difluoronitrobenzene as shown in Scheme 29. MS m/z: 453 (M+1). ¹H NMR (400 MHz, CD₃OD): δ ppm 3.03-3.15 (m, 2H), 3.47-3.55 (m, 1H), 3.62-3.68 (m, 1H), 3.81 (qd, J=7.11, 3.91 Hz, 1H), 6.95 (d, J=10.37 Hz, 1H), 7.37 (d, J=6.06 Hz, 1H), 7.43 (s, 1H), 7.53 (d, J=8.02 Hz, 2H), 7.68 (d, J=8.02 Hz, 2H).

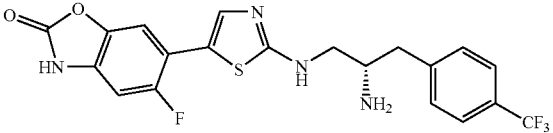

Scheme 29

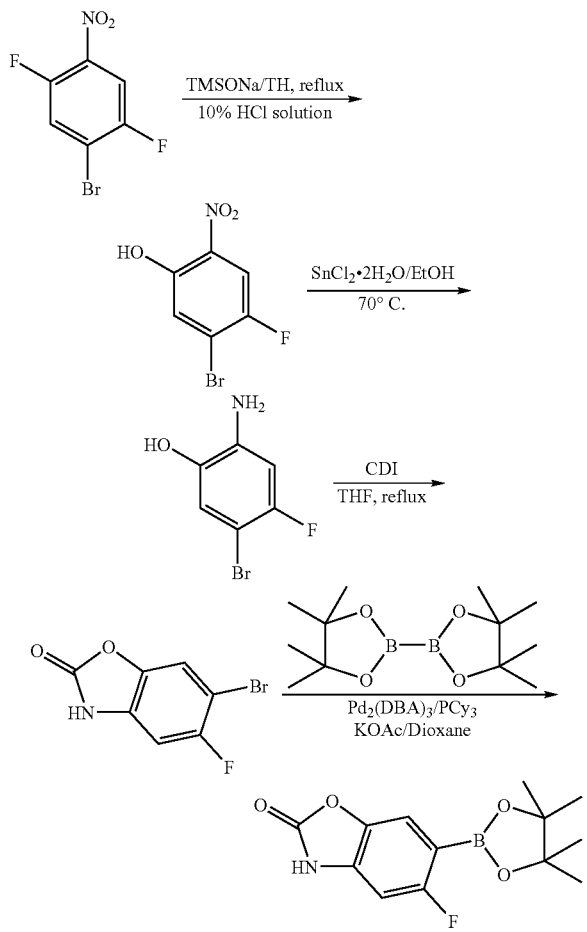

5-Bromo-4-fluoro-2-nitrophenol

A solution of 2 M sodium trimethylsilanolate (15.6, 31.1 mmol) in THF was added dropwise to 4-bromo-2,5-difluoronitrobenzene (2.47 g, 10.4 mmol) under a nitrogen atmosphere. A bright red suspension was formed, and the mixture was refluxed for 27 hours. The mixture was cooled to room temperature and concentrated. Water (6 mL) was added, and the solution was acidified with a 10% HCl solution, extracted with DCM (70 mL×2). The organic layers were combined and concentrated to give 5-bromo-4-fluoro-2-nitrophenol (5.05 g, 2.06%). MS m/z: 236(M+1). $^1$H NMR (400 MHz, CD$_3$OD) δ ppm 7.48 (d, J=5.87 Hz, 1H), 7.95 (d, J=8.41 Hz, 1H).

6-Bromo-5-fluorobenzo[d]oxazol-2(3H)-one

To a 100 mL of round bottom flask was added 5-bromo-4-fluoro-2-nitrophenol (0.98 g, 4.15 mmol), tin(II) chloride dihydrate (4.73 g, 20.76 mmol) and 5 mL of EtOH. The reaction mixture was heated to 70° C. for 30 minutes. The reaction mixture was concentrated and washed with saturated NaHCO$_3$ solution, and extracted with DCM (100 mL×3), and concentrated providing the crude product. 1,1'-Carbonyldiimidazole (808 mg, 4983 μmol) was added to the crude product in 20 mL of THF. The reaction mixture was heated at reflux overnight. The reaction mixture was concentrated and purified with silica gel column chromatography, eluting with 0-30% EtOAc/hexane to give 6-bromo-5-fluorobenzo[d]oxazol-2(3H)-one (690 mg, 71.6% yield). MS m/z: 232 (M+1).

5-Fluoro-6-(4,4,5,5-tetramethyl-1,3,2-dioxaborolan-2-yl)benzo[d]oxazol-2(3H)-one A glass microwave reaction vessel was charged with bis (pinacolato)diboron (867 mg, 3414 μmol), potassium acetate (267 μl, 4267 μmol), tricyclohexylphosphine (115 mg, 410 μmol), 6-bromo-5-fluorobenzo[d]oxazol-2(3H)-one (660 mg, 2845 μmol), Pd$_2$(dba)$_3$ (156 mg, 171 μmol), and 5 mL of dioxane. The reaction mixture was stirred and heated in a Smith Synthesizer® microwave reactor (Personal Chemistry, Inc., Upssala, Sweden) at 150° C. for 40 minutes. The reaction mixture was concentrated and dry-packed, then purified with silica gel column chromatography, eluting with 0-40% EtOAc/hexane providing 5-fluoro-6-(4,4,5,5-tetramethyl-1,3,2-dioxaborolan-2-yl)benzo[d]oxazol-2(3H)-one (680 mg, 85.7% yield) as light yellow solid. MS m/z: 280 (M+1).

Examples 113-116

Examples 113-116 were synthesized in a manner similar to that described for example 82.

Example 113

5-(2-((S)-2-Amino-3-(2,4-dichlorophenyl)propylamino)thiazol-5-yl)indolin-2-one

MS m/z: 433 (M+1). $^1$H NMR (400 MHz, CD$_3$OD) δ ppm 2.80 (dd, J=13.79, 7.53 Hz, 1H), 3.04 (dd, J=13.60, 5.97 Hz, 1H), 3.33-3.53 (m, 5H), 6.85 (d, J=8.02 Hz, 1H), 7.20-7.36 (m, 5H), 7.46 (d, J=1.96 Hz, 1H).

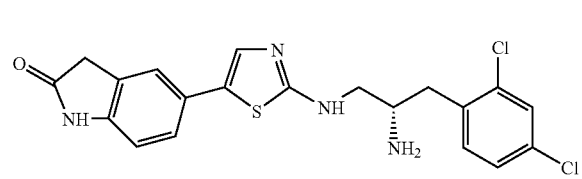

Example 114

5-(2-((S)-2-Amino-3-(3,4-dichlorophenyl)propylamino)thiazol-5-yl)indolin-2-one

MS m/z: 433 (M+1). $^1$H NMR (400 MHz, CD$_3$OD) δ ppm 2.65-2.74 (m, 1H), 2.88 (dd, J=13.60, 5.38 Hz, 1H), 3.55-3.25 (m, 5H, overlap with solvent), 6.85 (d, J=8.02 Hz, 1H), 7.17-7.28 (m, 3H), 7.34 (s, 1H), 7.45 (d, J=5.67 Hz, 2H).

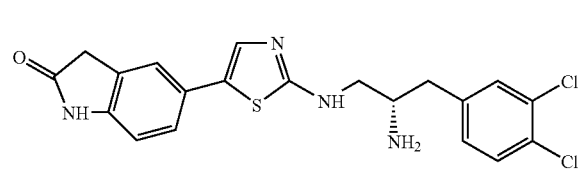

Example 115

6-(2-((S)-2-Amino-3-(3,4-dichlorophenyl)propylamino)thiazol-5-yl)benzo[d]oxazol-2(3H)-one MS m/z: 435 (M+1). $^1$H NMR (400 MHz, CD$_3$OD) δ ppm 2.92-2.96 (m, 1H), 3.00-3.05 (m, 1H), 3.46-3.52 (m, 1H), 3.61-3.65 (m, 1H), 3.65-3.75 (m, Hz, 1H), 7.06 (d, J=8.02 Hz, 1H), 7.25 (td, J=8.22, 1.76 Hz, 2H), 7.35 (s, 2H), 7.51-7.54 (m, 2H).

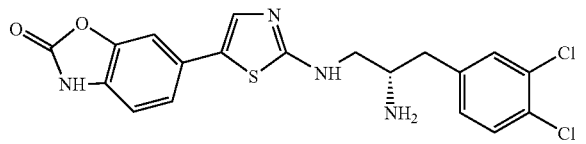

Example 116

5-(2-((S)-2-Amino-3-p-tolylpropylamino)thiazol-5-yl)indolin-2-one

MS m/z: 379 (M+1). $^1$H NMR (400 MHz, CD$_3$OD) δ ppm 2.33 (s, 3H), 2.98 (d, J=7.24 Hz, 2H), 3.51-3.68 (m, 4H), 3.74 (dt, J=7.24, 3.62 Hz, 1H), 6.90 (d, J=8.22 Hz, 1H), 7.20 (s, 4H), 7.30 (d, J=8.22 Hz, 1H), 7.38 (s, 2H).

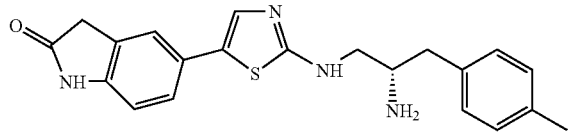

Example 117

Methyl 2-((S)-2-amino-3-(4-(trifluoromethyl)phenyl)-propylamino)-5-(isoquinolin-6-yl)thiazole-4carboxylate The title compound was synthesized in a manner similar to that described for Example 81 using methyl 5-bromo-2-(tert-butoxycarbonyl)thiazole-4-carboxylate as the starting material instead of 5-bromo-4-((dimethylamino)methyl)thiazole. 5-Bromo-2-(tert-butoxycarbonyl)thiazole-4-carboxylate was prepared as shown in Scheme 30. MS m/z: 487 (M+1). $^1$H NMR (400 MHz, CD$_3$OD) δ ppm 3.06-3.14 (m, 2H), 3.57-3.63 (m, 1H), 3.70-3.75 (m, 4H), 3.86 (m, 1H), 7.56 (d, J=8.02 Hz, 2H), 7.70 (d, J=8.22 Hz, 2H), 8.00 (dd, J=8.51, 1.47 Hz, 1H), 8.26 (s, 1H), 8.28 (d, J=6.46 Hz, 1H), 8.39 (d, J=8.61 Hz, 1H), 8.56 (d, J=6.46 Hz, 1H), 9.61 (s, 1H).

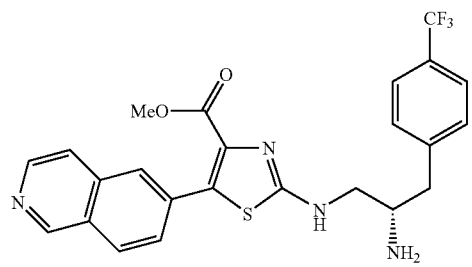

Scheme 30

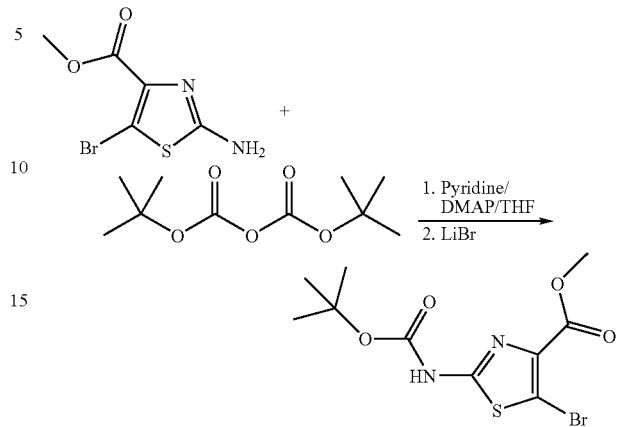

Methyl 5-bromo-2-(tert-butoxycarbonyl)thiazole-4-carboxylate

A suspension of methyl 2-amino-5-bromothiazole-4-carboxylate (2.62 g, 11.1 mmol) in 40 mL of THF was stirred at room temperature and treated with pyridine (8.94 mL, 111 mmol) and then with di-tert-butyl dicarbonate (3.62 g, 16.6 mmol). The reaction mixture was stirred for 1 hour. LC-MS showed that mono-Boc and di-Boc products were formed. The mixture was partitioned between EtOAc (100 mL) and 1 N HCl (50 mL). The aqueous layer was extracted again with EtOAc (50 mL), and the combined organic phases were concentrated to give crude product. Lithium bromide (0.831 mL, 33.2 mmol) and 20 mL of MeCN were added to the crude product. The reaction mixture was heated to 65° C. for 1 hour, and LC-MS showed that the di-Boc product was converted to the mono-Boc product. The reaction mixture was concentrated, 50 mL of saturated NaHCO$_3$ solution was added, and the resulting mixture was extracted twice with 70 mL of EtOAc. All organic layers were combined and concentrated and purified with silica gel column chromatography, eluting with 0-30% EtOAc/hexane to give methyl 5-bromo-2-(tert-butoxycarbonyl)thiazole-4-carboxylate (1.59 g, 42.7% yield). MS m/z: 337 (M+1). $^1$H NMR (400 MHz, CDCl$_3$) δ ppm 1.56 (s, 9H), 3.93 (s, 3H), 7.99 (br s, 1H).

Example 118

N-((S)-2-Amino-3-(4-(trifluoromethyl)phenyl)propyl)-5-(isoquinolin-6-yl)-4-(oxazol-5-yl)thiazol-2-amine The title compound was synthesized using the precursor of Example 117, methyl 2-(((S)-2-(tert-butoxycarbonylamino)-3-(4-(trifluoromethyl)phenyl)propyl)(tert-butoxycarbonyl) amino)-5-(isoquinolin-6-yl)thiazole-4-carboxylate, as the starting material as shown in Scheme 31. LCMS (M+H) calc. for C$_{25}$H$_{21}$F$_3$N$_5$OS 496.1. $^1$H NMR (400 MHz, CD$_3$OD): δ ppm 9.24 (s, 1H) 8.46 (d, J=5.87 Hz, 1H) 8.11 (d, J=8.61 Hz, 1H) 8.08 (s, 1H) 7.97 (s, 1H) 7.82 (d, J=6.06 Hz, 1H) 7.63-7.70 (m, 4H) 7.51 (d, J=7.82 Hz, 2H) 7.25 (s, 1H) 3.51-3.61 (m, 2H) 3.40-3.47 (m, 1H) 3.03 (dd, J=13.69, 6.06 Hz, 1H) 2.88 (dd, 1H).

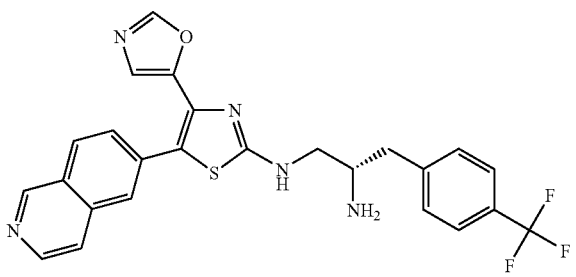

Scheme 31

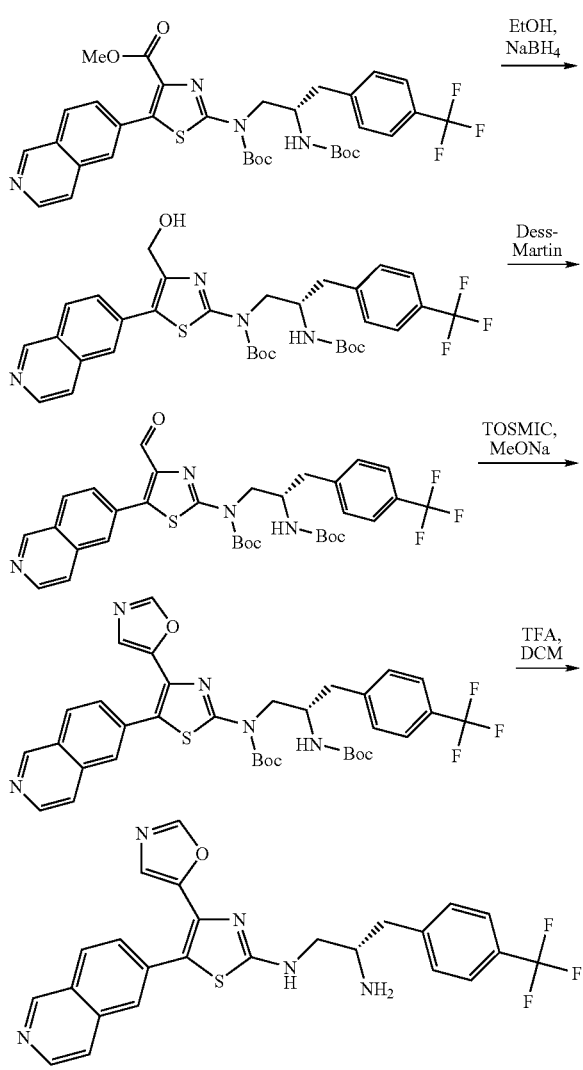

2-(((S)-2-(tert-butoxycarbonylamino)-3-(4-(trifluoromethyl)phenyl)-propyl)(tert-butoxycarbonyl)amino)-5-(isoquinolin-6-yl)thiazole-4-methylalcohol To a 100 mL round-bottomed flask was added methyl 2-(((S)-2-(tert-butoxycarbonylamino)-3-(4-(trifluoromethyl)phenyl)propyl)(tert-butoxycarbonyl)amino)-5-(isoquinolin-6-yl)thiazole-4-carboxylate (0.350 g, 0.51 mmol), EtOH (20.00 mL) and sodium borohydride (0.19 g, 5.1 mmol). The resulting mixture was stirred about 48 hours. LCMS indicated about 50% conversion of the starting material to the product. The reaction was partitioned between EtOAc and saturated sodium bicarbonate, and the aqueous layer was extracted with EtOAc. The combined organic layers were dried over sodium sulfate and filtered. The crude product was adsorbed onto a plug of silica gel and chromatographed through a Redi-Sep® pre-packed silica gel column (12 g), eluting with a gradient of 10% to 50% EtOAc in hexane to provide 2-(((S)-2-(tert-butoxycarbonylamino)-3-(4-(trifluoromethyl)phenyl)propyl)(tert-butoxycarbonyl)amino)-5-(isoquinolin-6-yl)thiazole-4-methylalcohol (0.098 g, 29% yield).

2-(((S)-2-(tert-butoxycarbonylamino)-3-(4-(trifluoromethyl)phenyl)-propyl)(tert-butoxycarbonyl)amino)-5-(isoquinolin-6-yl)thiazole-4-formaldehyde To a 100 mL round-bottomed flask was added 2-(((S)-2-(tert-butoxycarbonylamino)-3-(4-(trifluoromethyl)phenyl)propyl)(tert-butoxycarbonyl)amino)-5-(isoquinolin-6-yl)thiazole-4-methylalcohol (0.098 g, 0.15 mmol), DCM (0.0096 mL, 0.15 mmol), and Dess-Martin Periodinane (0.076 g, 0.18 mmol). The reaction was stirred open to the atmosphere, and followed by LCMS. LCMS showed clean conversion to the product so the reaction was quenched with sodium thiosulfate and sodium bicarbonate and extracted with EtOAc. The combined organic layers were washed with brine, dried with sodium sulfate, filtered, and reduced to give the crude product (0.098 g, 100% yield) which was used immediately in the next step.

N-((S)-2-amino-3-(4-(trifluoromethyl)phenyl)propyl)-5-(isoquinolin-6-yl)-4-(oxazol-5-yl)thiazol-2-amine To a 100 mL round-bottomed flask was added thiazole 4-carboxaldehyde tert-butyl (S)-1-(4-formyl-5-(isoquinolin-6-yl)thiazol-2-yl-(Boc)amino)-3-(4-(trifluoromethyl)phenyl)propan-2-ylcarbamate (0.098 g, 0.15 mmol), MeOH (0.0060 mL, 0.15 mmol), sodium methoxide (0.027 g, 0.51 mmol) and p-toluenesulfonylmethylisonitrile (0.035 g, 0.18 mmol). The resulting solution was stirred at reflux for about 1 hour until LCMS indicated that the reaction was complete. LCMS indicated complete conversion with removal of one of the Boc groups. The crude reaction was quenched with water and extracted three times with EtOAc. The combined organic layers were dried over sodium sulfate, filtered, and the solvent was removed. The crude product was used immediately in the next step. To a 100 mL round-bottomed flask was added the crude material from the previous step (0.100 g, 0.14 mmol), DCM (0.0092 mL, 0.14 mmol), TFA (0.011 mL, 0.14 mmol), and a few drops of triethylsilane. The reaction was stirred at room temperature and followed by LCMS. Toluene was added, and the solvent was removed. The residue was dissolved in 2 N ammonia in MeOH, and the crude product was adsorbed onto a plug of silica gel and chromatographed through a Redi-Sep® pre-packed silica gel column (12 g), eluting with a gradient of 1% to 10% MeOH in DCM, to provide N-((S)-2-amino-3-(4-(trifluoromethyl)phenyl)propyl)-5-(isoquinolin-6-yl)-4-(oxazol-5-yl)thiazol-2-amine (0.072 g, 101% yield).

Example 119

2-((S)-2-Amino-3-(4-(trifluoromethyl)phenyl)-propylamino)-N-(2-hydroxyethyl)-5-(isoquinolin-6-yl)thiazole-4-carboxamide The title compound was synthesized by treating the intermediate methyl 2-(((S)-2-(tert-butoxycarbonylamino)-3-(4-(trifluoromethyl)phenyl)propyl)(tert-butoxycarbonyl)amino)-5-(isoquinolin-6-yl)thiazole-4-carboxylate with 2-aminoethanol followed with a TFA treatment to remove the tert-butoxycarbonyl protecting groups. LCMS (M+H) calc. for $C_{25}H_{25}F_3N_5O_2S$ 516.2. $^1$H NMR (400 MHz, $CD_3OD$) δ ppm 9.70 (s, 1H) 8.53-8.60 (m, 1H) 8.38-8.46 (m, 2H) 8.36 (s, 1H) 8.10-8.19 (m, 1H) 7.73 (d, J=6.85 Hz, 2H) 7.58 (d, J=6.85 Hz, 2H) 4.52-4.61 (m, 1H) 3.93 (s, 1H) 3.78-3.87 (m, 1H) 3.71 (t, J=5.48 Hz, 2H) 3.63 (dd, J=14.67, 6.46 Hz, 1H) 3.44-3.51 (m, 2H) 3.06-3.23 (m, 2H).

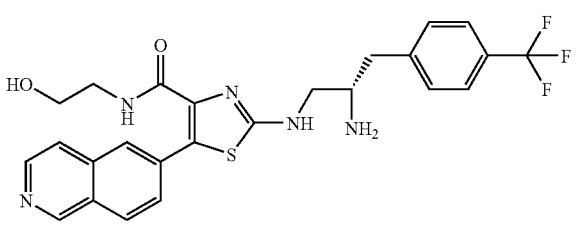

Example 120

2-((S)-2-amino-3-(4-(trifluoromethyl)phenyl)-propylamino)-5-(isoquinolin-6-yl)-N-methylthiazole-4-carboxamide The title compound was synthesized in a manner similar to that described for Example 119. LCMS m/z: 486 (M+1), $^1$H NMR (400 MHz, $CD_3OD$) δ ppm 2.77 (dd, J=13.50, 7.43 Hz, 1H) 2.85 (s, 3H) 2.98 (dd, J=13.50, 5.67 Hz, 1H) 3.37-3.40 (m, 1H) 3.45 (dd, J=11.44, 5.77 Hz, 1H) 3.47-3.52 (m, 1H) 7.49 (d, J=8.02 Hz, 2H) 7.64 (d, J=8.02 Hz, 2H) 7.79-7.84 (m, 2H) 8.02 (s, 1H) 8.06 (d, J=8.61 Hz, 1H) 8.43 (d, J=5.87 Hz, 1H) 9.22 (s, 1H).

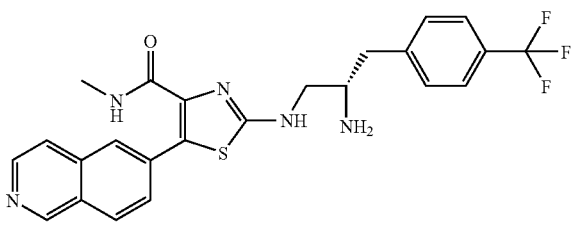

Example 121

2-((S)-2-amino-3-(4-(trifluoromethyl)phenyl)propylamino)-5-(isoquinolin-6-yl)thiazole-4-carboxamide The title compound was synthesized in a manner similar to that described for Example 119. LCMS m/z: 472 (M+1).

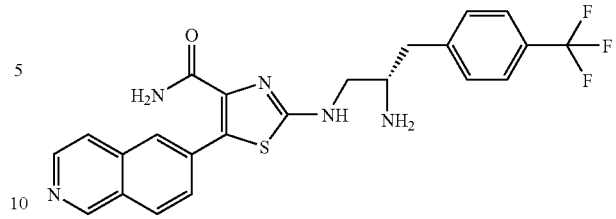

Example 122

Methyl 2-((S)-2-amino-3-(4-(trifluoromethyl)phenyl)propylamino)-5-(2-oxoindolin-5-yl)thiazole-4-carboxylate The title compound was synthesized in a manner similar to that described for Example 117. MS m/z: 491 (M+1). $^1$H NMR (400 MHz, $CD_3OD$): δ ppm 3.03-3.14 (m, 2H), 3.47-3.57 (m, 3H), 3.63-3.68 (m, 1H), 3.70 (s, 3H), 3.80 (br s, 1H), 6.90 (d, J=8.02 Hz, 1H), 7.28 (d, J=8.02 Hz, 1H), 7.33 (s, 1H), 7.54 (d, J=8.02 Hz, 2H), 7.69 (d, J=8.22 Hz, 2H).

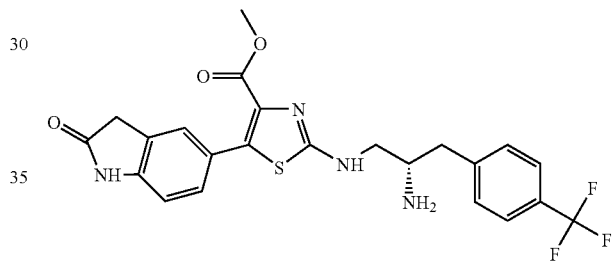

Example 123

5-(2-((S)-2-Amino-3-(4-(trifluoromethyl)phenyl)propylamino)-4-(hydroxymethyl)thiazol-5-yl)indolin-2-one To a 25 mL round-bottom flask was added methyl 2-(tert-butoxycarbonyl)-5-(2-oxoindolin-5-yl)thiazole-4-carboxylate (140 mg, 203 µmol), $NaBH_4$ (77 mg, 2027 µmol), and 2 mL of MeOH. The reaction mixture was stirred for 5 hours. 10 mL of water was then added to the reaction mixture, and the mixture was then extracted twice with 20 mL of EtOAc. The organic layers were combined, concentrated, and purified by preparative LC to give the Boc protected intermediate as an off-white solid. MS m/z: 663 (M+1). 5 mL of 70% TFA/DCM was added to the Boc protected intermediate. After 30 minutes, the reaction mixture was concentrated and purified by preparative LC to give 5-(2-((S)-2-amino-3-(4-(trifluoromethyl)phenyl)propylamino)-4-(hydroxymethyl)thiazol-5-yl)indolin-2-one (82 mg, 87% yield) as a white solid. MS m/z: 463 (M+1). $^1$H NMR (400 MHz, $CD_3OD$) δ ppm 3.05-3.16 (m, 2H), 3.51-3.58 (m, 3H), 3.63-3.70 (m, 1H), 3.83 (qd, J=7.08, 3.62 Hz, 1H), 4.46 (s, 2H), 6.94 (d, J=8.02 Hz, 1H), 7.27 (d, J=8.02 Hz, 1H), 7.31 (s, 1H), 7.54 (d, J=8.02 Hz, 2H), 7.69 (d, J=8.22 Hz, 2H).

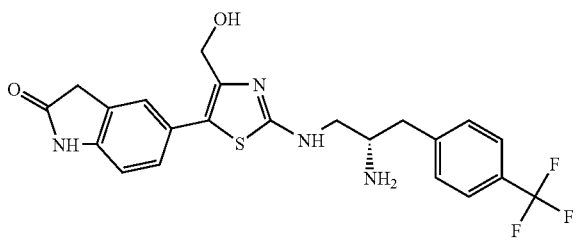

Example 124

Methyl 2-((S)-2-Amino-3-(4-(trifluoromethyl)phenyl)propylamino)-5-(2-oxo-2,3-dihydrobenzo[d]oxazol-6-yl)thiazole-4-carboxylate The title compound was synthesized in a manner similar to that described for Example 117. MS m/z: 493 (M+1). $^1$H NMR (400 MHz, CD$_3$OD) δ ppm 3.05-3.14 (m, 2H), 3.46-3.53 (m, 1H), 3.53-3.51 (m, 1H), 3.56-3.51(m 1H), 3.70 (s, 3), 7.10 (d, J=8.02 Hz, 1H), 7.23 (dd, J=8.02, 1.56 Hz, 1H), 7.33 (d, J=1.37 Hz, 1H), 7.54 (d, J=8.02 Hz, 2H), 7.69 (d, J=7.82 Hz, 2H).

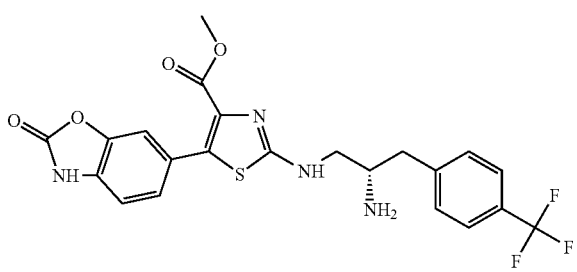

Example 125

6-(2-((S)-2-Amino-3-(4-(trifluoromethyl)phenyl)propylamino)-4-(hydroxymethyl)thiazol-5-yl)benzo[d]oxazol-2(3H)-one The title compound was synthesized in a manner similar to that described for Example 123. MS m/z: 463 (M+1). $^1$H NMR (400 MHz, CD$_3$OD) δ ppm 3.03-3.15 (m, 2H), 3.47-3.52 (m, 1H), 3.64-3.68 (m, 1H) 3.80 (br s, 1H), 4.46 (s, 2H), 7.11 (d, J=8.02 Hz, 1H), 7.21 (dd, J=8.02, 1.57 Hz, 1H), 7.30 (d, J=1.37 Hz, 1H), 7.54 (d, J=7.82 Hz, 2H), 7.69 (d, J=8.02 Hz, 2H).

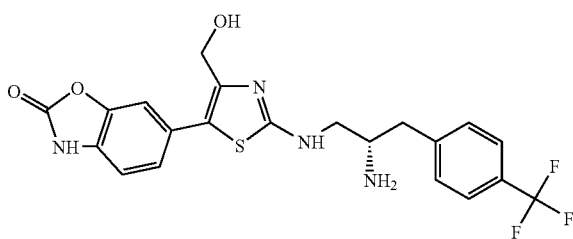

Example 126

5-(2-((S)-2-Amino-3-(3,4-difluorophenyl)propylamino)thiazol-5-yl)indolin-2-one

The title compound was synthesized in a manner similar to that described for Example 113. MS m/z: 401 (M+1). $^1$H NMR (400 MHz, CD$_3$OD): δ ppm 3.43 (d, J=7.43 Hz, 1H), 3.58 (d, J=5.48 Hz, 1H), 3.8-4.0 (m, 3H), 4.29 (br s, 2H), 7.58 (d, J=8.02 Hz, 1H), 8.00 (s, 1H), 8.08-8.20 (m, 4H), 8.55 (s, 1H), 11.22 (s, 1H).

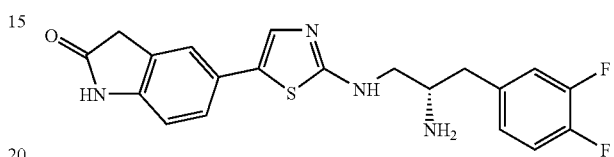

Example 127

6-(2-((S)-2-Amino-3-(3,4-difluorophenyl)propylamino)thiazol-5-yl)benzo[d]oxazol-2(3H)-one The title compound was synthesized in a manner similar to that described for Example 113. MS m/z: 403 (M+1). $^1$H NMR (400 MHz, (CD$_3$OD) δ ppm 2.90-3.06 (m, 2H), 3.47-3.53 (m, 1H), 3.61-3.67 (m, 1H), 3.70-3.77 (m, 1H), 7.06 (d, J=8.22 Hz, 1H), 7.14 (d, J=2.15 Hz, 1H), 7.22-7.31 (m, 31H), 7.35-7.38 (m, 2H).

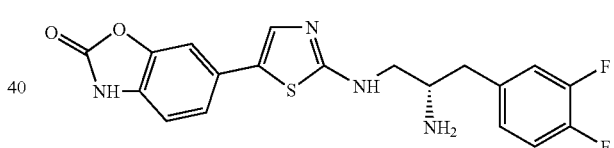

Example 128

N-((S)-1-(5-(2-Oxoindolin-5-yl)thiazol-2-ylamino)-3-(4-(trifluoro-methyl)phenyl)propan-2-yl)acetamide To a 25 mL round-bottom flask was added Example 42 (30 mg, 69 μmol), pyridine (27 mg, 347 μmol), acetic anhydride (14 mg, 139 μmol), and 2 mL of DCM. After 30 minutes, LC-MS showed that the reaction was complete. The reaction mixture was concentrated and dissolved in 2 mL of MeOH, then purified by preparative LC to give N-((S)-1-(5-(2-oxoindolin-5-yl)thiazol-2-ylamino)-3-(4-(trifluoromethyl)-phenyl)propan-2-yl)acetamide (26 mg, 79% yield). MS m/z: 475 (M+1). $^1$H NMR (400 MHz, CD$_3$OD) δ ppm 1.89 (s, 3H), 2.90 (dd, J=13.99, 9.29 Hz, 1H), 3.08 (dd, J=13.99, 5.18 Hz, 1H), 3.46-3.53 (m, 1H), 3.60 (s, 2H), 3.61-3.67 (m, 1H), 4.41-4.48 (m, 1H), 6.96 (d, J=8.22 Hz, 1H), 7.38 (dd, J=8.12, 1.86 Hz, 1H), 7.46-7.51 (m, 3H), 7.63 (d, J=8.02 Hz, 3H).

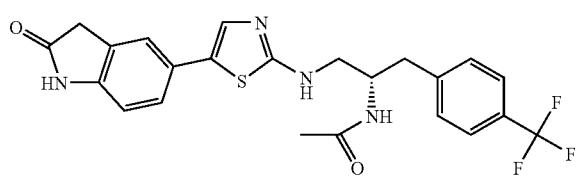

Example 129

6-(2-(2-Amino-3-(3-fluoro-4-methoxyphenyl)propylamino)-thiazol-5-yl)benzo[d]oxazol-2(3H)-one The title compound was synthesized in a manner similar to that described for Example 82 using the corresponding amino acid ester that was prepared as shown in Scheme 32 starting with commercially available 3-fluoro-4-methoxybenzaldehyde. MS m/z: 415 (M+1). $^1$H NMR (400 MHz, CD$_3$OD) δ ppm 2.88-3.02 (m, 2H), 3.48-3.54 (m, 1H), 3.62-3.74 (m, 2H), 3.89 (s, 3H), 7.06-7.14 (m, 4H), 7.27 (dd, J=8.12, 1.66 Hz, 1H), 7.38 (s, 2H).

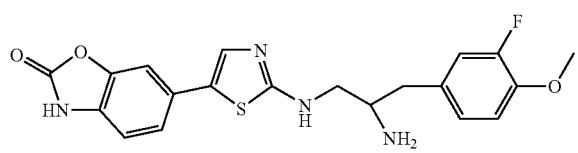

Scheme 32

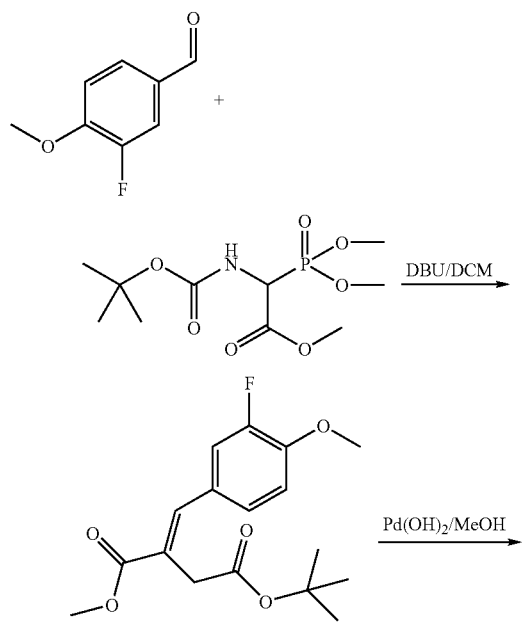

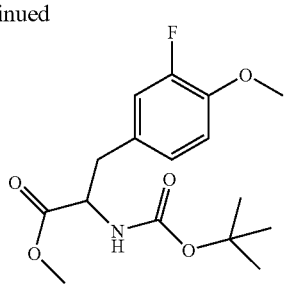

(E)-4-tert-Butyl 1-methyl 2-(3-fluoro-4-methoxybenzylidene)succinate

In a 1000 mL round bottom flask, (+/−)-Boc-alpha-phosphonoglycine trimethyl ester (29 g, 97 mmol) was dissolved in DCM (500 mL) and stirred in an ice bath at 0° C. DBU (15 mL, 97 mmol) was added, and the reaction was stirred for 10 minutes, then 3-fluoro-4-methoxybenzaldehyde (10 g, 65 mmol) was added in one portion. The reaction mixture was stirred for another 5 hours at room temperature. The reaction mixture was washed with 150 mL of 1N HCl aq. solution and 100 mL of brine. The organic layer was concentrated, and purified with silica gel column chromatography, eluting with 0-25%, EtOAc/hexane to give (E)-4-tert-butyl 1-methyl 2-(3-fluoro-4-methoxybenzylidene)succinate (17 g, 81% yield). MS m/z: 324 (M−1).

Methyl 2-(tert-butoxycarbonyl)-3-(3-fluoro-4-methoxyphenyl)propanoate

In a 500 mL round bottom flask, (Z)-methyl 2-(tert-butoxycarbonyl)-3-(3-fluoro-4-methoxyphenyl)acrylate (16 g, 49 mmol) was dissolved in MeOH (500 mL), and palladium hydroxide on carbon (0.069 g, 0.49 mmol) was added. The reaction mixture was stirred for 2 days under a hydrogen balloon and then filtered through Celite, and concentrated in vacuum to give the title compound as crude product. MS m/z: 326 (M−1).

Example 130

5-(2-(2-Amino-3-(3-fluoro-4-methoxyphenyl)propylamino)thiazol-5-yl)indolin-2-one The title compound was prepared in a manner similar to that described for Example 129. MS m/z: 413 (M+1). $^1$H NMR (400 MHz, CD$_3$OD) δ ppm 2.89-3.02 (m, 2H), 3.47-3.54 (m, 1H), 3.57 (s, 2H), 3.65-3.74 (m, 1H), 3.89 (s, 3H), 6.91 (d, J=8.22 Hz, 1H), 7.06-7.14 (m, 3H), 7.30-7.34 (m, 2H), 7.40 (s, 1H).

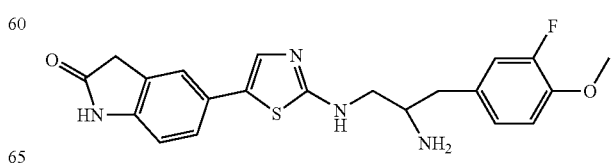

Example 131

N-(2-Amino-3-(3-fluoro-4-methoxyphenyl)propyl)-5-(isoquinolin-6-yl)thiazol-2-amine The title compound was prepared in a manner similar to that described for Example 129. MS m/z: 409 (M+1). $^1$H NMR (400 MHz, CD$_3$OD) δ ppm 2.92-3.03 (m, 2H), 3.57-3.66 (m, 1H), 3.73-3.81 (m, 2H), 3.89 (s, 3H), 7.07-7.16 (m, 3H), 8.02 (s, 1H), 8.12 (s, 1H), 8.26 (dd, J=8.80, 1.57 Hz, 1H), 8.33 (d, J=6.65 Hz, 1H), 8.41 (d, J=8.80 Hz, 1H), 8.48 (d, J=6.65 Hz, 1H), 9.57 (s, 1H).

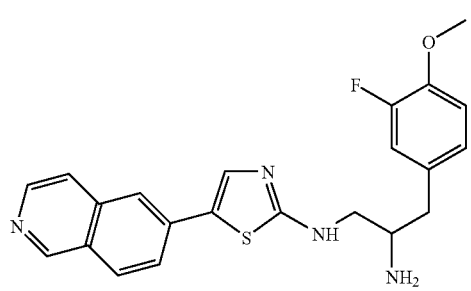

Example 132

N-((S)-2-Amino-3-(3,4-dichlorophenyl)propyl)-5-(isoquinolin-6-yl)thiazol-2-amine The title compound was prepared in a manner similar to that described for Example 81. MS m/z: 429 (M+1). $^1$H NMR (400 MHz, CD$_3$OD): δ ppm 2.97-3.10 (m, 2H), 3.59-3.65 (m, 1H), 3.74-3.71 (m, 1H), 3.82-3.88 (m, 1H), 7.30 (dd, J=8.22, 1.96 Hz, 1H), 7.54-7.58 (m, 2H), 8.00 (s, 1H), 8.11 (s, 1H), 8.25 (dd, J=8.80, 1.57 Hz, 1H), 8.30 (d, J=6.65 Hz, 1H), 8.39 (d, J=8.80 Hz, 1H), 8.48 (d, J=6.65 Hz, 1H), 9.55 (s, 1H).

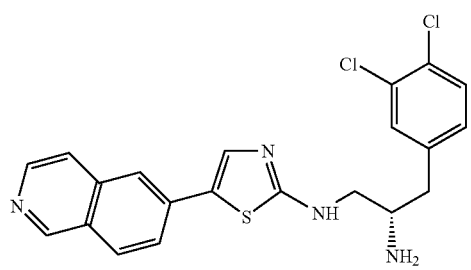

Example 133

5-(2-((S)-2-Amino-3-(4-(trifluoromethyl)phenyl)propylamino)-4-(1,1-difluoro-2-hydroxyethyl)thiazol-5-yl)indolin-2-one The title compound was synthesized in a manner similar to that described for Example 81 using (S)-2-(2-(2-(N-Boc-amino)-3-(4-(trifluoromethyl)phenyl)propyl(N-Boc-amino)-5-bromothiazol-4-yl)-2,2-difluoroethanol as the key intermediate starting with commercially available ethyl 2-(2-aminothiazol-4-yl)-2-oxoacetate as shown in Scheme 33. MS m/z: 513 (M+1). $^1$H NMR (400 MHz, CD$_3$OD): δ ppm 3.10 (d, J=7.24 Hz, 2H), 3.45-3.53 (m, 1H), 3.55 (s, 2H), 3.67 (dd, J=14.77, 3.03 Hz, 1H), 3.83-3.88 (m, 1H), 3.93 (ddd, J=14.92, 12.96, 12.62 Hz, 2H), 6.89 (d, J=8.02 Hz, 1H), 7.30 (d, J=8.02 Hz, 1H), 7.34 (s, 1H), 7.55 (d, J=8.02 Hz, 2H), 7.70 (d, J=8.02 Hz, 2H).

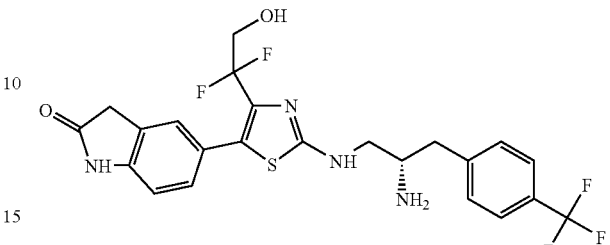

Scheme 33

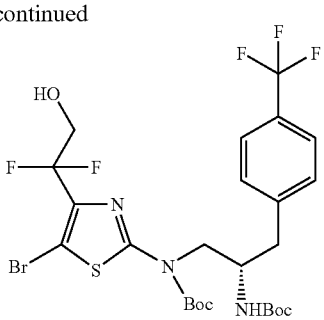

Ethyl 2-(2-(tert-butoxycarbonyl)thiazol-4-yl)-2-oxoacetate

A suspension of ethyl 2-(2-aminothiazol-4-yl)-2-oxoacetate (4.97 g, 25 mmol) in ACN (100 mL) was stirred at room temperature and treated with N,N'-tetramethylethylenediamine (8.7 g, 74 mmol) followed by di-tert-butylpyrocarbonate (5.4 g, 25 mmol). The reaction mixture was stirred at room temperature overnight. The solvent was reduced in vacuo to about 20 mL, and the mixture was partitioned between EtOAc (100 mL) and 1 N HCl (50 mL). The aqueous layer was extracted again with EtOAc (100 mL) and the combined organic phases were washed with 1 N HCl (75 mL), saturated NaHCO$_3$ (75 mL), saturated NaCl (50 mL), dried over Na$_2$SO$_4$, filtered and concentrated in vacuo, and purified with silica gel column chromatography, eluting with 25% EtOAc/hexane to give ethyl 2-(2-(tert-butoxycarbonyl)thiazol-4-yl)-2-oxoacetate (4.2 g, 56% yield). MS m/z: 300 (M+1). $^1$H NMR (400 MHz, CD$_3$OD) δ ppm 1.55 (s, 9H), 2.81 (d, J=13.50 Hz, 3H), 4.39 (q, J=7.11 Hz, 2H), 8.31 (s, 1H).

Ethyl 2-(2-(tert-butoxycarbonyl)thiazol-4-yl)-2,2-difluoroacetate

To a 100 mL Teflon® round bottom flask was added ethyl 2-(2-(tert-butoxycarbonyl)-thiazol-4-yl)-2-oxoacetate (1.6 g, 4.0 mmol), bis(2-methoxyethyl)aminosulfur trifluoride (2.7 g, 12 mmol), and 3 drops of EtOH. After 16 hours, 40 mL of saturated NaHCO$_3$ solution was added to the reaction mixture. The react mixture was extracted twice with 80 mL of EtOAc. The organic layers were combined and concentrated and purified with silica gel column chromatography, eluting with 20% EtOAc/hexane to give ethyl 2-(2-(tert-butoxycarbonyl)thiazol-4-yl)-2,2-difluoroacetate (1.6 g, 93% yield) as a white solid. MS m/z: 321 (M–1). $^1$H NMR (400 MHz, CD$_3$OD) δ ppm 1.30 (t, J=7.04 Hz, 3H), 1.55 (s, 9H), 4.33 (q, J=7.24 Hz, 3H), 7.45 (s, 1H).

(S)-Ethyl 2-(2-(2-(N-Boc-amino)-3-(4-(trifluoromethyl)phenyl)propyl(N-Boc-mino)thiazol-4-yl)-2,2-difluoroacetate To a solution of ethyl 2-(2-(tert-butoxycarbonyl)thiazol-4-yl)-2,2-difluoroacetate (1.6 g, 5.0 mmol) in 20 mL of DMF was added Cs$_2$CO$_3$ (3.2 g, 9.9 mmol). The mixture was heated to 50° C., and the cyclic sulfamidate (2.8 g, 7.4 mmol) in 15 mL of DMF was added slowly. After 10 minutes, 50 mL of a 1 N HCl solution was added to the reaction mixture, and the reaction mixture was extracted with 80 mL of EtOAc. The organic layer was concentrated and purified with silica gel column chromatography, eluting with 0-20% EtOAc/hexane to give (S)-ethyl 2-(2-(tert-butoxycarbonyl)thiazol-4-yl)-2,2-difluoroacetate (2.6 g, 84% yield). MS m/z: 660 (M+1).

(S)-2-(2-(2-(N-Boc-amino)-3-(4-(trifluoromethyl)phenyl)propyl(N-Boc-amino)thiazol-4-yl)-2,2-difluoroethanol To a 150 mL of round bottom flask was added (S)-ethyl 2-(2-(tert-butoxy-carbonyl)thiazol-4-yl)-2,2-difluoroacetate (2.5 g, 4.0 mmol), NaBH$_4$ (0.76 g, 20 mmol), and 40 mL of EtOH. The reaction mixture was stirred at room temperature for 2 hours. 50 mL of a saturated NH$_4$Cl solution was added dropwise, and the mixture was then extracted twice with 100 mL of EtOAc. The organic layers were combined and concentrated to give the title compound as a crude product. MS m/z: 580 (M–1).

(S)-2-(2-(2-(N-Boc-amino)-3-(4-(trifluoromethyl)phenyl)propyl(N-Boc-amino)-5-bromothiazol-4-yl)-2,2-difluoroethanol NBS (0.71 g, 4.0 mmol) was added to the crude product from the above step in 50 mL of CCl$_4$. After 4 hours, the reaction mixture was concentrated and purified with silica gel column chromatography, eluting with 0-30% EtOAc/hexane to give the title compound (2.0 g, 76% yield). MS m/z: 660 (M+1).

Example 134

2-(2-((S)-2-Amino-3-(4-(trifluoromethyl)phenyl)propylamino)-5-(isoquinolin-6-yl)thiazol-4-yl)-2,2-difluoroethanol The title compound was prepared in a manner similar to that described for Example 133. MS m/z: 509 (M+1). $^1$H NMR (400 MHz, (CD$_3$OD): δ ppm 3.11-3.15 (m, 2H), 3.56 (dd, J=14.77, 6.94 Hz, 1H), 3.71-3.78 (m, 1H), 3.89-3.96 (m, 1H), 4.05 (td, J=12.96, 3.03 Hz, 2H), 7.56 (d, J=8.02 Hz, 2H), 7.71 (d, J=8.22 Hz, 2H), 8.05 (d, J=8.61 Hz, 1H), 8.23-8.27 (m, 2H), 8.36 (d, J=8.61 Hz, 1H), 8.55 (d, J=6.46 Hz, 1H), 9.58 (s, 1H).

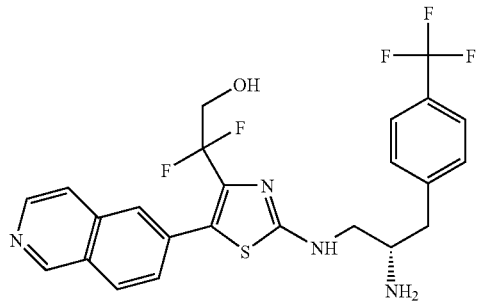

Example 135

6-(2-((S)-2-Amino-3-(4-(trifluoromethyl)phenyl)propylamino)-4-(1,1-difluoro-2-hydroxyethyl)thiazol-5-yl)benzo[d]oxazol-2(3H)-one The title compound was prepared in a manner similar to that described for Example 133. MS m/z: 515 (M+1). $^1$H NMR (400 MHz, CD$_3$OD): δ ppm 3.10 (d, J=7.43 Hz, 2H), 3.46-3.53 (m, 1H), 3.66-3.70 (m, 1H), 3.84-3.90 (m, J=7.09, 3.91, 3.59, 3.59 Hz, 1H), 3.96 (td, J=13.11, 2.35 Hz, 2H), 7.09 (d, J=8.22 Hz, 1H), 7.26 (dd, J=8.02, 1.57 Hz, 1H), 7.33 (s, 1H), 7.55 (d, J=8.02 Hz, 2H), 7.71 (d, J=8.22 Hz, 2H).

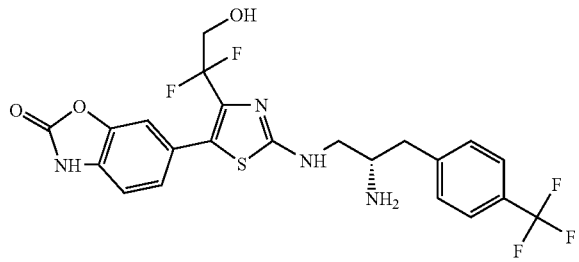

Example 136

6-(2-((S)-2-Amino-3-(4-(trifluoromethyl)phenyl)propylamino)-4-(1,1-difluoro-2-hydroxyethyl)thiazol-5-yl)-1-methyl-1H-benzo[d]imidazol-2(3H)-one The title compound was prepared in a manner similar to that described for Example 133. MS m/z: 528 (M+1). ¹H NMR (400 MHz, CD₃OD): δ ppm 3.10 (d, J=7.43 Hz, 2H), 3.39-3.41 (s, 3H), 3.47-3.66 (m, 1H), 3.70 (d, J=3.33 Hz, 2H), 3.84-3.90 (m, 1H), 3.95 (td, J=13.01, 2.15 Hz, 2H), 7.06-7.15 (m, 2H), 7.16-7.20 (m, 1H), 7.55 (d, J=8.02 Hz, 2H), 7.71 (d, J=8.02 Hz, 2H).

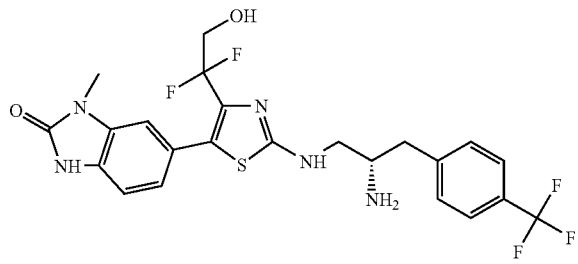

Example 137

5-(2-((R)-2-Amino-3-(4-(trifluoromethyl)phenyl)propylamino)thiazol-5-1)indolin-2-one The title compound was prepared in a manner similar to that described for Example 82 using 4-(trifluoromethyl)-D-phenylalanine purchased from PepTech as the starting material. MS m/z: 433 (M+1). ¹H NMR (400 MHz, CD₃OD): δ ppm 3.12-3.34 (m, 2H), 3.46-3.52 (m, 1H), 3.54 (s, 2H), 3.60-3.65 (m, 1H), 3.78 (br s, 1H), 6.87 (d, J=7.82 Hz, 1H), 7.28 (s, 2H), 7.37(s, 1H), 7.52 (d, J=8.22 Hz, 2H), 7.69 (d, J=8.02 Hz, 2H).

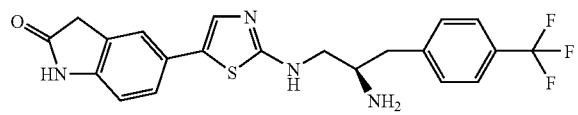

Examples 138-139

Examples 138-139 were synthesized via a cross coupling reaction of tert-butyl methyl(6-(4,4,5,5-tetramethyl-1,3,2-dioxaborolan-2-yl)isoquinolin-3-yl)carbamate, prepared as shown in Scheme 34, with the corresponding bromothiazole followed by Boc cleavage as previously described.

Scheme 34

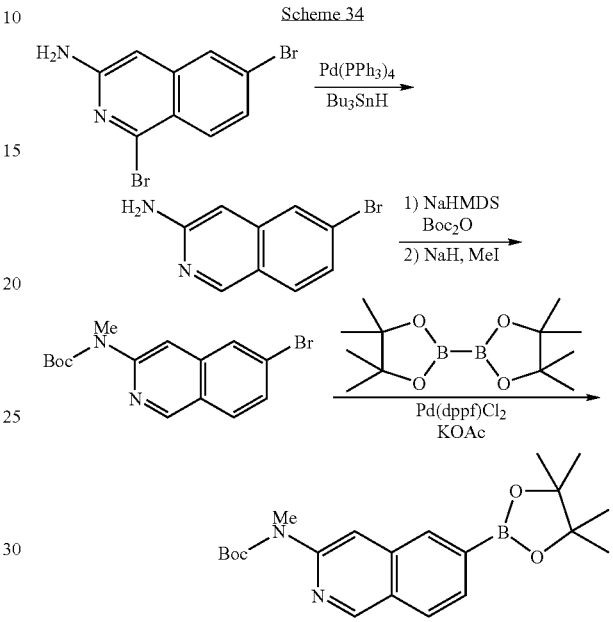

6-Bromoisoquinolin-3-amine

To a solution of 1,6-dibromoisoquinolin-3-amine (0.20 g, 0.66 mmol) and tributyltin hydride (0.19 mL, 0.73 mmol) in 6 mL of dioxane in a sealable tube was added palladium tetrakistriphenylphosphine (0.038 g, 0.033 mmol). The tube was sealed and heated to 100° C. in a Personal Chemistry microwave unit for 10 minutes. The mixture was then concentrated under reduced pressure, and the residue was purified by flash chromatography on silica gel (5% to 50% EtOAc/hexanes) affording 6-bromoisoquinolin-3-amine. ¹H NMR (400 MHz, CD₃OD) δ ppm 8.74 (s, 1H) 7.72 (s, 1H) 7.70 (d, J=8.80 Hz, 1H) 7.27 (dd, J=8.80, 1.76 Hz, 1H) 6.68 (s, 1H).

tert-Butyl 6-bromoisoquinolin-3-ylcarbamate

6-Bromoisoquinolin-3-amine (0.57 g, 2.6 mmol) was taken up in 10 mL of THF. NaHMDS (1M in THF (4.7 mL, 4.7 mmol)) was added, and the mixture was stirred for 15 minutes. Boc₂O (0.51 g, 2.3 mmol) was then added slowly in 3 mL of THF. The mixture was stirred for 30 minutes. The mixture was then quenched with 5 mL of aq. NH₄Cl. The mixture was diluted with 10 mL of water and extracted three times with 10 mL of EtOAc. The combined organic extracts were washed with 15 mL of brine and dried over MgSO₄. Filtration and concentration under reduced pressure, followed by flash chromatography on silica gel (2.5% to 20% EtOAc/hexanes) afforded tert-butyl 6-bromoisoquinolin-3-ylcarbamate (0.48 g, 64% yield) as a white solid. ¹H NMR (400 MHz, CDCl₃) δ ppm 8.93 (s, 1H) 8.16 (s, 1H) 7.93 (s, 1H) 7.71 (d, J=8.80 Hz, 1H) 7.49 (dd, J=8.61, 1.57 Hz, 1H) 1.59-1.53 (m, 9H).

tert-Butyl 6-bromoisoquinolin-3-yl(methyl)carbamate tert-Butyl 6-bromoisoquinolin-3-ylcarbamate (48 g, 1.5 mmol) was taken up in 10 mL of DMF and chilled to 0° C. Sodium hydride (0.074 g, 1.9 mmol) was added, and the mixture was stirred for 15 minutes. Iodomethane (0.10 mL, 1.6 mmol) was then added, and the mixture was stirred for 30 minutes. The reaction mixture was then quenched with 5 mL of aq NH$_4$Cl. The mixture was then diluted with 50 mL of EtOAc and transferred to a separatory funnel. The mixture was washed five times with 25 mL of water and once with 25 mL of brine. The remaining portion was dried over MgSO$_4$, filtered, and concentrated under reduced pressure. The residue was purified by flash chromatography on silica gel (0.5% to 7.5% EtOAc/hexanes), affording tert-butyl 6-bromoisoquinolin-3-yl(methyl)carbamate (0.39 g, 78% yield) as a yellow solid. $^1$H NMR (400 MHz, CDCl$_3$) δ ppm 9.04 (s, 1H) 7.95 (s, 1H) 7.88 (s, 1H) 7.77 (d, J=8.80 Hz, 1H) 7.56 (dd, J=8.61, 1.76 Hz, 1H) 3.48 (s, 3H) 1.57-1.52 (m, 9H).

tert-Butyl methyl(6-(4,4,5,5-tetramethyl-1,3,2-dioxaborolan-2-yl)isoquinolin-3-yl)carbamate tert-Butyl 6-bromoisoquinolin-3-yl(methyl)carbamate (0.170 g, 0.50 mmol) was taken up in 3 mL of DMSO and transferred to a sealable tube. Bis(pinacolato)diboron (0.15 g, 0.60 mmol), potassium acetate (0.074 g, 0.76 mmol), and 1,1'-bis(diphenylphosphino)ferrocene-palladium dichloride (0.01 8 g, 0.025 mmol) were added, and the mixture was purged with nitrogen. The tube was sealed. The mixture was heated to 80° C. and stirred for 2 hours. The mixture was then diluted with 30 mL of EtOAc and transferred to a separatory funnel. The mixture was washed three times with 20 mL of water and once with 20 mL of brine, then dried over MgSO$_4$. Filtration and concentration under reduced pressure, followed by flash chromatography on silica gel (2.5% to 15% EtOAc/hexanes) afforded tert-butyl methyl(6-(4,4,5,5-tetramethyl-1,3,2-dioxaborolan-2-yl)isoquinolin-3-yl)carbamate (0.15 g, 77% yield) as a clear oil. $^1$H NMR (400 MHz, CDCl$_3$) δ ppm 9.09 (s, 1H) 8.29 (s, 1H) 7.84-7.91 (m, 3H) 3.46 (s, 3H) 1.51 (s, 9H) 1.39 (s, 12H).

Example 138

6-(2-((S)-2-amino-3-(4-(trifluoromethyl)phenyl)propylamino)thiazol-5-yl)-N-methylisoquinolin-3-amine MS m/z: 458 (M+1) $^1$H NMR (400 MHz, CD$_3$OD): δ ppm 8.65 (s, 1H) 7.73 (d, J=8.61 Hz, 1H) 7.62 (d, J=8.22 Hz, 2H) 7.43-7.53 (m, 4H) 7.37 (d, J=8.80 Hz, 1H) 6.54 (s, 1H), 3.49-3.40 (m, 3H), 2.96 (dd, J=13.40, 5.18 Hz, 1H) 2.91 (s, 3H) 2.73 (dd, J=13.60, 7.34 Hz, 1H)

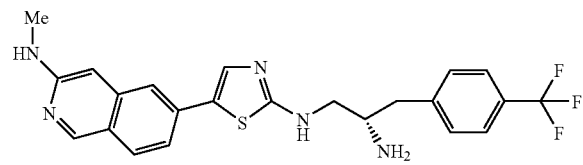

Example 139

6-(2-((S)-2-amino-3-(4-chlorophenyl)propylamino)thiazol-5-yl)-N-methylisoquinolin-3-amine MS m/z: 424 (M+1) $^1$H NMR (400 MHz, CD$_3$OD): δ ppm 8.65 (s, 1H) 7.73 (d, J=8.61 Hz, 1H) 7.52 (s, 1H) 7.45 (s, 1H) 7.30-7.38 (m, 3H) 7.23-7.27 (m, 2H) 6.55 (s, 1H) 3.45-3.23 (m, 3H) 2.91 (s, 3H) 2.86 (dd, J=13.40, 5.18 Hz, 1H) 2.66 (d, J=7.04 Hz, 1H).

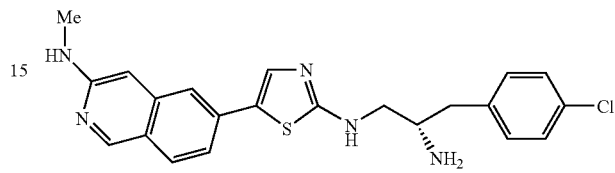

Examples 140-153

Examples 140-153 were synthesized in an manner similar to that described for Example 79 as shown in Scheme 20.

Example 140

3-(2-((S)-2-amino-3-(4-(trifluoromethyl)phenyl)propylamino)-5-(isoquinolin-6-yl)thiazol-4-yl)prop-2-yn-1-ol MS m/z: 483 (M+1). $^1$H NMR (400 MHz, DMSO-d$_6$) δ ppm 9.26 (s, 1H), 8.49 (d, J=5.67 Hz, 1H), 8.21 (s, 1H), 8.08-8.12 (m, 2H), 7.82 (d, J=5.87 Hz, 1H), 7.66 (d, J=8.22 Hz, 2H), 7.48 (d, J=8.02 Hz, 2H), 5.46 (t, J=6.06 Hz, 1H), 4.38 (d, J=6.06 Hz, 2H), 3.33-3.25 (m, 1H), 3.20-3.14 (m, 3H), 3.13 (s, 1H), 2.87 (dd, J=13.20, 4.40 Hz, 1H), 2.68-2.58 (m, 1H), 1.65-1.48 (broad s, 2H).

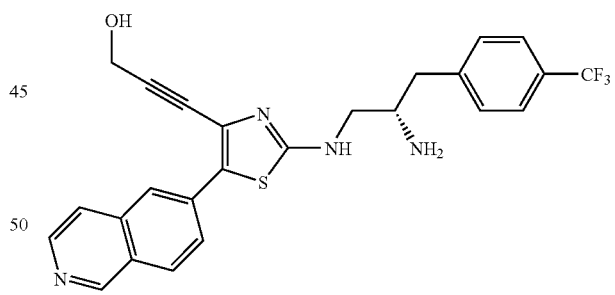

Example 141

4-(2-((S)-2-amino-3-(4-(trifluoromethyl)phenyl)propylamino)-5-(isoquinolin-6-yl)thiazol-4-yl)but-3-yn-2-ol MS m/z: 497 (M+1). $^1$H NMR (400 MHz, CD$_3$OD): δ ppm 9.17 (s, 1H), 8.41 (d, J=5.87 Hz, 1H), 8.27 (s, 1H), 8.14-8.07 (m, 2H), 7.80 (d, J=5.87 Hz, 1H), 7.62 (d, J=8.22 Hz, 2H), 7.47 (d, J=8.02 Hz, 2H), 4.75 (q, J=6.52 Hz, 1H), 3.51-3.25 (m, 3H), 2.96 (d, J=5.09 Hz, 1H), 2.74 (dd, J=13.60, 7.53 Hz, 1H), 1.53 (d, J=6.65 Hz, 3H).

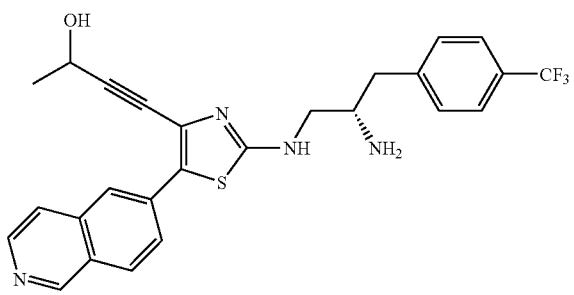

Example 142

1-(2-(2-((S)-2-amino-3-(4-(trifluoromethyl)phenyl) propylamino)-5-(isoquinolin-6-yl)thiazol-4-yl)ethynyl)cyclobutanol MS m/z: 523 (M+1). $^1$H NMR (400 MHz, CD$_3$OD): δ ppm 9.17 (s, 1H), 8.40 (d, J=5.87 Hz, 1H), 8.28 (s, 1H), 8.15-8.07 (m, 2H), 7.77 (d, J=5.67 Hz, 1H), 7.62 (d, J=8.02 Hz, 2H), 7.47 (d, J=8.02 Hz, 2H), 3.48-3.28 (m, 3H), 2.96 (s, 1H), 2.73 (dd, J=13.40, 7.34 Hz, 1H), 2.56-2.49 (m, 2H), 2.39-2.30 (m, 2H), 1.94-1.85 (m, 2H).

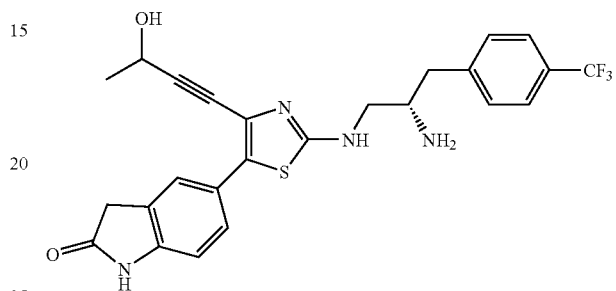

Example 143

N-((S)-2-amino-3-(4-(trifluoromethyl)phenyl)propyl)-5-(isoquinolin-6-yl)-4-(prop-1-ynyl)thiazol-2-amine MS m/z: 467 (M+1). $^1$H NMR (400 MHz, CD$_3$OD): δ ppm 9.14 (s, 1H), 8.38 (d, J=5.87 Hz, 1H), 8.16-8.12 (m, 2H), 8.07-8.02 (m, 1H), 7.75 (d, J=5.87 Hz, 1H), 7.61 (d, J=8.02 Hz, 2H), 7.46 (d, J=8.02 Hz, 2H), 3.43-3.25 (m, 3H), 3.00-2.93 (m, 1H), 2.71 (dd, J=13.50, 7.43 Hz, 1H), 2.13 (s, 3H).

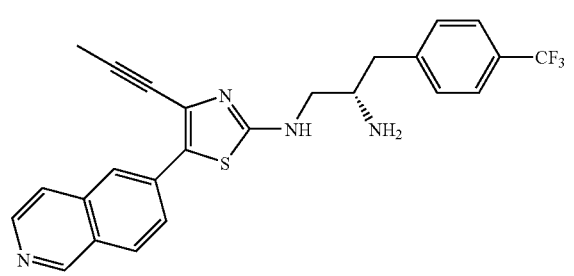

Example 144

5-(2-((S)-2-amino-3-(4-(trifluoromethyl)phenyl) propylamino)-4-(3-hydroxybut-1-ynyl)thiazol-5-yl) indolin-2-one MS m/z: 501 (M+1). $^1$H NMR (400 MHz, DMSO-d$_6$) δ ppm 7.79 (s, 1H) 7.65 (d, J=8.02 Hz, 2H) 7.57 (s, 1H) 7.51-7.44 (m, 3H) 6.82 (d, J=8.41 Hz, 1H) 5.45 (d, J=5.48 Hz, 1H) 4.54-4.61 (m, 1H), 3.49 (s, 2H), 3.45-3.08 (m, 3H), 3.88-3.82 (m, 1H), 2.64-2.56 (m, 1H), 1.37 (d, J=6.65 Hz, 3H).

Example 145

5-(2-((S)-2-amino-3-(4-(trifluoromethyl)phenyl) propylamino)-4-(3-hydroxyprop-1-ynyl)thiazol-5-yl) indolin-2-one MS m/z: 497 (M+1). $^1$H NMR (400 MHz, DMSO-d$_6$) δ ppm 10.48 (s, 1H), 7.82-7.79 (m, 1H), 7.65 (d, J=8.02 Hz, 2H), 7.45-7.53 (m, 3H), 6.82 (d, J=8.22 Hz, 1H), 5.33 (t, J=6.06 Hz, 1H), 4.29 (d, J=6.06 Hz, 2H), 3.50 (s, 2H), 3.25 (s, 1H), 3.11 (d, J=4.89 Hz, 2H), 2.85 (dd, J=13.50, 3.91 Hz, 1H), 2.59 (dd, J=13.11, 7.24 Hz, 1H).

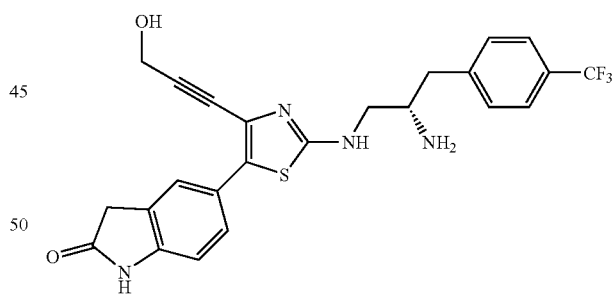

Example 146

N-((S)-2-amino-3-(4-(trifluoromethyl)phenyl)propyl)-5-(isoquinolin-6-yl)-4-(3-methoxyprop-1-ynyl) thiazol-2-amine MS m/z: 497 (M+1). $^1$H NMR (400 MHz, DMSO-d$_6$) δ ppm 9.27 (s, 1H) 8.49 (d, J=5.67 Hz, 1H) 8.11-8.20 (m, 3H) 8.08 (d, J=1.76 Hz, 1H) 7.80 (d, J=5.67 Hz, 1H) 7.66 (d, J=8.02 Hz, 2H) 7.48 (d, J=7.83 Hz, 2H) 4.40 (s, 2H) 3.35 (s, 3H) 3.28 (d, J=4.50 Hz, 1H) 3.17 (d, J=12.52 Hz, 2H) 2.89 (d, J=4.50 Hz, 1H) 2.86 (s, 1H) 2.64 (d, J=7.63 Hz, 1H).

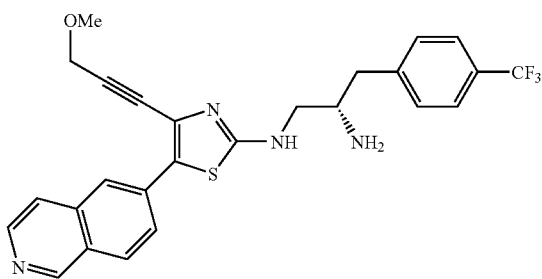

Example 147

N-((S)-2-amino-3-(4-(trifluoromethyl)phenyl)propyl)-4-(2-cyclopentenylethynyl)-5-(isoquinolin-6-yl)thiazol-2-amine MS m/z: 519 (M+1). $^1$H NMR (400 MHz, CD$_3$OD) δ ppm 9.20 (s, 1H), 8.44 (d, J=5.87 Hz, 1H), 8.25 (s, 1H), 8.10-8.17 (m, 2H), 7.79 (d, J=5.87 Hz, 1H), 7.65 (d, J=8.02 Hz, 2H), 7.50 (d, J=8.02 Hz, 2H), 6.28-6.26 (m, 1H), 3.52-3.25 (m, 3H), 2.99 (d, J=4.89 Hz, 1H), 2.76 (dd, J=13.40, 7.73 Hz, 1H), 2.53-2.65 (m, 4H), 1.99-2.07 (m, 2H).

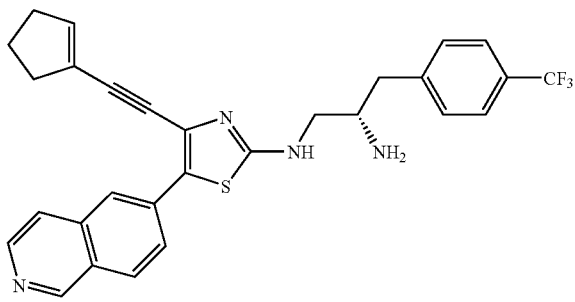

Example 148

1-(2-(2-((S)-2-amino-3-(4-(trifluoromethyl)phenyl)propylamino)-5-(isoquinolin-6-yl)thiazol-4-yl)ethynyl)cyclopentanol MS m/z: 537 (M+1). $^1$H NMR (400 MHz, CD$_3$OD) δ ppm 9.18 (s, 1H), 8.43 (d, J=5.87 Hz, 1H), 8.28 (s, 1H), 8.07-8.14 (m, 2H), 7.79 (d, J=5.87 Hz, 1H), 7.64 (d, J=8.22 Hz, 2H), 7.50 (d, J=8.02 Hz, 2H), 3.48-3.31 (m, 3H), 3.00 (dd, J=13.50, 4.89 Hz, 1H), 2.76 (dd, J=13.50, 7.43 Hz, 1H), 2.15-2.03 (m, 4H) 1.96-1.48 (m, 4H).

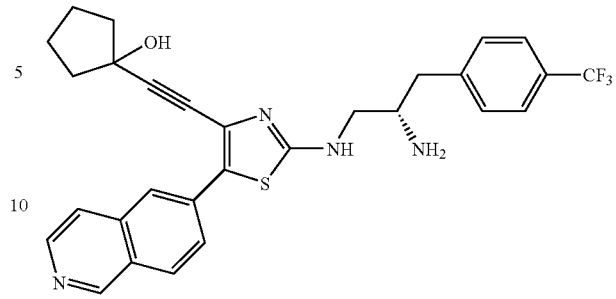

Example 149

3-(2-((S)-2-amino-3-(4-(trifluoromethyl)phenyl)propylamino)-5-(3-methyl-1H-indazol-5-yl)thiazol-4-yl)prop-2-yn-1-ol MS m/z: 486 (M+1). $^1$H NMR (400 MHz, CD$_3$OD) δ ppm 8.07 (s, 1H), 7.74 (dd, J=8.61, 1.56 Hz, 1H), 7.63 (d, J=8.22 Hz, 2H), 7.55-7.45 (m, 3H), 4.42 (s, 2H), 3.47-3.25 (m, 3H), 3.00 (s, 1H), 2.80 (s, 1H), 2.56 (s, 3H).

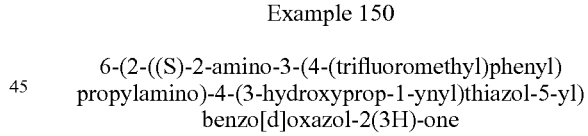

Example 150

6-(2-((S)-2-amino-3-(4-(trifluoromethyl)phenyl)propylamino)-4-(3-hydroxyprop-1-ynyl)thiazol-5-yl)benzo[d]oxazol-2(3H)-one MS m/z: 489 (M+1). $^1$H NMR (400 MHz, DMSO-d$_6$) δ ppm 7.90 (s, 1H) 7.62-7.67 (m, 3H) 7.48 (d, J=8.02 Hz, 2H) 7.35 (dd, J=8.12, 1.66 Hz, 1H) 7.07 (d, J=8.22 Hz, 1H) 5.37 (s, 1H) 4.30 (s, 2H) 3.30-3.12 (m, J=11.15 Hz, 3H) 2.85 (d, J=4.11 Hz, 1H) 2.62 (dd, J=13.30, 7.24 Hz, 1H).

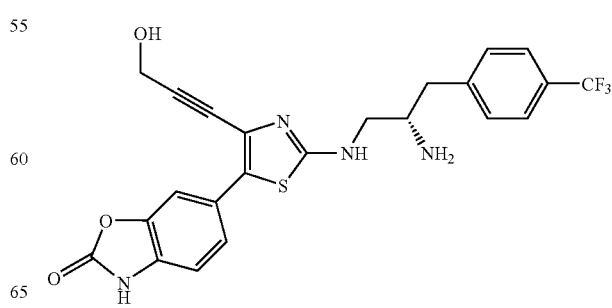

Example 151

N-(3-(2-((S)-2-amino-3-(4-(trifluoromethyl)phenyl)propylamino)-5-(isoquinolin-6-yl)thiazol-4-yl)prop-2-ynyl)methanesulfonamide MS m/z: 560 (M+1). $^1$H NMR (400 MHz, CD$_3$OD) δ ppm 9.16 (s, 1H), 8.40 (d, J=5.87 Hz, 1H), 8.24 (s, 1H), 8.09 (s, 2H), 7.86 (d, J=5.87 Hz, 1H), 7.61 (d, J=8.02 Hz, 2H), 7.46 (d, J=8.02 Hz, 2H), 4.21 (s, 2H), 3.48-3.25 (m, 3H), 2.99-2.93 (m, 4H), 2.72 (dd, J=13.40, 7.34 Hz, 1H).

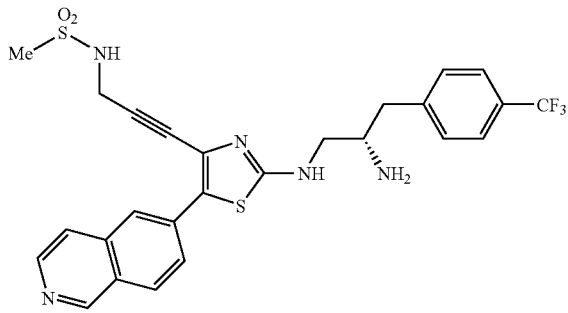

Example 152

5-(2-((S)-2-amino-3-(4-(trifluoromethyl)phenyl)propylamino)-4-(prop-1-ynyl)thiazol-5-yl)indolin-2-one MS m/z: 472 (M+1). $^1$H NMR (400 MHz, CD$_3$OD) δ ppm 7.62-7.66 (m, 3H) 7.57 (dd, J=8.22, 1.76 Hz, 1H) 7.48 (d, J=8.02 Hz, 2H) 6.91 (d, J=8.22 Hz, 1H) 3.44-3.23 (m, 5H) 2.97 (s, 1H) 2.74 (d, J=7.24 Hz, 1H) 2.08 (s, 3H).

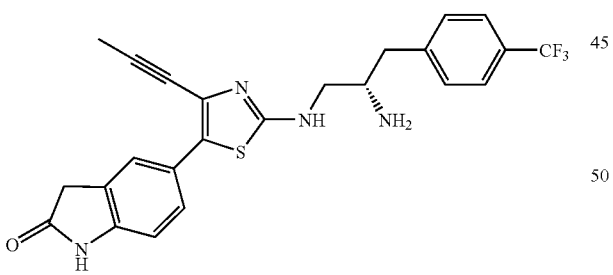

Example 153

N-((S)-2-amino-3-(4-(trifluoromethyl)phenyl)propyl)-5-(3-methyl-1H-indazol-5-yl)-4-(prop-1-ynyl)thiazol-2-amine MS m/z: 470 (M+1). $^1$H NMR (400 MHz, DMSO-d$_6$) δ ppm 12.7 (s, 2H) 7.95 (d, J=0.78 Hz, 1H) 7.77-7.82 (m, 1H) 7.62-7.68 (m, 3H) 7.47 (dd, J=8.02, 5.09 Hz, 3H) 3.21-3.30 (m, 1H) 3.12 (d, J=3.72 Hz, 2H) 2.87 (dd, J=13.20, 4.21 Hz, 1H) 2.61 (dd, J=13.40, 7.34 Hz, 1H) 2.06 (s, 3H).

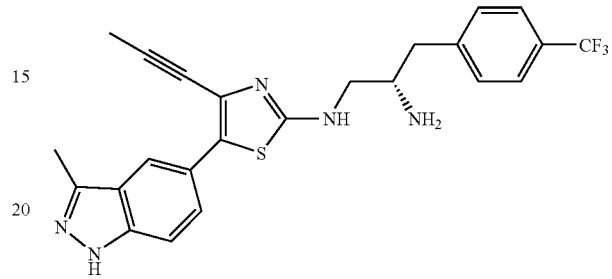

Example 154

N-((2S,3S,E)-2-amino-3-(4-(trifluoromethyl)phenyl)hex-4-enyl)-5-(isoquinolin-6-yl)thiazol-2-amine The title compound was synthesized in a manner similar to that described for Example 35 using a nosyl aziridine intermediate to introduce the (2S,3S,E)-2-amino-3-(4-(trifluoromethyl)phenyl)hex-4-enylamine side chain to make the bromothiazole intermediate that was coupled with isoquinolin-6-ylboronic acid. The nosyl aziridne was prepared in a similar manner to that described for Example 17 starting with (2S,3S,E)-2-amino-3-(4-(trifluoromethyl)phenyl)hex-4-en-1-ol which was prepared as shown in Scheme 35. MS m/z: 469 (M+1). $^1$H NMR (400 MHz, CD$_3$OD) δ ppm 9.12 (s, 1H) 8.38 (d, J=5.87 Hz, 1H) 8.03 (d, J=8.80 Hz, 1H) 7.86 (dd, J=8.61, 1.76 Hz, 1H) 7.70-7.80 (m, 2H) 7.65 (t, J=4.01 Hz, 3H) 7.50 (d, J=8.22 Hz, 2H) 5.63-5.83 (m, 2H) 3.65 (dd, J=13.11, 2.74 Hz, 1H) 3.37-3.44 (m, 2H) 3.21-3.30 (m, 1H) 1.73 (dd, J=6.26, 1.37 Hz, 3H).

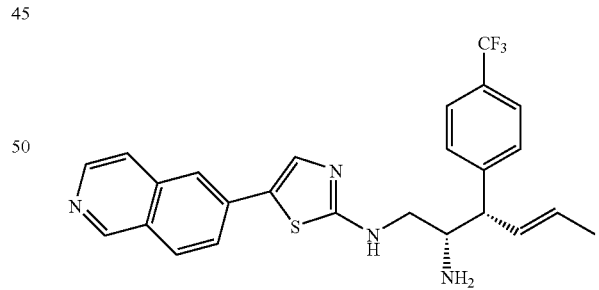

Scheme 35

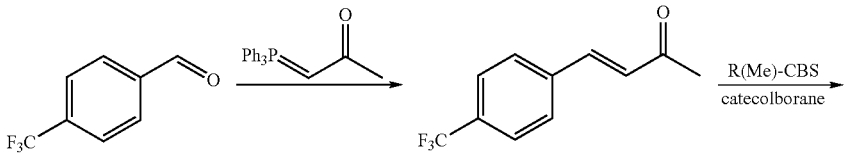

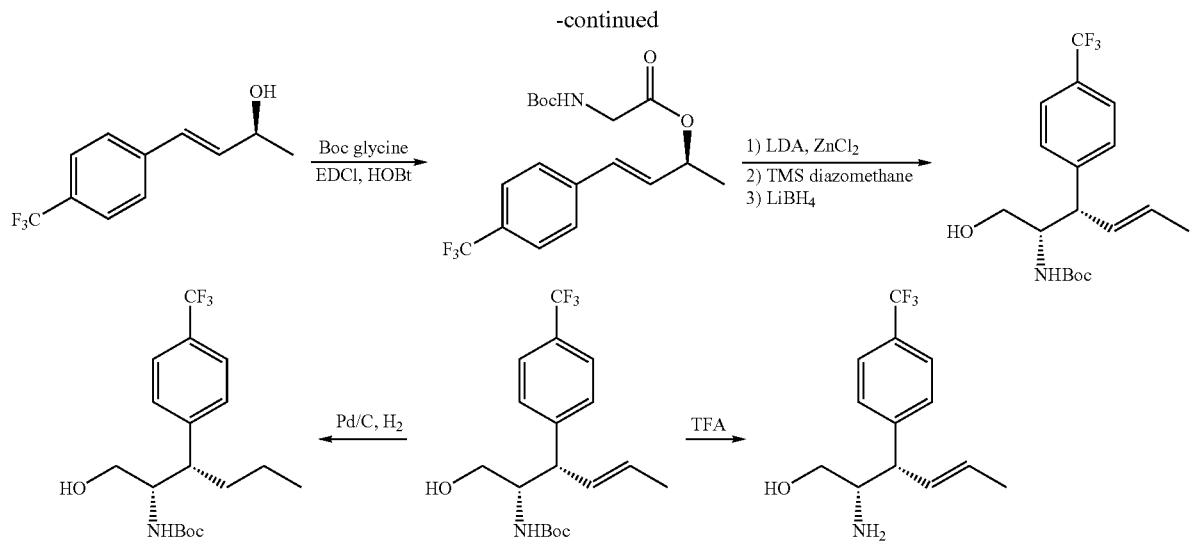

E-4-(4-(trifluoromethyl)phenyl)but-3-en-2-one 4-(Trifluoromethyl)benzaldehyde (25.0 g, 144 mmol) was taken up in 500 mL of DCM. 1-Triphenylphosphoranylidene-2-propanone (48.0 g, 151 mmol) was added. After 5 hours, an additional 3 g of 1-triphenylphosphoranylidene-2-propanone was added. The mixture was stirred for 10 hours. The solvent was removed under reduced pressure, and the residue was triturated with 500 mL of 5% EtOAc/hexanes. The mixture was filtered, removing a large amount of P(O)Ph$_3$. The residue was taken up in 300 mL of 2.5% EtOAc/hexanes and filtered through a pad of silica. The mixture was concentrated under reduced pressure and the residue was found to be (E)-4-(4-(trifluoromethyl)phenyl)but-3-en-2-one (28.3 g, 92.0% yield). $^1$H NMR (400 MHz, CDCl$_3$) δ ppm 7.68-7.60 (m, 4H), 7.52 (d, J=16.43 Hz, 1H), 6.78 (d, J=16.4 Hz, 1H), 2.41 (s, 3H).

(S,E)-4-(4-(trifluoromethyl)phenyl)but-3-en-2-ol (E)-4-(4-(trifluoromethyl)phenyl)but-3-en-2-one (15 g, 70 mmol) was taken up in 500 mL of toluene. (R)-2-Methyl-CBS-oxazaborolidine, 1.09 M in toluene (6.4 mL, 7.0 mmol) was added, and the mixture was chilled to −78° C. Catecholborane (13 mL, 119 mmol) was added dropwise via addition funnel in 125 mL of toluene. The mixture was stirred for 25 minutes and then gradually warmed to −45° C. and stirred for 2 hours. The yellow color taken on during the catecholborane addition faded during this time and the solution cleared. The mixture was quenched with 300 mL of water and warmed to room temperature. The mixture was partitioned in a separatory funnel. The organic portion was washed 3 times with 200 mL of 5% aq. KOH (to remove the catechol), twice with 200 mL of 10% aq. HCl (to remove the (R)-2-methyl-CBS-oxazaborolidine catalyst), and once with 200 mL of brine, then dried over MgSO$_4$. Filtration and concentration under reduced pressure afforded (S,E)-4-(4-(trifluoromethyl)phenyl)but-3-en-2-ol (15 g, 99% yield) as a yellow oil that slowly crystallized on the bench top. $^1$H NMR (400 MHz, CDCl$_3$) δ ppm 7.57 (d, J=8.22 Hz, 2H) 7.50-7.45 (m, 2H) 6.62 (d, J=16.04 Hz, 1H) 6.36 (dd, J=16.04, 6.06 Hz, 1H) 4.49-4.57 (m, 1H) 1.61 (d, J=4.30 Hz, 1H) 1.39 (d, J=6.46 Hz, 3H).

(S,E)-4-(4-Trifluoromethyl)phenyl)but-3-en-2-yl 2-(tert-butoxycarbonyl)acetate (S,E)-4-(4-(Trifluoromethyl)phenyl)but-3-en-2-ol (11.2 g, 51.8 mmol) was taken up in 240 mL of DMF. N-Boc glycine (22.7 g, 130 mmol), N1-((ethylimino)methylene)-N3,N3-dimethylpropane-1,3-diamine hydrochloride (29.8 g, 155 mmol), 1H-benzo[d][1,2,3]triazol-1-ol (21.0 g, 155 mmol), and Hunig's base (27.1 mL, 155 mmol) were added. After 12 hours, the solvent was removed under reduced pressure. The residue was taken up in 500 mL of EtOAc and transferred to a separatory funnel. The mixture was washed with 200 mL of 10% aqueous HCl, 200 mL of aqueous NaHCO$_3$, and 200 mL of brine, and then dried over MgSO$_4$. Filtration and concentration under reduced pressure, followed by flash chromatography on silica gel (2.5% to 15% EtOAc/hexanes) afforded (S,E)-4-(4-(trifluoromethyl)phenyl)but-3-en-2-yl 2-(tert-butoxycarbonyl)acetate (16.5 g, 85.3% yield) as a thick oil. $^1$H NMR (400 MHz, CDCl$_3$) δ ppm 7.59-7.52 (m, 2H) 7.47 (d, J=8.22 Hz, 2H) 6.64 (d, J=15.85 Hz, 1H) 6.26 (dd, J=15.94, 6.55 Hz, 1H) 5.60 (dq, J=6.55, 6.29 Hz, 1H) 5.00 (s, 1H) 3.85-4.00 (m, 2H), 1.46-1.43 (m, 12H).

tert-Butyl (2S,3S,E)-1-hydroxy-3-(4-(trifluoromethyl)phenyl)hex-4-en-2-ylcarbamate Diisopropylamine (8.3 mL, 59 mmol) was taken up in 45 mL of THF and chilled to −20° C. Butyllithium, 2.5 M in hexane (19 mL, 48 mmol) was added, and the mixture was stirred for 20 minutes. The mixture was then chilled to −78° C. (S,E)-4-(4-(Trifluoromethyl)phenyl)but-3-en-2-yl 2-(tert-butoxycarbonyl)acetate (8.1 g, 22 mmol) was added in 22 mL of THF at −78° C. by cannula. The mixture immediately turned purple. After 5 minutes, Zinc(II) chloride, 0.5 M in THF (50 mL, 25 mmol), was added slowly to the mixture. The mixture was then gradually warmed to room temperature over 1.5 hours. The mixture was quenched with 30 mL of 10% aq. HCl. The solvent was removed under reduced pressure. The residue was taken up in 400 mL of ether. The mixture was washed with 100 mL of 10% aq HCl. The mixture was then extracted twice with 125 mL of 1 M aq NaOH. The combined basic extracts were acidified with concentrated HCl. The mixture was then extracted three times with 200 mL of ether.

The combined ether extracts were dried over MgSO₄. Filtration and concentration under reduced pressure afforded (2S,3S,E)-2-(tert-butoxycarbonyl)-3-(4-(trifluoromethyl)phenyl)hex-4-enoic acid (5.3 g, 65% yield) which was carried on directly without any further purification.

(2S,3S,E)-2-(tert-butoxycarbonyl)-3-(4-(trifluoromethyl)phenyl)hex-4-enoic acid (5.3 g, 14 mmol) was taken up in 70 mL of 3.5:1 benzene:MeOH. TMS diazomethane, 2M in hexane (7.8 mL, 16 mmol) was added slowly to the mixture. Bubbling ensued. Approximately 2 mL excess TMS diazomethane reagent was added, presumably due to loss of titer of the reagent. The bubbling was monitored, and the addition was stopped when the bubbling ceased. The solvent was removed under reduced pressure. The mixture was triturated twice with 50 mL of 10% ether:hexanes, affording (2S,3S,E)-methyl 2-(tert-butoxycarbonyl)-3-(4-(trifluoromethyl)phenyl)hex-4-enoate (5.4 g, 98% yield) as a white solid. ¹H NMR (400 MHz, CDCl₃) δ ppm 7.59 (d, J=8.22 Hz, 2H) 7.34 (d, J=8.22 Hz, 2H) 5.75-5.59 (m, 2H) 4.92-4.84 (m, 1H) 4.70-4.63 (m, 1H) 3.78-3.72 (m, 1H) 3.68 (s, 3H) 1.72 (d, J=5.28 Hz, 3H) 1.37 (s, 9H).

(2S,3S,E)-Methyl 2-(tert-butoxycarbonyl)-3-(4-(trifluoromethyl)phenyl)hex-4-enoate (5.4 g, 14 mmol) was taken up in 140 mL of diethyl ether and chilled to 0° C. Lithium borohydride (1.2 g, 56 mmol) was added to the mixture. After 1.5 hours, approximately 10 mL of MeOH was added to the reaction. The mixture was stirred an additional 20 minutes and was then quenched by dropwise addition of aq NH₄Cl (20 mL). The mixture was then diluted with 50 mL of aq NH₄Cl and 50 mL of water. The mixture was partitioned and the aqueous portion was extracted with 120 mL of ether. The combined organic extracts were washed with 100 mL of brine and dried over MgSO₄ Filtration and concentration under reduced pressure, followed by flash chromatography on silica gel (5% to 30% EtOAc/hexanes) afforded tert-butyl (2S,3S,E)-1-hydroxy-3-(4-(trifluoromethyl)phenyl)hex-4-en-2-ylcarbamate (3.9 g, 78% yield) as a sticky solid. ¹H NMR (400 MHz, CDCl₃) δ ppm 7.56 (d, J=8.03 Hz, 2H) 7.34 (d, J=8.03 Hz, 2H) 5.59-5.69 (m, 2H) 4.60-4.50 (m, 1H) 3.94 (s, 1H) 3.80-3.70 (m, 2H) 3.63-3.55 (m, 1H) 2.15-2.07 (m, 1H) 1.69 (d, J=4.52 Hz, 3H) 1.29 (s, 9H).

(2S,3S,E)-2-amino-3-(4-(trifluoromethyl)phenyl)hex-4-en-1-ol

Tert-butyl (2S,3S,E)-1-hydroxy-3-(4-(trifluoromethyl)phenyl)hex-4-en-2-ylcarbamate (0.10 g, 0.28 mmol) was taken up in 3 mL of DCM. 1 mL of TFA was added. The mixture was stirred for 1 hour. The solvent was removed under reduced pressure, and the residue was taken up in 5 mL of DCM and 5 mL of 5% aq NaOH. The mixture was partitioned, and the aqueous portion was extracted three times with 5 mL of DCM. The combined organic extracts were dried over MgSO₄. Filtration and concentration under reduced pressure afforded (2S,3S,E)-2-amino-3-(4-(trifluoromethyl)phenyl)hex-4-en-1-ol, which was used without any further purification.

tert-butyl (2S,3S)-1-hydroxy-3-(4-(trifluoromethyl)phenyl)hexan-2-ylcarbamate

Tert-butyl (2S,3S,E)-1-hydroxy-3-(4-(trifluoromethyl)phenyl)hex-4-en-2-ylcarbamate (0.51 g, 1.4 mmol) was taken up in 10 mL of MeOH. 0.10 g of 10% Pd on carbon was added, and hydrogen was bubbled through the mixture. After 2 minutes, the bubbling was ceased and the reaction was kept under a balloon of hydrogen. After 2 hours, the mixture was filtered through Celite and concentrated under reduced pressure, affording tert-butyl (2S,3S)-1-hydroxy-3-(4-(trifluoromethyl)phenyl)hexan-2-ylcarbamate (0.50 g, 97% yield) as a white solid.

Example 155

5-(2-((2S,3S,E)-2-amino-3-(4-(trifluoromethyl)phenyl)hex-4-enylamino)thiazol-5-yl)indolin-2-one This compound was synthesized in a manner similar to that described for Example 154. MS m/z: 473 (M+1). ¹H NMR (400 MHz, CD₃OD) δ ppm 7.64 (d, J=8.02 Hz, 2H) 7.48 (d, J=8.02 Hz, 2H) 7.36 (s, 1H) 7.21-7.29 (m, 2H) 6.87 (d, J=8.02 Hz, 1H) 5.73-5.79 (m, 1H) 5.65 (dq, J=15.11, 6.24 Hz, 1H) 3.50-3.62 (m, 1H) 3.34-3.41 (m, 2H) 3.14-3.23 (m, 1H) 1.71 (d, J=8.0 Hz, 3H).

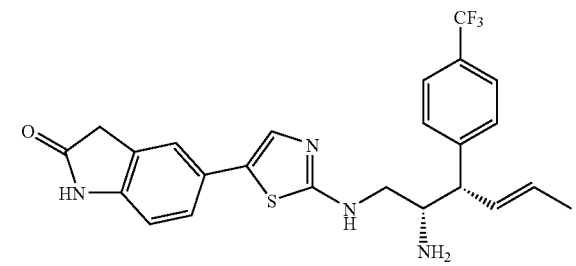

Examples 156-157

Examples 156-157 were prepared in a manner similar to that described for Example 81 using tert-butyl (2S,3S)-1-hydroxy-3-(4-(trifluoromethyl)phenyl)hexan-2-ylcarbamate as the starting material which was prepared as shown in Scheme 35.

Example 156

5-(2-((2S,3S)-2-amino-3-(4-(trifluoromethyl)phenyl)hexylamino)thiazol-5-yl)indolin-2-one MS m/z: 475 (M+1). ¹H NMR (400 MHz, CD₃OD) δ ppm 7.66 (d, J=8.22 Hz, 2H) 7.49 (d, J=8.22 Hz, 2H) 7.38 (d, J=1.37 Hz, 1H) 7.29 (dd, J=8.12, 1.86 Hz, 1H) 7.23 (s, 1H) 6.89 (d, J=8.22 Hz, 1H) 3.47-3.57 (m, 2H) 3.37 (s, 2H) 3.14-3.21 (m, 1H) 2.84-2.90 (m, 1H) 1.81-1.87 (m, 2H) 1.11-1.18 (m, 2H) 0.90 (t, J=7.34 Hz, 3H).

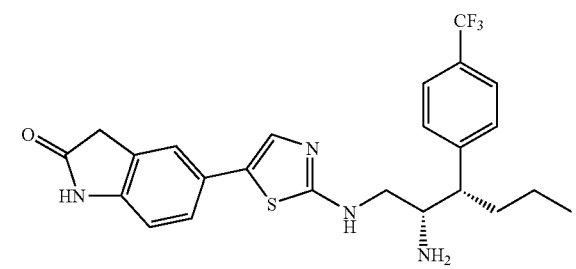

Example 157

N-((2S,3S)-2-amino-3-(4-(trifluoromethyl)phenyl)hexyl)-5-(isoquinolin-6-yl)thiazol-2-amine MS m/z: 471 (M+1). $^1$H NMR (400 MHz, CD$_3$OD) δ ppm 9.14 (s, 1H) 8.39 (d, J=6.02 Hz, 1H) 8.05 (d, J=9.03 Hz, 1H) 7.90 (d, J=9.03 Hz, 1H) 7.82 (s, 1H) 7.77 (d, J=6.02 Hz, 1H) 7.60-7.70 (m, 3H) 7.50 (d, J=8.03 Hz, 2H) 3.55 (dd, J=13.05, 4.02 Hz, 1H) 3.20-3.31 (m, 2H) 2.84-2.91 (m, 1H) 1.79-1.89 (m, 2H) 1.10-1.22 (m, 2H) 0.91 (t, J=7.28 Hz, 3H).

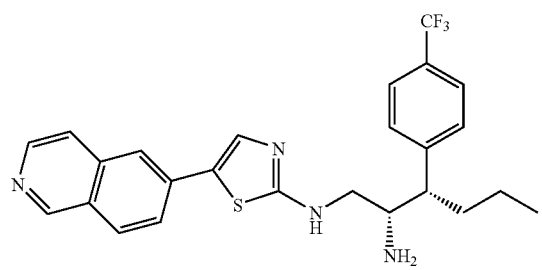

Example 158

5-(2-((2S,3S)-2-amino-4-hydroxy-3-(4-(trifluoromethyl)phenyl)butylamino)thiazol-5-yl)indolin-2-one This compound was synthesized in a manner similar to that described for Example 81 using (2S,3S)-3-(t-butoxylcarbonyl)amino-4-(5-bromothiazol-2-yl(t-butoxylcarbonyl)amino)-2-(4-(trifluoromethyl)phenyl)butan-1-ol as the starting material which was prepared as shown in Scheme 36. HRMS calc'd (M+1) 463.14101, found 463.14167. $^1$H NMR (400 MHz, CD$_3$OD) δ ppm 7.69 (d, J=8.03 Hz, 2H) 7.55-7.64 (m, 2H) 7.40 (s, 1H) 7.31 (d, J=8.03 Hz, 1H) 7.26 (s, 1H) 6.91 (d, J=8.03 Hz, 1H) 3.96-4.06 (m, 2H) 3.51-3.60 (m, 3H) 3.39 (s, 3H) 3.21-3.31 (m, 1H) 3.08 (q, J=6.02 Hz, 1H).

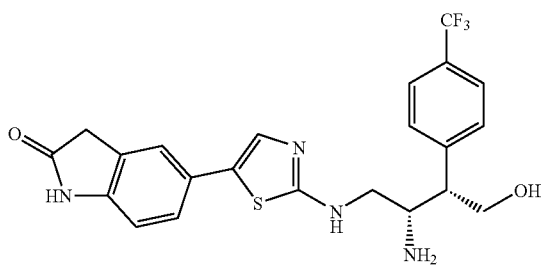

Scheme 36

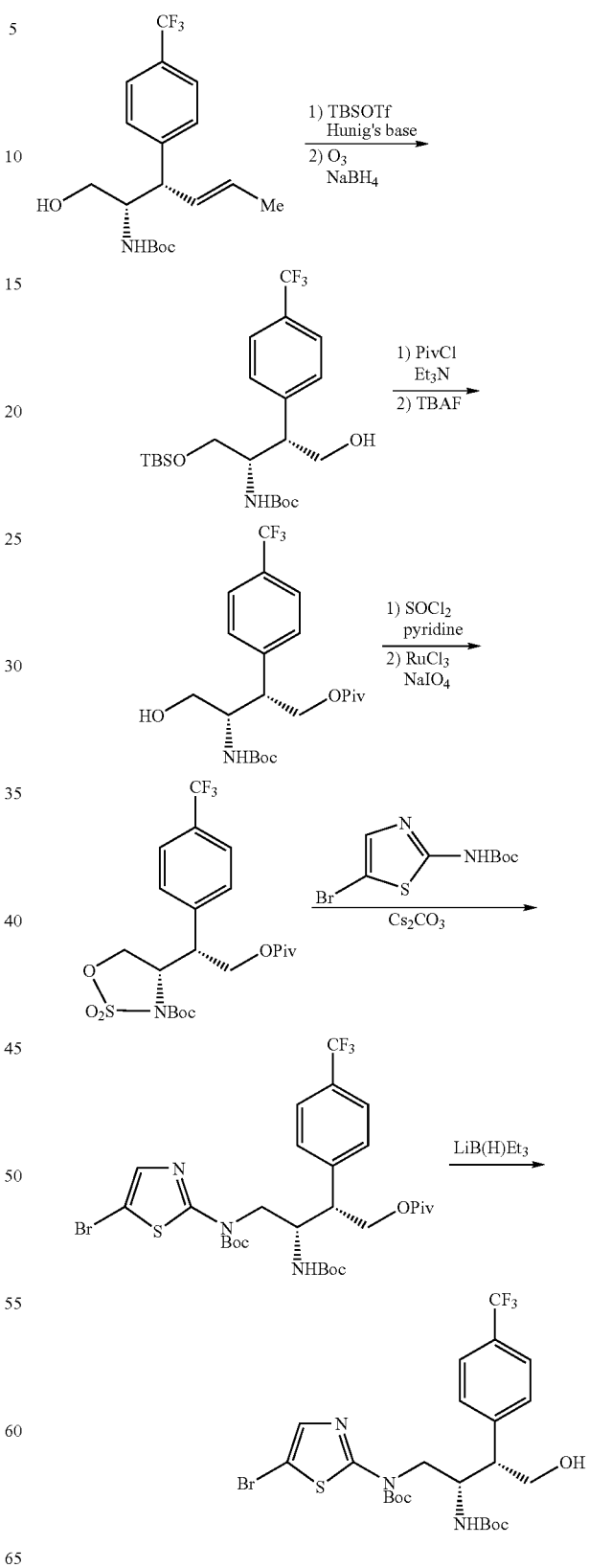

tert-Butyl (2S,3S)-1-(tert-butyldimethylsilyloxy)-4-hydroxy-3-(4-(trifluoromethyl)phenyl)butan-2-ylcarbamate Tert-butyl (2S,3S,E)-1-hydroxy-3-(4-(trifluoromethyl)phenyl)hex-4-en-2-ylcarbamate (1.94 g, 5.4 mmol) was taken up in 50 mL of DCM and chilled to 0° C. N,N-diisopropylethylamine (2.4 mL, 13 mmol) was added, followed by slow addition of tert-butyldimethylsilyl trifluoromethanesulfonate (TBSOTf) (1.5 mL, 6.5 mmol). After 45 minutes, an additional 0.20 mL of TBSOTf was added. After an addition 20 minutes, the reaction was quenched with 50 mL of aq NaHCO$_3$. The mixture was partitioned, and the aqueous portion was extracted twice with 50 mL of DCM. The combined organic extracts were dried over MgSO$_4$. Filtration and concentration under reduced pressure, followed by flash chromatography on silica gel (1% to 7.5% EtOAc/hexanes) afforded tert-butyl (2S,3S,E)-1-(tert-butyldimethylsilyloxy)-3-(4-(trifluoromethyl)phenyl)hex-4-en-2-ylcarbamate (2.0 g, 78% yield) as a clear oil. The oil crystallized on the bench top over 12 hours. $^1$H NMR (400 MHz, CDCl$_3$) δ ppm 7.54 (d, J=8.02 Hz, 2H) 7.35 (d, J=8.02 Hz, 2H) 5.61 (s, 1H) 5.59 (d, J=5.87 Hz, 1H) 4.62-4.60 (m, 1H) 3.97-3.92 (m, 1H) 3.79-3.76 (m, 1H) 3.66-3.59 (m, 2H) 1.69 (d, J=5.28 Hz, 3H) 1.26 (s, 9H) 0.92-0.97 (m, 9H) 0.06 (s, 6H).

Tert-butyl (2S,3S,E)-1-(tert-butyldimethylsilyloxy)-3-(4-(trifluoromethyl)phenyl)hex-4-en-2-ylcarbamate (2.0 g, 4.2 mmol) was dissolved in 40 mL of 1:1 MeOH/DCM, and the mixture was chilled to −78° C. Ozone was bubbled through the mixture until a blue color persisted. Nitrogen was then bubbled through the mixture for 15 minutes. NaBH$_4$ (0.80 g, 21 mmol) was added, and the mixture was warmed to room temperature. After 3 hours, the mixture was quenched with aq NH$_4$Cl. The mixture was extracted three times with 50 mL of DCM. The combined organic extracts were dried over MgSO$_4$. Filtration and concentration under reduced pressure afforded tert-butyl (2S,3S)-1-(tert-butyldimethylsilyloxy)-4-hydroxy-3-(4-(trifluoromethyl)phenyl)butan-2-ylcarbamate (1.9 g, 97% yield) as a white solid. $^1$H NMR (400 MHz, CDCl$_3$) δ ppm 7.56 (d, J=8.03 Hz, 2H) 7.32 (d, J=8.03 Hz, 2H) 4.51 (s, 1H) 4.22-4.16 (m, 1H) 3.90-3.66 (m, 3H) 3.47 (d, J=5.52 Hz, 2H) 3.15-3.20 (m, 1H) 1.45 (s, 9H) 0.84 (s, 9H) 0.01 (s, 3H) −0.01 (s, 3H).

(2S,3S)-3-(tert-butoxycarbonyl)-4-hydroxy-2-(4-(trifluoromethyl)phenyl)butyl pivalate Tert-butyl (2S,3S)-1-(tert-butyldimethylsilyloxy)-4-hydroxy-3-(4-(trifluoromethyl)phenyl)butan-2-ylcarbamate (1.9 g, 4.1 mmol) was taken up in 40 mL of DCM and chilled to 0° C. TEA (1.1 mL, 8.2 mmol), N,N-dimethylpyridin-4-amine (0.025 g, 0.20 mmol), and pivaloyl chloride (0.76 mL, 6.1 mmol) were added. The mixture was warmed to room temperature. After 12 hours, the reaction was quenched with 50 mL of aq NaHCO$_3$ and stirred for 10 minutes. The mixture was partitioned, and the aqueous portion was extracted twice with 50 mL of DCM. The combined organic extracts were washed with 50 mL of aq NaCHO$_3$ and 50 mL of aq NH$_4$Cl, and then dried over MgSO$_4$. Filtration and concentration under reduced pressure afforded a yellow oil that was carried on without any further purification.

(2S,3S)-3-(Tert-butoxycarbonyl)-4-(tert-butyldimethylsilyloxy)-2-(4-(trifluoromethyl)phenyl)butyl pivalate (2.2 g, 4.0 mmol) was taken up in 40 mL of THF and chilled to 0° C. TBAF, 1 M in THF (6.0 mL, 6.0 mmol) was added slowly. After 20 minutes, the mixture was warmed to room temperature and stirred for 1 hour. 0.5 mL of additional TBAF was added, and the mixture was stirred for 20 minutes. The mixture was quenched with 20 mL of aq NH$_4$Cl. The mixture was then diluted with 40 mL of water and extracted twice with 50 mL of EtOAc. The combined organic extracts were washed with 50 mL of brine and dried over MgSO$_4$. Filtration and concentration under reduced pressure, followed by flash chromatography on silica gel (5% to 40% EtOAc/hexanes) afforded (2S,3S)-3-(tert-butoxycarbonyl)-4-hydroxy-2-(4-(trifluoromethyl)phenyl)butyl pivalate (1.5 g, 86% yield) as a yellow solid. $^1$H NMR (400 MHz, CDCl$_3$) δ ppm 7.59 (d, J=8.22 Hz, 2H) 7.37 (d, J=8.02 Hz, 2H) 4.57 (d, J=6.4 Hz, 1H) 4.45-4.35 (m, 2H) 4.06 (s, 1H) 3.70 (s, 2H) 3.51-3,41 (m, 1H), 1.75 (broad s, 1H) 1.33 (s, 9H) 1.08 (s, 9H).

The cyclic sulfamidate

Thionyl chloride (0.63 mL, 8.7 mmol) was taken up in 30 mL of MeCN and chilled to −55° C. (2S,3S)-3-(Tert-butoxycarbonyl)-4-hydroxy-2-(4-(trifluoromethyl)phenyl)butyl pivalate (1.5 g, 3.5 mmol) was added slowly in 10 mL of MeCN. After 15 minutes, pyridine (1.4 mL, 17 mmol) was added, and the mixture was warmed to room temperature. The mixture was concentrated under reduced pressure. The residue was taken up in 100 mL of EtOAc and 100 mL of water. The mixture was partitioned, and the aqueous portion was extracted with 100 mL of EtOAc. The combined organic extracts were washed with 100 mL of brine and dried over MgSO$_4$. Filtration and concentration under reduced pressure, followed by flash chromatography on silica gel (2.5% to 20% EtOAc/hexanes) afforded the desired cyclic sulfamidite(1.1 g, 66% yield) as a white solid.

The cyclic sulfamidite (1.1 g, 2.3 mmol) was taken up in 18 mL of MeCN and 3 mL of EtOAc and chilled to 0° C. Sodium periodate (0.74 g, 3.4 mmol) was added in 6 mL of water, followed by ruthenium(III) chloride hydrate (0.0048 g, 0.023 mmol). The mixture was warmed to room temperature. After 1.5 hours, the solvent was removed under reduced pressure. The residue was taken in 20 mL of EtOAc and 20 mL of water. The aqueous portion was extracted twice with 20 mL of EtOAc, and the combined organic extracts were washed with 30 mL of brine. Filtration and concentration under reduced pressure afforded the desired cyclic sulfamidate (1.1 g, 97% yield) as a white solid. $^1$H NMR (400 MHz, CDCl$_3$) δ ppm 7.61 (d, J=8.03 Hz, 2H) 7.44 (d, J=8.03 Hz, 2H) 4.59-4.68 (m, 4H) 4.45 (dd, J=11.80, 5.27 Hz, 1H) 3.65 (d, J=5.52 Hz, 1H) 1.39 (s, 9H) 1.11-1.14 (m, 9H).

(2S,3S)-3-(Boc)amino-4-(5-bromothiazol-2-yl(Boc)amino)-2-(4-(trifluoromethyl)phenyl)butyl pivalate Tert-butyl 5-bromothiazol-2-ylcarbamate (0.59 g, 2.1 mmol) was taken up in 15 mL of DMF and heated to 50° C. Cs$_2$CO$_3$ (1.4 g, 4.2 mmol) was added, followed by the slow addition of cyclic sulfamidate (1.1 g, 2.2 mmol) in 10 mL of DMF After 1.5 hours, the solvent was removed under reduced pressure. The residue was taken up in 20 mL of EtOAc and 20 mL of 10% aq. HCl was then slowly added. The mixture was stirred for 20 minutes. The mixture was partitioned, and the aqueous portion was extracted twice with 20 mL of EtOAc. The combined organic extracts were washed with 20 mL of brine and dried over MgOS$_4$. Filtration and concentration under reduced pressure, followed by flash chromatography on silica gel (2.5% to 25% EtOAc/hexanes) afforded (2S,3S)-3-(Boc)amino-4-(5-bromothiazol-2-yl(Boc)amino)-2-(4-(trifluoromethyl)phenyl)butyl pivalate (1.2 g, 82% yield) as a white solid.

(2S,3S)-3-(Boc)amino-4-(5-bromothiazol-2-yl(Boc) amino)-2-(4-(trifluoromethyl)phenyl)butan-1-ol (2S,3S)-3-(Boc)amino-4-(5-bromothiazol-2-yl(Boc) amino)-2-(4-(trifluoromethyl)phenyl)butyl pivalate (0.66 g, 0.95 mmol) was taken up in 10 mL of THF and chilled to −78° C. Super hydride, 1M in THF (2.4 mL, 2.4 mmol) was added. The mixture was stirred for 5 minutes and then warmed to 0° C. The mixture was stirred for 15 minutes and then quenched with 5 mL of EtOAc. The mixture was diluted with 10 mL of aqueous NH$_4$Cl and partitioned in a separatory funnel. The aqueous portion was extracted twice with 20 mL of EtOAc, and the combined organic layers were washed with 10 mL of brine and dried over MgSO$_4$. Filtration and concentration under reduced pressure, followed by flash chromatography on silica gel (5% to 25% EtOAc/hexanes) afforded (2S,3S)-3-(Boc)amino-4-(5-bromothiazol-2-yl(Boc)amino)-2-(4-(trifluoromethyl)phenyl)butan-1-ol (0.51 g, 88% yield) 82646-5-1 as a white solid. $^1$H NMR (400 MHz, CDCl$_3$) δ ppm 7.61 (d, J=8.02 Hz, 2H) 7.35 (d, J=8.02 Hz, 2H) 5.16-5.02 (m, 1H) 4.60-4.51 (m, 1H), 4.33-4.20 (m 1H) 4.09-3.96 (m, 1H), 3.91-3.65 (m, 2H) 3.15-3.05 (m, 1H) 1.52 (s, 9H) 1.37 (s, 9H).

Example 159

(2S,3S)-3-amino-4-(5-(isoquinolin-6-yl)thiazol-2-ylamino)-2-(4-(trifluoromethyl)phenyl)butan-1-ol The title compound was synthesized in a manner similar to that described for Example 158. HRMS calc'd (M+1) 459.14609, found 463.16345. $^1$H NMR (400 MHz, CD$_3$OD) δ ppm 9.13 (s, 1H) 8.39 (d, J=5.52 Hz, 1H) 8.04 (d, J=8.53 Hz, 1H) 7.88 (d, J=8.53 Hz, 1H) 7.81 (s, 1H) 7.76 (d, J=6.02 Hz, 1H) 7.64-7.69 (m, 3H) 7.55 (d, J=8.03 Hz, 2H) 3.94-4.06 (m, 2H) 3.51-3.61 (m, 2H) 3.36 (s, 2H) 3.27 (dd, J=13.05, 7.03 Hz, 1H) 3.06 (q, J=6.19 Hz, 1H).

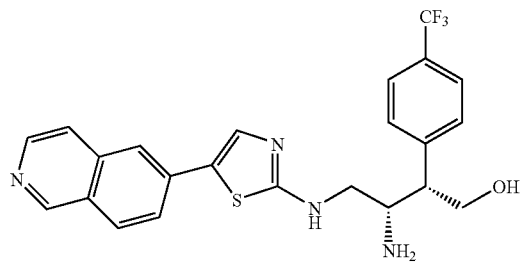

Example 160

6-(2-((2S,3S)-2-amino-4-hydroxy-3-(4-(trifluoromethyl)phenyl)butylamino)thiazol-5-yl)benzo[d]oxazol-2(3H)-one The title compound was synthesized in a manner similar to that described for Example 158. MS m/z: 465 (M+1). $^1$H NMR (400 MHz, CD$_3$OD) δ ppm 7.64-7.71 (m, 2H) 7.56 (d, J=8.02 Hz, 2H) 7.34 (d, J=1.37 Hz, 1H) 7.29 (s, 1H) 7.23 (dd, J=8.12, 1.66 Hz, 1H) 7.04-7.08 (m, 1H) 3.94-4.13 (m, 2H) 3.50-3.66 (m, 2H) 3.20-3.29 (m, 1H) 3.07 (q, J=6.26 Hz, 1H).

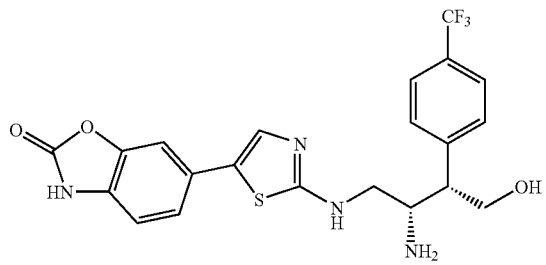

Examples 161-164

Examples 161-164 were synthesized in a manner similar to that described for Example 82 using 3,5-difluoro-1-phenylalanine purchased from PepTech as the starting material.

Example 161

N-((S)-2-amino-3-(3,5-difluorophenyl)propyl)-5-(isoquinolin-6-yl)thiazol-2-amine Theoretical (M+H) 397.2, found 397.3.

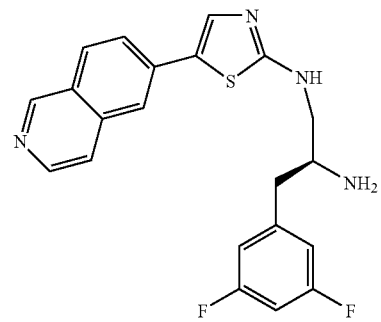

Example 162

6-(2-((S)-2-amino-3-(3,5-difluorophenyl)propylamino)thiazol-5-yl)-1-methyl-1H-benzo[d]imidazol-2(3H)one Theoretical (M+H) 398.1, found 398.1.

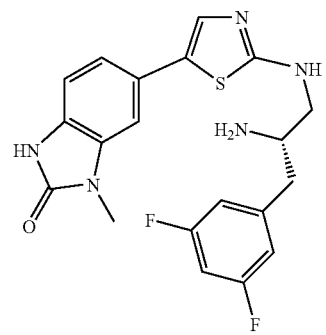

Example 163

5-(2-((S)-2-amino-3-(3,5-difluorophenyl)propy-lamino)thiazol-5-yl)indolin-2-one

Theoretical (M+H) 383.1, found 383.1.

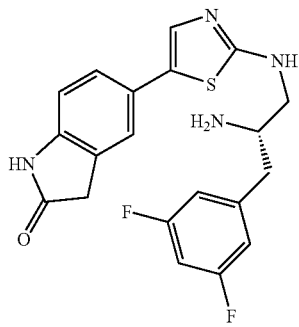

Example 164

6-(2-((S)2-amino-3-(3,5-difluorophenyl)propy-lamino)thiazol-5-yl)benzo[d]oxazol-2(3H)one Theoretical (M+H) 385.1, found 385.1.

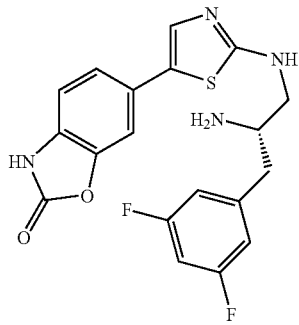

Example 165

N-((S)-2-amino-3-(4-chlorophenyl)propyl-5-(iso-quinolin-6-yl)-4-(trifluoromethyl)thiazol-2-amine The title compound was synthesized in a manner similar to that described for Example 82 using Boc protected 4-chloro-5-(isoquinolin-6-yl)thiazol-2-amine which was reacted with the cyclic sulfamidate. 4-chloro-5-(isoquinolin-6-yl)thiazol-2-amine was synthesized as shown in Scheme 37. Theoretical (M+H) 463.1, found 463.1.

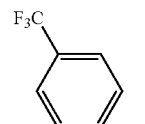

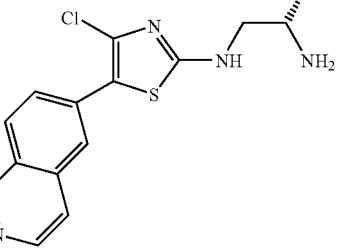

Scheme 37

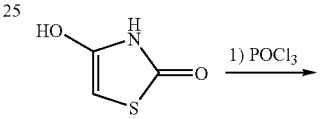

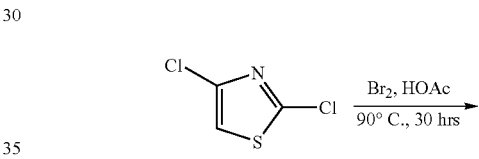

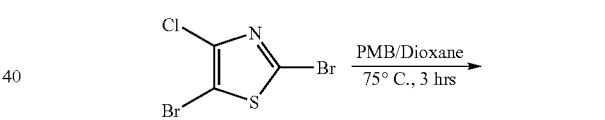

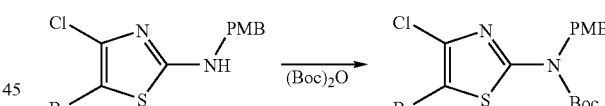

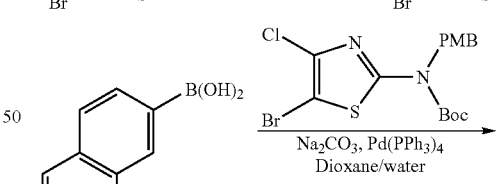

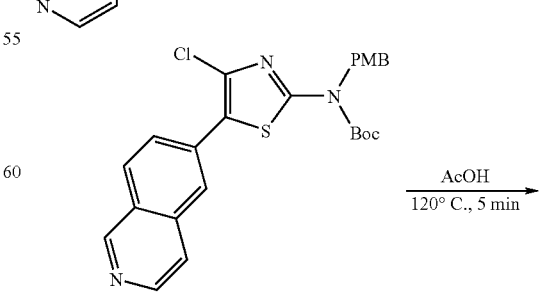

-continued

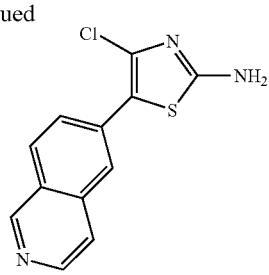

2,4-dichlorothiazole

To a 250 mL round-bottomed flask was added 2,4-thiazolidinedione (14.0 g, 120 mmol), phosphorous oxychloride (74.6 mL, 800 mmol), and anhydrous pyridine (9.33 mL, 114 mmol). The dark orange solution was stirred at reflux for 3 hours. After cooling, the mixture was concentrated and poured into ice water and extracted with diethyl ether. The combined organic layers were washed with 1N NaOH (2×100 mL), saturated sodium chloride, and concentrated. The crude solid was recrystallized with a solution (1:1) of EtOH/water to give 2,4-dichlorothiazole (12.5 g, 68% yield), m/z (%): 155.2 (100%, M$^+$+H).

2,5-Dibromo-4-chlorothiazole

To a 100 mL round-bottomed flask was added 2,4-dichlorothiazole (6.56 g, 43 mmol), and glacial AcOH (10.0 mL, 173 mmol). The resulting solution was treated slowly dropwise via addition funnel with Br$_2$ (3.2 mL, 62 mmol) over 5 minutes. The mixture was stirred at 90° C. for 3 hours. After cooling, the mixture was basified with solid Na$_2$CO$_3$, first, then 5% Na$_2$CO$_3$ (aq). The overall mixture was extracted with ether (3×100 mL), and the combined organic layers were washed with 5% Na$_2$CO$_3$, dried, and concentrated to give 2,5-dibromo-4-chlorothiazole (9.5 g, 80% yield), m/z (%): 278.1 (100%, M$^+$+H).

N-(4-methoxybenzyl)-5-bromo-4-chlorothiazol-2-amine

To a 250 mL round-bottomed flask was added 2,5-dibromo-4-chlorothiazole (5.9 g, 21 mmol), p-dioxane (50 mL, 587 mmol), and 4-methoxybenzylamine (3 mL, 21 mmol). The solution was stirred at 75° C. for 4 hours. The reaction was cooled to room temperature, and the solvent was removed. The residue was dissolved in EtOAc and washed with saturated NaHCO$_3$ (1×25 mL), saturated sodium chloride (1×25 mL), water (1×25 mL), and dried over Na$_2$SO$_4$, filtered and concentrated in vacuum. The crude product was adsorbed onto a plug of silica gel and chromatographed through a Redi-Sep® pre-packed silica gel column (40 g), eluting with a gradient (5%→50% EtOAc in hexane) to provide N-(4-methoxybenzyl)-5-bromo-4-chlorothiazol-2-amine (5.5 g, 80% yield), m/z (%): 334.1 (100%, M$^+$+H).

tert-butyl-4-methoxybenzyl(4-chloro-5-(isoquinolin-6-yl)thiazol-2-yl)carbamate

To a microwave tube was added isoquinolin-6-ylboronic acid (0.21 g, 1.2 mmol), anhydrous sodium carbonate (0.13 mL, 3.0 mmol), tert-butyl-4-methoxybenzyl(4-chloro-5-(isoquinolin-6-yl)thiazol-2-yl)carbamate (0.200 g, 0.60 mmol), p-dioxane (10 mL, 117 mmol), and water (2.5 mL, 0.60 mmol). The suspension was stirred and purged with nitrogen for 10 minutes and tetrakis(triphenylphosphine)palladium (0) (0.035 g, 0.030 mmol) was added. The suspension was stirred at 90° C. over night. The reaction mixture was filtered through Celite and concentrated. The reaction mixture was diluted with saturated NaHCO$_3$ (50 mL) and extracted with EtOAc (3×50mL). The organic extract was washed with saturated sodium chloride and water, dried over Na$_2$SO$_4$, filtered, and concentrated in vacuo. The crude product was adsorbed onto a plug of silica gel and chromatographed through a Redi-Sep® pre-packed silica gel column (12 g), eluting with a gradient (5%→50% EtOAc in hexane), to provide tert-butyl 4-methoxybenzyl(4-chloro-5-(isoquinolin-6-yl)thiazol-2-yl)carbamate (0.110 g, 48% yield), m/z (%): 482.1 (100%, M$^+$+H).

4-Chloro-5-(isoquinolin-6-yl)thiazol-2-amine

A glass microwave reaction vessel was charged with tert-butyl 4-methoxybenzyl(4-chloro-5-(isoquinolin-6-yl)thiazol-2-yl)carbamate(1.5 g, 3.12 mmol) and AcOH. The reaction mixture was stirred and heated in a Smith Synthesizer® microwave reactor (Personal Chemistry, Inc.,) at 120° C. for 5 minutes. Excess AcOH was removed under high vacuum. The residue was dissolved in DCM and washed with saturated NaHCO$_3$ (50 mL) and saturated sodium chloride. This intermediate was synthesized in the same manner as described previously and water dried over Na$_2$SO$_4$, filtered and concentrated in vacuo to provide 4-chloro-5-(isoquinolin-6-yl)thiazol-2-amine (0.7 g, 81% yield), m/z (%): 263.2 (100%, M$^+$+H).

Examples 166-167

Examples 166-167 were synthesized in an analogous manner as example 36 via a coupling reaction between the corresponding bromothiazole intermediate and the boronic acid or esters.

Example 166

4-(2-((S)-2-amino-3-(4-(trifluoromethyl)phenyl)propylamino)thiazol-5-yl)-2-fluorobenzonitrile Theoretical (M+H) 421.1, found 421.1.

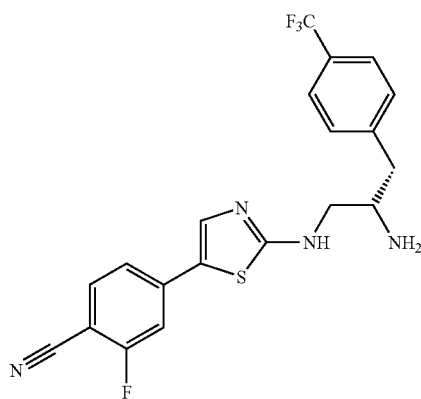

Example 167

N-((S)-2-amino-3-(4-(trifluoromethyl)phenyl)propyl)-5-(1-methyl-1H-indazol-6-yl)thiazol-2-amine Theoretical (M+H) 432.4, found 432.

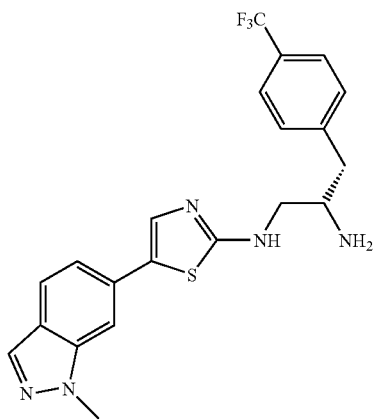

Example 168

N-((S)-2-amino-3-(4-chlorophenyl)propyl-5-(isoquinolin-6-yl)-4-(trifluoromethyl)thiazol-2-amine The title compound was synthesized in a manner similar manner to that described for Example 165 using 5-bromo-4-(trifluoromethyl)thiazol-2-amine as the starting material which was synthesized by treating 4-(trifluoromethyl)thiazol-2-amine with N-bromosuccinimide. Theoretical (M+H) 463.1 found 463.1.

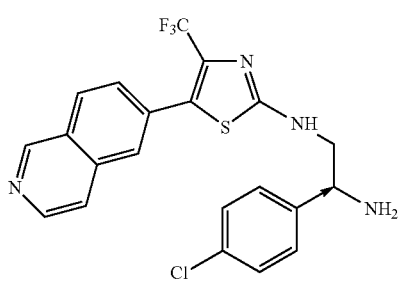

\5-Bromo-4-(trifluoromethyl)thiazol-2-amine

To a 250 mL round-bottomed flask were added 4-(trifluoromethyl)thiazol-2-amine (6 g, 36 mmol), ACN (90 mL, 1723 mmol), and N-bromosuccinimide (4 mL, 43 mmol). The solution was stirred at 60° C. for 3 hours. The reaction was cooled, and the solvent was removed in vacuo. The crude product was adsorbed onto a plug of silica gel and chromatographed through a Redi-Sep® pre-packed silica gel column (40 g), eluting with a gradient of (5%→50% EtOAc in hexane) to provide 5-bromo-4-(trifluoromethyl)thiazol-2-amine (8.1 g, 90% yield), m/z (%): 248.2 (100%, M⁺+H).

Example 169

N-((S)-2-amino-3-(4-trifluoromethyl)phenyl)propyl)-4-cyclopropyl-5-(isoquinolin-6-yl)thiazol-2-amine The title compound was synthesized in a manner similar to that described for Example 81 using tert-butyl 5-bromo-4-cyclopropylthiazol-2-ylcarbamate as the intermediate which was prepared as shown in Scheme 38. Theoretical (M+H) 468.1 found 468.1.

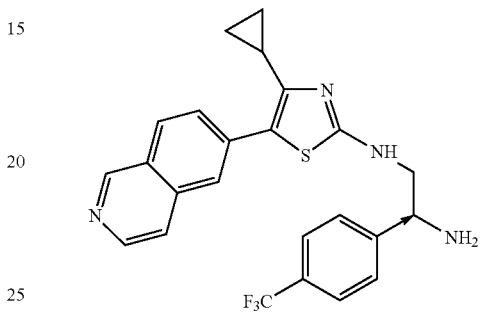

Scheme 38

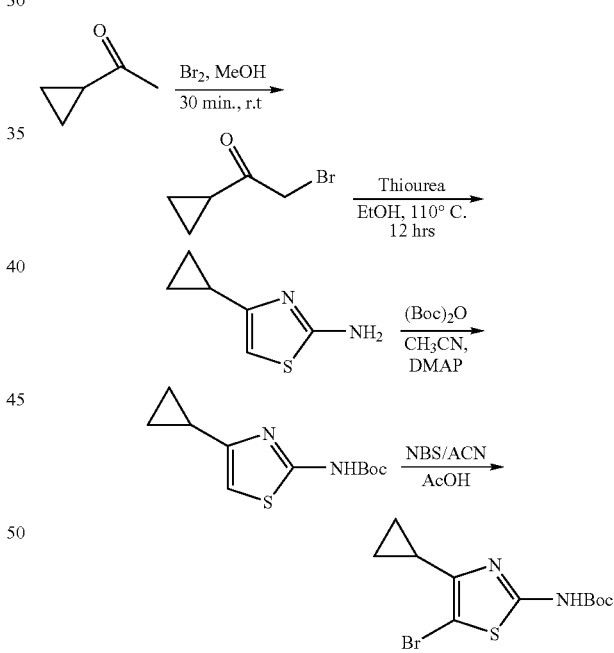

2-Bromo-1-cyclopropylethanone

To a 150 mL round-bottomed flask was added cyclopropyl methyl ketone (12 mL, 119 mmol) and MeOH (60 mL, 1482 mmol). The solution was stirred at 0° C. and treated drop wise with $Br_2$ (6.1 mL, 119 mmol). The resulting solution was stirred at 0° C. for 30 minutes. The suspension was diluted with water and extracted with ether (3×100 mL). The organics layers were washed with 10% $Na_2CO_3$ (1×50 mL), saturated sodium chloride (1×50 mL), water (1×50 mL), dried over Na₂SO₄, filtered, and concentrated in vacuo to give 2-bromo-1-cyclopropylethanone (16.7 g, 86% yield) m/z (%): 164.2 (100%, M⁺+H).

4-Cyclopropylthiazol-2-amine

To a 100 mL round-bottomed flask was added 2-bromo-1-cyclopropylethanone (7.9 g, 48 mmol), EtOH (70 mL, 1202 mmol), and thiourea (2.6 mL, 48 mmol). The solution was stirred at reflux for 6 hours. The reaction solution was cooled and concentrated under reduced pressure. The reaction mixture was diluted with water (200 mL), neutralized with NaHCO₃, and extracted with EtOAc (3×100 mL). The organic extract was washed with saturated sodium chloride (1×100 mL), water (1×100 mL), dried over Na₂SO₄, filtered and concentrated in vacuo to give 4-cyclopropylthiazol-2-amine. The crude product was adsorbed onto a plug of silica gel and chromatographed through a Redi-Sep® pre-packed silica gel column (40 g), eluting with a gradient (5%→50% n 2 M NH₃.MeOH in DCM), to provide 4-cyclopropylthiazol-2-amine (3.2 g, 48% yield), m/z (%): 141.3 (100%, M⁺+H).

tert-buty-4-cyclopropylthiazol-2-ylcarbamate

This intermediate was synthesized by treating 4-cyclopropylthiazol-2-amine with Boc₂O and a small amount of DMAP in ACN.

tert-butyl 5-bromo-4-cyclopropylthiazol-2-ylcarbamate

To a 250 mL round-bottomed flask was added tert-butyl 4-cyclopropylthiazol-2-ylcarbamate (9.5 g, 40 mmol), ACN 100% (100 mL, 1914 mmol), and glacial AcOH (6.8 mL, 119 mmol). The solution was stirred at 0° C. and treated in portions with N-bromosuccinimide (3.4 mL, 40 mmol). The suspension was stirred for 1 hour, diluted with NaHCO₃, and extracted with EtOAc. The organics were washed with saturated sodium chloride (1×50 mL) and water (1×50 mL), dried over Na₂SO₄, filtered, and concentrated in vacuo to give tert-butyl 5-bromo-4-cyclopropylthiazol-2-ylcarbamate (11 g, 86% yield), m/z (%): 320.3 (100%, M⁺+H).

Example 170

N-((S)-2-amino-3-(6-trifluoromethyl)pyridine-3-yl)propyl)-5-(isoquinolin-6-yl)thiazol-2-amine The title compound was synthesized in a manner similar to that described for Example 81 using (S)-tert-butyl 1-(5-bromothiazol-2-yl-(Boc)-amino)-3-(6-(trifluoromethyl)pyridin-3-yl)propan-2-ylcarbamate to couple with the boronic acid. (S)-tert-butyl 1-(5-bromothiazol-2-yl-(Boc)-amino)-3-(6-(trifluoromethyl)pyridin-3-yl)propan-2-ylcarbamate was synthesized as shown in Scheme 39. Theoretical (M+H) 430.4 found 430.4.

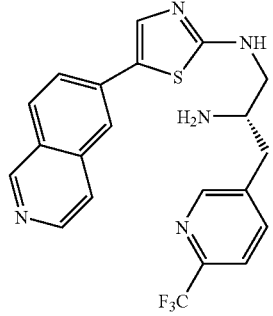

Scheme 39

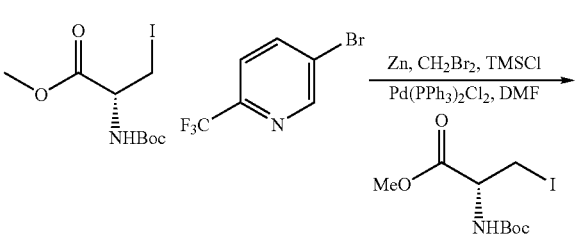

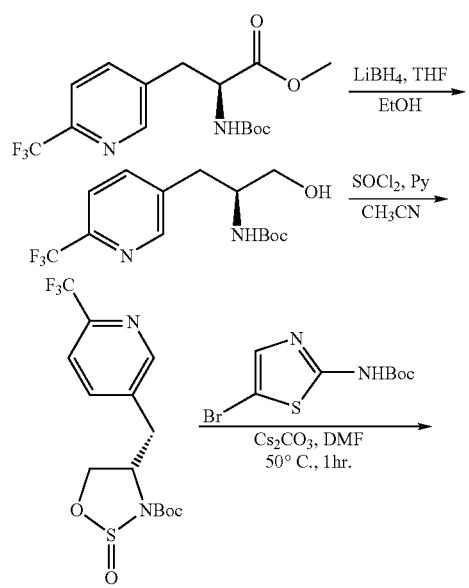

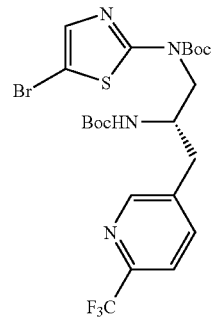

(R)-methyl 2-(tert-butoxycarbonyl)-3-(6-(trifluoromethyl)pyridin-3-yl)propanoate To a 250 mL round-bottomed flask was added zinc, nano-size activated powder (0.75 mL, 82 mmol), and DMF (14 mL, 177 mmol). The mixture was stirred and treated dropwise with 1,2-dibromoethane (0.35 mL, 4.1 mmol). The mixture was stirred at 90° C. for 30 minutes. After cooling, chlorotrimethylsilane (0.10 mL, 0.82 mmol) was added, and the mixture was stirred at room temperature for 30 minutes. To this stirred mixture, Boc-3-iodo-1-alanine methyl ester (4.5 g, 14 mmol) in 10 mL DMF was added dropwise via an addition funnel. After the addition, the combined mixture was stirred at room temperature for 4 hours. To this mixture was then added dichlorobis(triphenylphosphine)palladium(0) (0.48 g, 0.68 mmol) and a 10 mL DMF solution of 5-bromo-2-(trifluoromethyl)pyridine(4.0 g, 18 mmol). The resulting mixture was stirred at 25° C. overnight. The reaction mixture was filtered through Celite, diluted with $NH_4Cl$ and water (70 mL each), and diluted with EtOAc (200 mL). The aqueous layer was extracted with EtOAc (2×100 mL), saturated sodium chloride (1×50 mL), and water (1×50 mL), dried over $Na_2SO_4$, filtered, and concentrated in vacuo. The remaining residue was adsorbed onto a plug of silica gel and chromatographed through a Redi-Sep® pre-packed silica gel column (40 g), eluting with a gradient (5%→50% EtOAc in hexane) to provide (R)-methyl 2-(tert-butoxycarbonyl)-3-(6-(trifluoromethyl)pyridin-3-yl)propanoate (4.389 g, 93% yield) m/z (%): 349.3 (100%, $M^++H$).

(R)-tert-butyl 1-hydroxy-3-(6-(trifluoromethyl)pyridin-3-yl)propan-2-ylcarbamate This intermediate was synthesized as previously described by treating the amino ester with lithium borohydride in THF.

(S)-3-(tert-Butyloxycarbonyl)-4-((6-(trifluoromethyl)pyridin)[1,2,3]-oxathiazolidine-2-oxide To a 150 mL round-bottomed flask was added thionyl chloride ($SOCl_2$) (1.1 mL, 15 mmol), and ACN 100% (300 mL, 5742 mmol). The solution was stirred at −78° C. and treated dropwise via addition funnel with (R)-tert-butyl 1-hydroxy-3-(6-(trifluoromethyl)pyridin-3-yl)propan-2-ylcarbamate (1.9 g, 5.9 mmol) in 10 mL $CH_3CN$. The mixture was stirred at −78° C. for 30 minutes and treated in one portion with anhydrous pyridine (2.4 mL, 30 mmol). The suspension was warmed to room temperature and stirred overnight. The solution was concentrated under reduced pressure. The reaction mixture was diluted with water and EtOAc 1:1 (200 mL) and extracted with EtOAc (3×50 mL). The organic extract was washed with saturated sodium chloride (1×50 mL) and water (1×50 mL), dried over $Na_2SO_4$, filtered, and concentrated in vacuo. The crude product was adsorbed onto a plug of silica gel and chromatographed through a Redi-Sep® pre-packed silica gel column (40 g), eluting with gradient (5%→50% EtOAc in hexane) to provide (S)-3-(tert-butyloxycarbonyl)-4-((6-(trifluoromethyl)pyridin)[1,2,3]-oxathiazolidine-2-oxide (1.5 g, 69% yield) m/z (%): 367.3 (100%, $M^++H$).

(S)-tert-butyl 1-(5-bromothiazol-2-yl-(Boc)-amino)-3-(6-(trifluoromethyl)pyridin-3-yl)propan-2-ylcarbamate To a 100 mL round-bottomed flask was added tert-butyl 5-bromothiazol-2-ylcarbamate (1.5 g, 5.4 mmol), $Cs_2CO_3$ (3.5 g, 11 mmol), DMF (0.41 mL, 5.4 mmol). The mixture was stirred at 50° C. and treated dropwise via syringe with (S)-3-(tert-butyloxycarbonyl)-4-((6-(trifluoromethyl)pyridin)[1,2,3]-oxathiazolidine-2-oxide (2.4 g, 6.4 mmol) in DMF (1 mL). The mixture was then stirred at 50° C. for 1 hour. The mixture was diluted with ether and washed with brine, dried over $Na_2SO_4$, filtered, and concentrated in vacuo. The crude product was adsorbed onto a plug of silica gel and chromatographed through a Redi-Sep® pre-packed silica gel column (40 g), eluting with gradient (5%→50% EtOAc in hexane), to provide (S)-tert-butyl 1-(5-bromothiazol-2-yl-(Boc)-amino)-3-(6-(trifluoromethyl)pyridin-3-yl)propan-2-ylcarbamate (1.35 g, 43% yield) m/z (%): 582.2 (100%, $M^++H$).

Examples 171-172

Examples 171-172 were synthesized in an analogous manner Example 170.

Example 171

5-(2-((S)-2-amino-3-(6-(trifluoromethyl)pyridine-3-yl)propylamino)thiazol-5-yl)indolin-2-one Theoretical (M+H) 434.4, found 434.4.

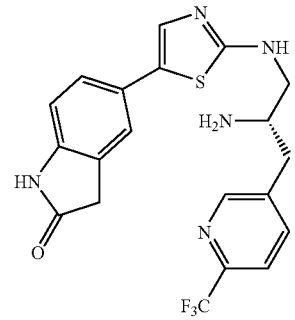

Example 172

6-(2-((S)-2-amino-3-(6-(trifluoromethyl)pyridine-3-yl)propylamino)thiazol-5-yl)benzo[d]oxazol-2(3H)-one Theoretical (M+H) 436.4, found 436.4.

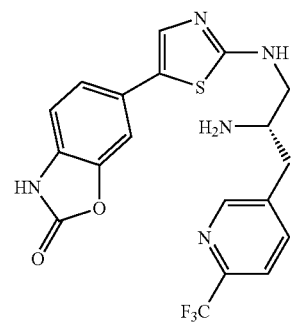

Example 173

N-((S)-2-amino-3-(5-methoxy-6-trifluoromethyl)pyridin-3-yl)propyl)-5-(isoquinolin-6-yl)thiazol-2-amine The title compound was synthesized in a manner similar to that described in Example 170 using the amino acid (S)-methyl 2-(tert-butoxycarbonyl)-3-(5-methoxy-6-(trifluoromethyl)pyridin-3-yl)propanoate as a key intermediate which was prepared as shown in Scheme 40. Theoretical (M+H) 460.1, found 460.1.

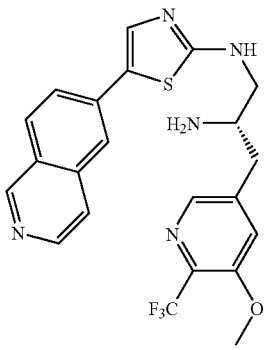

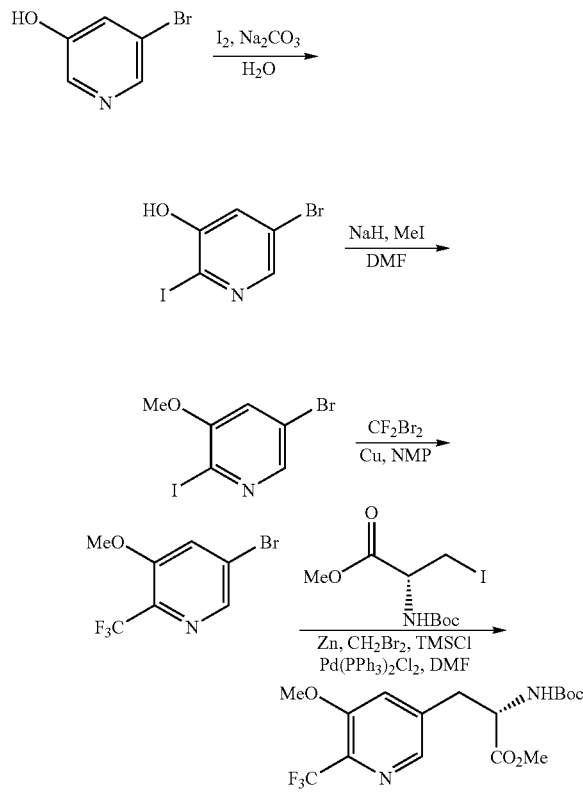

5-Bromo-2-iodopyridin-3-ol

To a mixture of sodium carbonate monohydrate (1.96 mL, 35.5 mmol) and 3-bromo-5-hydroxypyridine (2.06 g, 11.8 mmol) in H$_2$O (0.213 mL, 11.8 mmol) was added iodine crystals (0.640 mL, 12.4 mmol), and the overall mixture was stirred at room temperature overnight. The mixture was then poured slowly into 2M HCl(aq), and the pH was adjusted to ~3. The product was collected by filtration followed by crystallization from EtOH/water to afford 5-bromo-2-iodopyridin-3-ol as an off-white solid of (3.53 g, 99.4% yield) m/z (%): 301.2 (100%, M$^+$+H).

5-Bromo-2-iodo-3-methoxypyridine

To a stirred solution of 5-bromo-2-iodopyridin-3-ol (2.17 g, 7.2 mmol) in DMF (10.00 mL, 129 mmol) was added NaH (0.32 g, 8.0 mmol) at 0° C. The resulting mixture was stirred at 0° C. and MeI was added at 0° C. The resulting mixture was stirred at room temperature for 2 hours. The reaction mixture was diluted with NH$_4$Cl(aq) and water (10 mL each) at 0° C., and diluted with EtOAc (15 mL). The separated aqueous layer was extracted with EtOAc (2×15 mL) and the combined organic layers were washed with water and saturated sodium chloride, dried over Na$_2$SO$_4$, and concentrated to give the crude residue which was purified with flash column chromatography ((5%→50% EtOAc in hexane) to obtain 5-bromo-2-iodo-3-methoxypyridine as an off-white solid (1.77 g, 78% yield) m/z (%): 314.2 (100%, M$^+$+H).

5-Bromo-3-methoxy-2-(trifluoromethyl)pyridine

To a sealable vessel was added dibromodifluoromethane (1.9 g, 8.9 mmol), 5-bromo-2-iodo-3-methoxypyridine (0.56 g, 1.8 mmol), copper (1.1 g, 18 mmol), and NMP (2 mL). The overall mixture was sealed and heated at 100° C. overnight. After cooling, the overall mixture was passed through a short path of Celite, and the filtrate cake was washed with EtOAc (3×10 mL). The combined organic phases were washed with water and saturated sodium chloride, and then concentrated to give the crude residue. Flash column chromatography purification (short column, SiO$_2$, pure hexanes→30% EtOAc in hexanes) provided 5-bromo-3-methoxy-2-(trifluoromethyl)pyridine (0.35 g, 77% yield) as a pale yellow oil of m/z (%): 257.3 (100%, M$^+$+H).

(S)-Methyl 2-(tert-butoxycarbonyl)-3-(5-methoxy-6-(trifluoromethyl)pyridin-3-yl)propanoate This intermediate was synthesized in a similar manner to that described in Scheme 39 for Example 170.

Examples 174-175

Examples 174-175 were synthesized in an analogous manner to that described for Example 173.

Example 174

5-(2-((S)-2-amino-3-(5-methoxy-6-(trifluoromethyl)pyridin-3-yl)propylamino)thiazol-5-yl)indolin-2-one Theoretical (M+H) 464.1, found 464.1.

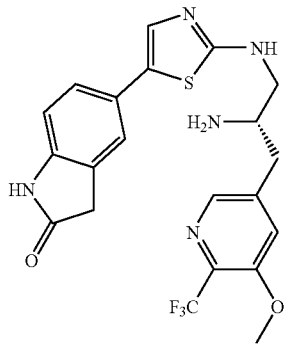

Example 175

6-(2-((S)-2-amino-3-(5-methoxy-6-(trifluoromethyl)pyridin-3-yl)propylamino)thiazol-5-yl)-1-methyl-1H-benzo[d]imidazol-2(3H)-one Theoretical (M+H) 479.1, found 479.1.

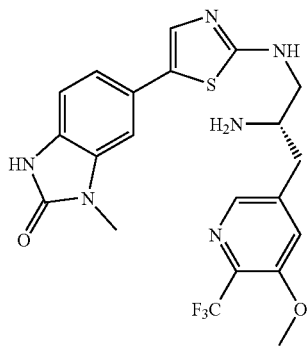

Examples 176-189

Examples 176-189 were synthesized in a manner similar to that described for Example 129. The optically pure compounds were separated from the racemic mixture by a chiral preparative HPLC procedure.

Example 176

5-(2-(-2-amino-3-(2-fluoro-4-(trifluoromethyl)phenyl)propylamino)thiazol-5-yl)indolin-2-one: LCMS (M+H) 451 for $C_{21}H_{18}F_4N_4OS$ 450.45.

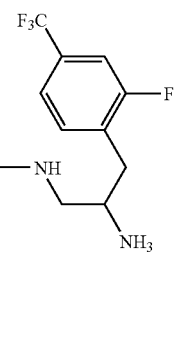

Example 177

N-(-2-amino-3-(2-fluoro-4-(trifluoromethyl)phenyl)propyl)-5-(isoquinolin-6-yl)thiazol-2-amine LCMS (M+H) 447 for $C_{22}H_{18}F_4N_4S$ 446.46.

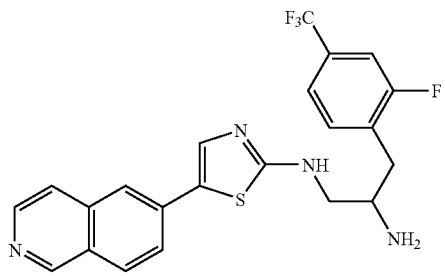

Example 178

6-(2-(-2-amino-3-(2-fluoro-4-(trifluoromethyl)phenyl)propylamino)thiazol-5-yl)benzo[d]oxazol-2(3H)-one LCMS (M+H) 453 for $C_{20}H_{16}F_4N_4O_2S$ 452.43.

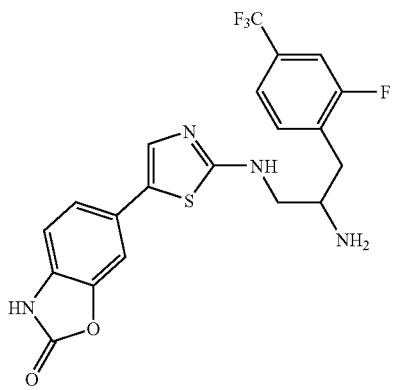

Example 179

5-(2-(-2-amino-3-(3-fluoro-4-(trifluoromethyl)phenyl)propylamino)thiazol-5-yl)indolin-2-one LCMS (M+H) 451 for $C_{21}H_{18}F_4N_4OS$ 450.45.

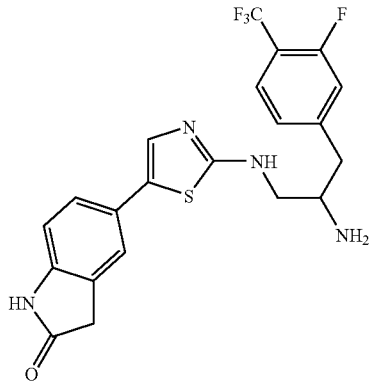

Example 180

N-((S)-2-amino-3-(3-fluoro-4-(trifluoromethyl)phenyl)propyl)-5-(isoquinolin-6-yl)thiazol-2-amine LCMS (M+H) 447 $C_{22}H_{18}F_4N_4S$ for 446.46.

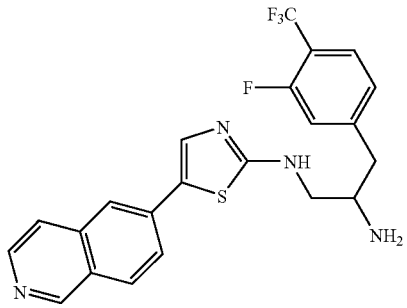

Example 181

6-(2-(2-amino-3-(3-fluoro-4-(trifluoromethyl)phenyl)propylamino)thiazol-5-yl)benzo[d]oxazol-2(3H)-one LCMS (M+H) 453 $C_{20}H_{16}F_4N_4O_2S$ Mol. Wt.: 452.43.

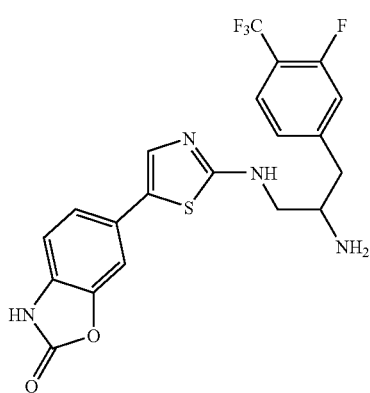

Example 182

6-(2-((R)-2-amino-3-(3-fluoro-4-(trifluoromethyl)phenyl)propylamino)thiazol-5-yl)benzo[d]oxazol-2(3H)-one

LCMS (M+H) 453 $C_{20}H_{16}F_4N_4O_2S$ 452.43.

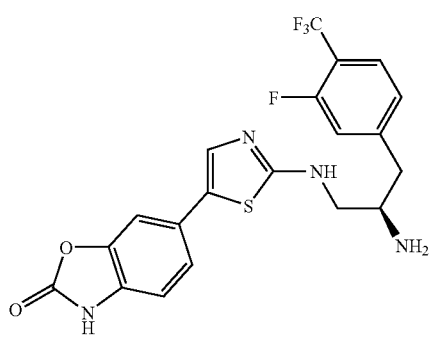

Example 183

6-(2-((S)-2-amino-3-(3-fluoro-4-(trifluoromethyl)phenyl)propylamino)thiazol-5-yl)benzo[d]oxazol-2(3H)-one LCMS (M+H) 453 for $C_{20}H_{16}F_4N_4O_2S$ 452.43.

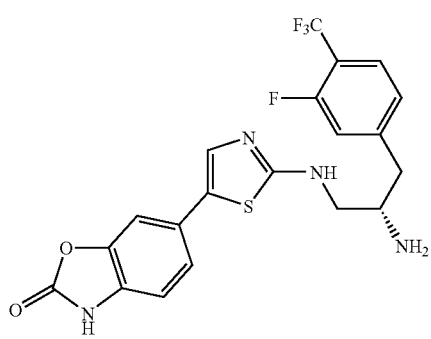

Example 184

6-(2-((S)-2-amino-3-(3-fluoro-4-(trifluoromethyl)phenyl)propylamino)thiazol-5-yl)-1-methyl-1H-benzo[d]imidazol-2(3H)-one LCMS (M+H) 466 for $C_{21}H_{19}F_4N_4OS$ 465.47.

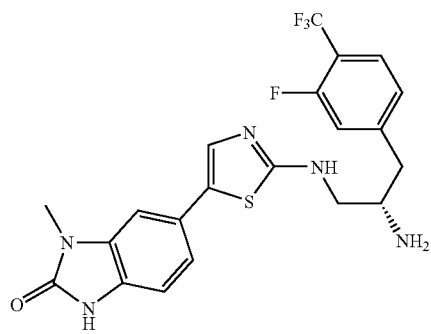

Example 185

5-(2-((S)-2-amino-3-(3-fluoro-4-(trifluoromethyl)phenyl)propylamino)thiazol-5-yl)indolin-2-one LCMS (M+H) 466 for $C_{21}H_{18}F_4N_4OS$ 465.45.

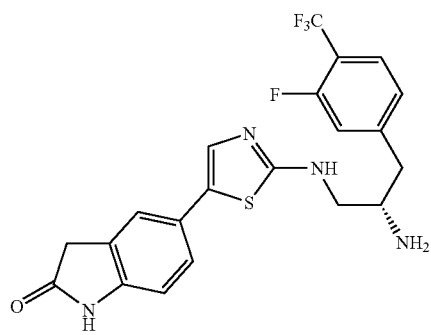

Example 186

N-((S)-2-amino-3-(3-fluoro-4-(trifluoromethyl)phenyl)propyl)-5-(1H-indazol-5-yl)thiazol-2-amine LCMS (M+H) 436 for $C_{20}H_{17}F_4N_5S$ 435.44.

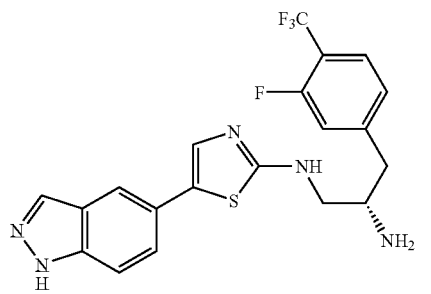

Example 187

6-(2-(-2-amino-3-(4-(trifluoromethoxy)phenyl)propylamino)thiazol-5-yl)benzo[d]oxazol-2(3H)-one LCMS (M+H) 451 for $C_{20}H_{17}F_3N_4O_3S$ 450.43.

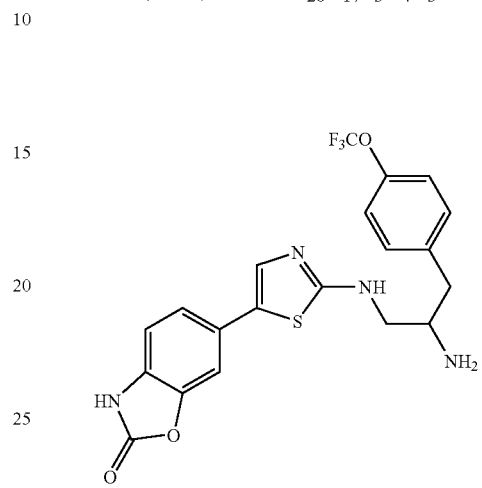

Example 188

5-(2-(-2-amino-3-(4-(trifluoromethoxy)phenyl)propylamino)thiazol-5-yl)indolin-2-one LCMS (M+H) 449 for $C_{21}H_{19}F_3N_4O_2S$ 448.46.

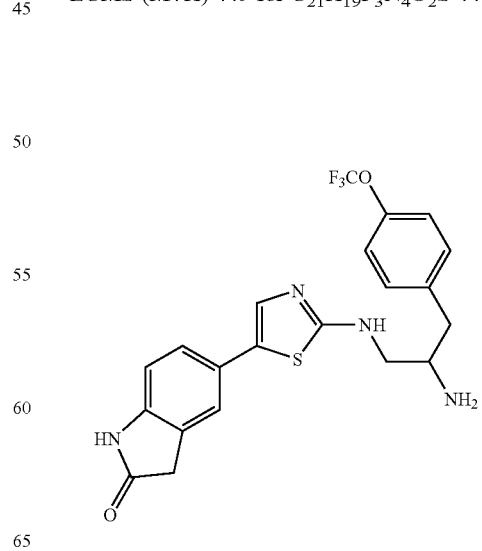

Example 189

N-(-2-amino-3-(4-(trifluoromethoxy)phenyl)propyl)-5-(isoquinolin-6-yl)thiazol-2-amine LCMS (M+H) 445 for $C_{22}H_{19}F_3N_4OS$ 444.47.

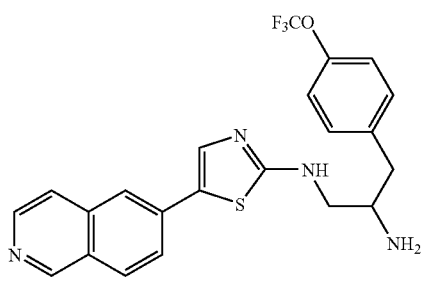

Examples 190-191

Examples 190-191 were prepared in a manner similar to that described for Example 129 using 2,3-difluoro-4-(trifluoromethyl)benzaldehyde purchased from Matrix Scientific as the starting material.

Example 190

N-(2-amino-3-(2,3-difluoro-4-(trifluoromethyl)phenyl)propyl)-5-(1H-indazol-5-yl)thiazol-2-amine LCMS (M+H) 454 for $C_{20}H_{16}F_5N_5S$ 453.43.

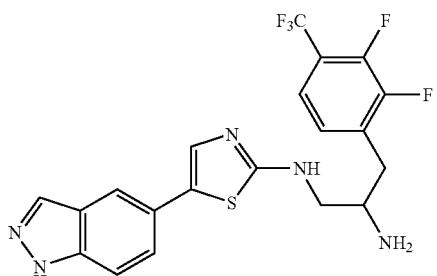

Example 191

6-(2-(2-amino-3-(2,3-difluoro-4-(trifluoromethyl)phenyl)propylamino)thiazol-5-yl)-1-methyl-1H-benzo[d]imidazol-2(3H)-one LCMS (M+H) 484 for $C_{21}H_{18}F_5N_5OS$ 483.46.

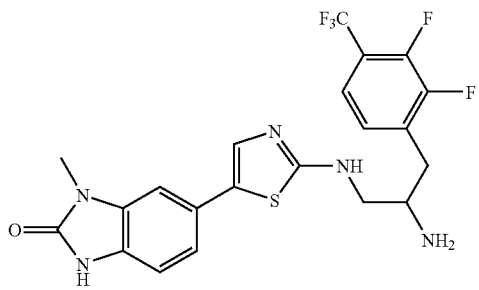

Example 192

5-(2-((S)-2-amino-3-(4-hydroxyphenyl)propylamino)thiazol-5-yl)indolin-2-one

This compound was synthesized in a manner similar to that described for Example 82 using L-tyrosine as the starting material. LCMS (M+H) 381 for $C_{20}H_{20}N_4O_2S$ 380.46.

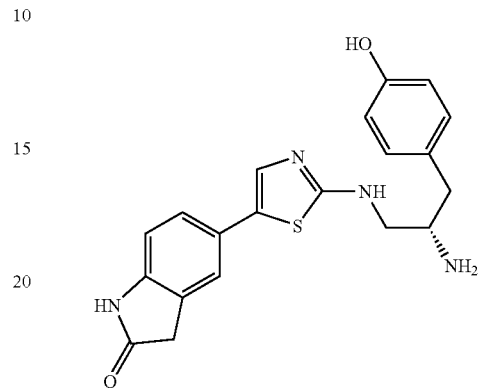

Example 193

5-(2-((S)-2-amino-3-(4-(trifluoromethyl)-phenyl)propylamino)thiazol-5-yl)-1H-benzo[d]imidazol-2(3H)-one This compound was synthesized in a similar manner to that described for Example 82. LCMS (M+H+) 434.5 calc. for $C_{20}H_{18}F_3N_5OS$; $^1H$ NMR (400 MHz, DMSO-d6) δ ppm 10.59 (b, 2H), 7.65 (m, 3H), 7.46 (d, 2H), 6.98 (d, 1H), 6.93 (s, 1H), 6.87 (d, 1H), 3.24 (m, 1H), 3.12 (m, 2H), 2.84 (m, 1H), 2.60 (m, 1H).

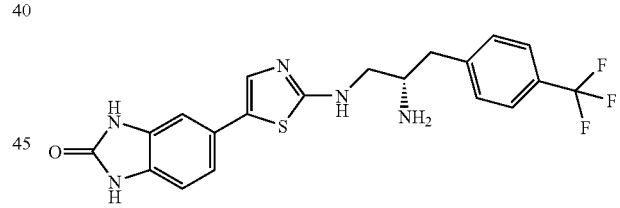

Examples 194-195

Examples 194-195 were synthesized by hydrolyzing the Boc protected intermediate for Example 117, methyl 2-(((S)-2-(tert-butoxycarbonylamino)-3-(4-(trifluoromethyl)phenyl)propyl)(tert-butoxycarbonyl)amino)-5-(isoquinolin-6-yl)thiazole-4-carboxylate, and coupling it with the corresponding amines using EDC as the coupling agent.

Example 194

2-((S)-2-amino-3-(4-(trifluoromethyl)phenyl)propylamino)-5-(isoquinolin-6-yl)-N,N-dimethylthiazole-4-carboxamide LCMS (M+H+) 500.5 calc. For $C_{25}H_{24}F_3N_5OS$; $^1H$ NMR (400 MHz, DMSO-d6) δ ppm 9.24 (s, 1H), 8.475 (d, 1H), 8.07 (d, 1H), 7.78 (d, 2H), 7.66 (d, 2H), 7.57 (d, 1H), 7.49 (d, 2H), 3.21 (d, 2H), 3.00 (m, 3H), 2.88 (m, 1H), 2.78 (m, 3H), 2.68 (m, 2H).

d6) δ ppm 9.28 (s, 1H), 8.49 (d, 1H), 8.13 (d, 1H), 7.90 (s, 1H), 7.815 (d, 1H), 7.71 (d, 1H), 7.35 (d, 2H), 7.27 (d, 2H), 4.76 (m, 1H), 4.105 (m, 1H), 3.86 (m, 1H), 2.76 (m, 1H), 3.165 (d, 2H), 3.09 (m, 2H), 2.72 (m, 1H), 2.55 (m, 1H), 2.19 (m, 1H), 2.06 (m, 2H), 1.90 (m, 2H).

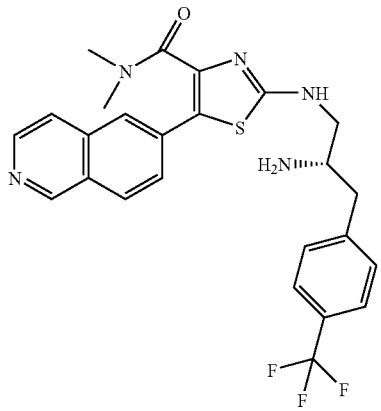

Example 195

(2-((S)-2-amino-3-(4-(trifluoromethyl)phenyl)propylamino)-5-(isoquinolin-6-yl)thiazol-4-yl)(pyrrolidin-1-yl)methanone LCMS (M+H$^+$) 526.5 calc. For $C_{27}H_{26}F_3N_5OS$; $^1$H NMR (400 MHz, DMSO-d6) δ ppm 9.23 (s, H), 8.475 (d, 1H), 8.07 (d, 1H), 7.79 (m, 2H), 7.64 (m, 3H), 7.48 (d, 2H), 3.46 (t, 2H), 3.16 (m, 4H), 2.89 (m, 1H), 2.86 (m, 1H), 2.64 (m, 1H), 1.75 (m, 4H).

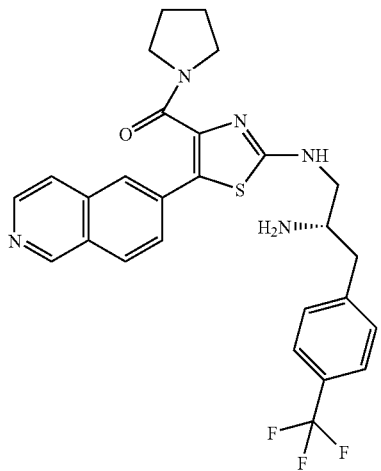

Example 196

N-((S)-2-amino-3-(4-chlorophenyl)propyl)-5-(isoquinolin-6-yl)-4-(tetrahydrofuran-2-yl)thiazol-2-amine This compound was synthesized in a manner similar to that described for Example 81 using tert-butyl 4-(tetrahydrofuran-2-yl)thiazol-2-ylcarbamate as the key intermediate which was synthesized as shown in Scheme 41. LCMS (M+H+) 466.0 calc. for $C_{25}H_{25}ClN_4OS$; $^1$H NMR (400 MHz, DMSO-

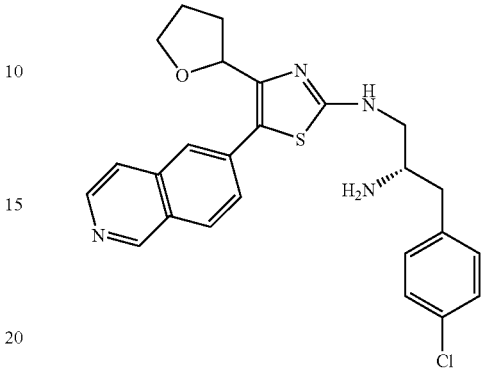

Scheme 41

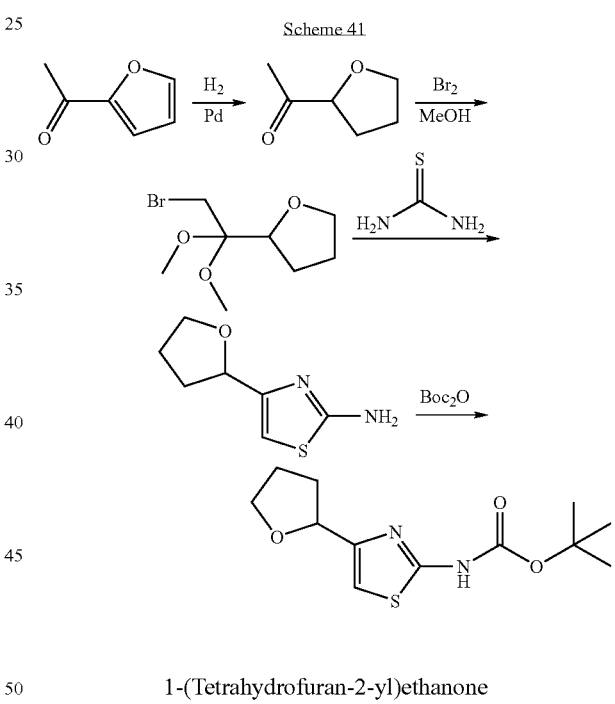

1-(Tetrahydrofuran-2-yl)ethanone

2-Acetylfuran (25 g, 227 mmol) was added to a par-shaker bottle. Ether (50 mL) and palladium on activated carbon 10% (0.20 mL, 23 mmol) were then added followed by more ether (75 mL). The reaction was run on the hydrogenation par-shaker with hydrogen gas pressure at approximately 30 psi. Hydrogen was consumed rapidly. The chamber was continually refilled with hydrogen gas from a storage cell. After about 5 hours, hydrogen gas consumption stopped. After filtration through a pad of Celite and removal of the ether under reduced pressure, the desired compound 1-(tetrahydrofuran-2-yl)ethanone was obtained (26 g, 100% yield).

4-Tetrahydrofuran-2-yl)thiazol-2-amine

To a 500 mL round-bottomed flask was added 1-(tetrahydrofuran-2-yl)ethanone (20 g, 175 mmol) and anhydrous MeOH (100 mL). The resulting mixture was then stirred in an ice bath at 0° C. for 15 minutes. Br₂ was added (9.0 mL, 175 mmol) dropwise via an addition funnel. After addition, the reaction mixture was stirred in an ice bath for 20 minutes and then stirred for 4 hours at room temperature. To this reaction mixture was added thiourea (9.1 mL, 167 mmol). The resulting mixture was heated at reflux for 2 hours. After removing the solvent under a reduced pressure, the remaining residue was absorbed onto a plug of silica gel and purified using a Redi-sep pre-packed silica gel column (4 g), eluting with 0% to 10% gradient of MeOH with DCM to yield the crude product. (23 g).

tert-Butyl 4-(tetrahydrofuran-2-yl)thiazol-2-ylcarbamate

The title compound was prepared by treating 4-(tetrahydrofuran-2-yl)thiazol-2-amine with di-tert-butyl dicarbonate in dioxane and pyridine at room temperature for 18 hours.

Example 197

5-(2-((S)-2-Amino-3-(4-chlorophenyl)propylamino)-4-(tetrahydrofuran-2-yl)thiazol-5-yl)indolin-2-one The title compound was synthesized in a manner similar to that described for Example 196. LCMS (M+H⁺) 466.0 calc. For C₂₄H₂₅ClN₄O₂S; ¹H NMR (400 MHz, DMSO-d6) δ ppm 10.45 (bs, 1H), 7.63 (t, 1H), 7.33 (d, 2H), 7.25 (d, 2H), 7.2 (s, 1H), 7.17 (d, 1H), 6.83 (d, 1H), 4.60 (m, 1H), 3.81 (m, 1H), 3.69 (m, 1H), 3.50 (s, 2H), 3.20 (m, 1H), 3.03 (m, 2H), 2.70 (m, 1H), 2.02 (m, 4H).

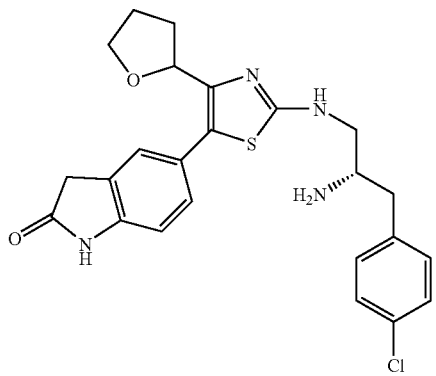

Example 198

N-((S)-2-Amino-3-(4-(trifluoromethyl)phenyl)propyl)-5-(isoquinolin-6-yl)-4-(tetrahydrofuran-2-yl)thiazol-2-amine The title compound was synthesized in a manner similar to that described for Example 196. LCMS (M+H⁺) 499.5 calc. For C₂₆H₂₅F₃N₄OS; ¹H NMR (400 MHz, DMSO-d6) δ ppm 9.26 (s, 1H), 8.49 (d, 1H), 8.13 (d, 1H), 7.90 (s, 1H), 7.81 (d, 1H), 7.71 (d, 1H), 7.65 (d, 2H), 7.48 (d, 2H), 4.75 (m, 1H), 3.83 (m, 1H), 3.75 (m, 1H), 3.165 (d, 2H), 2.82 (m, 1H), 2.67 (m, 1H), 2.20 (m, 1H), 2.06 (m, 2H), 1.90 (m, 2H).

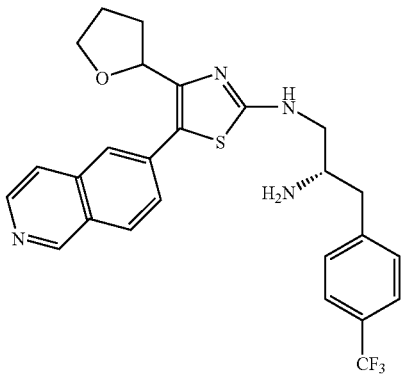

Examples 199-200

Examples 199-200 were synthesized in a manner similar to that described for Example 82 and Example 92 using 5'-(4,4,5,5-tetramethyl-1,3,2-dioxaborolan-2-yl)spiro[cyclopropane-1,3'-indol]-2'(1'H)-one to couple with the corresponding bromothiazole intermediate. 5'-(4,4,5,5-Tetramethyl-1,3,2-dioxaborolan-2-yl)spiro[cyclopropane-1,3'-indol]-2'(1'H)-one was prepared in a manner similar to that described in Scheme 1 using 5'-bromo-spiro[cyclopropane-1,3'-indol]-2' (1'H)-one as the starting material for reaction with bis(pinacolato)diboron. 5'-Bromo-spiro[cyclopropane-1,3'-indol]-2' (1'H)-one was prepared using a procedure similar to the literature procedure described by Robertson in J. Med. Chem., 30(5), 828 (1987).

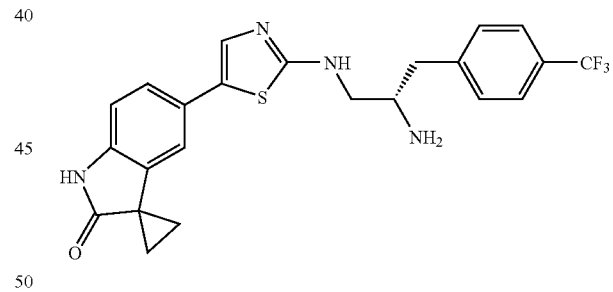

Example 199

5'-(2-((S)-2-amino-3-(4-(trifluoromethyl)phenyl) propylamino)thiazol-5-yl)spiro[cyclopropane-1,3'-indol]-2'(1'H)-one LCMS (M+H⁺) 459 for C₂₃H₂₁F₃N₄OS 458.5; ¹H NMR (400 MHz, CD₃OD) δ ppm 1.66 (s, 4H) 2.73 (dd, J=13.55, 7.53 Hz, 1H) 2.98 (dd, J=13.30, 5.27 Hz, 1H) 3.23-3.30 (m, 1H) 3.34-3.42 (m, 2H) 6.95 (d, J=8.03 Hz, 1H) 7.05 (s, 1H) 7.22-7.26 (m, 2H) 7.46 (d, J=7.53 Hz, 2H) 7.62 (s, 2H) (m, 2H).

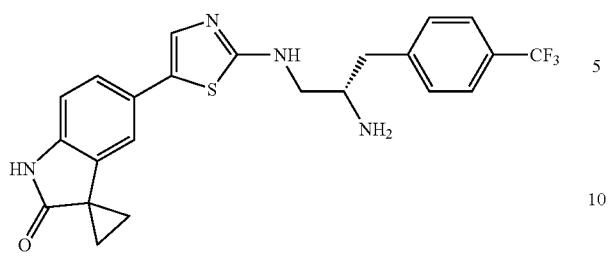

Example 200

5'-(2-((2S,3S)-2-amino-3-(4-(trifluoromethyl)phenyl)butylamino)thiazol-5-yl)spiro[cyclopropane-1,3'-indol]-2'(1'H)-one LCMS (M+H⁺) 473 for $C_{24}H_{23}F_3N_4OS$ 472.5. ¹H NMR (400 MHz, CD₃OD) δ ppm 1.39 (d, J=7.04 Hz, 3H) 1.66 (s, 4H) 2.92-3.00 (m, 1H) 3.20-3.27 (m, 2H) 3.51-3.58 (m, 1H) 6.95 (d, J=8.22 Hz, 1H) 7.05 (d, J=1.56 Hz, 1H) 7.23-7.26 (m, 2H) 7.50 (d, J=8.22 Hz, 2H) 7.65 (d, J=8.02 Hz, 2H).

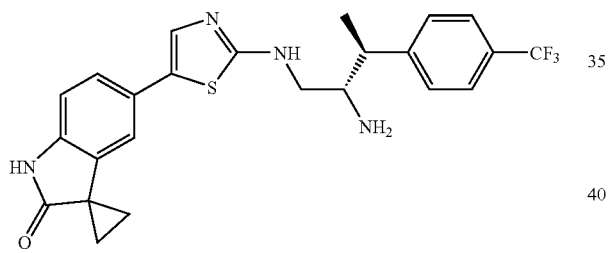

Examples 201-204

Examples 201-204 were synthesized in a manner similar to that described for Example 82.

Example 201

5-(2-((S)-2-amino-3-(naphthalen-2-yl)propylamino)thiazol-5-yl)indolin-2-one

LCMS (M+H), 415.0 for $C_{24}H_{22}N_4OS$ 414.5. ¹H NMR (400 MHz, CDCl₃) δ ppm 7.78-7.84 (m, 3H), 7.67 (s, 1H), 7.61 (s, 1H), 7.44-7.50 (m, 2H), 7.35 (m, 1H), 7.29 (s, 1H), 7.24 (s, 2H), 6.81 (d, J=8.0 Hz, 1H), 5.68 (bs, 1H), 3.55 (s, 2H), 3.50 (m, 1H), 3.43 (m, 1H), 3.23 (dd, J=7.6, 12.5 Hz, 1H), 3.06 (dd, J=4.9, 13.5 Hz, 1H), 2.77 (dd, J=8.6, 13.5 Hz, 1H).

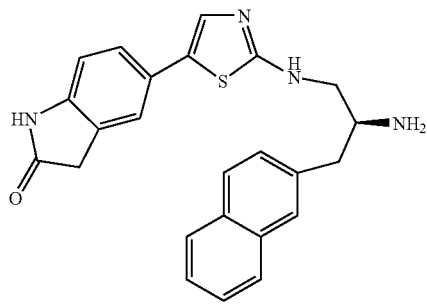

Example 202

N-((S)-2-amino-3-(naphthalen-2-yl)propyl)-5-(isoquinolin-6-yl)thiazol-2-amine

LCMS (M+H), 411.0 for $C_{25}H_{22}N_4S$ 410.5. ¹H NMR (400 MHz, CDCl₃) δ ppm 9.16 (s, 1H), 8.49 (d, J=5.7 Hz, 1H), 7.90 (d, J=8.6 Hz, 1H), 7.79-7.85 (m, 3H), 7.72 (dd, J=1.6 ,8.6 Hz, 1H), 7.67 (d, J=6.9 Hz, 2H), 7.58 (m, 2H), 7.47 (m, 2H), 7.36 (dd, J=1.5, 8.3 Hz, 1H), 6.10 (bs, 1H), 3.56 (dd, J=4.0, 12.6 Hz, 1H), 3.46 (m, 1H), 3.28 (m, 1H), 3.08 (dd, J=5.1, 13.5 Hz, 1H), 2.80 (dd, J=8.4, 13.5 Hz, 1H).

Example 203

6-(2-((S)-2-amino-3-(naphthalen-2-yl)propylamino)thiazol-5-yl)-1-methyl-1H-benzo[d]imidazol-2(3H)-one LCMS (M+H), 430.0 for $C_{24}H_{23}N_5OS$ 429.5. ¹H NMR (400 MHz, DMSO-d₆): δ ppm 10.97 (s, 1H), 8.24 (bs, 2H), 7.91-8.00 (m, 4H), 7.53-7.60 (m, 4H), 7.29 (s, 1H), 7.07 (m, 1H), 7.00 (d, J=8.0 Hz, 1H), 3.83 (m, 2H), 3.36 (s, 3H), 3.20 (m, 2H).

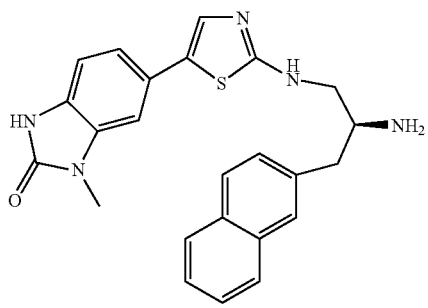

Example 204

6-(2-((S)-2-amino-3-(naphthalen-2-yl)propylamino)
thiazol-5-yl)benzo[d]oxazol-2(3H)-one LCMS (M+H), 417.0 $C_{23}H_{20}N_4O_2S$ 416.5. $^1$H NMR (400 MHz, DMSO-$d_6$) δ ppm 7.80-7.90 (m, 4H), 7.74 (s, 1H), 7.39-7.50 (m, 5H), 7.09 (m, 1H), 7.00 (d, J=8.0 Hz, 1H), 3.15 (m, 3H), 2.93 (m, 1H), 2.73 (m, 1H).

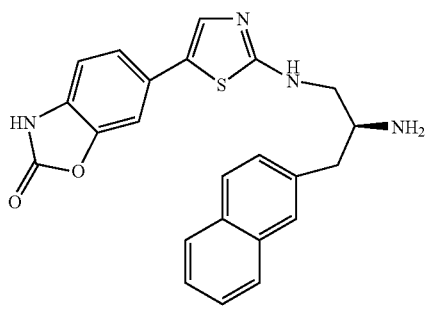

Example 205

N-((S)-2-amino-3-(3-methoxy-4-(trifluoromethyl)
phenyl)propyl)-5-(isoquinolin-6-yl)thiazol-2-amine The title compound was synthesized in a manner similar to that described for Example 170 in Scheme 39 using 4-bromo-2-methoxy-1-(trifluoromethyl)benzene as the starting material instead of 5-bromo-2-(trifluoromethyl)pyridine. 4-Bromo-2-methoxy-1-(trifluoromethyl)benzene was prepared as described in the following procedure. LCMS (M+H), 459 for $C_{23}H_{21}F_3N_4OS$ 458.5.

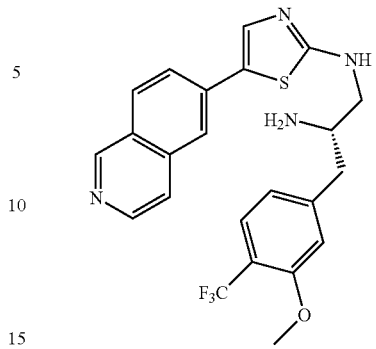

4-Bromo-2-methoxy-1-(trifluoromethyl)benzene

To a 250 mL round-bottomed flask was added 4-bromo-2-fluoro-1-(trifluoromethyl)benzene (12 mL, 50 mmol) and DMF (4.0 mL, 50 mmol). The solution was stirred at 0° C. and treated with sodium methoxide (4 g, 75 mmol). The reaction mixture was stirred at room temperature for 30 minutes and 60° C. for 2 hours. The resulting milky suspension was quenched with ice at 0° C. and the separated aqueous layer was extracted with EtOAc (3×50 mL). The combined organic layers were washed with saturated sodium chloride (1×25 mL), dried over $Na_2SO_4$, and concentrated to give the crude residue which was purified with flash column chromatography ((5%→20% EtOAc in hexane) to provide 4-bromo-2-methoxy-1-(trifluoromethyl)benzene (5.80 g, 46% yield) as a light yellow oil. m/z (%): 256.1.2 (100%, M$^+$+H).

Examples 206-207

Examples 206-207 were synthesized in a manner similar to that described for Example 173 via a coupling reaction between the corresponding bromothiazole intermediate and the boronic acid or esters.

Example 206

5-(2-((S)-2-amino-3-(3-methoxy-4-(trifluoromethyl)
phenyl) propylamino)thiazol-5-yl)indolin-2-one LCMS (M+H), 463 for $C_{22}H_{21}F_3N_4O_2S$ 462.4.

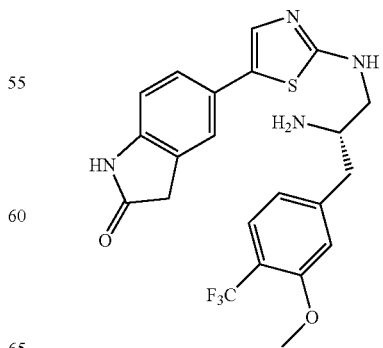

Example 207

6-(2-((S)-2-amino-3-(3-methoxy-4-(trifluoromethyl)phenyl)propylamino)thiazol-5-yl)benzo[d]oxazol-2(3H)-one Theoretical (M+H) 465.1, found 465.1.

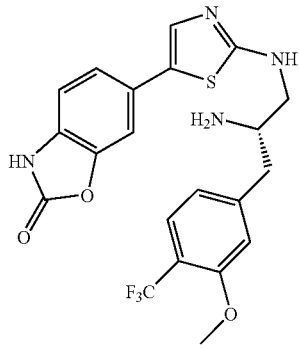

Example 208

5-((S)-2-amino-3-(5-(isoquinolin-6-yl)thiazol-2-ylamino)propyl)-2-(trifluoromethyl)phenol The title compound was prepared by treating Example 205 with boron tribromide as described in the following procedure. LCMS (M+H), 445.0 for $C_{22}H_{19}F_3N_4OS$ 444.4.

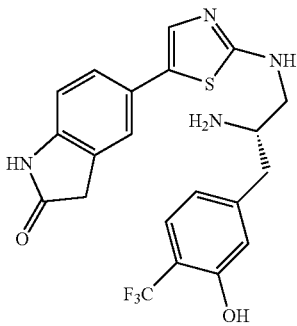

To a 50 mL round-bottomed flask was added anhydrous DCM (25 mL, 383 mmol) and N-((S)-2-amino-3-(3-methoxy-4-(trifluoromethyl)phenyl)-propyl)-5-(isoquinolin-7-yl)thiazol-2-amine (0.040 g, 0.086 mmol). The suspension was stirred at −78° C. and treated drop wise via syringe with boron tribromide (0.082 mL, 0.86 mmol). The solution was stirred at −78° C. for 1 hour and warmed to −12° C. and stirred for 1 hour and then stirred for 3 hours at room temperature. The reaction was quenched with $NaHCO_3$ and ether, and the separated aqueous layer was extracted with ether (3×50 mL). The combined organic layers were washed with saturated sodium chloride, dried over $Na_2SO_4$, and concentrated to give the crude residue which was purified with flash column chromatography ((5%→20% MeOH in DCM) to obtain the desired product as an off white solid of 5-((S)-2-amino-3-(5-(isoquinolin-7-yl)thiazol-2-ylamino)propyl)-2-(trifluoromethyl)phenol (0.018 g, 46% yield). m/z (%): 445.4 (100%, $M^+$+H).

Examples 209-210

Examples 209-210 were synthesized in a manner similar to that described for Example 208.

Example 209

5-(2-((S)-2-amino-3-(3-hydroxy-4-(trifluoromethyl)phenyl)propylamino)thiazol-5-yl)indolin-2-one Theoretical (M+H) 449.1 found 449.1.

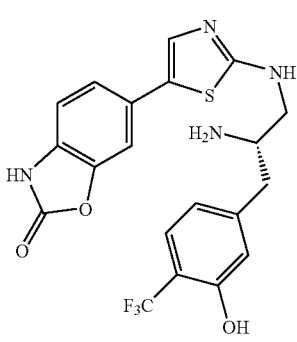

Example 210

6-(2-((S)-2-amino-3-(3-hydroxy-4-(trifluoromethylphenyl)propylamino)thiazol-5-yl)benzo[d]oxazol-2(3H)-one Theoretical (M+H) 451.1 found 451.1.

Examples 211-213

Examples 211-213 were synthesized in a manner similar to that described for Example 82.

Example 211

N-((S)-2-amino-3-(5-chlorothiophen-2-yl)propyl)-5-(isoquinolin-6-yl)thiazol-2-amine Theoretical (M+H) 401.1 found 401.1.

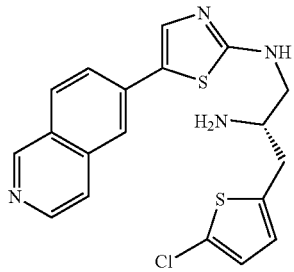

Example 212

5-(2-((S)-2-amino-3-(5-chlorothiophen-2-yl)propylamino)thiazol-5-yl)indolin-2-one Theoretical (M+H) 405.1 found 405.1.

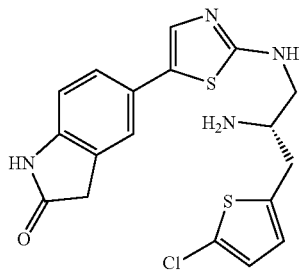

Example 213

6-(2-((S)-2-amino-3-(5-chlorothiophen-2-yl)propylamino)thiazol-5-yl)benzo[d]oxazol-2(3H)-one Theoretical (M+H) 407.1 found 407.1.

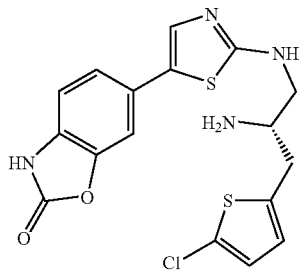

Example 214

5-(2-((S)-2-amino-3-(4-(trifluoromethylphenyl)propylamino)thiazol-5-yl)-6-fluoroindolin-2-one This compound was synthesized in a similar manner as Example 199. The starting material, 5-bromo-6-fluoroindolin-2-one, was synthesized as shown in Scheme 42. MS m/z: 451 (M+1). $^1$H NMR (400 MHz, CD$_3$OD) δ ppm 3.04-3.17 (m, 2H), 3.48-3.56 (m, 3H), 3.68 (d, J=3.72 Hz, 1H), 3.82 (tt, J=7.21, 3.45 Hz, 1H), 6.75 (d, J=10.96 Hz, 1H), 7.39-7.42 (m, 2H), 7.55 (d, J=8.22 Hz, 2H), 7.71 (d, J=8.22 Hz, 2H).

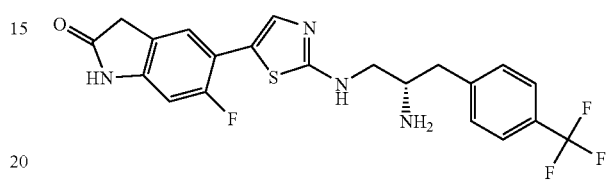

Scheme 42

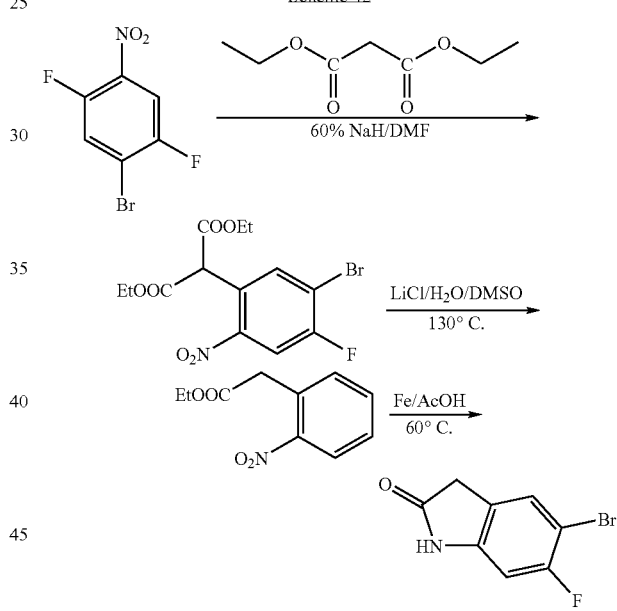

Diethyl 2-(5-bromo-4-fluoro-2-nitrophenyl)malonate

To a 250 mL round bottom flask was added sodium hydride, 60% dispersion in mineral oil (2.3 g, 58 mmol), and 70 mL of DMF at 0° C. Diethyl ester malonic acid (7 mL, 44 mmol) was then added dropwise. After 30 minutes, 4-bromo-2,5-difluoronitrobenzene (7 g, 29 mmol) was added to the reaction mixture. The reaction mixture was stirred at room temperature overnight. 50 mL of water was added to the reaction mixture, and the mixture was then extracted twice with 70 mL of EtOAc. The organic layers were combined and concentrated to give the crude product.

Ethyl 2-(5-bromo-4-fluoro-2-nitrophenyl)acetate 50 mL of DMSO, 10 g LiCl and 1 mL of water were added to the crude product from the above reaction. The reaction mixture was heated to 130° C. for 4 hours. The reaction was then cooled to room temperature. 70 mL of water was added, and the mixture was extracted twice with 70 mL of EtOAc. The organic layers were concentrated and purified with silica gel column chromatography, eluting with 0-10% EtOAc/hexane to give ethyl 2-(5-bromo-4-fluoro-2-nitrophenyl)acetate (5.5 g, 61% yield). $^1$H NMR (400 MHz, CDCl$_3$) δ ppm 1.28 (dq, J=7.28, 7.11 Hz, 3H), 3.98 (s, 2H), 4.18 (q, J=7.03 Hz, 2H), 7.60 (d, J=6.53 Hz, 1H), 7.92 (d, J=8.03 Hz, 1H).

5-Bromo-6-fluoroindolin-2-one

To a 250 mL round bottom flask was added ethyl 2-(5-bromo-4-fluoro-2-nitrophenyl)acetate (5.2 g, 17 mmol), iron (4.7 g, 85 mmol) and 50 mL of AcOH. The reaction mixture was heated at 60° C. for 1 hour. The reaction mixture was then concentrated, dissolved in 100 mL of EtOAc, filtered, and washed with 50 mL of a saturated NaHCO$_3$ solution. The organic layer was concentrated and purified with silica gel column chromatography, eluting with 40% EtOAc/hexane to give 5-bromo-6-fluoroindolin-2-one (3.4 g, 87% yield) as a white solid. MS m/z: 230 (M+1). $^1$H NMR (400 MHz, CD$_3$OD) δ ppm 3.49-3.54 (m, 2H), 6.77 (d, J=8.80 Hz, 1H), 7.45 (d, J=6.65 Hz, 1H).

Example 215

5-(2-((S)-2-amino-3-(6-(trifluoromethyl)pyridin-3-yl)propylamino)thiazol-5-yl)-6-fluoroindolin-2-one The title compound was prepared in a manner similar to that described for Example 214. MS m/z: 452 (M+1). $^1$H NMR (400 MHz, CD$_3$OD) δ ppm 3.09-3.26 (m, 2H), 3.49-3.62 (m, 3H), 3.68-3.76 (m, 1H), 3.91 (qd, J=7.04, 4.30 Hz, 1H), 6.75 (d, J=10.95 Hz, 1H), 7.41 (d, J=7.24 Hz, 1H), 7.44 (s, 1H), 7.84 (d, J=8.22 Hz, 1H), 8.05 (dd, J=8.02, 1.57 Hz, 1H), 8.72 (s, 1H).

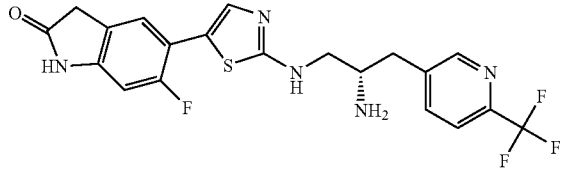

Example 216

6-(2-(2-Amino-3-(3-fluoro-4-hydroxyphenyl)propylamino)thiazol-5-yl)benzo[d]oxazol-2(3H)-one To a 25 mL round-bottomed flask was added 6-(2-(2-amino-3-(3-fluoro-4-methoxyphenyl)propylamino)thiazol-5-yl)benzo[d]oxazol-2(3H)-one (Example 129) (60 mg, 145 μmol) and 3 mL of DCM. The solution was cooled to −78° C., and treated dropwise with boron tribromide, 1.0 M in DCM (497 μL, 2895 μmol) via a syringe. The solution was stirred at −78° C. for 1 hour and then allowed to warm to room temperature overnight. The reaction mixture was concentrated, and 2 mL of MeOH was added dropwise. The reaction mixture was purified by preparative LC to give 6-(2-(2-amino-3-(3-fluoro-4-hydroxyphenyl)propylamino)thiazol-5-yl)benzo[d]oxazol-2((H)-one (20 mg, 35% yield). MS m/z: 401 (M+1). $^1$H NMR (400 MHz, CD$_3$OD) δ ppm 2.85-2.98 (m, 2H), 3.47-3.53 (m, 1H), 3.62-3.71 (m, 2H), 6.92-6.97 (m, 2H), 7.05-7.10 (m, 2H), 7.26 (dd, J=8.02, 1.57 Hz, 1H), 7.37 (s, 1H), 7.38 (d, J=1.37 Hz, 1H).

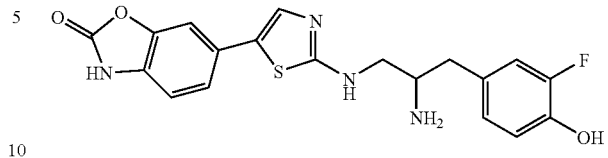

Example 217

5-(2-(2-Amino-3-(3-fluoro-4-hydroxyphenyl)propylamino)thiazol-5-yl)indolin-2-one The title compound was prepared according to the procedure as for Example 216 using Example 130 as the starting material. MS m/z: 399 (M+1). $^1$H NMR (400 MHz, CD$_3$OD) δ ppm 2.85-2.98 (m, 2H), 3.46-3.52 (m, 1H), 3.56 (s, 2H), 3.61-3.67 (m, 2H), 6.88-6.97 (m, 3H), 7.06 (d, J=12 Hz, 1H), 7.29-7.32 (m, 2H), 7.39 (s, 1H).

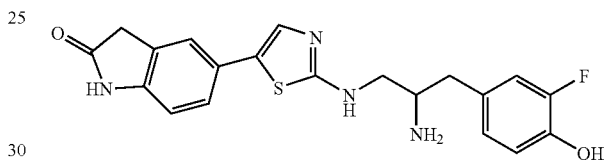

Example 218

4-(2-Amino-3-(5-(isoquinolin-6-yl)thiazol-2-ylamino)propyl)-2-fluorophenol

The title compound was prepared according to the procedure as for Example 216 using Example 131 as the starting material. MS m/z: 395 (M+1). $^1$H NMR (400 MHz, CD$_3$OD) δ ppm 2.88-3.00 (m, 2H), 3.57-3.64 (m, 1H), 3.71-3.77 (m, 2H), 6.92-6.99 (m, 2H), 7.08 (d, J=12.55 Hz, 1H), 7.98 (s, 1H), 8.09 (s, 1H), 8.21-8.29 (m, 2H), 8.37 (d, J=8.53 Hz, 1H), 8.47 (d, J=6.53 Hz, 1H), 9.52 (s, 1H).

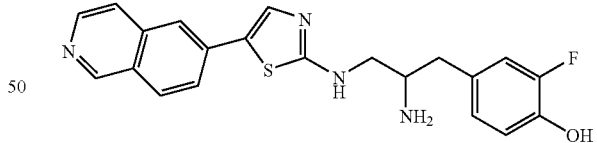

Example 219

6-(2-((S)-2-amino-3-(6-(trifluoromethyl)pyridin-3-yl)propylamino)thiazol-5-yl)-5-fluorobenzo[d]oxazol-2(3H)-one The title compound was prepared in a manner similar to that described for Example 214. MS m/z: 454 (M+1). $^1$H NMR (400 MHz, CD$_3$OD) δ ppm 3.08-3.15 (m, 1H), 3.19-3.22 (m, 1H), 3.53-3.59 (m, 1H), 3.68-3.72 (m, 1H), 3.89 (tt, J=7.07, 3.59 Hz, 1H), 6.97-6.99 (d, J=8.0 Hz, 1H), 7.40 (d, J=6.06 Hz, 1H), 7.45 (s, 1H), 7.84 (d, J=8.22 Hz, 1H), 8.03 (dd, J=8.12, 1.66 Hz, 1H), 8.71 (d, J=1.76 Hz, 1H).

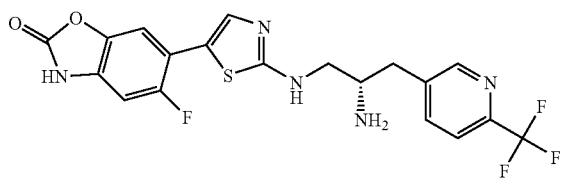

Example 220

5-(2-((S)-2-amino-3-(4-(trifluoromethyl)phenyl)propylamino)thiazol-5-yl)-7-fluoroindolin-2-one The title compound was prepared in a manner similar to that described for Example 214. The starting 5-bromo-7-fluoroindolin-2-one was prepared as shown in Scheme 43. MS m/z: 451 (M+1). $^1$H NMR (400 MHz, CD$_3$OD) δ ppm 3.06 (d, J=7.24 Hz, 1H), 3.10-3.16 (m, 1H), 3.47-3.66(m, 4H), 3.78 (br s, 1H), 7.16 (d, J=12.0 Hz, 1H), 7.21 (s, 1H), 7.35 (s, 1H), 7.54 (d, J=8.02 Hz, 2H), 7.71 (d, J=8.22 Hz, 2H).

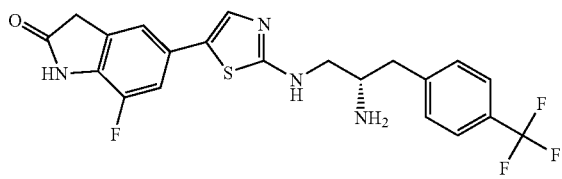

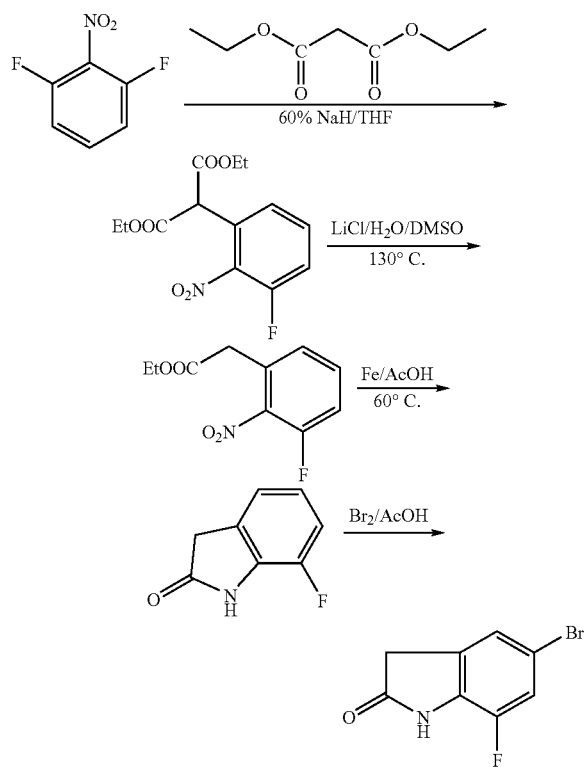

Scheme 43

Diethyl 2-(3-fluoro-2-nitrophenyl)malonate

To a 250 mL round bottom flask was added sodium hydride, 60% dispersion in mineral oil (2.5 g, 62 mmol), and 50 mL of THF at 0° C. Diethyl ester malonic acid (5.2 mL, 35 mmol) was then added dropwise. After 30 minutes, 1,3-difluoro-2-nitrobenzene (5000 mg, 31 mmol) was added to the reaction mixture. The reaction mixture was stirred at room temperature overnight. 50 mL of water was then added slowly to the reaction mixture, and the reaction mixture was extracted twice with 70 mL of EtOAc. The organic layers were combined and concentrated to give the title compound as a crude product.

Ethyl 2-(3-fluoro-2-nitrophenyl)acetate 50 mL of DMSO, 5 g LiCl, and 1 mL of water were added to the crude product from the above reaction. The reaction mixture was heated at 130° C. for 4 hours. The reaction mixture was then cooled to room temperature. 100 mL of water was added, and the mixture was extracted twice with 100 mL of EtOAc. The organic layers were concentrated and purified with silica gel column chromatography, eluting with 0-20% EtOAc/hexane to give ethyl 2-(3-fluoro-2-nitrophenyl)acetate (3.5 g, 49% yield). MS m/z: 228 (M+1). $^1$H NMR (400 MHz, CDCl$_3$) δ ppm 1.27 (dt, J=10.07, 7.09 Hz, 3H), 4.17 (q, J=7.04 Hz, 2H), 7.15-7.29 (m, 2H), 7.48 (td, J=8.12, 5.28 Hz, 1H).

7-Fluoroindolin-2-one

To a 250 mL round bottom flask was added ethyl 2-(3-fluoro-2-nitrophenyl)acetate (3.1 g, 14 mmol), iron (3.8 g, 68 mmol), and 50 mL of AcOH. The reaction mixture was heated at 60° C. for 1 hour. The reaction mixture was concentrated and dissolved in 100 mL of EtOAc, filtered, and washed with 50 mL of a saturated NaHCO$_3$ solution. The organic layer was concentrated and purified with silica gel column chromatography, eluting with 40% EtOAc/hexane to give 7-fluoroindolin-2-one (1.2 g, 58% yield) as a white solid. MS m/z: 152 (M+1). $^1$H NMR (400 MHz, CDCl$_3$) δ ppm 3.58 (s, 2H), 6.94-7.04 (m, 3H).

5-Bromo-7-fluoroindolin-2-one

7-Fluoroindolin-2-one (800 mg, 5293 μmol) was taken up in 30 mL of boiling water. Br$_2$ (273 μL, 5293 μmol) and KBr (1260 mg, 10586 μmol) were added dropwise in 5 mL of water over 10 minutes. A white precipitate began to form as the solution was added. The mixture was stirred for 20 minutes. The mixture was then chilled in an ice bath for 30 minutes, washed with 30 mL of a saturated NaHCO$_3$ solution and extracted twice with 50 mL of EtOAc. The organic layers were concentrated and purified with silica gel column chromatography, eluting with 0-35% EtOAc/hexane to give 5-bromo-7-fluoroindolin-2-one (913 mg, 75% yield). MS m/z: 230 (M+1). $^1$H NMR (400 MHz, CDCl$_3$) δ ppm 3.58 (s, 2H), 7.20 (dd, J=10.07, 0.88 Hz, 2H), 7.63 (s, 1H).

Example 221

5-(2-((S)-2-amino-3-(6-(trifluoromethyl)pyridin-3-yl)propylamino)thiazol-5-yl)-7-fluoroindolin-2-one The title compound was prepared according to a procedure similar to that described in Example 220. MS m/z: 452 (M+1). $^1$H NMR (400 MHz, CD$_3$OD) δ ppm 3.24-3.06 (m, 1H), 3.58-3.48 (m, 1H), 3.62 (s, 2H), 3.67-3.72 (m, 1H), 3.94-3.83 (m, 1H), 7.22 (d, J=1.17 Hz, 1H), 7.25 (s, 1H), 7.36 (s, 1H), 7.85 (d, J=8.22 Hz, 1H), 8.03 (s, 1H), 8.71 (s, 1H).

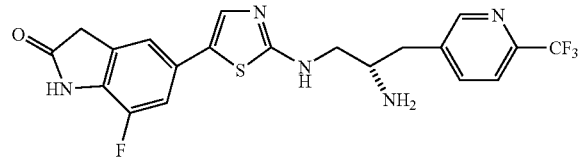

Example 222

5-(2-((2S,3S)-2-amino-3-(4-(trifluoromethyl)phenyl)butylamino)thiazol-5-yl)-7-fluoroindolin-2-one The title compound was prepared according to a procedure similar to that described in Example 220. MS m/z: 465 (M+1). $^1$H NMR (400 MHz, CD$_3$OD) δ ppm 1.49 (d, J=7.04 Hz, 3H), 3.18-3.27 (m, 2H), 3.62 (s, 2H), 3.64-3.71 (m, 1H), 3.76 (ddd, J=9.00, 6.36, 2.64 Hz, 1H), 3.84-3.87 (m, 1H), 7.16 (d, J=10.96 Hz, 1H), 7.21 (s, 1H), 7.36 (s, 1H), 7.57 (d, J=8.02 Hz, 2H), 7.74 (d, J=8.22 Hz, 2H).

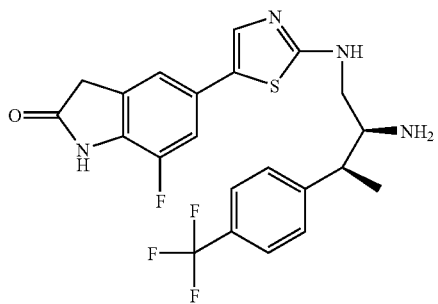

Example 223

Benzyl 4-((S)-2-amino-3-(5-(isoquinolin-6-yl)thiazol-2-ylamino)propyl)phenylcarbamate The title compound was synthesized in manner similar to that described for Example 82. MS m/z: 510 (M+1). $^1$H NMR (400 MHz, CDCl$_3$) δ ppm 2.93-2.99 (m, 2H), 3.48-3.58 (m, 1H), 3.69-3.76 (m, 2H), 5.17 (s, 2H), 7.25 (d, J=8.61 Hz, 2H), 7.31-7.42 (m, 5H), 7.47 (d, J=8.61 Hz, 2H), 7.96 (s, 1H), 8.06 (s, 1H), 8.18-8.22 (m, 1H), 8.24 (d, J=6.46 Hz, 1H), 8.34 (d, J=9.00 Hz, 1H), 8.44 (d, J=6.65 Hz, 1H), 9.49 (s, 1H).

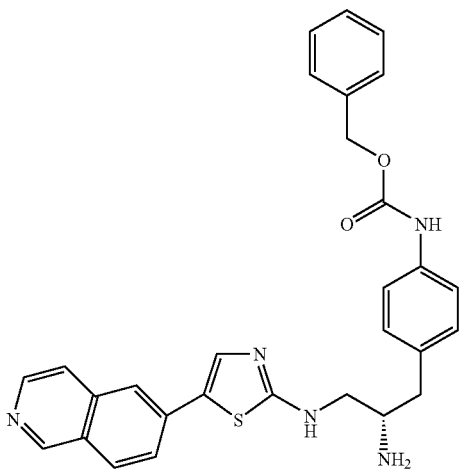

Example 224

5-(2-((S)-2-amino-3-(4-(trifluoromethyl)phenyl)propylamino)thiazol-5-yl)-4-fluoroindolin-2-one The title compound was prepared according to a procedure similar to that described in Example 220, starting from commercially available 1,2-difluoro-3-nitrobenzene. MS m/z: 451 (M+1). $^1$H NMR (400 MHz, CD$_3$OD) δ ppm 3.05-3.17 (m, 2H), 3.49-3.68 (m, 4H), 3.82 (dd, J=7.28, 3.76 Hz, 1H), 6.77 (d, J=8.03 Hz, 1H), 7.35-7.39 (m, 2H), 7.55 (d, J=8.03 Hz, 2H), 7.71 (d, J=8.03 Hz, 2H).

Example 225

5-(2-((2S,3S)-2-amino-3-(4-(trifluoromethyl)phenyl)butylamino)thiazol-5-yl)-4-fluoroindolin-2-one The title compound was prepared according to a procedure similar to that described in Example 220, starting from commercially available 1,2-difluoro-3-nitrobenzene. MS m/z: 465 (M+1). $^1$H NMR (400 MHz, CD$_3$OD) δ ppm 1.48 (d, J=7.03 Hz, 3H), 3.15-3.28 (m, 2H), 3.59-3.77 (m, 4H), 3.85 (dd, J=14.56, 2.01 Hz, 1H), 6.76 (d, J=8.03 Hz, 1H), 7.33-7.39 (m, 2H), 7.57 (d, J=8.03 Hz, 2H), 7.73 (d, J=8.03 Hz, 2H), 8.41 (s, 1H).

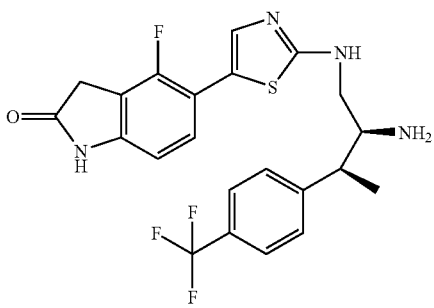

Examples 226-228

Examples 226-228 were synthesized in a manner similar to that described for Example 199 using commercially available 5-bromo-1H-pyrrolo[2,3-b]pyridin-2(3H)-one to make the corresponding boronic ester as the intermediate.

Example 226

5-(2-((S)-2-amino-3-(4-(trifluoromethyl)phenyl)propylamino)thiazol-5-yl)-1H-pyrrolo[2,3-b]pyridin-2(3H)-one MS m/z: 434 (M+1). $^1$H NMR (400 MHz, CD$_3$OD) δ ppm 3.05-3.18 (m, 2H), 3.49-3.57 (m, 1H), 3.62-3.70 (m, 3H), 3.80-3.87 (m, J=10.78, 7.12, 3.81, 3.52 Hz, 1H), 7.39 (s, 1H), 7.55 (d, J=8.02 Hz, 2H), 7.69-7.77 (m, 3H), 8.13 (d, J=2.15 Hz, 1H).

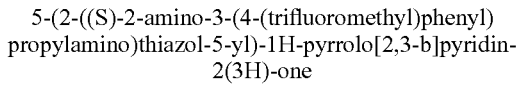

Example 227

5-(2-((S)-2-amino-3-(6-(trifluoromethyl)pyridin-3-yl)propylamino)thiazol-5-yl)-1H-pyrrolo[2,3-b]pyridin-2(3H)-one MS m/z: 435 (M+1). $^1$H NMR (400 MHz, CD$_3$OD) δ ppm 3.09-3.16 (m, 1H), 3.18-3.23 (m, 1H), 3.53-3.60 (m, 1H), 3.64 (s, 2H), 3.68-3.73 (m, 1H), 3.91 (qd, J=7.04, 4.11 Hz, 1H), 7.39 (s, 1H), 7.75-7.77 (m, 1H), 7.85 (d, J=8.02 Hz, 1H), 8.04 (dd, J=8.02, 1.76 Hz, 1H), 8.13 (d, J=2.15 Hz, 1H), 8.72 (d, J=1.56 Hz, 1H).

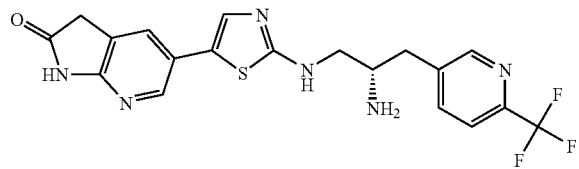

Example 228

5-(2-((2S,3S)-2-amino-3-(4-(trifluoromethyl)phenyl)butylamino)thiazol-5-yl)-1H-pyrrolo[2,3-b]pyridin-2(3H)-one MS m/z: 448 (M+1). $^1$H NMR (400 MHz, CD$_3$OD) δ ppm 1.45-1.52 (m, 3H), 3.19-3.29 (m, 1H), 3.61-3.89 (m, 6H), 7.39-7.59 (m, 3H), 7.72 (d, J=8.22 Hz, 2H), 7.75 (s, 1H), 8.13 (s, 1H).

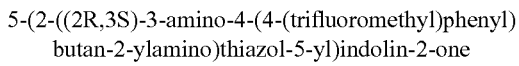

Example 229

5-(2-((2R,3S)-3-amino-4-(4-(trifluoromethyl)phenyl)butan-2-ylamino)thiazol-5-yl)indolin-2-one The title compound was prepared using tert-butyl (2S,3S)-3-hydroxy-1-(4-(trifluoromethyl)phenyl)butan-2-ylcarbamate cyclic sulfamidate according to the procedure described in Example 36. The tert-butyl (2S,3S)-3-hydroxy-1-(4-(trifluoromethyl)phenyl)butan-2-ylcarbamate cyclic sulfamidate intermediate was synthesized as shown in Scheme 44. HRMS 447.14504 (M+H) calcd for C$_{22}$H$_{21}$F$_3$N$_4$OS 447.14609. $^1$H NMR (400 MHz, CDCl$_3$) δ ppm 1.31 (d, J=6.46 Hz, 3H) 2.60 (dd, J=13.50, 9.59 Hz, 1H) 2.96 (dd, J=13.50, 4.30 Hz, 1H) 3.25 (ddd, J=9.19, 4.50, 4.30 Hz, 1H) 3.55 (s, 2H) 3.74 (s, 1H) 6.83 (d, J=8.22 Hz, 1H) 7.22 (s, 1H) 7.24 (d, J=8.02 Hz, 1H) 7.28 (s, 1H) 7.34 (d, J=8.02 Hz, 2H) 7.59 (d, J=8.22 Hz, 3H) 8.27 (s, 1H).

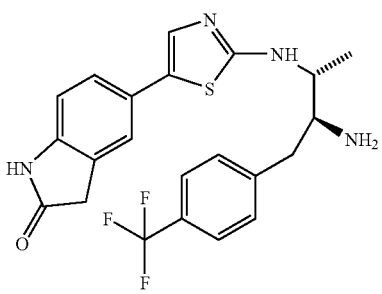

Scheme 44

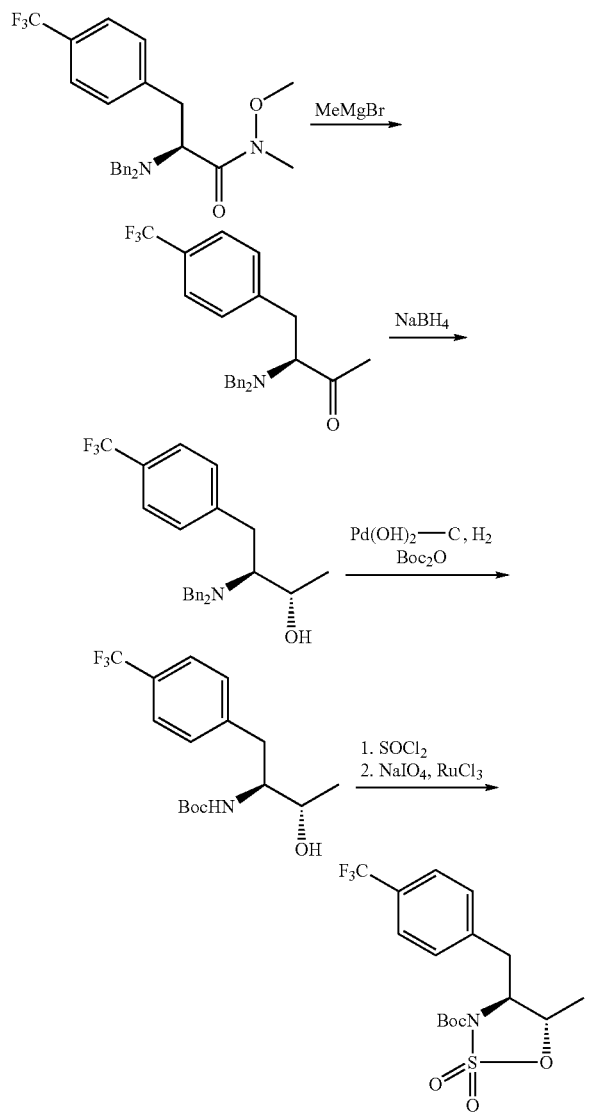

(S)-3-Dibenzylamino-4-(4-(trifluoromethyl)phenyl)butan-2-one

To a 250 mL round bottom flask containing (S)-2-(dibenzylamino)-N-methoxy-N-methyl-3-(4-(trifluoromethyl)phenyl)propanamide (10.49 g, 23.0 mmol) was added THF (200 mL), and the flask was cooled to 0° C. Methylmagnesium bromide (3.16 M in ether, 12.7 mL, 40.2 mmol) was added dropwise over 10 minutes. After 2 hours, additional methylmagnesium bromide, 3.16 in ether (12.7 mL, 40.2 mmol) was added dropwise over 10 minutes. After 1 hour, the mixture was poured into ammonium chloride—ice (200 mL), washed with brine (100 mL), dried over sodium sulfate, and stored at −20° C. for 15 hours. Plate-like crystals formed the next morning. The mixture was decanted from sodium sulfate and evaporated to provide a yellow oil that crystallized in the freezer over the weekend. The solid was triturated with hexane and chilled at −20° C. before filtration. The product was obtained as a white crystalline solid. The yellow filtrate was adsorbed onto silica gel and purified by chromatography through a Redi-Sep® pre-packed silica gel column (330 g), eluting with a gradient of 0% to 70% EtOAc in hexane to provide additional product as an oil that crystallized under hi vacuum. The two lots were combined to provide (S)-3-(dibenzylamino)-4-(4-(trifluoromethyl)phenyl)butan-2-one (8.09 g, 85.6% yield) as a white solid. LCMS (ES+) m/z=412.3 (M+H); $^1$H NMR (400 MHz, CDCl$_3$) δ ppm 2.13 (s, 3H) 2.93 (dd, J=13.30, 3.52 Hz, 2H) 3.21 (dd, J=13.30, 9.39 Hz, 1H) 3.50-3.60 (m, 3H) 3.82 (d, J=13.69 Hz, 2H) 7.19-7.30 (m, 4H) 7.30-7.35 (m, 8H) 7.46 (d, J=8.02 Hz, 2H).

(2S,3S)-3-Dibenzylamino)-4-(4-(trifluoromethyl)phenyl)butan-2-ol

To (S)-3-(dibenzylamino)-4-(4-(trifluoromethyl)phenyl)butan-2-one (8.00 g, 19.4 mmol) in a 1 L round bottom flask was added MeOH (106 mL) and THF (35 mL). The mixture was cooled to −20° C. in a dry ice/acetone bath, and sodium borohydride (1.54 g, 40.8 mmol) was added. After 50 minutes, brine (200 mL) was added, and the mixture was extracted with ether (2×200 mL). The ether was washed with brine (50 mL), dried over sodium sulfate, and evaporated to provide an aqueous/oily mixture. The mixture was taken up in EtOAc (100 mL), washed with brine (50 mL), and the brine was back extracted with EtOAc (2×50 mL). The combined organic layers were dried over sodium sulfate and evaporated to a colorless oil. The oil was taken up in hexane and a white precipitate quickly formed. The precipitate was dissolved in hot hexane and left to stand at room temperature. Needles slowly formed, and the flask was cooled at −20° C. for 16 hours. The solid was recovered by filtration through a medium scintered glass funnel. The filtrate was evaporated and 1.4 g of colorless oil was recovered. The oil was dissolved in 6 mL hexane and cooled at −20° C. After 6 hours, the hexane was decanted and the white solid was placed under high vacuum. The two crops were combined to provide (2S,3S)-3-(dibenzylamino)-4-(4-(trifluoromethyl)phenyl)butan-2-ol (7.30 g, 90.8% yield) as a white crystalline solid. LCMS (ES+) m/z=414.3; $^1$H NMR (400 MHz, CDCl$_3$) δ ppm 0.97 (d, J=6.06 Hz, 3H) 2.67-2.75 (m, 1H) 2.76-2.88 (m, 1H) 3.15 (dd, J=14.28, 5.67 Hz, 1H) 3.38 (d, J=13.30 Hz, 2H) 3.70-3.81 (m, 1H) 3.94 (d, J=13.30 Hz, 2H) 4.13 (s, 1H) 7.16-7.35 (m, 12H) 7.57 (d, J=7.83 Hz, 2H).

tert-Butyl (2S,3S)-3-hydroxy-1-(4-(trifluoromethyl)phenyl)butan-2-ylcarbamate To a 1 L flask containing (2S,3S)-3-(dibenzylamino)-4-(4-(trifluoromethyl)phenyl)butan-2-ol (7.30 g, 18 mmol), was added palladium hydroxide, 20 wt % pd (dry basis) on carbon, wet, degussa type e101 ne/w (1.2 g, 1.8 mmol) and MeOH (200 mL). The flask was purged with a balloon of hydrogen and then stirred under a balloon of hydrogen. After 3 hours, the hydrogen was purged with a stream of nitrogen and di-t-butyldicarbonate (7.7 g, 35 mmol) and DMAP (0.22 g, 1.8 mmol) were added. After 4 hours, the mixture was filtered through Celite and a medium scintered glass funnel to provide a colorless clear filtrate. The filtrate was evaporated providing a pale yellow solid. The solid was triturated with boiling hexane and allowed to cool to room temp before being placed in the freezer at −20° C. After 22 hours, the solid was recovered by filtration through a medium scintered glass funnel to provide tert-butyl (2S,3S)-3-hydroxy-1-(4-(trifluoromethyl)phenyl)butan-2-ylcarbamate (5.23 g, 89% yield) as an amorphous white solid. LCMS (ES+) m/z=234.2 (M−Boc); $^1$H NMR (400 MHz, DMSO-d$_6$) δ ppm 1.02 (d, J=6.26 Hz, 3H)

1.26 (s, 9H) 2.61-2.71 (m, 1H) 3.55-3.68 (m, 2H) 4.64 (d, J=5.28 Hz, 1H) 6.45 (d, J=9.19 Hz, 1H) 7.43 (d, J=8.02 Hz, 2H) 7.61 (d, J=8.02 Hz, 2H).

tert-Butyl (2S,3S)-3-hydroxy-1-(4-(trifluoromethyl) phenyl)butan-2-ylcarbamate cyclic sulfamidate A solution of tert-butyl (2S,3S)-3-hydroxy-1-(4-(trifluoromethyl)-phenyl)butan-2-ylcarbamate (2.00 g, 6.0 mmol) in 25 mL DCM and 25 mL ACN was added dropwise over 30 minutes by addition funnel to a solution of thionyl chloride (1.1 mL, 15 mmol) in 25 mL DCM at −60° C. After an additional 30 minutes, pyridine (2.4 mL, 30 mmol) was added, and the mixture was allowed to warm to room temperature over 15 hours. The mixture was evaporated, and the residue was washed with water (100 mL) and EtOAc (200 mL) in a separatory funnel. The organic layers were washed with brine/bicarbonate (1:1, 100 mL), dried over sodium sulfate, adsorbed onto a plug of silica gel and purified by chromatography through a Redi-Sep® pre-packed silica gel column (120 g), eluting with a gradient of 0% to 60% EtOAc in hexane, to provide a diastereomeric mixture of tert-butyl (2S,3S)-3-hydroxy-1-(4-(trifluoromethyl)phenyl)butan-2-ylcarbamate cyclic sulfamidite (1.53 g, 67% yield) as a colorless oil which was used without further purification. LCMS (ES+) m/z=324.1 (M−tBu). To a 1 L flask containing a diastereomeric mixture of tert-butyl (2S,3S)-3-hydroxy-1-(4-(trifluoromethyl)phenyl)butan-2-ylcarbamate cyclic sulfamidite (1.53 g, 4.03 mmol) in 22 mL ACN and 3 mL EtOAc was added sodium periodate (0.949 g, 4.44 mmol) in 11 mL water and ruthenium trichloride hydrate (9.09 mg, 0.0403 mmol). After 1 hour, the mixture was evaporated, and the residue was taken up in 1:1 EtOAc:brine (200 mL). The aqueous layer was extracted again with EA (100 mL), and the organic layers were dried over sodium sulfate and evaporated to provide tert-butyl (2S,3S)-3-hydroxy-1-(4-(trifluoromethyl)phenyl) butan-2-ylcarbamate cyclic sulfamidate (1.51 g, 94.7% yield) as a white solid. LCMS (ES+) m/z=340.1 (M−tBu); $^1$H NMR (400 MHz, CDCl$_3$) δ ppm 1.45 (d, J=6.65 Hz, 3H) 1.53 (s, 9H) 3.05 (d, J=9.00 Hz, 1H) 3.36-3.43 (m, 1H) 4.21-4.27 (m, 1H) 4.61 (dd, J=6.46, 2.93 Hz, 1H) 7.36 (d, J=8.02 Hz, 2H) 7.61 (d, J=8.22 Hz, 2H).

Examples 230-232

Examples 230-232 were synthesized in a manner similar to that described for Example 229.

Example 230

N-((2R,3S)-3-amino-4-(4-(trifluoromethyl)phenyl) butan-2-yl)-5-(isoquinolin-6-yl)thiazol-2-amine HRMS 443.15099 (M+H) calcd for C$_{23}$H$_{21}$F$_3$N$_4$S 443.15118. $^1$H NMR (400 MHz, CDCl$_3$) δ ppm 1.33 (d, J=6.46 Hz, 3H) 2.63 (dd, J=13.40, 9.68 Hz, 1H) 2.97 (dd, J=13.60, 4.40 Hz, 1H) 3.27 (ddd, J=9.19, 4.50, 4.30 Hz, 1H) 3.81 (dt, J=10.37, 6.55 Hz, 1H) 7.35 (d, J=8.02 Hz, 2H) 7.54-7.73 (m, 6H) 7.90 (d, J=8.61 Hz, 1H) 8.49 (d, J=5.67 Hz, 1H) 9.16 (s, 1H).

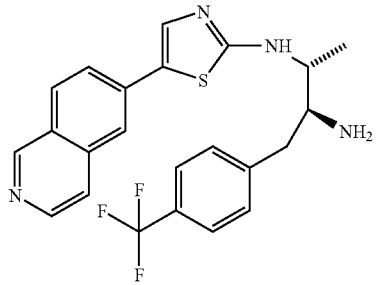

Example 231

6-(2-((2R,3S)-3-amino-4-(4-(trifluoromethyl)phenyl) butan-2-ylamino)thiazol-5-yl)benzo[d]oxazol-2(3H)-one HRMS 449.12536 (M+H) calcd for C$_{21}$H$_{19}$F$_3$N$_4$O$_2$S 449.12536. $^1$H NMR (400 MHz, CDCl$_3$) δ ppm 1.30 (d, J=6.65 Hz, 3H) 2.57-2.63 (m, 1H) 2.94-3.00 (m, 1H) 3.22-3.26 (m, 1H) 3.82-3.90 (m, 1H) 6.98 (d, 1H) 7.17 (dd, J=8.22, 1.57 Hz, 1H) 7.24 (d, J=1.37 Hz, 2H) 7.34 (d, J=8.22 Hz, 2H) 7.59 (d, J=7.83 Hz, 2H).

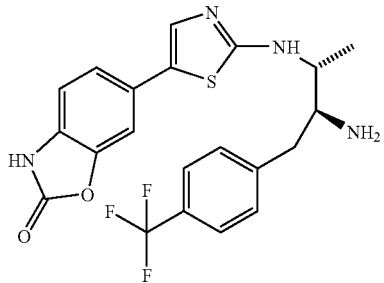

Example 232

6-(2-((2R,3S)-3-amino-4-(4-(trifluoromethyl)phenyl) butan-2-ylamino)thiazol-5-yl)-1-methyl-1H-benzo [d]imidazol-2(3H)-one MS m/z: 462 (M+1). $^1$H NMR (400 MHz, CD$_3$OD) δ ppm 1.38 (d, J=7.03 Hz, 3H), 2.97 (dd, J=14.31, 8.78 Hz, 1H), 3.24 (dd, J=14.56, 6.02 Hz, 1H), 3.43 (s, 3H), 3.84-3.88 (m, 1H), 4.14-4.20 (m, 1H), 7.07 (d, J=8.03 Hz, 1H), 7.18 (d, J=8.53 Hz, 1H), 7.24 (s, 1H), 7.39 (s, 1H), 7.57 (d, J=8.03 Hz, 2H), 7.71 (d, J=8.03 Hz, 2H).

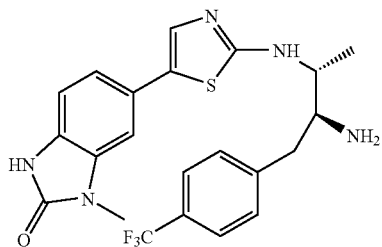

Example 233

5-(2-((2S,3S)-2-amino-3-(6-(trifluoromethyl)pyridin-3-yl)butylamino)thiazol-5-yl)indolin-2-one The title compound was prepared in a manner similar to that described in Example 109 using (E)-3-(6-(trifluoromethyl)pyridin-3-yl)acrylic acid instead of (E)-3-(4-(trifluoromethyl)phenyl)acrylic acid as the starting material as shown in Scheme 27. LCMS (M+H) 448 calc. for $C_{21}H_{21}F_3N_5OS$ 448.14. $^1H$ NMR (300 MHz, CD$_3$OD) δ ppm 8.65 (d, J=1.61 Hz, 1H) 7.99 (dd, J=8.04, 1.61 Hz, 1H) 7.78 (d, J=8.18 Hz, 1H) 7.35 (d, J=1.61 Hz, 1H) 7.26 (dd, J=8.11, 1.83 Hz, 1H) 7.21 (s, 1H) 6.86 (d, J=8.04 Hz, 1H) 3.48-3.58 (m, 1H) 3.35 (s, 2H, partially obscured) 3.20-3.26 (m, 1H) 3.00-3.11 (m, 1H) 1.93 (s, 1H) 1.43 (d, J=7.16 Hz, 3H) the NH protons are obscured in the solvent peaks.

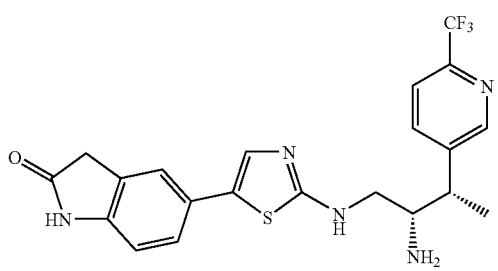

Example 234

5-(2-((2S,3S)-3-amino-4-(4-(trifluoromethyl)phenyl)butan-2-ylamino)thiazol-5-yl)indolin-2-one The title compound was prepared using tert-butyl (2S,3R)-3-hydroxy-1-(4-(trifluoromethyl)phenyl)butan-2-ylcarbamate cyclic sulfamidate according to the procedure described in Example 36. The tert-butyl (2S,3R)-3-hydroxy-1-(4-(trifluoromethyl)phenyl)butan-2-ylcarbamate cyclic sulfamidate was synthesized as shown in Scheme 45. HRMS 447.14636 (M+H) calcd for $C_{22}H_{21}F_3N_4OS$ 447.14609. $^1H$ NMR (400 MHz, CDCl$_3$) δ ppm 1.29-1.35 (m, 3H) 2.71 (dd, J=13.60, 8.90 Hz, 1H) 2.98 (dd, J=13.50, 5.28 Hz, 1H) 3.22 (ddd, J=8.75, 5.33, 3.13 Hz, 1H) 3.54 (s, 3H) 3.66-3.72 (m, J=6.50, 6.50, 6.36, 2.93 Hz, 1H) 6.83 (d, J=8.02 Hz, 1H) 7.21-7.26 (m, 2H) 7.28 (s, 1H) 7.32 (d, J=8.02 Hz, 2H) 7.57 (d, J=8.02 Hz, 2H) 8.42 (s, 1H).

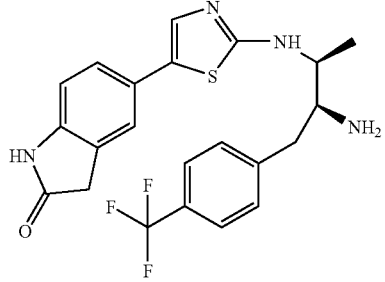

Scheme 45

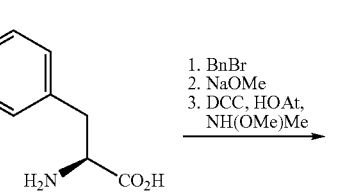

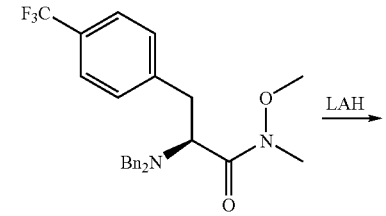

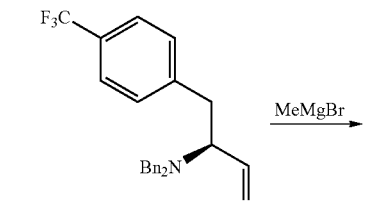

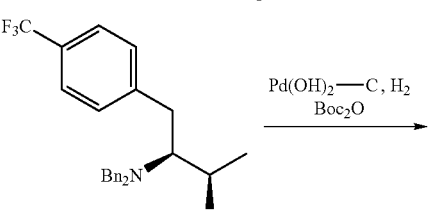

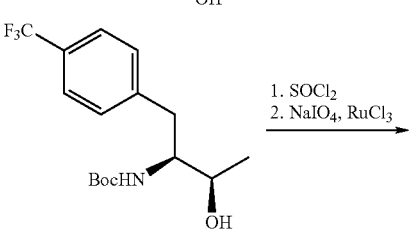

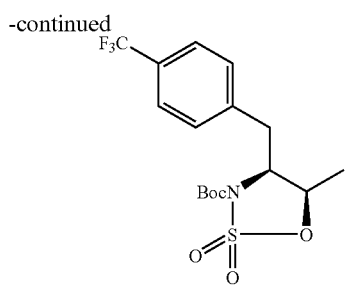

(S)-2-(Dibenzylamino)-N-methoxy-N-methyl-3-(4-(trifluoromethyl)phenyl)propanamide To a 1 L round bottom flask was added (S)-2-amino-3-(4-(trifluoromethyl)phenyl)propanoic acid (20.12 g, 86.28 mmol), 1-(bromomethyl)benzene (35.84 mL, 302.0 mmol), $K_2CO_3$ (53.66 g, 388.3 mmol), and EtOH (500 mL). The mixture was heated at 80° C. under a reflux condenser for 5 hours. The mixture was filtered through a coarse scintered glass funnel washing with EtOAc, and the filtrate was evaporated. The residue was taken up in DCM (500 mL) and washed with brine (100 mL), dried over sodium sulfate, and evaporated to a yellow oil. The crude product was stirred in 6:1:3 (dioxane 360 mL:MeOH 60 mL:2 N NaOH 120 mL, 600 mL) for 5 hours, 200 mL ether was added, but the phases did not separate. The mixture was evaporated to an aqueous solution and ether (300 mL) was added. The aqueous layer was extracted again with ether (100 mL), the ether was washed with brine (100 mL), dried over sodium sulfate, and evaporated to a yellow oil that was used without purification. LCMS m/z 414.2 (M+H).

To a 250 mL round bottom flask was added crude (S)-2-(dibenzylamino)-3-(4-(trifluoromethyl)phenyl)propanoic acid, DMF (700 mL), N,O-dimethylhydroxylamine hydrochloride (25.3 g, 259 mmol), TEA (36.0 mL, 259 mmol), 3H-[1,2,3]triazolo[4,5-b]pyridin-3-ol (17.6 g, 130 mmol), and 1,3-dicyclohexylcarbodiimide (26.7 g, 130 mmol) at 0° C. The mixture was allowed to warm to room temperature. After 18 hours, the mixture was diluted with 1 L ether, and the precipitate was filtered through a coarse scintered glass funnel washing with ether. The filtrate was washed with brine (4×200 mL) and the organic layer was again passed through a coarse scintered glass funnel. The aqueous layer was extracted with ether (200 mL), and the combined ether layers were washed with brine (100 mL) and passed through a coarse scintered glass funnel. The organic layers were dried over sodium sulfate and evaporated providing a cloudy yellow oil. The oil was passed through a medium scintered glass funnel washing with ether, and the filtrate was evaporated to provide a clear yellow oil. The crude product was loaded onto a 1.5 kg silica gel column in hexane and eluted at 400 mL/minute 0% to 70% EtOAc in hexane to provide (S)-2-(dibenzylamino)-N-methoxy-N-methyl-3-(4-(trifluoromethyl)phenyl)propanamide (26.52 g, 67.3% yield) as a light yellow oil. LCMS (ES+) m/z=457.3 (M+H). $^1$H NMR (400 MHz, DMSO-$d_6$) δ ppm 2.50 (dt, J=3.67, 1.79 Hz, 3H) 3.09-3.19 (m, 3H) 3.31 (s, 3H) 3.68-3.76 (m, 2H) 3.77-3.85 (m, 2H) 7.16-7.34 (m, 12H) 7.63 (d, J=8.22 Hz, 2H).

(S)-2-(Dibenzylamino)-3-(4-(trifluoromethyl)phenyl)propanal

To a 500 mL round-bottomed flask was added (S)-2-(dibenzylamino)-N-methoxy-N-methyl-3-(4-(trifluoromethyl)phenyl)propanamide (6.22 g, 13.6 mmol), THF (100 mL), and LAH, 1.0 M solution in THF (27.3 mL, 27.3 mmol), dropwise at 0° C. After 30 minutes, TLC (2:1 hexanes:EtOAc) showed that no starting material remained. The mixture was quenched by dropwise addition of water (6.82 mL), 2 N NaOH (6.82 mL), and water (9.83 mL). The solids were removed by filtration through a medium scintered glass funnel. The filtrate was dried over sodium sulfate and evaporated. The residue was taken up in EtOAc (200 mL) and washed with brine (50 mL). The organic layer was dried over sodium sulfate and evaporated to provide (S)-2-(dibenzylamino)-3-(4-(trifluoromethyl)phenyl)propanal (4.51 g, 83.3% yield) as a light yellow oil. LCMS (ES+) m/z=398.2. $^1$H NMR (400 MHz, CDCl$_3$) δ ppm 2.96 (dd, J=13.89, 5.67 Hz, 1H) 3.18 (dd, J=13.89, 7.43 Hz, 1H) 3.52-3.55 (m, 1H) 3.66-3.72 (m, 2H) 3.82-3.88 (m, 2H) 7.21-7.33 (m, 12H) 7.50 (d, J=8.02 Hz, 2H) 9.74 (s, 1H).

(2R,3S)-3-(Dibenzylamino)-4-(4-(trifluoromethyl)phenyl)butan-2-ol

Ether (100 mL) was added to a 500 mL round-bottom flask containing (S)-2-(dibenzylamino)-3-(4-(trifluoromethyl)phenyl)propanal (4.51 g, 11.3 mmol). The mixture was cooled to −78° C., and methylmagnesium bromide (3.16 M ether, 35.9 mL, 113 mmol) was added dropwise over 15 minutes. After 5 hours, ammonium chloride (50 mL) was added dropwise, and the mixture was warmed to room temperature. The mixture was extracted with EtOAc (2×500 mL), washed with brine (250 mL), dried over sodium sulfate, and purified by chromatography through a 300 g column eluting with a gradient of 0% to 70% EtOAc in hexane, to provide (2R,3S)-3-(dibenzylamino)-4-(4-(trifluoromethyl)phenyl)butan-2-ol (3.09 g, 65.9% yield) as a yellow oil. LCMS (ES+) m/z=414.3 (M+H). $^1$H NMR (400 MHz, CDCl$_3$) δ ppm 1.23-1.28 (m, 3H) 2.84-2.94 (m, 2H) 3.08 (dd, J=12.81, 6.36 Hz, 1H) 3.66-3.76 (m, 4H) 4.03 (dt, J=10.66, 6.41 Hz, 1H) 7.15-7.28 (m, 12H) 7.51 (d, J=8.02 Hz, 2H).

tert-Butyl (2S,3R)-3-hydroxy-1-(4-(trifluoromethyl)phenyl)butan-2-ylcarbamate To a 1 L flask containing (2R,3S)-3-(dibenzylamino)-4-(4-(trifluoromethyl)phenyl)butan-2-ol (3.09 g, 7.5 mmol), was added palladium hydroxide, 20 wt % Pd (dry basis) on carbon, wet, degussa type e101 ne/w (0.52 g, 0.75 mmol), and MeOH (70 mL). The flask was purged with a balloon of hydrogen and then stirred under a balloon of hydrogen. After 3 hours, the hydrogen was purged with a stream of nitrogen, and di-tert-butyldicarbonate (3.3 g, 15 mmol) and DMAP (0.091 g, 0.75 mmol) were added. After 1 hour, the mixture was filtered through Celite, washing with EtOAc to provide a colorless clear filtrate which was evaporated to a pale yellow solid. The solid was triturated with boiling hexane and allowed to cool to room temperature before being placed in a freezer at −20° C. After 16 hours, the solid was recovered by filtration through a medium scintered glass funnel to provide tert-butyl (2S,3R)-3-hydroxy-1-(4-(trifluoromethyl)phenyl)butan-2-ylcarbamate (1.922 g, 77% yield) as a white crystalline solid. LCMS (ES+) m/z=234.2 (M−Boc). $^1$H NMR (400 MHz, DMSO-$d_6$) δ ppm 1.08 (d, J=6.06 Hz, 3H) 1.22 (s, 9H) 2.56 (dd, J=13.50, 10.56 Hz, 1H) 3.09 (dd, J=13.40, 2.64 Hz, 1H) 3.40-3.54 (m, 2H) 4.72 (d, J=5.48 Hz, 1H) 6.59 (d, J=9.19 Hz, 1H) 7.39 (d, J=8.02 Hz, 2H) 7.59 (d, J=8.02 Hz, 2H).

tert-Butyl (2S,3R)-3-hydroxy-1-(4-(trifluoromethyl)phenyl)butan-2-ylcarbamate cyclic sulfamidate To a 250 mL round bottom flask was added thionyl chloride (1.05 mL, 14.4 mmol) and DCM (33 mL). The mixture was cooled to −60° C. tert-Butyl (2S,3R)-3-hydroxy-1-(4-(trifluoromethyl)phenyl)butan-2-ylcarbamate (1.922 g, 5.77 mmol) was added dropwise in DCM-ACN (1:1 40 mL) over 25 minutes. After 30 minutes, pyridine (2.33 mL, 28.8 mmol) was added. After 16 hours, the mixture was evaporated and the residue was taken up in brine:EtOAc (1:1, 100 mL). The organic layer was washed with brine (50 mL), ammonium chloride (50 mL), and brine (50 mL), and then dried over sodium sulfate, adsorbed onto a plug of silica gel and purified by chromatography through a Redi-Sep® pre-packed silica gel column (120 g), eluting with a gradient of 0% to 100% EtOAc in hexane, to give the intermediate sulfamidite as a mixture of diastereomers that was used without further purification (1.31 g, 59.9% yield). To a solution of the sulfamidites (1.31 g, 3.45 mmol) in 40 mL ACN and 8 mL EtOAc at 0° C. was added sodium periodate (0.812 g, 3.80 mmol) in 20 mL water, followed by ruthenium trichloride hydrate (7.8 mg, 0.0345 mmol). After 2 hours, the mixture was evaporated, and the residue was taken up in brine:EtOAc (1:1, 200 mL), and washed with brine (100 mL). The organic layer was dried over sodium sulfate and evaporated to provide tert-butyl (2S,3R)-3-hydroxy-1-(4-(trifluoromethyl)phenyl)butan-2-ylcarbamate cyclic sulfamidate (1.36 g, 99.6% yield) as a white amorphous solid. LCMS (ES+) m/z=340.1 (M−tBu). $^1$H NMR (400 MHz, CDCl$_3$) δ ppm 1.32 (s, 9H) 1.53 (d, J=6.46 Hz, 3H) 3.02-3.16 (m, 2H) 4.53 (ddd, J=9.49, 5.18, 4.89 Hz, 1H) 5.12 (dd, J=6.46, 4.50 Hz, 1H) 7.40 (d, J=8.22 Hz, 2H) 7.57 (d, J=8.02 Hz, 2H).

Examples 235-237

Examples 235-237 were synthesized in a manner similar to that described in Example 234.

Example 235

N-((2S,3S)-3-amino-4-(4-(trifluoromethyl)phenyl)butan-2-yl)-5-(isoquinolin-6-yl)thiazol-2-amine HRMS 443.15267 (H+H) calcd for C$_{23}$H$_{21}$F$_3$N$_4$S 443.15118. $^1$H NMR (400 MHz, CDCl$_3$) δ ppm 1.34 (t, J=6.06 Hz, 3H) 2.72 (dd, J=13.50, 8.80 Hz, 1H) 2.98 (dd, J=13.50, 5.28 Hz, 1H) 3.25 (ddd, J=8.66, 5.62, 2.74 Hz, 1H) 3.74 (qd, J=6.62, 2.64 Hz, 1H) 7.32 (d, J=8.02 Hz, 2H) 7.56 (s, 1H) 7.58 (d, J=7.43 Hz, 3H) 7.67 (s, 1H) 7.73 (dd, J=8.61, 1.76 Hz, 1H) 7.91 (d, J=8.61 Hz, 1H) 8.49 (d, J=5.87 Hz, 1H) 9.16 (s, 1H).

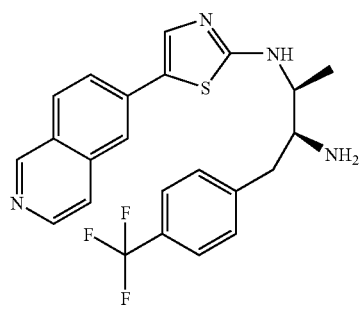

Example 236

6-(2-((2S,3S)-3-amino-4-(4-(trifluoromethyl)phenyl)butan-2-ylamino)thiazol-5-yl)benzo[d]oxazol-2(3H)-one HRMS 449.12438 (M+H) calcd for C$_{21}$H$_{19}$F$_3$N$_4$O$_2$S 449.12536. $^1$H NMR (400 MHz, CDCl$_3$) δ ppm 1.33 (d, J=6.65 Hz, 3H) 2.70 (dd, J=13.50, 9.00 Hz, 1H) 2.97 (dd, J=13.69, 5.28 Hz, 1H) 3.21 (ddd, J=8.75, 5.33, 2.93 Hz, 1H) 3.65-3.70 (m, 1H) 6.98-7.02 (d, 1H) 7.19 (dd, J=8.12, 1.66 Hz, 1H) 7.27 (s, 1H) 7.32 (d, J=7.82 Hz, 2H) 7.57 (d, J=8.02 Hz, 2H).

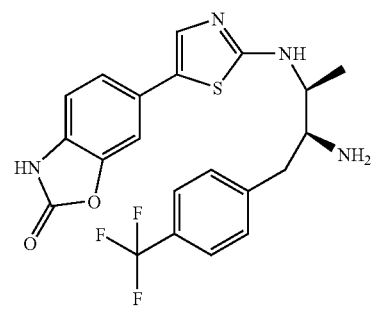

Example 237

6-(2-((2S,3S)-3-amino-4-(4-(trifluoromethyl)phenyl)butan-2-ylamino)thiazol-5-yl)-1l-methyl-1H-benzo[d]imidazol-2(3H)-one MS m/z: 462 (M+1). $^1$H NMR (400 MHz, CD$_3$OD) δ ppm 1.44 (d, J=6.85 Hz, 3H), 2.99 (dd, J=14.38, 8.51 Hz, 1H), 3.26 (d, J=5.48 Hz, 1H), 3.40-3.45 (m, 3H), 3.83 (dt, J=8.41, 5.87 Hz, 1H), 4.03-4.10 (m, 1H), 7.08 (d, J=8.02 Hz, 1H), 7.17-7.20 (m, 1H), 7.25 (d, J=1.37 Hz, 1H), 7.41 (s, 1H), 7.52 (d, J=8.02 Hz, 2H), 7.70 (d, J=8.22 Hz, 2H).

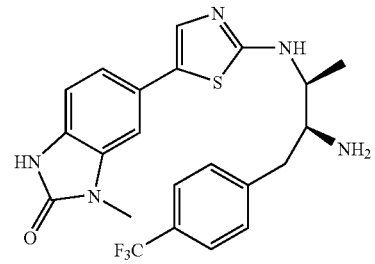

Example 238

5-(2-((S)-2-amino-3-(5-methoxy-6-(trifluoromethyl)pyridin-3-yl)propylamino)thiazol-5-yl)isoindolin-1-one The title compound was synthesized in a manner similar to that described in Example 173 using 5-(4,4,5,5-tetramethyl-1,3,2-dioxaborolan-2-yl)isoindolin-1-one instead of isoquinolin-6-ylboronic acid. 5-(4,4,5,5-Tetramethyl-1,3,2-dioxaborolan-2-yl)isoindolin-1-one was prepared in a manner similar to that described in Scheme 1 by reacting 5-bromoisoindolin-1-one with bis(pinacolato)diboron. 5-Bromoisoindolin-1-one was prepared according to procedures for the preparation of isoindolin-1-one analogs described in WO 2006/012374A1. LCMS (M+H) 464, calc. for $C_{21}H_{20}F_3N_5O_2S$ 463.5.

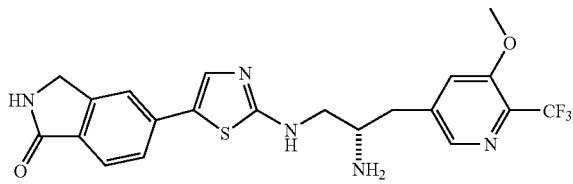

Example 239

3,5-(2-((S)-2-amino-3-(5-chlorothiophen-2-yl)propylamino)thiazol-5-yl)isoindolin-1-one This compound was synthesized in a manner similar to that described in Example 238. LCMS (M+H) 405, calc. for C18H17ClN4OS2 404.1.

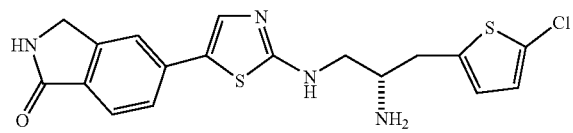

Example 240

5-(2-((S)-2-amino-3-(4-(trifluoromethyl)phenyl)propylamino)thiazol-5-yl)isoindolin-1-one The title compound was synthesized in a manner similar to that described for Example 238. LCMS (M+H) 433 calc. for C21H19F3N4OS 432.5.

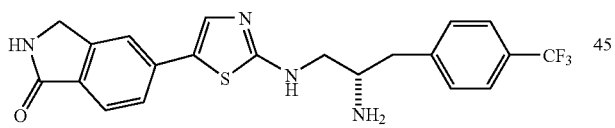

Example 241

5-(2-((2S,3S)-2-amino-4-methoxy-3-(4-(trifluoromethyl)phenyl)butylamino)thiazol-5-yl)indolin-2-one The title compound was synthesized in a manner similar to that described in Example 158 using tert-butyl (2S,3S)-1-hydroxy-4-methoxy-3-(4-(trifluoromethyl)phenyl)-butan-2-ylcarbamate instead of (2S,3S)-3-(tert-butoxycarbonyl)-4-hydroxy-2-(4-(trifluoromethyl)phenyl)butyl pivalate as shown in Scheme 36. Tert-butyl (2S,3S)-1-hydroxy-4-methoxy-3-(4-(trifluoromethyl)phenyl)butan-2-ylcarbamate was synthesized as shown in Scheme 46. MS m/z: 477 (M+1). $^1$H NMR (400 MHz, CD$_3$OD) δ ppm 7.66 (d, J=8.03 Hz, 2H) 7.51-7.59 (m, 2H) 7.38 (s, 1H) 7.23-7.34 (m, 2H) 6.88 (d, J=8.03 Hz, 1H) 3.67-3.87 (m, 2H) 3.43-3.52 (m, 2H) 3.36 (s, 3H) 3.18-3.29 (m, 1H) 3.16 (q, J=6.02 Hz, 1H).

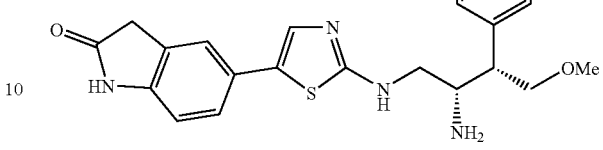

Scheme 46

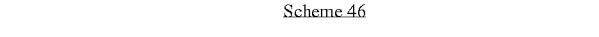

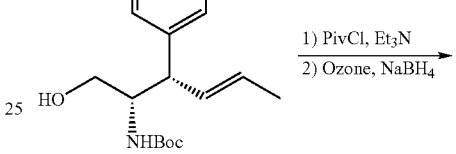

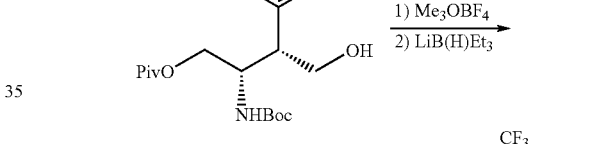

tert-Butyl (2S,3S)-1-hydroxy-4-methoxy-3-(4-(trifluoromethyl)phenyl)butan-2-ylcarbamate tert-Butyl (2S,3S,E)-1-hydroxy-3-(4-(trifluoromethyl)phenyl)hex-4-en-2-ylcarbamate (2.35 g, 6.5 mmol) was taken up in 60 mL of CH$_2$Cl$_2$ and chilled to 0° C. TEA (2.7 mL, 20 mmol), pivaloyl chloride (0.97 mL, 7.8 mmol), and N,N-dimethylpyridin-4-amine (0.040 g, 0.33 mmol) were added. The mixture was stirred for 12 hours. The reaction was quenched with 50 mL of aqueous NaHCO$_3$ and stirred for 10 minutes. The mixture was partitioned, and the aqueous portion was extracted with 50 mL of CH$_2$Cl$_2$. The combined organic extracts were dried over MgOS$_4$. Filtration and concentration under reduced pressure afforded a yellow solid that was taken up in 10% EtOAc/hexanes and filtered through a plug of silica gel. The solvent was removed under reduced pressure, affording (2S,3S,E)-2-(tert-butoxycarbonyl)-3-(4-

(trifluoromethyl)-phenyl)hex-4-enyl pivalate (1.8 g, 62% yield) as a light yellow solid that was carried on without any further purification.

(2S,3S,E)-2-(tert-Butoxycarbonyl)-3-(4-(trifluoromethyl)phenyl)hex-4-enyl pivalate (1.8 g, 4.1 mmol) was taken up in 40 mL of 1:1 MeOH:CH$_2$Cl$_2$ and chilled to −78° C. Ozone was bubbled through the mixture until a blue color persisted. Nitrogen was then bubbled through the mixture for 15 minutes. Sodium borohydride (0.77 g, 20 mmol) was added, and the mixture was warmed to room temperature. The mixture was stirred for 2 hours. The mixture was quenched with 40 mL of aqueous NH$_4$Cl. After 30 minutes, the mixture was diluted with 20 mL of water and extracted three times with 40 mL of CH$_2$Cl$_2$. The combined organic extracts were dried over MgSO$_4$. Filtration and concentration under reduced pressure afforded (2S,3S)-2-(tert-butoxycarbonyl)-4-hydroxy-3-(4-(trifluoromethyl)phenyl)butyl pivalate (1.8 g, 100% yield) as a white crystalline solid.

Trimethyloxonium tetrafluoroborate (2.3 g, 16 mmol) was taken up in 10 mL of CH$_2$Cl$_2$. Proton sponge (3.3 g, 16 mmol) and (2S,3S)-2-(tert-butoxycarbonyl)-4-hydroxy-3-(4-(trifluoromethyl)phenyl)butyl pivalate (2.25 g, 5.2 mmol) were added to the mixture in 15 mL of CH$_2$Cl$_2$. The mixture was shielded from light and stirred for 3 hours. The mixture was carefully quenched with 70 mL of 10% aq HCl and extracted three times with 100 mL of CH$_2$Cl$_2$. The combined organic extracts were dried over MgSO$_4$. Filtration and concentration under reduced pressure, followed by flash chromatography on silica gel (5% to 25% EtOAc/hexanes) afforded (2S,3S)-2-(tert-butoxycarbonyl)-4-methoxy-3-(4-(trifluoromethyl)phenyl)butyl pivalate (1.4 g, 60% yield) as a white solid. $^1$H NMR (400 MHz, CDCl$_3$) δ ppm 7.58 (d, J=8.02 Hz, 2H) 7.34 (d, J=8.02 Hz, 2H) 4.42-4.32 (m, 2H) 4.15-4.00 (m, 2H) 3.73-3.63 (m, 2H) 3.34 (s, 3H) 1.35 (s, 9H) 1.19 (s, 9H).

(2S,3S)-2-(Tert-butoxycarbonyl)-4-methoxy-3-(4-(trifluoromethyl)phenyl)butyl pivalate (1.5 g, 3.4 mmol) was taken up in 30 mL of THF and chilled to −78° C. Super hydride, 1.0 M in THF (8.4 mL, 8.4 mmol), was added slowly to the mixture. After 5 minutes, the mixture was warmed to 0° C. After 30 minutes, the mixture was quenched with 20 mL of aq NH$_4$Cl. The mixture was extracted twice with 30 mL of EtOAc, and the combined organic extracts were washed with 20 mL of brine and dried over MgSO$_4$. Filtration and concentration under reduced pressure, followed by flash chromatography on silica gel (20% to 50% EtOAc/hexanes) afforded tert-butyl (2S,3S)-1-hydroxy-4-methoxy-3-(4-(trifluoromethyl)phenyl)butan-2-ylcarbamate (0.85 g, 70% yield) as a white solid. $^1$H NMR (400 MHz, CDCl$_3$) δ ppm 7.57 (d, J=8.22 Hz, 2H) 7.39 (d, J=8.02 Hz, 2H) 4.84 (s, 1H) 4.02-3.91 (m, 1H) 3.78-3.59 (m, 4H) 3.39 (s, 3H) 3.30-3.22 (m, 1H) 2.83-2.76 (m, 1H) 1.33 (s, 9H).

Example 242

(2S,3S)-3-amino-4-(5-(2-oxoindolin-5-yl)thiazol-2-ylamino)-2-(4-(trifluoromethyl)phenyl)butyl pivalate The title compound was synthesized in a manner similar to the procedure described in Example 158. MS m/z: 554 (M+1); $^1$H NMR (400 MHz, DMSO-d6) δ ppm 7.72-2.67 (m, 3H), 7.54 (d, J=8.0 Hz, 2H), 7.29 (d, J=10.9 Hz, 1H), 7.28 (s, 1H), 7.20 (d, J=9.7 Hz, 1H), 6.69 (d, J=8/0 Hz, 1H), 4.47-4.34 (m, 2H), 3.53-2.95 (m, 6H), 0.96 (s, 9H).

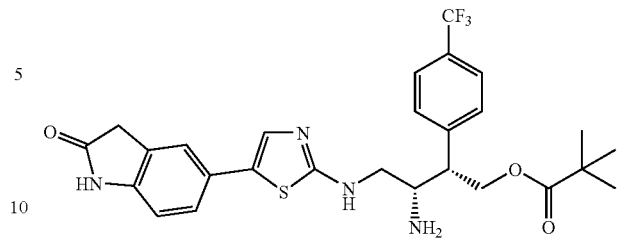

Example 243

5-(2-((2S,3S)-2-amino-4-hydroxy-3-(4-(trifluoromethyl)phenyl)pentylamino)thiazol-5-yl)indolin-2-one The title compound was synthesized in a manner similar to Example 158 starting with tert-butyl (2S,3S)-1-(5-bromothiazol-2-yl-(Boc)-amino)-4-hydroxy-3-(4-(trifluoromethyl)phenyl)butan-2-ylcarbamate as shown in Scheme 36. After an oxidation with Dess-Martin periodinane, tert-butyl (2S,3S)-1-(5-bromothiazol-2-yl-(Boc)-amino)-4-hydroxy-3-(4-(trifluoromethyl)phenyl)butan-2-ylcarbamate was converted to tert-butyl (2S,3S)-1-(5-bromothiazol-2-yl-(Boc)-amino)-4-oxo-3-(4-(trifluoromethyl)phenyl)butan-2-ylcarbamate. The aldehyde tert-butyl (2S,3S)-1-(5-bromothiazol-2-yl-(Boc)-amino)-4-oxo-3-(4-(trifluoromethyl)-phenyl)butan-2-ylcarbamate reacted with methylmagnesium bromide to generate tert-butyl (2S,3S,4S)-1-(5-bromothiazol-2-yl-(Boc)-amino)-4-hydroxy-3-(4-(trifluoromethyl)phenyl)pentan-2-ylcarbamate as the intermediate for the Suzuki reaction with 5-(4,4,5,5-tetramethyl-1,3,2-dioxaborolan-2-yl)indolin-2-one leading to the final product. MS m/z: 477 (M+1). $^1$H NMR (400 MHz, CD$_3$OD) δ ppm 7.68 (d, J=8.22 Hz, 2H) 7.54 (d, J=8.22 Hz, 2H) 7.34 (d, J=1.56 Hz, 1H) 7.26 (dd, J=8.12, 1.86 Hz, 1H) 6.87 (d, J=8.22 Hz, 1H) 4.39 (dd, J=9.00, 6.06 Hz, 1H) 3.77-3.82 (m, 1H) 3.41 (dd, J=13.69, 5.28 Hz, 1H) 3.37 (s, 3H) 3.20 (dd, J=13.50, 8.02 Hz, 1H) 2.92 (dd, J=9.00, 3.52 Hz, 1H) 1.08 (d, J=6.26 Hz, 3H).

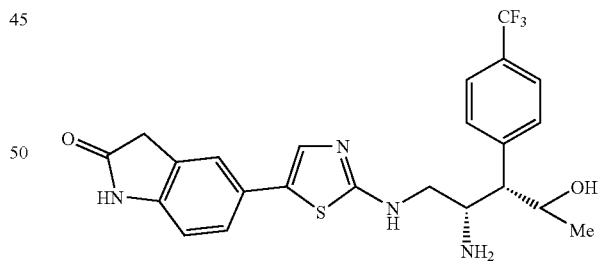

Example 244

5-(2-(2-amino-3-(methoxymethoxy)-3-(4-(trifluoromethyl)phenyl)propylamino)thiazol-5-yl)indolin-2-one This compound was synthesized in a manner similar to Example 241 using the Boc-protected amino alcohol intermediate tert-butyl 3-hydroxy-1-(methoxymethoxy)-1-(4-(trifluoromethyl)phenyl)propan-2-ylcarbamate which was synthesized as shown in Scheme 47. LCMS (API-ES) m/z: 493 (M$^+$+H).

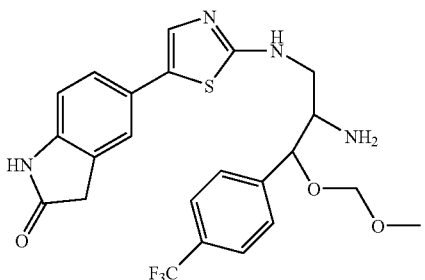

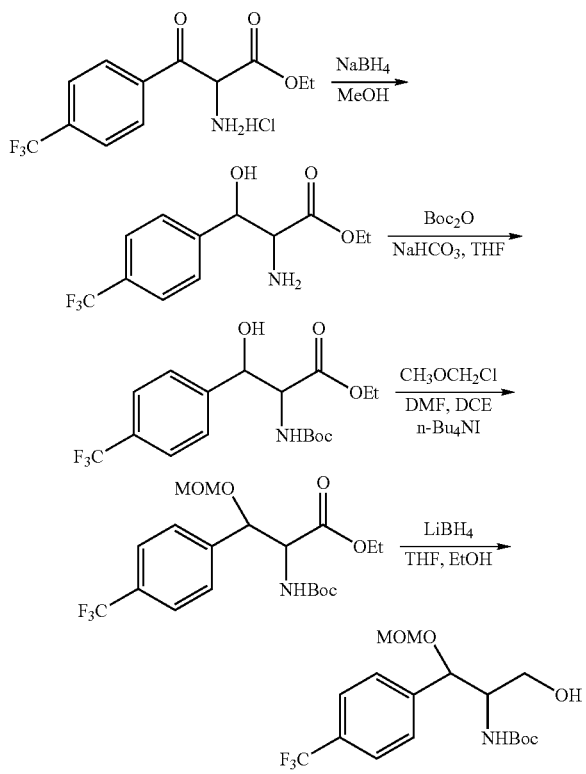

Ethyl 2-amino-3-hydroxy-3-(4-(trifluoromethyl)phenyl)propanoate

Ethyl 2-amino-3-oxo-3-(4-(trifluoromethyl)phenyl)propanoate hydrochloride (20.00 g, 64.17 mmol), was prepared as described by Singh, J., Tetrahedron Letters 34 (2), 211-214 (1993), was charged into a 500 mL round-bottomed flask and mixed with MeOH (160 mL). Sodium borohydride (3.641 g, 96.25 mmol) was added to the above mixture slowly at 0° C. The cooling bath was removed after the addition. The mixture was stirred at room temperature for 2 hours, and then filtered through a silica gel column in a funnel. The silica gel was washed with 10% MeOH (2.0M $NH_3$)—$CH_2Cl_2$. The filtrate was concentrated in vacuo, and the crude product was triturated with 25% EtOAc-Hexane to provide the pure product as a white solid. LCMS (API-ES) m/z (%): 278 ($M^+$+H).

Ethyl 2-(tert-butoxycarbonyl)-3-hydroxy-3-(4-(trifluoromethyl)phenyl)propanoate

To a solution of ethyl 2-amino-3-hydroxy-3-(4-(trifluoromethyl)phenyl)propanoate (7.27 g, 26.2 mmol) in THF (50 mL) was added di-tert-butyl dicarbonate (6.87 g, 31.5 mmol) and sodium bicarbonate (4.35 g, 52.4 mmol) at room temperature. The mixture was stirred at room temperature overnight, and the solid was filtered through a funnel. The filtrate was concentrated in vacuo to provide the product as a white solid. LCMS (API-ES) m/z (%): 278 ($M^+$+H−100).

Ethyl 2-(tert-butoxycarbonyl)-3-(methoxymethoxy)-3-(4-(trifluoromethyl)phenyl)propanoate To a solution of ethyl 2-(tert-butoxycarbonyl)-3-hydroxy-3-(4-(trifluoromethyl)phenyl)propanoate (9.25 g, 24.5 mmol) in DMF (3.78 mL, 49.0 mmol) and 1,2-dichloroethane (20 mL) was added tetra-n-butylammonium iodide (9.51 g, 25.7 mmol), chloromethyl methyl ether (5.59 mL, 73.5 mmol) and N,N-diisopropylethylamine (12.8 mL, 73.5 mmol). The mixture was gradually heated to 45° C. and stirred overnight. The crude product was concentrated in vacuo, diluted with $CH_2Cl_2$ and washed three times with water. The organic phase was dried over $Na_2SO_4$ and concentrated in vacuo. The crude product was purified by silica gel chromatography: 16%-20%-25% EtOAc-Hexane. The product was obtained as a white solid. LCMS (API-ES) m/z (%): 322 (M+1−100).

tert-Butyl 3-hydroxy-1-(methoxymethoxy)-1-(4-(trifluoromethyl)phenyl)propan-2-ylcarbamate To a solution of ethyl 2-(tert-butoxycarbonyl)-3-(methoxymethoxy)-3-(4-(trifluoromethyl)phenyl)propanoate (8.30 g, 20 mmol) in THF (100 mL) and EtOH (35 mL, 591 mmol) was added lithium borohydride, 2.0 M solution in THF (20 mL, 39 mmol) at 0° C. The reaction mixture was stirred at 0° C. for 1 hour. The cooling bath was removed, and the mixture was stirred at room temperature for 1 hour. The reaction was quenched with 5% citric acid in water. The resulting mixture was concentrated in vacuo, and the residue was extracted twice with EtOAc. The organic phase was washed with saturated $NaHCO_3$, water and brine, dried over $Na_2SO_4$, and concentrated in vacuo. The product was obtained as a white solid. LCMS (API-ES) m/z (%): 280 (M+1−100).

Examples 245-247

Examples 245-247 were synthesized in a manner similar to that described in Example 241.

Example 245

6-(2-((2S,3S)-2-amino-4-methoxy-3-(4-(trifluoromethyl)phenyl)butylamino)thiazol-5-yl)benzo[d]oxazol-2(3H)-one HRMS(M+1): Calcd 479.13592, found 479.14337. $^1$H NMR (400 MHz, $CD_3OD$) δ ppm 7.65 (d, J=8.2 Hz, 2H) 7.53 (d, J=8.2 Hz, 2H) 7.34 (d, J=1.6 Hz, 1H) 7.29 (s, 1H) 7.23 (dd, J=8.1 Hz, 1.6 Hz, 1H) 7.05 (d, J=8.2 Hz, 1H) 3.86-3.81 (m, 1H) 3.78-3.73 (m, 1H) 3.53-3.44 (m, 2H) 3.35 (s, 3H) 3.23 (d, J=5.9 Hz, 1H) 3.15 (d, J=6.1 Hz, 1H).

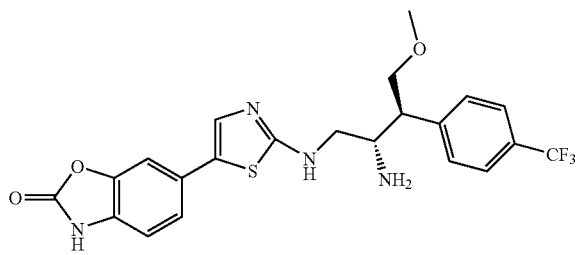

Example 246

N-((2S,3S)-2-amino-4-methoxy-3-(4-(trifluoromethyl)phenyl)butyl)-5-(isoquinolin-6-yl)thiazol-2-amine HRMS(M+1): Calcd 473.16174, found 473.17425; $^1$H NMR (400 MHz, CDCl$_3$) δ ppm 9.17 (s, 1H) 8.49 (d, J=5.87 Hz, 1H) 7.90 (d, J=8.61 Hz, 1H) 7.55-7.74 (m, 6H) 7.42 (d, J=8.02 Hz, 2H) 3.66-3.77 (m, 2H) 3.62 (dd, J=12.72, 3.91 Hz, 1H) 3.49 (td, J=7.34, 4.11 Hz, 1H) 3.34-3.39 (m, 3H) 3.26 (dd, J=12.81, 7.73 Hz, 1H) 3.01 (q, J=6.26 Hz, 1H).

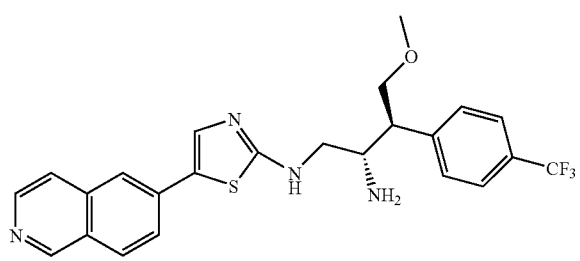

Example 247

6-(2-((2S,3S)-2-amino-4-methoxy-3-(4-(trifluoromethyl)phenyl)butylamino)thiazol-5-yl)-1-methyl-1H-benzo[d]imidazol-2(3H)-one HRMS(M+1): Calcd 492.16756, found 492.18182; $^1$H NMR (400 MHz, DMSO-d6) δ ppm 10.90 (broad s, 1H), 7.68 (d, J=7.8 Hz, 2H), 7.54 (d, J=8.2 Hz, 2H), 7.37 (s, 1H), 7.20 (s, 1H), 7.03 (d, J=7.2 Hz, 1H), 6.96 (1H, J=8.2 Hz), 3.78-3.43 (m, 2H), 3.37-3.25 (m, 2H), 3.30 (s, 3H), 3.23 (s, 3H), 3.19-3.12 (m, 1H), 3.06-2.98 (m, 1H).

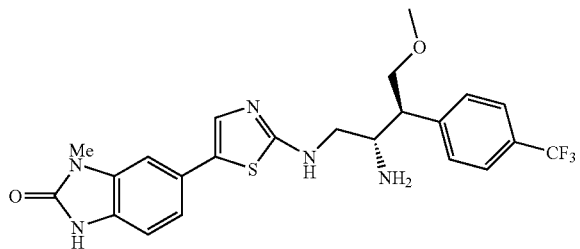

Example 248

(2S,3S)-3-amino-4-(5-(2-oxoindolin-5-yl)thiazol-2-ylamino)-2-(4-(trifluoromethyl)phenyl)butyl acetate The title compound was synthesized in a manner similar to that described in Example 243. MS m/z: 506 (M+1); $^1$H NMR (400 MHz, CD$_3$OD) δ ppm 7.67 (d, J=8.2 Hz, 2H), 7.53 (d, J=8.2 Hz, 2H), 7.37 (s, 1H), 7.28 (dd, J=1.8 Hz, 8.0 Hz, 1H), 7.23 (s, 1H), 6.87 (d, J=8.2 Hz, 1H), 5.54-5.44 (m, 2H), 3.57-3.13 (m, 6H), 1.95 (s, 3H).

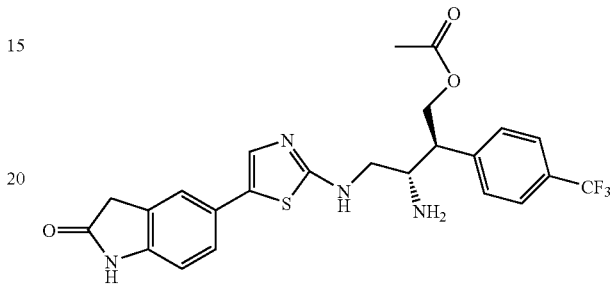

Example 249

6-(2-((S)-2-amino-3-(4-(trifluoromethyl)phenyl)propylamino)-4-(2-fluorophenyl)thiazol-5-yl)-1-methyl-1H-benzo[d]imidazol-2(3H)-one LCMS (M+H) 542 calc. for C$_{27}$H$_{24}$F$_4$N$_5$OS 542.16. $^1$H NMR (400 MHz, CD$_3$OD) δ ppm 7.64 (d, J=8.22 Hz, 2H) 7.51 (d, J=8.02 Hz, 2H) 7.33-7.42 (m, 2H) 7.16 (t, J=7.53 Hz, 1H) 7.10 (t, J=9.10 Hz, 1H) 6.85-6.95 (m, 2H) 6.81 (s, 1H) 3.60 (dd, J=6.85, 4.30 Hz, 1H) 3.50-3.57 (m, 1H) 3.35-3.45 (m, 1H) 3.21 (s, 3H) 3.05 (dd, J=13.69, 6.85 Hz, 1H) 2.90 (dd, J=13.79, 7.14 Hz, 1H).

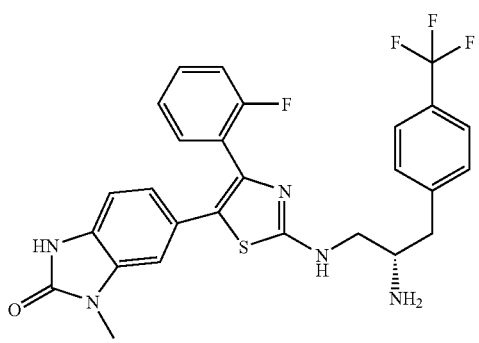

Example 250

6-(2-((S)-2-amino-3-(4-fluorophenyl)propylamino)-4-(2-fluorophenyl)thiazol-5-yl)-1-methyl-1H-benzo[d]imidazol-2(3H)-one LCMS (M+H) 492 calc. for C$_{26}$H$_{24}$F$_2$N$_5$OS 492.17. $^1$H NMR (400 MHz, CD$_3$OD) δ ppm 7.35-7.41 (m, 2H) 7.28-7.34 (m, 2H) 7.16 (t, J=7.53 Hz, 1H) 7.02-7.13 (m, 3H) 6.85-6.94 (m, 2H) 6.82 (s, 1H) 3.50-3.58 (m, 2H) 3.38-3.44 (m, 1H) 3.35-3.37 (m, 1H) 2.96 (dd, 3H) 2.82 (dd, 1H).

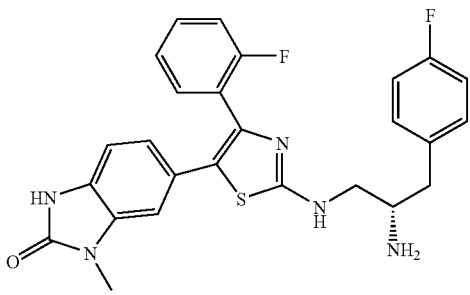

Example 251

N-((S)-2-amino-3-(1H-indol-3-yl)propyl)-5-(benzo[d][1,3]dioxol-5-yl)thiazol-2-amine The title compound was synthesized in a similar manner to that as described in Example 35. LCMS (M+1) 393 calc. For $C_{21}H_{21}N_4O_2S$ 393.5.

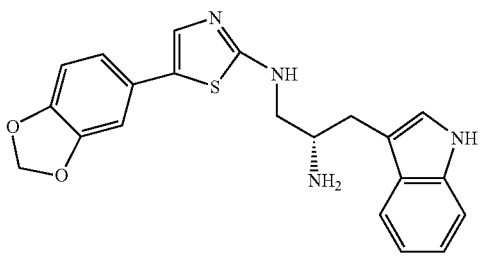

Example 252

7-(2-((S)-2-amino-3-(4-(trifluoromethyl)phenyl)propylamino)thiazol-5-yl)phthalazin-1(2H)-one The title compound was synthesized in a manner similar to that described in Example 82. LCMS (M+1) 446 calc. For $C_{21}H_{19}F_3N_5OS$ 446.5.

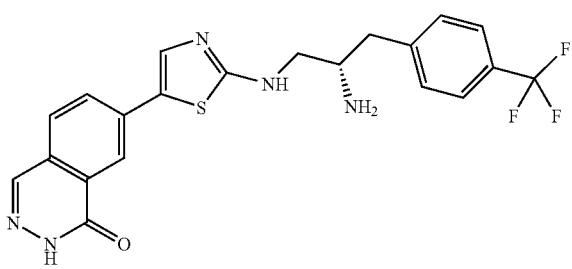

Example 253

N-((S)-2-Amino-3-(4-(trifluoromethyl)phenyl)propyl)-5-(quinazolin-7-yl)thiazol-2-amine LCMS (API-ES) m/z (%): 429.5 (100%, M+H). This compound was synthesized in four steps staring from 7-bromoquinazolin-2-amine.

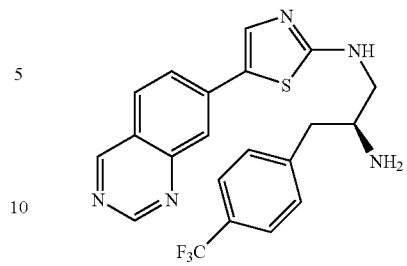

7-Bromo-2-iodoquinazoline

To a stirred suspension of 7-bromoquinazolin-2-amine (1.30 g, 5802 μmol) in THF (475 μL, 5802 μmol) was added CuI (1105 mg, 5802 μmol) and isoamyl nitrite (3897 μL, 29010 μmol), and the overall mixture was heated at reflux for 2 hours. After cooling, the mixture was diluted with EtOAc and 1 N HCl$_{(aq)}$. The separated aqueous layer was extracted with EtOAc (10 mL×2), and the combined organic layers were washed with brine, dried over $Na_2SO_4$, and concentrated to give the crude residue which was purified with flash column chromatography (ISCO Combiflash system, pure hexanes→20% ethyl acetates in hexanes) to obtain the desired product 7-bromo-2-iodoquinazoline (0.50 g, 26%) as a pale yellow solid. LCMS (API-ES) m/z (%): 335.9 (100%, M$^+$+H).

7-Bromoquinazoline

To a mixture of 7-bromo-2-iodoquinazoline (69 mg, 206 μmol), triphenylphosphine (5.4 mg, 21 μmol), and Pd(OAc)$_2$ (3.2 mg, 14 μmol) in DMF (4.0 mL) was added TEA (72 μL, 515 μmol) and formic acid (9.5 μL, 247 μmol). The reaction mixture was stirred at 70° C. overnight. After cooling, the reaction mixture was concentrated, and the crude residue was dissolved in DCM and mixed with SiO$_2$. The solvent was evaporated, and the residue was purified with flash column chromatography (pure DCM→3% MeOH in DCM) to obtain the desired product 7-bromoquinazoline (22 mg, 51%) as a white solid. LCMS (API-ES) m/z (%): 210.0 (100%, M$^+$+H).

tert-Butyl 5-(quinazolin-7-yl)thiazol-2-ylcarbamate

To a stirred mixture of flame-dried LiCl (45 mg, 1052 μmol), 7-bromoquinazoline (22 mg, 105 μmol), and Pd(Ph$_3$P)$_4$ (6.1 mg, 5.3 μmol), was added a solution of tert-butyl 5-(tributylstannyl)thiazol-2-ylcarbamate (77 mg, 158 μmol) in DMF (1.50 mL, 19372 μmol). The resulting mixture was stirred at 80° C. overnight. The mixture was concentrated, and the crude residue was dissolved in DCM and mixed with SiO$_2$. The solvent was evaporated, and the residue was purified with flash column chromatography (pure DCM→5% MeOH in DCM) followed by washing with ether to obtain the desired product tert-butyl 5-(quinazolin-7-yl)thiazol-2-ylcarbamate (16 mg, 46%) as a pale yellow solid. LCMS (API-ES) m/z (%): 329.4 (100%, M$^+$+H).

N-((S)-2-Amino-3-(4-(trifluoromethyl)phenyl)propyl)-5-(quinazolin-7-yl)thiazol-2-amine To a stirred orange mixture of tert-butyl 5-(quinazolin-7-yl)thiazol-2-ylcarbamate (22 mg, 67 μmol) and Cs$_2$CO$_3$ (44 mg, 134 μmol) in DMF (1.0 mL), was slowly added a solution of the cyclic sulfamidate (38 mg, 100 μmol) in DMF (0.5 mL) at 50° C. The resulting light yellow mixture was stirred at 50° C. for 30 minutes. The mixture was then cooled to 0° C. and was then diluted with EtOAc and 1N HCl$_{(aq)}$ and the entire mixture was stirred at room temperature for 30 minutes. The layers were separated, the aqueous layer was extracted with EtOAc (5 mL×3), and the combined organic layers were washed with brine, dried over Na$_2$SO$_4$, and concentrated to give the crude residue, which was taken up in a solution of DCM (1.5 mL), and TFA (1.5 mL) was slowly added. The overall solution was stirred at room temperature for 30 minutes and concentrated. The crude residue was dissolved in DCM and mixed with silica. The solvent was evaporated, and the residue was purified with flash column chromatography (pure DCM→10% MeOH in DCM) to obtain N-((S)-2-amino-3-(4-(trifluoromethyl)phenyl)propyl)-5-(quinazolin-7-yl)thiazol-2-amine (12 mg, 42%) as a yellow solid.

Example 254

N-((S)-2-amino-3-(4-(trifluoromethyl)phenyl)propyl)-5-(cinnolin-6-yl)thiazol-2-amine LCMS (API-ES) m/z (%): 430.5 (100%, M$^+$+H). The title compound was synthesized in a manner similar to that described in Example 253. tert-Butyl 5-(cinnolin-6-yl)thiazol-2-ylcarbamate was used as a intermediate instead of tert-Butyl 5-(quinazolin-7-yl)thiazol-2-ylcarbamate. tert-Butyl 5-(cinnolin-6-yl)thiazol-2-ylcarbamate was synthesized in two steps starting from 6-bromo-4-chlorocinnoline.

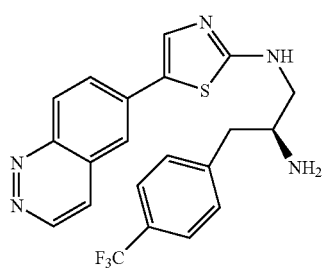

6-Bromocinnoline

To a stirred mixture of bis(pinacolato)diboron (6.4 g, 25 mmol), potassium acetate (6.8 g, 69 mmol), dichloro[1,1'bis(diphenylphoshino)ferrocene]palladium(II)dichloromethane adduct (0.50 g, 0.69 mmol), and 6-bromo-4-chlorocinnoline (5.60 g, 23 mmol), was added DMF (50.00 mL, 646 mmol) and the overall mixture was heated at 80° C. overnight. After cooling and checking by LC-MS, the overall mixture was concentrated with silica and purified with ISCO (40 g, hexanes/EA, 1:0 to 1:1) to provide the title compound 6-bromocinnoline (1.48, 31%) as a yellow solid. LCMS (API-ES) m/z (%): 210.0 (100%, M$^+$+H).

tert-Butyl 5-(cinnolin-6-yl)thiazol-2-ylcarbamate

The title compound (0.24 g, 60%) was synthesized in a manner similar to that described in Example 253 from 6-bromocinnoline (0.25 g, 1.0 mmol) and tert-butyl 5-(tributylstannyl)thiazol-2-ylcarbamate (0.90 g, 1.5 eq). LCMS (API-ES) m/z (%): 329.4 (100%, M$^+$+H).

Example 255

2-(2-((S)-2-amino-3-(4-(trifluoromethyl)phenyl)propylamino)-5-(isoquinolin-6-yl)thiazol-4-yl)ethanol This compound was synthesized in a manner similar to that described in Example 56 using (S)-2-(5-bromo-2-(N-(2-(tert-butoxycarbonyl)-3-(4-(trifluoromethyl)phenyl)propyl)acetamido)thiazol-4-yl)ethyl acetate to couple with isoquinolin-6-ylboronic acid. (S)-2-(5-Bromo-2-(N-(2-(tert-butoxycarbonyl)-3-(4-(trifluoromethyl)phenyl)propyl)acetamido)thiazol-4-yl)ethyl acetate was synthesized as shown in Scheme 46. LCMS (API-ES) m/z (%): 473.5 (100%, M$^+$+H).

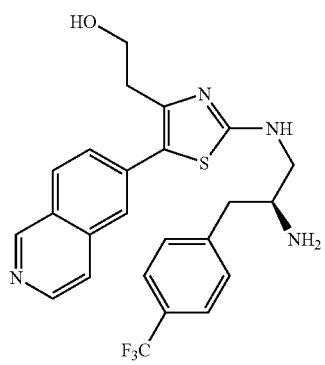

Scheme 46

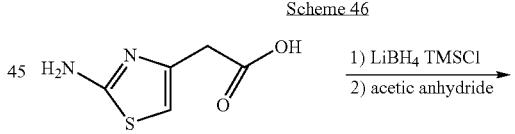

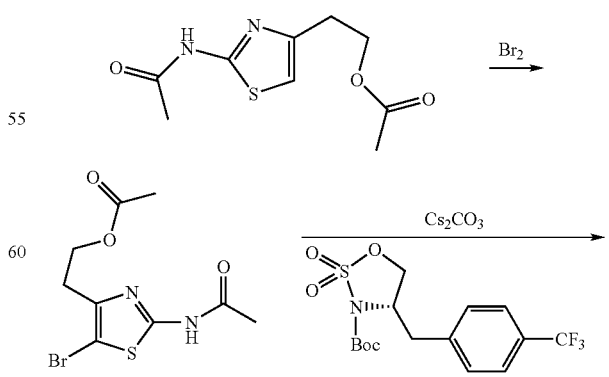

-continued

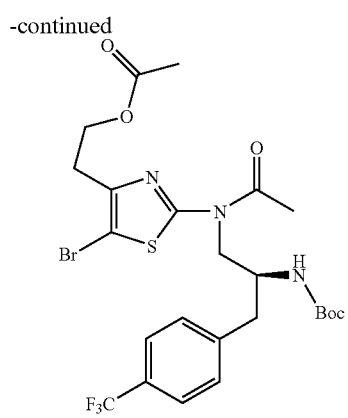

2-(2-acetamidothiazol-4-yl)ethyl acetate

To a solution of lithium borohydride (4.1 g, 190 mmol) in 100 mL THF at 0° C. under nitrogen, was added chlorotrimethylsilane (27.0 g, 253 mmol) by dropping funnel. A precipitate quickly formed. After the addition was complete, the reaction mixture was stirred for 3 more minutes before 2-(2-aminothiazol-4-yl) acetic acid (10.0 g, 63 mmol) was added in portions. After the addition, the ice water bath was taken away, and the reaction was stirred at room temperature for 3 hours. The reaction was quenched with acetic anhydride (100 mL) and was heated to 100° C. for 1 hour. The acetic anhydride was evaporated under reduced pressure. Saturated sodium bicarbonate was added to the residue, and the mixture was extracted into EtOAc (2×100 mL). The organic layer was washed with brine, dried over sodium sulfate, and evaporated to dryness. The collected solid was purified using silica gel chromatography with 50% EtOAc in hexane as the eluent to afford 2-(2-acetamidothiazol-4-yl)ethyl acetate(0.61 g, yield=4.2%) as a white solid. LCMS (API-ES) m/z (%): 229.1 (100%, M$^+$+H).

2-(2-acetamido-5-bromothiazol-4-yl)ethyl acetate

Br$_2$ (0.46 g, 2.9mmol) was dropped into 2-(2-acetamidothiazol-4-yl)ethyl acetate (0.60 g, 2.6 mmol) in 20 mL AcOH. The reaction was instantaneous. Acetic acid was evaporated from the reaction and saturated sodium bicarbonate was slowly added to the residue. The resulting mixture was extracted twice with EtOAc. The organic layer was washed with brine and dried over sodium sulfate. 2-(2-Acetamido-5-bromothiazol-4-yl)ethyl acetate (0.6 g, yield=74.3%) was obtained as a white solid. LCMS (API-ES) m/z (%): 309.0 (100%, M$^+$+H).

(S)-2-(5-bromo-2-(N-(2-(tert-butoxycarbonyl)-3-(4-(trifluoromethyl)phenyl)propyl)acetamido)thiazol-4-yl)ethyl acetate To a solution of 2-(2-acetamido-5-bromothiazol-4-yl) ethyl acetate (180 mg, 586 µmol) in 3.0 mL DMF was added Cs$_2$CO$_3$ (382 mg, 1172 µmol). The mixture was heated to 55° C., and the cyclic sulfamidate (268 mg, 703 µmol) was added in portions. The reaction was complete within 90 minutes at 55° C. After the reaction was complete, the solvent was evaporated, the residue was taken up in 50 mL EtOAc, and the flask was soaked in an ice water bath for 5 minutes. 50 mL of a 10% aqueous hydrochloride solution was added, and the mixture was stirred for 1 hour at room temperature. 100 mL saturated sodium bicarbonate along with 30 mL of a 10% sodium carbonate solution were added to the solution. The aqueous portion was extracted twice with 100 mL EtOAc. The combined organic layers were washed once with brine, dried over sodium sulfate, and evaporated to dryness. The collected solid was purified by silica gel chromatography with 30% EtOAc in hexane as the eluent to afford a white solid as the product (S)-2-(5-bromo-2-(N-(2-(tert-butoxycarbonyl)-3-(4-(trifluoromethyl)phenyl)propyl)acetamido)thiazol-4-yl)ethyl acetate (0.25 g, yield=70%). LCMS (API-ES) m/z (%): 610.1 (100%, M$^+$+H).

2.1 PKB Assay Testing

The kinase assay for evaluating PKB activity comprises active PKB enzymes, a PKB specific substrate, and P$^{33}$-labeled ATP. Two form of PKBα enzymes were used, the full length PKBα and a kinase domain of PKBα with pleckstrin domain (amino acids 1-117) deleted. Both PKB enzymes were obtained from Upstate cell signaling solutions (Cat.# 14-276 and 14-341). The PKB substrate used is a synthetic peptide (ARKRERTYSFGHHA (SEQ ID NO: 1)) as described in Obata et al., J. Biol. Chem. 275 (46), 36108-36115 (2000). The phosphorylated substrate was captured by a phosphocellulose membrane filter plate (MILLIPORE) and measured by a Wallac Microbeta liquid scintillation counter (Perkin Elmer). Table 1 provides the IC$_{50}$ values obtained for each of the examples with respect to PKBα.

PKB activity in cells was assayed in a PTEN null human breast tumor cell line MDA-MB-468 and U87-MG. The phosphorylation status of PKB substrate PRAS40, FKHRL1, GSK3a/b, and Tuberin were measured by immunoassays utilizing phospho-specific antibodies (Invitrogen, Cell signaling technology).

The effect of PKB inhibition on cell viability was measured in a range of human tumor cell lines including, but not limiting to, MDA-MB-468, MDA-MB-231, U87-MG, LN-229, PC3, DU145. The cells were treated in regular growth media for 72 hours and cell viability was measured by Alamar Blue (Invitrogen).

The effect of PKB inhibition on tumor growth in vivo is/was assessed in an established U87MG xenograft model. Athymic nude mice bearing U87MG tumors (approximately 200 mm$^3$) in the right flank are/were treated with the compound orally at the dosage of 15, 30, and 60 mg/kg/day (n=10) for 17 days. Tumor volume and body weight are/were measured twice per week. Data are/were expressed as means plus or minus standard errors and plotted as a function of time. Statistical significance of the effect is/was evaluated by Repeated Measures Analysis of Variance (RMANOVA) followed by Scheffe post hoc testing for multiple comparisons. Tumor stasis and regression are/were observed.

TABLE 1
| Example | Structure[a] | IC$_{50}$[b] |
|---|---|---|
| 1 | 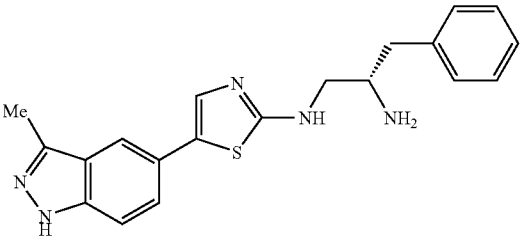 | +++ |
| 2 | 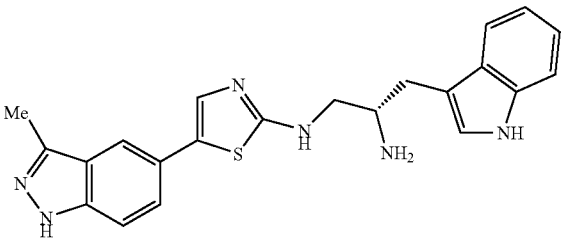 | +++ |
| 3 | 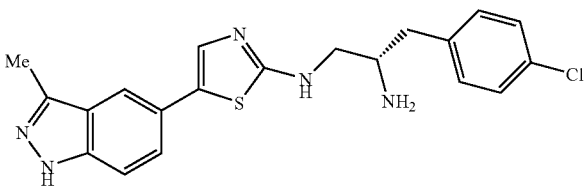 | +++ |
| 4 | 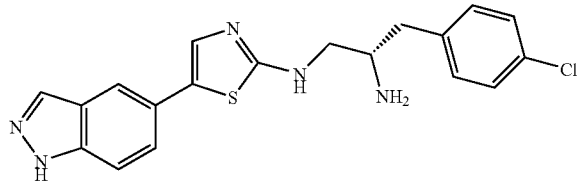 | ++++ |
| 5 | 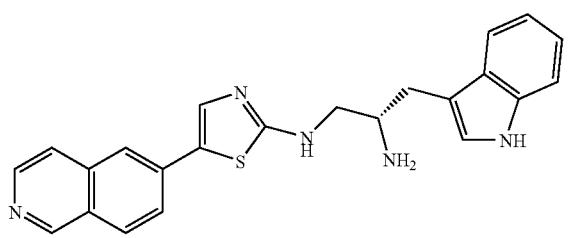 | +++ |
| 6 | 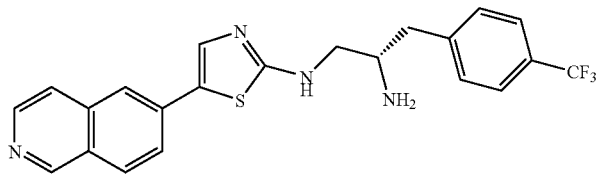 | ++++ |
| 7 | 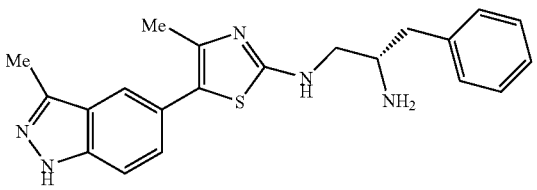 | ++ |

TABLE 1-continued
| Example | Structure[a] | IC$_{50}$[b] |
|---|---|---|
| 8 | 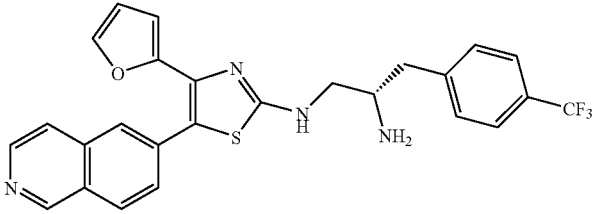 | +++ |
| 9 | 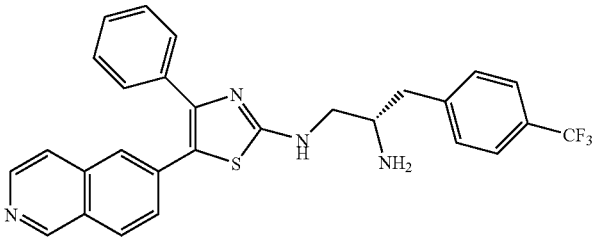 | +++ |
| 10 | 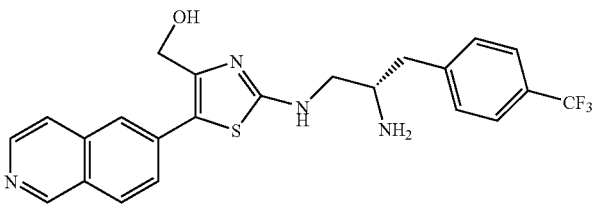 | ++++ |
| 11 | 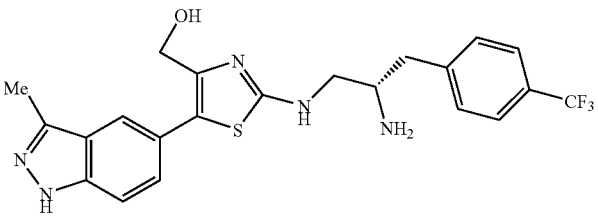 | ++++ |
| 12 | 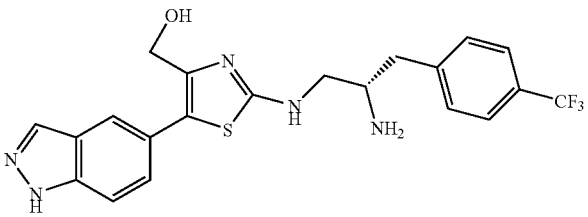 | ++++ |
| 13 | 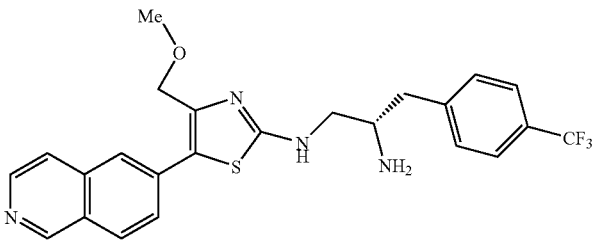 | ++++ |

TABLE 1-continued
| Example | Structure[a] | IC$_{50}$[b] |
|---|---|---|
| 14 | 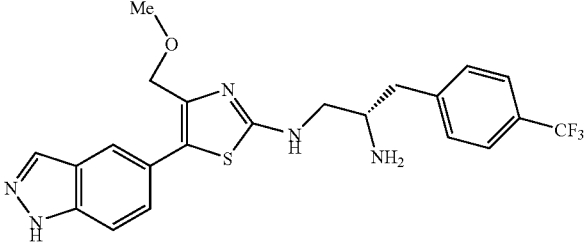 | ++++ |
| 15 | 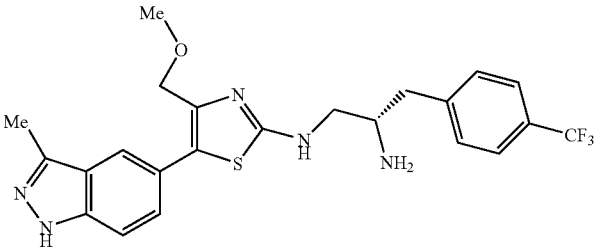 | +++ |
| 16 | 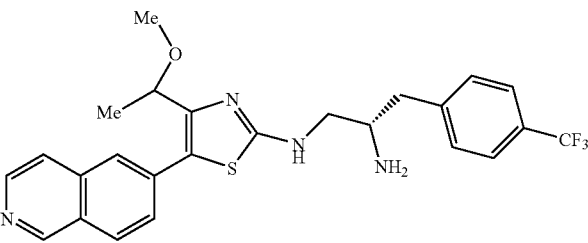 | +++ |
| 17 | 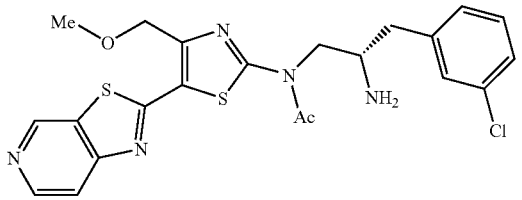 | ++ |
| 18 | 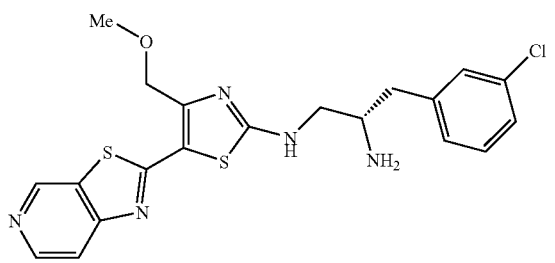 | ++ |
| 19 | 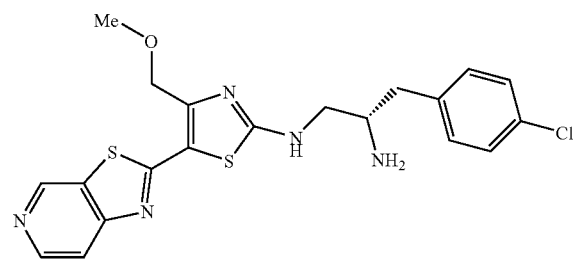 | ++++ |

TABLE 1-continued

| Example | Structure | IC$_{50}$$^b$ |
|---|---|---|
| 20 | | ++ |
| 21 | | +++ |
| 22 | | ++++ |
| 23 | | +++ |
| 24 | | +++ |
| 25 | | +++ |

TABLE 1-continued

| Example | Structure[a] | IC$_{50}$[b] |
|---|---|---|
| 26 | [Structure: pyrido-thiazole linked to thiazole with MeOCH$_2$ substituent, N(Ac) group connected to CH$_2$CH(NH$_2$)CH$_2$-C$_6$H$_4$-4-CF$_3$] | ++ |
| 27 | [Structure: pyrido-thiazole linked to thiazole with MeOCH$_2$ substituent, NH connected to CH$_2$CH(NH$_2$)CH$_2$-(1H-indol-3-yl)] | +++ |
| 28 | [Structure: pyrido-thiazole linked to thiazole, NH-CH$_2$-phenyl] | ++ |
| 29 | [Structure: pyrido-thiazole linked to thiazole, N(benzyl)-CH$_2$CH(NH$_2$)CH$_2$-C$_6$H$_4$-3-CF$_3$] | ++ |
| 30 | [Structure: pyrido-thiazole linked to thiazole, N(benzyl)-CH$_2$CH(NH$_2$)CH$_2$-C$_6$H$_4$-4-CF$_3$] | +++ |
| 31 | [Structure: pyrido-thiazole linked to thiazole, NH-CH$_2$CH(NH$_2$)CH$_2$-C$_6$H$_4$-3-CF$_3$] | ++ |
| 32 | [Structure: pyrido-thiazole linked to thiazole, NH-CH$_2$CH(NH$_2$)CH$_2$-C$_6$H$_4$-4-CF$_3$] | ++++ |

TABLE 1-continued

| Example | Structure | IC₅₀ |
|---|---|---|
| 33 | | + |
| 34 | | +++ |
| 35 | | +++ |
| 36 | | ++ |
| 37 | | ++ |

TABLE 1-continued

| Example | Structure[a] | IC$_{50}$[b] |
|---|---|---|
| 38 | | +++ |
| 39 | | +++ |
| 40 | | ++++ |
| 41 | | +++ |
| 42 | | ++++ |
| 43 | | ++++ |
| 44 | | +++ |
| 45 | | ++ |

TABLE 1-continued

| Example | Structure | IC$_{50}$$^b$ |
|---|---|---|
| 46 | | +++ |
| 47 | | +++ |
| 48 | | +++ |
| 49 | | ++ |
| 50 | | +++ |
| 51 | | +++ |
| 52 | | ++ |

TABLE 1-continued

| Example | Structure[a] | IC$_{50}$[b] |
|---|---|---|
| 53 | | ++ |
| 54 | | ++++ |
| 55 | | ++++ |
| 56 | | +++ |
| 57 | | ++++ |
| 58 | | +++ |

TABLE 1-continued

| Example | Structure | IC$_{50}$$^b$ |
|---|---|---|
| 59 | | ++++ |
| 60 | | ++ |
| 61 | | ++ |
| 62 | | ++ |
| 63 | | ++ |

TABLE 1-continued

| Example | Structure[a] | IC$_{50}$[b] |
|---|---|---|
| 64 | | +++ |
| 65 | | +++ |
| 66 | | ++++ |
| 67 | | +++ |
| 68 | | ++++ |
| 69 | | ++++ |
| 70 | | ++ |

TABLE 1-continued

| Example | Structure[a] | IC$_{50}$[b] |
|---|---|---|
| 71 | | ++++ |
| 72 | | +++ |
| | | |
| 73 | | +++ |
| | | |
| 74 | | ++ |

TABLE 1-continued
| Example | Structure | IC$_{50}$[b] |
|---|---|---|
| 75 | 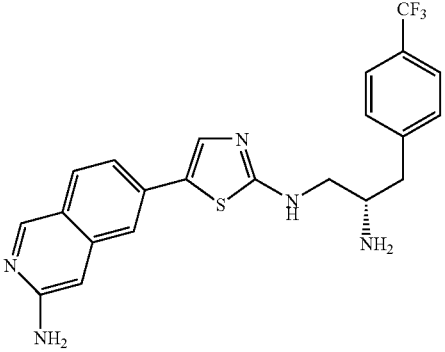 | ++++ |
| 76 | 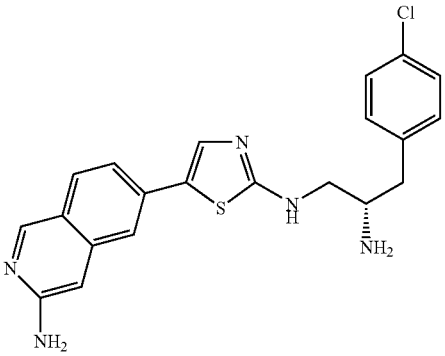 | ++++ |
| 77 | 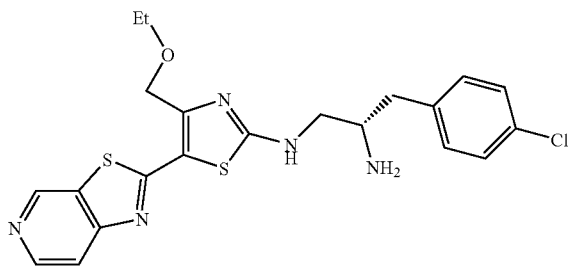 | +++ |
| 78 | 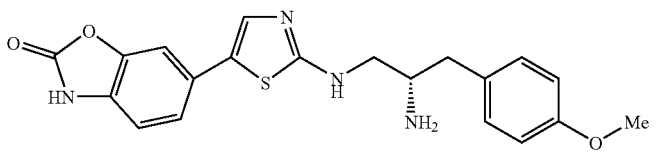 | +++ |
| 79 | 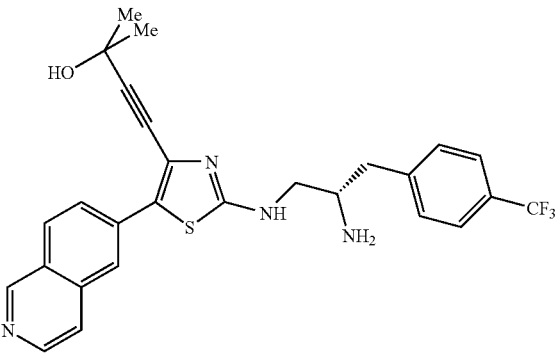 | +++ |

TABLE 1-continued

| Example | Structure | IC$_{50}$[b] |
|---|---|---|
| 80 | | +++ |
| 81 | | +++ |
| 82 | | +++ |
| 83 | | ++++ |
| 84 | | ++++ |
| 85 | | ++++ |
| 86 | | ++++ |

TABLE 1-continued

| Example | Structure | IC$_{50}$$^b$ |
|---|---|---|
| 87 | | ++++ |
| 88 | | ++ |
| 89 | | ++ |
| 90 | | ++ |
| 91 | | +++ |
| 92 | | ++++ |
| 93 | | +++ |

TABLE 1-continued
| Example | Structure | IC$_{50}$[b] |
|---|---|---|
| 94 | 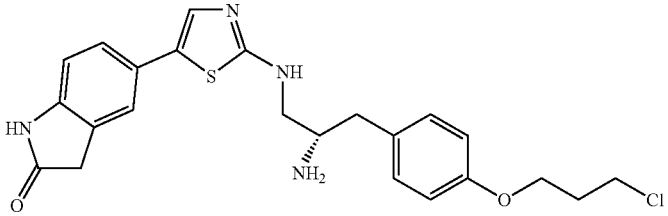 | ++ |
| 95 | 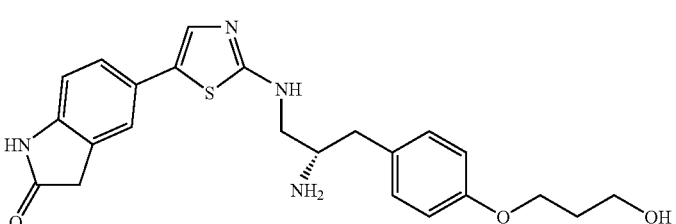 | ++ |
| 96 | 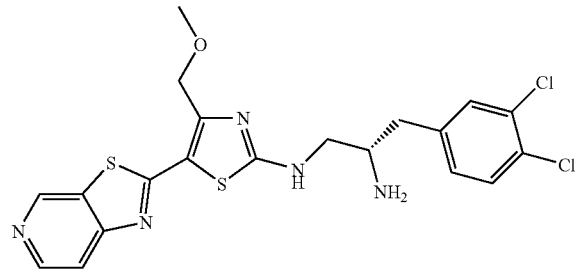 | ++++ |
| 97 | 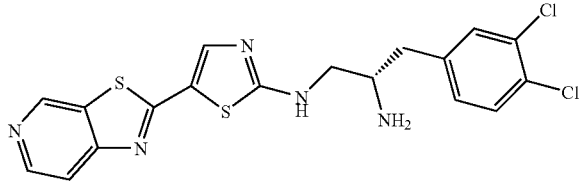 | +++ |
| 98 | 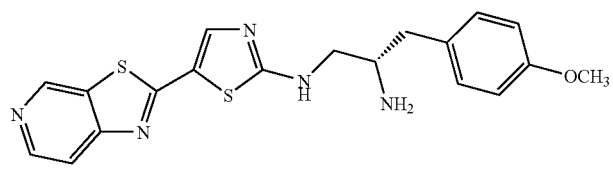 | +++ |
| 99 | 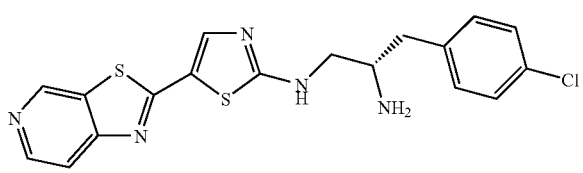 | ++++ |

TABLE 1-continued
| Example | Structure[a] | IC$_{50}$[b] |
|---|---|---|
| 100 | 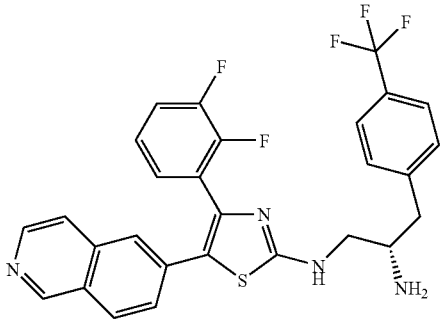 | +++ |
| 101 | 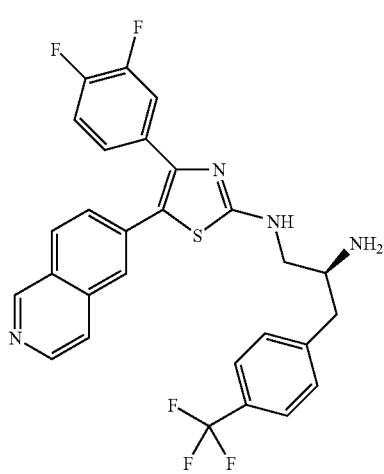 | +++ |
| 102 | 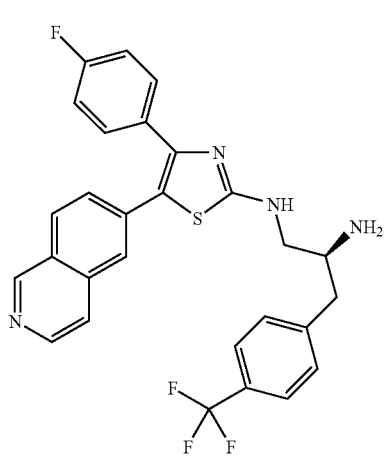 | +++ |

TABLE 1-continued

| Example | Structure | IC$_{50}$$^b$ |
|---|---|---|
| 103 | | +++ |
| 104 | | +++ |
| 105 | | ++++ |
| 106 | | +++ |

TABLE 1-continued
| Example | Structure | IC$_{50}$[b] |
|---|---|---|
| 107 | 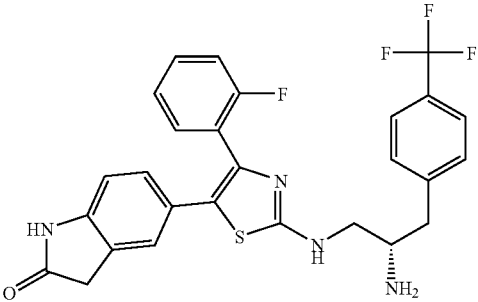 | ++ |
| 108 | 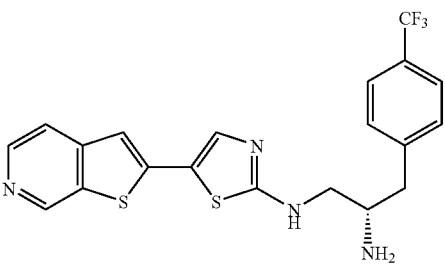 | ++++ |
| 109 | 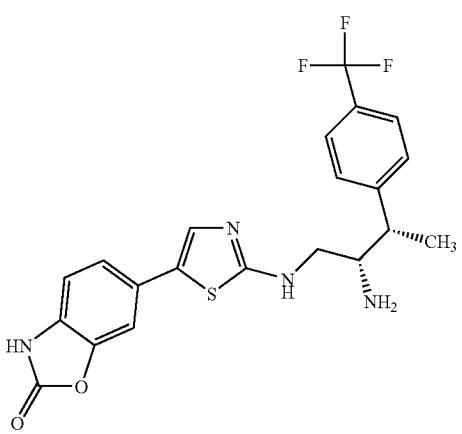 | ++++ |
| 110 | 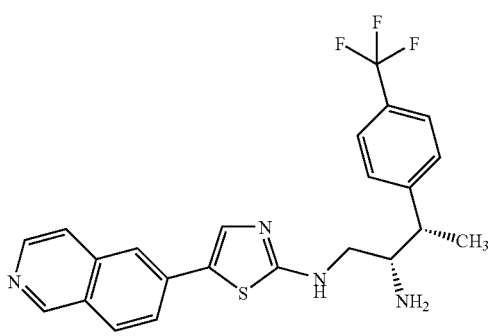 | ++++ |
| 111 | 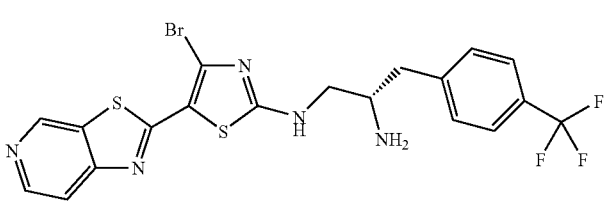 | +++ |

TABLE 1-continued

| Example | Structure | IC$_{50}$$^b$ |
|---|---|---|
| 112 | | ++++ |
| 113 | | +++ |
| 114 | | ++++ |
| 115 | | ++++ |
| 116 | | +++ |
| 117 | | ++++ |
| 118 | | +++ |
| 119 | | ++ |

TABLE 1-continued

| Example | Structure | IC$_{50}$$^b$ |
|---|---|---|
| 120 | | ++++ |
| 121 | | ++ |
| 122 | | +++ |
| 123 | | ++++ |
| 124 | | ++++ |
| 125 | | ++++ |

TABLE 1-continued

| Example | Structure<sup>a</sup> | IC<sub>50</sub><sup>b</sup> |
|---------|-----------|------|
| 126 | | +++ |
| 127 | | +++ |
| 128 | | ++ |
| 129 | | +++ |
| 130 | | +++ |
| 131 | | +++ |
| 132 | | ++++ |

TABLE 1-continued

| Example | Structure | IC$_{50}$$^b$ |
|---|---|---|
| 133 | | ++ |
| 134 | | +++ |
| 135 | | ++ |
| 136 | | ++ |
| 137 | | +++ |
| 138 | | ++++ |

TABLE 1-continued

| Example | Structure | IC$_{50}$$^b$ |
|---|---|---|
| 139 | | ++++ |
| 140 | | ++++ |
| 141 | | ++++ |
| 142 | | +++ |
| 143 | | ++++ |

TABLE 1-continued

| Example | Structure | IC$_{50}$$^b$ |
|---------|-----------|---------------|
| 144 | | ++++ |
| 145 | | ++++ |
| 146 | | +++ |
| 147 | | ++ |
| 148 | | +++ |

TABLE 1-continued
| Example | Structure | IC₅₀ |
|---|---|---|
| 149 | 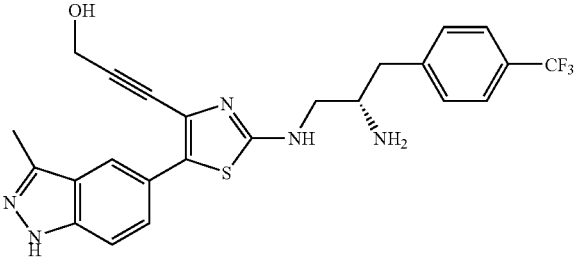 | ++++ |
| 150 | 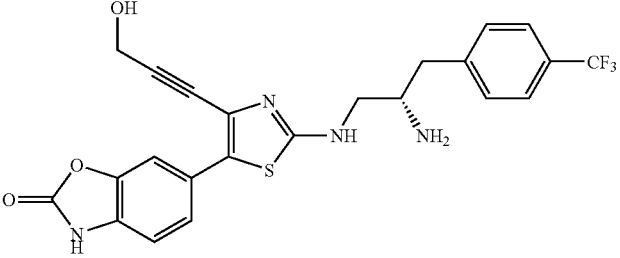 | ++++ |
| 151 | 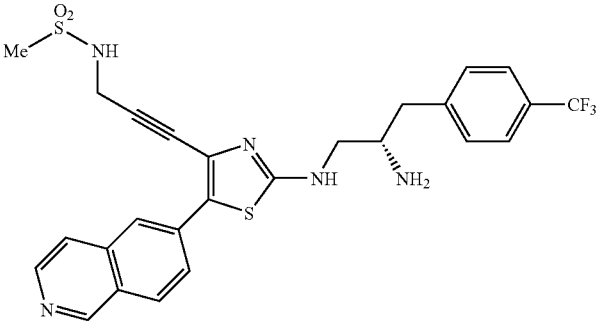 | ++ |
| 152 | 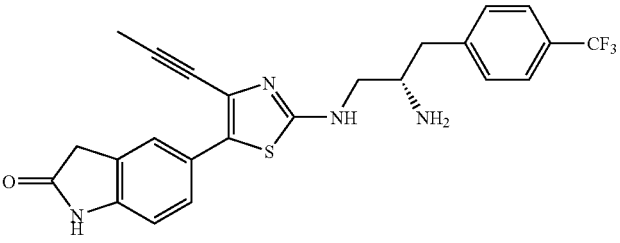 | ++++ |
| 153 | 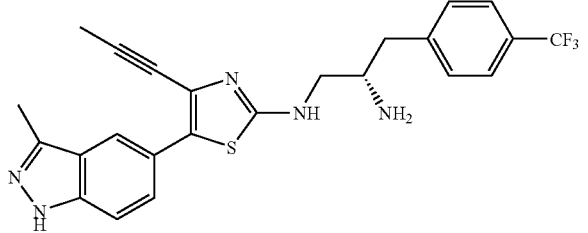 | ++++ |

TABLE 1-continued
| Example | Structure[a] | IC$_{50}$[b] |
|---|---|---|
| 154 | 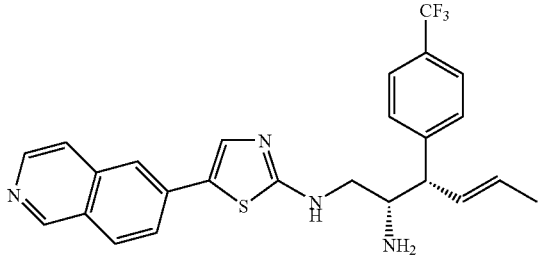 | ++++ |
| 155 | 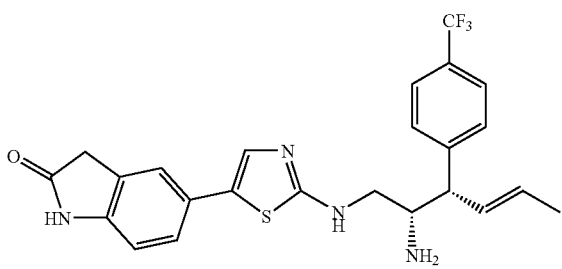 | ++++ |
| 156 | 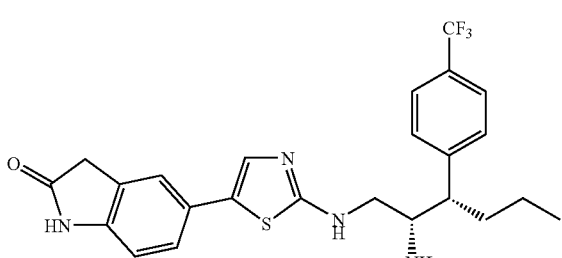 | +++ |
| 157 | 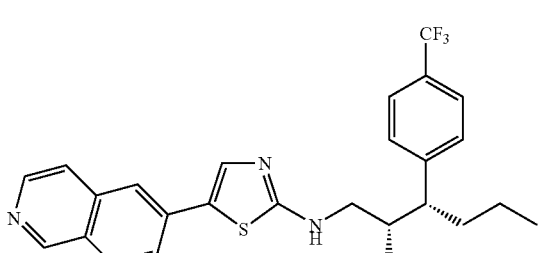 | ++++ |
| 158 | 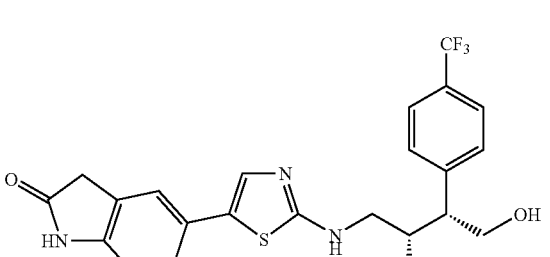 | ++++ |

TABLE 1-continued
| Example | Structure | IC$_{50}$[b] |
|---|---|---|
| 159 | 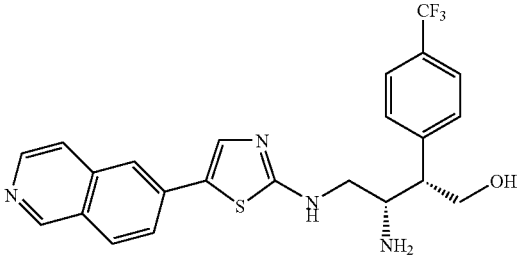 | ++++ |
| 160 | 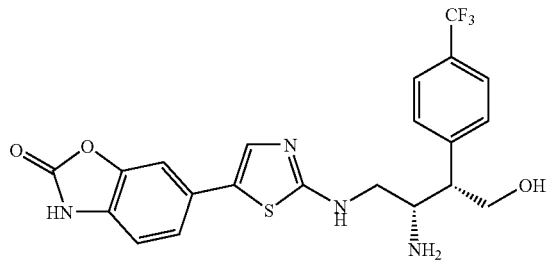 | ++++ |
| 161 | 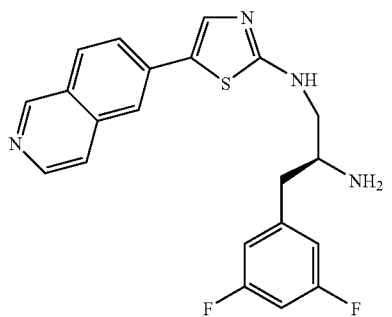 | +++ |
| 162 | 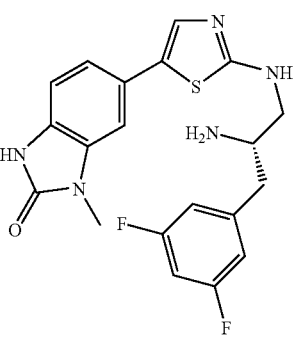 | ++ |
| 163 | 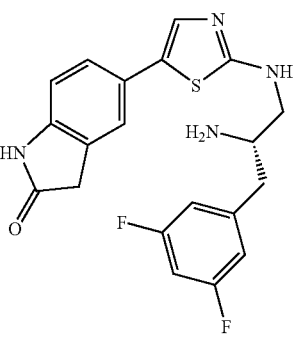 | ++ |

TABLE 1-continued

| Example | Structure | IC$_{50}$$^b$ |
|---|---|---|
| 164 | | +++ |
| 165 | | +++ |
| 166 | | +++ |

TABLE 1-continued
| Example | Structure | IC₅₀ |
|---------|-----------|------|
| 167 | 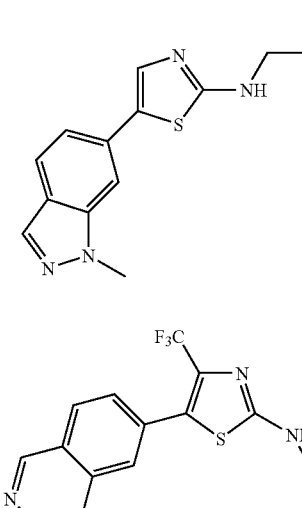 | ++ |
| 168 | 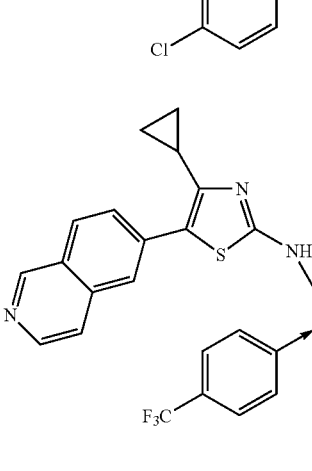 | +++ |
| 169 | 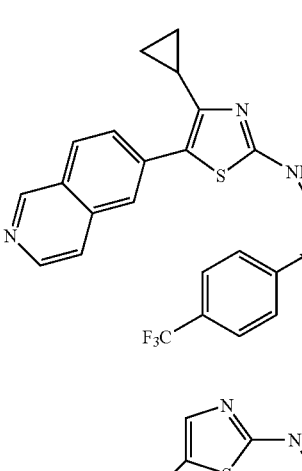 | +++ |
| 170 | 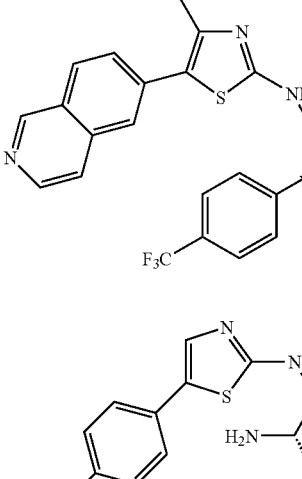 | ++++ |

TABLE 1-continued
| Example | Structure | IC$_{50}$[b] |
|---|---|---|
| 171 | 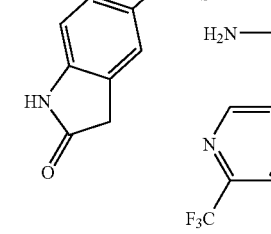 | ++++ |
| 172 | 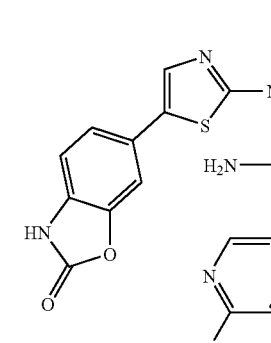 | ++++ |
| 173 | 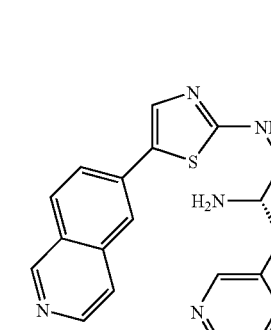 | ++++ |
| 174 | 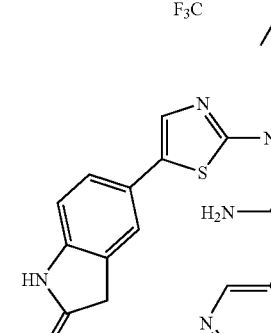 | +++ |

TABLE 1-continued
| Example | Structure | IC$_{50}$ |
|---|---|---|
| 175 | 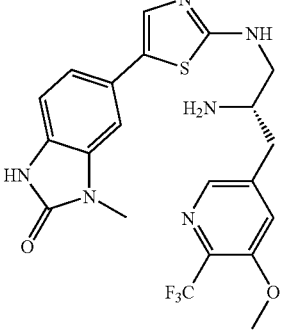 | ++++ |
| 176 | 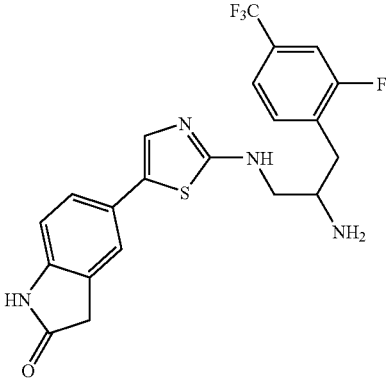 | +++ |
| 177 | 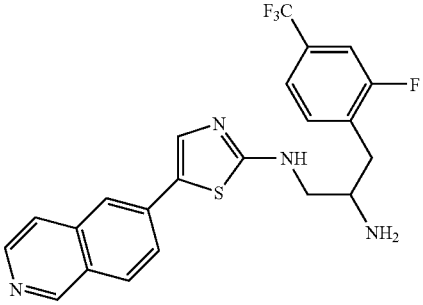 | ++++ |
| 178 | 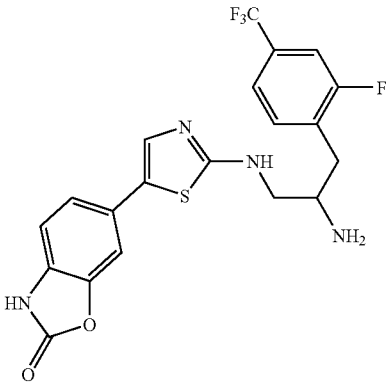 | ++++ |

TABLE 1-continued

| Example | Structure | IC$_{50}$[b] |
|---|---|---|
| 179 | | ++++ |
| 180 | | ++++ |
| 181 | | ++++ |
| 182 | | +++ |

TABLE 1-continued

| Example | Structure | IC$_{50}$$^b$ |
|---|---|---|
| 183 | | ++++ |
| 184 | | ++++ |
| 185 | | ++++ |
| 186 | | ++++ |

TABLE 1-continued

| Example | Structure | IC₅₀ |
|---------|-----------|------|
| 187 | | +++ |
| 188 | | ++++ |
| 189 | | ++++ |
| 190 | | ++++ |

TABLE 1-continued

| Example | Structure | IC$_{50}$$^b$ |
|---|---|---|
| 191 | | +++ |
| 192 | | ++ |
| 193 | | +++ |
| 194 | | +++ |

TABLE 1-continued

| Example | Structure | IC$_{50}$ |
|---|---|---|
| 195 | | ++ |
| 196 | | +++ |
| 197 | | ++ |

TABLE 1-continued
| Example | Structure | IC$_{50}$$^b$ |
|---|---|---|
| 198 | 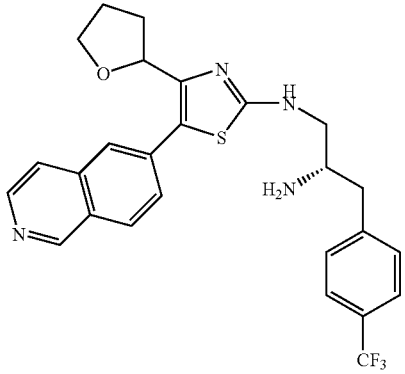 | ++++ |
| 199 | 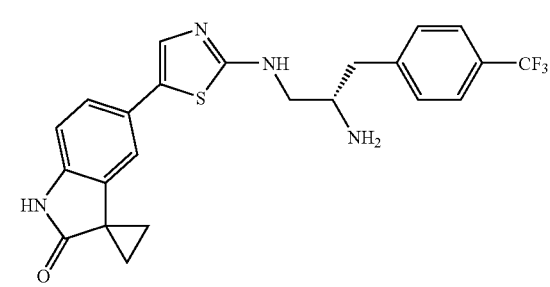 | +++ |
| 200 | 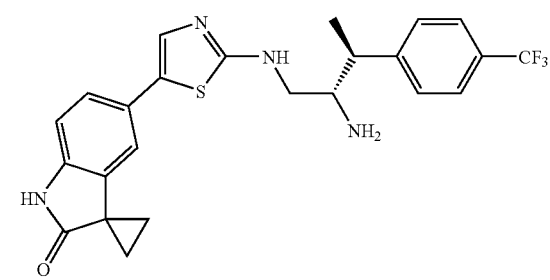 | +++ |
| 201 | 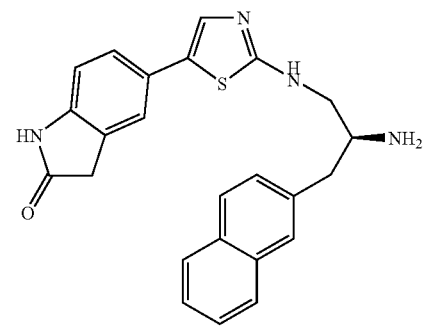 | +++ |

TABLE 1-continued
| Example | Structure | IC$_{50}$$^b$ |
|---|---|---|
| 202 | 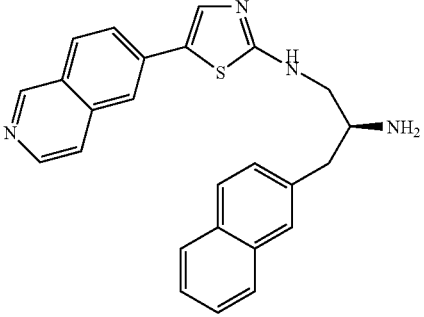 | ++++ |
| 203 | 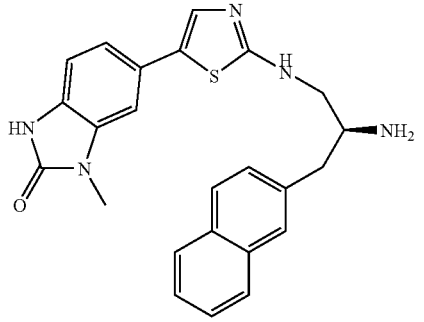 | +++ |
| 204 | 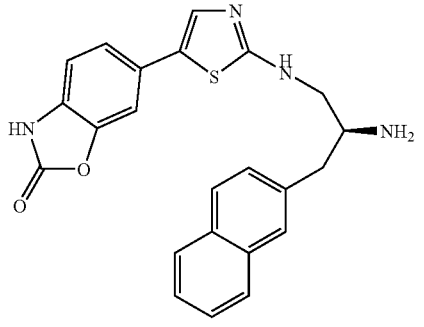 | ++++ |
| 205 | 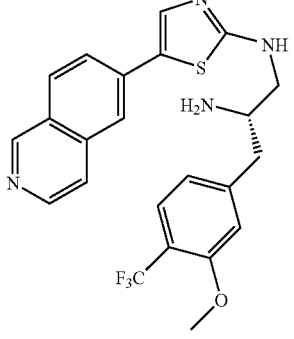 | ++++ |

TABLE 1-continued
| Example | Structure<sup>a</sup> | IC<sub>50</sub><sup>b</sup> |
|---|---|---|
| 206 | 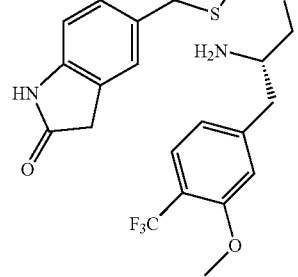 | ++++ |
| 207 | 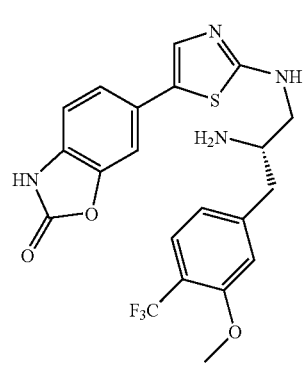 | ++++ |
| 208 | 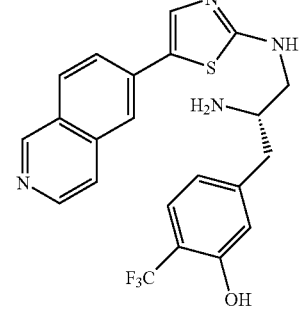 | ++++ |
| 209 | 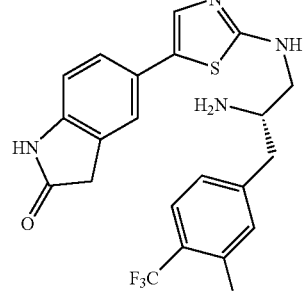 | +++ |

TABLE 1-continued

| Example | Structure$^a$ | IC$_{50}$$^b$ |
|---|---|---|
| 210 | | ++++ |
| 211 | | ++++ |
| 212 | | +++ |
| 213 | | +++ |
| 214 | | ++++ |
| 215 | | +++ |

TABLE 1-continued

| Example | Structure | IC$_{50}$$^b$ |
|---|---|---|
| 216 | | +++ |
| 217 | | +++ |
| 218 | | ++++ |
| 219 | | +++ |
| 220 | | ++++ |
| 221 | | ++++ |
| 222 | | +++ |

TABLE 1-continued

| Example | Structure | IC$_{50}$ |
|---|---|---|
| 223 | | ++ |
| 224 | | ++++ |
| 225 | | ++++ |
| 226 | | ++++ |
| 227 | | +++ |

TABLE 1-continued

| Example | Structure | IC$_{50}$$^b$ |
|---------|-----------|---------------|
| 228 | | +++ |
| 229 | | ++++ |
| 230 | | ++++ |
| 231 | | +++ |
| 232 | | +++ |

TABLE 1-continued

| Example | Structure[a] | IC$_{50}$[b] |
|---|---|---|
| 233 | | ++++ |
| 234 | | ++ |
| 235 | | +++ |
| 236 | | ++ |
| 237 | | ++ |

TABLE 1-continued

| Example | Structure[a] | IC$_{50}$[b] |
|---|---|---|
| 238 | | +++ |
| 239 | | ++ |
| 240 | | +++ |
| 241 | | ++++ |
| 242 | | +++ |
| 243 | | ++++ |

TABLE 1-continued
| Example | Structure | IC$_{50}$ |
|---|---|---|
| 244 | 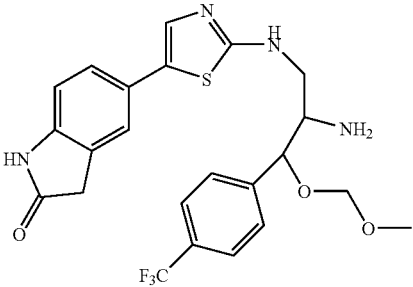 | ++ |
| 245 | 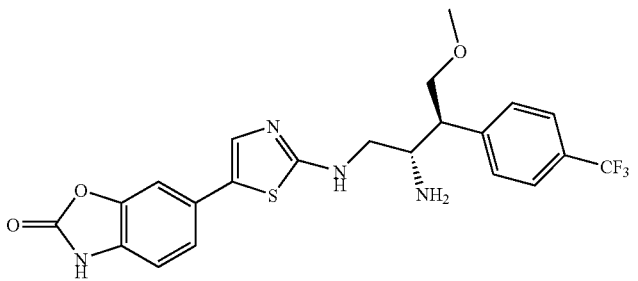 | ND[c] |
| 246 | 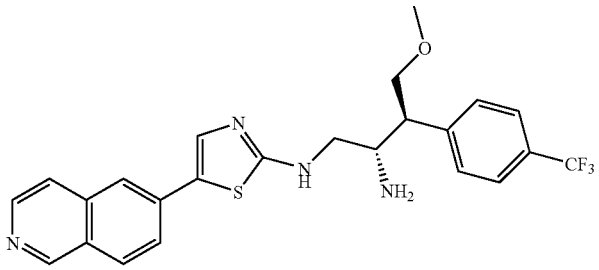 | ND |
| 247 | 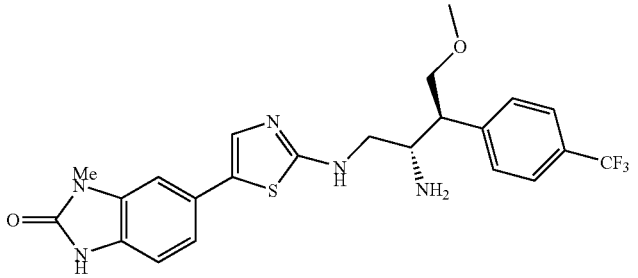 | ND |
| 248 | 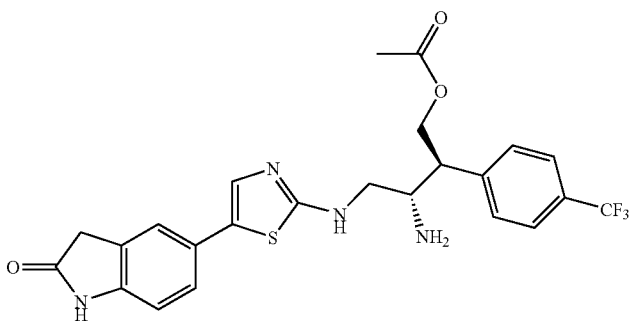 | +++ |

TABLE 1-continued

| Example | Structure | IC$_{50}$$^b$ |
|---------|-----------|---------------|
| 249 | | ++ |
| 250 | | ++ |
| 251 | | ++ |
| 252 | | ++ |
| 253 | | ++++ |

TABLE 1-continued

| Example | Structure[a] | IC$_{50}$[b] |
|---------|-----------|-----------|
| 254 | 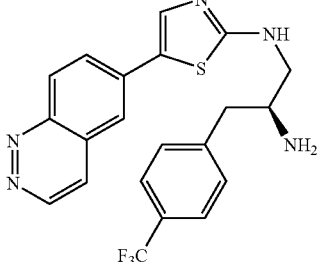 | +++ |
| 255 | 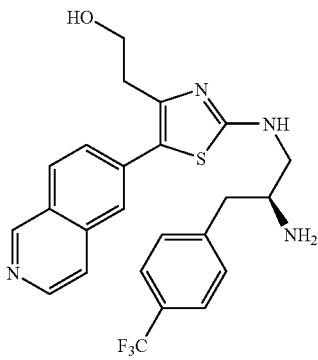 | +++ |

[a]When the stereochemistry is not specified at a carbon bonded to four different groups, this indicates a mixture of stereoisomers is present.
[b]IC$_{50}$ Ranges:
+ IC$_{50}$ > 10 μM
++ 1 μM ≦ IC$_{50}$ ≦ 10 μM
+++ 0.05 μM ≦ IC$_{50}$ < 1 μM
++++ IC$_{50}$ < 0.05 μM
[c]IC$_{50}$ value for this compound has not yet been determined.

Each of the compounds in the above table and tautomers, salts, neutral forms, solvates including hydrates, and stereoisomers thereof is preferred both individually and as a member of a group. Each of the groups in these compounds that corresponds to any of the variables in the compounds of Formula I and Formula II is also preferred.

The foregoing has demonstrated the pertinent and important features of the present invention. Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

All references cited herein are incorporated herein by reference in their entireties and for all purposes as if specifically set forth herein and to the same extent as if each individual publication or patent or patent application was specifically and individually indicated to be incorporated by reference in its entirety for all purposes.

What is claimed is:

1. A compound of Formula I

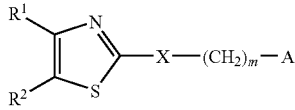

wherein:

A is

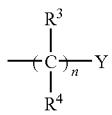

Y is —N(R$^5$)R$^6$;
X is —N(R$^7$);
R$^1$ is R$^8$, —CHR$^{11}$—N(H)—R$^8$, —CHR$^{11}$—O—R$^8$, C$_2$-C$_6$ alkynyl, C$_2$-C$_6$ hydroxyalkynyl, or —C≡N;
R$^2$ is unsubstituted or substituted aryl or unsubstituted or substituted heteroaryl
R$^3$ is —H, or unsubstituted C$_1$-C$_6$ alkyl;
R$^4$ is a —(CR$^9$R$^{10}$)$_t$(aryl) or —(CR$^9$R$^{10}$)$_t$(heteroaryl);
R$^5$ is —H, C$_1$-C$_8$ alkyl, —C(O)(CR$^9$R$^{10}$)$_t$)N(R$^7$)$_2$, —(CR$^9$R$^{10}$)$_t$(aryl), —(CR$^9$R$^{10}$)$_t$(heteroaryl), —(CR$^9$R$^{10}$)$_t$(cycloalkyl), or —(CR$^9$R$^{10}$)$_t$(heterocyclyl);
R$^6$ and R$^7$ are independently selected from —H, C$_1$-C$_8$ alkyl, —(C$_1$-C$_6$ alkyl)aryl, or —C(O)(C$_1$-C$_6$ alkyl),
R$^5$ and R$^6$, together with the nitrogen atom to which they are linked, join to form a 5 to 6-membered heterocyclic or heteroaryl ring;
R$^8$ is —H, C$_1$-C$_6$ alkyl, —(C$_1$-C$_6$ alkyl)aryl, aryl, or heteroaryl; and
R$^9$, R$^{10}$, and R$^{11}$ are independently selected from —H, C$_1$-C$_6$ alkyl, or aryl;
wherein n is 1; m is 1; and t is 1;
wherein each of the above alkyl, aryl, heteroaryl, cycloalkyl, and heterocyclyl moieties and heterocyclic and carbocyclic rings are optionally and independently substituted by 1-3 substituents selected from
amino,
aryl, heteroaryl, cycloalkyl, or heterocyclyl optionally substituted by 1-5 substituents selected from
C$_1$-C$_6$ alkoxy,
C$_1$-C$_6$ alkyl optionally substituted by halo,
aryl,
halo,
hydroxyl,
heteroaryl,
C$_1$-C$_6$ hydroxyalkyl, or
—NHS(O)$_2$—(C$_1$-C$_6$ alkyl);
C$_1$-C$_6$ alkyl, C$_1$-C$_6$ haloalkyl, C$_1$-C$_6$ hydroxyalkyl, C$_1$-C$_6$ alkoxy, C$_1$-C$_6$ alkylamino, C$_2$-C$_6$ alkenyl, or C$_2$-C$_6$ alkynyl, wherein each of which may be interrupted by one or more hetero
atoms,
cyano,
halo,
hydroxyl,
nitro, or
—O-aryl;

or a pharmaceutically acceptable salt, or stereoisomer thereof.

2. The compound of claim 1, wherein R$^2$ is optionally substituted heteroaryl, R$^3$ is —H, R$^5$, R$^6$, and R$^7$ are —H, and R$^9$ and R$^{10}$ are independently selected from H or C$_1$-C$_3$ alkyl.

3. The compound of claim 2, wherein R$^2$ is an optionally substituted bicyclic heteroaryl, R$^4$ is an optionally substituted —(CR$^9$R$^{10}$)$_t$(monocyclic aryl) or an optionally substituted —(CR$^9$R$^{10}$)$_t$(bicyclic heteroaryl), and R$^9$ and R$^{10}$ are —H.

4. The compound of claim 3, wherein the optionally substituted bicyclic heteroaryl group of R$^2$ is an optionally substituted isoquinolinyl, 1H-indazolyl, thiazolo[5,4-c]pyridinyl, benzo[d]thiazole-2(3H)-onyl, phthalazinyl, indolin-2-onyl, 3,4-dihydroquinolin-2(1H)-onyl, benzo[d]isoxazdiyl, benzo[d]oxazol-2(3H)-onyl, benzo[d]imidazol-2(3H)-onyl, or 1,6-naphthyridinyl; and the optionally substituted monocyclic aryl group of R$^4$ is phenyl, chlorophenyl, (trifluoromethyl)phenyl, or (C$_1$-C$_6$)alkoxyphenyl, or the optionally substituted bicyclic heteroaryl group of R$^4$ is 1H-indolyl.

5. The compound of claim 4, wherein the optionally substituted bicyclic heteroaryl group of R$^2$ is isoquinolin-6-yl, 3-aminoisoquinolin-6-yl, 1H-indazol-5-yl, 1H-indazol-6-yl, 3-amino-1H-indazol-5-yl, 3-amino-1H-indazol-6-yl, 3-amino-1-methyl-1H-indazol-6-yl, 3-methylanmino-1H-indazol-5-yl, 3-methyl-1H-indazol-5-yl, thiazolo[5,4-c]pyridin-2-yl, benzo[d]thiazole-2(3H)-on-6-yl, 1-hydroxyphthalazin-6-yl, phthalazin-6-yl, indolin-2-on-5-yl, 3-methylindolin-2-on-5-yl, 3-(furan-2-ylmethylene)indolin-2-on-5-yl, 3-(1H-imidazol-5-ylmethylene)indolin-2-on-5-yl, 3,3-difluoroindolin-2-on-5-yl, 3,4-dihydroquinolin-2(1H)-on-6-yl, benzo[d]isoxazol-5-yl, 3-aminobenzo[d]isoxazol-5-yl, benzo[d]oxazol-2(3H)-on-6-yl, 1-methyl-1H-benzo[d]imidazol-2(3H)-on-6-yl, or 1,6-naphthyridin-2-yl; and the optionally substituted monocyclic aryl group of R$^4$ is phenyl, 3-chlorophenyl, 4-chlorophenyl, 4-methoxyphenyl, 3-(trifluoromethyl)phenyl, or 4-(trifluoromethyl)phenyl, or the optionally substituted bicyclic heteroaryl group of R$^4$ is 1H-indol-3-yl.

6. The compound of claim 1, wherein R$^2$ is a an optionally substituted bicyclic heteroaryl, R$^3$ is —H, R$^4$ is an optionally substituted —(CR$^9$R$^{10}$)$_t$(monocyclic aryl), R$^5$, R$^6$, R$^7$, R$^9$ and R$^{10}$ are —H, the optionally substituted bicyclic heteroaryl group of R$^2$ is isoquinolin-6-yl, 3-aminoisoquinolin-6-yl, 1H-indazol-5-yl, 3-methyl-1H-indazol-5-yl, thiazolo[5,4-c]pyridin-2-yl, benzo[d]oxazol-2(3H)-on-6-yl, or 1,6-naphthyridin-2-yl, and the optionally substituted monocyclic aryl group of R$^4$ is 4-chlorophenyl, 3-(trifluoromethyl)phenyl, or 4-(trifluoromethyl)phenyl.

7. The compound claim 1, wherein R$^1$ is —H, —CH$_3$, —CH$_2$CH$_3$, —CH$_2$OCH$_3$, —CH$_2$OCH$_2$CH$_3$, —CH$_2$OH, —CH$_2$OCH$_2$CF$_3$, —CH$_2$N(H)CH$_3$, —CH(CH$_3$)OCH$_3$, furanyl, phenyl, pyridyl, or —C≡N.

8. The compound of claim 1, wherein R$^1$ is —(C$_1$-C$_6$ alkyl), —(C$_1$-C$_6$alkyl)aryl, aryl, heteroaryl, —CHR$^{11}$—N(H)—R$^8$, CHR$^{11}$—O—R$^8$, or —C≡N.

9. A pharmaceutical composition, comprising: a pharmaceutically-acceptable carrier and the compound of claim 1.

10. The composition of claim 9, further comprising at least one additional therapeutic agent.

11. A compound of Formula II

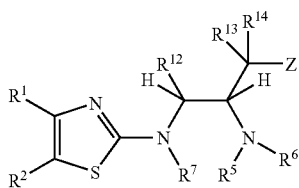

wherein:
R¹ is —H, halo, —OR⁸, $C_1$-$C_6$ alkyl, —($C_1$-$C_6$ alkyl)—O—R⁸, —($C_1$-$C_6$ haloalkyl)—O—R⁸, —($C_2$-$C_6$ alkenyl)—O—R⁸, —($C_1$-$C_6$ alkyl)N(R⁷)₂, —($C_1$-$C_6$ alkyl)aryl, —C(O)R⁸, —C(O)O—R⁸, —C(O)N(R⁷)₂, —CHR¹¹—N(H)—R⁸, —CHR¹¹—O—R⁸, $C_2$-$C_6$ alkynyl, ($C_2$-$C_6$ alkynyl)—O—R⁸, —C≡N, —($C_2$-$C_6$ alkynyl)($C_3$-$C_8$ cycloalkyl), —($C_2$-$C_6$ alkynyl)($C_5$-$C_8$ cycloalkenyl), —($C_2$-$C_6$ alkynyl) —N(R⁷)S(O)₂—R⁸, aryl, heteroaryl, cycloalkyl, or heterocyclyl;

R² is a unsubstituted or substituted carbocyclic ring system or is an unsubstituted or substituted hetrocyclic ring system R⁵ is —H, $C_1$-$C_8$ alkyl, —C(O)(CR⁹R¹⁰)$_t$)N(R⁷)₂, —(CR⁹R¹⁰)$_t$(heteroaryl), —(CR⁹R¹⁰)$_t$(cycloalkyl), or —(CR⁹R¹⁰)$_t$(heterocyclyl);

R⁶ and R⁷, in each instance, are independently selected from —H, $C_1$-$C_8$ alkyl, —($C_1$-$C_6$ alkyl)aryl, or —C(O)($C_1$-$C_6$ alkyl); R⁸ is selected from —H, $C_1$-$C_6$ alkyl, $C_1$-$C_6$ haloalkyl, —($C_1$-$C_6$ alkyl)aryl, aryl, heteroaryl, $C_1$-$C_6$ hydroxyalkyl, or —($C_1$-$C_6$ alkyl)—O—($C_1$-$C_6$ alkyl), cycloalkyl, or heterocyclyl;

R⁹ and R¹⁰, in each instance, and R¹¹ are independently selected from —H, $C_1$-$C_6$ alkyl, or aryl;

R¹² is —H, —OR⁸, —O—($C_1$-$C_6$ alkyl)—O—R⁸, $C_1$-$C_6$ alkyl, $C_2$-$C_6$ alkenyl, ($C_1$-$C_6$ alkyl)—O—R⁸, or —($C_1$-$C_6$ alkyl)—O—C(O)—R⁸;

R¹³ is —H, or $C_1$-$C_6$ alkyl;

R¹⁴ is —H, —OR⁸, —O—($C_1$-$C_6$ alkyl)—O—R⁸, $C_1$-$C_6$ alkyl, $C_2$-$C_6$ alkenyl, ($C_1$-$C_6$ alkyl)—O—R⁸, or —($C_1$-$C_6$ alkyl)—O—C(O)—R⁸;

each t is independently selected from 0, 1, 2, or 3; and

Z is aryl or heteroaryl;

wherein each of the above alkyl, aryl, heteroaryl, cycloalkyl, and heterocyclyl moieties and heterocyclic and carbocyclic rings are optionally and independently substituted by 1-3 substituents selected from amino, aryl, heteroaryl, cycloalkyl, or heterocyclic optionally substituted by 1-5 substituents selected from $C_1$-$C_6$ alkoxy, $C_1$-$C_6$ alkyl optionally substituted by halo;

aryl, halo, hydroxyl, heteroaryl, $C_1$-$C_6$ hydroxyalkyl, or —NHS(O)₂-($C_1$-$C_6$ alkyl);

$C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ hydroxyalkoxy, $C_1$-$C_6$ alkylamino, $C_2$-$C_6$ alkenyl, or $C_2$-$C_6$ alkynyl, wherein each of which may be interrupted by one or more hetero atoms, cyano, halo, hydroxyl, nitro, oxo, —NH(CO)—O—($C_1$-$C_6$ alkyl)aryl, —NH(CO)—O—($C_1$-$C_6$ alkyl), —N($C_1$-$C_6$ alkyl)(CO)—O—($C_1$-$C_6$ alkyl)aryl, —N($C_1$-$C_6$ alkyl)(CO)—O—($C_1$-$C_6$ alkyl), —C(O)OH, —C(O)O($C_1$-$C_6$ alkyl), —C(O)NH₂, —C(O)N(H)—($C_1$-$C_6$ alkyl), —C(O)N($C_1$-$C_6$ alkyl)₂, —NH($C_1$-$C_6$ alkyl), —N($C_1$-$C_6$ alkyl)₂, —($C_2$-$C_4$ alkenyl)heterocyclyl, or —($C_2$-$C_4$ alkenyl)cycloalkyl, or —O—aryl;

or a pharmaceutically acceptable salt, stereoisomer, or mixture thereof.

12. The compound of claim 11, wherein the compound of Formula II has the Formula IIA

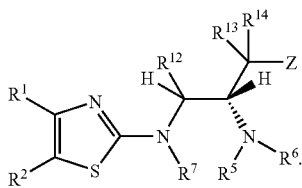

13. The compound of claim 11, wherein the compound of Formula II has the Formula IIB

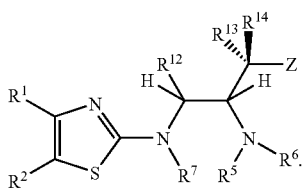

14. The compound of claim 11, wherein the compound of Formula II has the Formula IIC

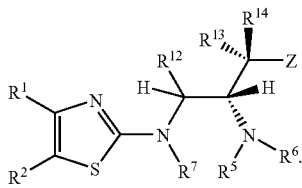

15. The compound of claim 11, wherein the compound of Formula II has the Formula IID

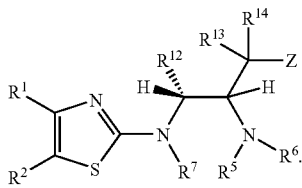

16. The compound of claim 11, wherein the compound of Formula II has the Formula IIE

IIE

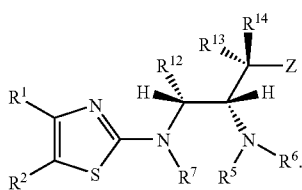

17. The compound of claim 11, wherein $R^1$ is —H.
18. The compound of claim 11, wherein $R^{12}$ is —H or $C_1$-$C_6$ alkyl.
19. The compound of claim 11, wherein $R^{13}$ is —H.
20. The compound of claim 11, wherein $R^{14}$ is —H.
21. The compound of claim 11, wherein $R^{14}$ is —$OR^8$, —O—($C_1$-$C_6$ alkyl)—O—$R^8$, $C_1$-$C_6$ alkyl, $C_2$-$C_6$ alkenyl, —($C_1$-$C_6$ alkyl)-O—$R^8$, or —($C_1$-$C_6$ alkyl)—O—C(O)—$R^8$.
22. The compound of claim 11, wherein $R^{14}$ is selected from —H, methyl, ethyl, propyl, ethenyl, propenyl, hydroxymethyl, methoxymethyl, —$CH_2$—O—C(O)—($C_1$-$C_6$ alkyl), 1-hydroxyethyl, or methoxymethoxy.
23. The compound of claim 11, wherein Z is selected from optionally substituted phenyl, optionally substituted indolyl, optionally substituted naphthyl, optionally substituted pyridyl, or optionally substituted thiophenyl.
24. The compound of claim 23, wherein Z is selected from phenyl, indolyl, naphthyl, pyridyl, orthiophenyl, each of which is optionally substituted with 1-3 substituents selected from —Cl, —F, —$CF_3$, —OH, —O—($C_1$-$C_6$ alkyl), —O—($C_1$-$C_6$ alkyl)—Cl, —O—($C_1$-$C_6$ alkyl)—OH, —$C_1$-$C_6$ alkyl, $OCF_3$, —NH(CO)—O—($C_1$-$C_6$ alkyl)aryl, or —NH(CO)—O—($C_1$-$C_6$ alkyl).
25. The compound of claim 24, wherein Z is selected from phenyl, indolyl, naphthyl, pyridyl, thiophenyl, 4-chlorophenyl, 4-trifluoromethylphenyl, 3-chlorophenyl, 3-trifluoromethylphenyl, 4-methoxyphenyl, 3-fluoro-4-trifluoromethylphenyl, 4-chloro-3-fluorophenyl, 4-(3-chloropropoxy)phenyl, 4-(3-hydroxypropoxy)phenyl, 3,4-dichlorophenyl, 4-fluorophenyl, 2,4-dichlorophenyl, 4-methylphenyl, 3,4-difluorophenyl, 3-fluoro-4-methoxyphenyl, 3,5-difluorophenyl, 6-trifluoromethylpyridin-3-yl, 5-methoxy-6-trifluoromethylpyridin-3-yl, 2-fluoro-4-trifluoromethylphenyl, 4-trifluoromethoxyphenyl, 2,3-difluoro-4-trifluoromethylphenyl, 4-hydroxyphenyl, 3-methoxy-4-trifluoromethylphenyl, 3-hydroxy-4-trifluoromethylphenyl, 5-chlorothiophen-2-yl, 3-fluoro-4-hydroxyphenyl or a phenyl substituted in the 4 position with —NH—C(O)—O—$CH_2$-phenyl.
26. The compound of claim 11, wherein $R^7$ is H.
27. The compound of claim 11, wherein $R^5$ and $R^6$ are each H.
28. The compound of claim 11, wherein $R^{12}$ is —H or $C_1$-$C_6$ alkyl, $R^{13}$ is —H, and $R^{14}$ is —H, —$OR^8$, —O—($C_1$-$C_6$ alkyl)—O—$R^8$, $C_1$-$C_6$ alkyl, $C_2$-$C_6$ alkenyl, —($C_1$-$C_6$ alkyl)—O—$R^8$, or —($C_1$-$C_6$ alkyl)—O—C(O)—$R^8$.
29. The compound of claim 28, wherein $R^5$, $R^6$, and $R^7$ are all H.
30. The compound of claim 11, wherein the carbocyclic ring system or the heterocyclic ring system of $R^2$ comprises at least one aromatic ring.
31. The compound of claim 11, wherein $R^2$ is selected from optionally substituted phenyl, pyridyl, indazolyl, isoquinolinyl, thiazolopyridinyl, benzothiazolonyl, dihydroquinolinonyl, benzoisoxazolyl, benzooxazolonyl, indolinonyl, benzoimidazolonyl, phthalazinyl, naphthyridinyl, thienopyridinyl, benzodioxolyl, isoindolinonyl, quinazolinyl, or cinnolinyl.
32. The compound of claim 11, wherein $R^2$ is selected from one of the following groups which may optionally be substituted and where the wavy line indicates the point of attachment to the thiazole:

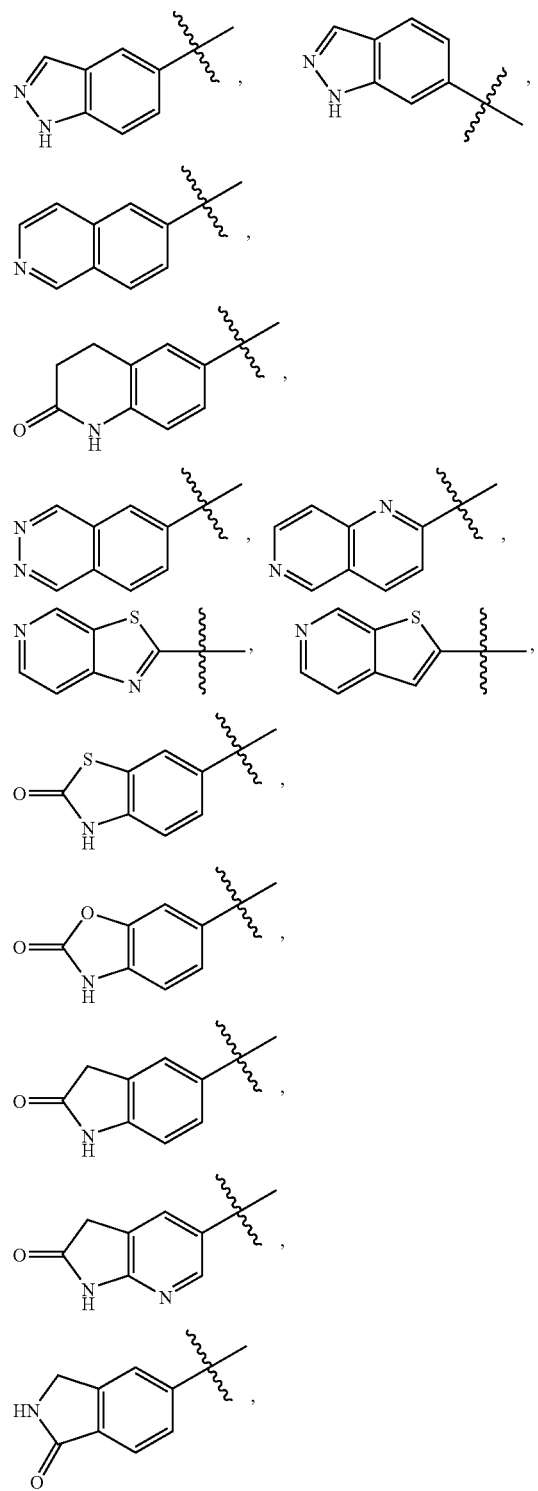

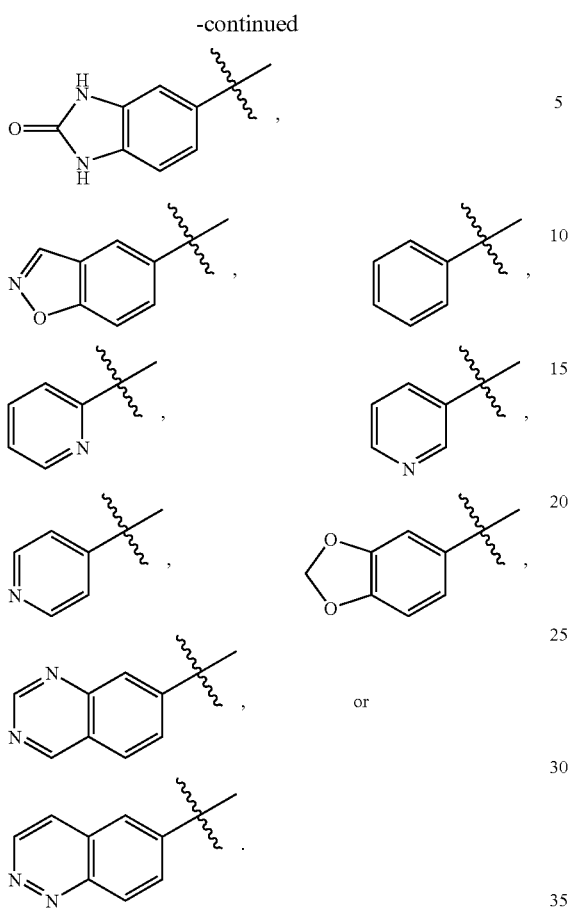
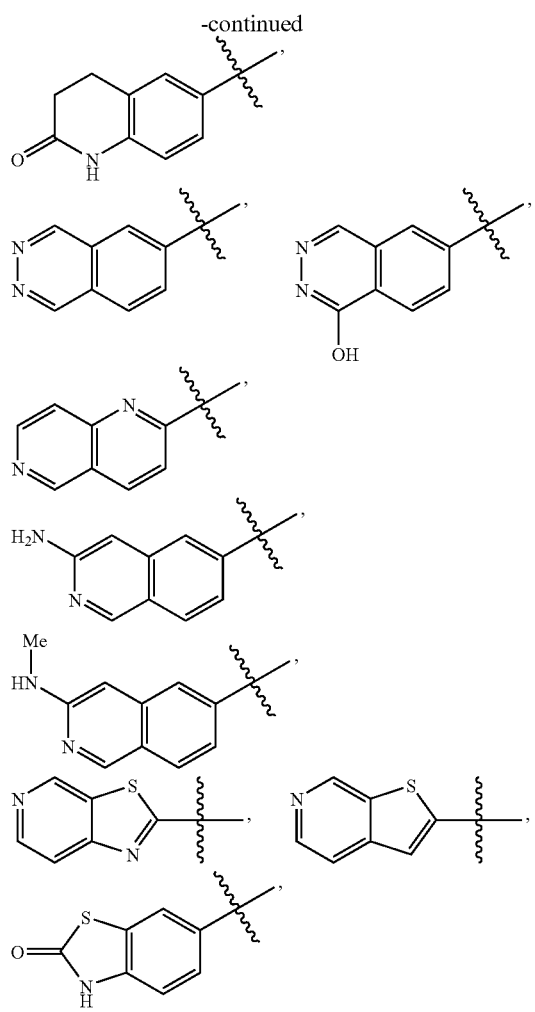
33. The compound of claim 11, wherein $R^2$ is selected from one of the following groups, where the wavy line indicates the point of attachment to the thiazole:
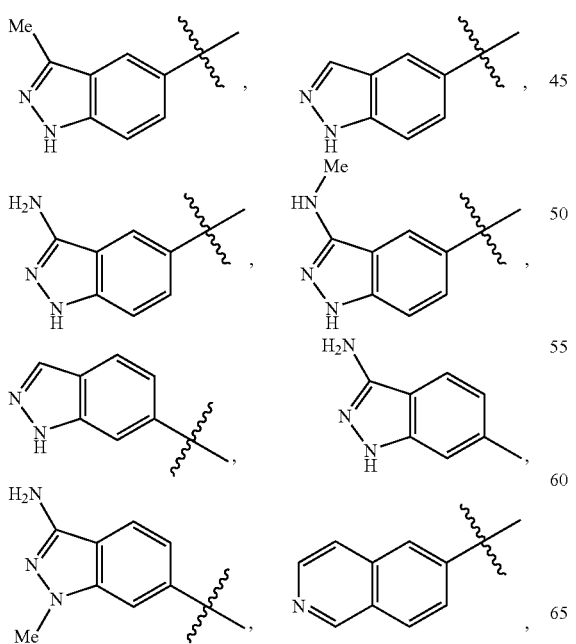
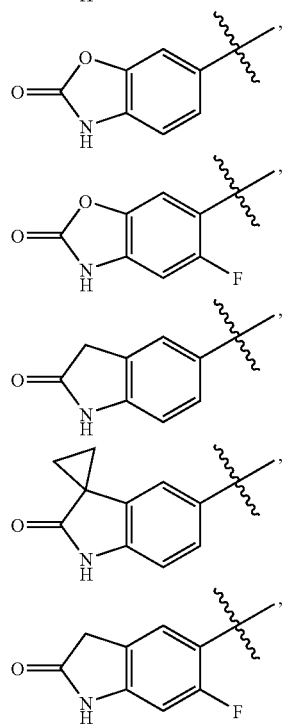

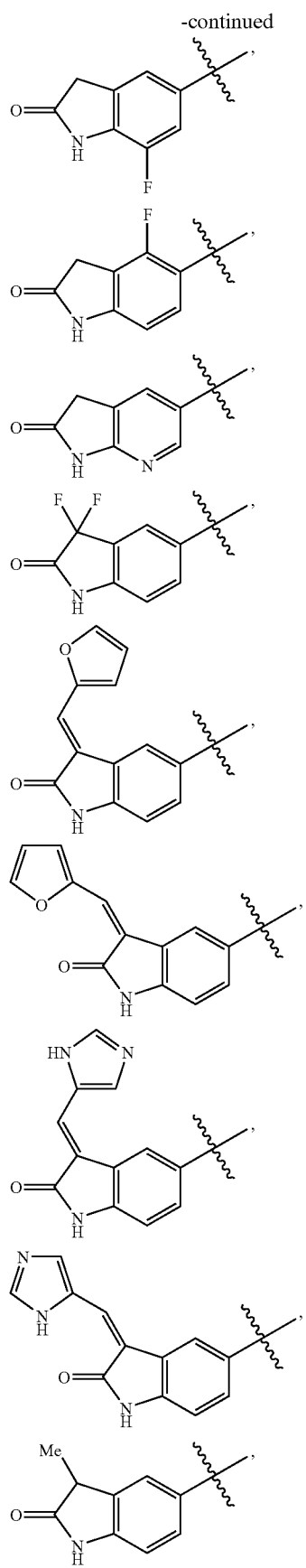
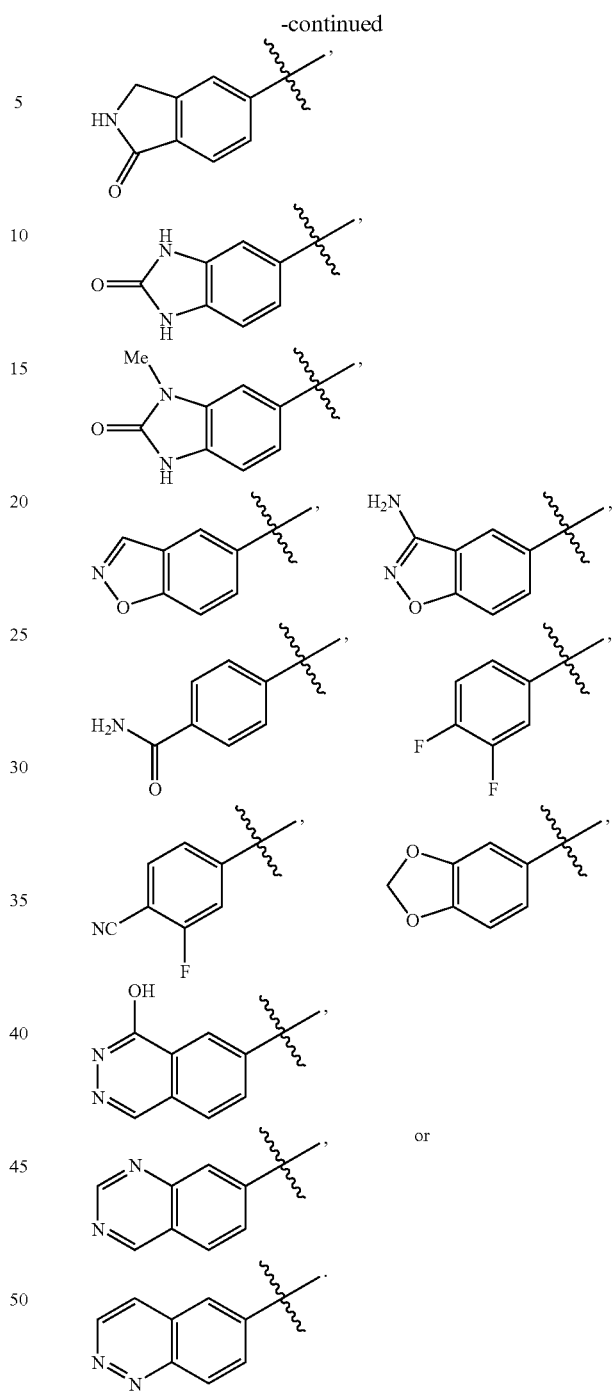

34. The compound of claim 11, wherein $R^1$ is selected from —H, —C≡N, —Br, —Cl, —OH, —CF$_3$, —CH$_3$, —CH$_2$CH$_3$, —CH$_2$CH$_2$OH, —C(H)(CH$_3$)OCH$_3$, —CH$_2$OCH$_2$CF$_3$, —CH$_2$N(H)CH$_3$, —CH$_2$N(CH$_3$)$_2$, —CF$_2$CH$_2$OH, cyclopropyl, furanyl, tetrahydrofuranyl phenyl, 2,3-difluorophenyl, 3,4-difluorophenyl, 4-fluorophenyl, 3-fluorophenyl, 2-fluorophenyl, pyridyl, oxazolyl, hydroxymethyl, methoxymethyl, ethoxymethyl, —C(O)OMe, —C(O)N(H)CH$_2$CH$_2$OH, —C(O)N(H)CH$_3$, —C(O)NH$_2$, —C(O)N(CH$_3$)$_2$, or a group selected from one of the following groups where the wavy line indicates the point of attachment to the thiazole:

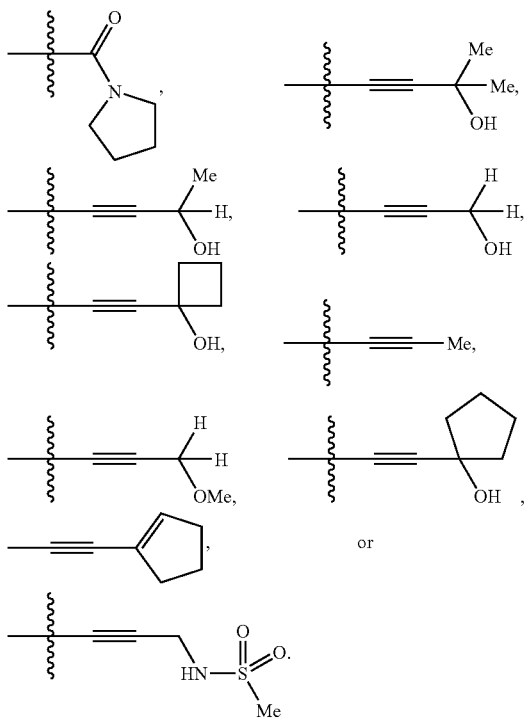

35. A pharmaceutical composition, comprising: a pharmaceutically-acceptable carrier and the compound of claim 11.

36. The composition of claim 35, further-comprising at least one additional therapeutic agent.

37. The compound of claim 1, wherein the compound is selected from

N-((S)-2-amino-3-phenylpropyl)-5-(3-methyl-1 H-indazol-5-yl)thiazol-2-amine,
N-((S)-2-amino-3-(1H-indol-3-yl)propyl)-5-(3-methyl-1H-indazol-5-yl)thiazol-2-amine,
N-((S)-2-amino-3-(4-chlorophenyl)propyl)-5-(3-methyl-1H-indazol-5-yl)thiazol-2-amine,
N-((S)-2-amino-3-(4-chlorophenyl)propyl)-5-( 1H-indazol-5-yl)thiazol-2-amine,
N-((S)-2-amino-3-(1H-indol-3-yl)propyl)-5-(isoquinolin-6-yl)thiazol-2-amine,
N-((S)-2-amino-3-(4-(trifluoromethyl)phenyl)propyl)-5-(isoquinolin-6-yl)thiazol-2-amine,
N-((S)-2-amino-3-phenylpropyl)-4-methyl-5-(3-methyl-1H-indazol-5-yl)thiazol-2-amine,
N-((S)-2-amino-3-(4-(trifluoromethyl)phenyl)propyl)-4-(furan-2-yl)-5-(isoquinolin-6-yl)thiazol-2-amine,
N-((S)2-amino-3-(4-(trifluoromethyl)phenyl)propyl)-5-(isoquinolin-6-yl)-4-phenylthiazol-2-amine,
(2-((S)-2-amino-3-(4-(trifluoromethyl)phenyl)propylamino)-5-(isoquinolin-6-yl)thiazol-4-yl)methanol,
(2-((S)-2-amino-3-(4-(trifluoromethyl)phenyl)propylamino)-5-(3-methyl- 1H-indazol-5-yl)thiazol-4-yl)methanol,
(2-((S)-2-amino-3-(4-(trifluoromethyl)phenyl)propylamino)-5-(1H-indazol-5-yl)thiazol-4-yl)methanol,
N-((S)-2-amino-3-(4-trifluoromethyl)phenyl)propyl)-5-(isoquinolin-6-yl)-4-(methoxymethyl)thiazol-2-amine,
N-((S)-2-amino-3-(4-(trifluoromethyl)phenyl)propyl)-5-(1H-indazol-5yl)-4-(methoxymethyl)thiazol-2-amine,
N-((S)-2-amino-3-(4-(trifluoromethyl)phenyl)propyl)-4-(methoxymethyl)-5-(3-methyl- 1H -indazol-5-yl)thiazol-2-amine,
N-((S)-2-amino-3-(4-(trifluoromethyl)phenyl)propyl)-5-(isoquinolin-6-yl)-4-(1-methoxyethyl)thiazol-2-amine,
N-((S)-amino-3-(3-chlorophenyl)propyl)4-(methoxymethyl)-5-(thiazolo[5,4-c]pyridin-2-yl)thiazol-2-amine,
N-((S)-2-amino-3-(4-chlorophenyl)propyl)-4-(methoxymethyl)-5-(thiazolo[5,4-c]pyridin-2-yl)thiazol-4-amine,
N-((S)-2-amino-3-(3-chlorophenyl)propyl)-5-(thiazolo[5,4-c]pyridin-2-yl)-4-((2,2,2-trifluoroethoxy)methyl)thiazol-2-amine,
N-((S)-2-amino-3-(4-chlorophenyl)propyl)-4-(ethoxymethyl)-5-(thiazolo[5,4-c]pyridin-2-yl)thiazol-2-amine,
N-((S)-2-amino-3-(4-(trifluoromethyl)phenyl)propyl)-4-(methoxymethyl)-5-(thiazolo[5,4-c]pyridin-2-yl)thiazol-2-amine,
N-((S)-2-amino-3-(4-(trifluoromethyl)phenyl)propyl)-4-ethyl-5-(thiazolo[5,4-c]pyridin-2-yl)thiazol-2-amine,
N-((S)-2-amino-3-(4-(trifluoromethyl)phenyl)propyl)-4-methyl-5-(thiazolo[5,4-c]pyridin-2-yl)thiazol-2-amine,
N-((S)-2-amino-3-(1H-indol-3-yl)propyl)-4-(methoxymethyl)-5-(thiazolo[5,4-c]pyridin-2-yl)thiazol-2-amine,
N-((S)-2-amino-3-(3-(trifluoromethyl)phenyl)propyl)-5-(thiazolo[5,4-c]pyridin-2-yl)thiazol-2-amine,
N-((S)-2-amino-3-(4-(trifluoromethyl)phenyl)propyl)-5-(thiazolo[5,4-c]pyridin-2-yl)thiazol-2-amine,
6-(2-((S)-2-amino-3-(4-(trifluoromethyl)phenyl)propylamino)thiazol-5-yl)-3,4-dihydroquinolin -2(1H)-one,
6-(2-((S)-2-amino-3-(1H-indol-3-yl)propylamino)thiazol-5-yl)benzo[d]thiazol-2(3H)-one,
5-(2-((S)-2-amino-3-(1H-indol-3-yl)propylamino)thiazol-5-yl)-1H-indazol-3-amine,
5-(2-((S)-2-amino-3-( 1H-indol-3-yl)propylamino)thiazol-5-yl)benzo[d]isoxazol-3-amine,
6-(2-((S)-2-amino-3-(1H-indol-3-yl)propylamino)thiazol-5-yl)benzo[d]oxazol-2(3H)-one,
6-(2-((S)-2-amino-3-(4-(trifluoromethyl)phenyl)propylamino)thiazol-5-yl)benzo[d]oxazol-2(3H) -one,
5-(2-((S)-2-amino-3-(4-(trifluoromethyl)phenyl)propylamino)thiazol-5-yl)-3,3-difluoroindolin-2-one,
5-(2-((S)-2-amino-3-(4-(trifluoromethyl)phenyl)propylamino)thiazol-5-yl)indolin-2-one,
6-(2-((S)-2-amino-3-(4-(trifluoromethyl)phenyl)propylamino)thiazol-5-yl)benzo[d]thiazol-2(3H) -one,
5-(2-((S)-2-amino-3-(3-(trifluoromethyl)phenyl)propylamino)thiazol-5-yl)indolin-2-one,
5-(2-((S)-2-amino-3-(1H-indol-3-yl)propylamino)thiazol-5-yl)-N-methyl-1H-indazol-3-amine,
6-(2-((S)-2-amino-3-(3-(trifluoromethyl)phenyl)propylamino)thiazol-5-yl)benzo[d]oxazol-2(3H)-one,
5-(2-((S)-2-amino-3-(4-(trifluoromethyl)phenyl) proplamino)thiazol-5-yl)-3-methylindolin-2-one,
N-((S)-2-amino-3-(4-(trifluoromethyl)phenyl)propyl)-5-(1H-indazol-6-yl)thiazol-2-amine,
5-(2-((S)-2-amino-3-(4-(trifluoromethyl)phenyl)propylamino)thiazol-5-yl)-1H-indazol-3-amine,
5-(2-((S)-2-amino-3-(4-(trifluoromethyl)phenyl)propylamino)thiazol-5-yl)benzo[d]isoxazol-3-amine,
6-(2-((S)-2-amino-3-(4-(trifluoromethyl)phenyl)propylamino)thiazol-5-yl)-1H-indazol-3-amine,
6-(2-((S)-2-amino-3-(4-(trifluoromethyl)phenyl)propylamino)thiazol-5-yl)-1-methyl-1H-indazo -3-amine,
5-(2-((S)-2-amino-3-(4chlorophenyl)propylamino)thiazol-5yl)indolin-2-one, 6-(2-((S)-2-amino-3-(4-chlorophenyl)propylamino)thiazol-5yl)benzo[d]oxazol-2(3H)-one,
N-((S)-2-amino-3-(4-(trifluoromethyl)phenyl)propyl)-5-(isoquinolin-6yl)-4-((methylamino)methyl)thiazol-2-amine,
6-2-((S)-2-amino-3-(4-trifluoromethyl)phenyl)propylamino)thiazol-5-yl)-1-methyl-1H-benzo[d]imidazol-2(3H)-one,
6-(2-((S)-2-amino-3-(4-(trifluoromethyl)phenyl)propylamino)-4-(methoxymethyl)thiazol-5-yl)-1-methyl-1H-benzo[d]imidazol-2(3H)-one,
6-(2-((S)-2-amino-3-(4-(trifluoromethyl)phenyl)propylamino)-4-(methoxymethyl)thiazol-5-yl)benzo[d]oxazol-2(3H)-one,
2-((S)-2-amino-3-(4-(trifluoromethyl)phenyl)propylamino)-5-(2-oxoindolin-5-yl)thiazole-4-carbonitrile,
2-((S)-2-amino-3-(4-(trifluoromethyl)phenyl)propylamino)-5-(3-methyl-2-oxo-2,3-dihydro-1H-benzo[d]imidazol-5-yl)thiazole-4-carbonitrile,
2-((S)-2-amino-3-(4-(trifluoromethyl)phenyl)propylamino)-5-(isoquinolin-6-yl)thiazole-4-carbonitrile,
N-((S)-2-amino-3-(4-(trifluoromethyl)phenyl)propyl)-5-(phthalazin-6-yl)thiazol-2-amine,
6-(2-((S)2-amino-3-(4-(trifluoromethyl)phenyl)propylamino)thiazol-5-yl)phthalazin-1-ol,
N—(S)-2-amino-3-(3-chlorophenyl)propyl)-5-(isoquinol in-6-yl)thiazol-2-amine,
5-(2-((S)-2-amino-3-(4-methoxyphenyl)propylamino)thiazol-5-yl)indolin-2-one,
N—((S)-2-amino-3-(4-(trifluoromethyl)phenyl)propyl)-5-(1,6-naphthyridin-2-yl)thiazol-2-amine,
5-(2-((S)-2-amino-3-(4-(trifluoromethyl)phenyl)propylamino)-4-(methoxymethyl)thiazol-5-yl)indolin-2-one,
5-(2-((S)-2-amino-3-phenylpropylamino)thiazol-5-yl)-3-methylindolin-2-one,
N—((S)-2-amino-3-(4-(trifluoromethyl)phenyl)propyl)-4-(methoxymethyl)-5-(1,6-naphthyridin-2-yl)thiazol-2-amine,
5-(2-((S)-2-amino-3-(1H-indol-3-yl)propylamino)thiazol-5-yl)indolin-2-one,
6-(2-((S)-2-amino-3-(4-(trifluoromethyl)phenyl)propylamino)thiazol-5-yl)isoquinolin-3-amine,
6-(2-((S)-2-amino-3-(4-chlorophenyl)propylamino)thiazol-5-yl)isoquinolin-3-amine,
6-(2-((S)-2-amino-3-(4-methoxyphenyl)propylamino)thiazol-5-yl)benzo[d]oxazol-2(3H)-one, or
4-(2-((S)-2-amino-3-(4-(trifluoromethyl)phenyl)propylamino)-5-(isoquinolin-6-yl)thiazole-4-yl)-2-methyl-but-3-yn-2-ol,
or a pharmaceutically acceptable salt or stereoisomer thereof.

38. The compound of claim 11, wherein the compound is

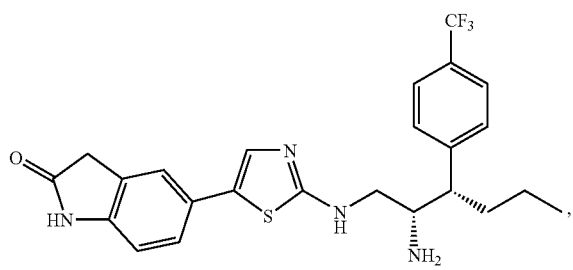

or a pharmaceutically acceptable salt or stereoisomer thereof.

39. The compound of claim 11, wherein the compound is

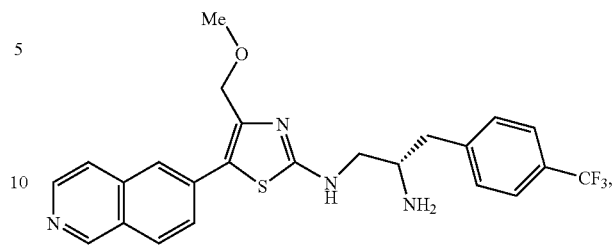

or a pharmaceutically acceptable salt or stereoisomer thereof.

40. The compound of claim 11, wherein the compound is

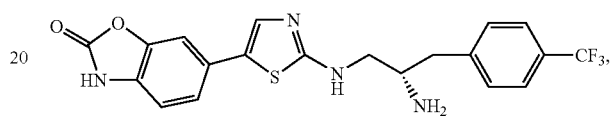

or a pharmaceutically acceptable salt or stereoisomer thereof.

41. The compound of claim 11, wherein the compound is

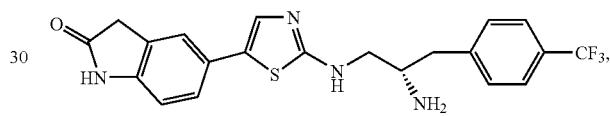

or a pharmaceutically acceptable salt or stereoisomer thereof.

42. The compound of claim 11, wherein the compound is

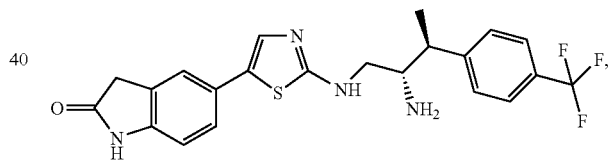

or a pharmaceutically acceptable salt or stereoisomer thereof.

43. The compound of claim 11, wherein the compound is

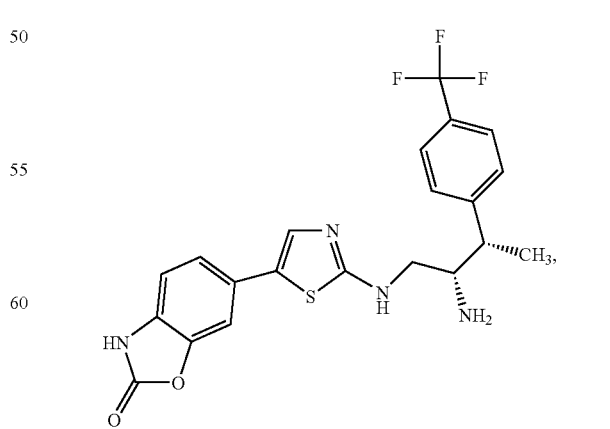

or a pharmaceutically acceptable salt or stereoisomer thereof.

44. The compound of claim 11, wherein the compound is

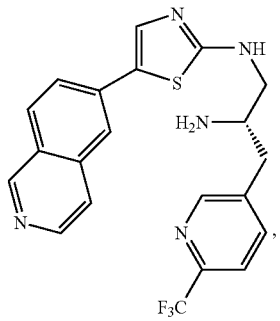

or a pharmaceutically acceptable salt or stereoisomer thereof.

45. The compound of claim 11, wherein the compound is

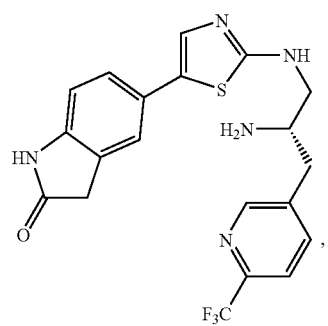

or a pharmaceutically acceptable salt or stereoisomer thereof.

46. The compound of claim 11, wherein the compound is

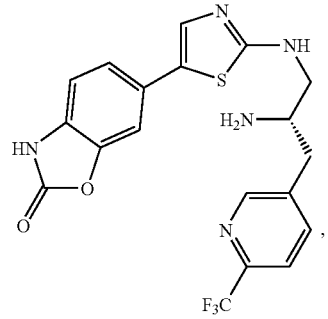

or a pharmaceutically acceptable salt or stereoisomer thereof.

47. The compound of claim 11, wherein the compound is

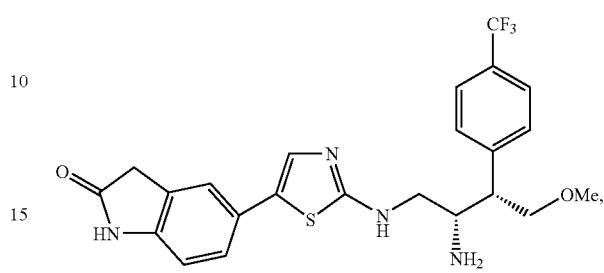

or a pharmaceutically acceptable salt or stereoisomer thereof.

48. The compound of claim 11, wherein the compound is

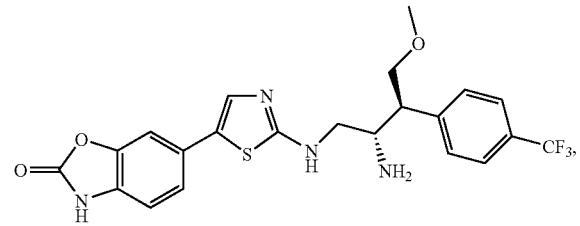

or a pharmaceutically acceptable salt or stereoisomer thereof.

* * * * *

UNITED STATES PATENT AND TRADEMARK OFFICE
CERTIFICATE OF CORRECTION

PATENT NO. : 7,514,566 B2
APPLICATION NO. : 11/652728
DATED : April 7, 2009
INVENTOR(S) : Zeng et al.

It is certified that error appears in the above-identified patent and that said Letters Patent is hereby corrected as shown below:

In claim 1, column 349, line 33, in the definition of the $R^6$ and $R^7$ variable, please replace ", or –C(O)($C_1$-$C_6$ alkyl)," with --, or –C(O)($C_1$-$C_6$ alkyl), or--.

In claim 5, column 350, lines 5 and 6 of the claim, replace "3-methylanmino-1H-indazol-5-yl" with --3-methylamino-1H-indazol-5-yl--.

In claim 11, column 351, line 31, in the definition of the $R^6$ and $R^7$ variable, please move the phrase beginning "$R^8$ is selected from" to the following line since this is the beginning of the definition of the $R^8$ variable.

In claim 11, column 351, line 51, please replace "heterocyclic" with --heterocyclyl--

In claim 24, column 353, line 2 of the claim, please replace "orthiophenyl" with --or thiophenyl--.

In claim 37, column 360, lines 8-10, please replace "N-((S)-2-amino-3-(4-chlorophenyl)propyl)-4-(methoxymethyl)-5-(thiazolo[5,4-c]pyridin-2-yl)thiazol-4-amine" with --N-((S)-2-amino-3-(4-chlorophenyl)propyl)-4-(methoxymethyl)-5-(thiazolo[5,4-c]pyridin-2-yl)thiazol-2-amine--.

In claim 37, column 361, lines 24-25, please replace "6-(2-((S)2-amino-3-(4-(trifluoromethyl)phenyl)propylamino)thiazol-5-yl)phthalazin-1-ol" with --6-(2-((S)-2-amino-3-(4-(trifluoromethyl)phenyl)propylamino)thiazol-5-yl)phthalazin-1-ol--.

Signed and Sealed this

Twenty-ninth Day of September, 2009

David J. Kappos
*Director of the United States Patent and Trademark Office*